US012668574B2

(12) United States Patent
Gilles

(10) Patent No.: US 12,668,574 B2
(45) Date of Patent: *Jun. 30, 2026

(54) 7-AZAINDOLE ANALOGS AND METHODS OF TREATING NEUROLOGICAL DISORDERS USING THE SAME

(71) Applicant: Kuleon LLC, Seattle, WA (US)

(72) Inventor: David Gilles, Tacoma, WA (US)

(73) Assignee: Kuleon LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/412,382

(22) Filed: Dec. 8, 2025

(65) Prior Publication Data

US 2026/0092034 A1 Apr. 2, 2026

Related U.S. Application Data

(63) Continuation of application No. 19/174,214, filed on Apr. 9, 2025, which is a continuation of application No. 18/741,888, filed on Jun. 13, 2024, now Pat. No. 12,275,701, which is a continuation of application No. 18/536,542, filed on Dec. 12, 2023, now Pat. No. 12,012,380, which is a continuation of application No. 18/360,976, filed on Jul. 28, 2023, now Pat. No. 12,187,678, which is a continuation of application No. 18/306,652, filed on Apr. 25, 2023, now Pat. No. 11,780,807, which is a continuation of application No. PCT/US2022/040048, filed on Aug. 11, 2022.

(60) Provisional application No. 63/325,515, filed on Mar. 30, 2022, provisional application No. 63/319,200, filed on Mar. 11, 2022, provisional application No. 63/314,378, filed on Feb. 26, 2022, provisional application No. 63/314,377, filed on Feb. 26, 2022, provisional application No. 63/314,379, filed on Feb. 26, 2022, provisional application No. 63/301,196, filed on Jan. 20, 2022, provisional application No. 63/292,567, filed on Dec. 22, 2021, provisional application No. 63/285,656, filed on Dec. 3, 2021, provisional application No. 63/285,679, filed on Dec. 3, 2021, provisional application No. 63/285,688, filed on Dec. 3, 2021, provisional application No. 63/239,963, filed on Sep. 2, 2021, provisional application No. 63/239,964, filed on Sep. 2, 2021, provisional application No. 63/239,965, filed on Sep. 2, 2021, provisional application No. 63/238,132, filed on Aug. 28, 2021, provisional application No. 63/238,133, filed on Aug. 28, 2021, provisional application No. 63/238,135, filed on Aug. 28, 2021, provisional application No. 63/238,134, filed on Aug. 28, 2021, provisional application No. 63/232,614, filed on Aug. 12, 2021, provisional application No. 63/232,548, filed on Aug. 12, 2021, provisional application No. 63/232,539, filed on Aug. 12, 2021.

(51) Int. Cl.
*C07D 209/04* (2006.01)

(52) U.S. Cl.
CPC .................................. *C07D 209/04* (2013.01)

(58) Field of Classification Search
CPC .................................................... C07D 209/04
See application file for complete search history.

(56) References Cited

U.S. PATENT DOCUMENTS

| | | | |
|---|---|---|---|
| 3,636,218 | A | 1/1972 | Suh |
| 4,137,414 | A | 1/1979 | Kukla |
| 5,494,910 | A | 2/1996 | North et al. |
| 5,792,763 | A | 8/1998 | Fritz et al. |
| 6,699,883 | B1 | 3/2004 | Doemling et al. |
| 8,680,135 | B2 | 3/2014 | Chaplin et al. |
| 9,365,590 | B2 | 6/2016 | Lim et al. |
| 10,933,073 | B2 | 3/2021 | Chadeayne |
| 11,292,765 | B2 | 4/2022 | Bryson |
| 11,780,807 | B2 | 10/2023 | Gilles |
| 12,012,380 | B1 | 6/2024 | Gilles |
| 2007/0293475 | A1 | 12/2007 | Mohapatra et al. |
| 2018/0221396 | A1 | 8/2018 | Chadeayne |
| 2019/0263757 | A1 | 8/2019 | Teegarden et al. |
| 2020/0030309 | A1 | 1/2020 | Olson |
| 2021/0188850 | A1 | 6/2021 | Mates et al. |
| 2023/0257346 | A1 | 8/2023 | Gilles |
| 2024/0124397 | A1 | 4/2024 | Gilles |
| 2024/0190819 | A1 | 6/2024 | Gilles |

FOREIGN PATENT DOCUMENTS

| | | | |
|---|---|---|---|
| AU | 585351 | A | 4/1986 |
| EP | 2762472 | A2 | 8/2014 |
| WO | 1995024200 | | 9/1995 |
| WO | 2007087684 | A1 | 8/2007 |
| WO | 2014018888 | A1 | 1/2014 |
| WO | 2018133854 | A1 | 7/2018 |
| WO | 2020176599 | A1 | 9/2020 |
| WO | 2020245133 | A1 | 12/2020 |
| WO | 2021041407 | A1 | 3/2021 |
| WO | 2021155470 | A1 | 8/2021 |
| WO | 2021252692 | A1 | 12/2021 |
| WO | 2022120181 | A1 | 6/2022 |

(Continued)

OTHER PUBLICATIONS

Gilles, David, File History of U.S. Appl. No. 18/716,589, filed Jun. 5, 2024.

(Continued)

*Primary Examiner* — Kamal A Saeed

(74) *Attorney, Agent, or Firm* — Kuleon IP Dept.

(57) ABSTRACT

Hallucinogenic and non-hallucinogenic serotonin receptor agonists are disclosed herein in addition to methods of making and using the same.

20 Claims, No Drawings

(56) References Cited

FOREIGN PATENT DOCUMENTS

| | | | |
|---|---|---|---|
| WO | 2022246554 | A1 | 12/2022 |
| WO | 2023101722 | A1 | 6/2023 |
| WO | 2023114238 | A1 | 6/2023 |
| WO | 2023115165 | A1 | 6/2023 |
| WO | 2023219789 | A1 | 11/2023 |
| WO | 2025000051 | A1 | 1/2025 |
| WO | 2023122135 | A1 | 6/2025 |

OTHER PUBLICATIONS

Gilles, David, File History of U.S. Appl. No. 18/360,976, filed Jul. 28, 2023.
PCT International Search Report and Written Opinion from PCT/US2022/053583, mailed Mar. 8, 2023, 8 pages.
Pubchem, SID 439594858, Modify Date: Jan. 15, 2021 [retrieved on 09 Feb. 1-5, 2023]., Retrieved from the Internet.
Pubchem, SID 440276851, Modify Date: Feb. 21, 2021 [retrieved on 09 Feb. 1-5, 2023]., Retrieved from the Internet.
Arsenyan, Pavel et al., "Synthesis, structure and cytotoxicity of 3-C, N, S, Se substituted benzo[b] selenophene derivatives", European Journal of Medicinal Chemistry 46 (2011) 3434-3443.
Bai, Chengfeng et al., "Benzothiophene derivatives as selective estrogen receptor covalent antagonists: Design, synthesis and anti-ER activities", Bioorg. Med. Chem. 47 (2021) 116395.
Berrade, Luis et al., "Novel Benzo[b]thiophene Derivatives as New Potential Antidepressants with Rapid Onset of Action", Journal of Medicinal Chemistry, 2011, 54, 3086-3090.
Blair, Joseph B. et al., "Thieno[3,2-b]- and Thieno[2,3-b]pyrrole Bioisosteric Analogues of the Hallucinogen and Serotonin Agonist N,N-Dimethyltryptamine", J. Med. Chem, 1999, 42, 1106-1111.
Bosin, T.R. et al., "Comparative toxicological studies of indole, benzo[b]thiophene, and 1-methylindole derivatives", Journal of Toxicology and Environmental Health, 1976, 1 :3, 515-520, doi: 10.1080/15287397609529350.
Campaigne, E. et al., "Benzo[b]thiophene Derivatives, XIX. The Sulfur Isosteres of Psilocin and Related Isomers", Journal of Heterocyclic Chemistry, vol. 10, No. 3, Jun. 1, 1973 (Jun. 1, 1973), pp. 297-305.
Campaigne, E. et al., Benzo[b]thiophene Derivatives. XII. Synthesis of Some 3-Benzo[b]thienylalkylamines and Comparison of Their Central Nervous System Activity with Tryptamine Isosteres, J. Med. Chem., Sep. 1968, 1049-1054.
Campaigne, E. et al., "Benzo[b]thiophene Derivatives. XVI. The Sulfur Isosteres of Melatonin, Bufotenine, 5-Hydroxytryptophan, and Related Structures", Journal of Medicinal Chemistry, 1970, vol. 13, No. 6, 1205-1208.
Campaigne, E. et al., "Biologically active benzo(b)thiophene derivatives", Adv Drug Ref. 1970; 5:1-54.
Casale, John F. et al., "The Characterization of 2-(5-Methoxy-1-benzofuran-3-yl)-N,N-dimethylethanamine (5-MeOBFe) and Differentiation from its N-Ethyl Analog", Microgram Journal, vol. 9, No. 1, 2012, 39-45.
Neidlein et al., Chemischer Informationsdienst 1978, 9, No. 14, Abstract 203, not in English (see scheme).
Dari, Abdelmjid et al., "Synthesis of Selenopsilocine (3-Dimethylaminoethyl-4-Hydroxybenzo[b]Selenophene)", Heterocycles, vol. 34, No. 9, 1992, 1737-1748.
Harris, R. Adron et al., "Structure-activity relationships among hallucinogenic tryptamine derivatives evaluated by schedule-controlled behaviour", J. Pharm. Pharmacol. 1981, 33: 320-322.
Harrison, Steadman D. Jr. et al., "Metabolism of 3-(2-Dimethylaminoethyl)Benzo[b]Thiophene In Vitro and In Vivo in the Rat", Drug Metabolism and Disposition, vol. 2, No. 3, 1974, 228-236.
Keri, Rangappa S. et al., "An overview of benzo[b]thiophene-based medicinal chemistry", European Journal of Medicinal Chemistry (2017), doi: 10.1016/j.ejmech.2017.07.038.
Krzyzanowski, Adrian et al., "Synthesis of Indole-, Benzo[b]thiophene-, and Benzo[b]selenophene-Based Analogues of the Resveratrol Dimers Viniferifuran and (±)-Dehydroampelopsin B", Org. Lett. 2018, 20, 6650-6654.
Malaca, Sara et al., "Toxicology and Analysis of Psychoactive Tryptamines", International Journal of Molecular Sciences, Dec. 4, 2020, 21, 9279, pp. 1-30.
Nakayama, Juzo et al., "Oxidation of Tetraarylselenophenes and Benzo[b ]selenophene with m-Chloroperbenzoic Acid", Chemistry Letters, 1995, 485-486.
PCT International Search Report and Written Opinion from PCT/US2022/040048 mailed Oct. 25, 2022, 8 pages.
Pubchem CID 6092, N-Ethyltryptamine, created Aug. 8, 2005.
Rudin, Deborah et al., "(2-Aminopropyl)benzo[B]thiophenes (APBTs) are novel monoamine transporter ligands that lack stimulant effects but display psychedelic-like activity in mice", Neuropsychopharmacology, 2022, 47(4) 914-923.
Staples, Maree K. et al., "Tandem free-radical additional substitution chemistry and its application to the preparation of novel AT1 receptor antagonists", Org. Biomol. Chem., 2011, 9, 473-479.
Neidlein, R. et al., "Synthese des Thiapsilocins," Archiv der Pharmazie 1974, 307(74), 232-234; not in English (see scheme).
Thiemann, Thies et al., "The chemistry of thiophene S-oxides and related compounds", Issue 5th Eurasian Conference on Heterocyclic Chemistry, 2009, 96-113.
Tomaszewski, Zbigniew et al., "Benzofuran Bioisosteres of Hallucinogenic Tryptamines", Journal of Medicinal Chemistry, 1992, vol. 35, No. 11, 2061-2064.
Winter, J.C. et al., "Synthesis of Some 3-Indenealkylamines. Comparison of the Biological Activity of 3-Indenealkylamines and 3-Benzo[b]thiophenealkylamines with Their Tryptamine Isosteres", J. Med. Chem. 1967, vol. 10, No. 5, pp. 856-859.
Zhang, Xue et al., "Metal-Free Synthesis of Aryl Selenocyanates and Selenaheterocycles with Elemental Selenium", Chemistry—A European Journal, 10.1002/chem.202004005, vol. 27, issue 3, Jan. 13, 2021, pp. 944-948.
Gilles, David, File History of U.S. Appl. No. 18/968,441, filed Dec. 4, 2024.

7-AZAINDOLE ANALOGS AND METHODS OF TREATING NEUROLOGICAL DISORDERS USING THE SAME

CROSS-REFERENCE TO RELATED APPLICATIONS

This application is a continuation of U.S. application Ser. No. 19/174,214, filed Apr. 9, 2025, which is a continuation of U.S. application Ser. No. 18/741,888, filed Jun. 13, 2024, now U.S. Pat. No. 12,275,701, which is a continuation of U.S. application Ser. No. 18/536,542, filed Dec. 12, 2023, now U.S. Pat. No. 12,012,380, which is a continuation of U.S. application Ser. No. 18/360,976, filed Jul. 28, 2023, now U.S. Pat. No. 12,187,678, which is a continuation of U.S. application Ser. No. 18/306,652, filed Apr. 25, 2023, now U.S. Pat. No. 11,780,807, which is a continuation of PCT/US2022/040048 filed Aug. 11, 2022, which claims priority to U.S. Provisional Application No. 63/325,515, filed Mar. 30, 2022, U.S. Provisional Application No. 63/319,200, filed Mar. 11, 2022, U.S. Provisional Application No. 63/314,379, filed Feb. 26, 2022, U.S. Provisional Application No. 63/314,378, filed Feb. 26, 2022, U.S. Provisional Application No. 63/314,377, filed Feb. 26, 2022, U.S. Provisional Application No. 63/301,196, filed Jan. 20, 2022, U.S. Provisional Application No. 63/292,567, filed Dec. 22, 2021, U.S. Provisional Application No. 63/285,688, filed Dec. 3, 2021, U.S. Provisional Application No. 63/285,679, filed Dec. 3, 2021, U.S. Provisional Application No. 63/285,656, filed Dec. 3, 2021, U.S. Provisional Application No. 63/239,965, filed Sep. 2, 2021, U.S. Provisional Application No. 63/239,964, filed Sep. 2, 2021, U.S. Provisional Application No. 63/239,963, filed Sep. 2, 2021, U.S. Provisional Application No. 63/238,135, filed Aug. 28, 2021, U.S. Provisional Application No. 63/238,134, filed Aug. 28, 2021, U.S. Provisional Application No. 63/238,133, filed Aug. 28, 2021, U.S. Provisional Application No. 63/238,132, filed Aug. 28, 2021, U.S. Provisional Application No. 63/232,614, filed Aug. 12, 2021, U.S. Provisional Application No. 63/232,548, filed Aug. 12, 2021, and U.S. Provisional Application No. 63/232,539, filed Aug. 12, 2021, the entire contents of each are incorporated by reference herein for all purposes.

TECHNICAL FIELD

This disclosure relates to hallucinogenic and non-hallucinogenic serotonin receptor agonist compounds, combinations thereof, and methods of using them for treating and preventing a variety of human conditions.

BACKGROUND

Many people worldwide are afflicted with psychological or mood disorders, such as depression, anxiety, compulsion, and post-traumatic stress disorders (PTSD). Altered synaptic connectivity has been observed in the brains of suffering from these types of diseases and disorders. Certain "psychedelic" drugs such as psilocybin and LSD have been found to alleviate symptoms of depression and PTSD in clinical trials. It is thought that this is due to the signaling of a 5-HT2A receptor, which sparks what's called neuroplasticity. Neuroplasticity helps the brain form new neural connections, which is believed to generate quick and lasting positive mood effects. In studies, psilocybin-based psychotherapy has been demonstrated to almost immediately reduce depressive symptoms in patients after a single high dose.

However, psychedelic-based drug therapies have several limitations that have inhibited their widespread adoption. Most notably, tryptamine drugs like psilocybin and LSD are hallucinogenic and must be administered in a clinical setting in the presence of a medical professional. Secondarily, well-known 5-HT2A receptor agonists like psilocin (the active compound of the prodrug psilocybin) are known to be cardiotoxic due to their strong agonistic effects at 5-HT2B receptor.

To date, very little (if any) work has been done in developing tryptamine-like analogs or tryptamine mimetics that are non-hallucinogenic and non-cardiotoxic, while maintaining their ability modulate a 5-HT2A receptor. Accordingly, there remains a need to develop novel active compounds exhibiting these properties to provide patients with therapeutic options that can be administered daily/weekly in the privacy of their own home without the oversight of medical professionals.

SUMMARY

Disclosed herein are hallucinogenic and non-hallucinogenic compounds of Formula I:

Formula I

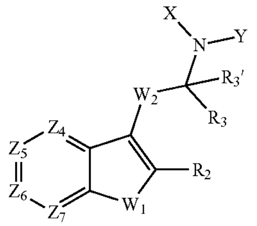

wherein

- X and Y are each independently selected from hydrogen, deuterium, optionally substituted $C_1$-$C_8$ alkyl, and optionally substituted $C_2$-$C_8$ alkenyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;
- $W_1$ is selected from $NR_1$, O, Se, Se(O), $SeO_2$, S, S(O), and $SO_2$;
- $W_2$ is selected from —$CD_2$-, —CHD-, —$(CD_2)_2$-, —$CH_2$— and —$(CH_2)_2$—;
- $Z_4$ is selected from N and $CR_4$;
- $Z_5$ is selected from N and $CR_5$;
- $Z_6$ is selected from N and $CR_6$;
- $Z_7$ is selected from N and $CR_7$;
- $R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)O_2(R_9)_2$, —$C(O)N(R_9)_2$, —$SOR_8$, and —$SO_2R_8$;
- $R_2$, $R_3$, $R_{3'}$, $R_6$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$;

$R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, —$C_1$-$C_8$alkoxy, —$OC(O)R_8$, —$OC(O)OR_8$, —$OP(O)O_2(R_9)_2$, and —$OSO_2R_8$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$alkyl, optionally substituted $C_2$-$C_8$ alkenyl, and optionally substituted aryl; and salts, solvates, hydrates, and prodrugs thereof.

The disclosure also relates to compositions comprising, consisting of, or consisting essentially of a compound of Formula I and an excipient. The disclosure further relates to pharmaceutical compositions comprising a therapeutically effective amount of a compound of Formula I, wherein the excipient is a pharmaceutically acceptable carrier.

The present disclosure further relates to a method of preventing or treating a psychological disorder comprising the step of administering to a subject in need thereof a therapeutically effective amount of a compound of Formula I or a pharmaceutical composition containing the same.

Embodiments of the disclosure also relate to a composition comprising, consisting of, or consisting essentially of a first compound selected from compounds of Formula I; and a second active compound. In certain embodiments, the second active compound comprises a serotonergic compound.

Also described herein are methods of preventing or treating inflammation and/or pain comprising administering to a subject in need thereof a therapeutically effective amount of a compound of Formula I, or a composition (e.g., a pharmaceutically-acceptable composition) containing said compound of Formula I.

Unless context indicates differently, reference to a compound of Formula I includes all subgenera of Formula I (e.g., Formulae Ia, Ib, II, etc.).

DETAILED DESCRIPTION

Compounds

Disclosed herein are compounds of Formula I:

Formula I

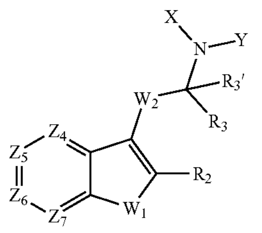

X and Y are each independently selected from hydrogen, deuterium, optionally substituted $C_1$-$C_8$ alkyl, and optionally substituted $C_2$-$C_8$ alkenyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from $NR_1$, O, Se, Se(O), $SeO_2$, S(O), and $SO_2$;

$W_2$ is selected from —$CD_2$-, —CHD-, —$(CD_2)_2$-, —$CH_2$— and —$(CH_2)_2$—;

$Z_4$ is selected from N and $CR_4$;

$Z_5$ is selected from N and $CR_5$;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)O_2(R_9)_2$, —$C(O)N(R_9)_2$, —$SOR_8$, and —$SO_2R_8$;

$R_2$, $R_3$, $R_{3'}$, $R_6$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$;

$R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, —$C_1$-$C_8$alkoxy, —$OC(O)R_8$, —$OC(O)OR_8$, —$OP(O)O_2(R_9)_2$, and —$OSO_2R_8$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$alkyl, optionally substituted $C_2$-$C_8$ alkenyl, and optionally substituted aryl; and salts, solvates, hydrates, and prodrugs thereof.

As used herein, the term "alkyl" refers to straight, branched or cyclic saturated hydrocarbon group. As used herein, alkyl has 1 to 20 carbon atoms, 1 to 10 carbon atoms, 1 to 8 carbon atoms, 1 to 6 carbon atoms or 1 to 3 carbon atoms. Examples of alkyl groups include methyl, ethyl, propyl, isopropyl, n-butyl, isobutyl, sec-butyl, tert-butyl pentyl, isopentyl, hexyl, heptyl, octyl, cyclopropyl, cyclobutyl, cyclopentyl, cyclohexyl, cycloheptyl, cyclooctyl, cyclononyl, and cyclodecyl. When an alkyl residue having a specific number of carbons is named by chemical name or identified by molecular formula, all positional isomers having that number of carbons may be encompassed; thus, for example, "butyl" includes n-butyl, isobutyl, sec-butyl, and tert-butyl; and "propyl" includes n-propyl and isopropyl. In some embodiments, a deuterium atom maybe be a replacement for a hydrogen atom. When the alkyl groups described herein are said to be "substituted," they may be substituted with any substituent or substituents as those found in the exemplary compounds and embodiments disclosed herein, as well as deuterium, aryl, heteroaryl, hydroxy, alkoxy, alkyl sulfonamido, aryl sulfonamido, and halo.

As used herein, the term "alkenyl" refers to an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, $CH{=}CH(CH_3)$, —$CH{=}C(CH_3)_2$, —$C(CH_3){=}CH_2$, —$C(CH_3){=}CH(CH_3)$, —$C(CH_2CH_3){=}CH_2$, —$C{\equiv}CH$, —$C{\equiv}C(CH_3)$, —$C{\equiv}C(CH_2CH_3)$, —$CH_2C{\equiv}CH$, $CH_2C{\equiv}C(CH_3)$ and $CH_2C{\equiv}C(CH_2CH_3)$, among others. When the alkenyl and alkynyl groups described herein are said to be "substituted," they may be substituted with any substituent or substituents as those found in the exemplary compounds and embodiments disclosed herein, as well as deuterium, aryl, heteroaryl, hydroxy, alkoxy, alkyl sulfonamido, aryl sulfonamido, and halo.

As used herein, the term "alkoxy" refers to —O-(alkyl), wherein alkyl is as defined above.

As used herein, the term "aryl" refers to an aromatic carbocyclic group of from 6 to 14 carbon atoms having a single ring (e.g., phenyl) or multiple condensed rings (e.g., naphthyl or anthryl). In some embodiments, aryl groups contain 6-14 carbons and in others from 6 to 12 or even 6 to 10 carbon atoms in the ring portions of the groups. Particular aryls include phenyl, biphenyl, naphthyl and the like. The phrase "aryl groups" also includes groups containing fused rings, such as fused aromatic-aliphatic ring systems (e.g., indanyl, tetrahydronaphthyl, and the like). When the aryl groups described herein are said to be "substituted," they may be substituted with any substituent or substituents as those found in the exemplary compounds and embodiments disclosed herein, as well as deuterium, aryl, alkyl, heteroaryl, hydroxyl, and halo.

As used herein, the term "heteroaryl" refers to an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic.

As used herein, the term "heterocyclic ring" or "heterocyclyl" or "heterocycloalkyl" refers to a non-aromatic cycloalkyl in which one to four of the ring carbon atoms are independently replaced with a heteroatom selected from O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass saturated and partially saturated ring systems. Further, the term heterocyclyl is intended to encompass any non-aromatic ring containing at least one heteroatom, which ring may be fused to an aryl or heteroaryl ring, regardless of the attachment to the remainder of the molecule. The phrase also includes bridged polycyclic ring systems containing a heteroatom.

As used herein, the term "heteromoieties" refers to any groups containing a heteroatom, for example, amino, O, Se, Se(O), $SeO_2$, S, S(O), and $SO_2$.

As used herein, the term "halo" or "halogen" refers to a fluorine, chlorine, bromine or iodine atom.

As used herein, the term "hydroxyl" refers to —OH group.

As used herein, the term "alkyl sulfonamido" refers to a moiety containing $-S(=O)_2-NR_2$, wherein each R group is chosen from an alkyl or H.

As used herein, the term "aryl sulfonamido" refers to a moiety containing $-S(=O)_2-NR_2$, wherein each R group is chosen from an aryl or H.

In some embodiments, the compound of Formula I contains one or more stereocenters.

In some circumstances, the compound of Formula I comprises a racemic mixture. In some embodiments, the compound of Formula I comprises the (S) enantiomer. In some embodiments, the compound of Formula I comprises the (R) enantiomer. In some embodiments, the (S) and (R) designations refer to the absolute stereochemistry of a compound having more than one stereocenter. In such cases, the conformation of one of those stereocenters may be referred to in terms of its relative (D) or (L) configuration.

In some embodiments, X and Y are independently selected from hydrogen, deuterium, and optionally substituted $C_1$-$C_8$ alkyl, wherein the alkyl group comprises a cycloalkyl moiety (e.g., cyclopropyl, cyclobutyl, etc.).

In some embodiments, $R_2$, $R_3$, $R_3$, $R_6$ and $R_7$ are each independently selected from hydrogen, deuterium, halo, $-N(R_9)_2$, $-SR_9$, optionally substituted $C_1$-$C_8$ alkyl, $-C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$. In some embodiments, $R_2$, $R_3$, $R_6$ and $R_7$ are each independently selected from hydrogen, deuterium, halo, optionally substituted $C_1$-$C_8$ alkyl, and optionally substituted $C_2$-$C_8$ alkenyl.

In some embodiments, $R_4$ and $R_5$ are each independently selected from hydrogen, deuterium, $-N(R_9)_2$, $-SR_9$, optionally substituted $C_1$-$C_8$ alkyl, optionally substituted $C_2$-$C_8$ alkenyl, halo, hydroxyl, $-C_1$-$C_8$ alkoxy, $-OC(O)R_8$, $-OC(O)OR_8$, $-OP(O)O_2(R_9)_2$, and $-OSO_2R_8$. In some embodiments, $R_4$ and $R_5$ are each independently selected from hydrogen, deuterium, optionally substituted $C_1$-$C_8$ alkyl, optionally substituted $C_2$-$C_8$ alkenyl, halo, hydroxyl, $-C_1$-$C_8$ alkoxy, $-OC(O)R_8$, $-OC(O)OR_8$, $-OP(O)O_2(R_9)_2$, and $-OSO_2R_8$.

In certain embodiments, at least one of $R_4$ and $R_5$ is selected from $C_1$-$C_8$ alkoxy group, or in some embodiments a $C_2$-$C_4$ alkoxy group, wherein it may be a straight chain or branched $C_1$-$C_5$ alkoxy group or $C_2$-$C_4$ alkoxy group, for example a straight chain, and may be methoxy or ethoxy. In some embodiments, $R_5$ is $C_1$-$C_5$ alkoxy. In some embodiments, $R_4$ is selected from hydrogen and fluorine, and $R_5$ is $C_1$-$C_5$ alkoxy. In some embodiments, at least one of $R_4$ and $R_5$ is selected from $C_1$-$C_5$ alkyl or $C_1$-$C_4$ alkyl, for example a straight chain $C_1$-$C_4$ alkyl. In some embodiments, $R_5$ is selected from methyl, ethyl, n-propyl or n-butyl, and for example methyl or ethyl. In some embodiments, at least one of $R_4$ and $R_5$ is halo. In some embodiments, $R_4$ is fluoro. In some embodiments, $R_4$ is fluoro and $R_5$ is selected from hydrogen and $C_1$-$C_5$ alkoxy. In some embodiments, at least one of $R_4$ and $R_5$ is $-OC(O)R_8$. In some embodiments $R_4$ is selected from $-OC(O)R_8$ and $R_5$ is hydrogen or fluoro.

In some embodiments, $R_8$ is selected from optionally substituted $C_1$-$C_8$ alkyl, optionally substituted $C_2$-$C_8$ alkenyl, and optionally substituted aryl. In some embodiments, $R_9$ is selected from hydrogen, deuterium, optionally substituted $C_1$-$C_8$ alkyl, optionally substituted $C_2$-$C_8$ alkenyl, and optionally substituted aryl. In some embodiments, $R_5$ is selected from methyl, ethyl, propyl, and isopropyl. In some embodiments, $R_9$ is selected from methyl, ethyl, propyl, and isopropyl.

Exemplary halo residues for compounds of Formula I include chloro, bromo, fluoro, and iodo. In certain embodiments, the compounds of Formula I comprise at least one fluoro residue.

In some embodiments, $W_1$ is selected from $NR_1$, O, Se, Se(O), $SeO_2$, S, S(O), and $SO_2$. In some embodiments, $W_1$ is $NR_1$. In some embodiments, $W_1$ is O. In some embodiments, $W_1$ is S. In some embodiments, $W_1$ is Se. In some embodiments, $Z_4$ is selected from N and $CR_4$; $Z_5$ is selected from N and $CR_5$; $Z_6$ is selected from N and $CR_6$; and $Z_7$ is selected from N and $CR_7$. In some embodiments, $Z_4$ is N. In some embodiments, $Z_5$ is N. In some embodiments, $Z_6$ is N. In some embodiments, $Z_7$ is N.

In some embodiments, $R_1$ is selected from hydrogen, deuterium, optionally substituted $C_1$-$C_8$ alkyl, optionally substituted $C_2$-$C_8$ alkenyl, —C(O)$R_8$, —C(O)O$R_8$, —P(O)$O_2(R_9)_2$, —C(O)N$(R_9)_2$, —SO$R_8$, and —$SO_2R_8$. In some embodiments, $R_1$ is hydrogen. In some embodiments, $R_1$ is optionally substituted $C_1$-$C_8$ alkyl. In some embodiments, $R_1$ is optionally substituted $C_2$-$C_4$ alkyl. In some embodiments, $R_1$ is methyl. In some embodiments, $R_1$ is ethyl. In some embodiments, $R_1$ is isopropyl.

In some embodiments, $W_2$ is selected from —$CD_2$-, —CDH—, —$(CD_2)_2$-, —$CH_2$— and —$(CH_2)_2$—. In some embodiments, $W_2$ is selected from —$CH_2$—. In some embodiments, $W_2$ is selected from —$(CH_2)_2$—. In some embodiments, $W_2$ is selected from —$CD_2$-. In some embodiments, $W_2$ is selected from —$(CD_2)_2$-. In some embodiments, $W_2$ is —CDH—. In some embodiments when $W_2$ is —CDH—, $W_2$ represents a stereocenter in the (R) or (S) conformation.

In certain embodiments, the alkyl groups of Formula I are selected from $C_1$-$C_8$ alkyl, $C_2$-$C_8$alkyl, $C_3$-$C_8$ alkyl, and $C_4$-$C_8$ alkyl, or methyl, ethyl, propyl, isopropyl, n-butyl, isobutyl, sec-butyl, tert-butyl pentyl, isopentyl, hexyl, heptyl, octyl, etc. In certain embodiments, the alkenyl groups of Formula I are selected from $C_2$-$C_8$ alkenyl, $C_3$-$C_8$ alkenyl, and $C_4$-$C_8$ alkenyl, or ethenyl, propenyl, butenyl, pentenyl, hexenyl, heptenyl, octenyl, etc. In certain embodiments, the alkyl and alkenyl groups of Formula I may be unsubstituted or substituted with one or more groups selected from aryl, heteroaryl, hydroxy, alkoxy, alkyl sulfonamido, aryl sulfonamido, and halo. In certain embodiments, the aryl groups of Formula I may be unsubstituted or substituted with one or more groups selected from aryl, alkyl, heteroaryl, hydroxyl, and halo. In certain embodiments, the alkoxy groups of Formula I may be unsubstituted or substituted with one or more groups selected from aryl, alkyl, heteroaryl, hydroxyl, and halo.

In some embodiments, X and/or Y may be a straight chain $C_1$-$C_4$ alkyl, or a $C_2$-$C_4$ alkenyl. In some embodiments, X and Y are each methyl, X and Y are each ethyl, or X is methyl and Y is ethyl. In certain embodiments X and/or Y are an $C_1$-$C_8$ alkyl or $C_2$-$C_8$ alkenyl optionally substituted with at least one halo group, such as fluorine. In certain embodiments, at least one of X or Y comprises a group selected from —$CF_3$, —$CHF_2$, —$CH_2F$, —$CH_2CF_3$, —$CH_2CHF_2$, and —$CH_2CH_2F$. In certain embodiments, at least one of X or Y comprises a group selected from —$CD_3$, —$CH_2CD_3$, —$CD_2CH_3$, and —$CD_2CD_3$.

In some embodiments, X is unsubstituted $C_1$-$C_8$ alkyl. In some embodiments, X is methyl. In some embodiments, X is ethyl. In some embodiments, X is n-propyl. In some embodiments, X is isopropyl. In some embodiments, X is cyclopropyl. In some embodiments, Y is hydrogen. In some embodiments, Y is unsubstituted $C_1$-$C_8$ alkyl. In some embodiments, Y is methyl. In some embodiments, Y is ethyl. In some embodiments, Y is n-propyl. In some embodiments, Y is isopropyl. In some embodiments, Y is cyclopropyl.

In some embodiments, $R_2$, $R_3$, $R_{3'}$, $R_6$ and $R_7$ are each independently selected from hydrogen, deuterium, halo, or $C_1$-$C_4$ alkyl, for example a straight chain $C_1$-$C_4$ alkyl. In some embodiments, $R_2$, $R_3$, $R_6$ and $R_7$ are each independently selected from hydrogen, deuterium, halo, methyl, ethyl, n-propyl, isopropyl, n-butyl and isobutyl. In other embodiments, $R_2$, $R_3$, $R_6$ and $R_7$ are each independently selected from hydrogen, deuterium, methyl, and ethyl.

In some embodiments, $R_2$ is hydrogen. In some embodiments, $R_3$ and $R_{3'}$ are each independently selected from hydrogen, methyl, and ethyl. In some embodiments, $R_3$ is hydrogen. In some embodiments, $R_3$ is methyl and $R_3$ is hydrogen. In some embodiments, $R_3$ and $R_{3'}$ are both hydrogen. In some embodiments, $R_3$ and $R_{3'}$ are both deuterium. In some embodiments, $R_3$ is hydrogen and $R_3$ is deuterium. In some embodiments, when $R_3$ and $R_{3'}$ are not the same, it represents a stereocenter wherein the compound of Formula I comprises a racemic mixture. In some embodiments, when $R_3$ and $R_{3'}$ are not the same, it represents a stereocenter wherein the compound of Formula I comprises the (S) enantiomer. In some embodiments, when $R_3$ is not hydrogen, it represents a stereocenter wherein the compound of Formula I comprises the (R) enantiomer. In some embodiments, a racemic mixture can be resolved to provide a pure enantiomer or a mixture enhanced with either the (R) or (S) enantiomer.

In some embodiments, $R_6$ and $R_7$ are each independently selected hydrogen, halo, methyl, ethyl, n-propyl, isopropyl, n-butyl and isobutyl. In some embodiments, $R_6$ is selected from hydrogen and halo. In some embodiments, $R_6$ is selected from hydrogen and fluorine. In some embodiments, $R_6$ is fluorine. In some embodiments, $R_7$ is selected from hydrogen and optionally substituted $C_1$-$C_4$ alkyl. In some embodiments, $R_7$ is selected from hydrogen, methyl and ethyl. In some embodiments, $R_7$ is optionally substituted $C_1$-$C_4$ alkyl. In some embodiments, when $R_6$ is fluoro, then $R_7$ is selected from hydrogen and optionally substituted $C_1$-$C_4$ alkyl.

In some embodiments, $R_4$ is hydrogen and $R_5$ is selected from optionally substituted $C_1$-$C_8$alkyl, optionally substituted $C_2$-$C_8$ alkenyl, halo, hydroxyl, —$C_1$-$C_8$ alkoxy, —OC(O)$R_8$, —OC(O)O$R_8$, —OP(O)$O_2(R_9)_2$, and —$OSO_2R_8$. In some embodiments, $R_5$ is selected from unsubstituted $C_1$-$C_8$ alkyl, hydroxyl, —$C_1$-$C_8$ alkoxy, —OC(O)$R_8$, —OC(O)O$R_8$, —OP(O)$O_2(R_9)_2$, and —$OSO_2R_8$. In some embodiments, $R_5$ is selected from unsubstituted $C_2$-$C_8$ alkyl, hydroxyl, —$C_1$-$C_8$alkoxy, —OC(O)$R_8$, —OC(O)O$R_8$, —OP(O)$O_2(R_9)_2$, and —$OSO_2R_8$. In some embodiments, $R_5$ is hydroxy. In some embodiments, $R_5$ is —OC(O)$R_8$. In some embodiments, $R_5$ is unsubstituted $C_1$-$C_4$alkyl. In some embodiments, $R_8$ is methyl.

In some embodiments, $R_5$ is hydrogen and $R_4$ is selected from optionally substituted $C_1$-$C_8$alkyl, optionally substituted $C_2$-$C_8$ alkenyl, halo, hydroxyl, —$C_1$-$C_8$ alkoxy, —OC(O)$R_8$, —OC(O)O$R_8$, —OP(O)$O_2(R_9)_2$, and —$OSO_2R_8$. In some embodiments, $R_4$ is selected from unsubstituted $C_1$-$C_8$ alkyl, hydroxyl, —$C_1$-$C_8$ alkoxy, —OC(O)$R_8$, —OC(O)O$R_8$, —OP(O)$O_2(R_9)_2$, and —$OSO_2R_8$. In some embodiments, $R_5$ is selected from unsubstituted $C_1$-$C_8$ alkyl, —$C_2$-$C_8$ alkoxy, —OC(O)$R_8$, —OC(O)O$R_8$, —OP(O)$O_2(R_9)_2$, and —$OSO_2R_8$. In some embodiments, $R_5$ is —OC(O)$R_8$. In some embodiments, $R_5$ is unsubstituted $C_1$-$C_4$ alkyl. In some embodiments, $R_5$ is methyl.

In certain embodiments, one or more hydrogen atoms on compounds of Formula I may be replaced with one or more deuterium atoms. For example, in certain embodiments $R_6$ may comprise a deuterium atom as a replacement for a hydrogen, or when $R_7$ is a —$CH_3$, each hydrogen atom may be replaced to form a —$CD_3$ residue. Similarly, another non-limiting example includes when X and/or Y is a —$CH_3$, each hydrogen atom may be replaced to form a —$CD_3$ residue.

In some embodiments, $R_4$ is not halo. In some embodiments, $R_5$ is not halo. In some embodiments, one of $R_4$ and $R_5$ is hydrogen and the other of $R_4$ and $R_5$ is selected from hydroxyl, —OC(O)$R_8$, —OC(O)O$R_8$, and —$C_1$-$C_8$ alkoxy; $R_6$ is selected from hydrogen and fluorine; and $R_7$ is selected from hydrogen, methyl and ethyl.

In some embodiments for compounds of Formula I, when X and Y are both methyl, $W_1$ is S, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_5$, $R_6$, and $R_7$ are all hydrogen, then $R_4$ is not hydroxyl or methoxy.

In some embodiments for compounds of Formula I, when X and Y are both methyl, $W_1$ is S, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_7$ are all hydrogen, then $R_5$ is not hydroxy or methoxy.

In some embodiments for compounds of Formula I, when X and Y are both ethyl, $W_1$ is S, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_7$ are all hydrogen, then $R_5$ is not methoxy.

In some embodiments for compounds of Formula I, when X and Y are both methyl, $W_1$ is S, $W_2$ is —$CH_2$—, $Z_4$ is $CR_4$, $Z_5$ is $CR_5$, $Z_6$ is $CR_6$ and $Z_7$ is $CR_7$, then at least one of $R_2$, $R_3$, $R_4$, $R_5$, $R_6$, or $R_7$ is not hydrogen.

In some embodiments for compounds of Formula I, when X and Y are both propyl, $W_1$ is S, $W_2$ is —$CH_2$—, $Z_4$ is $CR_4$, $Z_5$ is $CR_5$, $Z_6$ is $CR_6$ and $Z_7$ is $CR_7$, then at least one of $R_2$, $R_3$, $R_4$, $R_5$, $R_6$, or $R_7$ is not hydrogen.

In some embodiments for compounds of Formula I, when X methyl and Y is hydrogen, $W_1$ is S, $W_2$ is —$CH_2$—, $Z_4$ is $CR_4$, $Z_5$ is $CR_5$, $Z_6$ is $CR_6$ and $Z_7$ is $CR_7$, then at least one of $R_2$, $R_3$, $R_4$, $R_5$, $R_6$, or $R_7$ is not hydrogen.

In some embodiments for compounds of Formula I, when X ethyl and Y is hydrogen, $W_1$ is S, $W_2$ is —$CH_2$—, $Z_4$ is $CR_4$, $Z_5$ is $CR_5$, $Z_6$ is $CR_6$ and $Z_7$ is $CR_7$, then at least one of $R_2$, $R_3$, $R_4$, $R_5$, $R_6$, or $R_7$ is not hydrogen.

In some embodiments for compounds of Formula I, when X and Y are both methyl, $W_1$ is Se, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_5$, $R_6$, and $R_7$ are all hydrogen, then $R_4$ is not hydroxyl or methoxy.

In some embodiments for compounds of Formula I, when X and Y are both methyl, $W_1$ is O, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_7$ are all hydrogen, then $R_5$ is not hydroxy, methoxy, or bromo.

In some embodiments for compounds of Formula I, when X and Y are both methyl, $W_1$ is O, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_5$ are all hydrogen, then $R_7$ is not methoxy.

In some embodiments for compounds of Formula I, when X is methyl or ethyl and Y is hydrogen, $W_1$ is O, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_7$ are all hydrogen, then $R_5$ is not methoxy.

In some embodiments for compounds of Formula I, when X methyl and Y is hydrogen, $W_1$ is O, $W_2$ is —$CH_2$—, $Z_4$ is $CR_4$, $Z_5$ is $CR_5$, $Z_6$ is $CR_6$ and $Z_7$ is $CR_7$, then at least one of $R_2$, $R_3$, $R_4$, $R_5$, $R_6$, or $R_7$ is not hydrogen.

In some embodiments for compounds of Formula I, when X is methyl and Y is hydrogen, $W_1$ is O, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_7$ are all hydrogen, then $R_6$ is not methoxy.

In some embodiments for compounds of Formula I, when X is methyl and Y is hydrogen, $W_1$ is O, $W_2$ is —$CH_2$—, $Z_4$ is $CR_4$, $Z_5$ is $CR_5$, $Z_6$ is $CR_6$ and $Z_7$ is $CR_7$, and $R_2$, $R_3$, $R_4$, $R_5$, and $R_6$ are all hydrogen, then $R_7$ is not methoxy.

In some embodiments for compounds of Formula I, at least one of $R_2$, $R_3$, $R_5$, $R_6$ or $R_7$ is not hydrogen when X and Y are both methyl, $W_1$ is NH, $W_2$ is —$CH_2$—, $Z_4$ is N, $Z_5$ is $CR_5$, $Z_6$ is $CR_6$ and $Z_7$ is $CR_7$.

In some embodiments for compounds of Formula I, $R_5$ is not methyl or methoxy when X and Y are both methyl, $W_1$ is NH, $W_2$ is —$CH_2$—, $Z_4$ is N, $Z_5$ is $CR_5$, $Z_6$ is $CR_6$ and $Z_7$ is $CR_7$, and $R_2$, $R_3$, $R_6$ and $R_7$ are all hydrogen.

In some embodiments for compounds of Formula I, at least one of $R_2$, $R_3$, $R_4$, $R_6$ or $R_7$ is not hydrogen when X and Y are both methyl, $W_1$ is NH, $W_2$ is —$CH_2$—, $Z_4$ is $CR_4$, $Z_5$ is N, $Z_6$ is $CR_6$ and $Z_7$ is $CR_7$.

In some embodiments for compounds of Formula I, $R_2$ is not ethyl or iodo when X and Y are both methyl, $W_1$ is NH, $W_2$ is —$CH_2$—, $Z_4$ is $CR_4$, $Z_5$ is N, $Z_6$ is $CR_6$ and $Z_7$ is $CR_7$, and $R_3$, $R_4$, $R_6$ and $R_7$ are all hydrogen.

In some embodiments for compounds of Formula I, at least one of $R_2$, $R_3$, $R_4$, $R_5$ or $R_7$ is not hydrogen when X and Y are both ethyl, $W_1$ is NH, $W_2$ is —$CH_2$—, $Z_4$ is $CR_4$, $Z_5$ is $CR_5$, $Z_6$ is N and $Z_7$ is $CR_7$.

In some embodiments for compounds of Formula I, $R_6$ is not chloro when X and Y are both methyl, $W_1$ is NH, $W_2$ is —$CH_2$—, $Z_4$ is $CR_4$, $Z_5$ is $CR_5$, $Z_6$ is $CR_6$ and $Z_7$ is N, and $R_2$, $R_3$, $R_4$, and $R_5$ are all hydrogen.

In some embodiments for compounds of Formula I, $R_6$ is not chloro when X is hydrogen and Y is methyl, $W_1$ is NH, $W_2$ is —$CH_2$—, $Z_4$ is $CR_4$, $Z_5$ is $CR_5$, $Z_6$ is $CR_6$ and $Z_7$ is N, and $R_2$, $R_3$, $R_4$, and $R_5$ are all hydrogen.

In some embodiments for compounds of Formula I, at least one of $R_2$, $R_3$, $R_4$, $R_5$ or $R_6$ is not hydrogen when X and Y are both methyl, $W_1$ is NH, $W_2$ is —$CH_2$—, $Z_4$ is $CR_4$, $Z_5$ is $CR_5$, $Z_6$ is $CR_6$ and $Z_7$ is N.

In some embodiments, $R_2$ is not ethyl or iodo when X and Y are both methyl, $W_1$ is NH, $W_2$ is —$CH_2$—, $Z_4$ is $CR_4$, $Z_5$ is $CR_5$, $Z_6$ is $CR_6$ and $Z_7$ is N, and $R_3$, $R_4$, $R_5$ and $R_6$ are all hydrogen.

In some embodiments, the compounds of Formula I are represented by compounds of Formula II:

Formula II

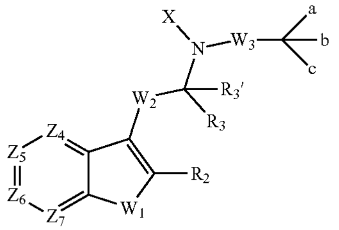

wherein

X is selected from hydrogen and deuterium;

$W_3$ is absent or is selected from —$(CZ'_2)_n$—, wherein n is an integer selected from 1 and 2, and each Z' is independently selected from hydrogen, deuterium, and fluorine;

a, b and c are each independently selected from hydrogen, deuterium, and fluorine; and all other variables are as defined above.

In certain embodiments for compounds of Formula II, $W_3$ is absent. In certain embodiments, n=1. In certain embodiments, $Z_4$ is $CR_4$ and $R_4$ is fluorine. In certain embodiments, $Z_6$ is $CR_6$ and $R_6$ is fluorine. In certain embodiments, $Z_4$ is N. In certain embodiments, $Z_5$ is N. In certain embodiments, $Z_6$ is N. In certain embodiments, $Z_7$ is N. In certain embodiments, $W_3$ is selected from —$CH_2$—, —CHF—, —$CF_2$—, and —$CD_2$-. In certain embodiments, a is fluorine, and b and c are each hydrogen. In certain embodiments, a is hydrogen, and b and c are each fluorine. In certain embodiments, a, b and c are all fluorine. In certain embodiments, a, b and c are all hydrogen. In certain embodiments, a, b and c are all deuterium.

In certain embodiments, $W_2$ is selected from —$CH_2$—, —$CD_2$- and —CHD-. In certain embodiments, $R_3$ and $R_{3'}$ are both hydrogen. In certain embodiments, $R_3$ and $R_{3'}$ are both deuterium. In certain embodiments, $R_3$ is hydrogen and $R_{3'}$ is deuterium. In certain embodiments, $W_2$ is —CHD-, $R_3$ is hydrogen and $R_{3'}$ is deuterium. In certain embodiments, $W_3$ is —$CH_2$—. In certain embodiments, $W_3$ is —$CD_2$-. In some embodiments, $W_2$ is —$CH_2$—, $R_3$ is hydrogen, $R_{3'}$ is deuterium, $Z_4$ is $CR_4$, $Z_5$ is $CR_5$, $Z_6$ is $CR_6$, $Z_7$ is $CR_7$, and $R_2$, $R_4$, $R_5$, $R_6$ and $R_7$ are all hydrogen. In some embodiments, $W_2$ is —$CH_2$—, $R_3$ is deuterium, $R_{3'}$ is hydrogen, $Z_4$ is $CR_4$, $Z_5$ is $CR_5$, $Z_6$ is $CR_6$, $Z_7$ is $CR_7$, and $R_2$, $R_4$, $R_5$, $R_6$ and $R_7$ are all hydrogen.

Exemplary compounds of Formula I include:

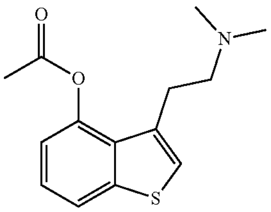

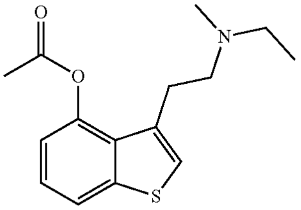

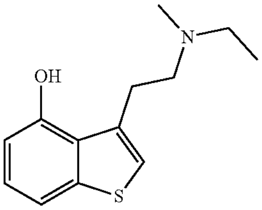

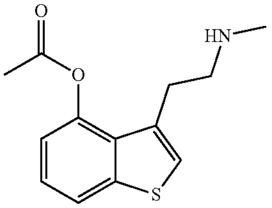

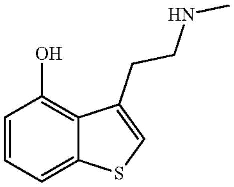

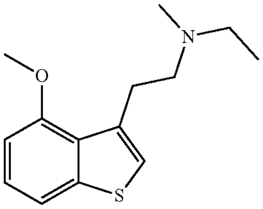

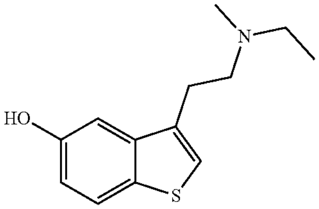

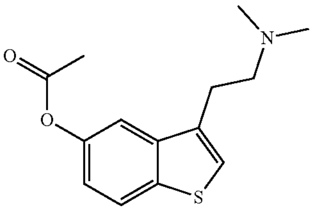

-continued

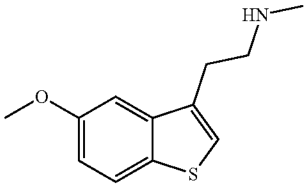

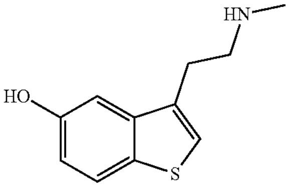

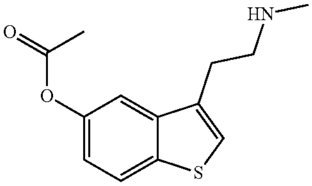

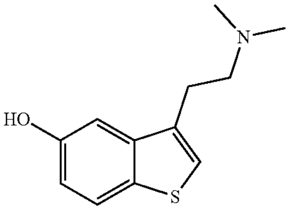

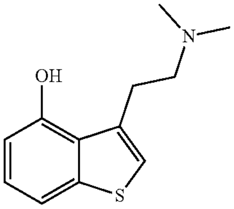

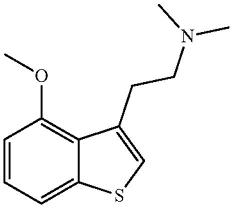

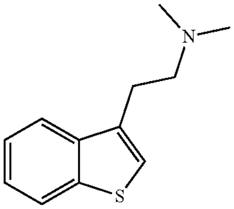

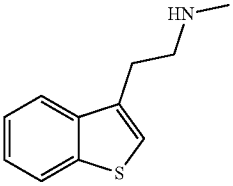

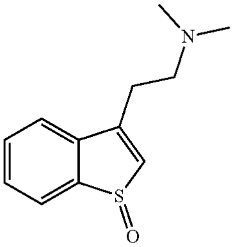

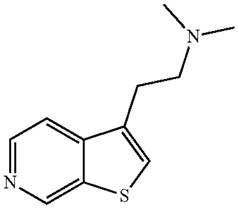

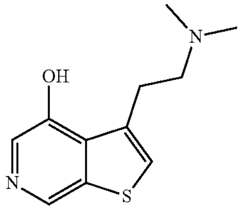

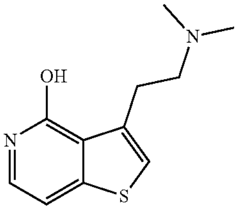

-continued
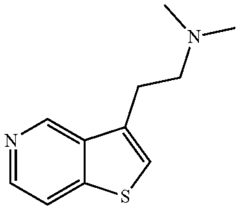
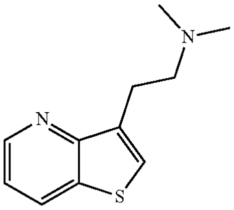
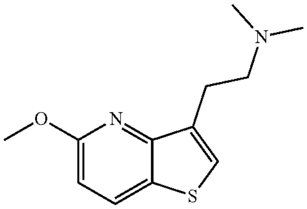
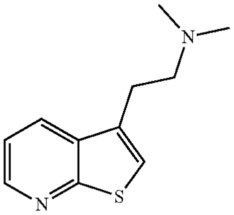
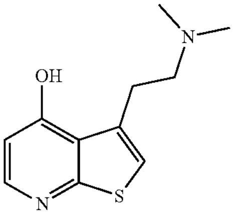
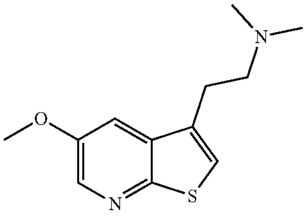
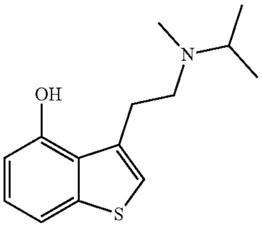
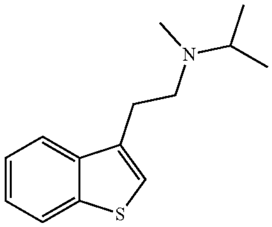 [SMILES: CC(C)N(C)CCc1csc2ccccc12]
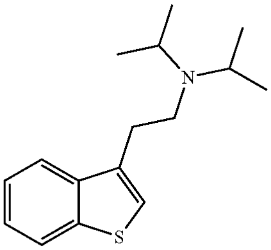
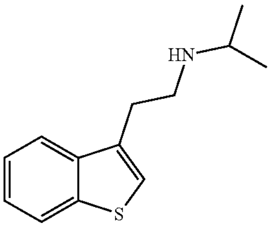
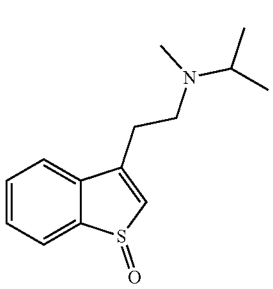
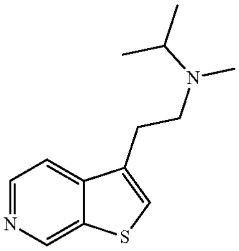
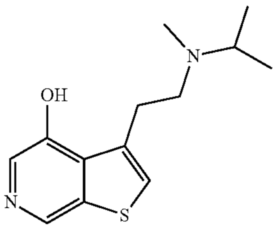
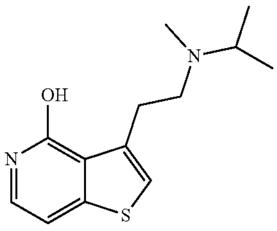
-continued
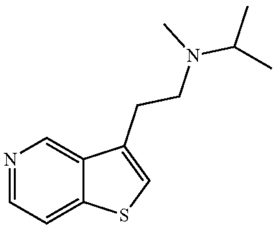
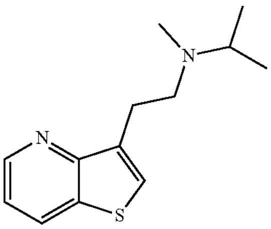
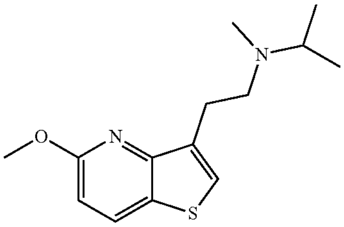
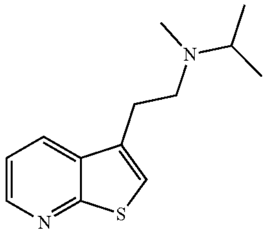
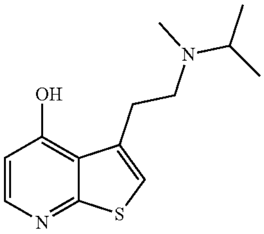
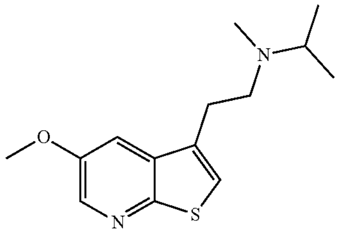
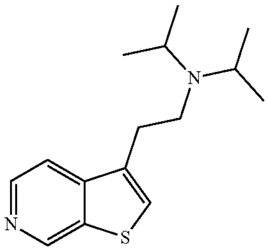
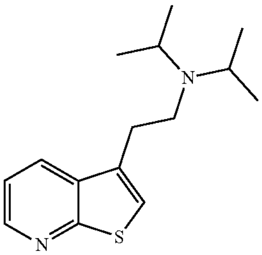
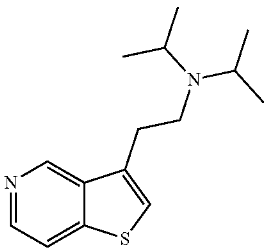
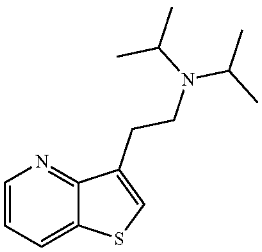
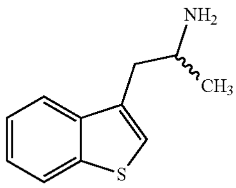
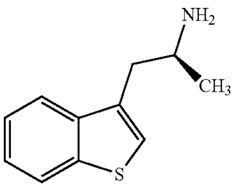

-continued
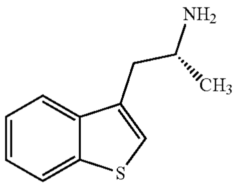
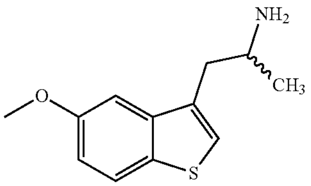
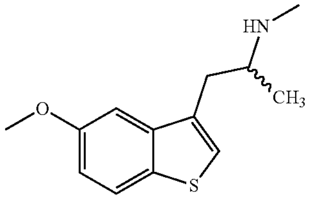
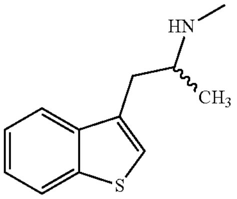
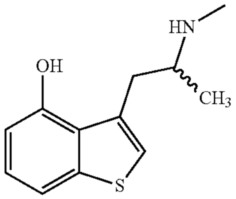
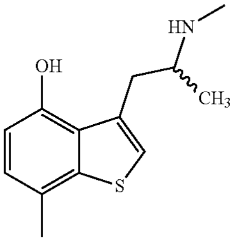
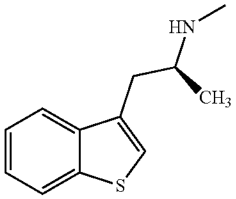
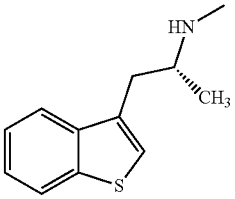
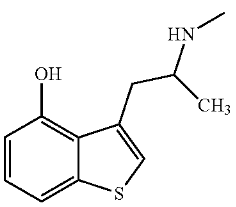
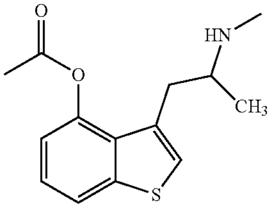
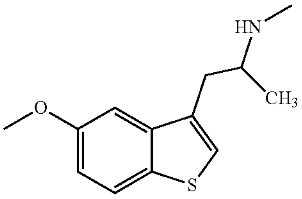
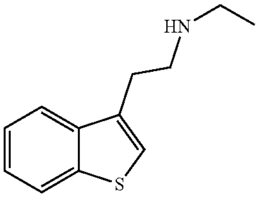
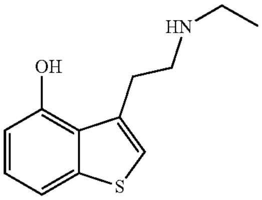
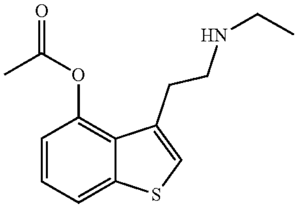
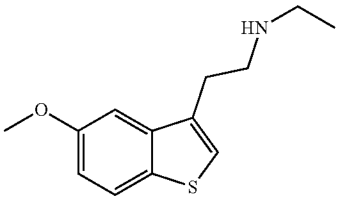
-continued
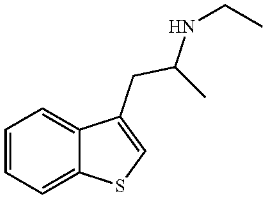
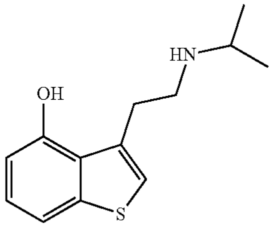
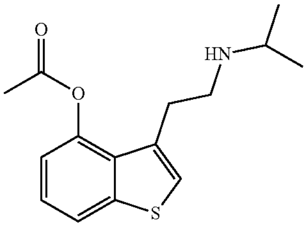
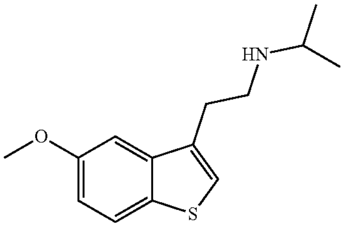
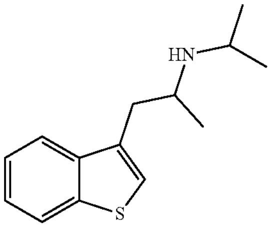
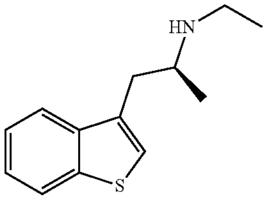
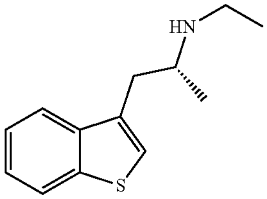
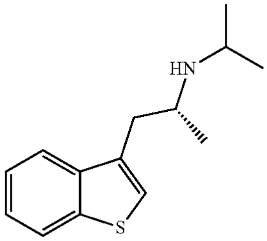
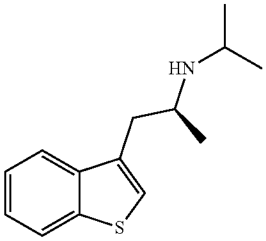
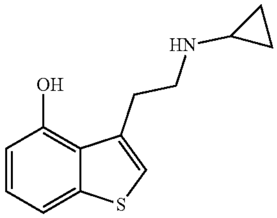

-continued
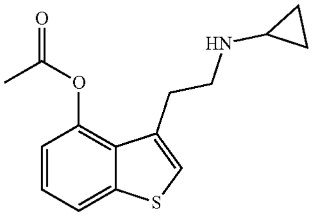
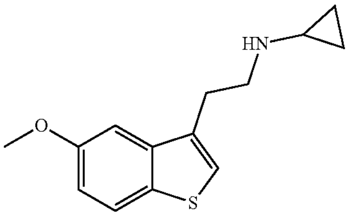
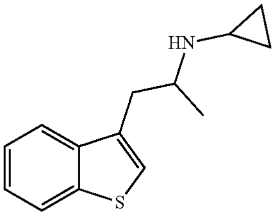
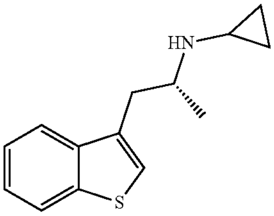
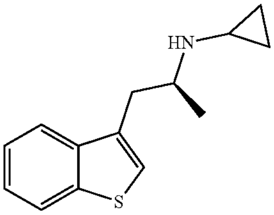
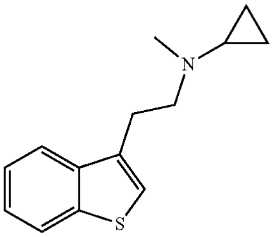
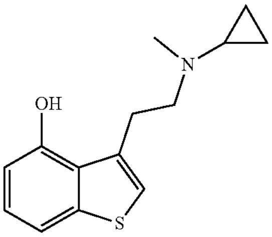
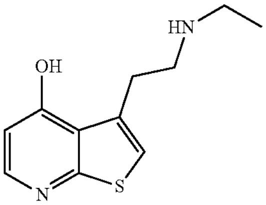
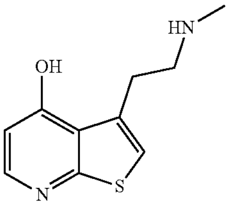
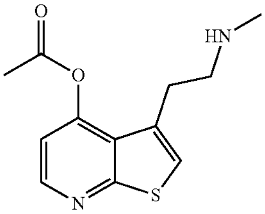
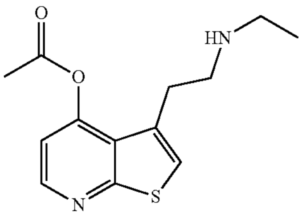
-continued
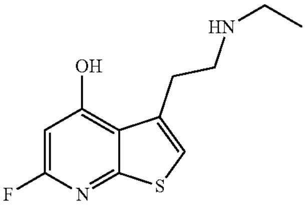
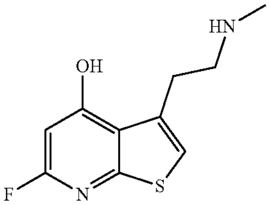
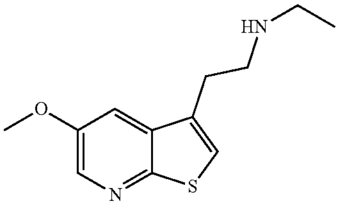
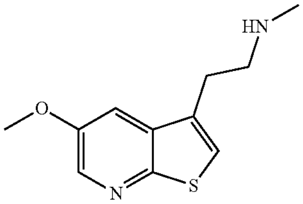
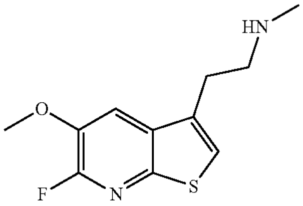
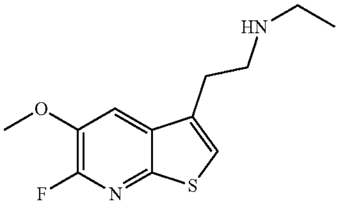
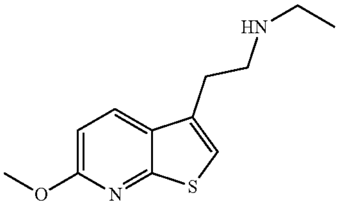
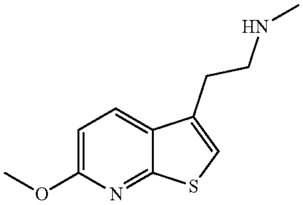

-continued
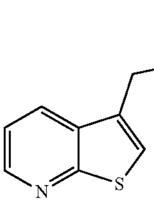
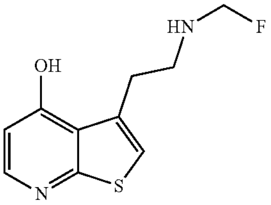
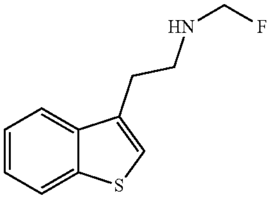
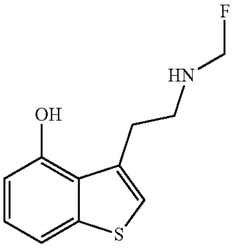
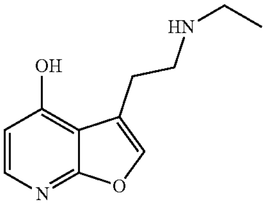
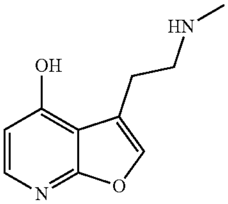
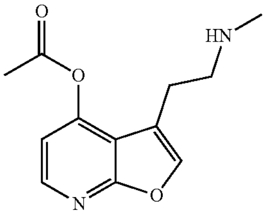
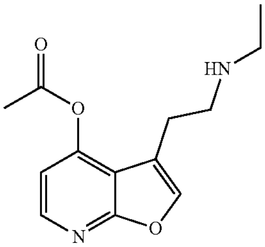
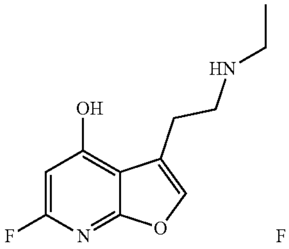
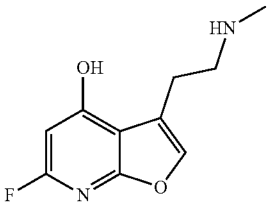
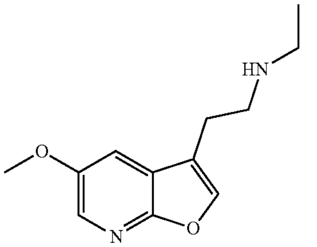
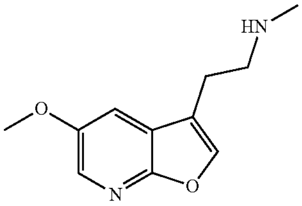
-continued
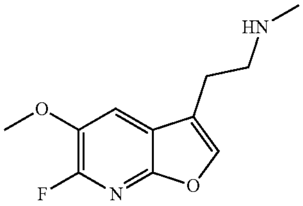
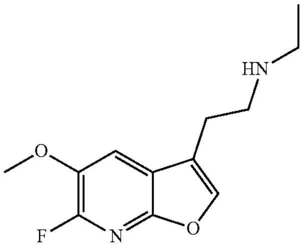
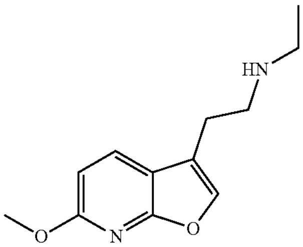
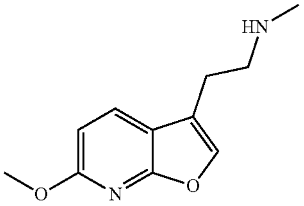
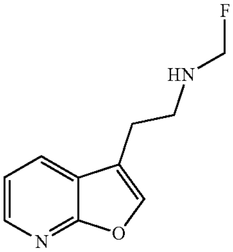
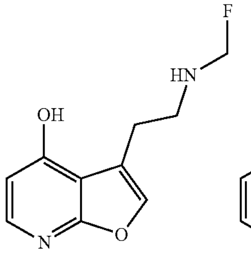
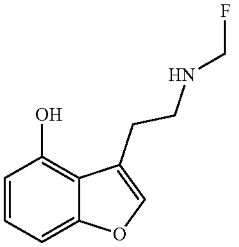
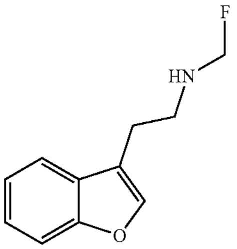
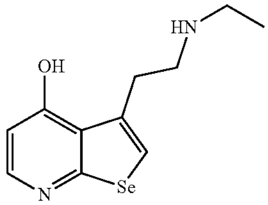
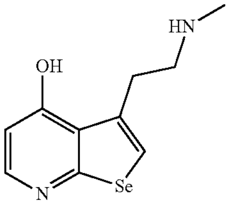

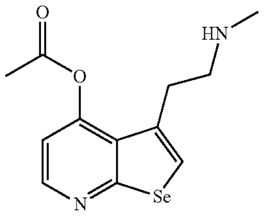
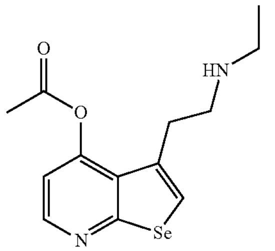
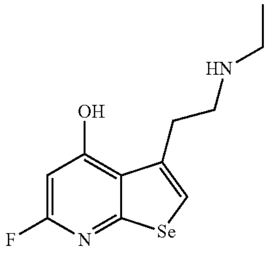
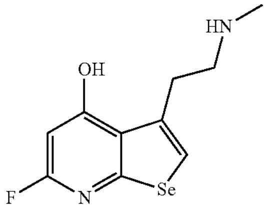
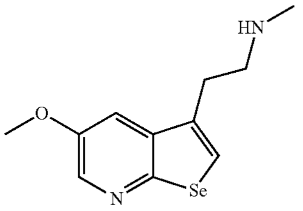
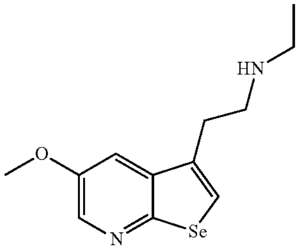
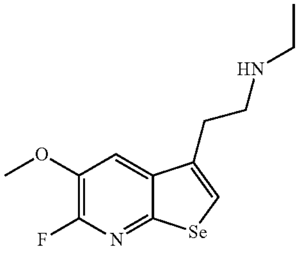
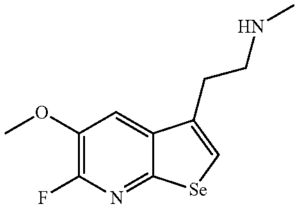
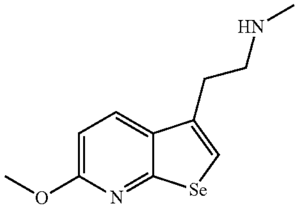
-continued
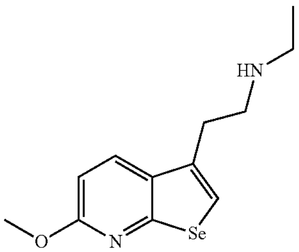
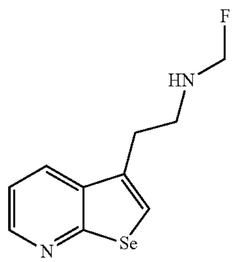
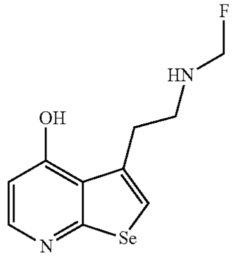
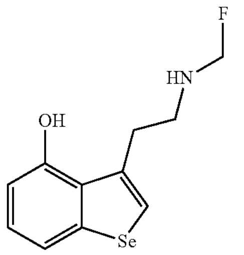
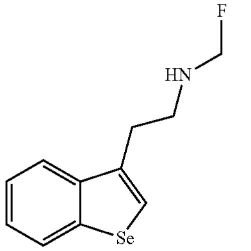
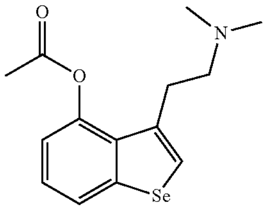
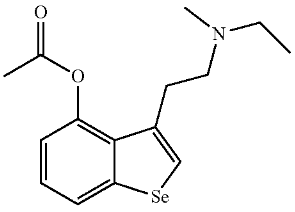
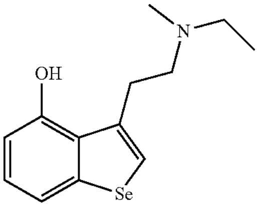
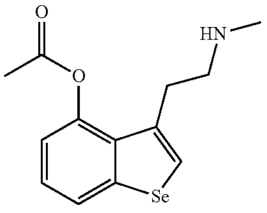
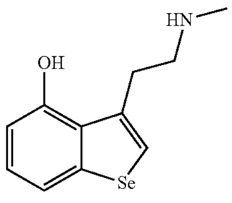
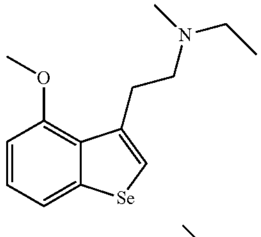
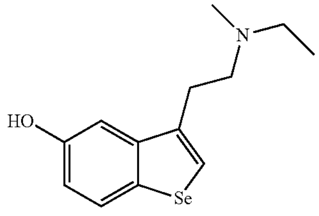

-continued
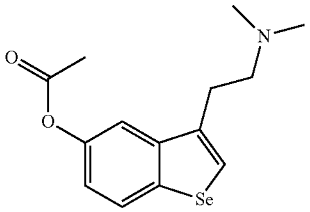
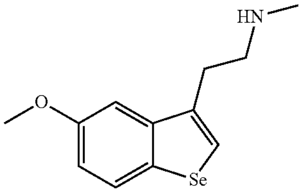
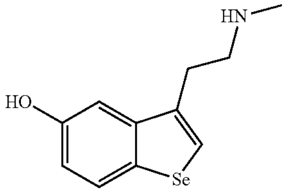
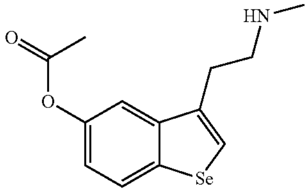
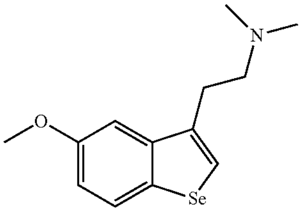
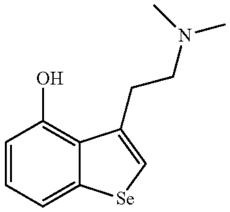
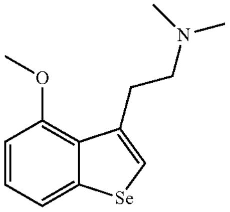
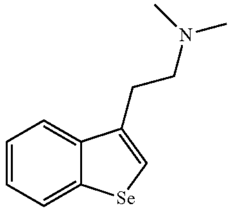
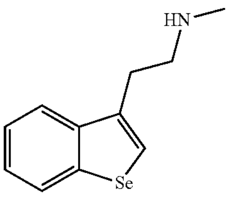
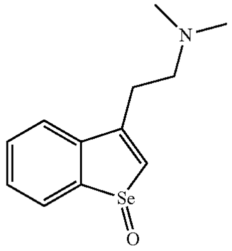
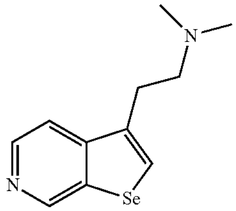
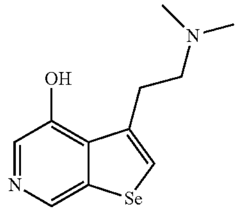
-continued
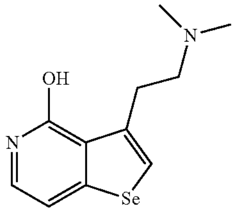
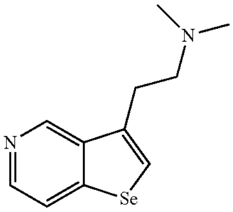
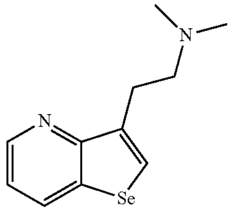
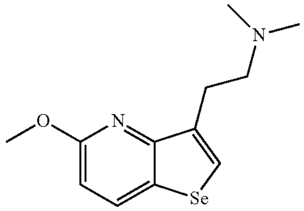
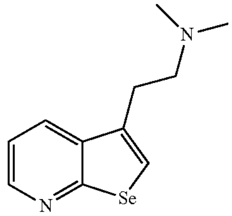
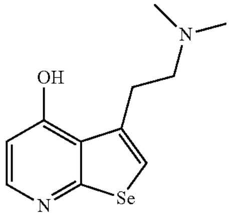
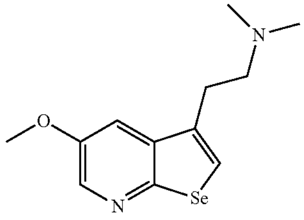
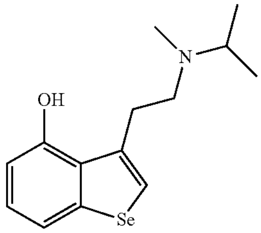
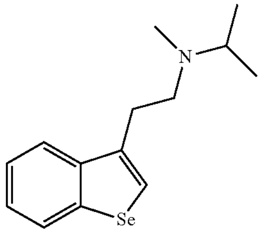
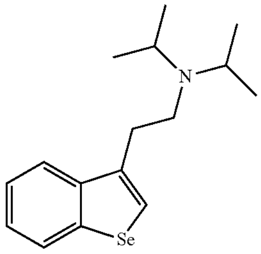
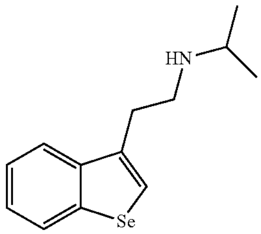
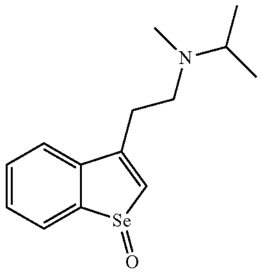
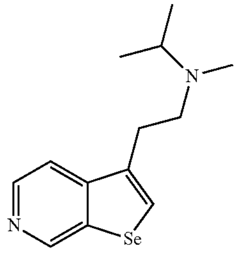
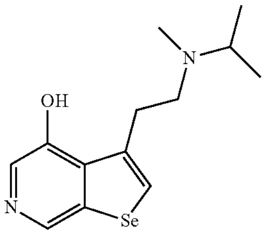

-continued
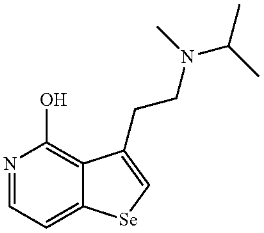
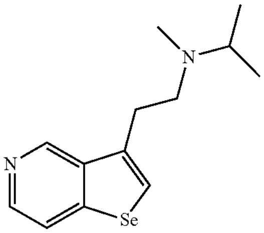
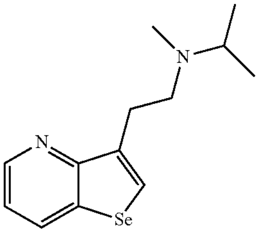
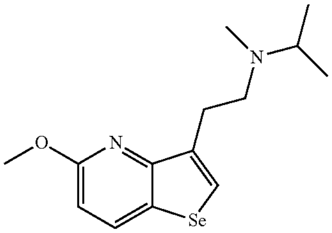
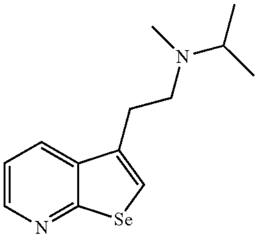
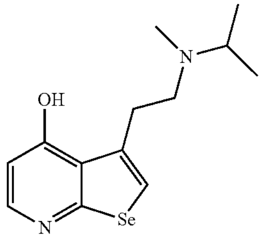
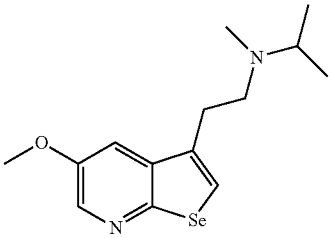
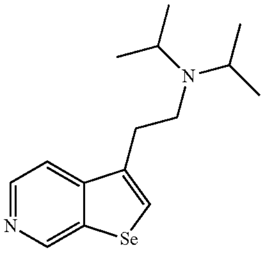
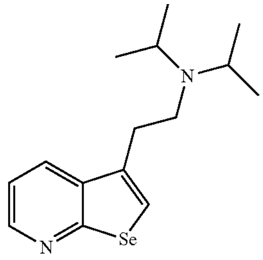
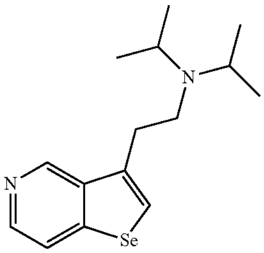
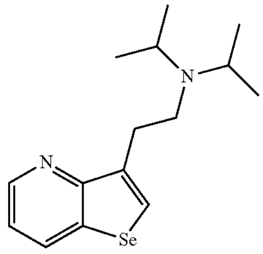
-continued
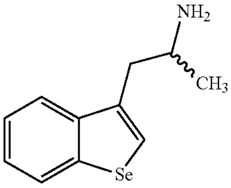
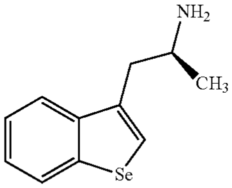
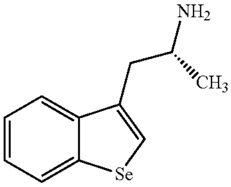
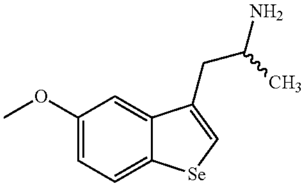
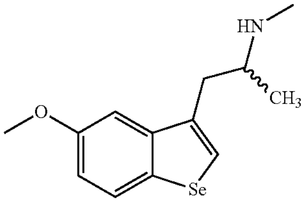
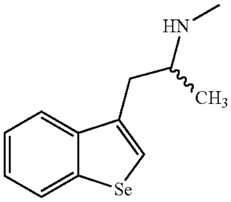
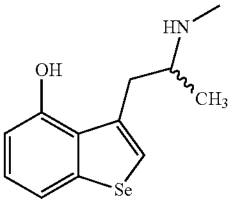
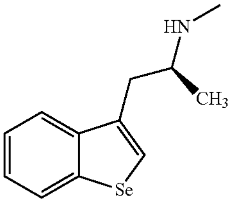
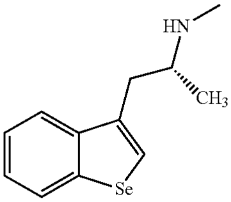
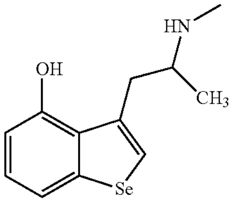
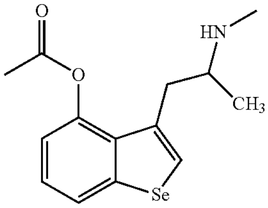
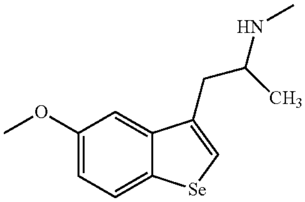
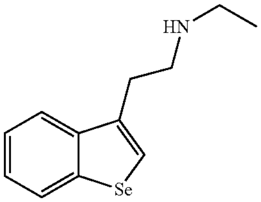
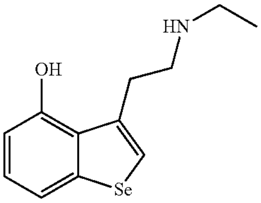
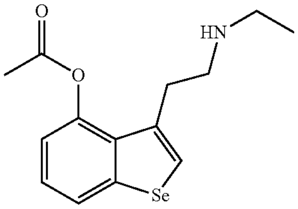

-continued
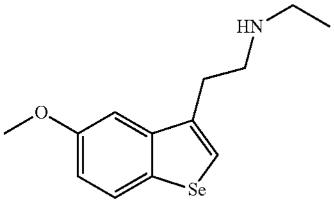
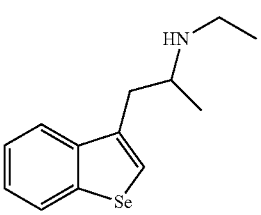
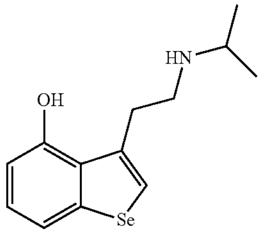
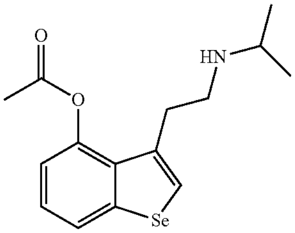
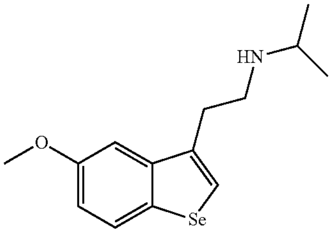
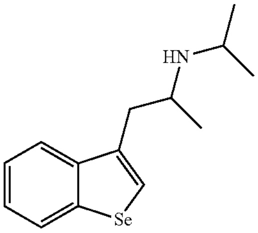
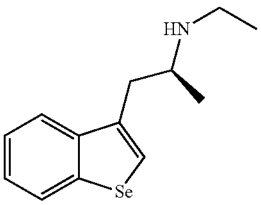
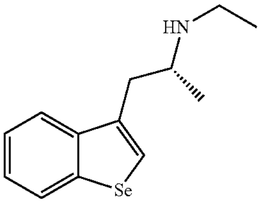
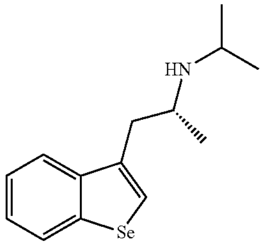
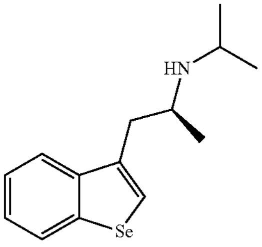
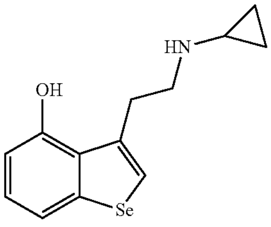
-continued
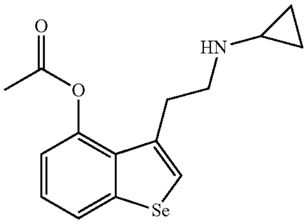
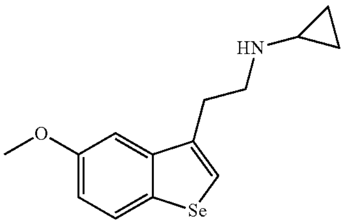
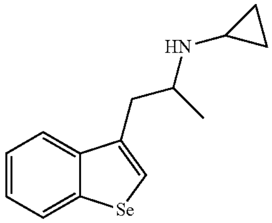
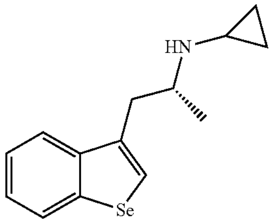
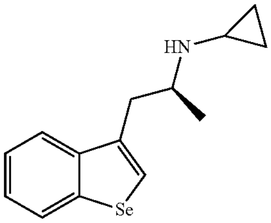
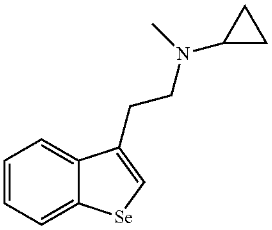
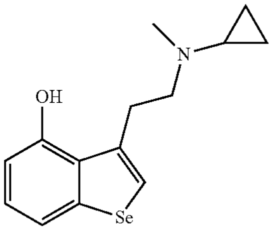
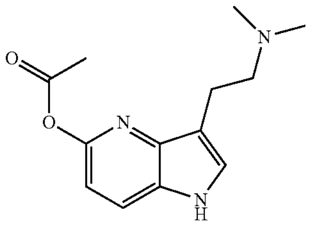

-continued
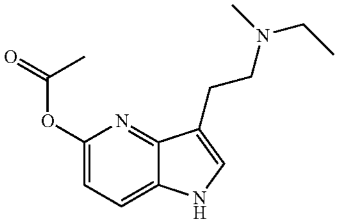
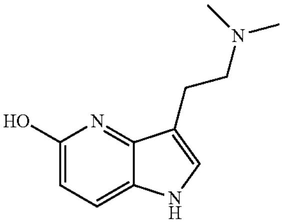
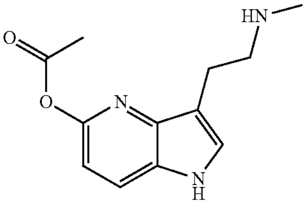
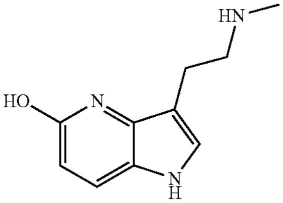
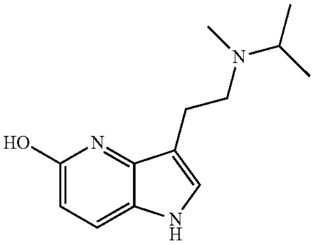
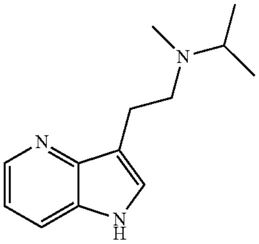
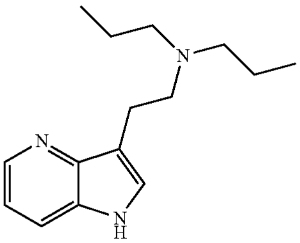
-continued
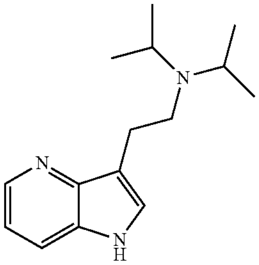
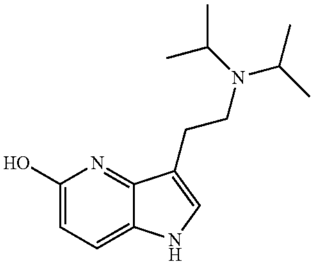
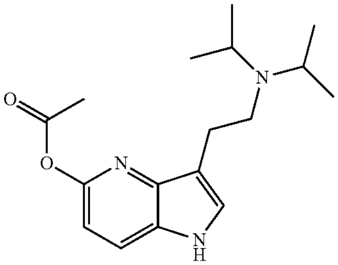
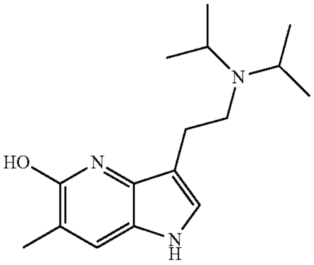
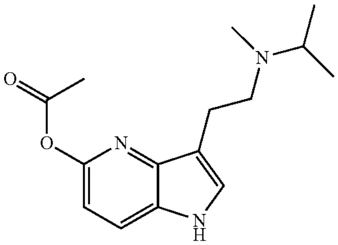
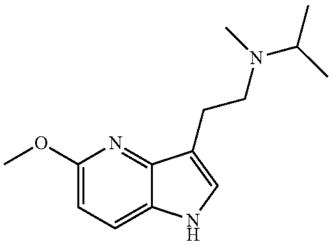
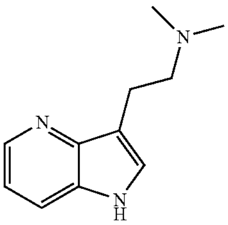

-continued
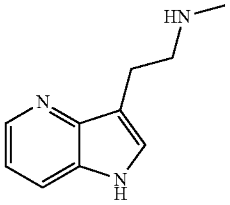
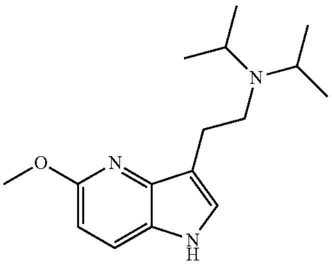
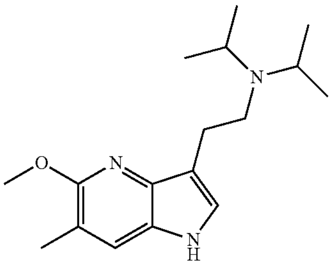
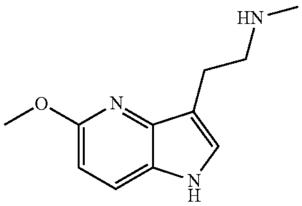
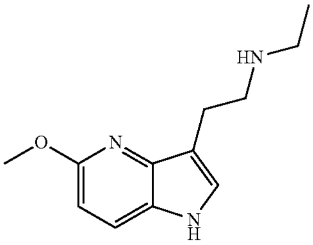
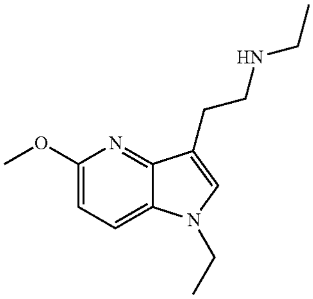
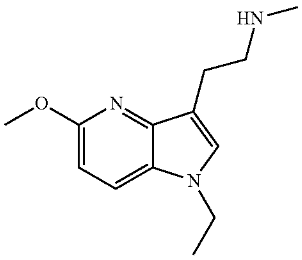
-continued
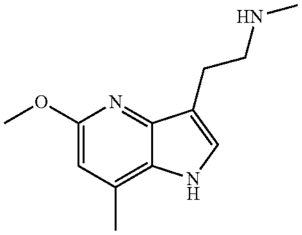
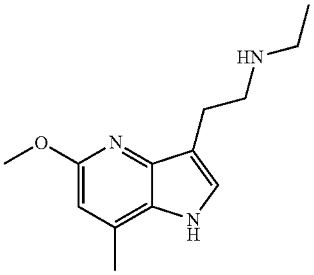
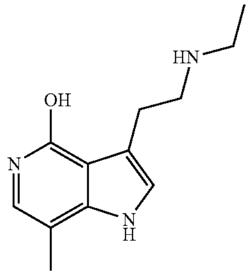
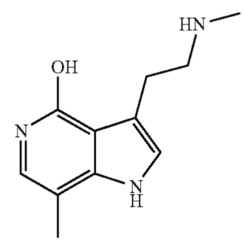
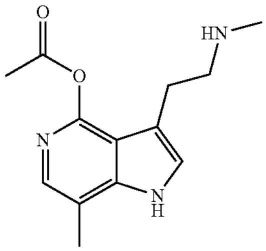
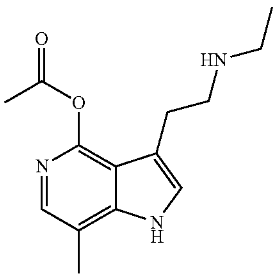
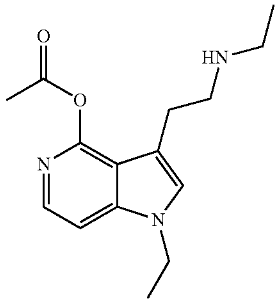
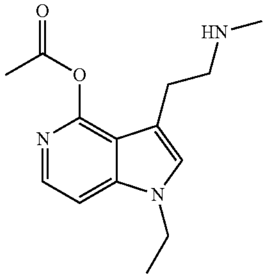
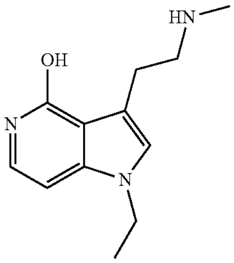
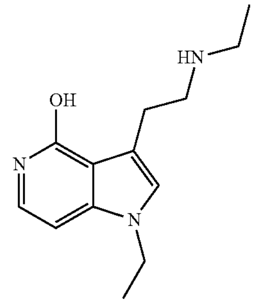
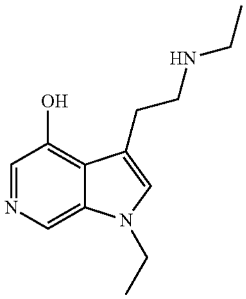

-continued
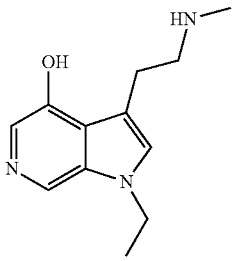
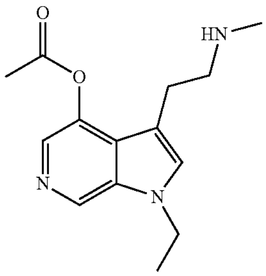
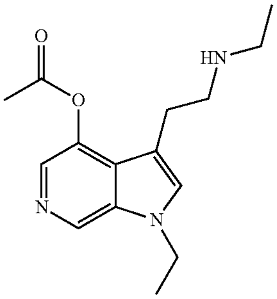
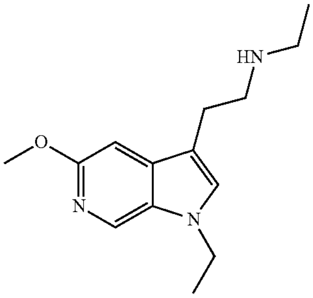
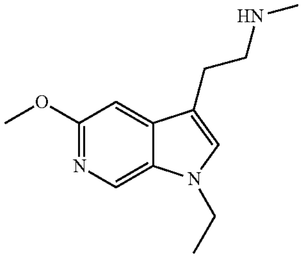
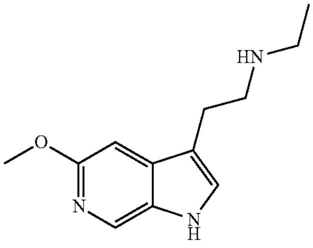
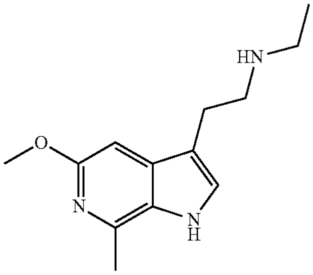
-continued
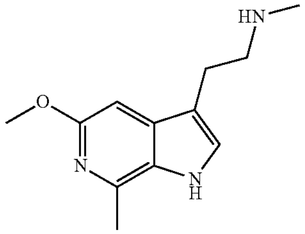
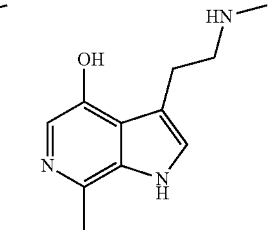
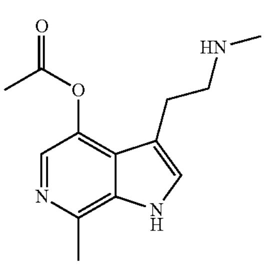
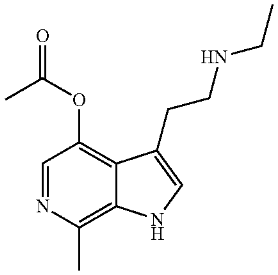
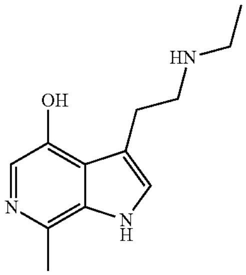
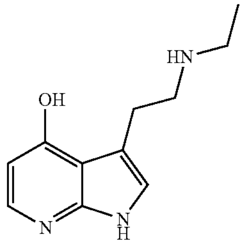
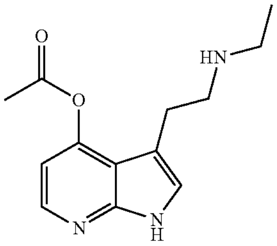
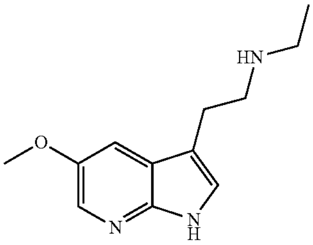
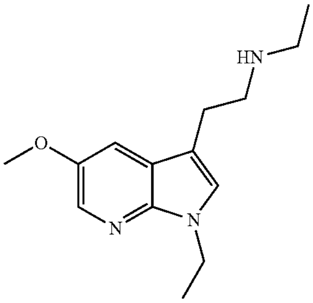

-continued
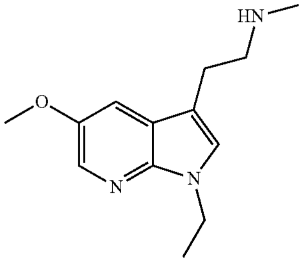
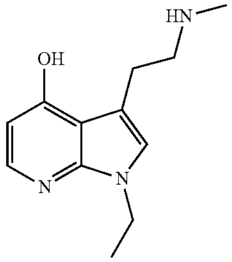
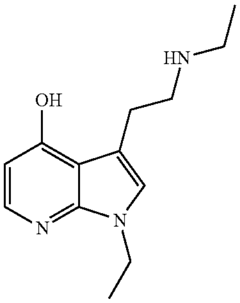
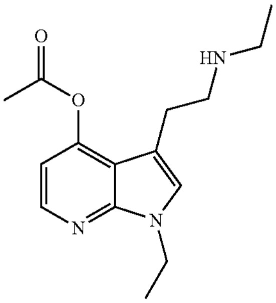
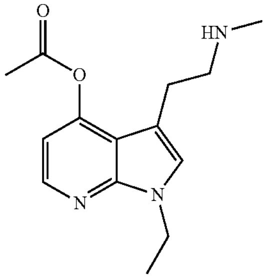
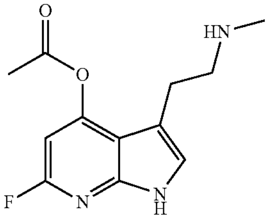
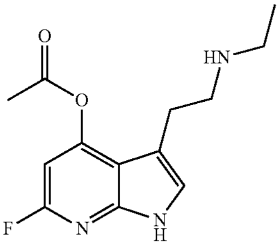
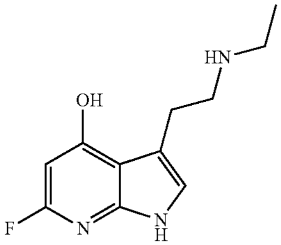
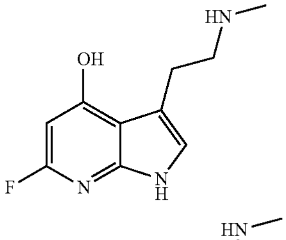
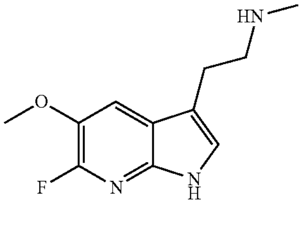
-continued
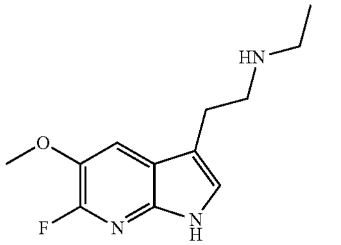
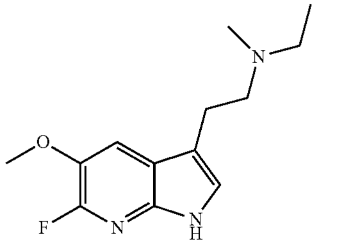
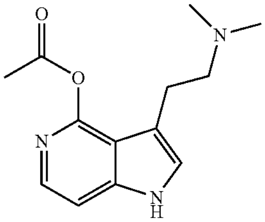
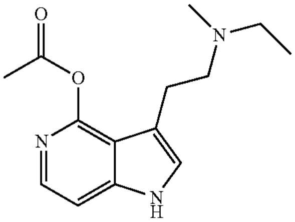
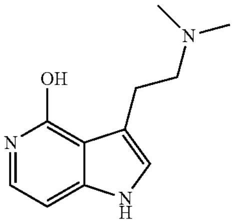
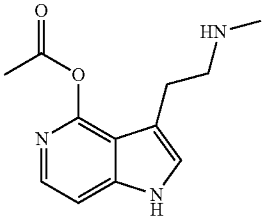
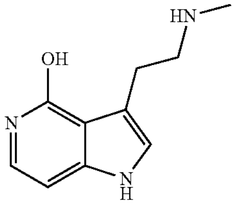
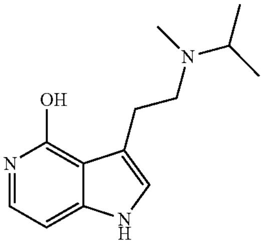
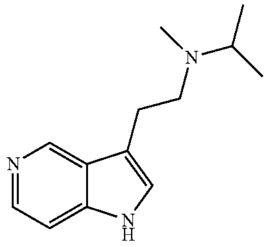
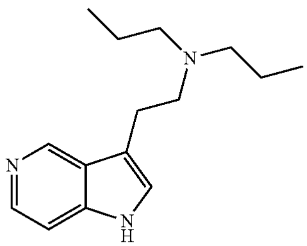

-continued
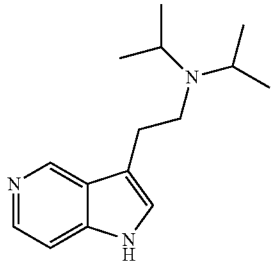
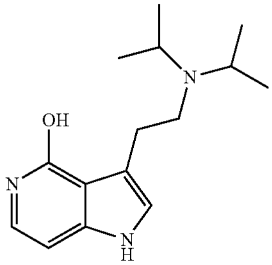
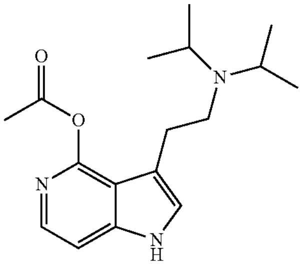
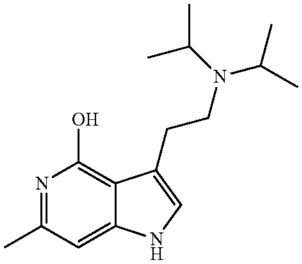
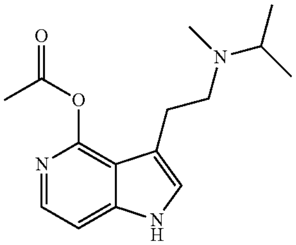
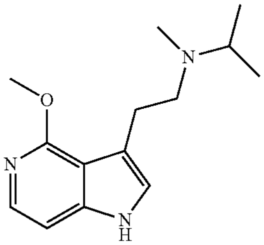
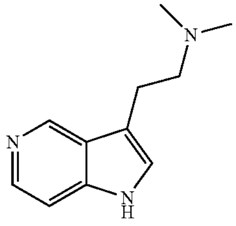
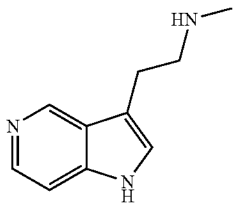
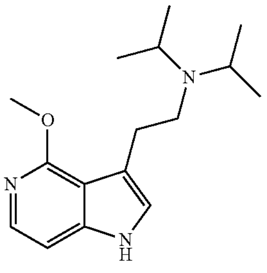
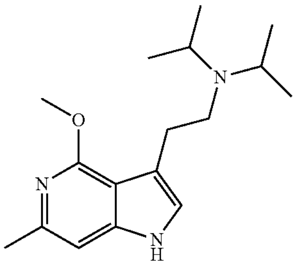
-continued
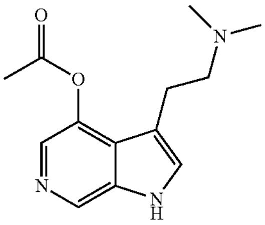
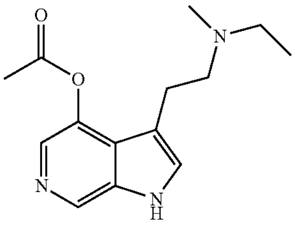
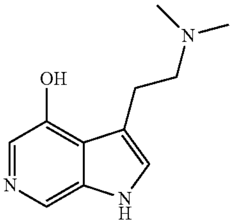
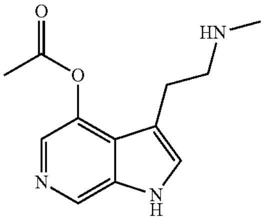
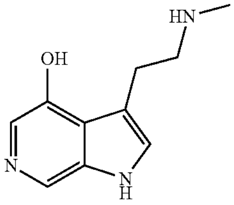
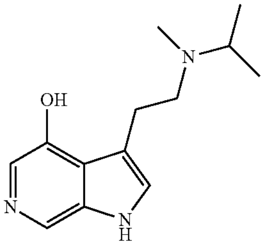
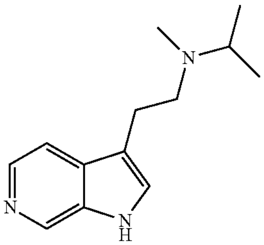
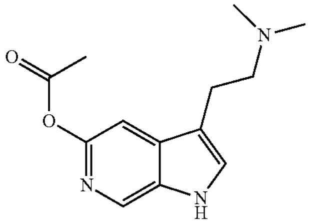
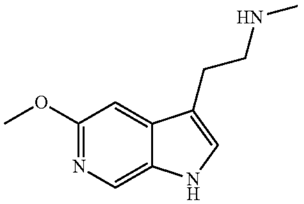
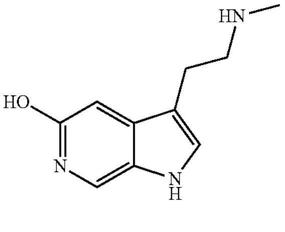

-continued
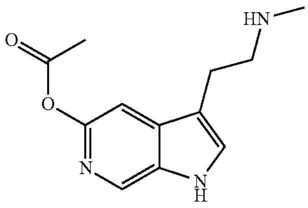
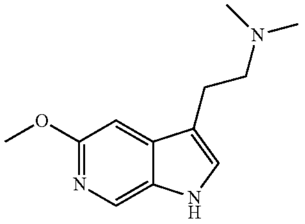
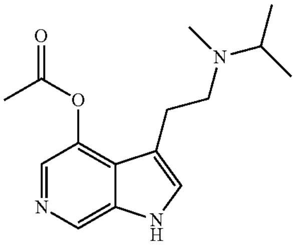
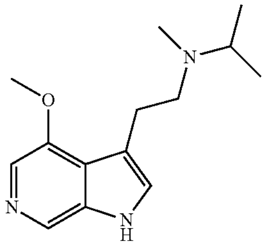
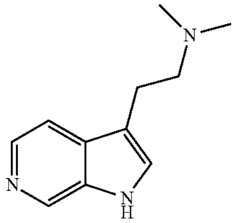
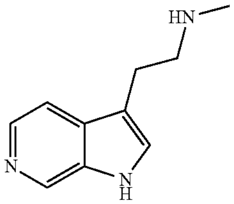
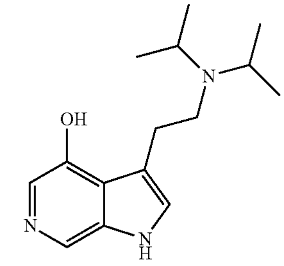
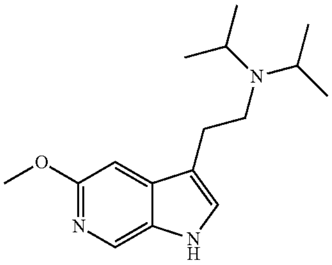
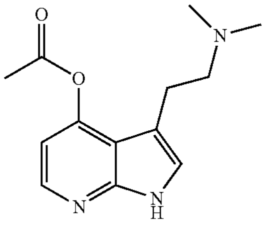
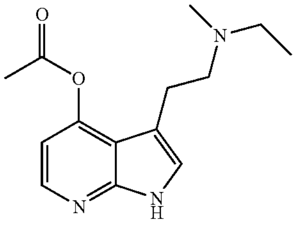
-continued
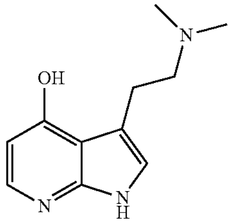
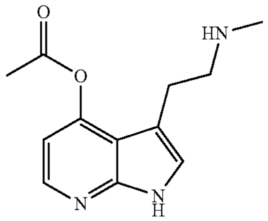
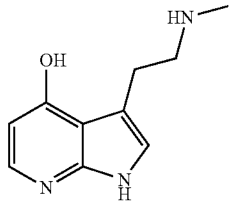
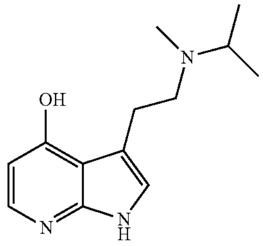
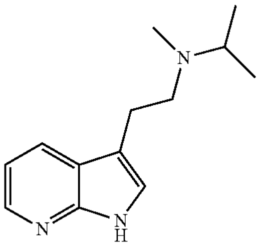
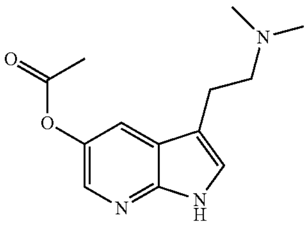
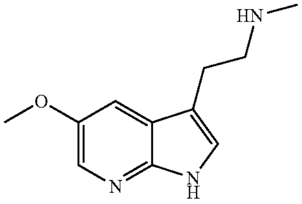
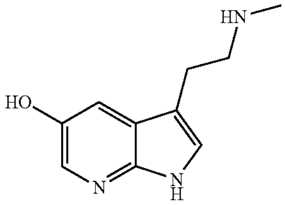
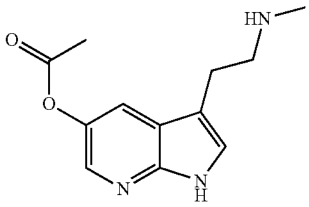
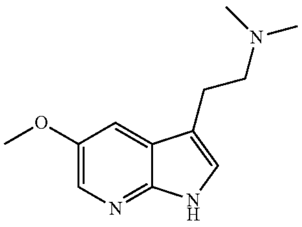

-continued

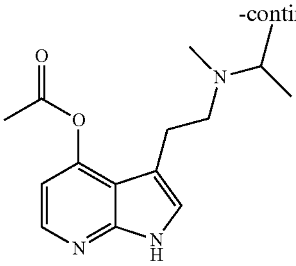

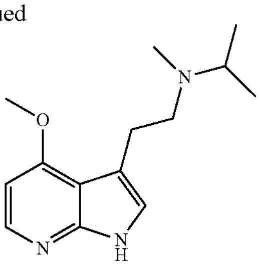

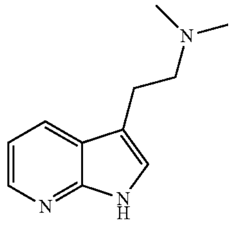

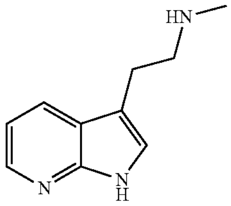

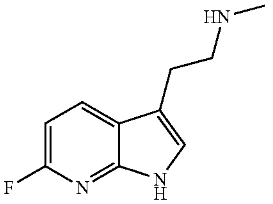

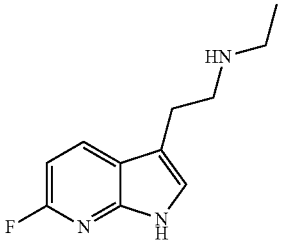

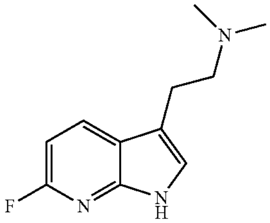

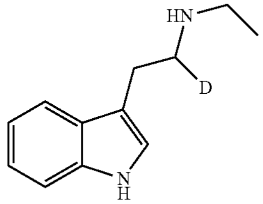

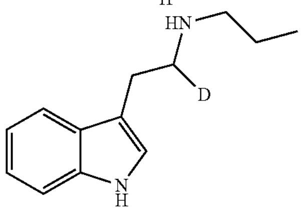

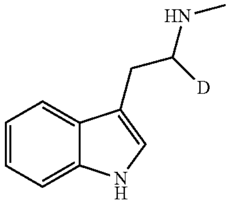

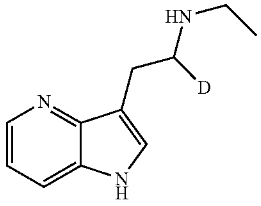

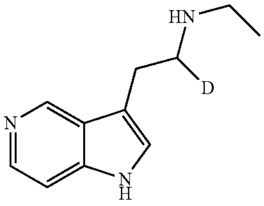

-continued

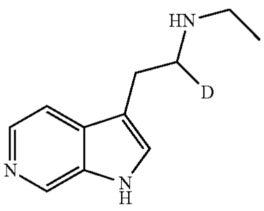

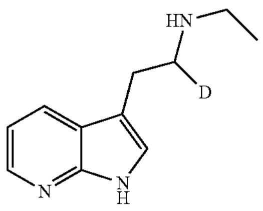

and salts, solvates, hydrates, and prodrugs of any of the foregoing compounds.

In some embodiments, the compounds of Formula I comprise salts. In some embodiments, the compounds of Formula I comprise pharmaceutically-acceptable salts. Exemplary salts include, but are not limited to, HCl, HI, HBr, HF, ascorbate, hydrofumarate, fumarate, oxalate, maleate, and the like. In certain embodiments, the compound of Formula I is in its free-base form. In some embodiments, the compound of Formula I comprises a salt, such as a [1:1] salt (e.g., HCl, hydrofumarate) or a [2:1] salt (e.g., oxalate, fumarate). For the [1:1] salts, one ammonium cation of one compound of Formula I is balanced by a single anion (Cl—, I—, etc.). For the [2:1] salts, two ammonium cations of two molecules of Formula I are balanced by a dianionic species, such as a dianion derived from di-acids such as oxalic acid and fumaric acid. Other exemplary salts include zwitterionic forms of compounds of Formula I, such as when $R_4$ is $—OP(O)O_2(R_9)_2$ and each $R_9$ is hydrogen, wherein deprotonation of an —OH on $R_4$ may result in intramolecular coordination of the resulting $—O^-$ with the quaternary ethylammonium residue (e.g., $—(CH_2)_2N^*H(CH_3)_2$).

Other exemplary compounds of Formula I include those below in Table 1, which is also represented by Formula Ia:

Formula Ia

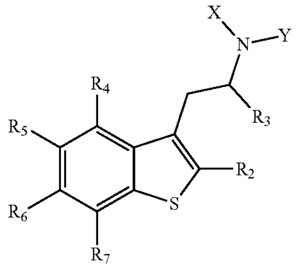

TABLE 1

| Ref. | X | Y | $R_2$ | $R_3$ | $R_4$ | $R_5$ | $R_6$ | $R_7$ |
|---|---|---|---|---|---|---|---|---|
| 1 | $—CH_3$ | $—CH_3$ | H | H | $—OCH_3$ | H | H | H |
| 2 | $—CH_3$ | $—CH_2CH_3$ | H | H | $—OCH_3$ | H | H | H |
| 3 | $—CH_3$ | $—(CH_2)_2CH_3$ | H | H | $—OCH_3$ | H | H | H |
| 4 | $—CH_3$ | $—CH(CH_3)_2$ | H | H | $—OCH_3$ | H | H | H |
| 5 | $—CH_3$ | $—(CH_2)_3CH_3$ | H | H | $—OCH_3$ | H | H | H |
| 6 | $—CH_3$ | $—CH_2—HC{=}CH_2$ | H | H | $—OCH_3$ | H | H | H |
| 7 | $—CH_2CH_3$ | $—CH_2CH_3$ | H | H | $—OCH_3$ | H | H | H |
| 8 | $—CH_2CH_3$ | $—(CH_2)_2CH_3$ | H | H | $—OCH_3$ | H | H | H |
| 9 | $—CH_2CH_3$ | $—CH(CH_3)_2$ | H | H | $—OCH_3$ | H | H | H |
| 10 | $—CH_2CH_3$ | $—(CH_2)_3CH_3$ | H | H | $—OCH_3$ | H | H | H |
| 11 | $—CH_2CH_3$ | $—CH_2—HC{=}CH_2$ | H | H | $—OCH_3$ | H | H | H |
| 12 | $—(CH_2)_2CH_3$ | $—(CH_2)_2CH_3$ | H | H | $—OCH_3$ | H | H | H |

TABLE 1-continued

| Ref. | X | Y | $R_2$ | $R_3$ | $R_4$ | $R_5$ | $R_6$ | $R_7$ |
|---|---|---|---|---|---|---|---|---|
| 13 | $-(CH_2)_2CH_3$ | $-CH(CH_3)_2$ | H | H | $-OCH_3$ | H | H | H |
| 14 | $-(CH_2)_2CH_3$ | $-(CH_2)_3CH_3$ | H | H | $-OCH_3$ | H | H | H |
| 15 | $-(CH_2)_2CH_3$ | $-CH_2-HC{=}CH_2$ | H | H | $-OCH_3$ | H | H | H |
| 16 | $-CH(CH_3)_2$ | $-CH(CH_3)_2$ | H | H | $-OCH_3$ | H | H | H |
| 17 | $-CH(CH_3)_2$ | $-(CH_2)_3CH_3$ | H | H | $-OCH_3$ | H | H | H |
| 18 | $-CH(CH_3)_2$ | $-CH_2-HC{=}CH_2$ | H | H | $-OCH_3$ | H | H | H |
| 19 | $-(CH_2)_3CH_3$ | $-(CH_2)_3CH_3$ | H | H | $-OCH_3$ | H | H | H |
| 20 | $-(CH_2)_3CH_3$ | $-CH_2-HC{=}CH_2$ | H | H | $-OCH_3$ | H | H | H |
| 21 | $-CH_2-HC{=}CH_2$ | $-CH_2-HC{=}CH_2$ | H | H | $-OCH_3$ | H | H | H |
| 22 | $-CH_3$ | $-CH_2CH_3$ | H | H | $-OH$ | H | H | H |
| 23 | $-CH_3$ | $-(CH_2)_2CH_3$ | H | H | $-OH$ | H | H | H |
| 24 | $-CH_3$ | $-CH(CH_3)_2$ | H | H | $-OH$ | H | H | H |
| 25 | $-CH_3$ | $-(CH_2)_3CH_3$ | H | H | $-OH$ | H | H | H |
| 26 | $-CH_3$ | $-CH_2-HC{=}CH_2$ | H | H | $-OH$ | H | H | H |
| 27 | $-CH_2CH_3$ | $-CH_2CH_3$ | H | H | $-OH$ | H | H | H |
| 28 | $-CH_2CH_3$ | $-(CH_2)_2CH_3$ | H | H | $-OH$ | H | H | H |
| 29 | $-CH_2CH_3$ | $-CH(CH_3)_2$ | H | H | $-OH$ | H | H | H |
| 30 | $-CH_2CH_3$ | $-(CH_2)_3CH_3$ | H | H | $-OH$ | H | H | H |
| 31 | $-CH_2CH_3$ | $-CH_2-HC{=}CH_2$ | H | H | $-OH$ | H | H | H |
| 32 | $-(CH_2)_2CH_3$ | $-(CH_2)_2CH_3$ | H | H | $-OH$ | H | H | H |
| 33 | $-(CH_2)_2CH_3$ | $-CH(CH_3)_2$ | H | H | $-OH$ | H | H | H |
| 34 | $-(CH_2)_2CH_3$ | $-(CH_2)_3CH_3$ | H | H | $-OH$ | H | H | H |
| 35 | $-(CH_2)_2CH_3$ | $-CH_2-HC{=}CH_2$ | H | H | $-OH$ | H | H | H |
| 36 | $-CH(CH_3)_2$ | $-CH(CH_3)_2$ | H | H | $-OH$ | H | H | H |
| 37 | $-CH(CH_3)_2$ | $(CH_2)_3CH_3$ | H | H | $-OH$ | H | H | H |
| 38 | $-CH(CH_3)_2$ | $-CH_2-HC{=}CH_2$ | H | H | $-OH$ | H | H | H |
| 39 | $-(CH_2)_3CH_3$ | $-(CH_2)_3CH_3$ | H | H | $-OH$ | H | H | H |
| 40 | $-(CH_2)_3CH_3$ | $-CH_2-HC{=}CH_2$ | H | H | $-OH$ | H | H | H |
| 41 | $-CH_2-HC{=}CH_2$ | $-CH_2-HC{=}CH_2$ | H | H | $-OH$ | H | H | H |
| 42 | $-CH_3$ | $-CH_3$ | H | H | $-OC(O)CH_3$ | H | H | H |
| 43 | $-CH_3$ | $-CH_2CH_3$ | H | H | $-OC(O)CH_3$ | H | H | H |
| 44 | $-CH_3$ | $-(CH_2)_2CH_3$ | H | H | $-OC(O)CH_3$ | H | H | H |
| 45 | $-CH_3$ | $-CH(CH_3)_2$ | H | H | $-OC(O)CH_3$ | H | H | H |
| 46 | $-CH_3$ | $-(CH_2)_3CH_3$ | H | H | $-OC(O)CH_3$ | H | H | H |
| 47 | $-CH_3$ | $-CH_2-HC{=}CH_2$ | H | H | $-OC(O)CH_3$ | H | H | H |
| 48 | $-CH_2CH_3$ | $-CH_2CH_3$ | H | H | $-OC(O)CH_3$ | H | H | H |
| 49 | $-CH_2CH_3$ | $-(CH_2)_2CH_3$ | H | H | $-OC(O)CH_3$ | H | H | H |
| 50 | $-CH_2CH_3$ | $-CH(CH_3)_2$ | H | H | $-OC(O)CH_3$ | H | H | H |
| 51 | $-CH_2CH_3$ | $-(CH_2)_3CH_3$ | H | H | $-OC(O)CH_3$ | H | H | H |
| 52 | $-CH_2CH_3$ | $-CH_2-HC{=}CH_2$ | H | H | $-OC(O)CH_3$ | H | H | H |
| 53 | $-(CH_2)_2CH_3$ | $-(CH_2)_2CH_3$ | H | H | $-OC(O)CH_3$ | H | H | H |
| 54 | $-(CH_2)_2CH_3$ | $-CH(CH_3)_2$ | H | H | $-OC(O)CH_3$ | H | H | H |
| 55 | $-(CH_2)_2CH_3$ | $-(CH_2)_3CH_3$ | H | H | $-OC(O)CH_3$ | H | H | H |
| 56 | $-(CH_2)_2CH_3$ | $-CH_2-HC{=}CH_2$ | H | H | $-OC(O)CH_3$ | H | H | H |
| 57 | $-CH(CH_3)_2$ | $-CH(CH_3)_2$ | H | H | $-OC(O)CH_3$ | H | H | H |
| 58 | $-CH(CH_3)_2$ | $-(CH_2)_3CH_3$ | H | H | $-OC(O)CH_3$ | H | H | H |
| 59 | $-CH(CH_3)_2$ | $-CH_2-HC{=}CH_2$ | H | H | $-OC(O)CH_3$ | H | H | H |
| 60 | $-(CH_2)_3CH_3$ | $-(CH_2)_3CH_3$ | H | H | $-OC(O)CH_3$ | H | H | H |
| 61 | $-(CH_2)_3CH_3$ | $-CH_2-HC{=}CH_2$ | H | H | $-OC(O)CH_3$ | H | H | H |
| 62 | $-CH_2-HC{=}CH_2$ | $-CH_2-HC{=}CH_2$ | H | H | $-OC(O)CH_3$ | H | H | H |
| 63 | $-CH_3$ | $-CH_3$ | H | H | H | $-OCH_2CH_3$ | H | H |
| 64 | $-CH_3$ | $-CH_2CH_3$ | H | H | H | $-OCH_3$ | H | H |
| 65 | $-CH_3$ | $(CH_2)_2CH_3$ | H | H | H | $-OCH_3$ | H | H |
| 66 | $-CH_3$ | $-CH(CH_3)_2$ | H | H | H | $-OCH_3$ | H | H |
| 67 | $-CH_3$ | $-(CH_2)_3CH_3$ | H | H | H | $-OCH_3$ | H | H |
| 68 | $-CH_3$ | $-CH_2-HC{=}CH_2$ | H | H | H | $-OCH_3$ | H | H |
| 69 | $-CH_2CH_3$ | $-CH_2CH_3$ | H | H | H | $-OCH_3$ | H | H |
| 70 | $-CH_2CH_3$ | $-(CH_2)_2CH_3$ | H | H | H | $-OCH_3$ | H | H |
| 71 | $-CH_2CH_3$ | $-CH(CH_3)_2$ | H | H | H | $-OCH_3$ | H | H |
| 72 | $-CH_2CH_3$ | $-(CH_2)_3CH_3$ | H | H | H | $-OCH_3$ | H | H |
| 73 | $-CH_2CH_3$ | $-CH_2-HC{=}CH_2$ | H | H | H | $-OCH_3$ | H | H |
| 74 | $-(CH_2)_2CH_3$ | $-(CH_2)_2CH_3$ | H | H | H | $-OCH_3$ | H | H |
| 75 | $-(CH_2)_2CH_3$ | $-CH(CH_3)_2$ | H | H | H | $-OCH_3$ | H | H |
| 76 | $-(CH_2)_2CH_3$ | $-(CH_2)_3CH_3$ | H | H | H | $-OCH_3$ | H | H |
| 77 | $-(CH_2)_2CH_3$ | $-CH_2-HC{=}CH_2$ | H | H | H | $-OCH_3$ | H | H |
| 78 | $-CH(CH_3)_2$ | $-CH(CH_3)_2$ | H | H | H | $-OCH_3$ | H | H |
| 79 | $-CH(CH_3)_2$ | $-(CH_2)_3CH_3$ | H | H | H | $-OCH_3$ | H | H |
| 80 | $-CH(CH_3)_2$ | $-CH_2-HC{=}CH_2$ | H | H | H | $-OCH_3$ | H | H |
| 81 | $-(CH_2)_3CH_3$ | $-(CH_2)_3CH_3$ | H | H | H | $-OCH_3$ | H | H |
| 82 | $-(CH_2)_3CH_3$ | $-CH_2-HC{=}CH_2$ | H | H | H | $-OCH_3$ | H | H |
| 83 | $-CH_2-HC{=}CH_2$ | $-CH_2-HC{=}CH_2$ | H | H | H | $-OCH_3$ | H | H |
| 84 | $-CH_3$ | $-CH_2CH_3$ | H | H | H | $-OH$ | H | H |
| 85 | $-CH_3$ | $-(CH_2)_2CH_3$ | H | H | H | $-OH$ | H | H |
| 86 | $-CH_3$ | $-CH(CH_3)_2$ | H | H | H | $-OH$ | H | H |
| 87 | $-CH_3$ | $-(CH_2)_3CH_3$ | H | H | H | $-OH$ | H | H |
| 88 | $-CH_3$ | $-CH_2-HC{=}CH_2$ | H | H | H | $-OH$ | H | H |
| 89 | $-CH_2CH_3$ | $-CH_2CH_3$ | H | H | H | $-OH$ | H | H |
| 90 | $-CH_2CH_3$ | $-(CH_2)_2CH_3$ | H | H | H | $-OH$ | H | H |

TABLE 1-continued

| Ref. | X | Y | $R_2$ | $R_3$ | $R_4$ | $R_5$ | $R_6$ | $R_7$ |
|---|---|---|---|---|---|---|---|---|
| 91 | $-CH_2CH_3$ | $-CH(CH_3)_2$ | H | H | H | $-OH$ | H | H |
| 92 | $-CH_2CH_3$ | $-(CH_2)_3CH_3$ | H | H | H | $-OH$ | H | H |
| 93 | $-CH_2CH_3$ | $-CH_2-HC{=}CH_2$ | H | H | H | $-OH$ | H | H |
| 94 | $-(CH_2)_2CH_3$ | $-(CH_2)_2CH_3$ | H | H | H | $-OH$ | H | H |
| 95 | $-(CH_2)_2CH_3$ | $-CH(CH_3)_2$ | H | H | H | $-OH$ | H | H |
| 96 | $-(CH_2)_2CH_3$ | $-(CH_2)_3CH_3$ | H | H | H | $-OH$ | H | H |
| 97 | $-(CH_2)_2CH_3$ | $-CH_2-HC{=}CH_2$ | H | H | H | $-OH$ | H | H |
| 98 | $-CH(CH_3)_2$ | $-CH(CH_3)_2$ | H | H | H | $-OH$ | H | H |
| 99 | $-CH(CH_3)_2$ | $-(CH_2)_3CH_3$ | H | H | H | $-OH$ | H | H |
| 100 | $-CH(CH_3)_2$ | $-CH_2-HC{=}CH_2$ | H | H | H | $-OH$ | H | H |
| 101 | $-(CH_2)_3CH_3$ | $-(CH_2)_3CH_3$ | H | H | H | $-OH$ | H | H |
| 102 | $-(CH_2)_3CH_3$ | $-CH_2-HC{=}CH_2$ | H | H | H | $-OH$ | H | H |
| 103 | $-CH_2-HC{=}CH_2$ | $-CH_2-HC{=}CH_2$ | H | H | H | $-OH$ | H | H |
| 104 | $-CH_3$ | $-CH_3$ | H | H | H | $-OC(O)CH_3$ | H | H |
| 105 | $-CH_3$ | $-CH_2CH_3$ | H | H | H | $-OC(O)CH_3$ | H | H |
| 106 | $-CH_3$ | $-(CH_2)_2CH_3$ | H | H | H | $-OC(O)CH_3$ | H | H |
| 107 | $-CH_3$ | $-CH(CH_3)_2$ | H | H | H | $-OC(O)CH_3$ | H | H |
| 108 | $-CH_3$ | $-(CH_2)_3CH_3$ | H | H | H | $-OC(O)CH_3$ | H | H |
| 109 | $-CH_3$ | $-CH_2-HC{=}CH_2$ | H | H | H | $-OC(O)CH_3$ | H | H |
| 110 | $-CH_2CH_3$ | $-CH_2CH_3$ | H | H | H | $-OC(O)CH_3$ | H | H |
| 111 | $-CH_2CH_3$ | $-(CH_2)_2CH_3$ | H | H | H | $-OC(O)CH_3$ | H | H |
| 112 | $-CH_2CH_3$ | $-CH(CH_3)_2$ | H | H | H | $-OC(O)CH_3$ | H | H |
| 113 | $-CH_2CH_3$ | $-(CH_2)_3CH_3$ | H | H | H | $-OC(O)CH_3$ | H | H |
| 114 | $-CH_2CH_3$ | $-CH_2-HC{=}CH_2$ | H | H | H | $-OC(O)CH_3$ | H | H |
| 115 | $-(CH_2)_2CH_3$ | $-(CH_2)_2CH_3$ | H | H | H | $-OC(O)CH_3$ | H | H |
| 116 | $-(CH_2)_2CH_3$ | $-CH(CH_3)_2$ | H | H | H | $-OC(O)CH_3$ | H | H |
| 117 | $-(CH_2)_2CH_3$ | $-(CH_2)_3CH_3$ | H | H | H | $-OC(O)CH_3$ | H | H |
| 118 | $-(CH_2)_2CH_3$ | $-CH_2-HC{=}CH_2$ | H | H | H | $-OC(O)CH_3$ | H | H |
| 119 | $-CH(CH_3)_2$ | $-CH(CH_3)_2$ | H | H | H | $-OC(O)CH_3$ | H | H |
| 120 | $-CH(CH_3)_2$ | $-(CH_2)_3CH_3$ | H | H | H | $-OC(O)CH_3$ | H | H |
| 121 | $-CH(CH_3)_2$ | $-CH_2-HC{=}CH_2$ | H | H | H | $-OC(O)CH_3$ | H | H |
| 122 | $-(CH_2)_3CH_3$ | $-(CH_2)_3CH_3$ | H | H | H | $-OC(O)CH_3$ | H | H |
| 123 | $-(CH_2)_3CH_3$ | $-CH_2-HC{=}CH_2$ | H | H | H | $-OC(O)CH_3$ | H | H |
| 124 | $-CH_2-HC{=}CH_2$ | $-CH_2-HC{=}CH_2$ | H | H | H | $-OC(O)CH_3$ | H | H |
| 125 | $-CH_3$ | $-CH_3$ | H | H | $-OCH_3$ | H | H | $-CH_3$ |
| 126 | $-CH_3$ | $-CH_2CH_3$ | H | H | $-OCH_3$ | H | H | $-CH_3$ |
| 127 | $-CH_3$ | $-(CH_2)_2CH_3$ | H | H | $-OCH_3$ | H | H | $-CH_3$ |
| 128 | $-CH_3$ | $-CH(CH_3)_2$ | H | H | $-OCH_3$ | H | H | $-CH_3$ |
| 129 | $-CH_3$ | $-(CH_2)_3CH_3$ | H | H | $-OCH_3$ | H | H | $-CH_3$ |
| 130 | $-CH_3$ | $-CH_2-HC{=}CH_2$ | H | H | $-OCH_3$ | H | H | $-CH_3$ |
| 131 | $-CH_2CH_3$ | $-CH_2CH_3$ | H | H | $-OCH_3$ | H | H | $-CH_3$ |
| 132 | $-CH_2CH_3$ | $-(CH_2)_2CH_3$ | H | H | $-OCH_3$ | H | H | $-CH_3$ |
| 133 | $-CH_2CH_3$ | $-CH(CH_3)_2$ | H | H | $-OCH_3$ | H | H | $-CH_3$ |
| 134 | $-CH_2CH_3$ | $-(CH_2)_3CH_3$ | H | H | $-OCH_3$ | H | H | $-CH_3$ |
| 135 | $-CH_2CH_3$ | $-CH_2-HC{=}CH_2$ | H | H | $-OCH_3$ | H | H | $-CH_3$ |
| 135 | $-(CH_2)_2CH_3$ | $-(CH_2)_2CH_3$ | H | H | $-OCH_3$ | H | H | $-CH_3$ |
| 137 | $-(CH_2)_2CH_3$ | $-CH(CH_3)_2$ | H | H | $-OCH_3$ | H | H | $-CH_3$ |
| 138 | $-(CH_2)_2CH_3$ | $-(CH_2)_3CH_3$ | H | H | $-OCH_3$ | H | H | $-CH_3$ |
| 139 | $-(CH_2)_2CH_3$ | $-CH_2-HC{=}CH_2$ | H | H | $-OCH_3$ | H | H | $-CH_3$ |
| 140 | $-CH(CH_3)_2$ | $-CH(CH_3)_2$ | H | H | $-OCH_3$ | H | H | $-CH_3$ |
| 141 | $-CH(CH_3)_2$ | $-(CH_2)_3CH_3$ | H | H | $-OCH_3$ | H | H | $-CH_3$ |
| 142 | $-CH(CH_3)_2$ | $-CH_2-HC{=}CH_2$ | H | H | $-OCH_3$ | H | H | $-CH_3$ |
| 143 | $-(CH_2)_3CH_3$ | $-(CH_2)_3CH_3$ | H | H | $-OCH_3$ | H | H | $-CH_3$ |
| 144 | $-(CH_2)_3CH_3$ | $-CH_2-HC{=}CH_2$ | H | H | $-OCH_3$ | H | H | $-CH_3$ |
| 145 | $-CH_2-HC{=}CH_2$ | $-CH_2-HC{=}CH_2$ | H | H | $-OCH_3$ | H | H | $-CH_3$ |
| 146 | $-CH_3$ | $-CH_2CH_3$ | H | H | $-OH$ | H | H | $-CH_3$ |
| 147 | $-CH_3$ | $-(CH_2)_2CH_3$ | H | H | $-OH$ | H | H | $-CH_3$ |
| 148 | $-CH_3$ | $-CH(CH_3)_2$ | H | H | $-OH$ | H | H | $-CH_3$ |
| 149 | $-CH_3$ | $-(CH_2)_3CH_3$ | H | H | $-OH$ | H | H | $-CH_3$ |
| 150 | $-CH_3$ | $-CH_2-HC{=}CH_2$ | H | H | $-OH$ | H | H | $-CH_3$ |
| 151 | $-CH_2CH_3$ | $-CH_2CH_3$ | H | H | $-OH$ | H | H | $-CH_3$ |
| 152 | $-CH_2CH_3$ | $-(CH_2)_2CH_3$ | H | H | $-OH$ | H | H | $-CH_3$ |
| 153 | $-CH_2CH_3$ | $-CH(CH_3)_2$ | H | H | $-OH$ | H | H | $-CH_3$ |
| 154 | $-CH_2CH_3$ | $-(CH_2)_3CH_3$ | H | H | $-OH$ | H | H | $-CH_3$ |
| 155 | $-CH_2CH_3$ | $-CH_2-HC{=}CH_2$ | H | H | $-OH$ | H | H | $-CH_3$ |
| 156 | $-(CH_2)_2CH_3$ | $-(CH_2)_2CH_3$ | H | H | $-OH$ | H | H | $-CH_3$ |
| 157 | $-(CH_2)_2CH_3$ | $-CH(CH_3)_2$ | H | H | $-OH$ | H | H | $-CH_3$ |
| 158 | $-(CH_2)_2CH_3$ | $-(CH_2)_3CH_3$ | H | H | $-OH$ | H | H | $-CH_3$ |
| 159 | $-(CH_2)_2CH_3$ | $-CH_2-HC{=}CH_2$ | H | H | $-OH$ | H | H | $-CH_3$ |
| 160 | $-CH(CH_3)_2$ | $-CH(CH_3)_2$ | H | H | $-OH$ | H | H | $-CH_3$ |
| 161 | $-CH(CH_3)_2$ | $-(CH_2)_3CH_3$ | H | H | $-OH$ | H | H | $-CH_3$ |
| 162 | $-CH(CH_3)_2$ | $-CH_2-HC{=}CH_2$ | H | H | $-OH$ | H | H | $-CH_3$ |
| 163 | $-(CH_2)_3CH_3$ | $-(CH_2)_3CH_3$ | H | H | $-OH$ | H | H | $-CH_3$ |
| 164 | $-(CH_2)_3CH_3$ | $-CH_2-HC{=}CH_2$ | H | H | $-OH$ | H | H | $-CH_3$ |
| 165 | $-CH_2-HC{=}CH_2$ | $-CH_2-HC{=}CH_2$ | H | H | $-OH$ | H | H | $-CH_3$ |
| 166 | $-CH_3$ | $-CH_3$ | H | H | $-OC(O)CH_3$ | H | H | $-CH_3$ |
| 167 | $-CH_3$ | $-CH_2CH_3$ | H | H | $-OC(O)CH_3$ | H | H | $-CH_3$ |
| 168 | $-CH_3$ | $-(CH_2)_2CH_3$ | H | H | $-OC(O)CH_3$ | H | H | $-CH_3$ |

TABLE 1-continued

| Ref. | X | Y | $R_2$ | $R_3$ | $R_4$ | $R_5$ | $R_6$ | $R_7$ |
|---|---|---|---|---|---|---|---|---|
| 169 | $-CH_3$ | $-CH(CH_3)_2$ | H | H | $-OC(O)CH_3$ | H | H | $-CH_3$ |
| 170 | $-CH_3$ | $-(CH_2)_3CH_3$ | H | H | $-OC(O)CH_3$ | H | H | $-CH_3$ |
| 171 | $-CH_3$ | $-CH_2-HC=CH_2$ | H | H | $-OC(O)CH_3$ | H | H | $-CH_3$ |
| 172 | $-CH_2CH_3$ | $-CH_2CH_3$ | H | H | $-OC(O)CH_3$ | H | H | $-CH_3$ |
| 173 | $-CH_2CH_3$ | $-(CH_2)_2CH_3$ | H | H | $-OC(O)CH_3$ | H | H | $-CH_3$ |
| 174 | $-CH_2CH_3$ | $-CH(CH_3)_2$ | H | H | $-OC(O)CH_3$ | H | H | $-CH_3$ |
| 175 | $-CH_2CH_3$ | $-(CH_2)_3CH_3$ | H | H | $-OC(O)CH_3$ | H | H | $-CH_3$ |
| 176 | $-CH_2CH_3$ | $-CH_2-HC=CH_2$ | H | H | $-OC(O)CH_3$ | H | H | $-CH_3$ |
| 177 | $-(CH_2)_2CH_3$ | $-(CH_2)_2CH_3$ | H | H | $-OC(O)CH_3$ | H | H | $-CH_3$ |
| 178 | $-(CH_2)_2CH_3$ | $-CH(CH_3)_2$ | H | H | $-OC(O)CH_3$ | H | H | $-CH_3$ |
| 179 | $-(CH_2)_2CH_3$ | $-(CH_2)_3CH_3$ | H | H | $-OC(O)CH_3$ | H | H | $-CH_3$ |
| 180 | $-(CH_2)_2CH_3$ | $-CH_2-HC=CH_2$ | H | H | $-OC(O)CH_3$ | H | H | $-CH_3$ |
| 181 | $-CH(CH_3)_2$ | $-CH(CH_3)_2$ | H | H | $-OC(O)CH_3$ | H | H | $-CH_3$ |
| 182 | $-CH(CH_3)_2$ | $-(CH_2)_3CH_3$ | H | H | $-OC(O)CH_3$ | H | H | $-CH_3$ |
| 183 | $-CH(CH_3)_2$ | $-CH_2-HC=CH_2$ | H | H | $-OC(O)CH_3$ | H | H | $-CH_3$ |
| 184 | $-(CH_2)_3CH_3$ | $-(CH_2)_3CH_3$ | H | H | $-OC(O)CH_3$ | H | H | $-CH_3$ |
| 185 | $-(CH_2)_3CH_3$ | $-CH_2-HC=CH_2$ | H | H | $-OC(O)CH_3$ | H | H | $-CH_3$ |
| 186 | $-CH_2-HC=CH_2$ | $-CH_2-HC=CH_2$ | H | H | $-OC(O)CH_3$ | H | H | $-CH_3$ |
| 187 | $-CH_3$ | $-CH_3$ | H | H | H | $-OCH_3$ | H | $-CH_3$ |
| 188 | $-CH_3$ | $-CH_2CH_3$ | H | H | H | $-OCH_3$ | H | $-CH_3$ |
| 189 | $-CH_3$ | $-(CH_2)_2CH_3$ | H | H | H | $-OCH_3$ | H | $-CH_3$ |
| 190 | $-CH_3$ | $-CH(CH_3)_2$ | H | H | H | $-OCH_3$ | H | $-CH_3$ |
| 191 | $-CH_3$ | $-(CH_2)_3CH_3$ | H | H | H | $-OCH_3$ | H | $-CH_3$ |
| 192 | $-CH_3$ | $-CH_2-HC=CH_2$ | H | H | H | $-OCH_3$ | H | $-CH_3$ |
| 193 | $-CH_2CH_3$ | $-CH_2CH_3$ | H | H | H | $-OCH_3$ | H | $-CH_3$ |
| 194 | $-CH_2CH_3$ | $-(CH_2)_2CH_3$ | H | H | H | $-OCH_3$ | H | $-CH_3$ |
| 195 | $-CH_2CH_3$ | $-CH(CH_3)_2$ | H | H | H | $-OCH_3$ | H | $-CH_3$ |
| 196 | $-CH_2CH_3$ | $-(CH_2)_3CH_3$ | H | H | H | $-OCH_3$ | H | $-CH_3$ |
| 197 | $-CH_2CH_3$ | $-CH_2-HC=CH_2$ | H | H | H | $-OCH_3$ | H | $-CH_3$ |
| 198 | $-(CH_2)_2CH_3$ | $-(CH_2)_2CH_3$ | H | H | H | $-OCH_3$ | H | $-CH_3$ |
| 199 | $-(CH_2)_2CH_3$ | $-CH(CH_3)_2$ | H | H | H | $-OCH_3$ | H | $-CH_3$ |
| 200 | $-(CH_2)_2CH_3$ | $-(CH_2)_3CH_3$ | H | H | H | $-OCH_3$ | H | $-CH_3$ |
| 201 | $-(CH_2)_2CH_3$ | $-CH_2-HC=CH_2$ | H | H | H | $-OCH_3$ | H | $-CH_3$ |
| 202 | $-CH(CH_3)_2$ | $-CH(CH_3)_2$ | H | H | H | $-OCH_3$ | H | $-CH_3$ |
| 203 | $-CH(CH_3)_2$ | $-(CH_2)_3CH_3$ | H | H | H | $-OCH_3$ | H | $-CH_3$ |
| 204 | $-CH(CH_3)_2$ | $-CH_2-HC=CH_2$ | H | H | H | $-OCH_3$ | H | $-CH_3$ |
| 205 | $-(CH_2)_3CH_3$ | $-(CH_2)_3CH_3$ | H | H | H | $-OCH_3$ | H | $-CH_3$ |
| 206 | $-(CH_2)_3CH_3$ | $-CH_2-HC=CH_2$ | H | H | H | $-OCH_3$ | H | $-CH_3$ |
| 207 | $-CH_2-HC=CH_2$ | $-CH_2-HC=CH_2$ | H | H | H | $-OCH_3$ | H | $-CH_3$ |
| 208 | $-CH_3$ | $-CH_2CH_3$ | H | H | H | $-OH$ | H | $-CH_3$ |
| 209 | $-CH_3$ | $-(CH_2)_2CH_3$ | H | H | H | $-OH$ | H | $-CH_3$ |
| 210 | $-CH_3$ | $-CH(CH_3)_2$ | H | H | H | $-OH$ | H | $-CH_3$ |
| 211 | $-CH_3$ | $-(CH_2)_3CH_3$ | H | H | H | $-OH$ | H | $-CH_3$ |
| 212 | $-CH_3$ | $-CH_2-HC=CH_2$ | H | H | H | $-OH$ | H | $-CH_3$ |
| 213 | $-CH_2CH_3$ | $-CH_2CH_3$ | H | H | H | $-OH$ | H | $-CH_3$ |
| 214 | $-CH_2CH_3$ | $-(CH_2)_2CH_3$ | H | H | H | $-OH$ | H | $-CH_3$ |
| 215 | $-CH_2CH_3$ | $-CH(CH_3)_2$ | H | H | H | $-OH$ | H | $-CH_3$ |
| 216 | $-CH_2CH_3$ | $-(CH_2)_3CH_3$ | H | H | H | $-OH$ | H | $-CH_3$ |
| 217 | $-CH_2CH_3$ | $-CH_2-HC=CH_2$ | H | H | H | $-OH$ | H | $-CH_3$ |
| 218 | $-(CH_2)_2CH_3$ | $-(CH_2)_2CH_3$ | H | H | H | $-OH$ | H | $-CH_3$ |
| 219 | $-(CH_2)_2CH_3$ | $-CH(CH_3)_2$ | H | H | H | $-OH$ | H | $-CH_3$ |
| 220 | $-(CH_2)_2CH_3$ | $-(CH_2)_3CH_3$ | H | H | H | $-OH$ | H | $-CH_3$ |
| 221 | $-(CH_2)_2CH_3$ | $-CH_2-HC=CH_2$ | H | H | H | $-OH$ | H | $-CH_3$ |
| 222 | $-CH(CH_3)_2$ | $-CH(CH_3)_2$ | H | H | H | $-OH$ | H | $-CH_3$ |
| 223 | $-CH(CH_3)_2$ | $-(CH_2)_3CH_3$ | H | H | H | $-OH$ | H | $-CH_3$ |
| 224 | $-CH(CH_3)_2$ | $-CH_2-HC=CH_2$ | H | H | H | $-OH$ | H | $-CH_3$ |
| 225 | $-(CH_2)_3CH_3$ | $-(CH_2)_3CH_3$ | H | H | H | $-OH$ | H | $-CH_3$ |
| 226 | $-(CH_2)_3CH_3$ | $-CH_2-HC=CH_2$ | H | H | H | $-OH$ | H | $-CH_3$ |
| 227 | $-CH_2-HC=CH_2$ | $-CH_2-HC=CH_2$ | H | H | H | $-OH$ | H | $-CH_3$ |
| 228 | $-CH_3$ | $-CH_3$ | H | H | H | $-OC(O)CH_3$ | H | $-CH_3$ |
| 229 | $-CH_3$ | $-CH_2CH_3$ | H | H | H | $-OC(O)CH_3$ | H | $-CH_3$ |
| 230 | $-CH_3$ | $-(CH_2)_2CH_3$ | H | H | H | $-OC(O)CH_3$ | H | $-CH_3$ |
| 231 | $-CH_3$ | $-CH(CH_3)_2$ | H | H | H | $-OC(O)CH_3$ | H | $-CH_3$ |
| 232 | $-CH_3$ | $-(CH_2)_3CH_3$ | H | H | H | $-OC(O)CH_3$ | H | $-CH_3$ |
| 233 | $-CH_3$ | $-CH_2-HC=CH_2$ | H | H | H | $-OC(O)CH_3$ | H | $-CH_3$ |
| 234 | $-CH_2CH_3$ | $-CH_2CH_3$ | H | H | H | $-OC(O)CH_3$ | H | $-CH_3$ |
| 235 | $-CH_2CH_3$ | $-(CH_2)_2CH_3$ | H | H | H | $-OC(O)CH_3$ | H | $-CH_3$ |
| 236 | $-CH_2CH_3$ | $-CH(CH_3)_2$ | H | H | H | $-OC(O)CH_3$ | H | $-CH_3$ |
| 237 | $-CH_2CH_3$ | $-(CH_2)_3CH_3$ | H | H | H | $-OC(O)CH_3$ | H | $-CH_3$ |
| 238 | $-CH_2CH_3$ | $-CH_2-HC=CH_2$ | H | H | H | $-OC(O)CH_3$ | H | $-CH_3$ |
| 239 | $-(CH_2)_2CH_3$ | $-(CH_2)_2CH_3$ | H | H | H | $-OC(O)CH_3$ | H | $-CH_3$ |
| 240 | $-(CH_2)_2CH_3$ | $-CH(CH_3)_2$ | H | H | H | $-OC(O)CH_3$ | H | $-CH_3$ |
| 241 | $-(CH_2)_2CH_3$ | $-(CH_2)_3CH_3$ | H | H | H | $-OC(O)CH_3$ | H | $-CH_3$ |
| 242 | $-(CH_2)_2CH_3$ | $-CH_2-HC=CH_2$ | H | H | H | $-OC(O)CH_3$ | H | $-CH_3$ |
| 243 | $-CH(CH_3)_2$ | $-CH(CH_3)_2$ | H | H | H | $-OC(O)CH_3$ | H | $-CH_3$ |
| 244 | $-CH(CH_3)_2$ | $-(CH_2)_3CH_3$ | H | H | H | $-OC(O)CH_3$ | H | $-CH_3$ |
| 245 | $-CH(CH_3)_2$ | $-CH_2-HC=CH_2$ | H | H | H | $-OC(O)CH_3$ | H | $-CH_3$ |
| 246 | $-(CH_2)_3CH_3$ | $-(CH_2)_3CH_3$ | H | H | H | $-OC(O)CH_3$ | H | $-CH_3$ |

TABLE 1-continued

| Ref. | X | Y | $R_2$ | $R_3$ | $R_4$ | $R_5$ | $R_6$ | $R_7$ |
|---|---|---|---|---|---|---|---|---|
| 247 | —$(CH_2)_3CH_3$ | —$CH_2$—HC=$CH_2$ | H | H | H | —OC(O)$CH_3$ | H | —$CH_3$ |
| 248 | —$CH_2$—HC=$CH_2$ | —$CH_2$—HC=$CH_2$ | H | H | H | OC(O)$CH_3$ | H | —$CH_3$ |
| 249 | —$CH_3$ | —$CH_3$ | —$CH_3$ | H | H | H | H | H |
| 250 | —$CH_3$ | —$CH_3$ | —$CH_3$ | H | —OH | H | H | H |
| 251 | —$CH_3$ | —$CH_3$ | —$CH_3$ | H | —OC(O)$CH_3$ | H | H | H |
| 252 | —$CH_3$ | —$CH_3$ | —$CH_3$ | H | —$OCH_3$ | H | H | H |
| 253 | —$CH_3$ | —$CH_2CH_3$ | —$CH_3$ | H | H | H | H | H |
| 254 | —$CH_3$ | —$CH_2(CH_3)_2$ | —$CH_3$ | H | H | H | H | H |
| 255 | —$CH_3$ | —$CH_3$ | —$CH_3$ | H | F | H | H | H |
| 256 | —$CH_3$ | —$CH_3$ | H | —$CH_3$ | H | H | H | H |
| 257 | —$CH_3$ | —$CH_3$ | H | —$CH_3$ | —OH | H | H | H |
| 258 | —$CH_3$ | —$CH_3$ | H | —$CH_3$ | —OC(O)$CH_3$ | H | H | H |
| 259 | —$CH_3$ | —$CH_3$ | H | —$CH_3$ | —$OCH_3$ | H | H | H |
| 260 | —$CH_3$ | —$CH_2CH_3$ | H | —$CH_3$ | H | H | H | H |
| 261 | —$CH_3$ | —$CH_2(CH_3)_2$ | H | —$CH_3$ | H | H | H | H |
| 262 | —$CH_3$ | —$CH_3$ | H | —$CH_3$ | F | H | H | H |
| 263 | —$CH_3$ | —$CH_3$ | H | H | H | H | F | H |
| 264 | —$CH_3$ | —$CH_3$ | H | H | —OH | H | F | H |
| 265 | —$CH_3$ | —$CH_3$ | H | H | —OC(O)$CH_3$ | H | F | H |
| 266 | —$CH_3$ | —$CH_3$ | H | H | —$OCH_3$ | H | F | H |
| 267 | —$CH_3$ | —$CH_2CH_3$ | H | H | H | H | F | H |
| 268 | —$CH_3$ | —$CH_2(CH_3)_2$ | H | H | H | H | F | H |
| 269 | —$CH_3$ | —$CH_3$ | H | H | F | H | F | H |
| 270 | —$CH_3$ | —$CH_3$ | H | H | H | H | H | —$CH_3$ |
| 271 | —$CH_3$ | —$CH_3$ | H | H | —OH | H | H | —$CH_3$ |
| 272 | —$CH_3$ | —$CH_3$ | H | H | —OC(O)$CH_3$ | H | H | —$CH_3$ |
| 273 | —$CH_3$ | —$CH_3$ | H | H | —$OCH_3$ | H | H | —$CH_3$ |
| 274 | —$CH_3$ | —$CH_2CH_3$ | H | H | H | H | H | —$CH_3$ |
| 275 | —$CH_3$ | —$CH_2(CH_3)_2$ | H | H | H | H | H | —$CH_3$ |
| 276 | —$CH_3$ | —$CH_3$ | H | H | F | H | H | —$CH_3$ |
| 277 | —$CH_3$ | —$CH_3$ | —$CH_3$ | H | H | —OH | H | H |
| 278 | —$CH_3$ | —$CH_3$ | —$CH_3$ | H | H | —OC(O)$CH_3$ | H | H |
| 279 | —$CH_3$ | —$CH_3$ | —$CH_3$ | H | H | —$OCH_3$ | H | H |
| 280 | —$CH_3$ | —$CH_2CH_3$ | —$CH_3$ | H | H | H | H | H |
| 281 | —$CH_3$ | —$CH_2(CH_3)_2$ | —$CH_3$ | H | H | H | H | H |
| 282 | —$CH_3$ | —$CH_3$ | —$CH_3$ | H | H | F | H | H |
| 283 | —$CH_3$ | —$CH_3$ | H | —$CH_3$ | H | H | H | H |
| 284 | —$CH_3$ | —$CH_3$ | H | —$CH_3$ | H | —OH | H | H |
| 285 | —$CH_3$ | —$CH_3$ | H | —$CH_3$ | H | —OC(O)$CH_3$ | H | H |
| 286 | —$CH_3$ | —$CH_3$ | H | —$CH_3$ | H | —$OCH_3$ | H | H |
| 287 | —$CH_3$ | —$CH_2CH_3$ | H | —$CH_3$ | H | H | H | H |
| 288 | —$CH_3$ | $CH_2(CH_3)_2$ | H | —$CH_3$ | H | H | H | H |
| 289 | —$CH_3$ | —$CH_3$ | H | —$CH_3$ | H | F | H | H |
| 290 | —$CH_3$ | —$CH_3$ | H | H | H | H | F | H |
| 291 | —$CH_3$ | —$CH_3$ | H | H | H | —OH | F | H |
| 292 | —$CH_3$ | —$CH_3$ | H | H | H | —OC(O)$CH_3$ | F | H |
| 293 | —$CH_3$ | —$CH_3$ | H | H | H | —$OCH_3$ | F | H |
| 294 | —$CH_3$ | —$CH_2CH_3$ | H | H | H | H | F | H |
| 295 | —$CH_3$ | —$CH_2(CH_3)_2$ | H | H | H | H | F | H |
| 296 | —$CH_3$ | —$CH_3$ | H | H | H | F | F | H |
| 297 | —$CH_3$ | —$CH_3$ | H | H | H | H | H | —$CH_3$ |
| 298 | —$CH_3$ | —$CH_3$ | H | H | H | —OH | H | —$CH_3$ |
| 299 | —$CH_3$ | —$CH_3$ | H | H | H | —OC(O)$CH_3$ | H | —$CH_3$ |
| 300 | —$CH_3$ | —$CH_3$ | H | H | H | —$OCH_3$ | H | —$CH_3$ |
| 301 | —$CH_3$ | —$CH_2CH_3$ | H | H | H | H | H | —$CH_3$ |
| 302 | —$CH_3$ | —$CH_2(CH_3)_2$ | H | H | H | H | H | —$CH_3$ |
| 303 | —$CH_3$ | —$CH_3$ | H | H | H | H | F | —$CH_3$ |
| 304 | H | —$CH_3$ | H | H | H | H | H | H |
| 305 | H | —$CH_2CH_3$ | H | H | H | H | H | H |
| 306 | H | —$(CH_2)_2CH_3$ | H | H | H | H | H | H |
| 307 | H | —$CH(CH_3)_2$ | H | H | H | H | H | H |
| 308 | H | —$(CH_2)_3CH_3$ | H | H | H | H | H | H |
| 309 | H | —$CH_2$—HC=$CH_2$ | H | H | H | H | H | H |
| 310 | H | —$CH_3$ | H | —$CH_3$ | H | H | H | H |
| 310a | H | —$CH_2CH_3$ | H | —$CH_3$ | H | H | H | H |
| 311 | H | —$(CH_2)_2CH_3$ | H | —$CH_3$ | H | H | H | H |
| 312 | H | —$CH(CH_3)_2$ | H | —$CH_3$ | H | H | H | H |
| 313 | H | —$(CH_2)_3CH_3$ | H | —$CH_3$ | H | H | H | H |
| 314 | H | —$CH_2$—HC=$CH_2$ | H | —$CH_3$ | H | H | H | H |
| 315 | H | —$CH_3$ | H | H | —OH | H | H | H |
| 316 | H | —$CH_2CH_3$ | H | H | —OH | H | H | H |
| 317 | H | —$(CH_2)_2CH_3$ | H | H | —OH | H | H | H |
| 318 | H | —$CH(CH_3)_2$ | H | H | —OH | H | H | H |
| 319 | H | —$(CH_2)_3CH_3$ | H | H | —OH | H | H | H |
| 320 | H | —$CH_2$—HC=$CH_2$ | H | H | —OH | H | H | H |
| 321 | H | —$CH_3$ | H | H | —OC(O)$CH_3$ | H | H | H |
| 322 | H | —$CH_2CH_3$ | H | H | —OC(O)$CH_3$ | H | H | H |
| 324 | H | —$(CH_2)_2CH_3$ | H | H | —OC(O)$CH_3$ | H | H | H |

TABLE 1-continued

| Ref. | X | Y | $R_2$ | $R_3$ | $R_4$ | $R_5$ | $R_6$ | $R_7$ |
|---|---|---|---|---|---|---|---|---|
| 325 | H | $—CH(CH_3)_2$ | H | H | $—OC(O)CH_3$ | H | H | H |
| 326 | H | $—(CH_2)_3CH_3$ | H | H | $—OC(O)CH_3$ | H | H | H |
| 327 | H | $—CH_2—HC{=}CH_2$ | H | H | $—OC(O)CH_3$ | H | H | H |
| 328 | H | $—CH_3$ | H | H | H | $—OCH_3$ | H | H |
| 329 | H | $—CH_2CH_3$ | H | H | H | $—OCH_3$ | H | H |
| 330 | H | $—(CH_2)_2CH_3$ | H | H | H | $—OCH_3$ | H | H |
| 331 | H | $—CH(CH_3)_2$ | H | H | H | $—OCH_3$ | H | H |
| 332 | H | $—(CH_2)_3CH_3$ | H | H | H | $—OCH_3$ | H | H |
| 333 | H | $—CH_2—HC{=}CH_2$ | H | H | H | $—OCH_3$ | H | H |
| 334 | H | $—CH_3$ | H | H | H | H | F | H |
| 335 | H | $—CH_2CH_3$ | H | H | H | H | F | H |
| 336 | H | $—(CH_2)_2CH_3$ | H | H | H | H | F | H |
| 337 | H | $—CH(CH_3)_2$ | H | H | H | H | F | H |
| 338 | H | $—(CH_2)_3CH_3$ | H | H | H | H | F | H |
| 339 | H | $—CH_2—HC{=}CH_2$ | H | H | H | H | F | H |
| 340 | H | $—CH_3$ | H | $—CH_3$ | —OH | H | H | H |
| 341 | H | $—CH_2CH_3$ | H | $—CH_3$ | —OH | H | H | H |
| 342 | H | $—(CH_2)_2CH_3$ | H | $—CH_3$ | —OH | H | H | H |
| 343 | H | $—CH(CH_3)_2$ | H | $—CH_3$ | —OH | H | H | H |
| 344 | H | $—(CH_2)_3CH_3$ | H | $—CH_3$ | —OH | H | H | H |
| 345 | H | $—CH_2—HC{=}CH_2$ | H | $—CH_3$ | —OH | H | H | H |
| 346 | H | $—CH_3$ | H | $—CH_3$ | $—OC(O)CH_3$ | H | H | H |
| 347 | H | $—CH_2CH_3$ | H | $—CH_3$ | $—OC(O)CH_3$ | H | H | H |
| 348 | H | $—(CH_2)_2CH_3$ | H | $—CH_3$ | $—OC(O)CH_3$ | H | H | H |
| 349 | H | $—CH(CH_3)_2$ | H | $—CH_3$ | $—OC(O)CH_3$ | H | H | H |
| 350 | H | $—(CH_2)_3CH_3$ | H | $—CH_3$ | $—OC(O)CH_3$ | H | H | H |
| 351 | H | $—CH_2—HC{=}CH_2$ | H | $—CH_3$ | $—OC(O)CH_3$ | H | H | H |
| 352 | H | $—CH_3$ | H | $—CH_3$ | H | $—OCH_3$ | H | H |
| 353 | H | $—CH_2CH_3$ | H | $—CH_3$ | H | $—OCH_3$ | H | H |
| 354 | H | $—(CH_2)_2CH_3$ | H | $—CH_3$ | H | $—OCH_3$ | H | H |
| 355 | H | $—CH(CH_3)_2$ | H | $—CH_3$ | H | $—OCH_3$ | H | H |
| 356 | H | $—(CH_2)_3CH_3$ | H | $—CH_3$ | H | $—OCH_3$ | H | H |
| 357 | H | $—CH_2—HC{=}CH_2$ | H | $—CH_3$ | H | $—OCH_3$ | H | H |
| 358 | H | $—CH_3$ | H | $—CH_3$ | H | H | F | H |
| 359 | H | $—CH_2CH_3$ | H | $—CH_3$ | H | H | F | H |
| 360 | H | $—(CH_2)_2CH_3$ | H | $—CH_3$ | H | H | F | H |
| 361 | H | $—CH(CH_3)_2$ | H | $—CH_3$ | H | H | F | H |
| 362 | H | $—(CH_2)_3CH_3$ | H | $—CH_3$ | H | H | F | H |
| 363 | H | $—CH_2—HC{=}CH_2$ | H | $—CH_3$ | H | H | F | H |
| 364 | H | cyclopropyl | H | H | H | H | H | H |
| 365 | H | cyclopropyl | H | $—CH_3$ | H | H | H | H |
| 366 | H | cyclopropyl | H | H | —OH | H | H | H |
| 367 | H | cyclopropyl | H | H | $—OC(O)CH_3$ | H | H | H |
| 368 | H | cyclopropyl | H | H | H | $—OCH_3$ | H | H |
| 369 | H | cyclopropyl | H | H | H | H | F | H |
| 370 | H | cyclopropyl | H | H | H | H | H | H |
| 371 | H | cyclopropyl | H | $—CH_3$ | —OH | H | F | H |
| 372 | H | cyclopropyl | H | $—CH_3$ | —OH | H | H | H |
| 373 | H | cyclopropyl | H | $—CH_3$ | $—OC(O)CH_3$ | H | H | H |
| 374 | H | cyclopropyl | H | $—CH_3$ | H | $—OCH_3$ | H | H |
| 375 | H | cyclopropyl | H | $—CH_3$ | H | H | F | H |
| 376 | $—CH_3$ | cyclopropyl | H | H | H | H | H | H |
| 377 | $—CH_3$ | cyclopropyl | H | $—CH_3$ | H | H | H | H |
| 378 | $—CH_3$ | cyclopropyl | H | H | —OH | H | H | H |
| 379 | $—CH_3$ | cyclopropyl | H | H | $—OC(O)CH_3$ | H | H | H |
| 380 | $—CH_3$ | cyclopropyl | H | H | H | $—OCH_3$ | H | H |
| 381 | $—CH_3$ | cyclopropyl | H | H | H | H | F | H |
| 382 | $—CH_3$ | cyclopropyl | H | H | H | H | H | H |
| 383 | $—CH_3$ | cyclopropyl | H | $—CH_3$ | —OH | H | F | H |
| 384 | $—CH_3$ | cyclopropyl | H | $—CH_3$ | —OH | H | H | H |
| 385 | $—CH_3$ | cyclopropyl | H | $—CH_3$ | $—OC(O)CH_3$ | H | H | H |
| 386 | $—CH_3$ | cyclopropyl | H | $—CH_3$ | H | $—OCH_3$ | H | H |
| 387 | $—CH_3$ | cyclopropyl | H | $—CH_3$ | H | H | F | H |
| 388 | $—CH_2CH_3$ | cyclopropyl | H | H | H | H | H | H |
| 389 | $—CH_2CH_3$ | cyclopropyl | H | $—CH_3$ | H | H | H | H |
| 390 | $—CH_2CH_3$ | cyclopropyl | H | H | —OH | H | H | H |
| 391 | $—CH_2CH_3$ | cyclopropyl | H | H | $—OC(O)CH_3$ | H | H | H |
| 392 | $—CH_2CH_3$ | cyclopropyl | H | H | H | $—OCH_3$ | H | H |
| 393 | $—CH_2CH_3$ | cyclopropyl | H | H | H | H | F | H |
| 394 | $—CH_2CH_3$ | cyclopropyl | H | H | H | H | H | H |
| 395 | $—CH_2CH_3$ | cyclopropyl | H | $—CH_3$ | —OH | H | F | H |
| 396 | $—CH_2CH_3$ | cyclopropyl | H | $—CH_3$ | —OH | H | H | H |
| 397 | $—CH_2CH_3$ | cyclopropyl | H | $—CH_3$ | $—OC(O)CH_3$ | H | H | H |
| 398 | $—CH_2CH_3$ | cyclopropyl | H | $—CH_3$ | H | $—OCH_3$ | H | H |
| 399 | $—CH_2CH_3$ | cyclopropyl | H | $—CH_3$ | H | H | F | H |
| 400 | $—(CH_2)_2CH_3$ | cyclopropyl | H | H | H | H | H | H |
| 401 | $—(CH_2)_2CH_3$ | cyclopropyl | H | $—CH_3$ | H | H | H | H |
| 402 | $—(CH_2)_2CH_3$ | cyclopropyl | H | H | —OH | H | H | H |

TABLE 1-continued

| Ref. | X | Y | $R_2$ | $R_3$ | $R_4$ | $R_5$ | $R_6$ | $R_7$ |
|---|---|---|---|---|---|---|---|---|
| 403 | $-(CH_2)_2CH_3$ | cyclopropyl | H | H | $-OC(O)CH_3$ | H | H | H |
| 404 | $-(CH_2)_2CH_3$ | cyclopropyl | H | H | H | $-OCH_3$ | H | H |
| 405 | $-(CH_2)_2CH_3$ | cyclopropyl | H | H | H | H | F | H |
| 406 | $-(CH_2)_2CH_3$ | cyclopropyl | H | H | H | H | H | H |
| 407 | $-(CH_2)_2CH_3$ | cyclopropyl | H | $-CH_3$ | $-OH$ | H | F | H |
| 408 | $-(CH_2)_2CH_3$ | cyclopropyl | H | $-CH_3$ | $-OH$ | H | H | H |
| 409 | $-(CH_2)_2CH_3$ | cyclopropyl | H | $-CH_3$ | $-OC(O)CH_3$ | H | H | H |
| 410 | $-(CH_2)_2CH_3$ | cyclopropyl | H | $-CH_3$ | H | $-OCH_3$ | H | H |
| 411 | $-(CH_2)_2CH_3$ | cyclopropyl | H | $-CH_3$ | H | H | F | H |
| 412 | $-CH_2(CH_3)_2$ | cyclopropyl | H | H | H | H | H | H |
| 413 | $-CH_2(CH_3)_2$ | cyclopropyl | H | $-CH_3$ | H | H | H | H |
| 414 | $-CH_2(CH_3)_2$ | cyclopropyl | H | H | $-OH$ | H | H | H |
| 415 | $-CH_2(CH_3)_2$ | cyclopropyl | H | H | $-OC(O)CH_3$ | H | H | H |
| 416 | $-CH_2(CH_3)_2$ | cyclopropyl | H | H | H | $-OCH_3$ | H | H |
| 417 | $-CH_2(CH_3)_2$ | cyclopropyl | H | H | H | H | F | H |
| 418 | $-CH_2(CH_3)_2$ | cyclopropyl | H | H | H | H | H | H |
| 419 | $-CH_2(CH_3)_2$ | cyclopropyl | H | $-CH_3$ | $-OH$ | H | F | H |
| 420 | $-CH_2(CH_3)_2$ | cyclopropyl | H | $-CH_3$ | $-OH$ | H | H | H |
| 421 | $-CH_2(CH_3)_2$ | cyclopropyl | H | $-CH_3$ | $-OC(O)CH_3$ | H | H | H |
| 422 | $-CH_2(CH_3)_2$ | cyclopropyl | H | $-CH_3$ | H | $-OCH_3$ | H | H |
| 423 | $-CH_2(CH_3)_2$ | cyclopropyl | H | $-CH_3$ | H | H | F | H |
| 424 | cyclopropyl | cyclopropyl | H | $-CH_3$ | H | H | H | H |
| 425 | cyclopropyl | cyclopropyl | H | H | $-OH$ | H | H | H |
| 426 | cyclopropyl | cyclopropyl | H | H | $-OC(O)CH_3$ | H | H | H |
| 427 | cyclopropyl | cyclopropyl | H | H | H | $-OCH_3$ | H | H |
| 428 | cyclopropyl | cyclopropyl | H | H | H | H | F | H |
| 429 | cyclopropyl | cyclopropyl | H | H | H | H | H | H |
| 430 | cyclopropyl | cyclopropyl | H | $-CH_3$ | $-OH$ | H | F | H |
| 431 | cyclopropyl | cyclopropyl | H | $-CH_3$ | $-OH$ | H | H | H |
| 432 | cyclopropyl | cyclopropyl | H | $-CH_3$ | $-OC(O)CH_3$ | H | H | H |
| 433 | cyclopropyl | cyclopropyl | H | $-CH_3$ | H | $-OCH_3$ | H | H |
| 434 | cyclopropyl | cyclopropyl | H | $-CH_3$ | H | H | F | H |
| 435 | H | $-CH_3$ | H | H | $-OH$ | H | H | $-CH_3$ |
| 436 | H | $-CH_2CH_3$ | H | H | $-OH$ | H | H | $-CH_3$ |
| 437 | H | $-(CH_2)_2CH_3$ | H | H | $-OH$ | H | H | $-CH_3$ |
| 438 | H | $-CH(CH_3)_2$ | H | H | $-OH$ | H | H | $-CH_3$ |
| 439 | H | $-(CH_2)_3CH_3$ | H | H | $-OH$ | H | H | $-CH_3$ |
| 440 | H | $-CH_2-HC{=}CH_2$ | H | H | $-OH$ | H | H | $-CH_3$ |
| 441 | H | $-CH_3$ | H | H | $-OC(O)CH_3$ | H | H | $-CH_3$ |
| 442 | H | $-CH_2CH_3$ | H | H | $-OC(O)CH_3$ | H | H | $-CH_3$ |
| 443 | H | $-(CH_2)_2CH_3$ | H | H | $-OC(O)CH_3$ | H | H | $-CH_3$ |
| 444 | H | $-CH(CH_3)_2$ | H | H | $-OC(O)CH_3$ | H | H | $-CH_3$ |
| 445 | H | $-(CH_2)_3CH_3$ | H | H | $-OC(O)CH_3$ | H | H | $-CH_3$ |
| 446 | H | $-CH_2-HC{=}CH_2$ | H | H | $-OC(O)CH_3$ | H | H | $-CH_3$ |
| 447 | H | $-CH_3$ | H | H | H | $-OCH_3$ | H | $-CH_3$ |
| 448 | H | $-CH_2CH_3$ | H | H | H | $-OCH_3$ | H | $-CH_3$ |
| 449 | H | $-(CH_2)_2CH_3$ | H | H | H | $-OCH_3$ | H | $-CH_3$ |
| 450 | H | $-CH(CH_3)_2$ | H | H | H | $-OCH_3$ | H | $-CH_3$ |
| 451 | H | $-(CH_2)_3CH_3$ | H | H | H | $-OCH_3$ | H | $-CH_3$ |
| 452 | H | $-CH_2-HC{=}CH_2$ | H | H | H | $-OCH_3$ | H | $-CH_3$ |
| 453 | H | $-CH_3$ | H | H | $-OH$ | H | F | H |
| 454 | H | $-CH_2CH_3$ | H | H | $-OH$ | H | F | H |
| 455 | H | $-(CH_2)_2CH_3$ | H | H | $-OH$ | H | F | H |
| 456 | H | $-CH(CH_3)_2$ | H | H | $-OH$ | H | F | H |
| 457 | H | $-(CH_2)_3CH_3$ | H | H | $-OH$ | H | F | H |
| 458 | H | $-CH_2-HC{=}CH_2$ | H | H | $-OH$ | H | F | H |
| 459 | H | $-CH_3$ | H | H | $-OC(O)CH_3$ | H | F | H |
| 460 | H | $-CH_2CH_3$ | H | H | $-OC(O)CH_3$ | H | F | H |
| 461 | H | $-(CH_2)_2CH_3$ | H | H | $-OC(O)CH_3$ | H | F | H |
| 462 | H | $-CH(CH_3)_2$ | H | H | $-OC(O)CH_3$ | H | F | H |
| 463 | H | $-(CH_2)_3CH_3$ | H | H | $-OC(O)CH_3$ | H | F | H |
| 464 | H | $-CH_2-HC{=}CH_2$ | H | H | $-OC(O)CH_3$ | H | F | H |
| 465 | H | $-CH_3$ | H | H | H | $-OCH_3$ | F | H |
| 466 | H | $-CH_2CH_3$ | H | H | H | $-OCH_3$ | F | H |
| 467 | H | $-(CH_2)_2CH_3$ | H | H | H | $-OCH_3$ | F | H |
| 468 | H | $-CH(CH_3)_2$ | H | H | H | $-OCH_3$ | F | H |
| 469 | H | $-(CH_2)_3CH_3$ | H | H | H | $-OCH_3$ | F | H |
| 470 | H | $-CH_2-HC{=}CH_2$ | H | H | H | $-OCH_3$ | F | H |
| 471 | H | $-CD_3$ | H | H | H | H | H | H |
| 472 | H | $-CD_3$ | H | H | $-OH$ | H | H | H |
| 473 | H | $-CD_3$ | H | H | $-OC(O)CH_3$ | H | H | H |
| 474 | H | $-CD_3$ | H | H | H | $-OCH_3$ | H | H |
| 475 | H | $-CD_3$ | H | H | H | H | F | H |
| 476 | H | $-CD_3$ | H | H | $-OH$ | H | F | H |
| 477 | H | $-CD_3$ | H | H | $-OC(O)CH_3$ | H | F | H |
| 478 | H | $-CD_3$ | H | H | H | $-OCH_3$ | F | H |
| 479 | H | $-CD_3$ | H | H | H | H | H | $-CH_3$ |
| 480 | H | $-CD_3$ | H | H | $-OH$ | H | H | $-CH_3$ |

TABLE 1-continued

| Ref. | X | Y | $R_2$ | $R_3$ | $R_4$ | $R_5$ | $R_6$ | $R_7$ |
|---|---|---|---|---|---|---|---|---|
| 481 | H | $—CD_3$ | H | H | $—OC(O)CH_3$ | H | H | $—CH_3$ |
| 482 | H | $—CD_3$ | H | H | H | $—OCH_3$ | H | $—CH_3$ |
| 483 | H | $—CD_3$ | H | H | H | H | F | $—CH_3$ |
| 484 | H | $—CD_3$ | H | H | —OH | H | F | $—CH_3$ |
| 485 | H | $—CD_3$ | H | H | $—OC(O)CH_3$ | H | F | $—CH_3$ |
| 486 | H | $—CD_3$ | H | H | H | $—OCH_3$ | F | $—CH_3$ |
| 487 | H | $—CD_2CD_3$ | H | H | H | H | H | H |
| 488 | H | $—CD_2CD_3$ | H | H | —OH | H | H | H |
| 489 | H | $—CD_2CD_3$ | H | H | $—OC(O)CH_3$ | H | H | H |
| 490 | H | $—CD_2CD_3$ | H | H | H | $—OCH_3$ | H | H |
| 491 | H | $—CD_2CD_3$ | H | H | H | H | F | H |
| 492 | H | $—CD_2CD_3$ | H | H | —OH | H | F | H |
| 493 | H | $—CD_2CD_3$ | H | H | $—OC(O)CH_3$ | H | F | H |
| 494 | H | $—CD_2CD_3$ | H | H | H | $—OCH_3$ | F | H |
| 495 | H | $—CD_2CD_3$ | H | H | H | H | H | $—CH_3$ |
| 496 | H | $—CD_2CD_3$ | H | H | —OH | H | H | $—CH_3$ |
| 497 | H | $—CD_2CD_3$ | H | H | $—OC(O)CH_3$ | H | H | $—CH_3$ |
| 498 | H | $—CD_2CD_3$ | H | H | H | $—OCH_3$ | H | $—CH_3$ |
| 499 | H | $—CD_2CD_3$ | H | H | H | H | F | $—CH_3$ |
| 500 | H | $—CD_2CD_3$ | H | H | —OH | H | F | $—CH_3$ |
| 501 | H | $—CD_2CD_3$ | H | H | $—OC(O)CH_3$ | H | F | $—CH_3$ |
| 502 | H | $—CD_2CD_3$ | H | H | H | $—OCH_3$ | F | $—CH_3$ |
| 503 | H | $—CH_3$ | H | H | —OH | H | F | $—CH_3$ |
| 504 | H | $—CH_2CH_3$ | H | H | —OH | H | F | $—CH_3$ |
| 505 | H | $—(CH_2)_2CH_3$ | H | H | —OH | H | F | $—CH_3$ |
| 506 | H | $—CH(CH_3)_2$ | H | H | —OH | H | F | $—CH_3$ |
| 507 | H | $—(CH_2)_3CH_3$ | H | H | —OH | H | F | $—CH_3$ |
| 508 | H | $—CH_2—HC{=}CH_2$ | H | H | —OH | H | F | $—CH_3$ |
| 509 | H | $—CH_3$ | H | H | $—OC(O)CH_3$ | H | F | $—CH_3$ |
| 510 | H | $—CH_2CH_3$ | H | H | $—OC(O)CH_3$ | H | F | $—CH_3$ |
| 511 | H | $—(CH_2)_2CH_3$ | H | H | $—OC(O)CH_3$ | H | F | $—CH_3$ |
| 512 | H | $—CH(CH_3)_2$ | H | H | $—OC(O)CH_3$ | H | F | $—CH_3$ |
| 513 | H | $—(CH_2)_3CH_3$ | H | H | $—OC(O)CH_3$ | H | F | $—CH_3$ |
| 514 | H | $—CH_2—HC{=}CH_2$ | H | H | $—OC(O)CH_3$ | H | F | $—CH_3$ |
| 515 | H | $—CH_3$ | H | H | H | $—OCH_3$ | F | $—CH_3$ |
| 516 | H | $—CH_2CH_3$ | H | H | H | $—OCH_3$ | F | $—CH_3$ |
| 517 | H | $—(CH_2)_2CH_3$ | H | H | H | $—OCH_3$ | F | $—CH_3$ |
| 518 | H | $—CH(CH_3)_2$ | H | H | H | $—OCH_3$ | F | $—CH_3$ |
| 519 | H | $—(CH_2)_3CH_3$ | H | H | H | $—OCH_3$ | F | $—CH_3$ |
| 520 | H | $—CH_2—HC{=}CH_2$ | H | H | H | $—OCH_3$ | F | $—CH_3$ |
| 521 | H | $—CH_3$ | H | D | H | H | H | H |
| 522 | H | $—CH_2CH_3$ | H | D | H | H | H | H |
| 523 | H | $—(CH_2)_2CH_3$ | H | D | H | H | H | H |
| 524 | H | $—CH(CH_3)_2$ | H | D | H | H | H | H |
| 525 | H | $—(CH_2)_3CH_3$ | H | D | H | H | H | H |
| 526 | H | $—CH_2—HC{=}CH_2$ | H | D | H | H | H | H |
| 527 | H | $—CH_3$ | H | D | —OH | H | H | H |
| 528 | H | $—CH_2CH_3$ | H | D | —OH | H | H | H |
| 529 | H | $—(CH_2)_2CH_3$ | H | D | —OH | H | H | H |
| 530 | H | $—CH(CH_3)_2$ | H | D | —OH | H | H | H |
| 531 | H | $—(CH_2)_3CH_3$ | H | D | —OH | H | H | H |
| 532 | H | $—CH_2—HC{=}CH_2$ | H | D | —OH | H | H | H |
| 533 | H | $—CH_3$ | H | D | $—OC(O)CH_3$ | H | H | H |
| 534 | H | $—CH_2CH_3$ | H | D | $—OC(O)CH_3$ | H | H | H |
| 535 | H | $—(CH_2)_2CH_3$ | H | D | $—OC(O)CH_3$ | H | H | H |
| 536 | H | $—CH(CH_3)_2$ | H | D | $—OC(O)CH_3$ | H | H | H |
| 537 | H | $—(CH_2)_3CH_3$ | H | D | $—OC(O)CH_3$ | H | H | H |
| 538 | H | $—CH_2—HC{=}CH_2$ | H | D | $—OC(O)CH_3$ | H | H | H |
| 539 | H | $—CH_3$ | H | D | H | $—OCH_3$ | H | H |
| 540 | H | $—CH_2CH_3$ | H | D | H | $—OCH_3$ | H | H |
| 541 | H | $—(CH_2)_2CH_3$ | H | D | H | $—OCH_3$ | H | H |
| 542 | H | $—CH(CH_3)_2$ | H | D | H | $—OCH_3$ | H | H |
| 543 | H | $—(CH_2)_3CH_3$ | H | D | H | $—OCH_3$ | H | H |
| 544 | H | $—CH_2—HC{=}CH_2$ | H | D | H | $—OCH_3$ | H | H |
| 545 | H | $—CH_3$ | H | D | H | H | F | H |
| 546 | H | $—CH_2CH_3$ | H | D | H | H | F | H |
| 547 | H | $—(CH_2)_2CH_3$ | H | D | H | H | F | H |
| 548 | H | $—CH(CH_3)_2$ | H | D | H | H | F | H |
| 549 | H | $—(CH_2)_3CH_3$ | H | D | H | H | F | H |
| 550 | H | $—CH_2—HC{=}CH_2$ | H | D | H | H | F | H |
| 551 | H | $—CH_3$ | H | D | H | H | F | $CH_3$ |
| 552 | H | $—CH_2CH_3$ | H | D | H | H | F | $CH_3$ |
| 553 | H | $—(CH_2)_2CH_3$ | H | D | H | H | F | $CH_3$ |
| 554 | H | $—CH(CH_3)_2$ | H | D | H | H | F | $CH_3$ |
| 555 | H | $—(CH_2)_3CH_3$ | H | D | H | H | F | $CH_3$ |
| 556 | H | $—CH_2—HC{=}CH_2$ | H | D | H | H | F | $CH_3$ |

Other exemplary compounds of Formula I include those below in Table 2, which is also represented by Formula Ib:

Formula Ib

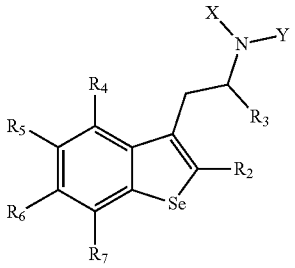

TABLE 2

| Ref. | X | Y | $R_2$ | $R_3$ | $R_4$ | $R_5$ | $R_6$ | $R_7$ |
|---|---|---|---|---|---|---|---|---|
| 1 | $—CH_3$ | $—CH_3$ | H | H | $—OCH_3$ | H | H | H |
| 2 | $—CH_3$ | $—CH_2CH_3$ | H | H | $—OCH_3$ | H | H | H |
| 3 | $—CH_3$ | $—(CH_2)_2CH_3$ | H | H | $—OCH_3$ | H | H | H |
| 4 | $—CH_3$ | $—CH(CH_3)_2$ | H | H | $—OCH_3$ | H | H | H |
| 5 | $—CH_3$ | $—(CH_2)_3CH_3$ | H | H | $—OCH_3$ | H | H | H |
| 6 | $—CH_3$ | $—CH_2—HC═CH_2$ | H | H | $—OCH_3$ | H | H | H |
| 7 | $—CH_2CH_3$ | $—CH_2CH_3$ | H | H | $—OCH_3$ | H | H | H |
| 8 | $—CH_2CH_3$ | $—(CH_2)_2CH_3$ | H | H | $—OCH_3$ | H | H | H |
| 9 | $—CH_2CH_3$ | $—CH(CH_3)_2$ | H | H | $—OCH_3$ | H | H | H |
| 10 | $—CH_2CH_3$ | $—(CH_2)_3CH_3$ | H | H | $—OCH_3$ | H | H | H |
| 11 | $—CH_2CH_3$ | $—CH_2—HC═CH_2$ | H | H | $—OCH_3$ | H | H | H |
| 12 | $—(CH_2)_2CH_3$ | $—(CH_2)_2CH_3$ | H | H | $—OCH_3$ | H | H | H |
| 13 | $—(CH_2)_2CH_3$ | $—CH(CH_3)_2$ | H | H | $—OCH_3$ | H | H | H |
| 14 | $—(CH_2)_2CH_3$ | $—(CH_2)_3CH_3$ | H | H | $—OCH_3$ | H | H | H |
| 15 | $—(CH_2)_2CH_3$ | $—CH_2—HC═CH_2$ | H | H | $—OCH_3$ | H | H | H |
| 16 | $—CH(CH_3)_2$ | $—CH(CH_3)_2$ | H | H | $—OCH_3$ | H | H | H |
| 17 | $—CH(CH_3)_2$ | $—(CH_2)_3CH_3$ | H | H | $—OCH_3$ | H | H | H |
| 18 | $—CH(CH_3)_2$ | $—CH_2—HC═CH_2$ | H | H | $—OCH_3$ | H | H | H |
| 19 | $—(CH_2)_3CH_3$ | $—(CH_2)_3CH_3$ | H | H | $—OCH_3$ | H | H | H |
| 20 | $—(CH_2)_3CH_3$ | $—CH_2—HC═CH_2$ | H | H | $—OCH_3$ | H | H | H |
| 21 | $—CH_2—HC═CH_2$ | $—CH_2—HC═CH_2$ | H | H | $—OCH_3$ | H | H | H |
| 22 | $—CH_3$ | $—CH_2CH_3$ | H | H | —OH | H | H | H |
| 23 | $—CH_3$ | $—(CH_2)_2CH_3$ | H | H | —OH | H | H | H |
| 24 | $—CH_3$ | $—CH(CH_3)_2$ | H | H | —OH | H | H | H |
| 25 | $—CH_3$ | $—(CH_2)_3CH_3$ | H | H | —OH | H | H | H |
| 26 | $—CH_3$ | $—CH_2—HC═CH_2$ | H | H | —OH | H | H | H |
| 27 | $—CH_2CH_3$ | $—CH_2CH_3$ | H | H | —OH | H | H | H |
| 28 | $—CH_2CH_3$ | $—(CH_2)_2CH_3$ | H | H | —OH | H | H | H |
| 29 | $—CH_2CH_3$ | $—CH(CH_3)_2$ | H | H | —OH | H | H | H |
| 30 | $—CH_2CH_3$ | $—(CH_2)_3CH_3$ | H | H | —OH | H | H | H |
| 31 | $—CH_2CH_3$ | $—CH_2—HC═CH_2$ | H | H | —OH | H | H | H |
| 32 | $—(CH_2)_2CH_3$ | $—(CH_2)_2CH_3$ | H | H | —OH | H | H | H |
| 33 | $—(CH_2)_2CH_3$ | $—CH(CH_3)_2$ | H | H | —OH | H | H | H |
| 34 | $—(CH_2)_2CH_3$ | $—(CH_2)_3CH_3$ | H | H | —OH | H | H | H |
| 35 | $—(CH_2)_2CH_3$ | $—CH_2—HC═CH_2$ | H | H | —OH | H | H | H |
| 36 | $—CH(CH_3)_2$ | $—CH(CH_3)_2$ | H | H | —OH | H | H | H |
| 37 | $—CH(CH_3)_2$ | $(CH_2)_3CH_3$ | H | H | —OH | H | H | H |
| 38 | $—CH(CH_3)_2$ | $—CH_2—HC═CH_2$ | H | H | —OH | H | H | H |
| 39 | $—(CH_2)_3CH_3$ | $—(CH_2)_3CH_3$ | H | H | —OH | H | H | H |
| 40 | $—(CH_2)_3CH_3$ | $—CH_2—HC═CH_2$ | H | H | —OH | H | H | H |
| 41 | $—CH_2—HC═CH_2$ | $—CH_2—HC═CH_2$ | H | H | —OH | H | H | H |
| 42 | $—CH_3$ | $—CH_3$ | H | H | $—OC(O)CH_3$ | H | H | H |
| 43 | $—CH_3$ | $—CH_2CH_3$ | H | H | $—OC(O)CH_3$ | H | H | H |
| 44 | $—CH_3$ | $—(CH_2)_2CH_3$ | H | H | $—OC(O)CH_3$ | H | H | H |
| 45 | $—CH_3$ | $—CH(CH_3)_2$ | H | H | $—OC(O)CH_3$ | H | H | H |
| 46 | $—CH_3$ | $—(CH_2)_3CH_3$ | H | H | $—OC(O)CH_3$ | H | H | H |
| 47 | $—CH_3$ | $—CH_2—HC═CH_2$ | H | H | $—OC(O)CH_3$ | H | H | H |
| 48 | $—CH_2CH_3$ | $—CH_2CH_3$ | H | H | $—OC(O)CH_3$ | H | H | H |
| 49 | $—CH_2CH_3$ | $—(CH_2)_2CH_3$ | H | H | $—OC(O)CH_3$ | H | H | H |
| 50 | $—CH_2CH_3$ | $—CH(CH_3)_2$ | H | H | $—OC(O)CH_3$ | H | H | H |
| 51 | $—CH_2CH_3$ | $—(CH_2)_3CH_3$ | H | H | $—OC(O)CH_3$ | H | H | H |
| 52 | $—CH_2CH_3$ | $—CH_2—HC═CH_2$ | H | H | $—OC(O)CH_3$ | H | H | H |
| 53 | $—(CH_2)_2CH_3$ | $—(CH_2)_2CH_3$ | H | H | $—OC(O)CH_3$ | H | H | H |
| 54 | $—(CH_2)_2CH_3$ | $—CH(CH_3)_2$ | H | H | $—OC(O)CH_3$ | H | H | H |
| 55 | $—(CH_2)_2CH_3$ | $—(CH_2)_3CH_3$ | H | H | $—OC(O)CH_3$ | H | H | H |
| 56 | $—(CH_2)_2CH_3$ | $—CH_2—HC═CH_2$ | H | H | $—OC(O)CH_3$ | H | H | H |

TABLE 2-continued

| Ref. | X | Y | $R_2$ | $R_3$ | $R_4$ | $R_5$ | $R_6$ | $R_7$ |
|---|---|---|---|---|---|---|---|---|
| 57 | —$CH(CH_3)_2$ | —$CH(CH_3)_2$ | H | H | —OC(O)$CH_3$ | H | H | H |
| 58 | —$CH(CH_3)_2$ | —$(CH_2)_3CH_3$ | H | H | —OC(O)$CH_3$ | H | H | H |
| 59 | —$CH(CH_3)_2$ | —$CH_2$—HC═$CH_2$ | H | H | —OC(O)$CH_3$ | H | H | H |
| 60 | —$(CH_2)_3CH_3$ | —$(CH_2)_3CH_3$ | H | H | —OC(O)$CH_3$ | H | H | H |
| 61 | $(CH_2)_3CH_3$ | —$CH_2$—HC═$CH_2$ | H | H | —OC(O)$CH_3$ | H | H | H |
| 62 | —$CH_2$—HC═$CH_2$ | —$CH_2$—HC═$CH_2$ | H | H | —OC(O)$CH_3$ | H | H | H |
| 63 | —$CH_3$ | —$CH_3$ | H | H | H | —$OCH_2CH_3$ | H | H |
| 64 | —$CH_3$ | —$CH_2CH_3$ | H | H | H | —$OCH_3$ | H | H |
| 65 | —$CH_3$ | $(CH_2)_2CH_3$ | H | H | H | —$OCH_3$ | H | H |
| 66 | —$CH_3$ | —$CH(CH_3)_2$ | H | H | H | —$OCH_3$ | H | H |
| 67 | —$CH_3$ | —$(CH_2)_3CH_3$ | H | H | H | —$OCH_3$ | H | H |
| 68 | —$CH_3$ | —$CH_2$—HC═$CH_2$ | H | H | H | —$OCH_3$ | H | H |
| 69 | —$CH_2CH_3$ | —$CH_2CH_3$ | H | H | H | —$OCH_3$ | H | H |
| 70 | —$CH_2CH_3$ | —$(CH_2)_2CH_3$ | H | H | H | —$OCH_3$ | H | H |
| 71 | —$CH_2CH_3$ | —$CH(CH_3)_2$ | H | H | H | —$OCH_3$ | H | H |
| 72 | —$CH_2CH_3$ | —$(CH_2)_3CH_3$ | H | H | H | —$OCH_3$ | H | H |
| 73 | —$CH_2CH_3$ | —$CH_2$—HC═$CH_2$ | H | H | H | —$OCH_3$ | H | H |
| 74 | —$(CH_2)_2CH_3$ | —$(CH_2)_2CH_3$ | H | H | H | —$OCH_3$ | H | H |
| 75 | —$(CH_2)_2CH_3$ | —$CH(CH_3)_2$ | H | H | H | —$OCH_3$ | H | H |
| 76 | —$(CH_2)_2CH_3$ | —$(CH_2)_3CH_3$ | H | H | H | —$OCH_3$ | H | H |
| 77 | —$(CH_2)_2CH_3$ | —$CH_2$—HC═$CH_2$ | H | H | H | —$OCH_3$ | H | H |
| 78 | —$CH(CH_3)_2$ | —$CH(CH_3)_2$ | H | H | H | —$OCH_3$ | H | H |
| 79 | —$CH(CH_3)_2$ | —$(CH_2)_3CH_3$ | H | H | H | —$OCH_3$ | H | H |
| 80 | —$CH(CH_3)_2$ | —$CH_2$—HC═$CH_2$ | H | H | H | —$OCH_3$ | H | H |
| 81 | —$(CH_2)_3CH_3$ | —$(CH_2)_3CH_3$ | H | H | H | —$OCH_3$ | H | H |
| 82 | —$(CH_2)_3CH_3$ | —$CH_2$—HC═$CH_2$ | H | H | H | —$OCH_3$ | H | H |
| 83 | —$CH_2$—HC═$CH_2$ | —$CH_2$—HC═$CH_2$ | H | H | H | —$OCH_3$ | H | H |
| 84 | —$CH_3$ | —$CH_2CH_3$ | H | H | H | —OH | H | H |
| 85 | —$CH_3$ | —$(CH_2)_2CH_3$ | H | H | H | —OH | H | H |
| 86 | —$CH_3$ | —$CH(CH_3)_2$ | H | H | H | —OH | H | H |
| 87 | —$CH_3$ | —$(CH_2)_3CH_3$ | H | H | H | —OH | H | H |
| 88 | —$CH_3$ | —$CH_2$—HC═$CH_2$ | H | H | H | —OH | H | H |
| 89 | —$CH_2CH_3$ | —$CH_2CH_3$ | H | H | H | —OH | H | H |
| 90 | —$CH_2CH_3$ | —$(CH_2)_2CH_3$ | H | H | H | —OH | H | H |
| 91 | —$CH_2CH_3$ | —$CH(CH_3)_2$ | H | H | H | —OH | H | H |
| 92 | —$CH_2CH_3$ | —$(CH_2)_3CH_3$ | H | H | H | —OH | H | H |
| 93 | —$CH_2CH_3$ | —$CH_2$—HC═$CH_2$ | H | H | H | —OH | H | H |
| 94 | —$(CH_2)_2CH_3$ | —$(CH_2)_2CH_3$ | H | H | H | —OH | H | H |
| 95 | —$(CH_2)_2CH_3$ | —$CH(CH_3)_2$ | H | H | H | —OH | H | H |
| 96 | —$(CH_2)_2CH_3$ | —$(CH_2)_3CH_3$ | H | H | H | —OH | H | H |
| 97 | —$(CH_2)_2CH_3$ | —$CH_2$—HC═$CH_2$ | H | H | H | —OH | H | H |
| 98 | —$CH(CH_3)_2$ | —$CH(CH_3)_2$ | H | H | H | —OH | H | H |
| 99 | —$CH(CH_3)_2$ | —$(CH_2)_3CH_3$ | H | H | H | —OH | H | H |
| 100 | —$CH(CH_3)_2$ | —$CH_2$—HC═$CH_2$ | H | H | H | —OH | H | H |
| 101 | —$(CH_2)_3CH_3$ | —$(CH_2)_3CH_3$ | H | H | H | —OH | H | H |
| 102 | —$(CH_2)_3CH_3$ | —$CH_2$—HC═$CH_2$ | H | H | H | —OH | H | H |
| 103 | —$CH_2$—HC═$CH_2$ | —$CH_2$—HC═$CH_2$ | H | H | H | —OH | H | H |
| 104 | —$CH_3$ | —$CH_3$ | H | H | H | —OC(O)$CH_3$ | H | H |
| 105 | —$CH_3$ | —$CH_2CH_3$ | H | H | H | —OC(O)$CH_3$ | H | H |
| 106 | —$CH_3$ | —$(CH_2)_2CH_3$ | H | H | H | —OC(O)$CH_3$ | H | H |
| 107 | —$CH_3$ | —$CH(CH_3)_2$ | H | H | H | —OC(O)$CH_3$ | H | H |
| 108 | —$CH_3$ | —$(CH_2)_3CH_3$ | H | H | H | —OC(O)$CH_3$ | H | H |
| 109 | —$CH_3$ | —$CH_2$—HC═$CH_2$ | H | H | H | —OC(O)$CH_3$ | H | H |
| 110 | —$CH_2CH_3$ | —$CH_2CH_3$ | H | H | H | —OC(O)$CH_3$ | H | H |
| 111 | —$CH_2CH_3$ | —$(CH_2)_2CH_3$ | H | H | H | —OC(O)$CH_3$ | H | H |
| 112 | —$CH_2CH_3$ | —$CH(CH_3)_2$ | H | H | H | —OC(O)$CH_3$ | H | H |
| 113 | —$CH_2CH_3$ | —$(CH_2)_3CH_3$ | H | H | H | —OC(O)$CH_3$ | H | H |
| 114 | —$CH_2CH_3$ | —$CH_2$—HC═$CH_2$ | H | H | H | —OC(O)$CH_3$ | H | H |
| 115 | —$(CH_2)_2CH_3$ | —$(CH_2)_2CH_3$ | H | H | H | —OC(O)$CH_3$ | H | H |
| 116 | —$(CH_2)_2CH_3$ | —$CH(CH_3)_2$ | H | H | H | —OC(O)$CH_3$ | H | H |
| 117 | —$(CH_2)_2CH_3$ | —$(CH_2)_3CH_3$ | H | H | H | —OC(O)$CH_3$ | H | H |
| 118 | —$(CH_2)_2CH_3$ | —$CH_2$—HC═$CH_2$ | H | H | H | —OC(O)$CH_3$ | H | H |
| 119 | —$CH(CH_3)_2$ | —$CH(CH_3)_2$ | H | H | H | —OC(O)$CH_3$ | H | H |
| 120 | —$CH(CH_3)_2$ | —$(CH_2)_3CH_3$ | H | H | H | —OC(O)$CH_3$ | H | H |
| 121 | —$CH(CH_3)_2$ | —$CH_2$—HC═$CH_2$ | H | H | H | —OC(O)$CH_3$ | H | H |
| 122 | —$(CH_2)_3CH_3$ | —$(CH_2)_3CH_3$ | H | H | H | —OC(O)$CH_3$ | H | H |
| 123 | —$(CH_2)_3CH_3$ | —$CH_2$—HC═$CH_2$ | H | H | H | —OC(O)$CH_3$ | H | H |
| 124 | —$CH_2$—HC═$CH_2$ | —$CH_2$—HC═$CH_2$ | H | H | H | —OC(O)$CH_3$ | H | H |
| 125 | —$CH_3$ | —$CH_3$ | H | H | —$OCH_3$ | H | H | —$CH_3$ |
| 126 | —$CH_3$ | —$CH_2CH_3$ | H | H | —$OCH_3$ | H | H | —$CH_3$ |
| 127 | —$CH_3$ | —$(CH_2)_2CH_3$ | H | H | —$OCH_3$ | H | H | —$CH_3$ |
| 128 | —$CH_3$ | —$CH(CH_3)_2$ | H | H | —$OCH_3$ | H | H | —$CH_3$ |
| 129 | —$CH_3$ | —$(CH_2)_3CH_3$ | H | H | —$OCH_3$ | H | H | —$CH_3$ |
| 130 | —$CH_3$ | —$CH_2$—HC═$CH_2$ | H | H | —$OCH_3$ | H | H | —$CH_3$ |
| 131 | —$CH_2CH_3$ | —$CH_2CH_3$ | H | H | —$OCH_3$ | H | H | —$CH_3$ |
| 132 | —$CH_2CH_3$ | —$(CH_2)_2CH_3$ | H | H | —$OCH_3$ | H | H | —$CH_3$ |
| 133 | —$CH_2CH_3$ | —$CH(CH_3)_2$ | H | H | —$OCH_3$ | H | H | —$CH_3$ |
| 134 | —$CH_2CH_3$ | —$(CH_2)_3CH_3$ | H | H | —$OCH_3$ | H | H | —$CH_3$ |

TABLE 2-continued

| Ref. | X | Y | $R_2$ | $R_3$ | $R_4$ | $R_5$ | $R_6$ | $R_7$ |
|---|---|---|---|---|---|---|---|---|
| 135 | —$CH_2CH_3$ | —$CH_2$—HC═$CH_2$ | H | H | —$OCH_3$ | H | H | —$CH_3$ |
| 135 | —$(CH_2)_2CH_3$ | —$(CH_2)_2CH_3$ | H | H | —$OCH_3$ | H | H | —$CH_3$ |
| 137 | —$(CH_2)_2CH_3$ | —$CH(CH_3)_2$ | H | H | —$OCH_3$ | H | H | —$CH_3$ |
| 138 | —$(CH_2)_2CH_3$ | —$(CH_2)_3CH_3$ | H | H | —$OCH_3$ | H | H | —$CH_3$ |
| 139 | —$(CH_2)_2CH_3$ | —$CH_2$—HC═$CH_2$ | H | H | —$OCH_3$ | H | H | —$CH_3$ |
| 140 | —$CH(CH_3)_2$ | —$CH(CH_3)_2$ | H | H | —$OCH_3$ | H | H | —$CH_3$ |
| 141 | —$CH(CH_3)_2$ | —$(CH_2)_3CH_3$ | H | H | —$OCH_3$ | H | H | —$CH_3$ |
| 142 | —$CH(CH_3)_2$ | —$CH_2$—HC═$CH_2$ | H | H | —$OCH_3$ | H | H | —$CH_3$ |
| 143 | —$(CH_2)_3CH_3$ | —$(CH_2)_3CH_3$ | H | H | —$OCH_3$ | H | H | —$CH_3$ |
| 144 | —$(CH_2)_3CH_3$ | —$CH_2$—HC═$CH_2$ | H | H | —$OCH_3$ | H | H | —$CH_3$ |
| 145 | —$CH_2$—HC═$CH_2$ | —$CH_2$—HC═$CH_2$ | H | H | —$OCH_3$ | H | H | —$CH_3$ |
| 146 | —$CH_3$ | —$CH_2CH_3$ | H | H | —OH | H | H | —$CH_3$ |
| 147 | —$CH_3$ | —$(CH_2)_2CH_3$ | H | H | —OH | H | H | —$CH_3$ |
| 148 | —$CH_3$ | —$CH(CH_3)_2$ | H | H | —OH | H | H | —$CH_3$ |
| 149 | —$CH_3$ | —$(CH_2)_3CH_3$ | H | H | —OH | H | H | —$CH_3$ |
| 150 | —$CH_3$ | —$CH_2$—HC═$CH_2$ | H | H | —OH | H | H | —$CH_3$ |
| 151 | —$CH_2CH_3$ | —$CH_2CH_3$ | H | H | —OH | H | H | —$CH_3$ |
| 152 | —$CH_2CH_3$ | —$(CH_2)_2CH_3$ | H | H | —OH | H | H | —$CH_3$ |
| 153 | —$CH_2CH_3$ | —$CH(CH_3)_2$ | H | H | —OH | H | H | —$CH_3$ |
| 154 | —$CH_2CH_3$ | —$(CH_2)_3CH_3$ | H | H | —OH | H | H | —$CH_3$ |
| 155 | —$CH_2CH_3$ | —$CH_2$—HC═$CH_2$ | H | H | —OH | H | H | —$CH_3$ |
| 156 | —$(CH_2)_2CH_3$ | —$(CH_2)_2CH_3$ | H | H | —OH | H | H | —$CH_3$ |
| 157 | —$(CH_2)_2CH_3$ | —$CH(CH_3)_2$ | H | H | —OH | H | H | —$CH_3$ |
| 158 | —$(CH_2)_2CH_3$ | —$(CH_2)_3CH_3$ | H | H | —OH | H | H | —$CH_3$ |
| 159 | —$(CH_2)_2CH_3$ | —$CH_2$—HC═$CH_2$ | H | H | —OH | H | H | —$CH_3$ |
| 160 | —$CH(CH_3)_2$ | —$CH(CH_3)_2$ | H | H | —OH | H | H | —$CH_3$ |
| 161 | —$CH(CH_3)_2$ | —$(CH_2)_3CH_3$ | H | H | —OH | H | H | —$CH_3$ |
| 162 | —$CH(CH_3)_2$ | —$CH_2$—HC═$CH_2$ | H | H | —OH | H | H | —$CH_3$ |
| 163 | —$(CH_2)_3CH_3$ | —$(CH_2)_3CH_3$ | H | H | —OH | H | H | —$CH_3$ |
| 164 | —$(CH_2)_3CH_3$ | —$CH_2$—HC═$CH_2$ | H | H | —OH | H | H | —$CH_3$ |
| 165 | —$CH_2$—HC═$CH_2$ | —$CH_2$—HC═$CH_2$ | H | H | —OH | H | H | —$CH_3$ |
| 166 | —$CH_3$ | —$CH_3$ | H | H | —OC(O)$CH_3$ | H | H | —$CH_3$ |
| 167 | —$CH_3$ | —$CH_2CH_3$ | H | H | —OC(O)$CH_3$ | H | H | —$CH_3$ |
| 168 | —$CH_3$ | —$(CH_2)_2CH_3$ | H | H | —OC(O)$CH_3$ | H | H | —$CH_3$ |
| 169 | —$CH_3$ | —$CH(CH_3)_2$ | H | H | —OC(O)$CH_3$ | H | H | —$CH_3$ |
| 170 | —$CH_3$ | —$(CH_2)_3CH_3$ | H | H | —OC(O)$CH_3$ | H | H | —$CH_3$ |
| 171 | —$CH_3$ | —$CH_2$—HC═$CH_2$ | H | H | —OC(O)$CH_3$ | H | H | —$CH_3$ |
| 172 | —$CH_2CH_3$ | —$CH_2CH_3$ | H | H | —OC(O)$CH_3$ | H | H | —$CH_3$ |
| 173 | —$CH_2CH_3$ | —$(CH_2)_2CH_3$ | H | H | —OC(O)$CH_3$ | H | H | —$CH_3$ |
| 174 | —$CH_2CH_3$ | —$CH(CH_3)_2$ | H | H | —OC(O)$CH_3$ | H | H | —$CH_3$ |
| 175 | —$CH_2CH_3$ | —$(CH_2)_3CH_3$ | H | H | —OC(O)$CH_3$ | H | H | —$CH_3$ |
| 176 | —$CH_2CH_3$ | —$CH_2$—HC═$CH_2$ | H | H | —OC(O)$CH_3$ | H | H | —$CH_3$ |
| 177 | —$(CH_2)_2CH_3$ | —$(CH_2)_2CH_3$ | H | H | —OC(O)$CH_3$ | H | H | —$CH_3$ |
| 178 | —$(CH_2)_2CH_3$ | —$CH(CH_3)_2$ | H | H | —OC(O)$CH_3$ | H | H | —$CH_3$ |
| 179 | —$(CH_2)_2CH_3$ | —$(CH_2)_3CH_3$ | H | H | —OC(O)$CH_3$ | H | H | —$CH_3$ |
| 180 | —$(CH_2)_2CH_3$ | —$CH_2$—HC═$CH_2$ | H | H | —OC(O)$CH_3$ | H | H | —$CH_3$ |
| 181 | —$CH(CH_3)_2$ | —$CH(CH_3)_2$ | H | H | —OC(O)$CH_3$ | H | H | —$CH_3$ |
| 182 | —$CH(CH_3)_2$ | —$(CH_2)_3CH_3$ | H | H | —OC(O)$CH_3$ | H | H | —$CH_3$ |
| 183 | —$CH(CH_3)_2$ | —$CH_2$—HC═$CH_2$ | H | H | —OC(O)$CH_3$ | H | H | —$CH_3$ |
| 184 | —$(CH_2)_3CH_3$ | —$(CH_2)_3CH_3$ | H | H | —OC(O)$CH_3$ | H | H | —$CH_3$ |
| 185 | —$(CH_2)_3CH_3$ | —$CH_2$—HC═$CH_2$ | H | H | —OC(O)$CH_3$ | H | H | —$CH_3$ |
| 186 | —$CH_2$—HC═$CH_2$ | —$CH_2$—HC═$CH_2$ | H | H | —OC(O)$CH_3$ | H | H | —$CH_3$ |
| 187 | —$CH_3$ | —$CH_3$ | H | H | H | —$OCH_3$ | H | —$CH_3$ |
| 188 | —$CH_3$ | —$CH_2CH_3$ | H | H | H | —$OCH_3$ | H | —$CH_3$ |
| 189 | —$CH_3$ | —$(CH_2)_2CH_3$ | H | H | H | —$OCH_3$ | H | —$CH_3$ |
| 190 | —$CH_3$ | —$CH(CH_3)_2$ | H | H | H | —$OCH_3$ | H | —$CH_3$ |
| 191 | —$CH_3$ | —$(CH_2)_3CH_3$ | H | H | H | —$OCH_3$ | H | —$CH_3$ |
| 192 | —$CH_3$ | —$CH_2$—HC═$CH_2$ | H | H | H | —$OCH_3$ | H | —$CH_3$ |
| 193 | —$CH_2CH_3$ | —$CH_2CH_3$ | H | H | H | —$OCH_3$ | H | —$CH_3$ |
| 194 | —$CH_2CH_3$ | —$(CH_2)_2CH_3$ | H | H | H | —$OCH_3$ | H | —$CH_3$ |
| 195 | —$CH_2CH_3$ | —$CH(CH_3)_2$ | H | H | H | —$OCH_3$ | H | —$CH_3$ |
| 196 | —$CH_2CH_3$ | —$(CH_2)_3CH_3$ | H | H | H | —$OCH_3$ | H | —$CH_3$ |
| 197 | —$CH_2CH_3$ | —$CH_2$—HC═$CH_2$ | H | H | H | —$OCH_3$ | H | —$CH_3$ |
| 198 | —$(CH_2)_2CH_3$ | —$(CH_2)_2CH_3$ | H | H | H | —$OCH_3$ | H | —$CH_3$ |
| 199 | —$(CH_2)_2CH_3$ | —$CH(CH_3)_2$ | H | H | H | —$OCH_3$ | H | —$CH_3$ |
| 200 | —$(CH_2)_2CH_3$ | —$(CH_2)_3CH_3$ | H | H | H | —$OCH_3$ | H | —$CH_3$ |
| 201 | —$(CH_2)_2CH_3$ | —$CH_2$—HC═$CH_2$ | H | H | H | —$OCH_3$ | H | —$CH_3$ |
| 202 | —$CH(CH_3)_2$ | —$CH(CH_3)_2$ | H | H | H | —$OCH_3$ | H | —$CH_3$ |
| 203 | —$CH(CH_3)_2$ | —$(CH_2)_3CH_3$ | H | H | H | —$OCH_3$ | H | —$CH_3$ |
| 204 | —$CH(CH_3)_2$ | —$CH_2$—HC═$CH_2$ | H | H | H | —$OCH_3$ | H | —$CH_3$ |
| 205 | —$(CH_2)_3CH_3$ | —$(CH_2)_3CH_3$ | H | H | H | —$OCH_3$ | H | —$CH_3$ |
| 206 | —$(CH_2)_3CH_3$ | —$CH_2$—HC═$CH_2$ | H | H | H | —$OCH_3$ | H | —$CH_3$ |
| 207 | —$CH_2$—HC═$CH_2$ | —$CH_2$—HC═$CH_2$ | H | H | H | —$OCH_3$ | H | —$CH_3$ |
| 208 | —$CH_3$ | —$CH_2CH_3$ | H | H | H | —OH | H | —$CH_3$ |
| 209 | —$CH_3$ | —$(CH_2)_2CH_3$ | H | H | H | —OH | H | —$CH_3$ |
| 210 | —$CH_3$ | —$CH(CH_3)_2$ | H | H | H | —OH | H | —$CH_3$ |
| 211 | —$CH_3$ | —$(CH_2)_3CH_3$ | H | H | H | —OH | H | —$CH_3$ |
| 212 | —$CH_3$ | —$CH_2$—HC═$CH_2$ | H | H | H | —OH | H | —$CH_3$ |

TABLE 2-continued

| Ref. | X | Y | $R_2$ | $R_3$ | $R_4$ | $R_5$ | $R_6$ | $R_7$ |
|---|---|---|---|---|---|---|---|---|
| 213 | $-CH_2CH_3$ | $-CH_2CH_3$ | H | H | H | $-OH$ | H | $-CH_3$ |
| 214 | $-CH_2CH_3$ | $-(CH_2)_2CH_3$ | H | H | H | $-OH$ | H | $-CH_3$ |
| 215 | $-CH_2CH_3$ | $-CH(CH_3)_2$ | H | H | H | $-OH$ | H | $-CH_3$ |
| 216 | $-CH_2CH_3$ | $-(CH_2)_3CH_3$ | H | H | H | $-OH$ | H | $-CH_3$ |
| 217 | $-CH_2CH_3$ | $-CH_2-HC{=}CH_2$ | H | H | H | $-OH$ | H | $-CH_3$ |
| 218 | $-(CH_2)_2CH_3$ | $-(CH_2)_2CH_3$ | H | H | H | $-OH$ | H | $-CH_3$ |
| 219 | $-(CH_2)_2CH_3$ | $-CH(CH_3)_2$ | H | H | H | $-OH$ | H | $-CH_3$ |
| 220 | $-(CH_2)_2CH_3$ | $-(CH_2)_3CH_3$ | H | H | H | $-OH$ | H | $-CH_3$ |
| 221 | $-(CH_2)_2CH_3$ | $-CH_2-HC{=}CH_2$ | H | H | H | $-OH$ | H | $-CH_3$ |
| 222 | $-CH(CH_3)_2$ | $-CH(CH_3)_2$ | H | H | H | $-OH$ | H | $-CH_3$ |
| 223 | $-CH(CH_3)_2$ | $-(CH_2)_3CH_3$ | H | H | H | $-OH$ | H | $-CH_3$ |
| 224 | $-CH(CH_3)_2$ | $-CH_2-HC{=}CH_2$ | H | H | H | $-OH$ | H | $-CH_3$ |
| 225 | $-(CH_2)_3CH_3$ | $-(CH_2)_3CH_3$ | H | H | H | $-OH$ | H | $-CH_3$ |
| 226 | $-(CH_2)_3CH_3$ | $-CH_2-HC{=}CH_2$ | H | H | H | $-OH$ | H | $-CH_3$ |
| 227 | $-CH_2-HC{=}CH_2$ | $-CH_2-HC{=}CH_2$ | H | H | H | $-OH$ | H | $-CH_3$ |
| 228 | $-CH_3$ | $-CH_3$ | H | H | H | $-OC(O)CH_3$ | H | $-CH_3$ |
| 229 | $-CH_3$ | $-CH_2CH_3$ | H | H | H | $-OC(O)CH_3$ | H | $-CH_3$ |
| 230 | $-CH_3$ | $-(CH_2)_2CH_3$ | H | H | H | $-OC(O)CH_3$ | H | $-CH_3$ |
| 231 | $-CH_3$ | $-CH(CH_3)_2$ | H | H | H | $-OC(O)CH_3$ | H | $-CH_3$ |
| 232 | $-CH_3$ | $-(CH_2)_3CH_3$ | H | H | H | $-OC(O)CH_3$ | H | $-CH_3$ |
| 233 | $-CH_3$ | $-CH_2-HC{=}CH_2$ | H | H | H | $-OC(O)CH_3$ | H | $-CH_3$ |
| 234 | $-CH_2CH_3$ | $-CH_2CH_3$ | H | H | H | $-OC(O)CH_3$ | H | $-CH_3$ |
| 235 | $-CH_2CH_3$ | $-(CH_2)_2CH_3$ | H | H | H | $-OC(O)CH_3$ | H | $-CH_3$ |
| 236 | $-CH_2CH_3$ | $-CH(CH_3)_2$ | H | H | H | $-OC(O)CH_3$ | H | $-CH_3$ |
| 237 | $-CH_2CH_3$ | $-(CH_2)_3CH_3$ | H | H | H | $-OC(O)CH_3$ | H | $-CH_3$ |
| 238 | $-CH_2CH_3$ | $-CH_2-HC{=}CH_2$ | H | H | H | $-OC(O)CH_3$ | H | $-CH_3$ |
| 239 | $-(CH_2)_2CH_3$ | $-(CH_2)_2CH_3$ | H | H | H | $-OC(O)CH_3$ | H | $-CH_3$ |
| 240 | $-(CH_2)_2CH_3$ | $-CH(CH_3)_2$ | H | H | H | $-OC(O)CH_3$ | H | $-CH_3$ |
| 241 | $-(CH_2)_2CH_3$ | $-(CH_2)_3CH_3$ | H | H | H | $-OC(O)CH_3$ | H | $-CH_3$ |
| 242 | $-(CH_2)_2CH_3$ | $-CH_2-HC{=}CH_2$ | H | H | H | $-OC(O)CH_3$ | H | $-CH_3$ |
| 243 | $-CH(CH_3)_2$ | $-CH(CH_3)_2$ | H | H | H | $-OC(O)CH_3$ | H | $-CH_3$ |
| 244 | $-CH(CH_3)_2$ | $-(CH_2)_3CH_3$ | H | H | H | $-OC(O)CH_3$ | H | $-CH_3$ |
| 245 | $-CH(CH_3)_2$ | $-CH_2-HC{=}CH_2$ | H | H | H | $-OC(O)CH_3$ | H | $-CH_3$ |
| 246 | $-(CH_2)_3CH_3$ | $-(CH_2)_3CH_3$ | H | H | H | $-OC(O)CH_3$ | H | $-CH_3$ |
| 247 | $-(CH_2)_3CH_3$ | $-CH_2-HC{=}CH_2$ | H | H | H | $-OC(O)CH_3$ | H | $-CH_3$ |
| 248 | $-CH_2-HC{=}CH_2$ | $-CH_2-HC{=}CH_2$ | H | H | H | $OC(O)CH_3$ | H | $-CH_3$ |
| 249 | $-CH_3$ | $-CH_3$ | $-CH_3$ | H | H | H | H | H |
| 250 | $-CH_3$ | $-CH_3$ | $-CH_3$ | H | $-OH$ | H | H | H |
| 251 | $-CH_3$ | $-CH_3$ | $-CH_3$ | H | $-OC(O)CH_3$ | H | H | H |
| 252 | $-CH_3$ | $-CH_3$ | $-CH_3$ | H | $-OCH_3$ | H | H | H |
| 253 | $-CH_3$ | $-CH_2CH_3$ | $-CH_3$ | H | H | H | H | H |
| 254 | $-CH_3$ | $-CH_2(CH_3)_2$ | $-CH_3$ | H | H | H | H | H |
| 255 | $-CH_3$ | $-CH_3$ | $-CH_3$ | H | F | H | H | H |
| 256 | $-CH_3$ | $-CH_3$ | H | $-CH_3$ | H | H | H | H |
| 257 | $-CH_3$ | $-CH_3$ | H | $-CH_3$ | $-OH$ | H | H | H |
| 258 | $-CH_3$ | $-CH_3$ | H | $-CH_3$ | $-OC(O)CH_3$ | H | H | H |
| 259 | $-CH_3$ | $-CH_3$ | H | $-CH_3$ | $-OCH_3$ | H | H | H |
| 260 | $-CH_3$ | $-CH_2CH_3$ | H | $-CH_3$ | H | H | H | H |
| 261 | $-CH_3$ | $-CH_2(CH_3)_2$ | H | $-CH_3$ | H | H | H | H |
| 262 | $-CH_3$ | $-CH_3$ | H | $-CH_3$ | F | H | H | H |
| 263 | $-CH_3$ | $-CH_3$ | H | H | H | H | F | H |
| 264 | $-CH_3$ | $-CH_3$ | H | H | $-OH$ | H | F | H |
| 265 | $-CH_3$ | $-CH_3$ | H | H | $-OC(O)CH_3$ | H | F | H |
| 266 | $-CH_3$ | $-CH_3$ | H | H | $-OCH_3$ | H | F | H |
| 267 | $-CH_3$ | $-CH_2CH_3$ | H | H | H | H | F | H |
| 268 | $-CH_3$ | $-CH_2(CH_3)_2$ | H | H | H | H | F | H |
| 269 | $-CH_3$ | $-CH_3$ | H | H | F | H | F | H |
| 270 | $-CH_3$ | $-CH_3$ | H | H | H | H | H | $-CH_3$ |
| 271 | $-CH_3$ | $-CH_3$ | H | H | $-OH$ | H | H | $-CH_3$ |
| 272 | $-CH_3$ | $-CH_3$ | H | H | $-OC(O)CH_3$ | H | H | $-CH_3$ |
| 273 | $-CH_3$ | $-CH_3$ | H | H | $-OCH_3$ | H | H | $-CH_3$ |
| 274 | $-CH_3$ | $-CH_2CH_3$ | H | H | H | H | H | $-CH_3$ |
| 275 | $-CH_3$ | $-CH_2(CH_3)_2$ | H | H | H | H | H | $-CH_3$ |
| 276 | $-CH_3$ | $-CH_3$ | H | H | F | H | H | $-CH_3$ |
| 277 | $-CH_3$ | $-CH_3$ | $-CH_3$ | H | H | $-OH$ | H | H |
| 278 | $-CH_3$ | $-CH_3$ | $-CH_3$ | H | H | $-OC(O)CH_3$ | H | H |
| 279 | $-CH_3$ | $-CH_3$ | $-CH_3$ | H | H | $-OCH_3$ | H | H |
| 280 | $-CH_3$ | $-CH_2CH_3$ | $-CH_3$ | H | H | H | H | H |
| 281 | $-CH_3$ | $-CH_2(CH_3)_2$ | $-CH_3$ | H | H | H | H | H |
| 282 | $-CH_3$ | $-CH_3$ | $-CH_3$ | H | H | F | H | H |
| 283 | $-CH_3$ | $-CH_3$ | H | $-CH_3$ | H | H | H | H |
| 284 | $-CH_3$ | $-CH_3$ | H | $-CH_3$ | H | $-OH$ | H | H |
| 285 | $-CH_3$ | $-CH_3$ | H | $-CH_3$ | H | $-OC(O)CH_3$ | H | H |
| 286 | $-CH_3$ | $-CH_3$ | H | $-CH_3$ | H | $-OCH_3$ | H | H |
| 287 | $-CH_3$ | $-CH_2CH_3$ | H | $-CH_3$ | H | H | H | H |
| 288 | $-CH_3$ | $-CH_2(CH_3)_2$ | H | $-CH_3$ | H | H | H | H |
| 289 | $-CH_3$ | $-CH_3$ | H | $-CH_3$ | H | F | H | H |
| 290 | $-CH_3$ | $-CH_3$ | H | H | H | H | F | H |

TABLE 2-continued

| Ref. | X | Y | $R_2$ | $R_3$ | $R_4$ | $R_5$ | $R_6$ | $R_7$ |
|---|---|---|---|---|---|---|---|---|
| 291 | $—CH_3$ | $—CH_3$ | H | H | H | —OH | F | H |
| 292 | $—CH_3$ | $—CH_3$ | H | H | H | $—OC(O)CH_3$ | F | H |
| 293 | $—CH_3$ | $—CH_3$ | H | H | H | $—OCH_3$ | F | H |
| 294 | $—CH_3$ | $—CH_2CH_3$ | H | H | H | H | F | H |
| 295 | $—CH_3$ | $—CH_2(CH_3)_2$ | H | H | H | H | F | H |
| 296 | $—CH_3$ | $—CH_3$ | H | H | H | F | F | H |
| 297 | $—CH_3$ | $—CH_3$ | H | H | H | H | H | $—CH_3$ |
| 298 | $—CH_3$ | $—CH_3$ | H | H | H | —OH | H | $—CH_3$ |
| 299 | $—CH_3$ | $—CH_3$ | H | H | H | $—OC(O)CH_3$ | H | $—CH_3$ |
| 300 | $—CH_3$ | $—CH_3$ | H | H | H | $—OCH_3$ | H | $—CH_3$ |
| 301 | $—CH_3$ | $—CH_2CH_3$ | H | H | H | H | H | $—CH_3$ |
| 302 | $—CH_3$ | $—CH_2(CH_3)_2$ | H | H | H | H | H | $—CH_3$ |
| 303 | $—CH_3$ | $—CH_3$ | H | H | H | H | F | $—CH_3$ |
| 304 | H | $—CH_3$ | H | H | H | H | H | H |
| 305 | H | $—CH_2CH_3$ | H | H | H | H | H | H |
| 306 | H | $—(CH_2)_2CH_3$ | H | H | H | H | H | H |
| 307 | H | $—CH(CH_3)_2$ | H | H | H | H | H | H |
| 308 | H | $—(CH_2)_3CH_3$ | H | H | H | H | H | H |
| 309 | H | $—CH_2—HC{=}CH_2$ | H | H | H | H | H | H |
| 310 | H | $—CH_3$ | H | $—CH_3$ | H | H | H | H |
| 310a | H | $—CH_2CH_3$ | H | $—CH_3$ | H | H | H | H |
| 311 | H | $—(CH_2)_2CH_3$ | H | $—CH_3$ | H | H | H | H |
| 312 | H | $—CH(CH_3)_2$ | H | $—CH_3$ | H | H | H | H |
| 313 | H | $—(CH_2)_3CH_3$ | H | $—CH_3$ | H | H | H | H |
| 314 | H | $—CH_2—HC{=}CH_2$ | H | $—CH_3$ | H | H | H | H |
| 315 | H | $—CH_3$ | H | H | —OH | H | H | H |
| 316 | H | $—CH_2CH_3$ | H | H | —OH | H | H | H |
| 317 | H | $—(CH_2)_2CH_3$ | H | H | —OH | H | H | H |
| 318 | H | $—CH(CH_3)_2$ | H | H | —OH | H | H | H |
| 319 | H | $—(CH_2)_3CH_3$ | H | H | —OH | H | H | H |
| 320 | H | $—CH_2—HC{=}CH_2$ | H | H | —OH | H | H | H |
| 321 | H | $—CH_3$ | H | H | $—OC(O)CH_3$ | H | H | H |
| 322 | H | $—CH_2CH_3$ | H | H | $—OC(O)CH_3$ | H | H | H |
| 324 | H | $—(CH_2)_2CH_3$ | H | H | $—OC(O)CH_3$ | H | H | H |
| 325 | H | $—CH(CH_3)_2$ | H | H | $—OC(O)CH_3$ | H | H | H |
| 326 | H | $—(CH_2)_3CH_3$ | H | H | $—OC(O)CH_3$ | H | H | H |
| 327 | H | $—CH_2—HC{=}CH_2$ | H | H | $—OC(O)CH_3$ | H | H | H |
| 328 | H | $—CH_3$ | H | H | H | $—OCH_3$ | H | H |
| 329 | H | $—CH_2CH_3$ | H | H | H | $—OCH_3$ | H | H |
| 330 | H | $—(CH_2)_2CH_3$ | H | H | H | $—OCH_3$ | H | H |
| 331 | H | $—CH(CH_3)_2$ | H | H | H | $—OCH_3$ | H | H |
| 332 | H | $—(CH_2)_3CH_3$ | H | H | H | $—OCH_3$ | H | H |
| 333 | H | $—CH_2—HC{=}CH_2$ | H | H | H | $—OCH_3$ | H | H |
| 334 | H | $—CH_3$ | H | H | H | H | F | H |
| 335 | H | $—CH_2CH_3$ | H | H | H | H | F | H |
| 336 | H | $—(CH_2)_2CH_3$ | H | H | H | H | F | H |
| 337 | H | $—CH(CH_3)_2$ | H | H | H | H | F | H |
| 338 | H | $—(CH_2)_3CH_3$ | H | H | H | H | F | H |
| 339 | H | $—CH_2—HC{=}CH_2$ | H | H | H | H | F | H |
| 340 | H | $—CH_3$ | H | $—CH_3$ | —OH | H | H | H |
| 341 | H | $—CH_2CH_3$ | H | $—CH_3$ | —OH | H | H | H |
| 342 | H | $—(CH_2)_2CH_3$ | H | $—CH_3$ | —OH | H | H | H |
| 343 | H | $—CH(CH_3)_2$ | H | $—CH_3$ | —OH | H | H | H |
| 344 | H | $—(CH_2)_3CH_3$ | H | $—CH_3$ | —OH | H | H | H |
| 345 | H | $—CH_2—HC{=}CH_2$ | H | $—CH_3$ | —OH | H | H | H |
| 346 | H | $—CH_3$ | H | $—CH_3$ | $—OC(O)CH_3$ | H | H | H |
| 347 | H | $—CH_2CH_3$ | H | $—CH_3$ | $—OC(O)CH_3$ | H | H | H |
| 348 | H | $—(CH_2)_2CH_3$ | H | $—CH_3$ | $—OC(O)CH_3$ | H | H | H |
| 349 | H | $—CH(CH_3)_2$ | H | $—CH_3$ | $—OC(O)CH_3$ | H | H | H |
| 350 | H | $—(CH_2)_3CH_3$ | H | $—CH_3$ | $—OC(O)CH_3$ | H | H | H |
| 351 | H | $—CH_2—HC{=}CH_2$ | H | $—CH_3$ | $—OC(O)CH_3$ | H | H | H |
| 352 | H | $—CH_3$ | H | $—CH_3$ | H | $—OCH_3$ | H | H |
| 353 | H | $—CH_2CH_3$ | H | $—CH_3$ | H | $—OCH_3$ | H | H |
| 354 | H | $—(CH_2)_2CH_3$ | H | $—CH_3$ | H | $—OCH_3$ | H | H |
| 355 | H | $—CH(CH_3)_2$ | H | $—CH_3$ | H | $—OCH_3$ | H | H |
| 356 | H | $—(CH_2)_3CH_3$ | H | $—CH_3$ | H | $—OCH_3$ | H | H |
| 357 | H | $—CH_2—HC{=}CH_2$ | H | $—CH_3$ | H | $—OCH_3$ | H | H |
| 358 | H | $—CH_3$ | H | $—CH_3$ | H | H | F | H |
| 359 | H | $—CH_2CH_3$ | H | $—CH_3$ | H | H | F | H |
| 360 | H | $—(CH_2)_2CH_3$ | H | $—CH_3$ | H | H | F | H |
| 361 | H | $—CH(CH_3)_2$ | H | $—CH_3$ | H | H | F | H |
| 362 | H | $—(CH_2)_3CH_3$ | H | $—CH_3$ | H | H | F | H |
| 363 | H | $—CH_2—HC{=}CH_2$ | H | $—CH_3$ | H | H | F | H |
| 364 | H | cyclopropyl | H | H | H | H | H | H |
| 365 | H | cyclopropyl | H | $—CH_3$ | H | H | H | H |
| 366 | H | cyclopropyl | H | H | —OH | H | H | H |
| 367 | H | cyclopropyl | H | H | $—OC(O)CH_3$ | H | H | H |
| 368 | H | cyclopropyl | H | H | H | $—OCH_3$ | H | H |

TABLE 2-continued

| Ref. | X | Y | $R_2$ | $R_3$ | $R_4$ | $R_5$ | $R_6$ | $R_7$ |
|---|---|---|---|---|---|---|---|---|
| 369 | H | cyclopropyl | H | H | H | H | F | H |
| 370 | H | cyclopropyl | H | H | H | H | H | H |
| 371 | H | cyclopropyl | H | $—CH_3$ | —OH | H | F | H |
| 372 | H | cyclopropyl | H | $—CH_3$ | —OH | H | H | H |
| 373 | H | cyclopropyl | H | $—CH_3$ | $—OC(O)CH_3$ | H | H | H |
| 374 | H | cyclopropyl | H | $—CH_3$ | H | $—OCH_3$ | H | H |
| 375 | H | cyclopropyl | H | $—CH_3$ | H | H | F | H |
| 376 | $—CH_3$ | cyclopropyl | H | H | H | H | H | H |
| 377 | $—CH_3$ | cyclopropyl | H | $—CH_3$ | H | H | H | H |
| 378 | $—CH_3$ | cyclopropyl | H | H | —OH | H | H | H |
| 379 | $—CH_3$ | cyclopropyl | H | H | $—OC(O)CH_3$ | H | H | H |
| 380 | $—CH_3$ | cyclopropyl | H | H | H | $—OCH_3$ | H | H |
| 381 | $—CH_3$ | cyclopropyl | H | H | H | H | F | H |
| 382 | $—CH_3$ | cyclopropyl | H | H | H | H | H | H |
| 383 | $—CH_3$ | cyclopropyl | H | $—CH_3$ | —OH | H | F | H |
| 384 | $—CH_3$ | cyclopropyl | H | $—CH_3$ | —OH | H | H | H |
| 385 | $—CH_3$ | cyclopropyl | H | $—CH_3$ | $—OC(O)CH_3$ | H | H | H |
| 386 | $—CH_3$ | cyclopropyl | H | $—CH_3$ | H | $—OCH_3$ | H | H |
| 387 | $—CH_3$ | cyclopropyl | H | $—CH_3$ | H | H | F | H |
| 388 | $—CH_2CH_3$ | cyclopropyl | H | H | H | H | H | H |
| 389 | $—CH_2CH_3$ | cyclopropyl | H | $—CH_3$ | H | H | H | H |
| 390 | $—CH_2CH_3$ | cyclopropyl | H | H | —OH | H | H | H |
| 391 | $—CH_2CH_3$ | cyclopropyl | H | H | $—OC(O)CH_3$ | H | H | H |
| 392 | $—CH_2CH_3$ | cyclopropyl | H | H | H | $—OCH_3$ | H | H |
| 393 | $—CH_2CH_3$ | cyclopropyl | H | H | H | H | F | H |
| 394 | $—CH_2CH_3$ | cyclopropyl | H | H | H | H | H | H |
| 395 | $—CH_2CH_3$ | cyclopropyl | H | $—CH_3$ | —OH | H | F | H |
| 396 | $—CH_2CH_3$ | cyclopropyl | H | $—CH_3$ | —OH | H | H | H |
| 397 | $—CH_2CH_3$ | cyclopropyl | H | $—CH_3$ | $—OC(O)CH_3$ | H | H | H |
| 398 | $—CH_2CH_3$ | cyclopropyl | H | $—CH_3$ | H | $—OCH_3$ | H | H |
| 399 | $—CH_2CH_3$ | cyclopropyl | H | $—CH_3$ | H | H | F | H |
| 400 | $—(CH_2)_2CH_3$ | cyclopropyl | H | H | H | H | H | H |
| 401 | $—(CH_2)_2CH_3$ | cyclopropyl | H | $—CH_3$ | H | H | H | H |
| 402 | $—(CH_2)_2CH_3$ | cyclopropyl | H | H | —OH | H | H | H |
| 403 | $—(CH_2)_2CH_3$ | cyclopropyl | H | H | $—OC(O)CH_3$ | H | H | H |
| 404 | $—(CH_2)_2CH_3$ | cyclopropyl | H | H | H | $—OCH_3$ | H | H |
| 405 | $—(CH_2)_2CH_3$ | cyclopropyl | H | H | H | H | F | H |
| 406 | $—(CH_2)_2CH_3$ | cyclopropyl | H | H | H | H | H | H |
| 407 | $—(CH_2)_2CH_3$ | cyclopropyl | H | $—CH_3$ | —OH | H | F | H |
| 408 | $—(CH_2)_2CH_3$ | cyclopropyl | H | $—CH_3$ | —OH | H | H | H |
| 409 | $—(CH_2)_2CH_3$ | cyclopropyl | H | $—CH_3$ | $—OC(O)CH_3$ | H | H | H |
| 410 | $—(CH_2)_2CH_3$ | cyclopropyl | H | $—CH_3$ | H | $—OCH_3$ | H | H |
| 411 | $—(CH_2)_2CH_3$ | cyclopropyl | H | $—CH_3$ | H | H | F | H |
| 412 | $—CH_2(CH_3)_2$ | cyclopropyl | H | H | H | H | H | H |
| 413 | $—CH_2(CH_3)_2$ | cyclopropyl | H | $—CH_3$ | H | H | H | H |
| 414 | $—CH_2(CH_3)_2$ | cyclopropyl | H | H | —OH | H | H | H |
| 415 | $—CH_2(CH_3)_2$ | cyclopropyl | H | H | $—OC(O)CH_3$ | H | H | H |
| 416 | $—CH_2(CH_3)_2$ | cyclopropyl | H | H | H | $—OCH_3$ | H | H |
| 417 | $—CH_2(CH_3)_2$ | cyclopropyl | H | H | H | H | F | H |
| 418 | $—CH_2(CH_3)_2$ | cyclopropyl | H | H | H | H | H | H |
| 419 | $—CH_2(CH_3)_2$ | cyclopropyl | H | $—CH_3$ | —OH | H | F | H |
| 420 | $—CH_2(CH_3)_2$ | cyclopropyl | H | $—CH_3$ | —OH | H | H | H |
| 421 | $—CH_2(CH_3)_2$ | cyclopropyl | H | $—CH_3$ | $—OC(O)CH_3$ | H | H | H |
| 422 | $—CH_2(CH_3)_2$ | cyclopropyl | H | $—CH_3$ | H | $—OCH_3$ | H | H |
| 423 | $—CH_2(CH_3)_2$ | cyclopropyl | H | $—CH_3$ | H | H | F | H |
| 424 | cyclopropyl | cyclopropyl | H | $—CH_3$ | H | H | H | H |
| 425 | cyclopropyl | cyclopropyl | H | H | —OH | H | H | H |
| 426 | cyclopropyl | cyclopropyl | H | H | $—OC(O)CH_3$ | H | H | H |
| 427 | cyclopropyl | cyclopropyl | H | H | H | $—OCH_3$ | H | H |
| 428 | cyclopropyl | cyclopropyl | H | H | H | H | F | H |
| 429 | cyclopropyl | cyclopropyl | H | H | H | H | H | H |
| 430 | cyclopropyl | cyclopropyl | H | $—CH_3$ | —OH | H | F | H |
| 431 | cyclopropyl | cyclopropyl | H | $—CH_3$ | —OH | H | H | H |
| 432 | cyclopropyl | cyclopropyl | H | $—CH_3$ | $—OC(O)CH_3$ | H | H | H |
| 433 | cyclopropyl | cyclopropyl | H | $—CH_3$ | H | $—OCH_3$ | H | H |
| 434 | cyclopropyl | cyclopropyl | H | $—CH_3$ | H | H | F | H |
| 435 | H | $—CH_3$ | H | H | —OH | H | H | $—CH_3$ |
| 436 | H | $—CH_2CH_3$ | H | H | —OH | H | H | $—CH_3$ |
| 437 | H | $—(CH_2)_2CH_3$ | H | H | —OH | H | H | $—CH_3$ |
| 438 | H | $—CH(CH_3)_2$ | H | H | —OH | H | H | $—CH_3$ |
| 439 | H | $—(CH_2)_3CH_3$ | H | H | —OH | H | H | $—CH_3$ |
| 440 | H | $—CH_2—HC{=}CH_2$ | H | H | —OH | H | H | $—CH_3$ |
| 441 | H | $—CH_3$ | H | H | $—OC(O)CH_3$ | H | H | $—CH_3$ |
| 442 | H | $—CH_2CH_3$ | H | H | $—OC(O)CH_3$ | H | H | $—CH_3$ |
| 443 | H | $—(CH_2)_2CH_3$ | H | H | $—OC(O)CH_3$ | H | H | $—CH_3$ |
| 444 | H | $—CH(CH_3)_2$ | H | H | $—OC(O)CH_3$ | H | H | $—CH_3$ |
| 445 | H | $—(CH_2)_3CH_3$ | H | H | $—OC(O)CH_3$ | H | H | $—CH_3$ |
| 446 | H | $—CH_2—HC{=}CH_2$ | H | H | $—OC(O)CH_3$ | H | H | $—CH_3$ |

TABLE 2-continued

| Ref. | X | Y | $R_2$ | $R_3$ | $R_4$ | $R_5$ | $R_6$ | $R_7$ |
|---|---|---|---|---|---|---|---|---|
| 447 | H | $—CH_3$ | H | H | H | $—OCH_3$ | H | $—CH_3$ |
| 448 | H | $—CH_2CH_3$ | H | H | H | $—OCH_3$ | H | $—CH_3$ |
| 449 | H | $—(CH_2)_2CH_3$ | H | H | H | $—OCH_3$ | H | $—CH_3$ |
| 450 | H | $—CH(CH_3)_2$ | H | H | H | $—OCH_3$ | H | $—CH_3$ |
| 451 | H | $—(CH_2)_3CH_3$ | H | H | H | $—OCH_3$ | H | $—CH_3$ |
| 452 | H | $—CH_2—HC{=}CH_2$ | H | H | H | $—OCH_3$ | H | $—CH_3$ |
| 453 | H | $—CH_3$ | H | H | —OH | H | F | H |
| 454 | H | $—CH_2CH_3$ | H | H | —OH | H | F | H |
| 455 | H | $—(CH_2)_2CH_3$ | H | H | —OH | H | F | H |
| 456 | H | $—CH(CH_3)_2$ | H | H | —OH | H | F | H |
| 457 | H | $—(CH_2)_3CH_3$ | H | H | —OH | H | F | H |
| 458 | H | $—CH_2—HC{=}CH_2$ | H | H | —OH | H | F | H |
| 459 | H | $—CH_3$ | H | H | $—OC(O)CH_3$ | H | F | H |
| 460 | H | $—CH_2CH_3$ | H | H | $—OC(O)CH_3$ | H | F | H |
| 461 | H | $—(CH_2)_2CH_3$ | H | H | $—OC(O)CH_3$ | H | F | H |
| 462 | H | $—CH(CH_3)_2$ | H | H | $—OC(O)CH_3$ | H | F | H |
| 463 | H | $—(CH_2)_3CH_3$ | H | H | $—OC(O)CH_3$ | H | F | H |
| 464 | H | $—CH_2—HC{=}CH_2$ | H | H | $—OC(O)CH_3$ | H | F | H |
| 465 | H | $—CH_3$ | H | H | H | $—OCH_3$ | F | H |
| 466 | H | $—CH_2CH_3$ | H | H | H | $—OCH_3$ | F | H |
| 467 | H | $—(CH_2)_2CH_3$ | H | H | H | $—OCH_3$ | F | H |
| 468 | H | $—CH(CH_3)_2$ | H | H | H | $—OCH_3$ | F | H |
| 469 | H | $—(CH_2)_3CH_3$ | H | H | H | $—OCH_3$ | F | H |
| 470 | H | $—CH_2—HC{=}CH_2$ | H | H | H | $—OCH_3$ | F | H |
| 471 | H | $—CD_3$ | H | H | H | H | H | H |
| 472 | H | $—CD_3$ | H | H | —OH | H | H | H |
| 473 | H | $—CD_3$ | H | H | $—OC(O)CH_3$ | H | H | H |
| 474 | H | $—CD_3$ | H | H | H | $—OCH_3$ | H | H |
| 475 | H | $—CD_3$ | H | H | H | H | F | H |
| 476 | H | $—CD_3$ | H | H | —OH | H | F | H |
| 477 | H | $—CD_3$ | H | H | $—OC(O)CH_3$ | H | F | H |
| 478 | H | $—CD_3$ | H | H | H | $—OCH_3$ | F | H |
| 479 | H | $—CD_3$ | H | H | H | H | H | $—CH_3$ |
| 480 | H | $—CD_3$ | H | H | —OH | H | H | $—CH_3$ |
| 481 | H | $—CD_3$ | H | H | $—OC(O)CH_3$ | H | H | $—CH_3$ |
| 482 | H | $—CD_3$ | H | H | H | $—OCH_3$ | H | $—CH_3$ |
| 483 | H | $—CD_3$ | H | H | H | H | F | $—CH_3$ |
| 484 | H | $—CD_3$ | H | H | —OH | H | F | $—CH_3$ |
| 485 | H | $—CD_3$ | H | H | $—OC(O)CH_3$ | H | F | $—CH_3$ |
| 486 | H | $—CD_3$ | H | H | H | $—OCH_3$ | F | $—CH_3$ |
| 487 | H | $—CD_2CD_3$ | H | H | H | H | H | H |
| 488 | H | $—CD_2CD_3$ | H | H | —OH | H | H | H |
| 489 | H | $—CD_2CD_3$ | H | H | $—OC(O)CH_3$ | H | H | H |
| 490 | H | $—CD_2CD_3$ | H | H | H | $—OCH_3$ | H | H |
| 491 | H | $—CD_2CD_3$ | H | H | H | H | F | H |
| 492 | H | $—CD_2CD_3$ | H | H | —OH | H | F | H |
| 493 | H | $—CD_2CD_3$ | H | H | $—OC(O)CH_3$ | H | F | H |
| 494 | H | $—CD_2CD_3$ | H | H | H | $—OCH_3$ | F | H |
| 495 | H | $—CD_2CD_3$ | H | H | H | H | H | $—CH_3$ |
| 496 | H | $—CD_2CD_3$ | H | H | —OH | H | H | $—CH_3$ |
| 497 | H | $—CD_2CD_3$ | H | H | $—OC(O)CH_3$ | H | H | $—CH_3$ |
| 498 | H | $—CD_2CD_3$ | H | H | H | $—OCH_3$ | H | $—CH_3$ |
| 499 | H | $—CD_2CD_3$ | H | H | H | H | F | $—CH_3$ |
| 500 | H | $—CD_2CD_3$ | H | H | —OH | H | F | $—CH_3$ |
| 501 | H | $—CD_2CD_3$ | H | H | $—OC(O)CH_3$ | H | F | $—CH_3$ |
| 502 | H | $—CD_2CD_3$ | H | H | H | $—OCH_3$ | F | $—CH_3$ |
| 503 | H | $—CH_3$ | H | H | —OH | H | F | $—CH_3$ |
| 504 | H | $—CH_2CH_3$ | H | H | —OH | H | F | $—CH_3$ |
| 505 | H | $—(CH_2)_2CH_3$ | H | H | —OH | H | F | $—CH_3$ |
| 506 | H | $—CH(CH_3)_2$ | H | H | —OH | H | F | $—CH_3$ |
| 507 | H | $—(CH_2)_3CH_3$ | H | H | —OH | H | F | $—CH_3$ |
| 508 | H | $—CH_2—HC{=}CH_2$ | H | H | —OH | H | F | $—CH_3$ |
| 509 | H | $—CH_3$ | H | H | $—OC(O)CH_3$ | H | F | $—CH_3$ |
| 510 | H | $—CH_2CH_3$ | H | H | $—OC(O)CH_3$ | H | F | $—CH_3$ |
| 511 | H | $—(CH_2)_2CH_3$ | H | H | $—OC(O)CH_3$ | H | F | $—CH_3$ |
| 512 | H | $—CH(CH_3)_2$ | H | H | $—OC(O)CH_3$ | H | F | $—CH_3$ |
| 513 | H | $—(CH_2)_3CH_3$ | H | H | $—OC(O)CH_3$ | H | F | $—CH_3$ |
| 514 | H | $—CH_2—HC{=}CH_2$ | H | H | $—OC(O)CH_3$ | H | F | $—CH_3$ |
| 515 | H | $—CH_3$ | H | H | H | $—OCH_3$ | F | $—CH_3$ |
| 516 | H | $—CH_2CH_3$ | H | H | H | $—OCH_3$ | F | $—CH_3$ |
| 517 | H | $—(CH_2)_2CH_3$ | H | H | H | $—OCH_3$ | F | $—CH_3$ |
| 518 | H | $—CH(CH_3)_2$ | H | H | H | $—OCH_3$ | F | $—CH_3$ |
| 519 | H | $—(CH_2)_3CH_3$ | H | H | H | $—OCH_3$ | F | $—CH_3$ |
| 520 | H | $—CH_2—HC{=}CH_2$ | H | H | H | $—OCH_3$ | F | $—CH_3$ |
| 521 | H | $—CH_3$ | H | D | H | H | H | H |
| 522 | H | $—CH_2CH_3$ | H | D | H | H | H | H |
| 523 | H | $—(CH_2)_2CH_3$ | H | D | H | H | H | H |
| 524 | H | $—CH(CH_3)_2$ | H | D | H | H | H | H |

TABLE 2-continued

| Ref. | X | Y | $R_2$ | $R_3$ | $R_4$ | $R_5$ | $R_6$ | $R_7$ |
|---|---|---|---|---|---|---|---|---|
| 525 | H | $—(CH_2)_3CH_3$ | H | D | H | H | H | H |
| 526 | H | $—CH_2—HC{=}CH_2$ | H | D | H | H | H | H |
| 527 | H | $—CH_3$ | H | D | —OH | H | H | H |
| 528 | H | $—CH_2CH_3$ | H | D | —OH | H | H | H |
| 529 | H | $—(CH_2)_2CH_3$ | H | D | —OH | H | H | H |
| 530 | H | $—CH(CH_3)_2$ | H | D | —OH | H | H | H |
| 531 | H | $—(CH_2)_3CH_3$ | H | D | —OH | H | H | H |
| 532 | H | $—CH_2—HC{=}CH_2$ | H | D | —OH | H | H | H |
| 533 | H | $—CH_3$ | H | D | $—OC(O)CH_3$ | H | H | H |
| 534 | H | $—CH_2CH_3$ | H | D | $—OC(O)CH_3$ | H | H | H |
| 535 | H | $—(CH_2)_2CH_3$ | H | D | $—OC(O)CH_3$ | H | H | H |
| 536 | H | $—CH(CH_3)_2$ | H | D | $—OC(O)CH_3$ | H | H | H |
| 537 | H | $—(CH_2)_3CH_3$ | H | D | $—OC(O)CH_3$ | H | H | H |
| 538 | H | $—CH_2—HC{=}CH_2$ | H | D | $—OC(O)CH_3$ | H | H | H |
| 539 | H | $—CH_3$ | H | D | H | $—OCH_3$ | H | H |
| 540 | H | $—CH_2CH_3$ | H | D | H | $—OCH_3$ | H | H |
| 541 | H | $—(CH_2)_2CH_3$ | H | D | H | $—OCH_3$ | H | H |
| 542 | H | $—CH(CH_3)_2$ | H | D | H | $—OCH_3$ | H | H |
| 543 | H | $—(CH_2)_3CH_3$ | H | D | H | $—OCH_3$ | H | H |
| 544 | H | $—CH_2—HC{=}CH_2$ | H | D | H | $—OCH_3$ | H | H |
| 545 | H | $—CH_3$ | H | D | H | H | F | H |
| 546 | H | $—CH_2CH_3$ | H | D | H | H | F | H |
| 547 | H | $—(CH_2)_2CH_3$ | H | D | H | H | F | H |
| 548 | H | $—CH(CH_3)_2$ | H | D | H | H | F | H |
| 549 | H | $—(CH_2)_3CH_3$ | H | D | H | H | F | H |
| 550 | H | $—CH_2—HC{=}CH_2$ | H | D | H | H | F | H |
| 551 | H | $—CH_3$ | H | D | H | H | F | $CH_3$ |
| 552 | H | $—CH_2CH_3$ | H | D | H | H | F | $CH_3$ |
| 553 | H | $—(CH_2)_2CH_3$ | H | D | H | H | F | $CH_3$ |
| 554 | H | $—CH(CH_3)_2$ | H | D | H | H | F | $CH_3$ |
| 555 | H | $—(CH_2)_3CH_3$ | H | D | H | H | F | $CH_3$ |
| 556 | H | $—CH_2—HC{=}CH_2$ | H | D | H | H | F | $CH_3$ |

Other exemplary compounds of Formula I include those below in Table 3, which is also represented by Formula Ic:

Formula Ic

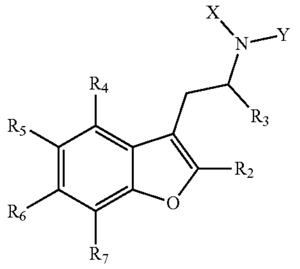

TABLE 3

| Ref. | X | Y | $R_2$ | $R_3$ | $R_4$ | $R_5$ | $R_6$ | $R_7$ |
|---|---|---|---|---|---|---|---|---|
| 1 | $—CH_3$ | $—CH_3$ | H | H | $—OCH_3$ | H | H | H |
| 2 | $—CH_3$ | $—CH_2CH_3$ | H | H | $—OCH_3$ | H | H | H |
| 3 | $—CH_3$ | $—(CH_2)_2CH_3$ | H | H | $—OCH_3$ | H | H | H |
| 4 | $—CH_3$ | $—CH(CH_3)_2$ | H | H | $—OCH_3$ | H | H | H |
| 5 | $—CH_3$ | $—(CH_2)_3CH_3$ | H | H | $—OCH_3$ | H | H | H |
| 6 | $—CH_3$ | $—CH_2—HC{=}CH_2$ | H | H | $—OCH_3$ | H | H | H |
| 7 | $—CH_2CH_3$ | $—CH_2CH_3$ | H | H | $—OCH_3$ | H | H | H |
| 8 | $—CH_2CH_3$ | $—(CH_2)_2CH_3$ | H | H | $—OCH_3$ | H | H | H |
| 9 | $—CH_2CH_3$ | $—CH(CH_3)_2$ | H | H | $—OCH_3$ | H | H | H |
| 10 | $—CH_2CH_3$ | $—(CH_2)_3CH_3$ | H | H | $—OCH_3$ | H | H | H |
| 11 | $—CH_2CH_3$ | $—CH_2—HC{=}CH_2$ | H | H | $—OCH_3$ | H | H | H |
| 12 | $—(CH_2)_2CH_3$ | $—(CH_2)_2CH_3$ | H | H | $—OCH_3$ | H | H | H |
| 13 | $—(CH_2)_2CH_3$ | $—CH(CH_3)_2$ | H | H | $—OCH_3$ | H | H | H |
| 14 | $—(CH_2)_2CH_3$ | $—(CH_2)_3CH_3$ | H | H | $—OCH_3$ | H | H | H |
| 15 | $—(CH_2)_2CH_3$ | $—CH_2—HC{=}CH_2$ | H | H | $—OCH_3$ | H | H | H |
| 16 | $—CH(CH_3)_2$ | $—CH(CH_3)_2$ | H | H | $—OCH_3$ | H | H | H |
| 17 | $—CH(CH_3)_2$ | $—(CH_2)_3CH_3$ | H | H | $—OCH_3$ | H | H | H |

TABLE 3-continued

| Ref. | X | Y | $R_2$ | $R_3$ | $R_4$ | $R_5$ | $R_6$ | $R_7$ |
|---|---|---|---|---|---|---|---|---|
| 18 | —$CH(CH_3)_2$ | —$CH_2$—HC=$CH_2$ | H | H | —$OCH_3$ | H | H | H |
| 19 | —$(CH_2)_3CH_3$ | —$(CH_2)_3CH_3$ | H | H | —$OCH_3$ | H | H | H |
| 20 | —$(CH_2)_3CH_3$ | —$CH_2$—HC=$CH_2$ | H | H | —$OCH_3$ | H | H | H |
| 21 | —$CH_2$—HC=$CH_2$ | —$CH_2$—HC=$CH_2$ | H | H | —$OCH_3$ | H | H | H |
| 22 | —$CH_3$ | —$CH_2CH_3$ | H | H | —OH | H | H | H |
| 23 | —$CH_3$ | —$(CH_2)_2CH_3$ | H | H | —OH | H | H | H |
| 24 | —$CH_3$ | —$CH(CH_3)_2$ | H | H | —OH | H | H | H |
| 25 | —$CH_3$ | —$(CH_2)_3CH_3$ | H | H | —OH | H | H | H |
| 26 | —$CH_3$ | —$CH_2$—HC=$CH_2$ | H | H | —OH | H | H | H |
| 27 | —$CH_2CH_3$ | —$CH_2CH_3$ | H | H | —OH | H | H | H |
| 28 | —$CH_2CH_3$ | —$(CH_2)_2CH_3$ | H | H | —OH | H | H | H |
| 29 | —$CH_2CH_3$ | —$CH(CH_3)_2$ | H | H | —OH | H | H | H |
| 30 | —$CH_2CH_3$ | —$(CH_2)_3CH_3$ | H | H | —OH | H | H | H |
| 31 | —$CH_2CH_3$ | —$CH_2$—HC=$CH_2$ | H | H | —OH | H | H | H |
| 32 | —$(CH_2)_2CH_3$ | —$(CH_2)_2CH_3$ | H | H | —OH | H | H | H |
| 33 | —$(CH_2)_2CH_3$ | —$CH(CH_3)_2$ | H | H | —OH | H | H | H |
| 34 | —$(CH_2)_2CH_3$ | —$(CH_2)_3CH_3$ | H | H | —OH | H | H | H |
| 35 | —$(CH_2)_2CH_3$ | —$CH_2$—HC=$CH_2$ | H | H | —OH | H | H | H |
| 36 | —$CH(CH_3)_2$ | —$CH(CH_3)_2$ | H | H | —OH | H | H | H |
| 37 | —$CH(CH_3)_2$ | —$(CH_2)_3CH_3$ | H | H | —OH | H | H | H |
| 38 | —$CH(CH_3)_2$ | —$CH_2$—HC=$CH_2$ | H | H | —OH | H | H | H |
| 39 | —$(CH_2)_3CH_3$ | —$(CH_2)_3CH_3$ | H | H | —OH | H | H | H |
| 40 | —$(CH_2)_3CH_3$ | —$CH_2$—HC=$CH_2$ | H | H | —OH | H | H | H |
| 41 | —$CH_2$—HC=$CH_2$ | —$CH_2$—HC=$CH_2$ | H | H | —OH | H | H | H |
| 42 | —$CH_3$ | —$CH_3$ | H | H | —OC(O)$CH_3$ | H | H | H |
| 43 | —$CH_3$ | —$CH_2CH_3$ | H | H | —OC(O)$CH_3$ | H | H | H |
| 44 | —$CH_3$ | —$(CH_2)_2CH_3$ | H | H | —OC(O)$CH_3$ | H | H | H |
| 45 | —$CH_3$ | —$CH(CH_3)_2$ | H | H | —OC(O)$CH_3$ | H | H | H |
| 46 | —$CH_3$ | —$(CH_2)_3CH_3$ | H | H | —OC(O)$CH_3$ | H | H | H |
| 47 | —$CH_3$ | —$CH_2$—HC=$CH_2$ | H | H | —OC(O)$CH_3$ | H | H | H |
| 48 | —$CH_2CH_3$ | —$CH_2CH_3$ | H | H | —OC(O)$CH_3$ | H | H | H |
| 49 | —$CH_2CH_3$ | —$(CH_2)_2CH_3$ | H | H | —OC(O)$CH_3$ | H | H | H |
| 50 | —$CH_2CH_3$ | —$CH(CH_3)_2$ | H | H | —OC(O)$CH_3$ | H | H | H |
| 51 | —$CH_2CH_3$ | —$(CH_2)_3CH_3$ | H | H | —OC(O)$CH_3$ | H | H | H |
| 52 | —$CH_2CH_3$ | —$CH_2$—HC=$CH_2$ | H | H | —OC(O)$CH_3$ | H | H | H |
| 53 | —$(CH_2)_2CH_3$ | —$(CH_2)_2CH_3$ | H | H | —OC(O)$CH_3$ | H | H | H |
| 54 | —$(CH_2)_2CH_3$ | —$CH(CH_3)_2$ | H | H | —OC(O)$CH_3$ | H | H | H |
| 55 | —$(CH_2)_2CH_3$ | —$(CH_2)_3CH_3$ | H | H | —OC(O)$CH_3$ | H | H | H |
| 56 | —$(CH_2)_2CH_3$ | —$CH_2$—HC=$CH_2$ | H | H | —OC(O)$CH_3$ | H | H | H |
| 57 | —$CH(CH_3)_2$ | —$CH(CH_3)_2$ | H | H | —OC(O)$CH_3$ | H | H | H |
| 58 | —$CH(CH_3)_2$ | —$(CH_2)_3CH_3$ | H | H | —OC(O)$CH_3$ | H | H | H |
| 59 | —$CH(CH_3)_2$ | —$CH_2$—HC=$CH_2$ | H | H | —OC(O)$CH_3$ | H | H | H |
| 60 | —$(CH_2)_3CH_3$ | —$(CH_2)_3CH_3$ | H | H | —OC(O)$CH_3$ | H | H | H |
| 61 | —$(CH_2)_3CH_3$ | —$CH_2$—HC=$CH_2$ | H | H | —OC(O)$CH_3$ | H | H | H |
| 62 | —$CH_2$—HC=$CH_2$ | —$CH_2$—HC=$CH_2$ | H | H | —OC(O)$CH_3$ | H | H | H |
| 63 | —$CH_3$ | —$CH_3$ | H | H | H | —$OCH_2CH_3$ | H | H |
| 64 | —$CH_3$ | —$CH_2CH_3$ | H | H | H | —$OCH_3$ | H | H |
| 65 | —$CH_3$ | —$(CH_2)_2CH_3$ | H | H | H | —$OCH_3$ | H | H |
| 66 | —$CH_3$ | —$CH(CH_3)_2$ | H | H | H | —$OCH_3$ | H | H |
| 67 | —$CH_3$ | —$(CH_2)_3CH_3$ | H | H | H | —$OCH_3$ | H | H |
| 68 | —$CH_3$ | —$CH_2$—HC=$CH_2$ | H | H | H | —$OCH_3$ | H | H |
| 69 | —$CH_2CH_3$ | —$CH_2CH_3$ | H | H | H | —$OCH_3$ | H | H |
| 70 | —$CH_2CH_3$ | —$(CH_2)_2CH_3$ | H | H | H | —$OCH_3$ | H | H |
| 71 | —$CH_2CH_3$ | —$CH(CH_3)_2$ | H | H | H | —$OCH_3$ | H | H |
| 72 | —$CH_2CH_3$ | —$(CH_2)_3CH_3$ | H | H | H | —$OCH_3$ | H | H |
| 73 | —$CH_2CH_3$ | —$CH_2$—HC=$CH_2$ | H | H | H | —$OCH_3$ | H | H |
| 74 | —$(CH_2)_2CH_3$ | —$(CH_2)_2CH_3$ | H | H | H | —$OCH_3$ | H | H |
| 75 | —$(CH_2)_2CH_3$ | —$CH(CH_3)_2$ | H | H | H | —$OCH_3$ | H | H |
| 76 | —$(CH_2)_2CH_3$ | —$(CH_2)_3CH_3$ | H | H | H | —$OCH_3$ | H | H |
| 77 | —$(CH_2)_2CH_3$ | —$CH_2$—HC=$CH_2$ | H | H | H | —$OCH_3$ | H | H |
| 78 | —$CH(CH_3)_2$ | —$CH(CH_3)_2$ | H | H | H | —$OCH_3$ | H | H |
| 79 | —$CH(CH_3)_2$ | —$(CH_2)_3CH_3$ | H | H | H | —$OCH_3$ | H | H |
| 80 | —$CH(CH_3)_2$ | —$CH_2$—HC=$CH_2$ | H | H | H | —$OCH_3$ | H | H |
| 81 | —$(CH_2)_3CH_3$ | —$(CH_2)_3CH_3$ | H | H | H | —$OCH_3$ | H | H |
| 82 | —$(CH_2)_3CH_3$ | —$CH_2$—HC=$CH_2$ | H | H | H | —$OCH_3$ | H | H |
| 83 | —$CH_2$—HC=$CH_2$ | —$CH_2$—HC=$CH_2$ | H | H | H | —$OCH_3$ | H | H |
| 84 | —$CH_3$ | —$CH_2CH_3$ | H | H | H | —OH | H | H |
| 85 | —$CH_3$ | —$(CH_2)_2CH_3$ | H | H | H | —OH | H | H |
| 86 | —$CH_3$ | —$CH(CH_3)_2$ | H | H | H | —OH | H | H |
| 87 | —$CH_3$ | —$(CH_2)_3CH_3$ | H | H | H | —OH | H | H |
| 88 | —$CH_3$ | —$CH_2$—HC=$CH_2$ | H | H | H | —OH | H | H |
| 89 | —$CH_2CH_3$ | —$CH_2CH_3$ | H | H | H | —OH | H | H |
| 90 | —$CH_2CH_3$ | —$(CH_2)_2CH_3$ | H | H | H | —OH | H | H |
| 91 | —$CH_2CH_3$ | —$CH(CH_3)_2$ | H | H | H | —OH | H | H |
| 92 | —$CH_2CH_3$ | —$(CH_2)_3CH_3$ | H | H | H | —OH | H | H |
| 93 | —$CH_2CH_3$ | —$CH_2$—HC=$CH_2$ | H | H | H | —OH | H | H |
| 94 | —$(CH_2)_2CH_3$ | —$(CH_2)_2CH_3$ | H | H | H | —OH | H | H |
| 95 | —$(CH_2)_2CH_3$ | —$CH(CH_3)_2$ | H | H | H | —OH | H | H |

TABLE 3-continued

| Ref. | X | Y | $R_2$ | $R_3$ | $R_4$ | $R_5$ | $R_6$ | $R_7$ |
|---|---|---|---|---|---|---|---|---|
| 96 | $-(CH_2)_2CH_3$ | $-(CH_2)_3CH_3$ | H | H | H | —OH | H | H |
| 97 | $-(CH_2)_2CH_3$ | $-CH_2-HC=CH_2$ | H | H | H | —OH | H | H |
| 98 | $-CH(CH_3)_2$ | $-CH(CH_3)_2$ | H | H | H | —OH | H | H |
| 99 | $-CH(CH_3)_2$ | $-(CH_2)_3CH_3$ | H | H | H | —OH | H | H |
| 100 | $-CH(CH_3)_2$ | $-CH_2-HC=CH_2$ | H | H | H | —OH | H | H |
| 101 | $-(CH_2)_3CH_3$ | $-(CH_2)_3CH_3$ | H | H | H | —OH | H | H |
| 102 | $-(CH_2)_3CH_3$ | $-CH_2-HC=CH_2$ | H | H | H | —OH | H | H |
| 103 | $-CH_2-HC=CH_2$ | $-CH_2-HC=CH_2$ | H | H | H | —OH | H | H |
| 104 | $-CH_3$ | $-CH_3$ | H | H | H | $-OC(O)CH_3$ | H | H |
| 105 | $-CH_3$ | $-CH_2CH_3$ | H | H | H | $-OC(O)CH_3$ | H | H |
| 106 | $-CH_3$ | $-(CH_2)_2CH_3$ | H | H | H | $-OC(O)CH_3$ | H | H |
| 107 | $-CH_3$ | $-CH(CH_3)_2$ | H | H | H | $-OC(O)CH_3$ | H | H |
| 108 | $-CH_3$ | $-(CH_2)_3CH_3$ | H | H | H | $-OC(O)CH_3$ | H | H |
| 109 | $-CH_3$ | $-CH_2-HC=CH_2$ | H | H | H | $-OC(O)CH_3$ | H | H |
| 110 | $-CH_2CH_3$ | $-CH_2CH_3$ | H | H | H | $-OC(O)CH_3$ | H | H |
| 111 | $-CH_2CH_3$ | $-(CH_2)_2CH_3$ | H | H | H | $-OC(O)CH_3$ | H | H |
| 112 | $-CH_2CH_3$ | $-CH(CH_3)_2$ | H | H | H | $-OC(O)CH_3$ | H | H |
| 113 | $-CH_2CH_3$ | $-(CH_2)_3CH_3$ | H | H | H | $-OC(O)CH_3$ | H | H |
| 114 | $-CH_2CH_3$ | $-CH_2-HC=CH_2$ | H | H | H | $-OC(O)CH_3$ | H | H |
| 115 | $-(CH_2)_2CH_3$ | $-(CH_2)_2CH_3$ | H | H | H | $-OC(O)CH_3$ | H | H |
| 116 | $-(CH_2)_2CH_3$ | $-CH(CH_3)_2$ | H | H | H | $-OC(O)CH_3$ | H | H |
| 117 | $-(CH_2)_2CH_3$ | $-(CH_2)_3CH_3$ | H | H | H | $-OC(O)CH_3$ | H | H |
| 118 | $-(CH_2)_2CH_3$ | $-CH_2-HC=CH_2$ | H | H | H | $-OC(O)CH_3$ | H | H |
| 119 | $-CH(CH_3)_2$ | $-CH(CH_3)_2$ | H | H | H | $-OC(O)CH_3$ | H | H |
| 120 | $-CH(CH_3)_2$ | $-(CH_2)_3CH_3$ | H | H | H | $-OC(O)CH_3$ | H | H |
| 121 | $-CH(CH_3)_2$ | $-CH_2-HC=CH_2$ | H | H | H | $-OC(O)CH_3$ | H | H |
| 122 | $-(CH_2)_3CH_3$ | $-(CH_2)_3CH_3$ | H | H | H | $-OC(O)CH_3$ | H | H |
| 123 | $-(CH_2)_3CH_3$ | $-CH_2-HC=CH_2$ | H | H | H | $-OC(O)CH_3$ | H | H |
| 124 | $-CH_2-HC=CH_2$ | $-CH_2-HC=CH_2$ | H | H | H | $-OC(O)CH_3$ | H | H |
| 125 | $-CH_3$ | $-CH_3$ | H | H | $-OCH_3$ | H | H | $-CH_3$ |
| 126 | $-CH_3$ | $-CH_2CH_3$ | H | H | $-OCH_3$ | H | H | $-CH_3$ |
| 127 | $-CH_3$ | $-(CH_2)_2CH_3$ | H | H | $-OCH_3$ | H | H | $-CH_3$ |
| 128 | $-CH_3$ | $-CH(CH_3)_2$ | H | H | $-OCH_3$ | H | H | $-CH_3$ |
| 129 | $-CH_3$ | $-(CH_2)_3CH_3$ | H | H | $-OCH_3$ | H | H | $-CH_3$ |
| 130 | $-CH_3$ | $-CH_2-HC=CH_2$ | H | H | $-OCH_3$ | H | H | $-CH_3$ |
| 131 | $-CH_2CH_3$ | $-CH_2CH_3$ | H | H | $-OCH_3$ | H | H | $-CH_3$ |
| 132 | $-CH_2CH_3$ | $-(CH_2)_2CH_3$ | H | H | $-OCH_3$ | H | H | $-CH_3$ |
| 133 | $-CH_2CH_3$ | $-CH(CH_3)_2$ | H | H | $-OCH_3$ | H | H | $-CH_3$ |
| 134 | $-CH_2CH_3$ | $-(CH_2)_3CH_3$ | H | H | $-OCH_3$ | H | H | $-CH_3$ |
| 135 | $-CH_2CH_3$ | $-CH_2-HC=CH_2$ | H | H | $-OCH_3$ | H | H | $-CH_3$ |
| 135 | $-(CH_2)_2CH_3$ | $-(CH_2)_2CH_3$ | H | H | $-OCH_3$ | H | H | $-CH_3$ |
| 137 | $-(CH_2)_2CH_3$ | $-CH(CH_3)_2$ | H | H | $-OCH_3$ | H | H | $-CH_3$ |
| 138 | $-(CH_2)_2CH_3$ | $-(CH_2)_3CH_3$ | H | H | $-OCH_3$ | H | H | $-CH_3$ |
| 139 | $-(CH_2)_2CH_3$ | $-CH_2-HC=CH_2$ | H | H | $-OCH_3$ | H | H | $-CH_3$ |
| 140 | $-CH(CH_3)_2$ | $-CH(CH_3)_2$ | H | H | $-OCH_3$ | H | H | $-CH_3$ |
| 141 | $-CH(CH_3)_2$ | $-(CH_2)_3CH_3$ | H | H | $-OCH_3$ | H | H | $-CH_3$ |
| 142 | $-CH(CH_3)_2$ | $-CH_2-HC=CH_2$ | H | H | $-OCH_3$ | H | H | $-CH_3$ |
| 143 | $-(CH_2)_3CH_3$ | $-(CH_2)_3CH_3$ | H | H | $-OCH_3$ | H | H | $-CH_3$ |
| 144 | $-(CH_2)_3CH_3$ | $-CH_2-HC=CH_2$ | H | H | $-OCH_3$ | H | H | $-CH_3$ |
| 145 | $-CH_2-HC=CH_2$ | $-CH_2-HC=CH_2$ | H | H | $-OCH_3$ | H | H | $-CH_3$ |
| 146 | $-CH_3$ | $-CH_2CH_3$ | H | H | —OH | H | H | $-CH_3$ |
| 147 | $-CH_3$ | $-(CH_2)_2CH_3$ | H | H | —OH | H | H | $-CH_3$ |
| 148 | $-CH_3$ | $-CH(CH_3)_2$ | H | H | —OH | H | H | $-CH_3$ |
| 149 | $-CH_3$ | $-(CH_2)_3CH_3$ | H | H | —OH | H | H | $-CH_3$ |
| 150 | $-CH_3$ | $-CH_2-HC=CH_2$ | H | H | —OH | H | H | $-CH_3$ |
| 151 | $-CH_2CH_3$ | $-CH_2CH_3$ | H | H | —OH | H | H | $-CH_3$ |
| 152 | $-CH_2CH_3$ | $-(CH_2)_2CH_3$ | H | H | —OH | H | H | $-CH_3$ |
| 153 | $-CH_2CH_3$ | $-CH(CH_3)_2$ | H | H | —OH | H | H | $-CH_3$ |
| 154 | $-CH_2CH_3$ | $-(CH_2)_3CH_3$ | H | H | —OH | H | H | $-CH_3$ |
| 155 | $-CH_2CH_3$ | $-CH_2-HC=CH_2$ | H | H | —OH | H | H | $-CH_3$ |
| 156 | $-(CH_2)_2CH_3$ | $-(CH_2)_2CH_3$ | H | H | —OH | H | H | $-CH_3$ |
| 157 | $-(CH_2)_2CH_3$ | $-CH(CH_3)_2$ | H | H | —OH | H | H | $-CH_3$ |
| 158 | $-(CH_2)_2CH_3$ | $-(CH_2)_3CH_3$ | H | H | —OH | H | H | $-CH_3$ |
| 159 | $-(CH_2)_2CH_3$ | $-CH_2-HC=CH_2$ | H | H | —OH | H | H | $-CH_3$ |
| 160 | $-CH(CH_3)_2$ | $-CH(CH_3)_2$ | H | H | —OH | H | H | $-CH_3$ |
| 161 | $-CH(CH_3)_2$ | $-(CH_2)_3CH_3$ | H | H | —OH | H | H | $-CH_3$ |
| 162 | $-CH(CH_3)_2$ | $-CH_2-HC=CH_2$ | H | H | —OH | H | H | $-CH_3$ |
| 163 | $-(CH_2)_3CH_3$ | $-(CH_2)_3CH_3$ | H | H | —OH | H | H | $-CH_3$ |
| 164 | $-(CH_2)_3CH_3$ | $-CH_2-HC=CH_2$ | H | H | —OH | H | H | $-CH_3$ |
| 165 | $-CH_2-HC=CH_2$ | $-CH_2-HC=CH_2$ | H | H | —OH | H | H | $-CH_3$ |
| 166 | $-CH_3$ | $-CH_3$ | H | H | $-OC(O)CH_3$ | H | H | $-CH_3$ |
| 167 | $-CH_3$ | $-CH_2CH_3$ | H | H | $-OC(O)CH_3$ | H | H | $-CH_3$ |
| 168 | $-CH_3$ | $-(CH_2)_2CH_3$ | H | H | $-OC(O)CH_3$ | H | H | $-CH_3$ |
| 169 | $-CH_3$ | $-CH(CH_3)_2$ | H | H | $-OC(O)CH_3$ | H | H | $-CH_3$ |
| 170 | $-CH_3$ | $-(CH_2)_3CH_3$ | H | H | $-OC(O)CH_3$ | H | H | $-CH_3$ |
| 171 | $-CH_3$ | $-CH_2-HC=CH_2$ | H | H | $-OC(O)CH_3$ | H | H | $-CH_3$ |
| 172 | $-CH_2CH_3$ | $-CH_2CH_3$ | H | H | $-OC(O)CH_3$ | H | H | $-CH_3$ |
| 173 | $-CH_2CH_3$ | $-(CH_2)_2CH_3$ | H | H | $-OC(O)CH_3$ | H | H | $-CH_3$ |

TABLE 3-continued

| Ref. | X | Y | $R_2$ | $R_3$ | $R_4$ | $R_5$ | $R_6$ | $R_7$ |
|---|---|---|---|---|---|---|---|---|
| 174 | $-CH_2CH_3$ | $-CH(CH_3)_2$ | H | H | $-OC(O)CH_3$ | H | H | $-CH_3$ |
| 175 | $-CH_2CH_3$ | $-(CH_2)_3CH_3$ | H | H | $-OC(O)CH_3$ | H | H | $-CH_3$ |
| 176 | $-CH_2CH_3$ | $-CH_2-HC=CH_2$ | H | H | $-OC(O)CH_3$ | H | H | $-CH_3$ |
| 177 | $-(CH_2)_2CH_3$ | $-(CH_2)_2CH_3$ | H | H | $-OC(O)CH_3$ | H | H | $-CH_3$ |
| 178 | $-(CH_2)_2CH_3$ | $-CH(CH_3)_2$ | H | H | $-OC(O)CH_3$ | H | H | $-CH_3$ |
| 179 | $-(CH_2)_2CH_3$ | $-(CH_2)_3CH_3$ | H | H | $-OC(O)CH_3$ | H | H | $-CH_3$ |
| 180 | $-(CH_2)_2CH_3$ | $-CH_2-HC=CH_2$ | H | H | $-OC(O)CH_3$ | H | H | $-CH_3$ |
| 181 | $-CH(CH_3)_2$ | $-CH(CH_3)_2$ | H | H | $-OC(O)CH_3$ | H | H | $-CH_3$ |
| 182 | $-CH(CH_3)_2$ | $-(CH_2)_3CH_3$ | H | H | $-OC(O)CH_3$ | H | H | $-CH_3$ |
| 183 | $-CH(CH_3)_2$ | $-CH_2-HC=CH_2$ | H | H | $-OC(O)CH_3$ | H | H | $-CH_3$ |
| 184 | $-(CH_2)_3CH_3$ | $-(CH_2)_3CH_3$ | H | H | $-OC(O)CH_3$ | H | H | $-CH_3$ |
| 185 | $-(CH_2)_3CH_3$ | $-CH_2-HC=CH_2$ | H | H | $-OC(O)CH_3$ | H | H | $-CH_3$ |
| 186 | $-CH_2-HC=CH_2$ | $-CH_2-HC=CH_2$ | H | H | $-OC(O)CH_3$ | H | H | $-CH_3$ |
| 187 | $-CH_3$ | $-CH_3$ | H | H | H | $-OCH_3$ | H | $-CH_3$ |
| 188 | $-CH_3$ | $-CH_2CH_3$ | H | H | H | $-OCH_3$ | H | $-CH_3$ |
| 189 | $-CH_3$ | $-(CH_2)_2CH_3$ | H | H | H | $-OCH_3$ | H | $-CH_3$ |
| 190 | $-CH_3$ | $-CH(CH_3)_2$ | H | H | H | $-OCH_3$ | H | $-CH_3$ |
| 191 | $-CH_3$ | $-(CH_2)_3CH_3$ | H | H | H | $-OCH_3$ | H | $-CH_3$ |
| 192 | $-CH_3$ | $-CH_2-HC=CH_2$ | H | H | H | $-OCH_3$ | H | $-CH_3$ |
| 193 | $-CH_2CH_3$ | $-CH_2CH_3$ | H | H | H | $-OCH_3$ | H | $-CH_3$ |
| 194 | $-CH_2CH_3$ | $-(CH_2)_2CH_3$ | H | H | H | $-OCH_3$ | H | $-CH_3$ |
| 195 | $-CH_2CH_3$ | $-CH(CH_3)_2$ | H | H | H | $-OCH_3$ | H | $-CH_3$ |
| 196 | $-CH_2CH_3$ | $-(CH_2)_3CH_3$ | H | H | H | $-OCH_3$ | H | $-CH_3$ |
| 197 | $-CH_2CH_3$ | $-CH_2-HC=CH_2$ | H | H | H | $-OCH_3$ | H | $-CH_3$ |
| 198 | $-(CH_2)_2CH_3$ | $-(CH_2)_2CH_3$ | H | H | H | $-OCH_3$ | H | $-CH_3$ |
| 199 | $-(CH_2)_2CH_3$ | $-CH(CH_3)_2$ | H | H | H | $-OCH_3$ | H | $-CH_3$ |
| 200 | $-(CH_2)_2CH_3$ | $-(CH_2)_3CH_3$ | H | H | H | $-OCH_3$ | H | $-CH_3$ |
| 201 | $-(CH_2)_2CH_3$ | $-CH_2-HC=CH_2$ | H | H | H | $-OCH_3$ | H | $-CH_3$ |
| 202 | $-CH(CH_3)_2$ | $-CH(CH_3)_2$ | H | H | H | $-OCH_3$ | H | $-CH_3$ |
| 203 | $-CH(CH_3)_2$ | $-(CH_2)_3CH_3$ | H | H | H | $-OCH_3$ | H | $-CH_3$ |
| 204 | $-CH(CH_3)_2$ | $-CH_2-HC=CH_2$ | H | H | H | $-OCH_3$ | H | $-CH_3$ |
| 205 | $-(CH_2)_3CH_3$ | $-(CH_2)_3CH_3$ | H | H | H | $-OCH_3$ | H | $-CH_3$ |
| 206 | $-(CH_2)_3CH_3$ | $-CH_2-HC=CH_2$ | H | H | H | $-OCH_3$ | H | $-CH_3$ |
| 207 | $-CH_2-HC=CH_2$ | $-CH_2-HC=CH_2$ | H | H | H | $-OCH_3$ | H | $-CH_3$ |
| 208 | $-CH_3$ | $-CH_2CH_3$ | H | H | H | $-OH$ | H | $-CH_3$ |
| 209 | $-CH_3$ | $-(CH_2)_2CH_3$ | H | H | H | $-OH$ | H | $-CH_3$ |
| 210 | $-CH_3$ | $-CH(CH_3)_2$ | H | H | H | $-OH$ | H | $-CH_3$ |
| 211 | $-CH_3$ | $-(CH_2)_3CH_3$ | H | H | H | $-OH$ | H | $-CH_3$ |
| 212 | $-CH_3$ | $-CH_2-HC=CH_2$ | H | H | H | $-OH$ | H | $-CH_3$ |
| 213 | $-CH_2CH_3$ | $-CH_2CH_3$ | H | H | H | $-OH$ | H | $-CH_3$ |
| 214 | $-CH_2CH_3$ | $-(CH_2)_2CH_3$ | H | H | H | $-OH$ | H | $-CH_3$ |
| 215 | $-CH_2CH_3$ | $-CH(CH_3)_2$ | H | H | H | $-OH$ | H | $-CH_3$ |
| 216 | $-CH_2CH_3$ | $-(CH_2)_3CH_3$ | H | H | H | $-OH$ | H | $-CH_3$ |
| 217 | $-CH_2CH_3$ | $-CH_2-HC=CH_2$ | H | H | H | $-OH$ | H | $-CH_3$ |
| 218 | $-(CH_2)_2CH_3$ | $-(CH_2)_2CH_3$ | H | H | H | $-OH$ | H | $-CH_3$ |
| 219 | $-(CH_2)_2CH_3$ | $-CH(CH_3)_2$ | H | H | H | $-OH$ | H | $-CH_3$ |
| 220 | $-(CH_2)_2CH_3$ | $-(CH_2)_3CH_3$ | H | H | H | $-OH$ | H | $-CH_3$ |
| 221 | $-(CH_2)_2CH_3$ | $-CH_2-HC=CH_2$ | H | H | H | $-OH$ | H | $-CH_3$ |
| 222 | $-CH(CH_3)_2$ | $-CH(CH_3)_2$ | H | H | H | $-OH$ | H | $-CH_3$ |
| 223 | $-CH(CH_3)_2$ | $-(CH_2)_3CH_3$ | H | H | H | $-OH$ | H | $-CH_3$ |
| 224 | $-CH(CH_3)_2$ | $-CH_2-HC=CH_2$ | H | H | H | $-OH$ | H | $-CH_3$ |
| 225 | $-(CH_2)_3CH_3$ | $-(CH_2)_3CH_3$ | H | H | H | $-OH$ | H | $-CH_3$ |
| 226 | $-(CH_2)_3CH_3$ | $-CH_2-HC=CH_2$ | H | H | H | $-OH$ | H | $-CH_3$ |
| 227 | $-CH_2-HC=CH_2$ | $-CH_2-HC=CH_2$ | H | H | H | $-OH$ | H | $-CH_3$ |
| 228 | $-CH_3$ | $-CH_3$ | H | H | H | $-OC(O)CH_3$ | H | $-CH_3$ |
| 229 | $-CH_3$ | $-CH_2CH_3$ | H | H | H | $-OC(O)CH_3$ | H | $-CH_3$ |
| 230 | $-CH_3$ | $-(CH_2)_2CH_3$ | H | H | H | $-OC(O)CH_3$ | H | $-CH_3$ |
| 231 | $-CH_3$ | $-CH(CH_3)_2$ | H | H | H | $-OC(O)CH_3$ | H | $-CH_3$ |
| 232 | $-CH_3$ | $-(CH_2)_3CH_3$ | H | H | H | $-OC(O)CH_3$ | H | $-CH_3$ |
| 233 | $-CH_3$ | $-CH_2-HC=CH_2$ | H | H | H | $-OC(O)CH_3$ | H | $-CH_3$ |
| 234 | $-CH_2CH_3$ | $-CH_2CH_3$ | H | H | H | $-OC(O)CH_3$ | H | $-CH_3$ |
| 235 | $-CH_2CH_3$ | $-(CH_2)_2CH_3$ | H | H | H | $-OC(O)CH_3$ | H | $-CH_3$ |
| 236 | $-CH_2CH_3$ | $-CH(CH_3)_2$ | H | H | H | $-OC(O)CH_3$ | H | $-CH_3$ |
| 237 | $-CH_2CH_3$ | $-(CH_2)_3CH_3$ | H | H | H | $-OC(O)CH_3$ | H | $-CH_3$ |
| 238 | $-CH_2CH_3$ | $-CH_2-HC=CH_2$ | H | H | H | $-OC(O)CH_3$ | H | $-CH_3$ |
| 239 | $-(CH_2)_2CH_3$ | $-(CH_2)_2CH_3$ | H | H | H | $-OC(O)CH_3$ | H | $-CH_3$ |
| 240 | $-(CH_2)_2CH_3$ | $-CH(CH_3)_2$ | H | H | H | $-OC(O)CH_3$ | H | $-CH_3$ |
| 241 | $-(CH_2)_2CH_3$ | $-(CH_2)_3CH_3$ | H | H | H | $-OC(O)CH_3$ | H | $-CH_3$ |
| 242 | $-(CH_2)_2CH_3$ | $-CH_2-HC=CH_2$ | H | H | H | $-OC(O)CH_3$ | H | $-CH_3$ |
| 243 | $-CH(CH_3)_2$ | $-CH(CH_3)_2$ | H | H | H | $-OC(O)CH_3$ | H | $-CH_3$ |
| 244 | $-CH(CH_3)_2$ | $-(CH_2)_3CH_3$ | H | H | H | $-OC(O)CH_3$ | H | $-CH_3$ |
| 245 | $-CH(CH_3)_2$ | $-CH_2-HC=CH_2$ | H | H | H | $-OC(O)CH_3$ | H | $-CH_3$ |
| 246 | $-(CH_2)_3CH_3$ | $-(CH_2)_3CH_3$ | H | H | H | $-OC(O)CH_3$ | H | $-CH_3$ |
| 247 | $-(CH_2)_3CH_3$ | $-CH_2-HC=CH_2$ | H | H | H | $-OC(O)CH_3$ | H | $-CH_3$ |
| 248 | $-CH_2-HC=CH_2$ | $-CH_2-HC=CH_2$ | H | H | H | $-OC(O)CH_3$ | H | $-CH_3$ |
| 249 | $-CH_3$ | $-CH_3$ | $-CH_3$ | H | H | H | H | H |
| 250 | $-CH_3$ | $-CH_3$ | $-CH_3$ | H | $-OH$ | H | H | H |
| 251 | $-CH_3$ | $-CH_3$ | $-CH_3$ | H | $-OC(O)CH_3$ | H | H | H |

TABLE 3-continued

| Ref. | X | Y | $R_2$ | $R_3$ | $R_4$ | $R_5$ | $R_6$ | $R_7$ |
|---|---|---|---|---|---|---|---|---|
| 252 | $-CH_3$ | $-CH_3$ | $-CH_3$ | H | $-OCH_3$ | H | H | H |
| 253 | $-CH_3$ | $-CH_2CH_3$ | $-CH_3$ | H | H | H | H | H |
| 254 | $-CH_3$ | $-CH_2(CH_3)_2$ | $-CH_3$ | H | H | H | H | H |
| 255 | $-CH_3$ | $-CH_3$ | $-CH_3$ | H | F | H | H | H |
| 256 | $-CH_3$ | $-CH_3$ | H | $-CH_3$ | H | H | H | H |
| 257 | $-CH_3$ | $-CH_3$ | H | $-CH_3$ | $-OH$ | H | H | H |
| 258 | $-CH_3$ | $-CH_3$ | H | $-CH_3$ | $-OC(O)CH_3$ | H | H | H |
| 259 | $-CH_3$ | $-CH_3$ | H | $-CH_3$ | $-OCH_3$ | H | H | H |
| 260 | $-CH_3$ | $-CH_2CH_3$ | H | $-CH_3$ | H | H | H | H |
| 261 | $-CH_3$ | $-CH_2(CH_3)_2$ | H | $-CH_3$ | H | H | H | H |
| 262 | $-CH_3$ | $-CH_3$ | H | $-CH_3$ | F | H | H | H |
| 263 | $-CH_3$ | $-CH_3$ | H | H | H | H | F | H |
| 264 | $-CH_3$ | $-CH_3$ | H | H | $-OH$ | H | F | H |
| 265 | $-CH_3$ | $-CH_3$ | H | H | $-OC(O)CH_3$ | H | F | H |
| 266 | $-CH_3$ | $-CH_3$ | H | H | $-OCH_3$ | H | F | H |
| 267 | $-CH_3$ | $-CH_2CH_3$ | H | H | H | H | F | H |
| 268 | $-CH_3$ | $-CH_2(CH_3)_2$ | H | H | H | H | F | H |
| 269 | $-CH_3$ | $-CH_3$ | H | H | F | H | F | H |
| 270 | $-CH_3$ | $-CH_3$ | H | H | H | H | H | $-CH_3$ |
| 271 | $-CH_3$ | $-CH_3$ | H | H | $-OH$ | H | H | $-CH_3$ |
| 272 | $-CH_3$ | $-CH_3$ | H | H | $-OC(O)CH_3$ | H | H | $-CH_3$ |
| 273 | $-CH_3$ | $-CH_3$ | H | H | $-OCH_3$ | H | H | $-CH_3$ |
| 274 | $-CH_3$ | $-CH_2CH_3$ | H | H | H | H | H | $-CH_3$ |
| 275 | $-CH_3$ | $-CH_2(CH_3)_2$ | H | H | H | H | H | $-CH_3$ |
| 276 | $-CH_3$ | $-CH_3$ | H | H | F | H | H | $-CH_3$ |
| 277 | $-CH_3$ | $-CH_3$ | $-CH_3$ | H | H | $-OH$ | H | H |
| 278 | $-CH_3$ | $-CH_3$ | $-CH_3$ | H | H | $-OC(O)CH_3$ | H | H |
| 279 | $-CH_3$ | $-CH_3$ | $-CH_3$ | H | H | $-OCH_3$ | H | H |
| 280 | $-CH_3$ | $-CH_2CH_3$ | $-CH_3$ | H | H | H | H | H |
| 281 | $-CH_3$ | $-CH_2(CH_3)_2$ | $-CH_3$ | H | H | H | H | H |
| 282 | $-CH_3$ | $-CH_3$ | $-CH_3$ | H | H | F | H | H |
| 283 | $-CH_3$ | $-CH_3$ | H | $-CH_3$ | H | H | H | H |
| 284 | $-CH_3$ | $-CH_3$ | H | $-CH_3$ | H | $-OH$ | H | H |
| 285 | $-CH_3$ | $-CH_3$ | H | $-CH_3$ | H | $-OC(O)CH_3$ | H | H |
| 286 | $-CH_3$ | $-CH_3$ | H | $-CH_3$ | H | $-OCH_3$ | H | H |
| 287 | $-CH_3$ | $-CH_2CH_3$ | H | $-CH_3$ | H | H | H | H |
| 288 | $-CH_3$ | $-CH_2(CH_3)_2$ | H | $-CH_3$ | H | H | H | H |
| 289 | $-CH_3$ | $-CH_3$ | H | $-CH_3$ | H | F | H | H |
| 290 | $-CH_3$ | $-CH_3$ | H | H | H | H | F | H |
| 291 | $-CH_3$ | $-CH_3$ | H | H | H | $-OH$ | F | H |
| 292 | $-CH_3$ | $-CH_3$ | H | H | H | $-OC(O)CH_3$ | F | H |
| 293 | $-CH_3$ | $-CH_3$ | H | H | H | $-OCH_3$ | F | H |
| 294 | $-CH_3$ | $-CH_2CH_3$ | H | H | H | H | F | H |
| 295 | $-CH_3$ | $-CH_2(CH_3)_2$ | H | H | H | H | F | H |
| 296 | $-CH_3$ | $-CH_3$ | H | H | H | F | F | H |
| 297 | $-CH_3$ | $-CH_3$ | H | H | H | H | H | $-CH_3$ |
| 298 | $-CH_3$ | $-CH_3$ | H | H | H | $-OH$ | H | $-CH_3$ |
| 299 | $-CH_3$ | $-CH_3$ | H | H | H | $-OC(O)CH_3$ | H | $-CH_3$ |
| 300 | $-CH_3$ | $-CH_3$ | H | H | H | $-OCH_3$ | H | $-CH_3$ |
| 301 | $-CH_3$ | $-CH_2CH_3$ | H | H | H | H | H | $-CH_3$ |
| 302 | $-CH_3$ | $-CH_2(CH_3)_2$ | H | H | H | H | H | $-CH_3$ |
| 303 | $-CH_3$ | $-CH_3$ | H | H | H | H | F | $-CH_3$ |
| 304 | H | $-CH_3$ | H | H | H | H | H | H |
| 305 | H | $-CH_2CH_3$ | H | H | H | H | H | H |
| 306 | H | $-(CH_2)_2CH_3$ | H | H | H | H | H | H |
| 307 | H | $-CH(CH_3)_2$ | H | H | H | H | H | H |
| 308 | H | $-(CH_2)_3CH_3$ | H | H | H | H | H | H |
| 309 | H | $-CH_2-HC=CH_2$ | H | H | H | H | H | H |
| 310 | H | $-CH_3$ | H | $-CH_3$ | H | H | H | H |
| 310a | H | $-CH_2CH_3$ | H | $-CH_3$ | H | H | H | H |
| 311 | H | $-(CH_2)_2CH_3$ | H | $-CH_3$ | H | H | H | H |
| 312 | H | $-CH(CH_3)_2$ | H | $-CH_3$ | H | H | H | H |
| 313 | H | $-(CH_2)_3CH_3$ | H | $-CH_3$ | H | H | H | H |
| 314 | H | $-CH_2-HC=CH_2$ | H | $-CH_3$ | H | H | H | H |
| 315 | H | $-CH_3$ | H | H | $-OH$ | H | H | H |
| 316 | H | $-CH_2CH_3$ | H | H | $-OH$ | H | H | H |
| 317 | H | $-(CH_2)_2CH_3$ | H | H | $-OH$ | H | H | H |
| 318 | H | $-CH(CH_3)_2$ | H | H | $-OH$ | H | H | H |
| 319 | H | $-(CH_2)_3CH_3$ | H | H | $-OH$ | H | H | H |
| 320 | H | $-CH_2-HC=CH_2$ | H | H | $-OH$ | H | H | H |
| 321 | H | $-CH_3$ | H | H | $-OC(O)CH_3$ | H | H | H |
| 322 | H | $-CH_2CH_3$ | H | H | $-OC(O)CH_3$ | H | H | H |
| 324 | H | $-(CH_2)_2CH_3$ | H | H | $-OC(O)CH_3$ | H | H | H |
| 325 | H | $-CH(CH_3)_2$ | H | H | $-OC(O)CH_3$ | H | H | H |
| 326 | H | $-(CH_2)_3CH_3$ | H | H | $-OC(O)CH_3$ | H | H | H |
| 327 | H | $-CH_2-HC=CH_2$ | H | H | $-OC(O)CH_3$ | H | H | H |
| 328 | H | $-CH_3$ | H | H | H | $-OCH_3$ | H | H |
| 329 | H | $-CH_2CH_3$ | H | H | H | $-OCH_3$ | H | H |

TABLE 3-continued

| Ref. | X | Y | $R_2$ | $R_3$ | $R_4$ | $R_5$ | $R_6$ | $R_7$ |
|---|---|---|---|---|---|---|---|---|
| 330 | H | $—(CH_2)_2CH_3$ | H | H | H | $—OCH_3$ | H | H |
| 331 | H | $—CH(CH_3)_2$ | H | H | H | $—OCH_3$ | H | H |
| 332 | H | $—(CH_2)_3CH_3$ | H | H | H | $—OCH_3$ | H | H |
| 333 | H | $—CH_2—HC{=}CH_2$ | H | H | H | $—OCH_3$ | H | H |
| 334 | H | $—CH_3$ | H | H | H | H | F | H |
| 335 | H | $—CH_2CH_3$ | H | H | H | H | F | H |
| 336 | H | $—(CH_2)_2CH_3$ | H | H | H | H | F | H |
| 337 | H | $—CH(CH_3)_2$ | H | H | H | H | F | H |
| 338 | H | $—(CH_2)_3CH_3$ | H | H | H | H | F | H |
| 339 | H | $—CH_2—HC{=}CH_2$ | H | H | H | H | F | H |
| 340 | H | $—CH_3$ | H | $—CH_3$ | —OH | H | H | H |
| 341 | H | $—CH_2CH_3$ | H | $—CH_3$ | —OH | H | H | H |
| 342 | H | $—(CH_2)_2CH_3$ | H | $—CH_3$ | —OH | H | H | H |
| 343 | H | $—CH(CH_3)_2$ | H | $—CH_3$ | —OH | H | H | H |
| 344 | H | $—(CH_2)_3CH_3$ | H | $—CH_3$ | —OH | H | H | H |
| 345 | H | $—CH_2—HC{=}CH_2$ | H | $—CH_3$ | —OH | H | H | H |
| 346 | H | $—CH_3$ | H | $—CH_3$ | $—OC(O)CH_3$ | H | H | H |
| 347 | H | $—CH_2CH_3$ | H | $—CH_3$ | $—OC(O)CH_3$ | H | H | H |
| 348 | H | $—(CH_2)_2CH_3$ | H | $—CH_3$ | $—OC(O)CH_3$ | H | H | H |
| 349 | H | $—CH(CH_3)_2$ | H | $—CH_3$ | $—OC(O)CH_3$ | H | H | H |
| 350 | H | $—(CH_2)_3CH_3$ | H | $—CH_3$ | $—OC(O)CH_3$ | H | H | H |
| 351 | H | $—CH_2—HC{=}CH_2$ | H | $—CH_3$ | $—OC(O)CH_3$ | H | H | H |
| 352 | H | $—CH_3$ | H | $—CH_3$ | H | $—OCH_3$ | H | H |
| 353 | H | $—CH_2CH_3$ | H | $—CH_3$ | H | $—OCH_3$ | H | H |
| 354 | H | $—(CH_2)_2CH_3$ | H | $—CH_3$ | H | $—OCH_3$ | H | H |
| 355 | H | $—CH(CH_3)_2$ | H | $—CH_3$ | H | $—OCH_3$ | H | H |
| 356 | H | $—(CH_2)_3CH_3$ | H | $—CH_3$ | H | $—OCH_3$ | H | H |
| 357 | H | $—CH_2—HC{=}CH_2$ | H | $—CH_3$ | H | $—OCH_3$ | H | H |
| 358 | H | $—CH_3$ | H | $—CH_3$ | H | H | F | H |
| 359 | H | $—CH_2CH_3$ | H | $—CH_3$ | H | H | F | H |
| 360 | H | $—(CH_2)_2CH_3$ | H | $—CH_3$ | H | H | F | H |
| 361 | H | $—CH(CH_3)_2$ | H | $—CH_3$ | H | H | F | H |
| 362 | H | $—(CH_2)_3CH_3$ | H | $—CH_3$ | H | H | F | H |
| 363 | H | $—CH_2—HC{=}CH_2$ | H | $—CH_3$ | H | H | F | H |
| 364 | H | cyclopropyl | H | H | H | H | H | H |
| 365 | H | cyclopropyl | H | $—CH_3$ | H | H | H | H |
| 366 | H | cyclopropyl | H | H | —OH | H | H | H |
| 367 | H | cyclopropyl | H | H | $—OC(O)CH_3$ | H | H | H |
| 368 | H | cyclopropyl | H | H | H | $—OCH_3$ | H | H |
| 369 | H | cyclopropyl | H | H | H | H | F | H |
| 370 | H | cyclopropyl | H | H | H | H | H | H |
| 371 | H | cyclopropyl | H | $—CH_3$ | —OH | H | F | H |
| 372 | H | cyclopropyl | H | $—CH_3$ | —OH | H | H | H |
| 373 | H | cyclopropyl | H | $—CH_3$ | $—OC(O)CH_3$ | H | H | H |
| 374 | H | cyclopropyl | H | $—CH_3$ | H | $—OCH_3$ | H | H |
| 375 | H | cyclopropyl | H | $—CH_3$ | H | H | F | H |
| 376 | $—CH_3$ | cyclopropyl | H | H | H | H | H | H |
| 377 | $—CH_3$ | cyclopropyl | H | $—CH_3$ | H | H | H | H |
| 378 | $—CH_3$ | cyclopropyl | H | H | —OH | H | H | H |
| 379 | $—CH_3$ | cyclopropyl | H | H | $—OC(O)CH_3$ | H | H | H |
| 380 | $—CH_3$ | cyclopropyl | H | H | H | $—OCH_3$ | H | H |
| 381 | $—CH_3$ | cyclopropyl | H | H | H | H | F | H |
| 382 | $—CH_3$ | cyclopropyl | H | H | H | H | H | H |
| 383 | $—CH_3$ | cyclopropyl | H | $—CH_3$ | —OH | H | F | H |
| 384 | $—CH_3$ | cyclopropyl | H | $—CH_3$ | —OH | H | H | H |
| 385 | $—CH_3$ | cyclopropyl | H | $—CH_3$ | $—OC(O)CH_3$ | H | H | H |
| 386 | $—CH_3$ | cyclopropyl | H | $—CH_3$ | H | $—OCH_3$ | H | H |
| 387 | $—CH_3$ | cyclopropyl | H | $—CH_3$ | H | H | F | H |
| 388 | $—CH_2CH_3$ | cyclopropyl | H | H | H | H | H | H |
| 389 | $—CH_2CH_3$ | cyclopropyl | H | $—CH_3$ | H | H | H | H |
| 390 | $—CH_2CH_3$ | cyclopropyl | H | H | —OH | H | H | H |
| 391 | $—CH_2CH_3$ | cyclopropyl | H | H | $—OC(O)CH_3$ | H | H | H |
| 392 | $—CH_2CH_3$ | cyclopropyl | H | H | H | $—OCH_3$ | H | H |
| 393 | $—CH_2CH_3$ | cyclopropyl | H | H | H | H | F | H |
| 394 | $—CH_2CH_3$ | cyclopropyl | H | H | H | H | H | H |
| 395 | $—CH_2CH_3$ | cyclopropyl | H | $—CH_3$ | —OH | H | F | H |
| 396 | $—CH_2CH_3$ | cyclopropyl | H | $—CH_3$ | —OH | H | H | H |
| 397 | $—CH_2CH_3$ | cyclopropyl | H | $—CH_3$ | $—OC(O)CH_3$ | H | H | H |
| 398 | $—CH_2CH_3$ | cyclopropyl | H | $—CH_3$ | H | $—OCH_3$ | H | H |
| 399 | $—CH_2CH_3$ | cyclopropyl | H | $—CH_3$ | H | H | F | H |
| 400 | $—(CH_2)_2CH_3$ | cyclopropyl | H | H | H | H | H | H |
| 401 | $—(CH_2)_2CH_3$ | cyclopropyl | H | $—CH_3$ | H | H | H | H |
| 402 | $—(CH_2)_2CH_3$ | cyclopropyl | H | H | —OH | H | H | H |
| 403 | $—(CH_2)_2CH_3$ | cyclopropyl | H | H | $—OC(O)CH_3$ | H | H | H |
| 404 | $—(CH_2)_2CH_3$ | cyclopropyl | H | H | H | $—OCH_3$ | H | H |
| 405 | $—(CH_2)_2CH_3$ | cyclopropyl | H | H | H | H | F | H |
| 406 | $—(CH_2)_2CH_3$ | cyclopropyl | H | H | H | H | H | H |
| 407 | $—(CH_2)_2CH_3$ | cyclopropyl | H | $—CH_3$ | —OH | H | F | H |

TABLE 3-continued

| Ref. | X | Y | $R_2$ | $R_3$ | $R_4$ | $R_5$ | $R_6$ | $R_7$ |
|---|---|---|---|---|---|---|---|---|
| 408 | $—(CH_2)_2CH_3$ | cyclopropyl | H | $—CH_3$ | —OH | H | H | H |
| 409 | $—(CH_2)_2CH_3$ | cyclopropyl | H | $—CH_3$ | $—OC(O)CH_3$ | H | H | H |
| 410 | $—(CH_2)_2CH_3$ | cyclopropyl | H | $—CH_3$ | H | $—OCH_3$ | H | H |
| 411 | $—(CH_2)_2CH_3$ | cyclopropyl | H | $—CH_3$ | H | H | F | H |
| 412 | $—CH_2(CH_3)_2$ | cyclopropyl | H | H | H | H | H | H |
| 413 | $—CH_2(CH_3)_2$ | cyclopropyl | H | $—CH_3$ | H | H | H | H |
| 414 | $—CH_2(CH_3)_2$ | cyclopropyl | H | H | —OH | H | H | H |
| 415 | $—CH_2(CH_3)_2$ | cyclopropyl | H | H | $—OC(O)CH_3$ | H | H | H |
| 416 | $—CH_2(CH_3)_2$ | cyclopropyl | H | H | H | $—OCH_3$ | H | H |
| 417 | $—CH_2(CH_3)_2$ | cyclopropyl | H | H | H | H | F | H |
| 418 | $—CH_2(CH_3)_2$ | cyclopropyl | H | H | H | H | H | H |
| 419 | $—CH_2(CH_3)_2$ | cyclopropyl | H | $—CH_3$ | —OH | H | F | H |
| 420 | $—CH_2(CH_3)_2$ | cyclopropyl | H | $—CH_3$ | —OH | H | H | H |
| 421 | $—CH_2(CH_3)_2$ | cyclopropyl | H | $—CH_3$ | $—OC(O)CH_3$ | H | H | H |
| 422 | $—CH_2(CH_3)_2$ | cyclopropyl | H | $—CH_3$ | H | $—OCH_3$ | H | H |
| 423 | $—CH_2(CH_3)_2$ | cyclopropyl | H | $—CH_3$ | H | H | F | H |
| 424 | cyclopropyl | cyclopropyl | H | $—CH_3$ | H | H | H | H |
| 425 | cyclopropyl | cyclopropyl | H | H | —OH | H | H | H |
| 426 | cyclopropyl | cyclopropyl | H | H | $—OC(O)CH_3$ | H | H | H |
| 427 | cyclopropyl | cyclopropyl | H | H | H | $—OCH_3$ | H | H |
| 428 | cyclopropyl | cyclopropyl | H | H | H | H | F | H |
| 429 | cyclopropyl | cyclopropyl | H | H | H | H | H | H |
| 430 | cyclopropyl | cyclopropyl | H | $—CH_3$ | —OH | H | F | H |
| 431 | cyclopropyl | cyclopropyl | H | $—CH_3$ | —OH | H | H | H |
| 432 | cyclopropyl | cyclopropyl | H | $—CH_3$ | $—OC(O)CH_3$ | H | H | H |
| 433 | cyclopropyl | cyclopropyl | H | $—CH_3$ | H | $—OCH_3$ | H | H |
| 434 | cyclopropyl | cyclopropyl | H | $—CH_3$ | H | H | F | H |
| 435 | H | $—CH_3$ | H | H | —OH | H | H | $—CH_3$ |
| 436 | H | $—CH_2CH_3$ | H | H | —OH | H | H | $—CH_3$ |
| 437 | H | $—(CH_2)_2CH_3$ | H | H | —OH | H | H | $—CH_3$ |
| 438 | H | $—CH(CH_3)_2$ | H | H | —OH | H | H | $—CH_3$ |
| 439 | H | $—(CH_2)_3CH_3$ | H | H | —OH | H | H | $—CH_3$ |
| 440 | H | $—CH_2—HC{=}CH_2$ | H | H | —OH | H | H | $—CH_3$ |
| 441 | H | $—CH_3$ | H | H | $—OC(O)CH_3$ | H | H | $—CH_3$ |
| 442 | H | $—CH_2CH_3$ | H | H | $—OC(O)CH_3$ | H | H | $—CH_3$ |
| 443 | H | $—(CH_2)_2CH_3$ | H | H | $—OC(O)CH_3$ | H | H | $—CH_3$ |
| 444 | H | $—CH(CH_3)_2$ | H | H | $—OC(O)CH_3$ | H | H | $—CH_3$ |
| 445 | H | $—(CH_2)_3CH_3$ | H | H | $—OC(O)CH_3$ | H | H | $—CH_3$ |
| 446 | H | $—CH_2—HC{=}CH_2$ | H | H | $—OC(O)CH_3$ | H | H | $—CH_3$ |
| 447 | H | $—CH_3$ | H | H | H | $—OCH_3$ | H | $—CH_3$ |
| 448 | H | $—CH_2CH_3$ | H | H | H | $—OCH_3$ | H | $—CH_3$ |
| 449 | H | $—(CH_2)_2CH_3$ | H | H | H | $—OCH_3$ | H | $—CH_3$ |
| 450 | H | $—CH(CH_3)_2$ | H | H | H | $—OCH_3$ | H | $—CH_3$ |
| 451 | H | $—(CH_2)_3CH_3$ | H | H | H | $—OCH_3$ | H | $—CH_3$ |
| 452 | H | $—CH_2—HC{=}CH_2$ | H | H | H | $—OCH_3$ | H | $—CH_3$ |
| 453 | H | $—CH_3$ | H | H | —OH | H | F | H |
| 454 | H | $—CH_2CH_3$ | H | H | —OH | H | F | H |
| 455 | H | $—(CH_2)_2CH_3$ | H | H | —OH | H | F | H |
| 456 | H | $—CH(CH_3)_2$ | H | H | —OH | H | F | H |
| 457 | H | $—(CH_2)_3CH_3$ | H | H | —OH | H | F | H |
| 458 | H | $—CH_2—HC{=}CH_2$ | H | H | —OH | H | F | H |
| 459 | H | $—CH_3$ | H | H | $—OC(O)CH_3$ | H | F | H |
| 460 | H | $—CH_2CH_3$ | H | H | $—OC(O)CH_3$ | H | F | H |
| 461 | H | $—(CH_2)_2CH_3$ | H | H | $—OC(O)CH_3$ | H | F | H |
| 462 | H | $—CH(CH_3)_2$ | H | H | $—OC(O)CH_3$ | H | F | H |
| 463 | H | $—(CH_2)_3CH_3$ | H | H | $—OC(O)CH_3$ | H | F | H |
| 464 | H | $—CH_2—HC{=}CH_2$ | H | H | $—OC(O)CH_3$ | H | F | H |
| 465 | H | $—CH_3$ | H | H | H | $—OCH_3$ | F | H |
| 466 | H | $—CH_2CH_3$ | H | H | H | $—OCH_3$ | F | H |
| 467 | H | $—(CH_2)_2CH_3$ | H | H | H | $—OCH_3$ | F | H |
| 468 | H | $—CH(CH_3)_2$ | H | H | H | $—OCH_3$ | F | H |
| 469 | H | $—(CH_2)_3CH_3$ | H | H | H | $—OCH_3$ | F | H |
| 470 | H | $—CH_2—HC{=}CH_2$ | H | H | H | $—OCH_3$ | F | H |
| 471 | H | $—CD_3$ | H | H | H | H | H | H |
| 472 | H | $—CD_3$ | H | H | —OH | H | H | H |
| 473 | H | $—CD_3$ | H | H | $—OC(O)CH_3$ | H | H | H |
| 474 | H | $—CD_3$ | H | H | H | $—OCH_3$ | H | H |
| 475 | H | $—CD_3$ | H | H | H | H | F | H |
| 476 | H | $—CD_3$ | H | H | —OH | H | F | H |
| 477 | H | $—CD_3$ | H | H | $—OC(O)CH_3$ | H | F | H |
| 478 | H | $—CD_3$ | H | H | H | $—OCH_3$ | F | H |
| 479 | H | $—CD_3$ | H | H | H | H | H | $—CH_3$ |
| 480 | H | $—CD_3$ | H | H | —OH | H | H | $—CH_3$ |
| 481 | H | $—CD_3$ | H | H | $—OC(O)CH_3$ | H | H | $—CH_3$ |
| 482 | H | $—CD_3$ | H | H | H | $—OCH_3$ | H | $—CH_3$ |
| 483 | H | $—CD_3$ | H | H | H | H | F | $—CH_3$ |
| 484 | H | $—CD_3$ | H | H | —OH | H | F | $—CH_3$ |
| 485 | H | $—CD_3$ | H | H | $—OC(O)CH_3$ | H | F | $—CH_3$ |

TABLE 3-continued

| Ref. | X | Y | $R_2$ | $R_3$ | $R_4$ | $R_5$ | $R_6$ | $R_7$ |
|---|---|---|---|---|---|---|---|---|
| 486 | H | $—CD_3$ | H | H | H | $—OCH_3$ | F | $—CH_3$ |
| 487 | H | $—CD_2CD_3$ | H | H | H | H | H | H |
| 488 | H | $—CD_2CD_3$ | H | H | —OH | H | H | H |
| 489 | H | $—CD_2CD_3$ | H | H | $—OC(O)CH_3$ | H | H | H |
| 490 | H | $—CD_2CD_3$ | H | H | H | $—OCH_3$ | H | H |
| 491 | H | $—CD_2CD_3$ | H | H | H | H | F | H |
| 492 | H | $—CD_2CD_3$ | H | H | —OH | H | F | H |
| 493 | H | $—CD_2CD_3$ | H | H | $—OC(O)CH_3$ | H | F | H |
| 494 | H | $—CD_2CD_3$ | H | H | H | $—OCH_3$ | F | H |
| 495 | H | $—CD_2CD_3$ | H | H | H | H | H | $—CH_3$ |
| 496 | H | $—CD_2CD_3$ | H | H | —OH | H | H | $—CH_3$ |
| 497 | H | $—CD_2CD_3$ | H | H | $—OC(O)CH_3$ | H | H | $—CH_3$ |
| 498 | H | $—CD_2CD_3$ | H | H | H | $—OCH_3$ | H | $—CH_3$ |
| 499 | H | $—CD_2CD_3$ | H | H | H | H | F | $—CH_3$ |
| 500 | H | $—CD_2CD_3$ | H | H | —OH | H | F | $—CH_3$ |
| 501 | H | $—CD_2CD_3$ | H | H | $—OC(O)CH_3$ | H | F | $—CH_3$ |
| 502 | H | $—CD_2CD_3$ | H | H | H | $—OCH_3$ | F | $—CH_3$ |
| 503 | H | $—CH_3$ | H | H | —OH | H | F | $—CH_3$ |
| 504 | H | $—CH_2CH_3$ | H | H | —OH | H | F | $—CH_3$ |
| 505 | H | $—(CH_2)_2CH_3$ | H | H | —OH | H | F | $—CH_3$ |
| 506 | H | $—CH(CH_3)_2$ | H | H | —OH | H | F | $—CH_3$ |
| 507 | H | $—(CH_2)_3CH_3$ | H | H | —OH | H | F | $—CH_3$ |
| 508 | H | $—CH_2—HC{=}CH_2$ | H | H | —OH | H | F | $—CH_3$ |
| 509 | H | $—CH_3$ | H | H | $—OC(O)CH_3$ | H | F | $—CH_3$ |
| 510 | H | $—CH_2CH_3$ | H | H | $—OC(O)CH_3$ | H | F | $—CH_3$ |
| 511 | H | $—(CH_2)_2CH_3$ | H | H | $—OC(O)CH_3$ | H | F | $—CH_3$ |
| 512 | H | $—CH(CH_3)_2$ | H | H | $—OC(O)CH_3$ | H | F | $—CH_3$ |
| 513 | H | $—(CH_2)_3CH_3$ | H | H | $—OC(O)CH_3$ | H | F | $—CH_3$ |
| 514 | H | $—CH_2—HC{=}CH_2$ | H | H | $—OC(O)CH_3$ | H | F | $—CH_3$ |
| 515 | H | $—CH_3$ | H | H | H | $—OCH_3$ | F | $—CH_3$ |
| 516 | H | $—CH_2CH_3$ | H | H | H | $—OCH_3$ | F | $—CH_3$ |
| 517 | H | $—(CH_2)_2CH_3$ | H | H | H | $—OCH_3$ | F | $—CH_3$ |
| 518 | H | $—CH(CH_3)_2$ | H | H | H | $—OCH_3$ | F | $—CH_3$ |
| 519 | H | $—(CH_2)_3CH_3$ | H | H | H | $—OCH_3$ | F | $—CH_3$ |
| 520 | H | $—CH_2—HC{=}CH_2$ | H | H | H | $—OCH_3$ | F | $—CH_3$ |
| 521 | H | $—CH_3$ | H | D | H | H | H | H |
| 522 | H | $—CH_2CH_3$ | H | D | H | H | H | H |
| 523 | H | $—(CH_2)_2CH_3$ | H | D | H | H | H | H |
| 524 | H | $—CH(CH_3)_2$ | H | D | H | H | H | H |
| 525 | H | $—(CH_2)_3CH_3$ | H | D | H | H | H | H |
| 526 | H | $—CH_2—HC{=}CH_2$ | H | D | H | H | H | H |
| 527 | H | $—CH_3$ | H | D | —OH | H | H | H |
| 528 | H | $—CH_2CH_3$ | H | D | —OH | H | H | H |
| 529 | H | $—(CH_2)_2CH_3$ | H | D | —OH | H | H | H |
| 530 | H | $—CH(CH_3)_2$ | H | D | —OH | H | H | H |
| 531 | H | $—(CH_2)_3CH_3$ | H | D | —OH | H | H | H |
| 532 | H | $—CH_2—HC{=}CH_2$ | H | D | —OH | H | H | H |
| 533 | H | $—CH_3$ | H | D | $—OC(O)CH_3$ | H | H | H |
| 534 | H | $—CH_2CH_3$ | H | D | $—OC(O)CH_3$ | H | H | H |
| 535 | H | $—(CH_2)_2CH_3$ | H | D | $—OC(O)CH_3$ | H | H | H |
| 536 | H | $—CH(CH_3)_2$ | H | D | $—OC(O)CH_3$ | H | H | H |
| 537 | H | $—(CH_2)_3CH_3$ | H | D | $—OC(O)CH_3$ | H | H | H |
| 538 | H | $—CH_2—HC{=}CH_2$ | H | D | $—OC(O)CH_3$ | H | H | H |
| 539 | H | $—CH_3$ | H | D | H | $—OCH_3$ | H | H |
| 540 | H | $—CH_2CH_3$ | H | D | H | $—OCH_3$ | H | H |
| 541 | H | $—(CH_2)_2CH_3$ | H | D | H | $—OCH_3$ | H | H |
| 542 | H | $—CH(CH_3)_2$ | H | D | H | $—OCH_3$ | H | H |
| 543 | H | $—(CH_2)_3CH_3$ | H | D | H | $—OCH_3$ | H | H |
| 544 | H | $—CH_2—HC{=}CH_2$ | H | D | H | $—OCH_3$ | H | H |
| 545 | H | $—CH_3$ | H | D | H | H | F | H |
| 546 | H | $—CH_2CH_3$ | H | D | H | H | F | H |
| 547 | H | $—(CH_2)_2CH_3$ | H | D | H | H | F | H |
| 548 | H | $—CH(CH_3)_2$ | H | D | H | H | F | H |
| 549 | H | $—(CH_2)_3CH_3$ | H | D | H | H | F | H |
| 550 | H | $—CH_2—HC{=}CH_2$ | H | D | H | H | F | H |
| 551 | H | $—CH_3$ | H | D | H | H | F | $CH_3$ |
| 552 | H | $—CH_2CH_3$ | H | D | H | H | F | $CH_3$ |
| 553 | H | $—(CH_2)_2CH_3$ | H | D | H | H | F | $CH_3$ |
| 554 | H | $—CH(CH_3)_2$ | H | D | H | H | F | $CH_3$ |
| 555 | H | $—(CH_2)_3CH_3$ | H | D | H | H | F | $CH_3$ |
| 556 | H | $—CH_2—HC{=}CH_2$ | H | D | H | H | F | $CH_3$ |

Other exemplary compounds of Formula I include those below in Table 4, which is also represented by Formula Id:

Formula Id

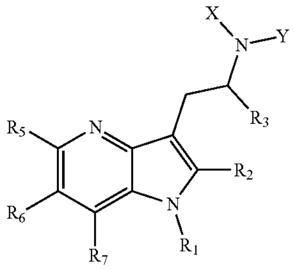

TABLE 4

| Ref. | X | Y | $R_2$ | $R_3$ | $R_5$ | $R_6$ | $R_7$ | $R_1$ |
|---|---|---|---|---|---|---|---|---|
| 1 | $-CH_3$ | $-CH_3$ | H | H | $-OCH_3$ | H | H | H |
| 2 | $-CH_3$ | $-CH_2CH_3$ | H | H | $-OCH_3$ | H | H | H |
| 3 | $-CH_3$ | $-(CH_2)_2CH_3$ | H | H | $-OCH_3$ | H | H | H |
| 4 | $-CH_3$ | $-CH(CH_3)_2$ | H | H | $-OCH_3$ | H | H | H |
| 5 | $-CH_3$ | $-(CH_2)_3CH_3$ | H | H | $-OCH_3$ | H | H | H |
| 6 | $-CH_3$ | $-CH_2-HC=CH_2$ | H | H | $-OCH_3$ | H | H | H |
| 7 | $-CH_2CH_3$ | $-CH_2CH_3$ | H | H | $-OCH_3$ | H | H | H |
| 8 | $-CH_2CH_3$ | $-(CH_2)_2CH_3$ | H | H | $-OCH_3$ | H | H | H |
| 9 | $-CH_2CH_3$ | $-CH(CH_3)_2$ | H | H | $-OCH_3$ | H | H | H |
| 10 | $-CH_2CH_3$ | $-(CH_2)_3CH_3$ | H | H | $-OCH_3$ | H | H | H |
| 11 | $-CH_2CH_3$ | $-CH_2-HC=CH_2$ | H | H | $-OCH_3$ | H | H | H |
| 12 | $-(CH_2)_2CH_3$ | $-(CH_2)_2CH_3$ | H | H | $-OCH_3$ | H | H | H |
| 13 | $-(CH_2)_2CH_3$ | $-CH(CH_3)_2$ | H | H | $-OCH_3$ | H | H | H |
| 14 | $-(CH_2)_2CH_3$ | $-(CH_2)_3CH_3$ | H | H | $-OCH_3$ | H | H | H |
| 15 | $-(CH_2)_2CH_3$ | $-CH_2-HC=CH_2$ | H | H | $-OCH_3$ | H | H | H |
| 16 | $-CH(CH_3)_2$ | $-CH(CH_3)_2$ | H | H | $-OCH_3$ | H | H | H |
| 17 | $-CH(CH_3)_2$ | $-(CH_2)_3CH_3$ | H | H | $-OCH_3$ | H | H | H |
| 18 | $-CH(CH_3)_2$ | $-CH_2-HC=CH_2$ | H | H | $-OCH_3$ | H | H | H |
| 19 | $-(CH_2)_3CH_3$ | $-(CH_2)_3CH_3$ | H | H | $-OCH_3$ | H | H | H |
| 20 | $-(CH_2)_3CH_3$ | $-CH_2-HC=CH_2$ | H | H | $-OCH_3$ | H | H | H |
| 21 | $-CH_2-HC=CH_2$ | $-CH_2-HC=CH_2$ | H | H | $-OCH_3$ | H | H | H |
| 22 | $-CH_3$ | $-CH_2CH_3$ | H | H | $-OH$ | H | H | H |
| 23 | $-CH_3$ | $-(CH_2)_2CH_3$ | H | H | $-OH$ | H | H | H |
| 24 | $-CH_3$ | $-CH(CH_3)_2$ | H | H | $-OH$ | H | H | H |
| 25 | $-CH_3$ | $-(CH_2)_3CH_3$ | H | H | $-OH$ | H | H | H |
| 26 | $-CH_3$ | $-CH_2-HC=CH_2$ | H | H | $-OH$ | H | H | H |
| 27 | $-CH_2CH_3$ | $-CH_2CH_3$ | H | H | $-OH$ | H | H | H |
| 28 | $-CH_2CH_3$ | $-(CH_2)_2CH_3$ | H | H | $-OH$ | H | H | H |
| 29 | $-CH_2CH_3$ | $-CH(CH_3)_2$ | H | H | $-OH$ | H | H | H |
| 30 | $-CH_2CH_3$ | $-(CH_2)_3CH_3$ | H | H | $-OH$ | H | H | H |
| 31 | $-CH_2CH_3$ | $-CH_2-HC=CH_2$ | H | H | $-OH$ | H | H | H |
| 32 | $-(CH_2)_2CH_3$ | $-(CH_2)_2CH_3$ | H | H | $-OH$ | H | H | H |
| 33 | $-(CH_2)_2CH_3$ | $-CH(CH_3)_2$ | H | H | $-OH$ | H | H | H |
| 34 | $-(CH_2)_2CH_3$ | $-(CH_2)_3CH_3$ | H | H | $-OH$ | H | H | H |
| 35 | $-(CH_2)_2CH_3$ | $-CH_2-HC=CH_2$ | H | H | $-OH$ | H | H | H |
| 36 | $-CH(CH_3)_2$ | $-CH(CH_3)_2$ | H | H | $-OH$ | H | H | H |
| 37 | $-CH(CH_3)_2$ | $-(CH_2)_3CH_3$ | H | H | $-OH$ | H | H | H |
| 38 | $-CH(CH_3)_2$ | $-CH_2-HC=CH_2$ | H | H | $-OH$ | H | H | H |
| 39 | $-(CH_2)_3CH_3$ | $-(CH_2)_3CH_3$ | H | H | $-OH$ | H | H | H |
| 40 | $-(CH_2)_3CH_3$ | $-CH_2-HC=CH_2$ | H | H | $-OH$ | H | H | H |
| 41 | $-CH_2-HC=CH_2$ | $-CH_2-HC=CH_2$ | H | H | $-OH$ | H | H | H |
| 42 | $-CH_3$ | $-CH_3$ | H | H | $-OC(O)CH_3$ | H | H | H |
| 43 | $-CH_3$ | $-CH_2CH_3$ | H | H | $-OC(O)CH_3$ | H | H | H |
| 44 | $-CH_3$ | $-(CH_2)_2CH_3$ | H | H | $-OC(O)CH_3$ | H | H | H |
| 45 | $-CH_3$ | $-CH(CH_3)_2$ | H | H | $-OC(O)CH_3$ | H | H | H |
| 46 | $-CH_3$ | $-(CH_2)_3CH_3$ | H | H | $-OC(O)CH_3$ | H | H | H |
| 47 | $-CH_3$ | $-CH_2-HC=CH_2$ | H | H | $-OC(O)CH_3$ | H | H | H |
| 48 | $-CH_2CH_3$ | $-CH_2CH_3$ | H | H | $-OC(O)CH_3$ | H | H | H |
| 49 | $-CH_2CH_3$ | $-(CH_2)_2CH_3$ | H | H | $-OC(O)CH_3$ | H | H | H |
| 50 | $-CH_2CH_3$ | $-CH(CH_3)_2$ | H | H | $-OC(O)CH_3$ | H | H | H |
| 51 | $-CH_2CH_3$ | $-(CH_2)_3CH_3$ | H | H | $-OC(O)CH_3$ | H | H | H |
| 52 | $-CH_2CH_3$ | $-CH_2-HC=CH_2$ | H | H | $-OC(O)CH_3$ | H | H | H |
| 53 | $-(CH_2)_2CH_3$ | $-(CH_2)_2CH_3$ | H | H | $-OC(O)CH_3$ | H | H | H |
| 54 | $-(CH_2)_2CH_3$ | $-CH(CH_3)_2$ | H | H | $-OC(O)CH_3$ | H | H | H |
| 55 | $-(CH_2)_2CH_3$ | $-(CH_2)_3CH_3$ | H | H | $-OC(O)CH_3$ | H | H | H |
| 56 | $-(CH_2)_2CH_3$ | $-CH_2-HC=CH_2$ | H | H | $-OC(O)CH_3$ | H | H | H |

TABLE 4-continued

| Ref. | X | Y | $R_2$ | $R_3$ | $R_5$ | $R_6$ | $R_7$ | $R_1$ |
|---|---|---|---|---|---|---|---|---|
| 57 | $-CH(CH_3)_2$ | $-CH(CH_3)_2$ | H | H | $-OC(O)CH_3$ | H | H | H |
| 58 | $-CH(CH_3)_2$ | $-(CH_2)_3CH_3$ | H | H | $-OC(O)CH_3$ | H | H | H |
| 59 | $-CH(CH_3)_2$ | $-CH_2-HC=CH_2$ | H | H | $-OC(O)CH_3$ | H | H | H |
| 60 | $-(CH_2)_3CH_3$ | $-(CH_2)_3CH_3$ | H | H | $-OC(O)CH_3$ | H | H | H |
| 61 | $-(CH_2)_3CH_3$ | $-CH_2-HC=CH_2$ | H | H | $-OC(O)CH_3$ | H | H | H |
| 62 | $-CH_2-HC=CH_2$ | $-CH_2-HC=CH_2$ | H | H | $-OC(O)CH_3$ | H | H | H |
| 63 | $-CH_3$ | $-CH_3$ | H | H | $-OCH_3$ | H | H | $-CH_2CH_3$ |
| 64 | $-CH_3$ | $-CH_2CH_3$ | H | H | $-OCH_3$ | H | H | $-CH_2CH_3$ |
| 65 | $-CH_3$ | $-(CH_2)_2CH_3$ | H | H | $-OCH_3$ | H | H | $-CH_2CH_3$ |
| 66 | $-CH_3$ | $-CH(CH_3)_2$ | H | H | $-OCH_3$ | H | H | $-CH_2CH_3$ |
| 67 | $-CH_3$ | $-(CH_2)_3CH_3$ | H | H | $-OCH_3$ | H | H | $-CH_2CH_3$ |
| 68 | $-CH_3$ | $-CH_2-HC=CH_2$ | H | H | $-OCH_3$ | H | H | $-CH_2CH_3$ |
| 69 | $-CH_2CH_3$ | $-CH_2CH_3$ | H | H | $-OCH_3$ | H | H | $-CH_2CH_3$ |
| 70 | $-CH_2CH_3$ | $-(CH_2)_2CH_3$ | H | H | $-OCH_3$ | H | H | $-CH_2CH_3$ |
| 71 | $-CH_2CH_3$ | $-CH(CH_3)_2$ | H | H | $-OCH_3$ | H | H | $-CH_2CH_3$ |
| 72 | $-CH_2CH_3$ | $-(CH_2)_3CH_3$ | H | H | $-OCH_3$ | H | H | $-CH_2CH_3$ |
| 73 | $-CH_2CH_3$ | $-CH_2-HC=CH_2$ | H | H | $-OCH_3$ | H | H | $-CH_2CH_3$ |
| 74 | $-(CH_2)_2CH_3$ | $-(CH_2)_2CH_3$ | H | H | $-OCH_3$ | H | H | $-CH_2CH_3$ |
| 75 | $-(CH_2)_2CH_3$ | $-CH(CH_3)_2$ | H | H | $-OCH_3$ | H | H | $-CH_2CH_3$ |
| 76 | $-(CH_2)_2CH_3$ | $-(CH_2)_3CH_3$ | H | H | $-OCH_3$ | H | H | $-CH_2CH_3$ |
| 77 | $-(CH_2)_2CH_3$ | $-CH_2-HC=CH_2$ | H | H | $-OCH_3$ | H | H | $-CH_2CH_3$ |
| 78 | $-CH(CH_3)_2$ | $-CH(CH_3)_2$ | H | H | $-OCH_3$ | H | H | $-CH_2CH_3$ |
| 79 | $-CH(CH_3)_2$ | $-(CH_2)_3CH_3$ | H | H | $-OCH_3$ | H | H | $-CH_2CH_3$ |
| 80 | $-CH(CH_3)_2$ | $-CH_2-HC=CH_2$ | H | H | $-OCH_3$ | H | H | $-CH_2CH_3$ |
| 81 | $-(CH_2)_3CH_3$ | $-(CH_2)_3CH_3$ | H | H | $-OCH_3$ | H | H | $-CH_2CH_3$ |
| 82 | $-(CH_2)_3CH_3$ | $-CH_2-HC=CH_2$ | H | H | $-OCH_3$ | H | H | $-CH_2CH_3$ |
| 83 | $-CH_2-HC=CH_2$ | $-CH_2-HC=CH_2$ | H | H | $-OCH_3$ | H | H | $-CH_2CH_3$ |
| 84 | $-CH_3$ | $-CH_2CH_3$ | H | H | H | F | H | H |
| 85 | $-CH_3$ | $-(CH_2)_2CH_3$ | H | H | H | F | H | H |
| 86 | $-CH_3$ | $-CH(CH_3)_2$ | H | H | H | F | H | H |
| 87 | $-CH_3$ | $-(CH_2)_3CH_3$ | H | H | H | F | H | H |
| 88 | $-CH_3$ | $-CH_2-HC=CH_2$ | H | H | H | F | H | H |
| 89 | $-CH_2CH_3$ | $-CH_2CH_3$ | H | H | H | F | H | H |
| 90 | $-CH_2CH_3$ | $-(CH_2)_2CH_3$ | H | H | H | F | H | H |
| 91 | $-CH_2CH_3$ | $-CH(CH_3)_2$ | H | H | H | F | H | H |
| 92 | $-CH_2CH_3$ | $-(CH_2)_3CH_3$ | H | H | H | F | H | H |
| 93 | $-CH_2CH_3$ | $-CH_2-HC=CH_2$ | H | H | H | F | H | H |
| 94 | $-(CH_2)_2CH_3$ | $-(CH_2)_2CH_3$ | H | H | H | F | H | H |
| 95 | $-(CH_2)_2CH_3$ | $-CH(CH_3)_2$ | H | H | H | F | H | H |
| 96 | $-(CH_2)_2CH_3$ | $-(CH_2)_3CH_3$ | H | H | H | F | H | H |
| 97 | $-(CH_2)_2CH_3$ | $-CH_2-HC=CH_2$ | H | H | H | F | H | H |
| 98 | $-CH(CH_3)_2$ | $-CH(CH_3)_2$ | H | H | H | F | H | H |
| 99 | $-CH(CH_3)_2$ | $-(CH_2)_3CH_3$ | H | H | H | F | H | H |
| 100 | $-CH(CH_3)_2$ | $-CH_2-HC=CH_2$ | H | H | H | F | H | H |
| 101 | $-(CH_2)_3CH_3$ | $-(CH_2)_3CH_3$ | H | H | H | F | H | H |
| 102 | $-(CH_2)_3CH_3$ | $-CH_2-HC=CH_2$ | H | H | H | F | H | H |
| 103 | $-CH_2-HC=CH_2$ | $-CH_2-HC=CH_2$ | H | H | H | F | H | H |
| 104 | $-CH_3$ | $-CH_3$ | H | H | H | H | $-CH_3$ | H |
| 105 | $-CH_3$ | $-CH_2CH_3$ | H | H | H | H | $-CH_3$ | H |
| 106 | $-CH_3$ | $-(CH_2)_2CH_3$ | H | H | H | H | $-CH_3$ | H |
| 107 | $-CH_3$ | $-CH(CH_3)_2$ | H | H | H | H | $-CH_3$ | H |
| 108 | $-CH_3$ | $-(CH_2)_3CH_3$ | H | H | H | H | $-CH_3$ | H |
| 109 | $-CH_3$ | $-CH_2-HC=CH_2$ | H | H | H | H | $-CH_3$ | H |
| 110 | $-CH_2CH_3$ | $-CH_2CH_3$ | H | H | H | H | $-CH_3$ | H |
| 111 | $-CH_2CH_3$ | $-(CH_2)_2CH_3$ | H | H | H | H | $-CH_3$ | H |
| 112 | $-CH_2CH_3$ | $-CH(CH_3)_2$ | H | H | H | H | $-CH_3$ | H |
| 113 | $-CH_2CH_3$ | $-(CH_2)_3CH_3$ | H | H | H | H | $-CH_3$ | H |
| 114 | $-CH_2CH_3$ | $-CH_2-HC=CH_2$ | H | H | H | H | $-CH_3$ | H |
| 115 | $-(CH_2)_2CH_3$ | $-(CH_2)_2CH_3$ | H | H | H | H | $-CH_3$ | H |
| 116 | $-(CH_2)_2CH_3$ | $-CH(CH_3)_2$ | H | H | H | H | $-CH_3$ | H |
| 117 | $-(CH_2)_2CH_3$ | $-(CH_2)_3CH_3$ | H | H | H | H | $-CH_3$ | H |
| 118 | $-(CH_2)_2CH_3$ | $-CH_2-HC=CH_2$ | H | H | H | H | $-CH_3$ | H |
| 119 | $-CH(CH_3)_2$ | $-CH(CH_3)_2$ | H | H | H | H | $-CH_3$ | H |
| 120 | $-CH(CH_3)_2$ | $-(CH_2)_3CH_3$ | H | H | H | H | $-CH_3$ | H |
| 121 | $-CH(CH_3)_2$ | $-CH_2-HC=CH_2$ | H | H | H | H | $-CH_3$ | H |
| 122 | $-(CH_2)_3CH_3$ | $-(CH_2)_3CH_3$ | H | H | H | H | $-CH_3$ | H |
| 123 | $-(CH_2)_3CH_3$ | $-CH_2-HC=CH_2$ | H | H | H | H | $-CH_3$ | H |
| 124 | $-CH_2-HC=CH_2$ | $-CH_2-HC=CH_2$ | H | H | H | H | $-CH_3$ | H |
| 125 | $-CH_3$ | $-CH_3$ | H | H | $-OCH_3$ | H | $-CH_3$ | H |
| 126 | $-CH_3$ | $-CH_2CH_3$ | H | H | $-OCH_3$ | H | $-CH_3$ | H |
| 127 | $-CH_3$ | $-(CH_2)_2CH_3$ | H | H | $-OCH_3$ | H | $-CH_3$ | H |
| 128 | $-CH_3$ | $-CH(CH_3)_2$ | H | H | $-OCH_3$ | H | $-CH_3$ | H |
| 129 | $-CH_3$ | $-(CH_2)_3CH_3$ | H | H | $-OCH_3$ | H | $-CH_3$ | H |
| 130 | $-CH_3$ | $-CH_2-HC=CH_2$ | H | H | $-OCH_3$ | H | $-CH_3$ | H |
| 131 | $-CH_2CH_3$ | $-CH_2CH_3$ | H | H | $-OCH_3$ | H | $-CH_3$ | H |
| 132 | $-CH_2CH_3$ | $-(CH_2)_2CH_3$ | H | H | $-OCH_3$ | H | $-CH_3$ | H |
| 133 | $-CH_2CH_3$ | $-CH(CH_3)_2$ | H | H | $-OCH_3$ | H | $-CH_3$ | H |
| 134 | $-CH_2CH_3$ | $-(CH_2)_3CH_3$ | H | H | $-OCH_3$ | H | $-CH_3$ | H |

TABLE 4-continued

| Ref. | X | Y | $R_2$ | $R_3$ | $R_5$ | $R_6$ | $R_7$ | $R_1$ |
|---|---|---|---|---|---|---|---|---|
| 135 | $—CH_2CH_3$ | $—CH_2—HC{=}CH_2$ | H | H | $—OCH_3$ | H | $—CH_3$ | H |
| 135 | $—(CH_2)_2CH_3$ | $—(CH_2)_2CH_3$ | H | H | $—OCH_3$ | H | $—CH_3$ | H |
| 137 | $—(CH_2)_2CH_3$ | $—CH(CH_3)_2$ | H | H | $—OCH_3$ | H | $—CH_3$ | H |
| 138 | $—(CH_2)_2CH_3$ | $—(CH_2)_3CH_3$ | H | H | $—OCH_3$ | H | $—CH_3$ | H |
| 139 | $—(CH_2)_2CH_3$ | $—CH_2—HC{=}CH_2$ | H | H | $—OCH_3$ | H | $—CH_3$ | H |
| 140 | $—CH(CH_3)_2$ | $—CH(CH_3)_2$ | H | H | $—OCH_3$ | H | $—CH_3$ | H |
| 141 | $—CH(CH_3)_2$ | $—(CH_2)_3CH_3$ | H | H | $—OCH_3$ | H | $—CH_3$ | H |
| 142 | $—CH(CH_3)_2$ | $—CH_2—HC{=}CH_2$ | H | H | $—OCH_3$ | H | $—CH_3$ | H |
| 143 | $—(CH_2)_3CH_3$ | $—(CH_2)_3CH_3$ | H | H | $—OCH_3$ | H | $—CH_3$ | H |
| 144 | $—(CH_2)_3CH_3$ | $—CH_2—HC{=}CH_2$ | H | H | $—OCH_3$ | H | $—CH_3$ | H |
| 145 | $—CH_2—HC{=}CH_2$ | $—CH_2—HC{=}CH_2$ | H | H | $—OCH_3$ | H | $—CH_3$ | H |
| 146 | $—CH_3$ | $—CH_2CH_3$ | H | H | $—OCH_3$ | F | H | H |
| 147 | $—CH_3$ | $—(CH_2)_2CH_3$ | H | H | $—OCH_3$ | F | H | H |
| 148 | $—CH_3$ | $—CH(CH_3)_2$ | H | H | $—OCH_3$ | F | H | H |
| 149 | $—CH_3$ | $—(CH_2)_3CH_3$ | H | H | $—OCH_3$ | F | H | H |
| 150 | $—CH_3$ | $—CH_2—HC{=}CH_2$ | H | H | $—OCH_3$ | F | H | H |
| 151 | $—CH_2CH_3$ | $—CH_2CH_3$ | H | H | $—OCH_3$ | F | H | H |
| 152 | $—CH_2CH_3$ | $—(CH_2)_2CH_3$ | H | H | $—OCH_3$ | F | H | H |
| 153 | $—CH_2CH_3$ | $—CH(CH_3)_2$ | H | H | $—OCH_3$ | F | H | H |
| 154 | $—CH_2CH_3$ | $—(CH_2)_3CH_3$ | H | H | $—OCH_3$ | F | H | H |
| 155 | $—CH_2CH_3$ | $—CH_2—HC{=}CH_2$ | H | H | $—OCH_3$ | F | H | H |
| 156 | $—(CH_2)_2CH_3$ | $—(CH_2)_2CH_3$ | H | H | $—OCH_3$ | F | H | H |
| 157 | $—(CH_2)_2CH_3$ | $—CH(CH_3)_2$ | H | H | $—OCH_3$ | F | H | H |
| 158 | $—(CH_2)_2CH_3$ | $—(CH_2)_3CH_3$ | H | H | $—OCH_3$ | F | H | H |
| 159 | $—(CH_2)_2CH_3$ | $—CH_2—HC{=}CH_2$ | H | H | $—OCH_3$ | F | H | H |
| 160 | $—CH(CH_3)_2$ | $—CH(CH_3)_2$ | H | H | $—OCH_3$ | F | H | H |
| 161 | $—CH(CH_3)_2$ | $—(CH_2)_3CH_3$ | H | H | $—OCH_3$ | F | H | H |
| 162 | $—CH(CH_3)_2$ | $—CH_2—HC{=}CH_2$ | H | H | $—OCH_3$ | F | H | H |
| 163 | $—(CH_2)_3CH_3$ | $—(CH_2)_3CH_3$ | H | H | $—OCH_3$ | F | H | H |
| 164 | $—(CH_2)_3CH_3$ | $—CH_2—HC{=}CH_2$ | H | H | $—OCH_3$ | F | H | H |
| 165 | $—CH_2—HC{=}CH_2$ | $—CH_2—HC{=}CH_2$ | H | H | $—OCH_3$ | F | H | H |
| 166 | H | $—CH_3$ | H | H | H | H | H | $—CH_2CH_3$ |
| 167 | H | $—CH_2CH_3$ | H | H | H | H | H | $—CH_2CH_3$ |
| 168 | H | $—(CH_2)_2CH_3$ | H | H | H | H | H | $—CH_2CH_3$ |
| 169 | H | $—CH(CH_3)_2$ | H | H | H | H | H | $—CH_2CH_3$ |
| 170 | H | $—(CH_2)_3CH_3$ | H | H | H | H | H | $—CH_2CH_3$ |
| 171 | H | $—CH_2—HC{=}CH_2$ | H | H | H | H | H | $—CH_2CH_3$ |
| 171a | H | $—CH_3$ | H | H | $—OCH_3$ | H | H | H |
| 172 | H | $—CH_2CH_3$ | H | H | $—OCH_3$ | H | H | H |
| 173 | H | $—(CH_2)_2CH_3$ | H | H | $—OCH_3$ | H | H | H |
| 174 | H | $—CH(CH_3)_2$ | H | H | $—OCH_3$ | H | H | H |
| 175 | H | $—(CH_2)_3CH_3$ | H | H | $—OCH_3$ | H | H | H |
| 176 | H | $—CH_2—HC{=}CH_2$ | H | H | $—OCH_3$ | H | H | H |
| 177 | H | $—CH_3$ | H | H | $—OCH_3$ | H | H | $—CH_2CH_3$ |
| 178 | H | $—CH_2CH_3$ | H | H | $—OCH_3$ | H | H | $—CH_2CH_3$ |
| 179 | H | $—(CH_2)_2CH_3$ | H | H | $—OCH_3$ | H | H | $—CH_2CH_3$ |
| 180 | H | $—CH(CH_3)_2$ | H | H | $—OCH_3$ | H | H | $—CH_2CH_3$ |
| 181 | H | $—(CH_2)_3CH_3$ | H | H | $—OCH_3$ | H | H | $—CH_2CH_3$ |
| 182 | H | $—CH_2—HC{=}CH_2$ | H | H | $—OCH_3$ | H | H | $—CH_2CH_3$ |
| 183 | H | $—CH_3$ | H | H | $—OCH_3$ | H | $—CH_3$ | H |
| 184 | H | $—CH_2CH_3$ | H | H | $—OCH_3$ | H | $—CH_3$ | H |
| 185 | H | $—(CH_2)_2CH_3$ | H | H | $—OCH_3$ | H | $—CH_3$ | H |
| 186 | H | $—CH(CH_3)_2$ | H | H | $—OCH_3$ | H | $—CH_3$ | H |
| 187 | H | $—(CH_2)_3CH_3$ | H | H | $—OCH_3$ | H | $—CH_3$ | H |
| 188 | H | $—CH_2—HC{=}CH_2$ | H | H | $—OCH_3$ | H | $—CH_3$ | H |
| 189 | H | $—CH_3$ | H | H | H | F | $—CH_3$ | H |
| 190 | H | $—CH_2CH_3$ | H | H | H | F | $—CH_3$ | H |
| 191 | H | $—(CH_2)_2CH_3$ | H | H | H | F | $—CH_3$ | H |
| 192 | H | $—CH(CH_3)_2$ | H | H | H | F | $—CH_3$ | H |
| 193 | H | $—(CH_2)_3CH_3$ | H | H | H | F | $—CH_3$ | H |
| 194 | H | $—CH_2—HC{=}CH_2$ | H | H | H | F | $—CH_3$ | H |
| 195 | H | $—CH_3$ | H | H | $—OCH_3$ | F | H | H |
| 196 | H | $—CH_2CH_3$ | H | H | $—OCH_3$ | F | H | H |
| 197 | H | $—(CH_2)_2CH_3$ | H | H | $—OCH_3$ | F | H | H |
| 198 | H | $—CH(CH_3)_2$ | H | H | $—OCH_3$ | F | H | H |
| 199 | H | $—(CH_2)_3CH_3$ | H | H | $—OCH_3$ | F | H | H |
| 200 | H | $—CH_2—HC{=}CH_2$ | H | H | $—OCH_3$ | F | H | H |
| 201 | H | $—CH_3$ | H | H | H | H | $—CH_3$ | H |
| 202 | H | $—CH_2CH_3$ | H | H | H | H | $—CH_3$ | H |
| 203 | H | $—(CH_2)_2CH_3$ | H | H | H | H | $—CH_3$ | H |
| 204 | H | $—CH(CH_3)_2$ | H | H | H | H | $—CH_3$ | H |
| 205 | H | $—(CH_2)_3CH_3$ | H | H | H | H | $—CH_3$ | H |
| 206 | H | $—CH_2—HC{=}CH_2$ | H | H | H | H | $—CH_3$ | H |
| 207 | H | $—CH_3$ | H | H | H | F | H | H |
| 208 | H | $—CH_2CH_3$ | H | H | H | F | H | H |
| 209 | H | $—(CH_2)_2CH_3$ | H | H | H | F | H | H |
| 210 | H | $—CH(CH_3)_2$ | H | H | H | F | H | H |
| 211 | H | $—(CH_2)_3CH_3$ | H | H | H | F | H | H |

TABLE 4-continued

| Ref. | X | Y | $R_2$ | $R_3$ | $R_5$ | $R_6$ | $R_7$ | $R_1$ |
|---|---|---|---|---|---|---|---|---|
| 212 | H | $—CH_2—HC═CH_2$ | H | H | H | F | H | H |
| 212a | cyclopropyl | $—CH_3$ | H | H | H | H | H | H |
| 213 | cyclopropyl | $—CH_2CH_3$ | H | H | H | H | H | H |
| 214 | cyclopropyl | $—(CH_2)_2CH_3$ | H | H | H | H | H | H |
| 215 | cyclopropyl | $—CH(CH_3)_2$ | H | H | H | H | H | H |
| 216 | cyclopropyl | $—(CH_2)_3CH_3$ | H | H | H | H | H | H |
| 217 | cyclopropyl | $—CH_2—HC═CH_2$ | H | H | H | H | H | H |
| 218 | cyclopropyl | $—CH_3$ | H | H | $—OCH_3$ | H | H | H |
| 219 | cyclopropyl | $—CH_2CH_3$ | H | H | $—OCH_3$ | H | H | H |
| 220 | cyclopropyl | $—(CH_2)_2CH_3$ | H | H | $—OCH_3$ | H | H | H |
| 221 | cyclopropyl | $—CH(CH_3)_2$ | H | H | $—OCH_3$ | H | H | H |
| 222 | cyclopropyl | $—(CH_2)_3CH_3$ | H | H | $—OCH_3$ | H | H | H |
| 223 | cyclopropyl | $—CH_2—HC═CH_2$ | H | H | $—OCH_3$ | H | H | H |
| 224 | cyclopropyl | $—CH_3$ | H | H | —OH | H | H | H |
| 225 | cyclopropyl | $—CH_2CH_3$ | H | H | —OH | H | H | H |
| 226 | cyclopropyl | $—(CH_2)_2CH_3$ | H | H | —OH | H | H | H |
| 227 | cyclopropyl | $—CH(CH_3)_2$ | H | H | —OH | H | H | H |
| 228 | cyclopropyl | $—(CH_2)_3CH_3$ | H | H | —OH | H | H | H |
| 229 | cyclopropyl | $—CH_2—HC═CH_2$ | H | H | —OH | H | H | H |
| 230 | cyclopropyl | $—CH_3$ | H | H | $—OC(O)CH_3$ | H | H | H |
| 231 | cyclopropyl | $—CH_2CH_3$ | H | H | $—OC(O)CH_3$ | H | H | H |
| 232 | cyclopropyl | $—(CH_2)_2CH_3$ | H | H | $—OC(O)CH_3$ | H | H | H |
| 233 | cyclopropyl | $—CH(CH_3)_2$ | H | H | $—OC(O)CH_3$ | H | H | H |
| 234 | cyclopropyl | $—(CH_2)_3CH_3$ | H | H | $—OC(O)CH_3$ | H | H | H |
| 235 | cyclopropyl | $—CH_2—HC═CH_2$ | H | H | $—OC(O)CH_3$ | H | H | H |
| 236 | cyclopropyl | $—CH_3$ | H | H | H | H | H | $—CH_2CH_3$ |
| 237 | cyclopropyl | $—CH_2CH_3$ | H | H | H | H | H | $—CH_2CH_3$ |
| 238 | cyclopropyl | $—(CH_2)_2CH_3$ | H | H | H | H | H | $—CH_2CH_3$ |
| 239 | cyclopropyl | $—CH(CH_3)_2$ | H | H | H | H | H | $—CH_2CH_3$ |
| 240 | cyclopropyl | $—(CH_2)_3CH_3$ | H | H | H | H | H | $—CH_2CH_3$ |
| 241 | cyclopropyl | $—CH_2—HC═CH_2$ | H | H | H | H | H | $—CH_2CH_3$ |
| 242 | cyclopropyl | $—CH_3$ | H | H | $—OCH_3$ | H | H | $—CH_2CH_3$ |
| 243 | cyclopropyl | $—CH_2CH_3$ | H | H | $—OCH_3$ | H | H | $—CH_2CH_3$ |
| 244 | cyclopropyl | $—(CH_2)_2CH_3$ | H | H | $—OCH_3$ | H | H | $—CH_2CH_3$ |
| 245 | cyclopropyl | $—CH(CH_3)_2$ | H | H | $—OCH_3$ | H | H | $—CH_2CH_3$ |
| 246 | cyclopropyl | $—(CH_2)_3CH_3$ | H | H | $—OCH_3$ | H | H | $—CH_2CH_3$ |
| 247 | cyclopropyl | $—CH_2—HC═CH_2$ | H | H | $—OCH_3$ | H | H | $—CH_2CH_3$ |
| 248 | H | $—CH_3$ | H | H | H | H | H | H |
| 249 | H | $—CH_2CH_3$ | H | H | H | H | H | H |
| 250 | H | $—(CH_2)_2CH_3$ | H | H | H | H | H | H |
| 251 | H | $—CH(CH_3)_2$ | H | H | H | H | H | H |
| 252 | H | $—(CH_2)_3CH_3$ | H | H | H | H | H | H |
| 253 | H | $—CH_2—HC═CH_2$ | H | H | H | H | H | H |
| 254 | H | cyclopropyl | H | H | H | H | H | H |
| 255 | H | $—CH_3$ | H | $—CH_3$ | H | H | H | H |
| 256 | H | $—CH_2CH_3$ | H | $—CH_3$ | H | H | H | H |
| 257 | H | $—(CH_2)_2CH_3$ | H | $—CH_3$ | H | H | H | H |
| 258 | H | $—CH(CH_3)_2$ | H | $—CH_3$ | H | H | H | H |
| 259 | H | $—(CH_2)_3CH_3$ | H | $—CH_3$ | H | H | H | H |
| 260 | H | $—CH_2—HC═CH_2$ | H | $—CH_3$ | H | H | H | H |
| 261 | H | cyclopropyl | H | $—CH_3$ | H | H | H | H |
| 262 | H | $—CH_3$ | H | $—CH_3$ | $—OCH_3$ | H | H | H |
| 263 | H | $—CH_2CH_3$ | H | $—CH_3$ | $—OCH_3$ | H | H | H |
| 264 | H | $—(CH_2)_2CH_3$ | H | $—CH_3$ | $—OCH_3$ | H | H | H |
| 265 | H | $—CH(CH_3)_2$ | H | $—CH_3$ | $—OCH_3$ | H | H | H |
| 266 | H | $—(CH_2)_3CH_3$ | H | $—CH_3$ | $—OCH_3$ | H | H | H |
| 267 | H | $—CH_2—HC═CH_2$ | H | $—CH_3$ | $—OCH_3$ | H | H | H |
| 268 | H | cyclopropyl | H | $—CH_3$ | $—OCH_3$ | H | H | H |
| 269 | H | $—CH_3$ | H | $—CH_3$ | H | H | H | $—CH_2CH_3$ |
| 270 | H | $—CH_2CH_3$ | H | $—CH_3$ | H | H | H | $—CH_2CH_3$ |
| 271 | H | $—(CH_2)_2CH_3$ | H | $—CH_3$ | H | H | H | $—CH_2CH_3$ |
| 272 | H | $—CH(CH_3)_2$ | H | $—CH_3$ | H | H | H | $—CH_2CH_3$ |
| 273 | H | $—(CH_2)_3CH_3$ | H | $—CH_3$ | H | H | H | $—CH_2CH_3$ |
| 274 | H | $—CH_2—HC═CH_2$ | H | $—CH_3$ | H | H | H | $—CH_2CH_3$ |
| 275 | H | cyclopropyl | H | $—CH_3$ | H | H | H | $—CH_2CH_3$ |
| 276 | H | $—CH_3$ | H | $—CH_3$ | $—OCH_3$ | H | H | $—CH_2CH_3$ |
| 277 | H | $—CH_2CH_3$ | H | $—CH_3$ | $—OCH_3$ | H | H | $—CH_2CH_3$ |
| 278 | H | $—(CH_2)_2CH_3$ | H | $—CH_3$ | $—OCH_3$ | H | H | $—CH_2CH_3$ |
| 279 | H | $—CH(CH_3)_2$ | H | $—CH_3$ | $—OCH_3$ | H | H | $—CH_2CH_3$ |
| 280 | H | $—(CH_2)_3CH_3$ | H | $—CH_3$ | $—OCH_3$ | H | H | $—CH_2CH_3$ |
| 281 | H | $—CH_2—HC═CH_2$ | H | $—CH_3$ | $—OCH_3$ | H | H | $—CH_2CH_3$ |
| 282 | H | cyclopropyl | H | $—CH_3$ | $—OCH_3$ | H | H | $—CH_2CH_3$ |
| 283 | H | $—CH_3$ | H | $—CH_3$ | H | H | $—CH_3$ | H |
| 284 | H | $—CH_2CH_3$ | H | $—CH_3$ | H | H | $—CH_3$ | H |
| 285 | H | $—(CH_2)_2CH_3$ | H | $—CH_3$ | H | H | $—CH_3$ | H |
| 286 | H | $—CH(CH_3)_2$ | H | $—CH_3$ | H | H | $—CH_3$ | H |
| 287 | H | $—(CH_2)_3CH_3$ | H | $—CH_3$ | H | H | $—CH_3$ | H |
| 288 | H | $—CH_2—HC═CH_2$ | H | $—CH_3$ | H | H | $—CH_3$ | H |

TABLE 4-continued

| Ref. | X | Y | $R_2$ | $R_3$ | $R_5$ | $R_6$ | $R_7$ | $R_1$ |
|---|---|---|---|---|---|---|---|---|
| 289 | H | cyclopropyl | H | $-CH_3$ | H | H | $-CH_3$ | H |
| 290 | H | $-CH_3$ | H | $-CH_3$ | H | F | H | H |
| 291 | H | $-CH_2CH_3$ | H | $-CH_3$ | H | F | H | H |
| 292 | H | $-(CH_2)_2CH_3$ | H | $-CH_3$ | H | F | H | H |
| 293 | H | $-CH(CH_3)_2$ | H | $-CH_3$ | H | F | H | H |
| 294 | H | $-(CH_2)_3CH_3$ | H | $-CH_3$ | H | F | H | H |
| 295 | H | $-CH_2-HC=CH_2$ | H | $-CH_3$ | H | F | H | H |
| 296 | H | cyclopropyl | H | $-CH_3$ | H | F | H | H |
| 297 | H | $-CH_3$ | H | $-CH_3$ | $-OCH_3$ | H | $-CH_3$ | H |
| 298 | H | $-CH_2CH_3$ | H | $-CH_3$ | $-OCH_3$ | H | $-CH_3$ | H |
| 299 | H | $-(CH_2)_2CH_3$ | H | $-CH_3$ | $-OCH_3$ | H | $-CH_3$ | H |
| 300 | H | $-CH(CH_3)_2$ | H | $-CH_3$ | $-OCH_3$ | H | $-CH_3$ | H |
| 301 | H | $-(CH_2)_3CH_3$ | H | $-CH_3$ | $-OCH_3$ | H | $-CH_3$ | H |
| 302 | H | $-CH_2-HC=CH_2$ | H | $-CH_3$ | $-OCH_3$ | H | $-CH_3$ | H |
| 303 | H | cyclopropyl | H | $-CH_3$ | $-OCH_3$ | H | $-CH_3$ | H |
| 304 | H | $-CH_3$ | H | $-CH_3$ | $-OCH_3$ | F | H | H |
| 305 | H | $-CH_2CH_3$ | H | $-CH_3$ | $-OCH_3$ | F | H | H |
| 306 | H | $-(CH_2)_2CH_3$ | H | $-CH_3$ | $-OCH_3$ | F | H | H |
| 307 | H | $-CH(CH_3)_2$ | H | $-CH_3$ | $-OCH_3$ | F | H | H |
| 308 | H | $-(CH_2)_3CH_3$ | H | $-CH_3$ | $-OCH_3$ | F | H | H |
| 309 | H | $-CH_2-HC=CH_2$ | H | $-CH_3$ | $-OCH_3$ | F | H | H |
| 310 | H | cyclopropyl | H | $-CH_3$ | $-OCH_3$ | F | H | H |
| 311 | H | H | H | $-CH_3$ | H | H | H | H |
| 312 | H | H | H | $-CH_3$ | $-OCH_3$ | H | H | H |
| 313 | H | H | H | $-CH_3$ | H | F | H | H |
| 314 | H | H | H | $-CH_3$ | H | H | $-CH_3$ | H |
| 315 | H | H | H | $-CH_3$ | H | H | H | $-CH_2CH_3$ |
| 316 | H | H | H | $-CH_3$ | $-OCH_3$ | H | H | $-CH_2CH_3$ |
| 317 | H | H | H | $-CH_3$ | $-OCH_3$ | H | $-CH_3$ | H |
| 318 | H | H | H | $-CH_3$ | $-OCH_3$ | F | $-CH_3$ | H |
| 319 | H | H | H | $-CH_3$ | $-OH$ | F | H | H |
| 320 | H | H | H | $-CH_3$ | $-OCH_3$ | H | H | $-CH_3$ |
| 321 | $-CH_3$ | $-CH_3$ | H | H | H | H | H | H |
| 322 | $-CH_3$ | $-CH_2CH_3$ | H | H | H | H | H | H |
| 323 | $-CH_3$ | $-(CH_2)_2CH_3$ | H | H | H | H | H | H |
| 324 | $-CH_3$ | $-CH(CH_3)_2$ | H | H | H | H | H | H |
| 325 | $-CH_3$ | $-(CH_2)_3CH_3$ | H | H | H | H | H | H |
| 326 | $-CH_3$ | $-CH_2-HC=CH_2$ | H | H | H | H | H | H |
| 327 | $-CH_2CH_3$ | $-CH_2CH_3$ | H | H | H | H | H | H |
| 328 | $-CH_2CH_3$ | $-(CH_2)_2CH_3$ | H | H | H | H | H | H |
| 329 | $-CH_2CH_3$ | $-CH(CH_3)_2$ | H | H | H | H | H | H |
| 330 | $-CH_2CH_3$ | $-(CH_2)_3CH_3$ | H | H | H | H | H | H |
| 331 | $-CH_2CH_3$ | $-CH_2-HC=CH_2$ | H | H | H | H | H | H |
| 332 | $-(CH_2)_2CH_3$ | $-(CH_2)_2CH_3$ | H | H | H | H | H | H |
| 333 | $-(CH_2)_2CH_3$ | $-CH(CH_3)_2$ | H | H | H | H | H | H |
| 334 | $-(CH_2)_2CH_3$ | $-(CH_2)_3CH_3$ | H | H | H | H | H | H |
| 335 | $-(CH_2)_2CH_3$ | $-CH_2-HC=CH_2$ | H | H | H | H | H | H |
| 336 | $-CH(CH_3)_2$ | $-CH(CH_3)_2$ | H | H | H | H | H | H |
| 337 | $-CH(CH_3)_2$ | $-(CH_2)_3CH_3$ | H | H | H | H | H | H |
| 338 | $-CH(CH_3)_2$ | $-CH_2-HC=CH_2$ | H | H | H | H | H | H |
| 339 | $-(CH_2)_3CH_3$ | $-(CH_2)_3CH_3$ | H | H | H | H | H | H |
| 340 | $-(CH_2)_3CH_3$ | $-CH_2-HC=CH_2$ | H | H | H | H | H | H |
| 341 | $-CH_2-HC=CH_2$ | $-CH_2-HC=CH_2$ | H | H | H | H | H | H |
| 342 | H | $-CD_3$ | H | H | H | H | H | H |
| 343 | H | $-CD_3$ | H | H | $-OH$ | H | H | H |
| 344 | H | $-CD_3$ | H | H | $-OC(O)CH_3$ | H | H | H |
| 345 | H | $-CD_3$ | H | H | $-OCH_3$ | H | H | H |
| 346 | H | $-CD_3$ | H | H | H | F | H | H |
| 347 | H | $-CD_3$ | H | H | $-OH$ | F | H | H |
| 348 | H | $-CD_3$ | H | H | $-OC(O)CH_3$ | F | H | H |
| 349 | H | $-CD_3$ | H | H | $-OCH_3$ | F | H | H |
| 350 | H | $-CD_3$ | H | H | H | H | $-CH_3$ | H |
| 351 | H | $-CD_3$ | H | H | $-OH$ | H | $-CH_3$ | H |
| 352 | H | $-CD_3$ | H | H | $-OC(O)CH_3$ | H | $-CH_3$ | H |
| 353 | H | $-CD_3$ | H | H | $-OCH_3$ | H | $-CH_3$ | H |
| 354 | H | $-CD_3$ | H | H | H | H | H | $-CH_2CH_3$ |
| 355 | H | $-CD_3$ | H | H | $-OH$ | H | H | $-CH_2CH_3$ |
| 356 | H | $-CD_3$ | H | H | $-OC(O)CH_3$ | H | H | $-CH_2CH_3$ |
| 357 | H | $-CD_3$ | H | H | $-OCH_3$ | H | H | $-CH_2CH_3$ |
| 358 | H | $-CD_2CD_3$ | H | H | H | H | H | H |
| 359 | H | $-CD_2CD_3$ | H | H | $-OH$ | H | H | H |
| 360 | H | $-CD_2CD_3$ | H | H | $-OC(O)CH_3$ | H | H | H |
| 361 | H | $-CD_2CD_3$ | H | H | $-OCH_3$ | H | H | H |
| 362 | H | $-CD_2CD_3$ | H | H | H | F | H | H |
| 363 | H | $-CD_2CD_3$ | H | H | $-OH$ | F | H | H |
| 364 | H | $-CD_2CD_3$ | H | H | $-OC(O)CH_3$ | F | H | H |
| 365 | H | $-CD_2CD_3$ | H | H | $-OCH_3$ | F | H | H |
| 366 | H | $-CD_2CD_3$ | H | H | H | H | $-CH_3$ | H |

TABLE 4-continued

| Ref. | X | Y | $R_2$ | $R_3$ | $R_5$ | $R_6$ | $R_7$ | $R_1$ |
|---|---|---|---|---|---|---|---|---|
| 367 | H | $-CD_2CD_3$ | H | H | $-OH$ | H | $-CH_3$ | H |
| 368 | H | $-CD_2CD_3$ | H | H | $-OC(O)CH_3$ | H | $-CH_3$ | H |
| 369 | H | $-CD_2CD_3$ | H | H | $-OCH_3$ | H | $-CH_3$ | H |
| 370 | H | $-CD_2CD_3$ | H | H | H | H | H | $-CH_2CH_3$ |
| 371 | H | $-CD_2CD_3$ | H | H | $-OH$ | H | H | $-CH_2CH_3$ |
| 372 | H | $-CD_2CD_3$ | H | H | $-OC(O)CH_3$ | H | H | $-CH_2CH_3$ |
| 373 | H | $-CD_2CD_3$ | H | H | $-OCH_3$ | H | H | $-CH_2CH_3$ |
| 374 | H | $-CH_3$ | H | D | H | H | H | H |
| 375 | H | $-CH_2CH_3$ | H | D | H | H | H | H |
| 376 | H | $-(CH_2)_2CH_3$ | H | D | H | H | H | H |
| 377 | H | $-CH(CH_3)_2$ | H | D | H | H | H | H |
| 378 | H | $-(CH_2)_3CH_3$ | H | D | H | H | H | H |
| 379 | H | $-CH_2-HC=CH_2$ | H | D | H | H | H | H |
| 380 | H | $-CH_3$ | H | D | $-OCH_3$ | H | H | H |
| 381 | H | $-CH_2CH_3$ | H | D | $-OCH_3$ | H | H | H |
| 382 | H | $-(CH_2)_2CH_3$ | H | D | $-OCH_3$ | H | H | H |
| 383 | H | $-CH(CH_3)_2$ | H | D | $-OCH_3$ | H | H | H |
| 384 | H | $-(CH_2)_3CH_3$ | H | D | $-OCH_3$ | H | H | H |
| 385 | H | $-CH_2-HC=CH_2$ | H | D | $-OCH_3$ | H | H | H |
| 386 | H | $-CH_3$ | H | D | $-OCH_3$ | F | H | H |
| 387 | H | $-CH_2CH_3$ | H | D | $-OCH_3$ | F | H | H |
| 388 | H | $-(CH_2)_2CH_3$ | H | D | $-OCH_3$ | F | H | H |
| 389 | H | $-CH(CH_3)_2$ | H | D | $-OCH_3$ | F | H | H |
| 390 | H | $-(CH_2)_3CH_3$ | H | D | $-OCH_3$ | F | H | H |
| 391 | H | $-CH_2-HC=CH_2$ | H | D | $-OCH_3$ | F | H | H |
| 392 | H | $-CH_3$ | H | D | $-OCH_3$ | H | $-CH_3$ | H |
| 393 | H | $-CH_2CH_3$ | H | D | $-OCH_3$ | H | $-CH_3$ | H |
| 394 | H | $-(CH_2)_2CH_3$ | H | D | $-OCH_3$ | H | $-CH_3$ | H |
| 395 | H | $-CH(CH_3)_2$ | H | D | $-OCH_3$ | H | $-CH_3$ | H |
| 396 | H | $-(CH_2)_3CH_3$ | H | D | $-OCH_3$ | H | $-CH_3$ | H |
| 397 | H | $-CH_2-HC=CH_2$ | H | D | $-OCH_3$ | H | $-CH_3$ | H |
| 398 | H | $-CH_3$ | H | D | H | F | $-CH_3$ | H |
| 399 | H | $-CH_2CH_3$ | H | D | H | F | $-CH_3$ | H |
| 400 | H | $-(CH_2)_2CH_3$ | H | D | H | F | $-CH_3$ | H |
| 401 | H | $-CH(CH_3)_2$ | H | D | H | F | $-CH_3$ | H |
| 402 | H | $-(CH_2)_3CH_3$ | H | D | H | F | $-CH_3$ | H |
| 403 | H | $-CH_2-HC=CH_2$ | H | D | H | F | $-CH_3$ | H |
| 404 | H | $-CH_3$ | H | D | H | F | H | H |
| 405 | H | $-CH_2CH_3$ | H | D | H | F | H | H |
| 406 | H | $-(CH_2)_2CH_3$ | H | D | H | F | H | H |
| 407 | H | $-CH(CH_3)_2$ | H | D | H | F | H | H |
| 408 | H | $-(CH_2)_3CH_3$ | H | D | H | F | H | H |
| 409 | H | $-CH_2-HC=CH_2$ | H | D | H | F | H | H |
| 410 | H | $-CH_3$ | H | D | H | H | $-CH_3$ | H |
| 411 | H | $-CH_2CH_3$ | H | D | H | H | $-CH_3$ | H |
| 412 | H | $-(CH_2)_2CH_3$ | H | D | H | H | $-CH_3$ | H |
| 413 | H | $-CH(CH_3)_2$ | H | D | H | H | $-CH_3$ | H |
| 414 | H | $-(CH_2)_3CH_3$ | H | D | H | H | $-CH_3$ | H |
| 415 | H | $-CH_2-HC=CH_2$ | H | D | H | H | $-CH_3$ | H |

Other exemplary compounds of Formula I include those below in Table 5, which is also represented by Formula Ie:

Formula Ie

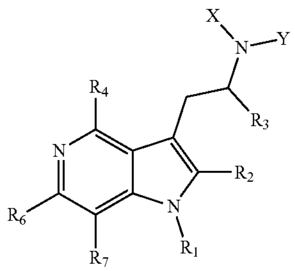

TABLE 5

| Ref. | X | Y | $R_2$ | $R_3$ | $R_4$ | $R_6$ | $R_7$ | $R_1$ |
|---|---|---|---|---|---|---|---|---|
| 1 | $—CH_3$ | $—CH_3$ | H | H | $—OCH_3$ | H | H | H |
| 2 | $—CH_3$ | $—CH_2CH_3$ | H | H | $—OCH_3$ | H | H | H |
| 3 | $—CH_3$ | $—(CH_2)_2CH_3$ | H | H | $—OCH_3$ | H | H | H |
| 4 | $—CH_3$ | $—CH(CH_3)_2$ | H | H | $—OCH_3$ | H | H | H |
| 5 | $—CH_3$ | $—(CH_2)_3CH_3$ | H | H | $—OCH_3$ | H | H | H |
| 6 | $—CH_3$ | $—CH_2—HC{=}CH_2$ | H | H | $—OCH_3$ | H | H | H |
| 7 | $—CH_2CH_3$ | $—CH_2CH_3$ | H | H | $—OCH_3$ | H | H | H |
| 8 | $—CH_2CH_3$ | $—(CH_2)_2CH_3$ | H | H | $—OCH_3$ | H | H | H |
| 9 | $—CH_2CH_3$ | $—CH(CH_3)_2$ | H | H | $—OCH_3$ | H | H | H |
| 10 | $—CH_2CH_3$ | $—(CH_2)_3CH_3$ | H | H | $—OCH_3$ | H | H | H |
| 11 | $—CH_2CH_3$ | $—CH_2—HC{=}CH_2$ | H | H | $—OCH_3$ | H | H | H |
| 12 | $—(CH_2)_2CH_3$ | $—(CH_2)_2CH_3$ | H | H | $—OCH_3$ | H | H | H |
| 13 | $—(CH_2)_2CH_3$ | $—CH(CH_3)_2$ | H | H | $—OCH_3$ | H | H | H |
| 14 | $—(CH_2)_2CH_3$ | $—(CH_2)_3CH_3$ | H | H | $—OCH_3$ | H | H | H |
| 15 | $—(CH_2)_2CH_3$ | $—CH_2—HC{=}CH_2$ | H | H | $—OCH_3$ | H | H | H |
| 16 | $—CH(CH_3)_2$ | $—CH(CH_3)_2$ | H | H | $—OCH_3$ | H | H | H |
| 17 | $—CH(CH_3)_2$ | $—(CH_2)_3CH_3$ | H | H | $—OCH_3$ | H | H | H |
| 18 | $—CH(CH_3)_2$ | $—CH_2—HC{=}CH_2$ | H | H | $—OCH_3$ | H | H | H |
| 19 | $—(CH_2)_3CH_3$ | $—(CH_2)_3CH_3$ | H | H | $—OCH_3$ | H | H | H |
| 20 | $—(CH_2)_3CH_3$ | $—CH_2—HC{=}CH_2$ | H | H | $—OCH_3$ | H | H | H |
| 21 | $—CH_2—HC{=}CH_2$ | $—CH_2—HC{=}CH_2$ | H | H | $—OCH_3$ | H | H | H |
| 22 | $—CH_3$ | $—CH_2CH_3$ | H | H | —OH | H | H | H |
| 23 | $—CH_3$ | $—(CH_2)_2CH_3$ | H | H | —OH | H | H | H |
| 24 | $—CH_3$ | $—CH(CH_3)_2$ | H | H | —OH | H | H | H |
| 25 | $—CH_3$ | $—(CH_2)_3CH_3$ | H | H | —OH | H | H | H |
| 26 | $—CH_3$ | $—CH_2—HC{=}CH_2$ | H | H | —OH | H | H | H |
| 27 | $—CH_2CH_3$ | $—CH_2CH_3$ | H | H | —OH | H | H | H |
| 28 | $—CH_2CH_3$ | $—(CH_2)_2CH_3$ | H | H | —OH | H | H | H |
| 29 | $—CH_2CH_3$ | $—CH(CH_3)_2$ | H | H | —OH | H | H | H |
| 30 | $—CH_2CH_3$ | $—(CH_2)_3CH_3$ | H | H | —OH | H | H | H |
| 31 | $—CH_2CH_3$ | $—CH_2—HC{=}CH_2$ | H | H | —OH | H | H | H |
| 32 | $—(CH_2)_2CH_3$ | $—(CH_2)_2CH_3$ | H | H | —OH | H | H | H |
| 33 | $—(CH_2)_2CH_3$ | $—CH(CH_3)_2$ | H | H | —OH | H | H | H |
| 34 | $—(CH_2)_2CH_3$ | $—(CH_2)_3CH_3$ | H | H | —OH | H | H | H |
| 35 | $—(CH_2)_2CH_3$ | $—CH_2—HC{=}CH_2$ | H | H | —OH | H | H | H |
| 36 | $—CH(CH_3)_2$ | $—CH(CH_3)_2$ | H | H | —OH | H | H | H |
| 37 | $—CH(CH_3)_2$ | $—(CH_2)_3CH_3$ | H | H | —OH | H | H | H |
| 38 | $—CH(CH_3)_2$ | $—CH_2—HC{=}CH_2$ | H | H | —OH | H | H | H |
| 39 | $—(CH_2)_3CH_3$ | $—(CH_2)_3CH_3$ | H | H | —OH | H | H | H |
| 40 | $—(CH_2)_3CH_3$ | $—CH_2—HC{=}CH_2$ | H | H | —OH | H | H | H |
| 41 | $—CH_2—HC{=}CH_2$ | $—CH_2—HC{=}CH_2$ | H | H | —OH | H | H | H |
| 42 | $—CH_3$ | $—CH_3$ | H | H | $—OC(O)CH_3$ | H | H | H |
| 43 | $—CH_3$ | $—CH_2CH_3$ | H | H | $—OC(O)CH_3$ | H | H | H |
| 44 | $—CH_3$ | $—(CH_2)_2CH_3$ | H | H | $—OC(O)CH_3$ | H | H | H |
| 45 | $—CH_3$ | $—CH(CH_3)_2$ | H | H | $—OC(O)CH_3$ | H | H | H |
| 46 | $—CH_3$ | $—(CH_2)_3CH_3$ | H | H | $—OC(O)CH_3$ | H | H | H |
| 47 | $—CH_3$ | $—CH_2—HC{=}CH_2$ | H | H | $—OC(O)CH_3$ | H | H | H |
| 48 | $—CH_2CH_3$ | $—CH_2CH_3$ | H | H | $—OC(O)CH_3$ | H | H | H |
| 49 | $—CH_2CH_3$ | $—(CH_2)_2CH_3$ | H | H | $—OC(O)CH_3$ | H | H | H |
| 50 | $—CH_2CH_3$ | $—CH(CH_3)_2$ | H | H | $—OC(O)CH_3$ | H | H | H |
| 51 | $—CH_2CH_3$ | $—(CH_2)_3CH_3$ | H | H | $—OC(O)CH_3$ | H | H | H |
| 52 | $—CH_2CH_3$ | $—CH_2—HC{=}CH_2$ | H | H | $—OC(O)CH_3$ | H | H | H |
| 53 | $—(CH_2)_2CH_3$ | $—(CH_2)_2CH_3$ | H | H | $—OC(O)CH_3$ | H | H | H |
| 54 | $—(CH_2)_2CH_3$ | $—CH(CH_3)_2$ | H | H | $—OC(O)CH_3$ | H | H | H |
| 55 | $—(CH_2)_2CH_3$ | $—(CH_2)_3CH_3$ | H | H | $—OC(O)CH_3$ | H | H | H |
| 56 | $—(CH_2)_2CH_3$ | $—CH_2—HC{=}CH_2$ | H | H | $—OC(O)CH_3$ | H | H | H |
| 57 | $—CH(CH_3)_2$ | $—CH(CH_3)_2$ | H | H | $—OC(O)CH_3$ | H | H | H |
| 58 | $—CH(CH_3)_2$ | $—(CH_2)_3CH_3$ | H | H | $—OC(O)CH_3$ | H | H | H |
| 59 | $—CH(CH_3)_2$ | $—CH_2—HC{=}CH_2$ | H | H | $—OC(O)CH_3$ | H | H | H |
| 60 | $—(CH_2)_3CH_3$ | $—(CH_2)_3CH_3$ | H | H | $—OC(O)CH_3$ | H | H | H |
| 61 | $—(CH_2)_3CH_3$ | $—CH_2—HC{=}CH_2$ | H | H | $—OC(O)CH_3$ | H | H | H |
| 62 | $—CH_2—HC{=}CH_2$ | $—CH_2—HC{=}CH_2$ | H | H | $—OC(O)CH_3$ | H | H | H |
| 63 | $—CH_3$ | $—CH_3$ | H | H | —OH | H | H | $—CH_2CH_3$ |
| 64 | $—CH_3$ | $—CH_2CH_3$ | H | H | —OH | H | H | $—CH_2CH_3$ |
| 65 | $—CH_3$ | $—(CH_2)_2CH_3$ | H | H | —OH | H | H | $—CH_2CH_3$ |
| 66 | $—CH_3$ | $—CH(CH_3)_2$ | H | H | —OH | H | H | $—CH_2CH_3$ |
| 67 | $—CH_3$ | $—(CH_2)_3CH_3$ | H | H | —OH | H | H | $—CH_2CH_3$ |
| 68 | $—CH_3$ | $—CH_2—HC{=}CH_2$ | H | H | —OH | H | H | $—CH_2CH_3$ |
| 69 | $—CH_2CH_3$ | $—CH_2CH_3$ | H | H | —OH | H | H | $—CH_2CH_3$ |
| 70 | $—CH_2CH_3$ | $—(CH_2)_2CH_3$ | H | H | —OH | H | H | $—CH_2CH_3$ |
| 71 | $—CH_2CH_3$ | $—CH(CH_3)_2$ | H | H | —OH | H | H | $—CH_2CH_3$ |
| 72 | $—CH_2CH_3$ | $—(CH_2)_3CH_3$ | H | H | —OH | H | H | $—CH_2CH_3$ |
| 73 | $—CH_2CH_3$ | $—CH_2—HC{=}CH_2$ | H | H | —OH | H | H | $—CH_2CH_3$ |
| 74 | $—(CH_2)_2CH_3$ | $—(CH_2)_2CH_3$ | H | H | —OH | H | H | $—CH_2CH_3$ |
| 75 | $—(CH_2)_2CH_3$ | $—CH(CH_3)_2$ | H | H | —OH | H | H | $—CH_2CH_3$ |
| 76 | $—(CH_2)_2CH_3$ | $—(CH_2)_3CH_3$ | H | H | —OH | H | H | $—CH_2CH_3$ |
| 77 | $—(CH_2)_2CH_3$ | $—CH_2—HC{=}CH_2$ | H | H | —OH | H | H | $—CH_2CH_3$ |
| 78 | $—CH(CH_3)_2$ | $—CH(CH_3)_2$ | H | H | —OH | H | H | $—CH_2CH_3$ |

TABLE 5-continued

| Ref. | X | Y | $R_2$ | $R_3$ | $R_4$ | $R_6$ | $R_7$ | $R_1$ |
|---|---|---|---|---|---|---|---|---|
| 79 | —$CH(CH_3)_2$ | —$(CH_2)_3CH_3$ | H | H | —OH | H | H | —$CH_2CH_3$ |
| 80 | —$CH(CH_3)_2$ | —$CH_2$—HC═$CH_2$ | H | H | —OH | H | H | —$CH_2CH_3$ |
| 81 | —$(CH_2)_3CH_3$ | —$(CH_2)_3CH_3$ | H | H | —OH | H | H | —$CH_2CH_3$ |
| 82 | —$(CH_2)_3CH_3$ | —$CH_2$—HC═$CH_2$ | H | H | —OH | H | H | —$CH_2CH_3$ |
| 83 | —$CH_2$—HC═$CH_2$ | —$CH_2$—HC═$CH_2$ | H | H | —OH | H | H | —$CH_2CH_3$ |
| 84 | —$CH_3$ | —$CH_2CH_3$ | H | H | H | F | H | H |
| 85 | —$CH_3$ | —$(CH_2)_2CH_3$ | H | H | H | F | H | H |
| 86 | —$CH_3$ | —$CH(CH_3)_2$ | H | H | H | F | H | H |
| 87 | —$CH_3$ | —$(CH_2)_3CH_3$ | H | H | H | F | H | H |
| 88 | —$CH_3$ | —$CH_2$—HC═$CH_2$ | H | H | H | F | H | H |
| 89 | —$CH_2CH_3$ | —$CH_2CH_3$ | H | H | H | F | H | H |
| 90 | —$CH_2CH_3$ | —$(CH_2)_2CH_3$ | H | H | H | F | H | H |
| 91 | —$CH_2CH_3$ | —$CH(CH_3)_2$ | H | H | H | F | H | H |
| 92 | —$CH_2CH_3$ | —$(CH_2)_3CH_3$ | H | H | H | F | H | H |
| 93 | —$CH_2CH_3$ | —$CH_2$—HC═$CH_2$ | H | H | H | F | H | H |
| 94 | —$(CH_2)_2CH_3$ | —$(CH_2)_2CH_3$ | H | H | H | F | H | H |
| 95 | —$(CH_2)_2CH_3$ | —$CH(CH_3)_2$ | H | H | H | F | H | H |
| 96 | —$(CH_2)_2CH_3$ | —$(CH_2)_3CH_3$ | H | H | H | F | H | H |
| 97 | —$(CH_2)_2CH_3$ | —$CH_2$—HC═$CH_2$ | H | H | H | F | H | H |
| 98 | —$CH(CH_3)_2$ | —$CH(CH_3)_2$ | H | H | H | F | H | H |
| 99 | —$CH(CH_3)_2$ | —$(CH_2)_3CH_3$ | H | H | H | F | H | H |
| 100 | —$CH(CH_3)_2$ | —$CH_2$—HC═$CH_2$ | H | H | H | F | H | H |
| 101 | —$(CH_2)_3CH_3$ | —$(CH_2)_3CH_3$ | H | H | H | F | H | H |
| 102 | —$(CH_2)_3CH_3$ | —$CH_2$—HC═$CH_2$ | H | H | H | F | H | H |
| 103 | —$CH_2$—HC═$CH_2$ | —$CH_2$—HC═$CH_2$ | H | H | H | F | H | H |
| 104 | —$CH_3$ | —$CH_3$ | H | H | H | H | —$CH_3$ | H |
| 105 | —$CH_3$ | —$CH_2CH_3$ | H | H | H | H | —$CH_3$ | H |
| 106 | —$CH_3$ | —$(CH_2)_2CH_3$ | H | H | H | H | —$CH_3$ | H |
| 107 | —$CH_3$ | —$CH(CH_3)_2$ | H | H | H | H | —$CH_3$ | H |
| 108 | —$CH_3$ | —$(CH_2)_3CH_3$ | H | H | H | H | —$CH_3$ | H |
| 109 | —$CH_3$ | —$CH_2$—HC═$CH_2$ | H | H | H | H | —$CH_3$ | H |
| 110 | —$CH_2CH_3$ | —$CH_2CH_3$ | H | H | H | H | —$CH_3$ | H |
| 111 | —$CH_2CH_3$ | —$(CH_2)_2CH_3$ | H | H | H | H | —$CH_3$ | H |
| 112 | —$CH_2CH_3$ | —$CH(CH_3)_2$ | H | H | H | H | —$CH_3$ | H |
| 113 | —$CH_2CH_3$ | —$(CH_2)_3CH_3$ | H | H | H | H | —$CH_3$ | H |
| 114 | —$CH_2CH_3$ | —$CH_2$—HC═$CH_2$ | H | H | H | H | —$CH_3$ | H |
| 115 | —$(CH_2)_2CH_3$ | —$(CH_2)_2CH_3$ | H | H | H | H | —$CH_3$ | H |
| 116 | —$(CH_2)_2CH_3$ | —$CH(CH_3)_2$ | H | H | H | H | —$CH_3$ | H |
| 117 | —$(CH_2)_2CH_3$ | —$(CH_2)_3CH_3$ | H | H | H | H | —$CH_3$ | H |
| 118 | —$(CH_2)_2CH_3$ | —$CH_2$—HC═$CH_2$ | H | H | H | H | —$CH_3$ | H |
| 119 | —$CH(CH_3)_2$ | —$CH(CH_3)_2$ | H | H | H | H | —$CH_3$ | H |
| 120 | —$CH(CH_3)_2$ | —$(CH_2)_3CH_3$ | H | H | H | H | —$CH_3$ | H |
| 121 | —$CH(CH_3)_2$ | —$CH_2$—HC═$CH_2$ | H | H | H | H | —$CH_3$ | H |
| 122 | —$(CH_2)_3CH_3$ | —$(CH_2)_3CH_3$ | H | H | H | H | —$CH_3$ | H |
| 123 | —$(CH_2)_3CH_3$ | —$CH_2$—HC═$CH_2$ | H | H | H | H | —$CH_3$ | H |
| 124 | —$CH_2$—HC═$CH_2$ | —$CH_2$—HC═$CH_2$ | H | H | H | H | —$CH_3$ | H |
| 125 | —$CH_3$ | —$CH_3$ | H | H | —OH | H | —$CH_3$ | H |
| 126 | —$CH_3$ | —$CH_2CH_3$ | H | H | —OH | H | —$CH_3$ | H |
| 127 | —$CH_3$ | —$(CH_2)_2CH_3$ | H | H | —OH | H | —$CH_3$ | H |
| 128 | —$CH_3$ | —$CH(CH_3)_2$ | H | H | —OH | H | —$CH_3$ | H |
| 129 | —$CH_3$ | —$(CH_2)_3CH_3$ | H | H | —OH | H | —$CH_3$ | H |
| 130 | —$CH_3$ | —$CH_2$—HC═$CH_2$ | H | H | —OH | H | —$CH_3$ | H |
| 131 | —$CH_2CH_3$ | —$CH_2CH_3$ | H | H | —OH | H | —$CH_3$ | H |
| 132 | —$CH_2CH_3$ | —$(CH_2)_2CH_3$ | H | H | —OH | H | —$CH_3$ | H |
| 133 | —$CH_2CH_3$ | —$CH(CH_3)_2$ | H | H | —OH | H | —$CH_3$ | H |
| 134 | —$CH_2CH_3$ | —$(CH_2)_3CH_3$ | H | H | —OH | H | —$CH_3$ | H |
| 135 | —$CH_2CH_3$ | —$CH_2$—HC═$CH_2$ | H | H | —OH | H | —$CH_3$ | H |
| 135 | —$(CH_2)_2CH_3$ | —$(CH_2)_2CH_3$ | H | H | —OH | H | —$CH_3$ | H |
| 137 | —$(CH2)_2CH_3$ | —$CH(CH_3)_2$ | H | H | —OH | H | —$CH_3$ | H |
| 138 | —$(CH2)_2CH_3$ | —$(CH_2)_3CH_3$ | H | H | —OH | H | —$CH_3$ | H |
| 139 | —$(CH2)_2CH_3$ | —$CH_2$—HC═$CH_2$ | H | H | —OH | H | —$CH_3$ | H |
| 140 | —$CH(CH_3)_2$ | —$CH(CH_3)_2$ | H | H | —OH | H | —$CH_3$ | H |
| 141 | —$CH(CH_3)_2$ | —$(CH_2)_3CH_3$ | H | H | —OH | H | —$CH_3$ | H |
| 142 | —$CH(CH_3)_2$ | —$CH_2$—HC═$CH_2$ | H | H | —OH | H | —$CH_3$ | H |
| 143 | —$(CH_2)_3CH_3$ | —$(CH_2)_3CH_3$ | H | H | —OH | H | —$CH_3$ | H |
| 144 | —$(CH_2)_3CH_3$ | —$CH_2$—HC═$CH_2$ | H | H | —OH | H | —$CH_3$ | H |
| 145 | —$CH_2$—HC═$CH_2$ | —$CH_2$—HC═$CH_2$ | H | H | —OH | H | —$CH_3$ | H |
| 146 | —$CH_3$ | —$CH_2CH_3$ | H | H | —OH | F | H | H |
| 147 | —$CH_3$ | —$(CH_2)_2CH_3$ | H | H | —OH | F | H | H |
| 148 | —$CH_3$ | —$CH(CH_3)_2$ | H | H | —OH | F | H | H |
| 149 | —$CH_3$ | —$(CH_2)_3CH_3$ | H | H | —OH | F | H | H |
| 150 | —$CH_3$ | —$CH_2$—HC═$CH_2$ | H | H | —OH | F | H | H |
| 151 | —$CH_2CH_3$ | —$CH_2CH_3$ | H | H | —OH | F | H | H |
| 152 | —$CH_2CH_3$ | —$(CH_2)_2CH_3$ | H | H | —OH | F | H | H |
| 153 | —$CH_2CH_3$ | —$CH(CH_3)_2$ | H | H | —OH | F | H | H |
| 154 | —$CH_2CH_3$ | —$(CH_2)_3CH_3$ | H | H | —OH | F | H | H |
| 155 | —$CH_2CH_3$ | —$CH_2$—HC═$CH_2$ | H | H | —OH | F | H | H |
| 156 | —$(CH_2)_2CH_3$ | —$(CH_2)_2CH_3$ | H | H | —OH | F | H | H |

TABLE 5-continued

| Ref. | X | Y | $R_2$ | $R_3$ | $R_4$ | $R_6$ | $R_7$ | $R_1$ |
|---|---|---|---|---|---|---|---|---|
| 157 | $-(CH_2)_2CH_3$ | $-CH(CH_3)_2$ | H | H | —OH | F | H | H |
| 158 | $-(CH_2)_2CH_3$ | $-(CH_2)_3CH_3$ | H | H | —OH | F | H | H |
| 159 | —(CH2)$_2CH_3$ | $-CH_2-HC{=}CH_2$ | H | H | —OH | F | H | H |
| 160 | $-CH(CH_3)_2$ | $-CH(CH_3)_2$ | H | H | —OH | F | H | H |
| 161 | $-CH(CH_3)_2$ | $-(CH_2)_3CH_3$ | H | H | —OH | F | H | H |
| 162 | $-CH(CH_3)_2$ | $-CH_2-HC{=}CH_2$ | H | H | —OH | F | H | H |
| 163 | $-(CH_2)_3CH_3$ | $-(CH_2)_3CH_3$ | H | H | —OH | F | H | H |
| 164 | $-(CH_2)_3CH_3$ | $-CH_2-HC{=}CH_2$ | H | H | —OH | F | H | H |
| 165 | $-CH_2-HC{=}CH_2$ | $-CH_2-HC{=}CH_2$ | H | H | —OH | F | H | H |
| 166 | H | $-CH_3$ | H | H | H | H | H | $-CH_2CH_3$ |
| 167 | H | $-CH_2CH_3$ | H | H | H | H | H | $-CH_2CH_3$ |
| 168 | H | $-(CH_2)_2CH_3$ | H | H | H | H | H | $-CH_2CH_3$ |
| 169 | H | $-CH(CH_3)_2$ | H | H | H | H | H | $-CH_2CH_3$ |
| 170 | H | $-(CH_2)_3CH_3$ | H | H | H | H | H | $-CH_2CH_3$ |
| 171 | H | $-CH_2-HC{=}CH_2$ | H | H | H | H | H | $-CH_2CH_3$ |
| 171a | H | $-CH_3$ | H | H | —OH | H | H | H |
| 172 | H | $-CH_2CH_3$ | H | H | —OH | H | H | H |
| 173 | H | $-(CH_2)_2CH_3$ | H | H | —OH | H | H | H |
| 174 | H | $-CH(CH_3)_2$ | H | H | —OH | H | H | H |
| 175 | H | $-(CH_2)_3CH_3$ | H | H | —OH | H | H | H |
| 176 | H | $-CH_2-HC{=}CH_2$ | H | H | —OH | H | H | H |
| 177 | H | $-CH_3$ | H | H | —OH | H | H | $-CH_2CH_3$ |
| 178 | H | $-CH_2CH_3$ | H | H | —OH | H | H | $-CH_2CH_3$ |
| 179 | H | $-(CH_2)_2CH_3$ | H | H | —OH | H | H | $-CH_2CH_3$ |
| 180 | H | $-CH(CH_3)_2$ | H | H | —OH | H | H | $-CH_2CH_3$ |
| 181 | H | $-(CH_2)_3CH_3$ | H | H | —OH | H | H | $-CH_2CH_3$ |
| 182 | H | $-CH_2-HC{=}CH_2$ | H | H | —OH | H | H | $-CH_2CH_3$ |
| 183 | H | $-CH_3$ | H | H | —OH | H | $-CH_3$ | H |
| 184 | H | $-CH_2CH_3$ | H | H | —OH | H | $-CH_3$ | H |
| 185 | H | $-(CH_2)_2CH_3$ | H | H | —OH | H | $-CH_3$ | H |
| 186 | H | $-CH(CH_3)_2$ | H | H | —OH | H | $-CH_3$ | H |
| 187 | H | $-(CH_2)_3CH_3$ | H | H | —OH | H | $-CH_3$ | H |
| 188 | H | $-CH_2-HC{=}CH_2$ | H | H | —OH | H | $-CH_3$ | H |
| 189 | H | $-CH_3$ | H | H | H | F | $-CH_3$ | H |
| 190 | H | $-CH_2CH_3$ | H | H | H | F | $-CH_3$ | H |
| 191 | H | $-(CH_2)_2CH_3$ | H | H | H | F | $-CH_3$ | H |
| 192 | H | $-CH(CH_3)_2$ | H | H | H | F | $-CH_3$ | H |
| 193 | H | $-(CH_2)_3CH_3$ | H | H | H | F | $-CH_3$ | H |
| 194 | H | $-CH_2-HC{=}CH_2$ | H | H | H | F | $-CH_3$ | H |
| 195 | H | $-CH_3$ | H | H | —OH | F | H | H |
| 196 | H | $-CH_2CH_3$ | H | H | —OH | F | H | H |
| 197 | H | $-(CH_2)_2CH_3$ | H | H | —OH | F | H | H |
| 198 | H | $-CH(CH_3)_2$ | H | H | —OH | F | H | H |
| 199 | H | $-(CH_2)_3CH_3$ | H | H | —OH | F | H | H |
| 200 | H | $-CH_2-HC{=}CH_2$ | H | H | —OH | F | H | H |
| 201 | H | $-CH_3$ | H | H | H | H | $-CH_3$ | H |
| 202 | H | $-CH_2CH_3$ | H | H | H | H | $-CH_3$ | H |
| 203 | H | $-(CH_2)_2CH_3$ | H | H | H | H | $-CH_3$ | H |
| 204 | H | $-CH(CH_3)_2$ | H | H | H | H | $-CH_3$ | H |
| 205 | H | $-(CH_2)_3CH_3$ | H | H | H | H | $-CH_3$ | H |
| 206 | H | $-CH_2-HC{=}CH_2$ | H | H | H | H | $-CH_3$ | H |
| 207 | H | $-CH_3$ | H | H | H | F | H | H |
| 208 | H | $-CH_2CH_3$ | H | H | H | F | H | H |
| 209 | H | $-(CH_2)_2CH_3$ | H | H | H | F | H | H |
| 210 | H | $-CH(CH_3)_2$ | H | H | H | F | H | H |
| 211 | H | $-(CH_2)_3CH_3$ | H | H | H | F | H | H |
| 212 | H | $-CH_2-HC{=}CH_2$ | H | H | H | F | H | H |
| 212a | cyclopropyl | $-CH_3$ | H | H | H | H | H | H |
| 213 | cyclopropyl | $-CH_2CH_3$ | H | H | H | H | H | H |
| 214 | cyclopropyl | $-(CH_2)_2CH_3$ | H | H | H | H | H | H |
| 215 | cyclopropyl | $-CH(CH_3)_2$ | H | H | H | H | H | H |
| 216 | cyclopropyl | $-(CH_2)_3CH_3$ | H | H | H | H | H | H |
| 217 | cyclopropyl | $-CH_2-HC{=}CH_2$ | H | H | H | H | H | H |
| 218 | cyclopropyl | $-CH_3$ | H | H | $-OCH_3$ | H | H | H |
| 219 | cyclopropyl | $-CH_2CH_3$ | H | H | $-OCH_3$ | H | H | H |
| 220 | cyclopropyl | $-(CH_2)_2CH_3$ | H | H | $-OCH_3$ | H | H | H |
| 221 | cyclopropyl | $-CH(CH_3)_2$ | H | H | $-OCH_3$ | H | H | H |
| 222 | cyclopropyl | $-(CH_2)_3CH_3$ | H | H | $-OCH_3$ | H | H | H |
| 223 | cyclopropyl | $-CH_2-HC{=}CH_2$ | H | H | $-OCH_3$ | H | H | H |
| 224 | cyclopropyl | $-CH_3$ | H | H | —OH | H | H | H |
| 225 | cyclopropyl | $-CH_2CH_3$ | H | H | —OH | H | H | H |
| 226 | cyclopropyl | $-(CH_2)_2CH_3$ | H | H | —OH | H | H | H |
| 227 | cyclopropyl | $-CH(CH_3)_2$ | H | H | —OH | H | H | H |
| 228 | cyclopropyl | $-(CH_2)_3CH_3$ | H | H | —OH | H | H | H |
| 229 | cyclopropyl | $-CH_2-HC{=}CH_2$ | H | H | —OH | H | H | H |
| 230 | cyclopropyl | $-CH_3$ | H | H | $-OC(O)CH_3$ | H | H | H |
| 231 | cyclopropyl | $-CH_2CH_3$ | H | H | $-OC(O)CH_3$ | H | H | H |
| 232 | cyclopropyl | $-(CH_2)_2CH_3$ | H | H | $-OC(O)CH_3$ | H | H | H |

TABLE 5-continued

| Ref. | X | Y | $R_2$ | $R_3$ | $R_4$ | $R_6$ | $R_7$ | $R_1$ |
|---|---|---|---|---|---|---|---|---|
| 233 | cyclopropyl | $—CH(CH_3)_2$ | H | H | —OC(O)$CH_3$ | H | H | H |
| 234 | cyclopropyl | $—(CH_2)_3CH_3$ | H | H | —OC(O)$CH_3$ | H | H | H |
| 235 | cyclopropyl | $—CH_2—HC{=}CH_2$ | H | H | —OC(O)$CH_3$ | H | H | H |
| 236 | cyclopropyl | $—CH_3$ | H | H | H | H | H | $—CH_2CH_3$ |
| 237 | cyclopropyl | $—CH_2CH_3$ | H | H | H | H | H | $—CH_2CH_3$ |
| 238 | cyclopropyl | $—(CH_2)_2CH_3$ | H | H | H | H | H | $—CH_2CH_3$ |
| 239 | cyclopropyl | $—CH(CH_3)_2$ | H | H | H | H | H | $—CH_2CH_3$ |
| 240 | cyclopropyl | $—(CH_2)_3CH_3$ | H | H | H | H | H | $—CH_2CH_3$ |
| 241 | cyclopropyl | $—CH_2—HC{=}CH_2$ | H | H | H | H | H | $—CH_2CH_3$ |
| 242 | cyclopropyl | $—CH_3$ | H | H | —OH | H | H | $—CH_2CH_3$ |
| 243 | cyclopropyl | $—CH_2CH_3$ | H | H | —OH | H | H | $—CH_2CH_3$ |
| 244 | cyclopropyl | $—(CH_2)_2CH_3$ | H | H | —OH | H | H | $—CH_2CH_3$ |
| 245 | cyclopropyl | $—CH(CH_3)_2$ | H | H | —OH | H | H | $—CH_2CH_3$ |
| 246 | cyclopropyl | $—(CH_2)_3CH_3$ | H | H | —OH | H | H | $—CH_2CH_3$ |
| 247 | cyclopropyl | $—CH_2—HC{=}CH_2$ | H | H | —OH | H | H | $—CH_2CH_3$ |
| 248 | H | $—CH_3$ | H | H | H | H | H | H |
| 249 | H | $—CH_2CH_3$ | H | H | H | H | H | H |
| 250 | H | $—(CH_2)_2CH_3$ | H | H | H | H | H | H |
| 251 | H | $—CH(CH_3)_2$ | H | H | H | H | H | H |
| 252 | H | $—(CH_2)_3CH_3$ | H | H | H | H | H | H |
| 253 | H | $—CH_2—HC{=}CH_2$ | H | H | H | H | H | H |
| 254 | H | cyclopropyl | H | H | H | H | H | H |
| 255 | H | $—CH_3$ | H | $—CH_3$ | H | H | H | H |
| 256 | H | $—CH_2CH_3$ | H | $—CH_3$ | H | H | H | H |
| 257 | H | $—(CH_2)_2CH_3$ | H | $—CH_3$ | H | H | H | H |
| 258 | H | $—CH(CH_3)_2$ | H | $—CH_3$ | H | H | H | H |
| 259 | H | $—(CH_2)_3CH_3$ | H | $—CH_3$ | H | H | H | H |
| 260 | H | $—CH_2—HC{=}CH_2$ | H | $—CH_3$ | H | H | H | H |
| 261 | H | cyclopropyl | H | $—CH_3$ | H | H | H | H |
| 262 | H | $—CH_3$ | H | $—CH_3$ | —OH | H | H | H |
| 263 | H | $—CH_2CH_3$ | H | $—CH_3$ | —OH | H | H | H |
| 264 | H | $—(CH_2)_2CH_3$ | H | $—CH_3$ | —OH | H | H | H |
| 265 | H | $—CH(CH_3)_2$ | H | $—CH_3$ | —OH | H | H | H |
| 266 | H | $—(CH_2)_3CH_3$ | H | $—CH_3$ | —OH | H | H | H |
| 267 | H | $—CH_2—HC{=}CH_2$ | H | $—CH_3$ | —OH | H | H | H |
| 268 | H | cyclopropyl | H | $—CH_3$ | —OH | H | H | H |
| 269 | H | $—CH_3$ | H | $—CH_3$ | H | H | H | $—CH_2CH_3$ |
| 270 | H | $—CH_2CH_3$ | H | $—CH_3$ | H | H | H | $—CH_2CH_3$ |
| 271 | H | $—(CH_2)_2CH_3$ | H | $—CH_3$ | H | H | H | $—CH_2CH_3$ |
| 272 | H | $—CH(CH_3)_2$ | H | $—CH_3$ | H | H | H | $—CH_2CH_3$ |
| 273 | H | $—(CH_2)_3CH_3$ | H | $—CH_3$ | H | H | H | $—CH_2CH_3$ |
| 274 | H | $—CH_2—HC{=}CH_2$ | H | $—CH_3$ | H | H | H | $—CH_2CH_3$ |
| 275 | H | cyclopropyl | H | $—CH_3$ | H | H | H | $—CH_2CH_3$ |
| 276 | H | $—CH_3$ | H | $—CH_3$ | —OH | H | H | $—CH_2CH_3$ |
| 277 | H | $—CH_2CH_3$ | H | $—CH_3$ | —OH | H | H | $—CH_2CH_3$ |
| 278 | H | $—(CH_2)_2CH_3$ | H | $—CH_3$ | —OH | H | H | $—CH_2CH_3$ |
| 279 | H | $—CH(CH_3)_2$ | H | $—CH_3$ | —OH | H | H | $—CH_2CH_3$ |
| 280 | H | $—(CH_2)_3CH_3$ | H | $—CH_3$ | —OH | H | H | $—CH_2CH_3$ |
| 281 | H | $—CH_2—HC{=}CH_2$ | H | $—CH_3$ | —OH | H | H | $—CH_2CH_3$ |
| 282 | H | cyclopropyl | H | $—CH_3$ | —OH | H | H | $—CH_2CH_3$ |
| 283 | H | $—CH_3$ | H | $—CH_3$ | H | H | $—CH_3$ | H |
| 284 | H | $—CH_2CH_3$ | H | $—CH_3$ | H | H | $—CH_3$ | H |
| 285 | H | $—(CH_2)_2CH_3$ | H | $—CH_3$ | H | H | $—CH_3$ | H |
| 286 | H | $—CH(CH_3)_2$ | H | $—CH_3$ | H | H | $—CH_3$ | H |
| 287 | H | $—(CH_2)_3CH_3$ | H | $—CH_3$ | H | H | $—CH_3$ | H |
| 288 | H | $—CH_2—HC{=}CH_2$ | H | $—CH_3$ | H | H | $—CH_3$ | H |
| 289 | H | cyclopropyl | H | $—CH_3$ | H | H | $—CH_3$ | H |
| 290 | H | $—CH_3$ | H | $—CH_3$ | H | F | H | H |
| 291 | H | $—CH_2CH_3$ | H | $—CH_3$ | H | F | H | H |
| 292 | H | $—(CH_2)_2CH_3$ | H | $—CH_3$ | H | F | H | H |
| 293 | H | $—CH(CH_3)_2$ | H | $—CH_3$ | H | F | H | H |
| 294 | H | $—(CH_2)_3CH_3$ | H | $—CH_3$ | H | F | H | H |
| 295 | H | $—CH_2—HC{=}CH_2$ | H | $—CH_3$ | H | F | H | H |
| 296 | H | cyclopropyl | H | $—CH_3$ | H | F | H | H |
| 297 | H | $—CH_3$ | H | $—CH_3$ | —OH | H | $—CH_3$ | H |
| 298 | H | $—CH_2CH_3$ | H | $—CH_3$ | —OH | H | $—CH_3$ | H |
| 299 | H | $—(CH_2)_2CH_3$ | H | $—CH_3$ | —OH | H | $—CH_3$ | H |
| 300 | H | $—CH(CH_3)_2$ | H | $—CH_3$ | —OH | H | $—CH_3$ | H |
| 301 | H | $—(CH_2)_3CH_3$ | H | $—CH_3$ | —OH | H | $—CH_3$ | H |
| 302 | H | $—CH_2—HC{=}CH_2$ | H | $—CH_3$ | —OH | H | $—CH_3$ | H |
| 303 | H | cyclopropyl | H | $—CH_3$ | —OH | H | $—CH_3$ | H |
| 304 | H | $—CH_3$ | H | $—CH_3$ | —OH | F | H | H |
| 305 | H | $—CH_2CH_3$ | H | $—CH_3$ | —OH | F | H | H |
| 306 | H | $—(CH_2)_2CH_3$ | H | $—CH_3$ | —OH | F | H | H |
| 307 | H | $—CH(CH_3)_2$ | H | $—CH_3$ | —OH | F | H | H |
| 308 | H | $—(CH_2)_3CH_3$ | H | $—CH_3$ | —OH | F | H | H |
| 309 | H | $—CH_2—HC{=}CH_2$ | H | $—CH_3$ | —OH | F | H | H |
| 310 | H | cyclopropyl | H | $—CH_3$ | —OH | F | H | H |

TABLE 5-continued

| Ref. | X | Y | $R_2$ | $R_3$ | $R_4$ | $R_6$ | $R_7$ | $R_1$ |
|---|---|---|---|---|---|---|---|---|
| 311 | H | H | H | $-CH_3$ | H | H | H | H |
| 312 | H | H | H | $-CH_3$ | —OH | H | H | H |
| 313 | H | H | H | $-CH_3$ | H | F | H | H |
| 314 | H | H | H | $-CH_3$ | H | H | $-CH_3$ | H |
| 315 | H | H | H | $-CH_3$ | H | H | H | $-CH_2CH_3$ |
| 316 | H | H | H | $-CH_3$ | —OH | H | H | $-CH_2CH_3$ |
| 317 | H | H | H | $-CH_3$ | —OH | H | $-CH_3$ | H |
| 318 | H | H | H | $-CH_3$ | —OH | F | $-CH_3$ | H |
| 319 | H | H | H | $-CH_3$ | —OH | F | H | H |
| 320 | H | H | H | $-CH_3$ | —OH | H | H | $-CH_3$ |
| 321 | $-CH_3$ | $-CH_3$ | H | H | H | H | H | H |
| 322 | $-CH_3$ | $-CH_2CH_3$ | H | H | H | H | H | H |
| 323 | $-CH_3$ | $-(CH_2)_2CH_3$ | H | H | H | H | H | H |
| 324 | $-CH_3$ | $-CH(CH_3)_2$ | H | H | H | H | H | H |
| 325 | $-CH_3$ | $-(CH_2)_3CH_3$ | H | H | H | H | H | H |
| 326 | $-CH_3$ | $-CH_2-HC{=}CH_2$ | H | H | H | H | H | H |
| 327 | $-CH_2CH_3$ | $-CH_2CH_3$ | H | H | H | H | H | H |
| 328 | $-CH_2CH_3$ | $-(CH_2)_2CH_3$ | H | H | H | H | H | H |
| 329 | $-CH_2CH_3$ | $-CH(CH_3)_2$ | H | H | H | H | H | H |
| 330 | $-CH_2CH_3$ | $-(CH_2)_3CH_3$ | H | H | H | H | H | H |
| 331 | $-CH_2CH_3$ | $-CH_2-HC{=}CH_2$ | H | H | H | H | H | H |
| 332 | $-(CH_2)_2CH_3$ | $-(CH_2)_2CH_3$ | H | H | H | H | H | H |
| 333 | $-(CH_2)_2CH_3$ | $-CH(CH_3)_2$ | H | H | H | H | H | H |
| 334 | $-(CH_2)_2CH_3$ | $-(CH_2)_3CH_3$ | H | H | H | H | H | H |
| 335 | $-(CH_2)_2CH_3$ | $-CH_2-HC{=}CH_2$ | H | H | H | H | H | H |
| 336 | $-CH(CH_3)_2$ | $-CH(CH_3)_2$ | H | H | H | H | H | H |
| 337 | $-CH(CH_3)_2$ | $-(CH_2)_3CH_3$ | H | H | H | H | H | H |
| 338 | $-CH(CH_3)_2$ | $-CH_2-HC{=}CH_2$ | H | H | H | H | H | H |
| 339 | $-(CH_2)_3CH_3$ | $-(CH_2)_3CH_3$ | H | H | H | H | H | H |
| 340 | $-(CH_2)_3CH_3$ | $-CH_2-HC{=}CH_2$ | H | H | H | H | H | H |
| 341 | $-CH_2-HC{=}CH_2$ | $-CH_2-HC{=}CH_2$ | H | H | H | H | H | H |
| 342 | H | $-CD_3$ | H | H | H | H | H | H |
| 343 | H | $-CD_3$ | H | H | —OH | H | H | H |
| 344 | H | $-CD_3$ | H | H | $-OC(O)CH_3$ | H | H | H |
| 345 | H | $-CD_3$ | H | H | $-OCH_3$ | H | H | H |
| 346 | H | $-CD_3$ | H | H | H | F | H | H |
| 347 | H | $-CD_3$ | H | H | —OH | F | H | H |
| 348 | H | $-CD_3$ | H | H | $-OC(O)CH_3$ | F | H | H |
| 349 | H | $-CD_3$ | H | H | $-OCH_3$ | F | H | H |
| 350 | H | $-CD_3$ | H | H | H | H | $-CH_3$ | H |
| 351 | H | $-CD_3$ | H | H | —OH | H | $-CH_3$ | H |
| 352 | H | $-CD_3$ | H | H | $-OC(O)CH_3$ | H | $-CH_3$ | H |
| 353 | H | $-CD_3$ | H | H | $-OCH_3$ | H | $-CH_3$ | H |
| 354 | H | $-CD_3$ | H | H | H | H | H | $-CH_2CH_3$ |
| 355 | H | $-CD_3$ | H | H | —OH | H | H | $-CH_2CH_3$ |
| 356 | H | $-CD_3$ | H | H | $-OC(O)CH_3$ | H | H | $-CH_2CH_3$ |
| 357 | H | $-CD_3$ | H | H | $-OCH_3$ | H | H | $-CH_2CH_3$ |
| 358 | H | $-CD_2CD_3$ | H | H | H | H | H | H |
| 359 | H | $-CD_2CD_3$ | H | H | —OH | H | H | H |
| 360 | H | $-CD_2CD_3$ | H | H | $-OC(O)CH_3$ | H | H | H |
| 361 | H | $-CD_2CD_3$ | H | H | $-OCH_3$ | H | H | H |
| 362 | H | $-CD_2CD_3$ | H | H | H | F | H | H |
| 363 | H | $-CD_2CD_3$ | H | H | —OH | F | H | H |
| 364 | H | $-CD_2CD_3$ | H | H | $-OC(O)CH_3$ | F | H | H |
| 365 | H | $-CD_2CD_3$ | H | H | $-OCH_3$ | F | H | H |
| 366 | H | $-CD_2CD_3$ | H | H | H | H | $-CH_3$ | H |
| 367 | H | $-CD_2CD_3$ | H | H | —OH | H | $-CH_3$ | H |
| 368 | H | $-CD_2CD_3$ | H | H | $-OC(O)CH_3$ | H | $-CH_3$ | H |
| 369 | H | $-CD_2CD_3$ | H | H | $-OCH_3$ | H | $-CH_3$ | H |
| 370 | H | $-CD_2CD_3$ | H | H | H | H | H | $-CH_2CH_3$ |
| 371 | H | $-CD_2CD_3$ | H | H | —OH | H | H | $-CH_2CH_3$ |
| 372 | H | $-CD_2CD_3$ | H | H | $-OC(O)CH_3$ | H | H | $-CH_2CH_3$ |
| 373 | H | $-CD_2CD_3$ | H | H | $-OCH_3$ | H | H | $-CH_2CH_3$ |
| 374 | H | $-CH_3$ | H | D | H | H | H | H |
| 375 | H | $-CH_2CH_3$ | H | D | H | H | H | H |
| 376 | H | $-(CH_2)_2CH_3$ | H | D | H | H | H | H |
| 377 | H | $-CH(CH_3)_2$ | H | D | H | H | H | H |
| 378 | H | $-(CH_2)_3CH_3$ | H | D | H | H | H | H |
| 379 | H | $-CH_2-HC{=}CH_2$ | H | D | H | H | H | H |
| 380 | H | $-CH_3$ | H | D | —OH | H | H | H |
| 381 | H | $-CH_2CH_3$ | H | D | —OH | H | H | H |
| 382 | H | $-(CH_2)_2CH_3$ | H | D | —OH | H | H | H |
| 383 | H | $-CH(CH_3)_2$ | H | D | —OH | H | H | H |
| 384 | H | $-(CH_2)_3CH_3$ | H | D | —OH | H | H | H |
| 385 | H | $-CH_2-HC{=}CH_2$ | H | D | —OH | H | H | H |
| 386 | H | $-CH_3$ | H | D | —OH | F | H | H |
| 387 | H | $-CH_2CH_3$ | H | D | —OH | F | H | H |
| 388 | H | $-(CH_2)_2CH_3$ | H | D | —OH | F | H | H |

TABLE 5-continued

| Ref. | X | Y | $R_2$ | $R_3$ | $R_4$ | $R_6$ | $R_7$ | $R_1$ |
|---|---|---|---|---|---|---|---|---|
| 389 | H | $—CH(CH_3)_2$ | H | D | —OH | F | H | H |
| 390 | H | $—(CH_2)_3CH_3$ | H | D | —OH | F | H | H |
| 391 | H | $—CH_2—HC{=}CH_2$ | H | D | —OH | F | H | H |
| 392 | H | $—CH_3$ | H | D | —OH | H | $—CH_3$ | H |
| 393 | H | $—CH_2CH_3$ | H | D | —OH | H | $—CH_3$ | H |
| 394 | H | $—(CH_2)_2CH_3$ | H | D | —OH | H | $—CH_3$ | H |
| 395 | H | $—CH(CH_3)_2$ | H | D | —OH | H | $—CH_3$ | H |
| 396 | H | $—(CH_2)_3CH_3$ | H | D | —OH | H | $—CH_3$ | H |
| 397 | H | $—CH_2—HC{=}CH_2$ | H | D | —OH | H | $—CH_3$ | H |
| 398 | H | $—CH_3$ | H | D | H | F | $—CH_3$ | H |
| 399 | H | $—CH_2CH_3$ | H | D | H | F | $—CH_3$ | H |
| 400 | H | $—(CH_2)_2CH_3$ | H | D | H | F | $—CH_3$ | H |
| 401 | H | $—CH(CH_3)_2$ | H | D | H | F | $—CH_3$ | H |
| 402 | H | $—(CH_2)_3CH_3$ | H | D | H | F | $—CH_3$ | H |
| 403 | H | $—CH_2—HC{=}CH_2$ | H | D | H | F | $—CH_3$ | H |
| 404 | H | $—CH_3$ | H | D | H | F | H | H |
| 405 | H | $—CH_2CH_3$ | H | D | H | F | H | H |
| 406 | H | $—(CH_2)_2CH_3$ | H | D | H | F | H | H |
| 407 | H | $—CH(CH_3)_2$ | H | D | H | F | H | H |
| 408 | H | $—(CH_2)_3CH_3$ | H | D | H | F | H | H |
| 409 | H | $—CH_2—HC{=}CH_2$ | H | D | H | F | H | H |
| 410 | H | $—CH_3$ | H | D | H | H | $—CH_3$ | H |
| 411 | H | $—CH_2CH_3$ | H | D | H | H | $—CH_3$ | H |
| 412 | H | $—(CH_2)_2CH_3$ | H | D | H | H | $—CH_3$ | H |
| 413 | H | $—CH(CH_3)_2$ | H | D | H | H | $—CH_3$ | H |
| 414 | H | $—(CH_2)_3CH_3$ | H | D | H | H | $—CH_3$ | H |
| 415 | H | $—CH_2—HC{=}CH_2$ | H | D | H | H | $—CH_3$ | H |

Other exemplary compounds of Formula I include those below in Table 6, which is also represented by Formula If:

Formula If

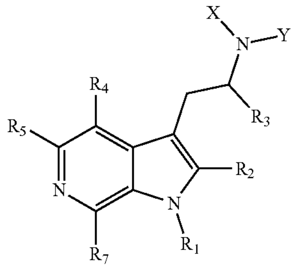

TABLE 6

| Ref. | X | Y | $R_2$ | $R_3$ | $R_4$ | $R_5$ | $R_7$ | $R_1$ |
|---|---|---|---|---|---|---|---|---|
| 1 | $—CH_3$ | $—CH_3$ | H | H | $—OCH_3$ | H | H | H |
| 2 | $—CH_3$ | $—CH_2CH_3$ | H | H | $—OCH_3$ | H | H | H |
| 3 | $—CH_3$ | $—(CH_2)_2CH_3$ | H | H | $—OCH_3$ | H | H | H |
| 4 | $—CH_3$ | $—CH(CH_3)_2$ | H | H | $—OCH_3$ | H | H | H |
| 5 | $—CH_3$ | $—(CH_2)_3CH_3$ | H | H | $—OCH_3$ | H | H | H |
| 6 | $—CH_3$ | $—CH_2—HC{=}CH_2$ | H | H | $—OCH_3$ | H | H | H |
| 7 | $—CH_2CH_3$ | $—CH_2CH_3$ | H | H | $—OCH_3$ | H | H | H |
| 8 | $—CH_2CH_3$ | $—(CH_2)_2CH_3$ | H | H | $—OCH_3$ | H | H | H |
| 9 | $—CH_2CH_3$ | $—CH(CH_3)_2$ | H | H | $—OCH_3$ | H | H | H |
| 10 | $—CH_2CH_3$ | $—(CH_2)_3CH_3$ | H | H | $—OCH_3$ | H | H | H |
| 11 | $—CH_2CH_3$ | $—CH_2—HC{=}CH_2$ | H | H | $—OCH_3$ | H | H | H |
| 12 | $—(CH_2)_2CH_3$ | $—(CH_2)_2CH_3$ | H | H | $—OCH_3$ | H | H | H |
| 13 | $—(CH_2)_2CH_3$ | $—CH(CH_3)_2$ | H | H | $—OCH_3$ | H | H | H |
| 14 | $—(CH_2)_2CH_3$ | $—(CH_2)_3CH_3$ | H | H | $—OCH_3$ | H | H | H |
| 15 | $—(CH_2)_2CH_3$ | $—CH_2—HC{=}CH_2$ | H | H | $—OCH_3$ | H | H | H |
| 16 | $—CH(CH_3)_2$ | $—CH(CH_3)_2$ | H | H | $—OCH_3$ | H | H | H |
| 17 | $—CH(CH_3)_2$ | $—(CH_2)_3CH_3$ | H | H | $—OCH_3$ | H | H | H |
| 18 | $—CH(CH_3)_2$ | $—CH_2—HC{=}CH_2$ | H | H | $—OCH_3$ | H | H | H |
| 19 | $—(CH_2)_3CH_3$ | $—(CH_2)_3CH_3$ | H | H | $—OCH_3$ | H | H | H |
| 20 | $—(CH_2)_3CH_3$ | $—CH_2—HC{=}CH_2$ | H | H | $—OCH_3$ | H | H | H |
| 21 | $—CH_2—HC{=}CH_2$ | $—CH_2—HC{=}CH_2$ | H | H | $—OCH_3$ | H | H | H |
| 22 | $—CH_3$ | $—CH_2CH_3$ | H | H | —OH | H | H | H |

TABLE 6-continued

| Ref. | X | Y | $R_2$ | $R_3$ | $R_4$ | $R_5$ | $R_7$ | $R_1$ |
|---|---|---|---|---|---|---|---|---|
| 23 | $-CH_3$ | $-(CH_2)_2CH_3$ | H | H | —OH | H | H | H |
| 24 | $-CH_3$ | $-CH(CH_3)_2$ | H | H | —OH | H | H | H |
| 25 | $-CH_3$ | $-(CH_2)_3CH_3$ | H | H | —OH | H | H | H |
| 26 | $-CH_3$ | $-CH_2-HC{=}CH_2$ | H | H | —OH | H | H | H |
| 27 | $-CH_2CH_3$ | $-CH_2CH_3$ | H | H | —OH | H | H | H |
| 28 | $-CH_2CH_3$ | $-(CH_2)_2CH_3$ | H | H | —OH | H | H | H |
| 29 | $-CH_2CH_3$ | $-CH(CH_3)_2$ | H | H | —OH | H | H | H |
| 30 | $-CH_2CH_3$ | $-(CH_2)_3CH_3$ | H | H | —OH | H | H | H |
| 31 | $-CH_2CH_3$ | $-CH_2-HC{=}CH_2$ | H | H | —OH | H | H | H |
| 32 | $-(CH_2)_2CH_3$ | $-(CH_2)_2CH_3$ | H | H | —OH | H | H | H |
| 33 | $-(CH_2)_2CH_3$ | $-CH(CH_3)_2$ | H | H | —OH | H | H | H |
| 34 | $-(CH_2)_2CH_3$ | $-(CH_2)_3CH_3$ | H | H | —OH | H | H | H |
| 35 | $-(CH_2)_2CH_3$ | $-CH_2-HC{=}CH_2$ | H | H | —OH | H | H | H |
| 36 | $-CH(CH_3)_2$ | $-CH(CH_3)_2$ | H | H | —OH | H | H | H |
| 37 | $-CH(CH_3)_2$ | $-(CH_2)_3CH_3$ | H | H | —OH | H | H | H |
| 38 | $-CH(CH_3)_2$ | $-CH_2-HC{=}CH_2$ | H | H | —OH | H | H | H |
| 39 | $-(CH_2)_3CH_3$ | $-(CH_2)_3CH_3$ | H | H | —OH | H | H | H |
| 40 | $-(CH_2)_3CH_3$ | $-CH_2-HC{=}CH_2$ | H | H | —OH | H | H | H |
| 41 | $-CH_2-HC{=}CH_2$ | $-CH_2-HC{=}CH_2$ | H | H | —OH | H | H | H |
| 42 | $-CH_3$ | $-CH_3$ | H | H | $-OC(O)CH_3$ | H | H | H |
| 43 | $-CH_3$ | $-CH_2CH_3$ | H | H | $-OC(O)CH_3$ | H | H | H |
| 44 | $-CH_3$ | $-(CH_2)_2CH_3$ | H | H | $-OC(O)CH_3$ | H | H | H |
| 45 | $-CH_3$ | $-CH(CH_3)_2$ | H | H | $-OC(O)CH_3$ | H | H | H |
| 46 | $-CH_3$ | $-(CH_2)_3CH_3$ | H | H | $-OC(O)CH_3$ | H | H | H |
| 47 | $-CH_3$ | $-CH_2-HC{=}CH_2$ | H | H | $-OC(O)CH_3$ | H | H | H |
| 48 | $-CH_2CH_3$ | $-CH_2CH_3$ | H | H | $-OC(O)CH_3$ | H | H | H |
| 49 | $-CH_2CH_3$ | $-(CH_2)_2CH_3$ | H | H | $-OC(O)CH_3$ | H | H | H |
| 50 | $-CH_2CH_3$ | $-CH(CH_3)_2$ | H | H | $-OC(O)CH_3$ | H | H | H |
| 51 | $-CH_2CH_3$ | $-(CH_2)_3CH_3$ | H | H | $-OC(O)CH_3$ | H | H | H |
| 52 | $-CH_2CH_3$ | $-CH_2-HC{=}CH_2$ | H | H | $-OC(O)CH_3$ | H | H | H |
| 53 | $-(CH_2)_2CH_3$ | $-(CH_2)_2CH_3$ | H | H | $-OC(O)CH_3$ | H | H | H |
| 54 | $-(CH_2)_2CH_3$ | $-CH(CH_3)_2$ | H | H | $-OC(O)CH_3$ | H | H | H |
| 55 | $-(CH_2)_2CH_3$ | $-(CH_2)_3CH_3$ | H | H | $-OC(O)CH_3$ | H | H | H |
| 56 | $-(CH_2)_2CH_3$ | $-CH_2-HC{=}CH_2$ | H | H | $-OC(O)CH_3$ | H | H | H |
| 57 | $-CH(CH_3)_2$ | $-CH(CH_3)_2$ | H | H | $-OC(O)CH_3$ | H | H | H |
| 58 | $-CH(CH_3)_2$ | $-(CH_2)_3CH_3$ | H | H | $-OC(O)CH_3$ | H | H | H |
| 59 | $-CH(CH_3)_2$ | $-CH_2-HC{=}CH_2$ | H | H | $-OC(O)CH_3$ | H | H | H |
| 60 | $-(CH_2)_3CH_3$ | $-(CH_2)_3CH_3$ | H | H | $-OC(O)CH_3$ | H | H | H |
| 61 | $-(CH_2)_3CH_3$ | $-CH_2-HC{=}CH_2$ | H | H | $-OC(O)CH_3$ | H | H | H |
| 62 | $-CH_2-HC{=}CH_2$ | $-CH_2-HC{=}CH_2$ | H | H | $-OC(O)CH_3$ | H | H | H |
| 63 | $-CH_3$ | $-CH_3$ | H | H | H | $-OCH_3$ | H | H |
| 64 | $-CH_3$ | $-CH_2CH_3$ | H | H | H | $-OCH_3$ | H | H |
| 65 | $-CH_3$ | $-(CH_2)_2CH_3$ | H | H | H | $-OCH_3$ | H | H |
| 66 | $-CH_3$ | $-CH(CH_3)_2$ | H | H | H | $-OCH_3$ | H | H |
| 67 | $-CH_3$ | $-(CH_2)_3CH_3$ | H | H | H | $-OCH_3$ | H | H |
| 68 | $-CH_3$ | $-CH_2-HC{=}CH_2$ | H | H | H | $-OCH_3$ | H | H |
| 69 | $-CH_2CH_3$ | $-CH_2CH_3$ | H | H | H | $-OCH_3$ | H | H |
| 70 | $-CH_2CH_3$ | $-(CH_2)_2CH_3$ | H | H | H | $-OCH_3$ | H | H |
| 71 | $-CH_2CH_3$ | $-CH(CH_3)_2$ | H | H | H | $-OCH_3$ | H | H |
| 72 | $-CH_2CH_3$ | $-(CH_2)_3CH_3$ | H | H | H | $-OCH_3$ | H | H |
| 73 | $-CH_2CH_3$ | $-CH_2-HC{=}CH_2$ | H | H | H | $-OCH_3$ | H | H |
| 74 | $-(CH_2)_2CH_3$ | $-(CH_2)_2CH_3$ | H | H | H | $-OCH_3$ | H | H |
| 75 | $-(CH_2)_2CH_3$ | $-CH(CH_3)_2$ | H | H | H | $-OCH_3$ | H | H |
| 76 | $-(CH_2)_2CH_3$ | $-(CH_2)_3CH_3$ | H | H | H | $-OCH_3$ | H | H |
| 77 | $-(CH_2)_2CH_3$ | $-CH_2-HC{=}CH_2$ | H | H | H | $-OCH_3$ | H | H |
| 78 | $-CH(CH_3)_2$ | $-CH(CH_3)_2$ | H | H | H | $-OCH_3$ | H | H |
| 79 | $-CH(CH_3)_2$ | $-(CH_2)_3CH_3$ | H | H | H | $-OCH_3$ | H | H |
| 80 | $-CH(CH_3)_2$ | $-CH_2-HC{=}CH_2$ | H | H | H | $-OCH_3$ | H | H |
| 81 | $-(CH_2)_3CH_3$ | $-(CH_2)_3CH_3$ | H | H | H | $-OCH_3$ | H | H |
| 82 | $-(CH_2)_3CH_3$ | $-CH_2-HC{=}CH_2$ | H | H | H | $-OCH_3$ | H | H |
| 83 | $-CH_2-HC{=}CH_2$ | $-CH_2-HC{=}CH_2$ | H | H | H | $-OCH_3$ | H | H |
| 83b | $-CH_3$ | $-CH_3$ | H | H | H | —OH | H | H |
| 84 | $-CH_3$ | $-CH_2CH_3$ | H | H | H | —OH | H | H |
| 85 | $-CH_3$ | $-(CH_2)_2CH_3$ | H | H | H | —OH | H | H |
| 86 | $-CH_3$ | $-CH(CH_3)_2$ | H | H | H | —OH | H | H |
| 87 | $-CH_3$ | $-(CH_2)_3CH_3$ | H | H | H | —OH | H | H |
| 88 | $-CH_3$ | $-CH_2-HC{=}CH_2$ | H | H | H | —OH | H | H |
| 89 | $-CH_2CH_3$ | $-CH_2CH_3$ | H | H | H | —OH | H | H |
| 90 | $-CH_2CH_3$ | $-(CH_2)_2CH_3$ | H | H | H | —OH | H | H |
| 91 | $-CH_2CH_3$ | $-CH(CH_3)_2$ | H | H | H | —OH | H | H |
| 92 | $-CH_2CH_3$ | $-(CH_2)_3CH_3$ | H | H | H | —OH | H | H |
| 93 | $-CH_2CH_3$ | $-CH_2-HC{=}CH_2$ | H | H | H | —OH | H | H |
| 94 | $-(CH_2)_2CH_3$ | $-(CH_2)_2CH_3$ | H | H | H | —OH | H | H |
| 95 | $-(CH_2)_2CH_3$ | $-CH(CH_3)_2$ | H | H | H | —OH | H | H |
| 96 | $-(CH_2)_2CH_3$ | $-(CH_2)_3CH_3$ | H | H | H | —OH | H | H |
| 97 | $-(CH_2)_2CH_3$ | $-CH_2-HC{=}CH_2$ | H | H | H | —OH | H | H |
| 98 | $-CH(CH_3)_2$ | $-CH(CH_3)_2$ | H | H | H | —OH | H | H |
| 99 | $-CH(CH_3)_2$ | $-(CH_2)_3CH_3$ | H | H | H | —OH | H | H |

TABLE 6-continued

| Ref. | X | Y | $R_2$ | $R_3$ | $R_4$ | $R_5$ | $R_7$ | $R_1$ |
|---|---|---|---|---|---|---|---|---|
| 100 | $-CH(CH_3)_2$ | $-CH_2-HC=CH_2$ | H | H | H | $-OH$ | H | H |
| 101 | $-(CH_2)_3CH_3$ | $-(CH_2)_3CH_3$ | H | H | H | $-OH$ | H | H |
| 102 | $-(CH_2)_3CH_3$ | $-CH_2-HC=CH_2$ | H | H | H | $-OH$ | H | H |
| 103 | $-CH_2-HC=CH_2$ | $-CH_2-HC=CH_2$ | H | H | H | $-OH$ | H | H |
| 104 | $-CH_3$ | $-CH_3$ | H | H | H | $-OC(O)CH_3$ | H | H |
| 105 | $-CH_3$ | $-CH_2CH_3$ | H | H | H | $-OC(O)CH_3$ | H | H |
| 106 | $-CH_3$ | $-(CH_2)_2CH_3$ | H | H | H | $-OC(O)CH_3$ | H | H |
| 107 | $-CH_3$ | $-CH(CH_3)_2$ | H | H | H | $-OC(O)CH_3$ | H | H |
| 108 | $-CH_3$ | $-(CH_2)_3CH_3$ | H | H | H | $-OC(O)CH_3$ | H | H |
| 109 | $-CH_3$ | $-CH_2-HC=CH_2$ | H | H | H | $-OC(O)CH_3$ | H | H |
| 110 | $-CH_2CH_3$ | $-CH_2CH_3$ | H | H | H | $-OC(O)CH_3$ | H | H |
| 111 | $-CH_2CH_3$ | $-(CH_2)_2CH_3$ | H | H | H | $-OC(O)CH_3$ | H | H |
| 112 | $-CH_2CH_3$ | $-CH(CH_3)_2$ | H | H | H | $-OC(O)CH_3$ | H | H |
| 113 | $-CH_2CH_3$ | $-(CH_2)_3CH_3$ | H | H | H | $-OC(O)CH_3$ | H | H |
| 114 | $-CH_2CH_3$ | $-CH_2-HC=CH_2$ | H | H | H | $-OC(O)CH_3$ | H | H |
| 115 | $-(CH_2)_2CH_3$ | $-(CH_2)_2CH_3$ | H | H | H | $-OC(O)CH_3$ | H | H |
| 116 | $-(CH_2)_2CH_3$ | $-CH(CH_3)_2$ | H | H | H | $-OC(O)CH_3$ | H | H |
| 117 | $-(CH_2)_2CH_3$ | $-(CH_2)_3CH_3$ | H | H | H | $-OC(O)CH_3$ | H | H |
| 118 | $-(CH_2)_2CH_3$ | $-CH_2-HC=CH_2$ | H | H | H | $-OC(O)CH_3$ | H | H |
| 119 | $-CH(CH_3)_2$ | $-CH(CH_3)_2$ | H | H | H | $-OC(O)CH_3$ | H | H |
| 120 | $-CH(CH_3)_2$ | $-(CH_2)_3CH_3$ | H | H | H | $-OC(O)CH_3$ | H | H |
| 121 | $-CH(CH_3)_2$ | $-CH_2-HC=CH_2$ | H | H | H | $-OC(O)CH_3$ | H | H |
| 122 | $-(CH_2)_3CH_3$ | $-(CH_2)_3CH_3$ | H | H | H | $-OC(O)CH_3$ | H | H |
| 123 | $-(CH_2)_3CH_3$ | $-CH_2-HC=CH_2$ | H | H | H | $-OC(O)CH_3$ | H | H |
| 124 | $-CH_2-HC=CH_2$ | $-CH_2-HC=CH_2$ | H | H | H | $-OC(O)CH_3$ | H | H |
| 125 | $-CH_3$ | $-CH_3$ | H | H | $-OH$ | H | H | $-CH_2CH_3$ |
| 126 | $-CH_3$ | $-CH_2CH_3$ | H | H | $-OH$ | H | H | $-CH_2CH_3$ |
| 127 | $-CH_3$ | $-(CH_2)_2CH_3$ | H | H | $-OH$ | H | H | $-CH_2CH_3$ |
| 128 | $-CH_3$ | $-CH(CH_3)_2$ | H | H | $-OH$ | H | H | $-CH_2CH_3$ |
| 129 | $-CH_3$ | $-(CH_2)_3CH_3$ | H | H | $-OH$ | H | H | $-CH_2CH_3$ |
| 130 | $-CH_3$ | $-CH_2-HC=CH_2$ | H | H | $-OH$ | H | H | $-CH_2CH_3$ |
| 131 | $-CH_2CH_3$ | $-CH_2CH_3$ | H | H | $-OH$ | H | H | $-CH_2CH_3$ |
| 132 | $-CH_2CH_3$ | $-(CH_2)_2CH_3$ | H | H | $-OH$ | H | H | $-CH_2CH_3$ |
| 133 | $-CH_2CH_3$ | $-CH(CH_3)_2$ | H | H | $-OH$ | H | H | $-CH_2CH_3$ |
| 134 | $-CH_2CH_3$ | $-(CH_2)_3CH_3$ | H | H | $-OH$ | H | H | $-CH_2CH_3$ |
| 135 | $-CH_2CH_3$ | $-CH_2-HC=CH_2$ | H | H | $-OH$ | H | H | $-CH_2CH_3$ |
| 135 | $-(CH_2)_2CH_3$ | $-(CH_2)_2CH_3$ | H | H | $-OH$ | H | H | $-CH_2CH_3$ |
| 137 | $-(CH_2)_2CH_3$ | $-CH(CH_3)_2$ | H | H | $-OH$ | H | H | $-CH_2CH_3$ |
| 138 | $-(CH_2)_2CH_3$ | $-(CH_2)_3CH_3$ | H | H | $-OH$ | H | H | $-CH_2CH_3$ |
| 139 | $-(CH_2)_2CH_3$ | $-CH_2-HC=CH_2$ | H | H | $-OH$ | H | H | $-CH_2CH_3$ |
| 140 | $-CH(CH_3)_2$ | $-CH(CH_3)_2$ | H | H | $-OH$ | H | H | $-CH_2CH_3$ |
| 141 | $-CH(CH_3)_2$ | $-(CH_2)_3CH_3$ | H | H | $-OH$ | H | H | $-CH_2CH_3$ |
| 142 | $-CH(CH_3)_2$ | $-CH_2-HC=CH_2$ | H | H | $-OH$ | H | H | $-CH_2CH_3$ |
| 143 | $-(CH_2)_3CH_3$ | $-(CH_2)_3CH_3$ | H | H | $-OH$ | H | H | $-CH_2CH_3$ |
| 144 | $-(CH_2)_3CH_3$ | $-CH_2-HC=CH_2$ | H | H | $-OH$ | H | H | $-CH_2CH_3$ |
| 145 | $-CH_2-HC=CH_2$ | $-CH_2-HC=CH_2$ | H | H | $-OH$ | H | H | $-CH_2CH_3$ |
| 145b | $-CH_3$ | $-CH_3$ | H | H | $-OH$ | H | $-CH_3$ | H |
| 146 | $-CH_3$ | $-CH_2CH_3$ | H | H | $-OH$ | H | $-CH_3$ | H |
| 147 | $-CH_3$ | $-(CH_2)_2CH_3$ | H | H | $-OH$ | H | $-CH_3$ | H |
| 148 | $-CH_3$ | $-CH(CH_3)_2$ | H | H | $-OH$ | H | $-CH_3$ | H |
| 149 | $-CH_3$ | $-(CH_2)_3CH_3$ | H | H | $-OH$ | H | $-CH_3$ | H |
| 150 | $-CH_3$ | $-CH_2-HC=CH_2$ | H | H | $-OH$ | H | $-CH_3$ | H |
| 151 | $-CH_2CH_3$ | $-CH_2CH_3$ | H | H | $-OH$ | H | $-CH_3$ | H |
| 152 | $-CH_2CH_3$ | $-(CH_2)_2CH_3$ | H | H | $-OH$ | H | $-CH_3$ | H |
| 153 | $-CH_2CH_3$ | $-CH(CH_3)_2$ | H | H | $-OH$ | H | $-CH_3$ | H |
| 154 | $-CH_2CH_3$ | $-(CH_2)_3CH_3$ | H | H | $-OH$ | H | $-CH_3$ | H |
| 155 | $-CH_2CH_3$ | $-CH_2-HC=CH_2$ | H | H | $-OH$ | H | $-CH_3$ | H |
| 156 | $-(CH_2)_2CH_3$ | $-(CH_2)_2CH_3$ | H | H | $-OH$ | H | $-CH_3$ | H |
| 157 | $-(CH_2)_2CH_3$ | $-CH(CH_3)_2$ | H | H | $-OH$ | H | $-CH_3$ | H |
| 158 | $-(CH_2)_2CH_3$ | $-(CH_2)_3CH_3$ | H | H | $-OH$ | H | $-CH_3$ | H |
| 159 | $-(CH_2)_2CH_3$ | $-CH_2-HC=CH_2$ | H | H | $-OH$ | H | $-CH_3$ | H |
| 160 | $-CH(CH_3)_2$ | $-CH(CH_3)_2$ | H | H | $-OH$ | H | $-CH_3$ | H |
| 161 | $-CH(CH_3)_2$ | $-(CH_2)_3CH_3$ | H | H | $-OH$ | H | $-CH_3$ | H |
| 162 | $-CH(CH_3)_2$ | $-CH_2-HC=CH_2$ | H | H | $-OH$ | H | $-CH_3$ | H |
| 163 | $-(CH_2)_3CH_3$ | $-(CH_2)_3CH_3$ | H | H | $-OH$ | H | $-CH_3$ | H |
| 164 | $-(CH_2)_3CH_3$ | $-CH_2-HC=CH_2$ | H | H | $-OH$ | H | $-CH_3$ | H |
| 165 | $-CH_2-HC=CH_2$ | $-CH_2-HC=CH_2$ | H | H | $-OH$ | H | $-CH_3$ | H |
| 166 | $-CH_3$ | $-CH_3$ | H | H | $-OC(O)CH_3$ | H | H | $-CH_2CH_3$ |
| 167 | $-CH_3$ | $-CH_2CH_3$ | H | H | $-OC(O)CH_3$ | H | H | $-CH_2CH_3$ |
| 168 | $-CH_3$ | $-(CH_2)_2CH_3$ | H | H | $-OC(O)CH_3$ | H | H | $-CH_2CH_3$ |
| 169 | $-CH_3$ | $-CH(CH_3)_2$ | H | H | $-OC(O)CH_3$ | H | H | $-CH_2CH_3$ |
| 170 | $-CH_3$ | $-(CH_2)_3CH_3$ | H | H | $-OC(O)CH_3$ | H | H | $-CH_2CH_3$ |
| 171 | $-CH_3$ | $-CH_2-HC=CH_2$ | H | H | $-OC(O)CH_3$ | H | H | $-CH_2CH_3$ |
| 172 | $-CH_2CH_3$ | $-CH_2CH_3$ | H | H | $-OC(O)CH_3$ | H | H | $-CH_2CH_3$ |
| 173 | $-CH_2CH_3$ | $-(CH_2)_2CH_3$ | H | H | $-OC(O)CH_3$ | H | H | $-CH_2CH_3$ |
| 174 | $-CH_2CH_3$ | $-CH(CH_3)_2$ | H | H | $-OC(O)CH_3$ | H | H | $-CH_2CH_3$ |
| 175 | $-CH_2CH_3$ | $-(CH_2)_3CH_3$ | H | H | $-OC(O)CH_3$ | H | H | $-CH_2CH_3$ |
| 176 | $-CH_2CH_3$ | $-CH_2-HC=CH_2$ | H | H | $-OC(O)CH_3$ | H | H | $-CH_2CH_3$ |

TABLE 6-continued

| Ref. | X | Y | $R_2$ | $R_3$ | $R_4$ | $R_5$ | $R_7$ | $R_1$ |
|---|---|---|---|---|---|---|---|---|
| 177 | $-(CH_2)_2CH_3$ | $-(CH_2)_2CH_3$ | H | H | $-OC(O)CH_3$ | H | H | $-CH_2CH_3$ |
| 178 | $-(CH_2)_2CH_3$ | $-CH(CH_3)_2$ | H | H | $-OC(O)CH_3$ | H | H | $-CH_2CH_3$ |
| 179 | $-(CH_2)_2CH_3$ | $-(CH_2)_3CH_3$ | H | H | $-OC(O)CH_3$ | H | H | $-CH_2CH_3$ |
| 180 | $-(CH_2)_2CH_3$ | $-CH_2-HC=CH_2$ | H | H | $-OC(O)CH_3$ | H | H | $-CH_2CH_3$ |
| 181 | $-CH(CH_3)_2$ | $-CH(CH_3)_2$ | H | H | $-OC(O)CH_3$ | H | H | $-CH_2CH_3$ |
| 182 | $-CH(CH_3)_2$ | $-(CH_2)_3CH_3$ | H | H | $-OC(O)CH_3$ | H | H | $-CH_2CH_3$ |
| 183 | $-CH(CH_3)_2$ | $-CH_2-HC=CH_2$ | H | H | $-OC(O)CH_3$ | H | H | $-CH_2CH_3$ |
| 184 | $-(CH_2)_3CH_3$ | $-(CH_2)_3CH_3$ | H | H | $-OC(O)CH_3$ | H | H | $-CH_2CH_3$ |
| 185 | $-(CH_2)_3CH_3$ | $-CH_2-HC=CH_2$ | H | H | $-OC(O)CH_3$ | H | H | $-CH_2CH_3$ |
| 186 | $-CH_2-HC=CH_2$ | $-CH_2-HC=CH_2$ | H | H | $-OC(O)CH_3$ | H | H | $-CH_2CH_3$ |
| 187 | $-CH_3$ | $-CH_3$ | H | H | $-OC(O)CH_3$ | H | $-CH_3$ | H |
| 188 | $-CH_3$ | $-CH_2CH_3$ | H | H | $-OC(O)CH_3$ | H | $-CH_3$ | H |
| 189 | $-CH_3$ | $-(CH_2)_2CH_3$ | H | H | $-OC(O)CH_3$ | H | $-CH_3$ | H |
| 190 | $-CH_3$ | $-CH(CH_3)_2$ | H | H | $-OC(O)CH_3$ | H | $-CH_3$ | H |
| 191 | $-CH_3$ | $-(CH_2)_3CH_3$ | H | H | $-OC(O)CH_3$ | H | $-CH_3$ | H |
| 192 | $-CH_3$ | $-CH_2-HC=CH_2$ | H | H | $-OC(O)CH_3$ | H | $-CH_3$ | H |
| 193 | $-CH_2CH_3$ | $-CH_2CH_3$ | H | H | $-OC(O)CH_3$ | H | $-CH_3$ | H |
| 194 | $-CH_2CH_3$ | $-(CH_2)_2CH_3$ | H | H | $-OC(O)CH_3$ | H | $-CH_3$ | H |
| 195 | $-CH_2CH_3$ | $-CH(CH_3)_2$ | H | H | $-OC(O)CH_3$ | H | $-CH_3$ | H |
| 196 | $-CH_2CH_3$ | $-(CH_2)_3CH_3$ | H | H | $-OC(O)CH_3$ | H | $-CH_3$ | H |
| 197 | $-CH_2CH_3$ | $-CH_2-HC=CH_2$ | H | H | $-OC(O)CH_3$ | H | $-CH_3$ | H |
| 198 | $-(CH_2)_2CH_3$ | $-(CH_2)_2CH_3$ | H | H | $-OC(O)CH_3$ | H | $-CH_3$ | H |
| 199 | $-(CH_2)_2CH_3$ | $-CH(CH_3)_2$ | H | H | $-OC(O)CH_3$ | H | $-CH_3$ | H |
| 200 | $-(CH_2)_2CH_3$ | $-(CH_2)_3CH_3$ | H | H | $-OC(O)CH_3$ | H | $-CH_3$ | H |
| 201 | $-(CH_2)_2CH_3$ | $-CH_2-HC=CH_2$ | H | H | $-OC(O)CH_3$ | H | $-CH_3$ | H |
| 202 | $-CH(CH_3)_2$ | $-CH(CH_3)_2$ | H | H | $-OC(O)CH_3$ | H | $-CH_3$ | H |
| 203 | $-CH(CH_3)_2$ | $-(CH_2)_3CH_3$ | H | H | $-OC(O)CH_3$ | H | $-CH_3$ | H |
| 204 | $-CH(CH_3)_2$ | $-CH_2-HC=CH_2$ | H | H | $-OC(O)CH_3$ | H | $-CH_3$ | H |
| 205 | $-(CH_2)_3CH_3$ | $-(CH_2)_3CH_3$ | H | H | $-OC(O)CH_3$ | H | $-CH_3$ | H |
| 206 | $-(CH_2)_3CH_3$ | $-CH_2-HC=CH_2$ | H | H | $-OC(O)CH_3$ | H | $-CH_3$ | H |
| 207 | $-CH_2-HC=CH_2$ | $-CH_2-HC=CH_2$ | H | H | $-OC(O)CH_3$ | H | $-CH_3$ | H |
| 207b | $-CH_3$ | $-CH_3$ | H | H | H | $-OCH_3$ | H | $-CH_2CH_3$ |
| 208 | $-CH_3$ | $-CH_2CH_3$ | H | H | H | $-OCH_3$ | H | $-CH_2CH_3$ |
| 209 | $-CH_3$ | $-(CH_2)_2CH_3$ | H | H | H | $-OCH_3$ | H | $-CH_2CH_3$ |
| 210 | $-CH_3$ | $-CH(CH_3)_2$ | H | H | H | $-OCH_3$ | H | $-CH_2CH_3$ |
| 211 | $-CH_3$ | $-(CH_2)_3CH_3$ | H | H | H | $-OCH_3$ | H | $-CH_2CH_3$ |
| 212 | $-CH_3$ | $-CH_2-HC=CH_2$ | H | H | H | $-OCH_3$ | H | $-CH_2CH_3$ |
| 213 | $-CH_2CH_3$ | $-CH_2CH_3$ | H | H | H | $-OCH_3$ | H | $-CH_2CH_3$ |
| 214 | $-CH_2CH_3$ | $-(CH_2)_2CH_3$ | H | H | H | $-OCH_3$ | H | $-CH_2CH_3$ |
| 215 | $-CH_2CH_3$ | $-CH(CH_3)_2$ | H | H | H | $-OCH_3$ | H | $-CH_2CH_3$ |
| 216 | $-CH_2CH_3$ | $-(CH_2)_3CH_3$ | H | H | H | $-OCH_3$ | H | $-CH_2CH_3$ |
| 217 | $-CH_2CH_3$ | $-CH_2-HC=CH_2$ | H | H | H | $-OCH_3$ | H | $-CH_2CH_3$ |
| 218 | $-(CH_2)_2CH_3$ | $-(CH_2)_2CH_3$ | H | H | H | $-OCH_3$ | H | $-CH_2CH_3$ |
| 219 | $-(CH_2)_2CH_3$ | $-CH(CH_3)_2$ | H | H | H | $-OCH_3$ | H | $-CH_2CH_3$ |
| 220 | $-(CH_2)_2CH_3$ | $-(CH_2)_3CH_3$ | H | H | H | $-OCH_3$ | H | $-CH_2CH_3$ |
| 221 | $-(CH_2)_2CH_3$ | $-CH_2-HC=CH_2$ | H | H | H | $-OCH_3$ | H | $-CH_2CH_3$ |
| 222 | $-CH(CH_3)_2$ | $-CH(CH_3)_2$ | H | H | H | $-OCH_3$ | H | $-CH_2CH_3$ |
| 223 | $-CH(CH_3)_2$ | $-(CH_2)_3CH_3$ | H | H | H | $-OCH_3$ | H | $-CH_2CH_3$ |
| 224 | $-CH(CH_3)_2$ | $-CH_2-HC=CH_2$ | H | H | H | $-OCH_3$ | H | $-CH_2CH_3$ |
| 225 | $-(CH_2)_3CH_3$ | $-(CH_2)_3CH_3$ | H | H | H | $-OCH_3$ | H | $-CH_2CH_3$ |
| 226 | $-(CH_2)_3CH_3$ | $-CH_2-HC=CH_2$ | H | H | H | $-OCH_3$ | H | $-CH_2CH_3$ |
| 227 | $-CH_2-HC=CH_2$ | $-CH_2-HC=CH_2$ | H | H | H | $-OCH_3$ | H | $-CH_2CH_3$ |
| 228 | $-CH_3$ | $-CH_3$ | H | H | H | $-OCH_3$ | $-CH_3$ | H |
| 229 | $-CH_3$ | $-CH_2CH_3$ | H | H | H | $-OCH_3$ | $-CH_3$ | H |
| 230 | $-CH_3$ | $-(CH_2)_2CH_3$ | H | H | H | $-OCH_3$ | $-CH_3$ | H |
| 231 | $-CH_3$ | $-CH(CH_3)_2$ | H | H | H | $-OCH_3$ | $-CH_3$ | H |
| 232 | $-CH_3$ | $-(CH_2)_3CH_3$ | H | H | H | $-OCH_3$ | $-CH_3$ | H |
| 233 | $-CH_3$ | $-CH_2-HC=CH_2$ | H | H | H | $-OCH_3$ | $-CH_3$ | H |
| 234 | $-CH_2CH_3$ | $-CH_2CH_3$ | H | H | H | $-OCH_3$ | $-CH_3$ | H |
| 235 | $-CH_2CH_3$ | $-(CH_2)_2CH_3$ | H | H | H | $-OCH_3$ | $-CH_3$ | H |
| 236 | $-CH_2CH_3$ | $-CH(CH_3)_2$ | H | H | H | $-OCH_3$ | $-CH_3$ | H |
| 237 | $-CH_2CH_3$ | $-(CH_2)_3CH_3$ | H | H | H | $-OCH_3$ | $-CH_3$ | H |
| 238 | $-CH_2CH_3$ | $-CH_2-HC=CH_2$ | H | H | H | $-OCH_3$ | $-CH_3$ | H |
| 239 | $-(CH_2)_2CH_3$ | $-(CH_2)_2CH_3$ | H | H | H | $-OCH_3$ | $-CH_3$ | H |
| 240 | $-(CH_2)_2CH_3$ | $-CH(CH_3)_2$ | H | H | H | $-OCH_3$ | $-CH_3$ | H |
| 241 | $-(CH_2)_2CH_3$ | $-(CH_2)_3CH_3$ | H | H | H | $-OCH_3$ | $-CH_3$ | H |
| 242 | $-(CH_2)_2CH_3$ | $-CH_2-HC=CH_2$ | H | H | H | $-OCH_3$ | $-CH_3$ | H |
| 243 | $-CH(CH_3)_2$ | $-CH(CH_3)_2$ | H | H | H | $-OCH_3$ | $-CH_3$ | H |
| 244 | $-CH(CH_3)_2$ | $-(CH_2)_3CH_3$ | H | H | H | $-OCH_3$ | $-CH_3$ | H |
| 245 | $-CH(CH_3)_2$ | $-CH_2-HC=CH_2$ | H | H | H | $-OCH_3$ | $-CH_3$ | H |
| 246 | $-(CH_2)_3CH_3$ | $-(CH_2)_3CH_3$ | H | H | H | $-OCH_3$ | $-CH_3$ | H |
| 247 | $-(CH_2)_3CH_3$ | $-CH_2-HC=CH_2$ | H | H | H | $-OCH_3$ | $-CH_3$ | H |
| 248 | $-CH_2-HC=CH_2$ | $-CH_2-HC=CH_2$ | H | H | H | $-OCH_3$ | $-CH_3$ | H |
| 249 | H | $-CH_3$ | H | H | H | H | H | $-CH_2CH_3$ |
| 250 | H | $-CH_2CH_3$ | H | H | H | H | H | $-CH_2CH_3$ |
| 251 | H | $-(CH_2)_2CH_3$ | H | H | H | H | H | $-CH_2CH_3$ |
| 252 | H | $-CH(CH_3)_2$ | H | H | H | H | H | $-CH_2CH_3$ |
| 253 | H | $-(CH_2)_3CH_3$ | H | H | H | H | H | $-CH_2CH_3$ |

TABLE 6-continued

| Ref. | X | Y | $R_2$ | $R_3$ | $R_4$ | $R_5$ | $R_7$ | $R_1$ |
|---|---|---|---|---|---|---|---|---|
| 254 | H | $-CH_2-HC=CH_2$ | H | H | H | H | H | $-CH_2CH_3$ |
| 255 | H | $-CH_3$ | H | H | $-OH$ | H | H | H |
| 256 | H | $-CH_2CH_3$ | H | H | $-OH$ | H | H | H |
| 257 | H | $-(CH_2)_2CH_3$ | H | H | $-OH$ | H | H | H |
| 258 | H | $-CH(CH_3)_2$ | H | H | $-OH$ | H | H | H |
| 259 | H | $-(CH_2)_3CH_3$ | H | H | $-OH$ | H | H | H |
| 260 | H | $-CH_2-HC=CH_2$ | H | H | $-OH$ | H | H | H |
| 261 | H | $-CH_3$ | H | H | $-OH$ | H | H | $-CH_2CH_3$ |
| 262 | H | $-CH_2CH_3$ | H | H | $-OH$ | H | H | $-CH_2CH_3$ |
| 263 | H | $-(CH_2)_2CH_3$ | H | H | $-OH$ | H | H | $-CH_2CH_3$ |
| 264 | H | $-CH(CH_3)_2$ | H | H | $-OH$ | H | H | $-CH_2CH_3$ |
| 265 | H | $-(CH_2)_3CH_3$ | H | H | $-OH$ | H | H | $-CH_2CH_3$ |
| 266 | H | $-CH_2-HC=CH_2$ | H | H | $-OH$ | H | H | $-CH_2CH_3$ |
| 267 | H | $-CH_3$ | H | H | $-OH$ | H | $-CH_3$ | H |
| 268 | H | $-CH_2CH_3$ | H | H | $-OH$ | H | $-CH_3$ | H |
| 269 | H | $-(CH_2)_2CH_3$ | H | H | $-OH$ | H | $-CH_3$ | H |
| 270 | H | $-CH(CH_3)_2$ | H | H | $-OH$ | H | $-CH_3$ | H |
| 271 | H | $-(CH_2)_3CH_3$ | H | H | $-OH$ | H | $-CH_3$ | H |
| 272 | H | $-CH_2-HC=CH_2$ | H | H | $-OH$ | H | $-CH_3$ | H |
| 273 | H | $-CH_3$ | H | H | H | $-OCH_3$ | $-CH_3$ | H |
| 274 | H | $-CH_2CH_3$ | H | H | H | $-OCH_3$ | $-CH_3$ | H |
| 275 | H | $-(CH_2)_2CH_3$ | H | H | H | $-OCH_3$ | $-CH_3$ | H |
| 276 | H | $-CH(CH_3)_2$ | H | H | H | $-OCH_3$ | $-CH_3$ | H |
| 277 | H | $-(CH_2)_3CH_3$ | H | H | H | $-OCH_3$ | $-CH_3$ | H |
| 278 | H | $-CH_2-HC=CH_2$ | H | H | H | $-OCH_3$ | $-CH_3$ | H |
| 279 | H | $-CH_3$ | H | H | $-OC(O)CH_3$ | H | H | H |
| 280 | H | $-CH_2CH_3$ | H | H | $-OC(O)CH_3$ | H | H | H |
| 281 | H | $-(CH_2)_2CH_3$ | H | H | $-OC(O)CH_3$ | H | H | H |
| 282 | H | $-CH(CH_3)_2$ | H | H | $-OC(O)CH_3$ | H | H | H |
| 283 | H | $-(CH_2)_3CH_3$ | H | H | $-OC(O)CH_3$ | H | H | H |
| 284 | H | $-CH_2-HC=CH_2$ | H | H | $-OC(O)CH_3$ | H | H | H |
| 285 | H | $-CH_3$ | H | H | H | H | $-CH_3$ | H |
| 286 | H | $-CH_2CH_3$ | H | H | H | H | $-CH_3$ | H |
| 287 | H | $-(CH_2)_2CH_3$ | H | H | H | H | $-CH_3$ | H |
| 288 | H | $-CH(CH_3)_2$ | H | H | H | H | $-CH_3$ | H |
| 289 | H | $-(CH_2)_3CH_3$ | H | H | H | H | $-CH_3$ | H |
| 290 | H | $-CH_2-HC=CH_2$ | H | H | H | H | $-CH_3$ | H |
| 291 | H | $-CH_3$ | H | H | H | $-OCH_3$ | H | H |
| 292 | H | $-CH_2CH_3$ | H | H | H | $-OCH_3$ | H | H |
| 293 | H | $-(CH_2)_2CH_3$ | H | H | H | $-OCH_3$ | H | H |
| 294 | H | $-CH(CH_3)_2$ | H | H | H | $-OCH_3$ | H | H |
| 295 | H | $-(CH_2)_3CH_3$ | H | H | H | $-OCH_3$ | H | H |
| 296 | H | $-CH_2-HC=CH_2$ | H | H | H | $-OCH_3$ | H | H |
| 297 | cyclopropyl | $-CH_3$ | H | H | H | H | H | H |
| 298 | cyclopropyl | $-CH_2CH_3$ | H | H | H | H | H | H |
| 299 | cyclopropyl | $-(CH_2)_2CH_3$ | H | H | H | H | H | H |
| 300 | cyclopropyl | $-CH(CH_3)_2$ | H | H | H | H | H | H |
| 301 | cyclopropyl | $-(CH_2)_3CH_3$ | H | H | H | H | H | H |
| 302 | cyclopropyl | $-CH_2-HC=CH_2$ | H | H | H | H | H | H |
| 303 | cyclopropyl | $-CH_3$ | H | H | $-OCH_3$ | H | H | H |
| 304 | cyclopropyl | $-CH_2CH_3$ | H | H | $-OCH_3$ | H | H | H |
| 305 | cyclopropyl | $-(CH_2)_2CH_3$ | H | H | $-OCH_3$ | H | H | H |
| 306 | cyclopropyl | $-CH(CH_3)_2$ | H | H | $-OCH_3$ | H | H | H |
| 307 | cyclopropyl | $-(CH_2)_3CH_3$ | H | H | $-OCH_3$ | H | H | H |
| 308 | cyclopropyl | $-CH_2-HC=CH_2$ | H | H | $-OCH_3$ | H | H | H |
| 309 | cyclopropyl | $-CH_3$ | H | H | $-OH$ | H | H | H |
| 310 | cyclopropyl | $-CH_2CH_3$ | H | H | $-OH$ | H | H | H |
| 311 | cyclopropyl | $-(CH_2)_2CH_3$ | H | H | $-OH$ | H | H | H |
| 312 | cyclopropyl | $-CH(CH_3)_2$ | H | H | $-OH$ | H | H | H |
| 313 | cyclopropyl | $-(CH_2)_3CH_3$ | H | H | $-OH$ | H | H | H |
| 314 | cyclopropyl | $-CH_2-HC=CH_2$ | H | H | $-OH$ | H | H | H |
| 315 | cyclopropyl | $-CH_3$ | H | H | $-OC(O)CH_3$ | H | H | H |
| 316 | cyclopropyl | $-CH_2CH_3$ | H | H | $-OC(O)CH_3$ | H | H | H |
| 317 | cyclopropyl | $-(CH_2)_2CH_3$ | H | H | $-OC(O)CH_3$ | H | H | H |
| 318 | cyclopropyl | $-CH(CH_3)_2$ | H | H | $-OC(O)CH_3$ | H | H | H |
| 319 | cyclopropyl | $-(CH_2)_3CH_3$ | H | H | $-OC(O)CH_3$ | H | H | H |
| 320 | cyclopropyl | $-CH_2-HC=CH_2$ | H | H | $-OC(O)CH_3$ | H | H | H |
| 321 | cyclopropyl | $-CH_3$ | H | H | H | H | H | $-CH_2CH_3$ |
| 322 | cyclopropyl | $-CH_2CH_3$ | H | H | H | H | H | $-CH_2CH_3$ |
| 323 | cyclopropyl | $-(CH_2)_2CH_3$ | H | H | H | H | H | $-CH_2CH_3$ |
| 324 | cyclopropyl | $-CH(CH_3)_2$ | H | H | H | H | H | $-CH_2CH_3$ |
| 325 | cyclopropyl | $-(CH_2)_3CH_3$ | H | H | H | H | H | $-CH_2CH_3$ |
| 326 | cyclopropyl | $-CH_2-HC=CH_2$ | H | H | H | H | H | $-CH_2CH_3$ |
| 327 | cyclopropyl | $-CH_3$ | H | H | $-OH$ | H | H | $-CH_2CH_3$ |
| 328 | cyclopropyl | $-CH_2CH_3$ | H | H | $-OH$ | H | H | $-CH_2CH_3$ |
| 329 | cyclopropyl | $-(CH_2)_2CH_3$ | H | H | $-OH$ | H | H | $-CH_2CH_3$ |
| 330 | cyclopropyl | $-CH(CH_3)_2$ | H | H | $-OH$ | H | H | $-CH_2CH_3$ |
| 331 | cyclopropyl | $-(CH_2)_3CH_3$ | H | H | $-OH$ | H | H | $-CH_2CH_3$ |

TABLE 6-continued

| Ref. | X | Y | $R_2$ | $R_3$ | $R_4$ | $R_5$ | $R_7$ | $R_1$ |
|---|---|---|---|---|---|---|---|---|
| 332 | cyclopropyl | $-CH_2-HC{=}CH_2$ | H | H | $-OH$ | H | H | $-CH_2CH_3$ |
| 333 | H | $-CH_3$ | H | H | H | H | H | H |
| 334 | H | $-CH_2CH_3$ | H | H | H | H | H | H |
| 335 | H | $-(CH_2)_2CH_3$ | H | H | H | H | H | H |
| 336 | H | $-CH(CH_3)_2$ | H | H | H | H | H | H |
| 337 | H | $-(CH_2)_3CH_3$ | H | H | H | H | H | H |
| 338 | H | $-CH_2-HC{=}CH_2$ | H | H | H | H | H | H |
| 339 | H | cyclopropyl | H | H | H | H | H | H |
| 340 | H | $-CH_3$ | H | $-CH_3$ | H | H | H | H |
| 341 | H | $-CH_2CH_3$ | H | $-CH_3$ | H | H | H | H |
| 342 | H | $-(CH_2)_2CH_3$ | H | $-CH_3$ | H | H | H | H |
| 343 | H | $-CH(CH_3)_2$ | H | $-CH_3$ | H | H | H | H |
| 344 | H | $-(CH_2)_3CH_3$ | H | $-CH_3$ | H | H | H | H |
| 345 | H | $-CH_2-HC{=}CH_2$ | H | $-CH_3$ | H | H | H | H |
| 346 | H | cyclopropyl | H | $-CH_3$ | H | H | H | H |
| 347 | H | $-CH_3$ | H | $-CH_3$ | $-OH$ | H | H | H |
| 348 | H | $-CH_2CH_3$ | H | $-CH_3$ | $-OH$ | H | H | H |
| 349 | H | $-(CH_2)_2CH_3$ | H | $-CH_3$ | $-OH$ | H | H | H |
| 350 | H | $-CH(CH_3)_2$ | H | $-CH_3$ | $-OH$ | H | H | H |
| 351 | H | $-(CH_2)_3CH_3$ | H | $-CH_3$ | $-OH$ | H | H | H |
| 352 | H | $-CH_2-HC{=}CH_2$ | H | $-CH_3$ | $-OH$ | H | H | H |
| 353 | H | cyclopropyl | H | $-CH_3$ | $-OH$ | H | H | H |
| 354 | H | $-CH_3$ | H | $-CH_3$ | H | H | H | $-CH_2CH_3$ |
| 355 | H | $-CH_2CH_3$ | H | $-CH_3$ | H | H | H | $-CH_2CH_3$ |
| 356 | H | $-(CH_2)_2CH_3$ | H | $-CH_3$ | H | H | H | $-CH_2CH_3$ |
| 357 | H | $-CH(CH_3)_2$ | H | $-CH_3$ | H | H | H | $-CH_2CH_3$ |
| 358 | H | $-(CH_2)_3CH_3$ | H | $-CH_3$ | H | H | H | $-CH_2CH_3$ |
| 359 | H | $-CH_2-HC{=}CH_2$ | H | $-CH_3$ | H | H | H | $-CH_2CH_3$ |
| 360 | H | cyclopropyl | H | $-CH_3$ | H | H | H | $-CH_2CH_3$ |
| 361 | H | $-CH_3$ | H | $-CH_3$ | $-OH$ | H | H | $-CH_2CH_3$ |
| 362 | H | $-CH_2CH_3$ | H | $-CH_3$ | $-OH$ | H | H | $-CH_2CH_3$ |
| 363 | H | $-(CH_2)_2CH_3$ | H | $-CH_3$ | $-OH$ | H | H | $-CH_2CH_3$ |
| 364 | H | $-CH(CH_3)_2$ | H | $-CH_3$ | $-OH$ | H | H | $-CH_2CH_3$ |
| 365 | H | $-(CH_2)_3CH_3$ | H | $-CH_3$ | $-OH$ | H | H | $-CH_2CH_3$ |
| 366 | H | $-CH_2-HC{=}CH_2$ | H | $-CH_3$ | $-OH$ | H | H | $-CH_2CH_3$ |
| 367 | H | cyclopropyl | H | $-CH_3$ | $-OH$ | H | H | $-CH_2CH_3$ |
| 368 | H | $-CH_3$ | H | $-CH_3$ | H | H | $-CH_3$ | H |
| 369 | H | $-CH_2CH_3$ | H | $-CH_3$ | H | H | $-CH_3$ | H |
| 370 | H | $-(CH_2)_2CH_3$ | H | $-CH_3$ | H | H | $-CH_3$ | H |
| 371 | H | $-CH(CH_3)_2$ | H | $-CH_3$ | H | H | $-CH_3$ | H |
| 372 | H | $-(CH_2)_3CH_3$ | H | $-CH_3$ | H | H | $-CH_3$ | H |
| 373 | H | $-CH_2-HC{=}CH_2$ | H | $-CH_3$ | H | H | $-CH_3$ | H |
| 374 | H | cyclopropyl | H | $-CH_3$ | H | H | $-CH_3$ | H |
| 375 | H | $-CH_3$ | H | $-CH_3$ | H | $-OCH_3$ | H | H |
| 376 | H | $-CH_2CH_3$ | H | $-CH_3$ | H | $-OCH_3$ | H | H |
| 377 | H | $-(CH_2)_2CH_3$ | H | $-CH_3$ | H | $-OCH_3$ | H | H |
| 378 | H | $-CH(CH_3)_2$ | H | $-CH_3$ | H | $-OCH_3$ | H | H |
| 379 | H | $-(CH_2)_3CH_3$ | H | $-CH_3$ | H | $-OCH_3$ | H | H |
| 380 | H | $-CH_2-HC{=}CH_2$ | H | $-CH_3$ | H | $-OCH_3$ | H | H |
| 381 | H | cyclopropyl | H | $-CH_3$ | H | $-OCH_3$ | H | H |
| 382 | H | $-CH_3$ | H | $-CH_3$ | $-OH$ | H | $-CH_3$ | H |
| 383 | H | $-CH_2CH_3$ | H | $-CH_3$ | $-OH$ | H | $-CH_3$ | H |
| 384 | H | $-(CH_2)_2CH_3$ | H | $-CH_3$ | $-OH$ | H | $-CH_3$ | H |
| 385 | H | $-CH(CH_3)_2$ | H | $-CH_3$ | $-OH$ | H | $-CH_3$ | H |
| 386 | H | $-(CH_2)_3CH_3$ | H | $-CH_3$ | $-OH$ | H | $-CH_3$ | H |
| 387 | H | $-CH_2-HC{=}CH_2$ | H | $-CH_3$ | $-OH$ | H | $-CH_3$ | H |
| 388 | H | cyclopropyl | H | $-CH_3$ | $-OH$ | H | $-CH_3$ | H |
| 389 | H | $-CH_3$ | H | $-CH_3$ | $-OC(O)CH_3$ | H | H | H |
| 390 | H | $-CH_2CH_3$ | H | $-CH_3$ | $-OC(O)CH_3$ | H | H | H |
| 391 | H | $-(CH_2)_2CH_3$ | H | $-CH_3$ | $-OC(O)CH_3$ | H | H | H |
| 392 | H | $-CH(CH_3)_2$ | H | $-CH_3$ | $-OC(O)CH_3$ | H | H | H |
| 393 | H | $-(CH_2)_3CH_3$ | H | $-CH_3$ | $-OC(O)CH_3$ | H | H | H |
| 394 | H | $-CH_2-HC{=}CH_2$ | H | $-CH_3$ | $-OC(O)CH_3$ | H | H | H |
| 395 | H | cyclopropyl | H | $-CH_3$ | $-OC(O)CH_3$ | H | H | H |
| 396 | H | H | H | $-CH_3$ | H | H | H | H |
| 397 | H | H | H | $-CH_3$ | $-OH$ | H | H | H |
| 398 | H | H | H | $-CH_3$ | H | $-OCH_3$ | H | H |
| 399 | H | H | H | $-CH_3$ | H | H | $-CH_3$ | H |
| 400 | H | H | H | $-CH_3$ | H | H | H | $-CH_2CH_3$ |
| 401 | H | H | H | $-CH_3$ | $-OH$ | H | H | $-CH_2CH_3$ |
| 402 | H | H | H | $-CH_3$ | $-OH$ | H | $-CH_3$ | H |
| 403 | H | H | H | $-CH_3$ | $-OH$ | $-OCH_3$ | $-CH_3$ | H |
| 404 | H | H | H | $-CH_3$ | $-OH$ | F | H | H |
| 405 | H | H | H | $-CH_3$ | $-OH$ | H | H | $-CH_3$ |
| 406 | $-CH_3$ | $-CH_3$ | H | H | H | H | H | H |
| 407 | $-CH_3$ | $-CH_2CH_3$ | H | H | H | H | H | H |
| 408 | $-CH_3$ | $-(CH_2)_2CH_3$ | H | H | H | H | H | H |
| 409 | $-CH_3$ | $-CH(CH_3)_2$ | H | H | H | H | H | H |

TABLE 6-continued

| Ref. | X | Y | $R_2$ | $R_3$ | $R_4$ | $R_5$ | $R_7$ | $R_1$ |
|---|---|---|---|---|---|---|---|---|
| 410 | $—CH_3$ | $—(CH_2)_3CH_3$ | H | H | H | H | H | H |
| 411 | $—CH_3$ | $—CH_2—HC═CH_2$ | H | H | H | H | H | H |
| 412 | $—CH_2CH_3$ | $—CH_2CH_3$ | H | H | H | H | H | H |
| 413 | $—CH_2CH_3$ | $—(CH_2)_2CH_3$ | H | H | H | H | H | H |
| 414 | $—CH_2CH_3$ | $—CH(CH_3)_2$ | H | H | H | H | H | H |
| 415 | $—CH_2CH_3$ | $—(CH_2)_3CH_3$ | H | H | H | H | H | H |
| 416 | $—CH_2CH_3$ | $—CH_2—HC═CH_2$ | H | H | H | H | H | H |
| 417 | $—(CH_2)_2CH_3$ | $—(CH_2)_2CH_3$ | H | H | H | H | H | H |
| 418 | $—(CH_2)_2CH_3$ | $—CH(CH_3)_2$ | H | H | H | H | H | H |
| 419 | $—(CH_2)_2CH_3$ | $—(CH_2)_3CH_3$ | H | H | H | H | H | H |
| 420 | $—(CH_2)_2CH_3$ | $—CH_2—HC═CH_2$ | H | H | H | H | H | H |
| 421 | $—CH(CH_3)_2$ | $—CH(CH_3)_2$ | H | H | H | H | H | H |
| 422 | $—CH(CH_3)_2$ | $—(CH_2)_3CH_3$ | H | H | H | H | H | H |
| 423 | $—CH(CH_3)_2$ | $—CH_2—HC═CH_2$ | H | H | H | H | H | H |
| 424 | $—(CH_2)_3CH_3$ | $—(CH_2)_3CH_3$ | H | H | H | H | H | H |
| 425 | $—(CH_2)_3CH_3$ | $—CH_2—HC═CH_2$ | H | H | H | H | H | H |
| 426 | $—CH_2—HC═CH_2$ | $—CH_2—HC═CH_2$ | H | H | H | H | H | H |
| 427 | H | $—CD_3$ | H | H | H | H | H | H |
| 428 | H | $—CD_3$ | H | H | —OH | H | H | H |
| 429 | H | $—CD_3$ | H | H | $—OC(O)CH_3$ | H | H | H |
| 430 | H | $—CD_3$ | H | H | H | $—OCH_3$ | H | H |
| 431 | H | $—CD_3$ | H | H | H | H | H | H |
| 432 | H | $—CD_3$ | H | H | —OH | H | H | H |
| 433 | H | $—CD_3$ | H | H | $—OC(O)CH_3$ | H | H | H |
| 434 | H | $—CD_3$ | H | H | H | $—OCH_3$ | H | H |
| 435 | H | $—CD_3$ | H | H | H | H | $—CH_3$ | H |
| 436 | H | $—CD_3$ | H | H | —OH | H | $—CH_3$ | H |
| 437 | H | $—CD_3$ | H | H | $—OC(O)CH_3$ | H | $—CH_3$ | H |
| 438 | H | $—CD_3$ | H | H | H | $—OCH_3$ | $—CH_3$ | H |
| 439 | H | $—CD_3$ | H | H | H | H | H | $—CH_2CH_3$ |
| 440 | H | $—CD_3$ | H | H | —OH | H | H | $—CH_2CH_3$ |
| 441 | H | $—CD_3$ | H | H | $—OC(O)CH_3$ | H | H | $—CH_2CH_3$ |
| 442 | H | $—CD_3$ | H | H | H | $—OCH_3$ | H | $—CH_2CH_3$ |
| 443 | H | $—CD_2CD_3$ | H | H | H | H | H | H |
| 444 | H | $—CD_2CD_3$ | H | H | —OH | H | H | H |
| 445 | H | $—CD_2CD_3$ | H | H | $—OC(O)CH_3$ | H | H | H |
| 446 | H | $—CD_2CD_3$ | H | H | H | $—OCH_3$ | H | H |
| 447 | H | $—CD_2CD_3$ | H | H | H | H | H | H |
| 448 | H | $—CD_2CD_3$ | H | H | —OH | H | H | H |
| 449 | H | $—CD_2CD_3$ | H | H | $—OC(O)CH_3$ | H | H | H |
| 450 | H | $—CD_2CD_3$ | H | H | H | $—OCH_3$ | H | H |
| 451 | H | $—CD_2CD_3$ | H | H | H | H | $—CH_3$ | H |
| 452 | H | $—CD_2CD_3$ | H | H | —OH | H | $—CH_3$ | H |
| 453 | H | $—CD_2CD_3$ | H | H | $—OC(O)CH_3$ | H | $—CH_3$ | H |
| 454 | H | $—CD_2CD_3$ | H | H | H | $—OCH_3$ | $—CH_3$ | H |
| 455 | H | $—CD_2CD_3$ | H | H | H | H | H | $—CH_2CH_3$ |
| 456 | H | $—CD_2CD_3$ | H | H | —OH | H | H | $—CH_2CH_3$ |
| 457 | H | $—CD_2CD_3$ | H | H | $—OC(O)CH_3$ | H | H | $—CH_2CH_3$ |
| 458 | H | $—CD_2CD_3$ | H | H | H | $—OCH_3$ | H | $—CH_2CH_3$ |
| 458 | H | $—CH_3$ | H | D | H | H | H | H |
| 459 | H | $—CH_2CH_3$ | H | D | H | H | H | H |
| 460 | H | $—(CH_2)_2CH_3$ | H | D | H | H | H | H |
| 461 | H | $—CH(CH_3)_2$ | H | D | H | H | H | H |
| 462 | H | $—(CH_2)_3CH_3$ | H | D | H | H | H | H |
| 463 | H | $—CH_2—HC═CH_2$ | H | D | H | H | H | H |
| 464 | H | $—CH_3$ | H | D | —OH | H | H | H |
| 465 | H | $—CH_2CH_3$ | H | D | —OH | H | H | H |
| 466 | H | $—(CH_2)_2CH_3$ | H | D | —OH | H | H | H |
| 467 | H | $—CH(CH_3)_2$ | H | D | —OH | H | H | H |
| 468 | H | $—(CH_2)_3CH_3$ | H | D | —OH | H | H | H |
| 469 | H | $—CH_2—HC═CH_2$ | H | D | —OH | H | H | H |
| 470 | H | $—CH_3$ | H | D | $—OC(O)CH_3$ | H | H | H |
| 471 | H | $—CH_2CH_3$ | H | D | $—OC(O)CH_3$ | H | H | H |
| 472 | H | $—(CH_2)_2CH_3$ | H | D | $—OC(O)CH_3$ | H | H | H |
| 473 | H | $—CH(CH_3)_2$ | H | D | $—OC(O)CH_3$ | H | H | H |
| 474 | H | $—(CH_2)_3CH_3$ | H | D | $—OC(O)CH_3$ | H | H | H |
| 475 | H | $—CH_2—HC═CH_2$ | H | D | $—OC(O)CH_3$ | H | H | H |
| 476 | H | $—CH_3$ | H | D | —OH | H | $—CH_3$ | H |
| 477 | H | $—CH_2CH_3$ | H | D | —OH | H | $—CH_3$ | H |
| 478 | H | $—(CH_2)_2CH_3$ | H | D | —OH | H | $—CH_3$ | H |
| 479 | H | $—CH(CH_3)_2$ | H | D | —OH | H | $—CH_3$ | H |
| 480 | H | $—(CH_2)_3CH_3$ | H | D | —OH | H | $—CH_3$ | H |
| 481 | H | $—CH_2—HC═CH_2$ | H | D | —OH | H | $—CH_3$ | H |
| 482 | H | $—CH_3$ | H | D | H | —OMe | $—CH_3$ | H |
| 483 | H | $—CH_2CH_3$ | H | D | H | —OMe | $—CH_3$ | H |
| 484 | H | $—(CH_2)_2CH_3$ | H | D | H | —OMe | $—CH_3$ | H |
| 485 | H | $—CH(CH_3)_2$ | H | D | H | —OMe | $—CH_3$ | H |
| 486 | H | $—(CH_2)_3CH_3$ | H | D | H | —OMe | $—CH_3$ | H |

TABLE 6-continued

| Ref. | X | Y | $R_2$ | $R_3$ | $R_4$ | $R_5$ | $R_7$ | $R_1$ |
|---|---|---|---|---|---|---|---|---|
| 487 | H | $—CH_2—HC{=}CH_2$ | H | D | H | —OMe | $—CH_3$ | H |
| 488 | H | $—CH_3$ | H | D | H | —OMe | H | H |
| 489 | H | $—CH_2CH_3$ | H | D | H | —OMe | H | H |
| 490 | H | $—(CH_2)_2CH_3$ | H | D | H | —OMe | H | H |
| 491 | H | $—CH(CH_3)_2$ | H | D | H | —OMe | H | H |
| 492 | H | $—(CH_2)_3CH_3$ | H | D | H | —OMe | H | H |
| 493 | H | $—CH_2—HC{=}CH_2$ | H | D | H | —OMe | H | H |
| 494 | H | $—CH_3$ | H | D | H | H | $—CH_3$ | H |
| 495 | H | $—CH_2CH_3$ | H | D | H | H | $—CH_3$ | H |
| 496 | H | $—(CH_2)_2CH_3$ | H | D | H | H | $—CH_3$ | H |
| 497 | H | $—CH(CH_3)_2$ | H | D | H | H | $—CH_3$ | H |
| 498 | H | $—(CH_2)_3CH_3$ | H | D | H | H | $—CH_3$ | H |
| 499 | H | $—CH_2—HC{=}CH_2$ | H | D | H | H | $—CH_3$ | H |

Other exemplary compounds of Formula I include those below in Table 7, which is also represented by Formula Ig:

Formula Ig

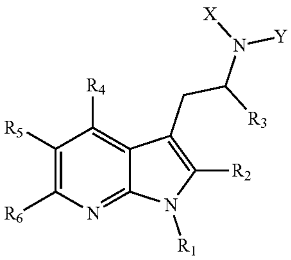

TABLE 7

| Ref. | X | Y | $R_2$ | $R_3$ | $R_4$ | $R_5$ | $R_6$ | $R_1$ |
|---|---|---|---|---|---|---|---|---|
| 1 | $—CH_3$ | $—CH_3$ | H | H | $—OCH_3$ | H | H | H |
| 2 | $—CH_3$ | $—CH_2CH_3$ | H | H | $—OCH_3$ | H | H | H |
| 3 | $—CH_3$ | $—(CH_2)_2CH_3$ | H | H | $—OCH_3$ | H | H | H |
| 4 | $—CH_3$ | $—CH(CH_3)_2$ | H | H | $—OCH_3$ | H | H | H |
| 5 | $—CH_3$ | $—(CH_2)_3CH_3$ | H | H | $—OCH_3$ | H | H | H |
| 6 | $—CH_3$ | $—CH_2—HC{=}CH_2$ | H | H | $—OCH_3$ | H | H | H |
| 7 | $—CH_2CH_3$ | $—CH_2CH_3$ | H | H | $—OCH_3$ | H | H | H |
| 8 | $—CH_2CH_3$ | $—(CH_2)_2CH_3$ | H | H | $—OCH_3$ | H | H | H |
| 9 | $—CH_2CH_3$ | $—CH(CH_3)_2$ | H | H | $—OCH_3$ | H | H | H |
| 10 | $—CH_2CH_3$ | $—(CH_2)_3CH_3$ | H | H | $—OCH_3$ | H | H | H |
| 11 | $—CH_2CH_3$ | $—CH_2—HC{=}CH_2$ | H | H | $—OCH_3$ | H | H | H |
| 12 | $—(CH_2)_2CH_3$ | $—(CH_2)_2CH_3$ | H | H | $—OCH_3$ | H | H | H |
| 13 | $—(CH_2)_2CH_3$ | $—CH(CH_3)_2$ | H | H | $—OCH_3$ | H | H | H |
| 14 | $—(CH_2)_2CH_3$ | $—(CH_2)_3CH_3$ | H | H | $—OCH_3$ | H | H | H |
| 15 | $—(CH_2)_2CH_3$ | $—CH_2—HC{=}CH_2$ | H | H | $—OCH_3$ | H | H | H |
| 16 | $—CH(CH_3)_2$ | $—CH(CH_3)_2$ | H | H | $—OCH_3$ | H | H | H |
| 17 | $—CH(CH_3)_2$ | $—(CH_2)_3CH_3$ | H | H | $—OCH_3$ | H | H | H |
| 18 | $—CH(CH_3)_2$ | $—CH_2—HC{=}CH_2$ | H | H | $—OCH_3$ | H | H | H |
| 19 | $—(CH_2)_3CH_3$ | $—(CH_2)_3CH_3$ | H | H | $—OCH_3$ | H | H | H |
| 20 | $—(CH_2)_3CH_3$ | $—CH_2—HC{=}CH_2$ | H | H | $—OCH_3$ | H | H | H |
| 21 | $—CH_2—HC{=}CH_2$ | $—CH_2—HC{=}CH_2$ | H | H | $—OCH_3$ | H | H | H |
| 22 | $—CH_3$ | $—CH_2CH_3$ | H | H | —OH | H | H | H |
| 23 | $—CH_3$ | $—(CH_2)_2CH_3$ | H | H | —OH | H | H | H |
| 24 | $—CH_3$ | $—CH(CH_3)_2$ | H | H | —OH | H | H | H |
| 25 | $—CH_3$ | $—(CH_2)_3CH_3$ | H | H | —OH | H | H | H |
| 26 | $—CH_3$ | $—CH_2—HC{=}CH_2$ | H | H | —OH | H | H | H |
| 27 | $—CH_2CH_3$ | $—CH_2CH_3$ | H | H | —OH | H | H | H |
| 28 | $—CH_2CH_3$ | $—(CH_2)_2CH_3$ | H | H | —OH | H | H | H |
| 29 | $—CH_2CH_3$ | $—CH(CH_3)_2$ | H | H | —OH | H | H | H |
| 30 | $—CH_2CH_3$ | $—(CH_2)_3CH_3$ | H | H | —OH | H | H | H |
| 31 | $—CH_2CH_3$ | $—CH_2—HC{=}CH_2$ | H | H | —OH | H | H | H |
| 32 | $—(CH_2)_2CH_3$ | $—(CH_2)_2CH_3$ | H | H | —OH | H | H | H |
| 33 | $—(CH_2)_2CH_3$ | $—CH(CH_3)_2$ | H | H | —OH | H | H | H |
| 34 | $—(CH_2)_2CH_3$ | $—(CH_2)_3CH_3$ | H | H | —OH | H | H | H |
| 35 | $—(CH_2)_2CH_3$ | $—CH_2—HC{=}CH_2$ | H | H | —OH | H | H | H |
| 36 | $—CH(CH_3)_2$ | $—CH(CH_3)_2$ | H | H | —OH | H | H | H |
| 37 | $—CH(CH_3)_2$ | $—(CH_2)_3CH_3$ | H | H | —OH | H | H | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 38 | $—CH(CH_3)_2$ | $—CH_2—HC═CH_2$ | H | H | —OH | H | H | H |
| 39 | $—(CH_2)_3CH_3$ | $—(CH_2)_3CH_3$ | H | H | —OH | H | H | H |
| 40 | $—(CH_2)_3CH_3$ | $—CH_2—HC═CH_2$ | H | H | —OH | H | H | H |
| 41 | $—CH_2—HC═CH_2$ | $—CH_2—HC═CH_2$ | H | H | —OH | H | H | H |
| 42 | $—CH_3$ | $—CH_3$ | H | H | $—OC(O)CH_3$ | H | H | H |
| 43 | $—CH_3$ | $—CH_2CH_3$ | H | H | $—OC(O)CH_3$ | H | H | H |
| 44 | $—CH_3$ | $—(CH_2)_2CH_3$ | H | H | $—OC(O)CH_3$ | H | H | H |
| 45 | $—CH_3$ | $—CH(CH_3)_2$ | H | H | $—OC(O)CH_3$ | H | H | H |
| 46 | $—CH_3$ | $—(CH_2)_3CH_3$ | H | H | $—OC(O)CH_3$ | H | H | H |
| 47 | $—CH_3$ | $—CH_2—HC═CH_2$ | H | H | $—OC(O)CH_3$ | H | H | H |
| 48 | $—CH_2CH_3$ | $—CH_2CH_3$ | H | H | $—OC(O)CH_3$ | H | H | H |
| 49 | $—CH_2CH_3$ | $—(CH_2)_2CH_3$ | H | H | $—OC(O)CH_3$ | H | H | H |
| 50 | $—CH_2CH_3$ | $—CH(CH_3)_2$ | H | H | $—OC(O)CH_3$ | H | H | H |
| 51 | $—CH_2CH_3$ | $—(CH_2)_3CH_3$ | H | H | $—OC(O)CH_3$ | H | H | H |
| 52 | $—CH_2CH_3$ | $—CH_2—HC═CH_2$ | H | H | $—OC(O)CH_3$ | H | H | H |
| 53 | $—(CH_2)_2CH_3$ | $—(CH_2)_2CH_3$ | H | H | $—OC(O)CH_3$ | H | H | H |
| 54 | $—(CH_2)_2CH_3$ | $—CH(CH_3)_2$ | H | H | $—OC(O)CH_3$ | H | H | H |
| 55 | $—(CH_2)_2CH_3$ | $—(CH_2)_3CH_3$ | H | H | $—OC(O)CH_3$ | H | H | H |
| 56 | $—(CH_2)_2CH_3$ | $—CH_2—HC═CH_2$ | H | H | $—OC(O)CH_3$ | H | H | H |
| 57 | $—CH(CH_3)_2$ | $—CH(CH_3)_2$ | H | H | $—OC(O)CH_3$ | H | H | H |
| 58 | $—CH(CH_3)_2$ | $—(CH_2)_3CH_3$ | H | H | $—OC(O)CH_3$ | H | H | H |
| 59 | $—CH(CH_3)_2$ | $—CH_2—HC═CH_2$ | H | H | $—OC(O)CH_3$ | H | H | H |
| 60 | $—(CH_2)_3CH_3$ | $—(CH_2)_3CH_3$ | H | H | $—OC(O)CH_3$ | H | H | H |
| 61 | $—(CH_2)_3CH_3$ | $—CH_2—HC═CH_2$ | H | H | $—OC(O)CH_3$ | H | H | H |
| 62 | $—CH_2—HC═CH_2$ | $—CH_2—HC═CH_2$ | H | H | $—OC(O)CH_3$ | H | H | H |
| 63 | $—CH_3$ | $—CH_3$ | H | H | H | $—OCH_3$ | H | H |
| 64 | $—CH_3$ | $—CH_2CH_3$ | H | H | H | $—OCH_3$ | H | H |
| 65 | $—CH_3$ | $—(CH_2)_2CH_3$ | H | H | H | $—OCH_3$ | H | H |
| 66 | $—CH_3$ | $—CH(CH_3)_2$ | H | H | H | $—OCH_3$ | H | H |
| 67 | $—CH_3$ | $—(CH_2)_3CH_3$ | H | H | H | $—OCH_3$ | H | H |
| 68 | $—CH_3$ | $—CH_2—HC═CH_2$ | H | H | H | $—OCH_3$ | H | H |
| 69 | $—CH_2CH_3$ | $—CH_2CH_3$ | H | H | H | $—OCH_3$ | H | H |
| 70 | $—CH_2CH_3$ | $—(CH_2)_2CH_3$ | H | H | H | $—OCH_3$ | H | H |
| 71 | $—CH_2CH_3$ | $—CH(CH_3)_2$ | H | H | H | $—OCH_3$ | H | H |
| 72 | $—CH_2CH_3$ | $—(CH_2)_3CH_3$ | H | H | H | $—OCH_3$ | H | H |
| 73 | $—CH_2CH_3$ | $—CH_2—HC═CH_2$ | H | H | H | $—OCH_3$ | H | H |
| 74 | $—(CH_2)_2CH_3$ | $—(CH_2)_2CH_3$ | H | H | H | $—OCH_3$ | H | H |
| 75 | $—(CH_2)_2CH_3$ | $—CH(CH_3)_2$ | H | H | H | $—OCH_3$ | H | H |
| 76 | $—(CH_2)_2CH_3$ | $—(CH_2)_3CH_3$ | H | H | H | $—OCH_3$ | H | H |
| 77 | $—(CH_2)_2CH_3$ | $—CH_2—HC═CH_2$ | H | H | H | $—OCH_3$ | H | H |
| 78 | $—CH(CH_3)_2$ | $—CH(CH_3)_2$ | H | H | H | $—OCH_3$ | H | H |
| 79 | $—CH(CH_3)_2$ | $—(CH_2)_3CH_3$ | H | H | H | $—OCH_3$ | H | H |
| 80 | $—CH(CH_3)_2$ | $—CH_2—HC═CH_2$ | H | H | H | $—OCH_3$ | H | H |
| 81 | $—(CH_2)_3CH_3$ | $—(CH_2)_3CH_3$ | H | H | H | $—OCH_3$ | H | H |
| 82 | $—(CH_2)_3CH_3$ | $—CH_2—HC═CH_2$ | H | H | H | $—OCH_3$ | H | H |
| 83 | $—CH_2—HC═CH_2$ | $—CH_2—HC═CH_2$ | H | H | H | $—OCH_3$ | H | H |
| 83b | $—CH_3$ | $—CH_3$ | H | H | H | —OH | H | H |
| 84 | $—CH_3$ | $—CH_2CH_3$ | H | H | H | —OH | H | H |
| 85 | $—CH_3$ | $—(CH_2)_2CH_3$ | H | H | H | —OH | H | H |
| 86 | $—CH_3$ | $—CH(CH_3)_2$ | H | H | H | —OH | H | H |
| 87 | $—CH_3$ | $—(CH_2)_3CH_3$ | H | H | H | —OH | H | H |
| 88 | $—CH_3$ | $—CH_2—HC═CH_2$ | H | H | H | —OH | H | H |
| 89 | $—CH_2CH_3$ | $—CH_2CH_3$ | H | H | H | —OH | H | H |
| 90 | $—CH_2CH_3$ | $—(CH_2)_2CH_3$ | H | H | H | —OH | H | H |
| 91 | $—CH_2CH_3$ | $—CH(CH_3)_2$ | H | H | H | —OH | H | H |
| 92 | $—CH_2CH_3$ | $—(CH_2)_3CH_3$ | H | H | H | —OH | H | H |
| 93 | $—CH_2CH_3$ | $—CH_2—HC═CH_2$ | H | H | H | —OH | H | H |
| 94 | $—(CH_2)_2CH_3$ | $—(CH_2)_2CH_3$ | H | H | H | —OH | H | H |
| 95 | $—(CH_2)_2CH_3$ | $—CH(CH_3)_2$ | H | H | H | —OH | H | H |
| 96 | $—(CH_2)_2CH_3$ | $—(CH_2)_3CH_3$ | H | H | H | —OH | H | H |
| 97 | $—(CH_2)_2CH_3$ | $—CH_2—HC═CH_2$ | H | H | H | —OH | H | H |
| 98 | $—CH(CH_3)_2$ | $—CH(CH_3)_2$ | H | H | H | —OH | H | H |
| 99 | $—CH(CH_3)_2$ | $—(CH_2)_3CH_3$ | H | H | H | —OH | H | H |
| 100 | $—CH(CH_3)_2$ | $—CH_2—HC═CH_2$ | H | H | H | —OH | H | H |
| 101 | $—(CH_2)_3CH_3$ | $—(CH_2)_3CH_3$ | H | H | H | —OH | H | H |
| 102 | $—(CH_2)_3CH_3$ | $—CH_2—HC═CH_2$ | H | H | H | —OH | H | H |
| 103 | $—CH_2—HC═CH_2$ | $—CH_2—HC═CH_2$ | H | H | H | —OH | H | H |
| 104 | $—CH_3$ | $—CH_3$ | H | H | H | $—OC(O)CH_3$ | H | H |
| 105 | $—CH_3$ | $—CH_2CH_3$ | H | H | H | $—OC(O)CH_3$ | H | H |
| 106 | $—CH_3$ | $—(CH_2)_2CH_3$ | H | H | H | $—OC(O)CH_3$ | H | H |
| 107 | $—CH_3$ | $—CH(CH_3)_2$ | H | H | H | $—OC(O)CH_3$ | H | H |
| 108 | $—CH_3$ | $—(CH_2)_3CH_3$ | H | H | H | $—OC(O)CH_3$ | H | H |
| 109 | $—CH_3$ | $—CH_2—HC═CH_2$ | H | H | H | $—OC(O)CH_3$ | H | H |
| 110 | $—CH_2CH_3$ | $—CH_2CH_3$ | H | H | H | $—OC(O)CH_3$ | H | H |
| 111 | $—CH_2CH_3$ | $—(CH_2)_2CH_3$ | H | H | H | $—OC(O)CH_3$ | H | H |
| 112 | $—CH_2CH_3$ | $—CH(CH_3)_2$ | H | H | H | $—OC(O)CH_3$ | H | H |
| 113 | $—CH_2CH_3$ | $—(CH_2)_3CH_3$ | H | H | H | $—OC(O)CH_3$ | H | H |
| 114 | $—CH_2CH_3$ | $—CH_2—HC═CH_2$ | H | H | H | $—OC(O)CH_3$ | H | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 115 | $—(CH_2)_2CH_3$ | $—(CH_2)_2CH_3$ | H | H | H | $—OC(O)CH_3$ | H | H |
| 116 | $—(CH_2)_2CH_3$ | $—CH(CH_3)_2$ | H | H | H | $—OC(O)CH_3$ | H | H |
| 117 | $—(CH_2)_2CH_3$ | $—(CH_2)_3CH_3$ | H | H | H | $—OC(O)CH_3$ | H | H |
| 118 | $—(CH_2)_2CH_3$ | $—CH_2—HC{=}CH_2$ | H | H | H | $—OC(O)CH_3$ | H | H |
| 119 | $—CH(CH_3)_2$ | $—CH(CH_3)_2$ | H | H | H | $—OC(O)CH_3$ | H | H |
| 120 | $—CH(CH_3)_2$ | $—(CH_2)_3CH_3$ | H | H | H | $—OC(O)CH_3$ | H | H |
| 121 | $—CH(CH_3)_2$ | $—CH_2—HC{=}CH_2$ | H | H | H | $—OC(O)CH_3$ | H | H |
| 122 | $—(CH_2)_3CH_3$ | $—(CH_2)_3CH_3$ | H | H | H | $—OC(O)CH_3$ | H | H |
| 123 | $—(CH_2)_3CH_3$ | $—CH_2—HC{=}CH_2$ | H | H | H | $—OC(O)CH_3$ | H | H |
| 124 | $—CH_2—HC{=}CH_2$ | $—CH_2—HC{=}CH_2$ | H | H | H | $—OC(O)CH_3$ | H | H |
| 125 | $—CH_3$ | $—CH_3$ | H | H | —OH | H | H | $—CH_2CH_3$ |
| 126 | $—CH_3$ | $—CH_2CH_3$ | H | H | —OH | H | H | $—CH_2CH_3$ |
| 127 | $—CH_3$ | $—(CH_2)_2CH_3$ | H | H | —OH | H | H | $—CH_2CH_3$ |
| 128 | $—CH_3$ | $—CH(CH_3)_2$ | H | H | —OH | H | H | $—CH_2CH_3$ |
| 129 | $—CH_3$ | $—(CH_2)_3CH_3$ | H | H | —OH | H | H | $—CH_2CH_3$ |
| 130 | $—CH_3$ | $—CH_2—HC{=}CH_2$ | H | H | —OH | H | H | $—CH_2CH_3$ |
| 131 | $—CH_2CH_3$ | $—CH_2CH_3$ | H | H | —OH | H | H | $—CH_2CH_3$ |
| 132 | $—CH_2CH_3$ | $—(CH_2)_2CH_3$ | H | H | —OH | H | H | $—CH_2CH_3$ |
| 133 | $—CH_2CH_3$ | $—CH(CH_3)_2$ | H | H | —OH | H | H | $—CH_2CH_3$ |
| 134 | $—CH_2CH_3$ | $—(CH_2)_3CH_3$ | H | H | —OH | H | H | $—CH_2CH_3$ |
| 135 | $—CH_2CH_3$ | $—CH_2—HC{=}CH_2$ | H | H | —OH | H | H | $—CH_2CH_3$ |
| 135 | $—(CH_2)_2CH_3$ | $—(CH_2)_2CH_3$ | H | H | —OH | H | H | $—CH_2CH_3$ |
| 137 | $—(CH_2)_2CH_3$ | $—CH(CH_3)_2$ | H | H | —OH | H | H | $—CH_2CH_3$ |
| 138 | $—(CH_2)_2CH_3$ | $—(CH_2)_3CH_3$ | H | H | —OH | H | H | $—CH_2CH_3$ |
| 139 | $—(CH_2)_2CH_3$ | $—CH_2—HC{=}CH_2$ | H | H | —OH | H | H | $—CH_2CH_3$ |
| 140 | $—CH(CH_3)_2$ | $—CH(CH_3)_2$ | H | H | —OH | H | H | $—CH_2CH_3$ |
| 141 | $—CH(CH_3)_2$ | $—(CH_2)_3CH_3$ | H | H | —OH | H | H | $—CH_2CH_3$ |
| 142 | $—CH(CH_3)_2$ | $—CH_2—HC{=}CH_2$ | H | H | —OH | H | H | $—CH_2CH_3$ |
| 143 | $—(CH_2)_3CH_3$ | $—(CH_2)_3CH_3$ | H | H | —OH | H | H | $—CH_2CH_3$ |
| 144 | $—(CH_2)_3CH_3$ | $—CH_2—HC{=}CH_2$ | H | H | —OH | H | H | $—CH_2CH_3$ |
| 145 | $—CH_2—HC{=}CH_2$ | $—CH_2—HC{=}CH_2$ | H | H | —OH | H | H | $—CH_2CH_3$ |
| 145b | $—CH_3$ | $—CH_3$ | H | H | —OH | H | F | H |
| 146 | $—CH_3$ | $—CH_2CH_3$ | H | H | —OH | H | F | H |
| 147 | $—CH_3$ | $—(CH_2)_2CH_3$ | H | H | —OH | H | F | H |
| 148 | $—CH_3$ | $—CH(CH_3)_2$ | H | H | —OH | H | F | H |
| 149 | $—CH_3$ | $—(CH_2)_3CH_3$ | H | H | —OH | H | F | H |
| 150 | $—CH_3$ | $—CH_2—HC{=}CH_2$ | H | H | —OH | H | F | H |
| 151 | $—CH_2CH_3$ | $—CH_2CH_3$ | H | H | —OH | H | F | H |
| 152 | $—CH_2CH_3$ | $—(CH_2)_2CH_3$ | H | H | —OH | H | F | H |
| 153 | $—CH_2CH_3$ | $—CH(CH_3)_2$ | H | H | —OH | H | F | H |
| 154 | $—CH_2CH_3$ | $—(CH_2)_3CH_3$ | H | H | —OH | H | F | H |
| 155 | $—CH_2CH_3$ | $—CH_2—HC{=}CH_2$ | H | H | —OH | H | F | H |
| 156 | $—(CH_2)_2CH_3$ | $—(CH_2)_2CH_3$ | H | H | —OH | H | F | H |
| 157 | $—(CH_2)_2CH_3$ | $—CH(CH_3)_2$ | H | H | —OH | H | F | H |
| 158 | $—(CH_2)_2CH_3$ | $—(CH_2)_3CH_3$ | H | H | —OH | H | F | H |
| 159 | $—(CH_2)_2CH_3$ | $—CH_2—HC{=}CH_2$ | H | H | —OH | H | F | H |
| 160 | $—CH(CH_3)_2$ | $—CH(CH_3)_2$ | H | H | —OH | H | F | H |
| 161 | $—CH(CH_3)_2$ | $—(CH_2)_3CH_3$ | H | H | —OH | H | F | H |
| 162 | $—CH(CH_3)_2$ | $—CH_2—HC{=}CH_2$ | H | H | —OH | H | F | H |
| 163 | $—(CH_2)_3CH_3$ | $—(CH_2)_3CH_3$ | H | H | —OH | H | F | H |
| 164 | $—(CH_2)_3CH_3$ | $—CH_2—HC{=}CH_2$ | H | H | —OH | H | F | H |
| 165 | $—CH_2—HC{=}CH_2$ | $—CH_2—HC{=}CH_2$ | H | H | —OH | H | F | H |
| 166 | $—CH_3$ | $—CH_3$ | H | H | $—OC(O)CH_3$ | H | H | $—CH_2CH_3$ |
| 167 | $—CH_3$ | $—CH_2CH_3$ | H | H | $—OC(O)CH_3$ | H | H | $—CH_2CH_3$ |
| 168 | $—CH_3$ | $—(CH_2)_2CH_3$ | H | H | $—OC(O)CH_3$ | H | H | $—CH_2CH_3$ |
| 169 | $—CH_3$ | $—CH(CH_3)_2$ | H | H | $—OC(O)CH_3$ | H | H | $—CH_2CH_3$ |
| 170 | $—CH_3$ | $—(CH_2)_3CH_3$ | H | H | $—OC(O)CH_3$ | H | H | $—CH_2CH_3$ |
| 171 | $—CH_3$ | $—CH_2—HC{=}CH_2$ | H | H | $—OC(O)CH_3$ | H | H | $—CH_2CH_3$ |
| 172 | $—CH_2CH_3$ | $—CH_2CH_3$ | H | H | $—OC(O)CH_3$ | H | H | $—CH_2CH_3$ |
| 173 | $—CH_2CH_3$ | $—(CH_2)_2CH_3$ | H | H | $—OC(O)CH_3$ | H | H | $—CH_2CH_3$ |
| 174 | $—CH_2CH_3$ | $—CH(CH_3)_2$ | H | H | $—OC(O)CH_3$ | H | H | $—CH_2CH_3$ |
| 175 | $—CH_2CH_3$ | $—(CH_2)_3CH_3$ | H | H | $—OC(O)CH_3$ | H | H | $—CH_2CH_3$ |
| 176 | $—CH_2CH_3$ | $—CH_2—HC{=}CH_2$ | H | H | $—OC(O)CH_3$ | H | H | $—CH_2CH_3$ |
| 177 | $—(CH_2)_2CH_3$ | $—(CH_2)_2CH_3$ | H | H | $—OC(O)CH_3$ | H | H | $—CH_2CH_3$ |
| 178 | $—(CH_2)_2CH_3$ | $—CH(CH_3)_2$ | H | H | $—OC(O)CH_3$ | H | H | $—CH_2CH_3$ |
| 179 | $—(CH_2)_2CH_3$ | $—(CH_2)_3CH_3$ | H | H | $—OC(O)CH_3$ | H | H | $—CH_2CH_3$ |
| 180 | $—(CH_2)_2CH_3$ | $—CH_2—HC{=}CH_2$ | H | H | $—OC(O)CH_3$ | H | H | $—CH_2CH_3$ |
| 181 | $—CH(CH_3)_2$ | $—CH(CH_3)_2$ | H | H | $—OC(O)CH_3$ | H | H | $—CH_2CH_3$ |
| 182 | $—CH(CH_3)_2$ | $—(CH_2)_3CH_3$ | H | H | $—OC(O)CH_3$ | H | H | $—CH_2CH_3$ |
| 183 | $—CH(CH_3)_2$ | $—CH_2—HC{=}CH_2$ | H | H | $—OC(O)CH_3$ | H | H | $—CH_2CH_3$ |
| 184 | $—(CH_2)_3CH_3$ | $—(CH_2)_3CH_3$ | H | H | $—OC(O)CH_3$ | H | H | $—CH_2CH_3$ |
| 185 | $—(CH_2)_3CH_3$ | $—CH_2—HC{=}CH_2$ | H | H | $—OC(O)CH_3$ | H | H | $—CH_2CH_3$ |
| 186 | $—CH_2—HC{=}CH_2$ | $—CH_2—HC{=}CH_2$ | H | H | $—OC(O)CH_3$ | H | H | $—CH_2CH_3$ |
| 187 | $—CH_3$ | $—CH_3$ | H | H | $—OC(O)CH_3$ | H | F | H |
| 188 | $—CH_3$ | $—CH_2CH_3$ | H | H | $—OC(O)CH_3$ | H | F | H |
| 189 | $—CH_3$ | $—(CH_2)_2CH_3$ | H | H | $—OC(O)CH_3$ | H | F | H |
| 190 | $—CH_3$ | $—CH(CH_3)_2$ | H | H | $—OC(O)CH_3$ | H | F | H |
| 191 | $—CH_3$ | $—(CH_2)_3CH_3$ | H | H | $—OC(O)CH_3$ | H | F | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 192 | $—CH_3$ | $—CH_2—HC{=}CH_2$ | H | H | $—OC(O)CH_3$ | H | F | H |
| 193 | $—CH_2CH_3$ | $—CH_2CH_3$ | H | H | $—OC(O)CH_3$ | H | F | H |
| 194 | $—CH_2CH_3$ | $—(CH_2)_2CH_3$ | H | H | $—OC(O)CH_3$ | H | F | H |
| 195 | $—CH_2CH_3$ | $—CH(CH_3)_2$ | H | H | $—OC(O)CH_3$ | H | F | H |
| 196 | $—CH_2CH_3$ | $—(CH_2)_3CH_3$ | H | H | $—OC(O)CH_3$ | H | F | H |
| 197 | $—CH_2CH_3$ | $—CH_2—HC{=}CH_2$ | H | H | $—OC(O)CH_3$ | H | F | H |
| 198 | $—(CH_2)_2CH_3$ | $—(CH_2)_2CH_3$ | H | H | $—OC(O)CH_3$ | H | F | H |
| 199 | $—(CH_2)_2CH_3$ | $—CH(CH_3)_2$ | H | H | $—OC(O)CH_3$ | H | F | H |
| 200 | $—(CH_2)_2CH_3$ | $—(CH_2)_3CH_3$ | H | H | $—OC(O)CH_3$ | H | F | H |
| 201 | $—(CH_2)_2CH_3$ | $—CH_2—HC{=}CH_2$ | H | H | $—OC(O)CH_3$ | H | F | H |
| 202 | $—CH(CH_3)_2$ | $—CH(CH_3)_2$ | H | H | $—OC(O)CH_3$ | H | F | H |
| 203 | $—CH(CH_3)_2$ | $—(CH_2)_3CH_3$ | H | H | $—OC(O)CH_3$ | H | F | H |
| 204 | $—CH(CH_3)_2$ | $—CH_2—HC{=}CH_2$ | H | H | $—OC(O)CH_3$ | H | F | H |
| 205 | $—(CH_2)_3CH_3$ | $—(CH_2)_3CH_3$ | H | H | $—OC(O)CH_3$ | H | F | H |
| 206 | $—(CH_2)_3CH_3$ | $—CH_2—HC{=}CH_2$ | H | H | $—OC(O)CH_3$ | H | F | H |
| 207 | $—CH_2—HC{=}CH_2$ | $—CH_2—HC{=}CH_2$ | H | H | $—OC(O)CH_3$ | H | F | H |
| 207b | $—CH_3$ | $—CH_3$ | H | H | H | $—OCH_3$ | H | $—CH_2CH_3$ |
| 208 | $—CH_3$ | $—CH_2CH_3$ | H | H | H | $—OCH_3$ | H | $—CH_2CH_3$ |
| 209 | $—CH_3$ | $—(CH_2)_2CH_3$ | H | H | H | $—OCH_3$ | H | $—CH_2CH_3$ |
| 210 | $—CH_3$ | $—CH(CH_3)_2$ | H | H | H | $—OCH_3$ | H | $—CH_2CH_3$ |
| 211 | $—CH_3$ | $—(CH_2)_3CH_3$ | H | H | H | $—OCH_3$ | H | $—CH_2CH_3$ |
| 212 | $—CH_3$ | $—CH_2—HC{=}CH_2$ | H | H | H | $—OCH_3$ | H | $—CH_2CH_3$ |
| 213 | $—CH_2CH_3$ | $—CH_2CH_3$ | H | H | H | $—OCH_3$ | H | $—CH_2CH_3$ |
| 214 | $—CH_2CH_3$ | $—(CH_2)_2CH_3$ | H | H | H | $—OCH_3$ | H | $—CH_2CH_3$ |
| 215 | $—CH_2CH_3$ | $—CH(CH_3)_2$ | H | H | H | $—OCH_3$ | H | $—CH_2CH_3$ |
| 216 | $—CH_2CH_3$ | $—(CH_2)_3CH_3$ | H | H | H | $—OCH_3$ | H | $—CH_2CH_3$ |
| 217 | $—CH_2CH_3$ | $—CH_2—HC{=}CH_2$ | H | H | H | $—OCH_3$ | H | $—CH_2CH_3$ |
| 218 | $—(CH_2)_2CH_3$ | $—(CH_2)_2CH_3$ | H | H | H | $—OCH_3$ | H | $—CH_2CH_3$ |
| 219 | $—(CH_2)_2CH_3$ | $—CH(CH_3)_2$ | H | H | H | $—OCH_3$ | H | $—CH_2CH_3$ |
| 220 | $—(CH_2)_2CH_3$ | $—(CH_2)_3CH_3$ | H | H | H | $—OCH_3$ | H | $—CH_2CH_3$ |
| 221 | $—(CH_2)_2CH_3$ | $—CH_2—HC{=}CH_2$ | H | H | H | $—OCH_3$ | H | $—CH_2CH_3$ |
| 222 | $—CH(CH_3)_2$ | $—CH(CH_3)_2$ | H | H | H | $—OCH_3$ | H | $—CH_2CH_3$ |
| 223 | $—CH(CH_3)_2$ | $—(CH_2)_3CH_3$ | H | H | H | $—OCH_3$ | H | $—CH_2CH_3$ |
| 224 | $—CH(CH_3)_2$ | $—CH_2—HC{=}CH_2$ | H | H | H | $—OCH_3$ | H | $—CH_2CH_3$ |
| 225 | $—(CH_2)_3CH_3$ | $—(CH_2)_3CH_3$ | H | H | H | $—OCH_3$ | H | $—CH_2CH_3$ |
| 226 | $—(CH_2)_3CH_3$ | $—CH_2—HC{=}CH_2$ | H | H | H | $—OCH_3$ | H | $—CH_2CH_3$ |
| 227 | $—CH_2—HC{=}CH_2$ | $—CH_2—HC{=}CH_2$ | H | H | H | $—OCH_3$ | H | $—CH_2CH_3$ |
| 228 | $—CH_3$ | $—CH_3$ | H | H | H | $—OCH_3$ | F | H |
| 229 | $—CH_3$ | $—CH_2CH_3$ | H | H | H | $—OCH_3$ | F | H |
| 230 | $—CH_3$ | $—(CH_2)_2CH_3$ | H | H | H | $—OCH_3$ | F | H |
| 231 | $—CH_3$ | $—CH(CH_3)_2$ | H | H | H | $—OCH_3$ | F | H |
| 232 | $—CH_3$ | $—(CH_2)_3CH_3$ | H | H | H | $—OCH_3$ | F | H |
| 233 | $—CH_3$ | $—CH_2—HC{=}CH_2$ | H | H | H | $—OCH_3$ | F | H |
| 234 | $—CH_2CH_3$ | $—CH_2CH_3$ | H | H | H | $—OCH_3$ | F | H |
| 235 | $—CH_2CH_3$ | $—(CH_2)_2CH_3$ | H | H | H | $—OCH_3$ | F | H |
| 236 | $—CH_2CH_3$ | $—CH(CH_3)_2$ | H | H | H | $—OCH_3$ | F | H |
| 237 | $—CH_2CH_3$ | $—(CH_2)_3CH_3$ | H | H | H | $—OCH_3$ | F | H |
| 238 | $—CH_2CH_3$ | $—CH_2—HC{=}CH_2$ | H | H | H | $—OCH_3$ | F | H |
| 239 | $—(CH_2)_2CH_3$ | $—(CH_2)_2CH_3$ | H | H | H | $—OCH_3$ | F | H |
| 240 | $—(CH_2)_2CH_3$ | $—CH(CH_3)_2$ | H | H | H | $—OCH_3$ | F | H |
| 241 | $—(CH_2)_2CH_3$ | $—(CH_2)_3CH_3$ | H | H | H | $—OCH_3$ | F | H |
| 242 | $—(CH_2)_2CH_3$ | $—CH_2—HC{=}CH_2$ | H | H | H | $—OCH_3$ | F | H |
| 243 | $—CH(CH_3)_2$ | $—CH(CH_3)_2$ | H | H | H | $—OCH_3$ | F | H |
| 244 | $—CH(CH_3)_2$ | $—(CH_2)_3CH_3$ | H | H | H | $—OCH_3$ | F | H |
| 245 | $—CH(CH_3)_2$ | $—CH_2—HC{=}CH_2$ | H | H | H | $—OCH_3$ | F | H |
| 246 | $—(CH_2)_3CH_3$ | $—(CH_2)_3CH_3$ | H | H | H | $—OCH_3$ | F | H |
| 247 | $—(CH_2)_3CH_3$ | $—CH_2—HC{=}CH_2$ | H | H | H | $—OCH_3$ | F | H |
| 248 | $—CH_2—HC{=}CH_2$ | $—CH_2—HC{=}CH_2$ | H | H | H | $—OCH_3$ | F | H |
| 249 | H | $—CH_3$ | H | H | H | H | H | $—CH_2CH_3$ |
| 250 | H | $—CH_2CH_3$ | H | H | H | H | H | $—CH_2CH_3$ |
| 251 | H | $—(CH_2)_2CH_3$ | H | H | H | H | H | $—CH_2CH_3$ |
| 252 | H | $—CH(CH_3)_2$ | H | H | H | H | H | $—CH_2CH_3$ |
| 253 | H | $—(CH_2)_3CH_3$ | H | H | H | H | H | $—CH_2CH_3$ |
| 254 | H | $—CH_2—HC{=}CH_2$ | H | H | H | H | H | $—CH_2CH_3$ |
| 255 | H | $—CH_3$ | H | H | —OH | H | H | H |
| 256 | H | $—CH_2CH_3$ | H | H | —OH | H | H | H |
| 257 | H | $—(CH_2)_2CH_3$ | H | H | —OH | H | H | H |
| 258 | H | $—CH(CH_3)_2$ | H | H | —OH | H | H | H |
| 259 | H | $—(CH_2)_3CH_3$ | H | H | —OH | H | H | H |
| 260 | H | $—CH_2—HC{=}CH_2$ | H | H | —OH | H | H | H |
| 261 | H | $—CH_3$ | H | H | —OH | H | H | $—CH_2CH_3$ |
| 262 | H | $—CH_2CH_3$ | H | H | —OH | H | H | $—CH_2CH_3$ |
| 263 | H | $—(CH_2)_2CH_3$ | H | H | —OH | H | H | $—CH_2CH_3$ |
| 264 | H | $—CH(CH_3)_2$ | H | H | —OH | H | H | $—CH_2CH_3$ |
| 265 | H | $—(CH_2)_3CH_3$ | H | H | —OH | H | H | $—CH_2CH_3$ |
| 266 | H | $—CH_2—HC{=}CH_2$ | H | H | —OH | H | H | $—CH_2CH_3$ |
| 267 | H | $—CH_3$ | H | H | —OH | H | F | H |
| 268 | H | $—CH_2CH_3$ | H | H | —OH | H | F | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 269 | H | $—(CH_2)_2CH_3$ | H | H | —OH | H | F | H |
| 270 | H | $—CH(CH_3)_2$ | H | H | —OH | H | F | H |
| 271 | H | $—(CH_2)_3CH_3$ | H | H | —OH | H | F | H |
| 272 | H | $—CH_2—HC═CH_2$ | H | H | —OH | H | F | H |
| 273 | H | $—CH_3$ | H | H | H | $—OCH_3$ | F | H |
| 274 | H | $—CH_2CH_3$ | H | H | H | $—OCH_3$ | F | H |
| 275 | H | $—(CH_2)_2CH_3$ | H | H | H | $—OCH_3$ | F | H |
| 276 | H | $—CH(CH_3)_2$ | H | H | H | $—OCH_3$ | F | H |
| 277 | H | $—(CH_2)_3CH_3$ | H | H | H | $—OCH_3$ | F | H |
| 278 | H | $—CH_2—HC═CH_2$ | H | H | H | $—OCH_3$ | F | H |
| 279 | H | $—CH_3$ | H | H | $—OC(O)CH_3$ | H | H | H |
| 280 | H | $—CH_2CH_3$ | H | H | $—OC(O)CH_3$ | H | H | H |
| 281 | H | $—(CH_2)_2CH_3$ | H | H | $—OC(O)CH_3$ | H | H | H |
| 282 | H | $—CH(CH_3)_2$ | H | H | $—OC(O)CH_3$ | H | H | H |
| 283 | H | $—(CH_2)_3CH_3$ | H | H | $—OC(O)CH_3$ | H | H | H |
| 284 | H | $—CH_2—HC═CH_2$ | H | H | $—OC(O)CH_3$ | H | H | H |
| 285 | H | $—CH_3$ | H | H | H | H | F | H |
| 286 | H | $—CH_2CH_3$ | H | H | H | H | F | H |
| 287 | H | $—(CH_2)_2CH_3$ | H | H | H | H | F | H |
| 288 | H | $—CH(CH_3)_2$ | H | H | H | H | F | H |
| 289 | H | $—(CH_2)_3CH_3$ | H | H | H | H | F | H |
| 290 | H | $—CH_2—HC═CH_2$ | H | H | H | H | F | H |
| 291 | H | $—CH_3$ | H | H | H | $—OCH_3$ | H | H |
| 292 | H | $—CH_2CH_3$ | H | H | H | $—OCH_3$ | H | H |
| 293 | H | $—(CH_2)_2CH_3$ | H | H | H | $—OCH_3$ | H | H |
| 294 | H | $—CH(CH_3)_2$ | H | H | H | $—OCH_3$ | H | H |
| 295 | H | $—(CH_2)_3CH_3$ | H | H | H | $—OCH_3$ | H | H |
| 296 | H | $—CH_2—HC═CH_2$ | H | H | H | $—OCH_3$ | H | H |
| 297 | cyclopropyl | $—CH_3$ | H | H | H | H | H | H |
| 298 | cyclopropyl | $—CH_2CH_3$ | H | H | H | H | H | H |
| 299 | cyclopropyl | $—(CH_2)_2CH_3$ | H | H | H | H | H | H |
| 300 | cyclopropyl | $—CH(CH_3)_2$ | H | H | H | H | H | H |
| 301 | cyclopropyl | $—(CH_2)_3CH_3$ | H | H | H | H | H | H |
| 302 | cyclopropyl | $—CH_2—HC═CH_2$ | H | H | H | H | H | H |
| 303 | cyclopropyl | $—CH_3$ | H | H | $—OCH_3$ | H | H | H |
| 304 | cyclopropyl | $—CH_2CH_3$ | H | H | $—OCH_3$ | H | H | H |
| 305 | cyclopropyl | $—(CH_2)_2CH_3$ | H | H | $—OCH_3$ | H | H | H |
| 306 | cyclopropyl | $—CH(CH_3)_2$ | H | H | $—OCH_3$ | H | H | H |
| 307 | cyclopropyl | $—(CH_2)_3CH_3$ | H | H | $—OCH_3$ | H | H | H |
| 308 | cyclopropyl | $—CH_2—HC═CH_2$ | H | H | $—OCH_3$ | H | H | H |
| 309 | cyclopropyl | $—CH_3$ | H | H | —OH | H | H | H |
| 310 | cyclopropyl | $—CH_2CH_3$ | H | H | —OH | H | H | H |
| 311 | cyclopropyl | $—(CH_2)_2CH_3$ | H | H | —OH | H | H | H |
| 312 | cyclopropyl | $—CH(CH_3)_2$ | H | H | —OH | H | H | H |
| 313 | cyclopropyl | $—(CH_2)_3CH_3$ | H | H | —OH | H | H | H |
| 314 | cyclopropyl | $—CH_2—HC═CH_2$ | H | H | —OH | H | H | H |
| 315 | cyclopropyl | $—CH_3$ | H | H | $—OC(O)CH_3$ | H | H | H |
| 316 | cyclopropyl | $—CH_2CH_3$ | H | H | $—OC(O)CH_3$ | H | H | H |
| 317 | cyclopropyl | $—(CH_2)_2CH_3$ | H | H | $—OC(O)CH_3$ | H | H | H |
| 318 | cyclopropyl | $—CH(CH_3)_2$ | H | H | $—OC(O)CH_3$ | H | H | H |
| 319 | cyclopropyl | $—(CH_2)_3CH_3$ | H | H | $—OC(O)CH_3$ | H | H | H |
| 320 | cyclopropyl | $—CH_2—HC═CH_2$ | H | H | $—OC(O)CH_3$ | H | H | H |
| 321 | cyclopropyl | $—CH_3$ | H | H | H | H | H | $—CH_2CH_3$ |
| 322 | cyclopropyl | $—CH_2CH_3$ | H | H | H | H | H | $—CH_2CH_3$ |
| 323 | cyclopropyl | $—(CH_2)_2CH_3$ | H | H | H | H | H | $—CH_2CH_3$ |
| 324 | cyclopropyl | $—CH(CH_3)_2$ | H | H | H | H | H | $—CH_2CH_3$ |
| 325 | cyclopropyl | $—(CH_2)_3CH_3$ | H | H | H | H | H | $—CH_2CH_3$ |
| 326 | cyclopropyl | $—CH_2—HC═CH_2$ | H | H | H | H | H | $—CH_2CH_3$ |
| 327 | cyclopropyl | $—CH_3$ | H | H | —OH | H | H | $—CH_2CH_3$ |
| 328 | cyclopropyl | $—CH_2CH_3$ | H | H | —OH | H | H | $—CH_2CH_3$ |
| 329 | cyclopropyl | $—(CH_2)_2CH_3$ | H | H | —OH | H | H | $—CH_2CH_3$ |
| 330 | cyclopropyl | $—CH(CH_3)_2$ | H | H | —OH | H | H | $—CH_2CH_3$ |
| 331 | cyclopropyl | $—(CH_2)_3CH_3$ | H | H | —OH | H | H | $—CH_2CH_3$ |
| 332 | cyclopropyl | $—CH_2—HC═CH_2$ | H | H | —OH | H | H | $—CH_2CH_3$ |
| 333 | H | $—CH_3$ | H | H | H | H | H | H |
| 334 | H | $—CH_2CH_3$ | H | H | H | H | H | H |
| 335 | H | $—(CH_2)_2CH_3$ | H | H | H | H | H | H |
| 336 | H | $—CH(CH_3)_2$ | H | H | H | H | H | H |
| 337 | H | $—(CH_2)_3CH_3$ | H | H | H | H | H | H |
| 338 | H | $—CH_2—HC═CH_2$ | H | H | H | H | H | H |
| 339 | H | cyclopropyl | H | H | H | H | H | H |
| 340 | H | $—CH_3$ | H | $—CH_3$ | H | H | H | H |
| 341 | H | $—CH_2CH_3$ | H | $—CH_3$ | H | H | H | H |
| 342 | H | $—(CH_2)_2CH_3$ | H | $—CH_3$ | H | H | H | H |
| 343 | H | $—CH(CH_3)_2$ | H | $—CH_3$ | H | H | H | H |
| 344 | H | $—(CH_2)_3CH_3$ | H | $—CH_3$ | H | H | H | H |
| 345 | H | $—CH_2—HC═CH_2$ | H | $—CH_3$ | H | H | H | H |
| 346 | H | cyclopropyl | H | $—CH_3$ | H | H | H | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 347 | H | $—CH_3$ | H | $—CH_3$ | —OH | H | H | H |
| 348 | H | $—CH_2CH_3$ | H | $—CH_3$ | —OH | H | H | H |
| 349 | H | $—(CH_2)_2CH_3$ | H | $—CH_3$ | —OH | H | H | H |
| 350 | H | $—CH(CH_3)_2$ | H | $—CH_3$ | —OH | H | H | H |
| 351 | H | $—(CH_2)_3CH_3$ | H | $—CH_3$ | —OH | H | H | H |
| 352 | H | $—CH_2—HC{=}CH_2$ | H | $—CH_3$ | —OH | H | H | H |
| 353 | H | cyclopropyl | H | $—CH_3$ | —OH | H | H | H |
| 354 | H | $—CH_3$ | H | $—CH_3$ | H | H | H | $—CH_2CH_3$ |
| 355 | H | $—CH_2CH_3$ | H | $—CH_3$ | H | H | H | $—CH_2CH_3$ |
| 356 | H | $—(CH_2)_2CH_3$ | H | $—CH_3$ | H | H | H | $—CH_2CH_3$ |
| 357 | H | $—CH(CH_3)_2$ | H | $—CH_3$ | H | H | H | $—CH_2CH_3$ |
| 358 | H | $—(CH_2)_3CH_3$ | H | $—CH_3$ | H | H | H | $—CH_2CH_3$ |
| 359 | H | $—CH_2—HC{=}CH_2$ | H | $—CH_3$ | H | H | H | $—CH_2CH_3$ |
| 360 | H | cyclopropyl | H | $—CH_3$ | H | H | H | $—CH_2CH_3$ |
| 361 | H | $—CH_3$ | H | $—CH_3$ | —OH | H | H | $—CH_2CH_3$ |
| 362 | H | $—CH_2CH_3$ | H | $—CH_3$ | —OH | H | H | $—CH_2CH_3$ |
| 363 | H | $—(CH_2)_2CH_3$ | H | $—CH_3$ | —OH | H | H | $—CH_2CH_3$ |
| 364 | H | $—CH(CH_3)_2$ | H | $—CH_3$ | —OH | H | H | $—CH_2CH_3$ |
| 365 | H | $—(CH_2)_3CH_3$ | H | $—CH_3$ | —OH | H | H | $—CH_2CH_3$ |
| 366 | H | $—CH_2—HC{=}CH_2$ | H | $—CH_3$ | —OH | H | H | $—CH_2CH_3$ |
| 367 | H | cyclopropyl | H | $—CH_3$ | —OH | H | H | $—CH_2CH_3$ |
| 368 | H | $—CH_3$ | H | $—CH_3$ | H | H | F | H |
| 369 | H | $—CH_2CH_3$ | H | $—CH_3$ | H | H | F | H |
| 370 | H | $—(CH_2)_2CH_3$ | H | $—CH_3$ | H | H | F | H |
| 371 | H | $—CH(CH_3)_2$ | H | $—CH_3$ | H | H | F | H |
| 372 | H | $—(CH_2)_3CH_3$ | H | $—CH_3$ | H | H | F | H |
| 373 | H | $—CH_2—HC{=}CH_2$ | H | $—CH_3$ | H | H | F | H |
| 374 | H | cyclopropyl | H | $—CH_3$ | H | H | F | H |
| 375 | H | $—CH_3$ | H | $—CH_3$ | H | $—OCH_3$ | H | H |
| 376 | H | $—CH_2CH_3$ | H | $—CH_3$ | H | $—OCH_3$ | H | H |
| 377 | H | $—(CH_2)_2CH_3$ | H | $—CH_3$ | H | $—OCH_3$ | H | H |
| 378 | H | $—CH(CH_3)_2$ | H | $—CH_3$ | H | $—OCH_3$ | H | H |
| 379 | H | $—(CH_2)_3CH_3$ | H | $—CH_3$ | H | $—OCH_3$ | H | H |
| 380 | H | $—CH_2—HC{=}CH_2$ | H | $—CH_3$ | H | $—OCH_3$ | H | H |
| 381 | H | cyclopropyl | H | $—CH_3$ | H | $—OCH_3$ | H | H |
| 382 | H | $—CH_3$ | H | $—CH_3$ | —OH | H | F | H |
| 383 | H | $—CH_2CH_3$ | H | $—CH_3$ | —OH | H | F | H |
| 384 | H | $—(CH_2)_2CH_3$ | H | $—CH_3$ | —OH | H | F | H |
| 385 | H | $—CH(CH_3)_2$ | H | $—CH_3$ | —OH | H | F | H |
| 386 | H | $—(CH_2)_3CH_3$ | H | $—CH_3$ | —OH | H | F | H |
| 387 | H | $—CH_2—HC{=}CH_2$ | H | $—CH_3$ | —OH | H | F | H |
| 388 | H | cyclopropyl | H | $—CH_3$ | —OH | H | F | H |
| 389 | H | $—CH_3$ | H | $—CH_3$ | $—OC(O)CH_3$ | H | H | H |
| 390 | H | $—CH_2CH_3$ | H | $—CH_3$ | $—OC(O)CH_3$ | H | H | H |
| 391 | H | $—(CH_2)_2CH_3$ | H | $—CH_3$ | $—OC(O)CH_3$ | H | H | H |
| 392 | H | $—CH(CH_3)_2$ | H | $—CH_3$ | $—OC(O)CH_3$ | H | H | H |
| 393 | H | $—(CH_2)_3CH_3$ | H | $—CH_3$ | $—OC(O)CH_3$ | H | H | H |
| 394 | H | $—CH_2—HC{=}CH_2$ | H | $—CH_3$ | $—OC(O)CH_3$ | H | H | H |
| 395 | H | cyclopropyl | H | $—CH_3$ | $—OC(O)CH_3$ | H | H | H |
| 396 | H | H | H | $—CH_3$ | H | H | H | H |
| 397 | H | H | H | $—CH_3$ | —OH | H | H | H |
| 398 | H | H | H | $—CH_3$ | H | $—OCH_3$ | H | H |
| 399 | H | H | H | $—CH_3$ | H | H | F | H |
| 400 | H | H | H | $—CH_3$ | H | H | H | $—CH_2CH_3$ |
| 401 | H | H | H | $—CH_3$ | —OH | H | H | $—CH_2CH_3$ |
| 402 | H | H | H | $—CH_3$ | —OH | H | F | H |
| 403 | H | H | H | $—CH_3$ | —OH | $—OCH_3$ | F | H |
| 404 | H | H | H | $—CH_3$ | —OH | F | H | H |
| 405 | H | H | H | $—CH_3$ | —OH | H | H | $—CH_3$ |
| 406 | $—CH_3$ | $—CH_3$ | H | H | H | H | H | H |
| 407 | $—CH_3$ | $—CH_2CH_3$ | H | H | H | H | H | H |
| 408 | $—CH_3$ | $—(CH_2)_2CH_3$ | H | H | H | H | H | H |
| 409 | $—CH_3$ | $—CH(CH_3)_2$ | H | H | H | H | H | H |
| 410 | $—CH_3$ | $—(CH_2)_3CH_3$ | H | H | H | H | H | H |
| 411 | $—CH_3$ | $—CH_2—HC{=}CH_2$ | H | H | H | H | H | H |
| 412 | $—CH_2CH_3$ | $—CH_2CH_3$ | H | H | H | H | H | H |
| 413 | $—CH_2CH_3$ | $—(CH_2)_2CH_3$ | H | H | H | H | H | H |
| 414 | $—CH_2CH_3$ | $—CH(CH_3)_2$ | H | H | H | H | H | H |
| 415 | $—CH_2CH_3$ | $—(CH_2)_3CH_3$ | H | H | H | H | H | H |
| 416 | $—CH_2CH_3$ | $—CH_2—HC{=}CH_2$ | H | H | H | H | H | H |
| 417 | $—(CH_2)_2CH_3$ | $—(CH_2)_2CH_3$ | H | H | H | H | H | H |
| 418 | $—(CH_2)_2CH_3$ | $—CH(CH_3)_2$ | H | H | H | H | H | H |
| 419 | $—(CH_2)_2CH_3$ | $—(CH_2)_3CH_3$ | H | H | H | H | H | H |
| 420 | $—(CH_2)_2CH_3$ | $—CH_2—HC{=}CH_2$ | H | H | H | H | H | H |
| 421 | $—CH(CH_3)_2$ | $—CH(CH_3)_2$ | H | H | H | H | H | H |
| 422 | $—CH(CH_3)_2$ | $—(CH_2)_3CH_3$ | H | H | H | H | H | H |
| 423 | $—CH(CH_3)_2$ | $—CH_2—HC{=}CH_2$ | H | H | H | H | H | H |
| 424 | $—(CH_2)_3CH_3$ | $—(CH_2)_3CH_3$ | H | H | H | H | H | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 425 | $-(CH_2)_3CH_3$ | $-CH_2-HC=CH_2$ | H | H | H | H | H | H |
| 426 | $-CH_2-HC=CH_2$ | $-CH_2-HC=CH_2$ | H | H | H | H | H | H |
| 427 | $-CH_3$ | $-CH_3$ | H | H | H | H | —OMe | H |
| 428 | $-CH_3$ | $-CH_2CH_3$ | H | H | H | H | —OMe | H |
| 429 | $-CH_3$ | $-(CH_2)_2CH_3$ | H | H | H | H | —OMe | H |
| 430 | $-CH_3$ | $-CH(CH_3)_2$ | H | H | H | H | —OMe | H |
| 431 | $-CH_3$ | $-(CH_2)_3CH_3$ | H | H | H | H | —OMe | H |
| 432 | $-CH_3$ | $-CH_2-HC=CH_2$ | H | H | H | H | —OMe | H |
| 433 | $-CH_2CH_3$ | $-CH_2CH_3$ | H | H | H | H | —OMe | H |
| 434 | $-CH_2CH_3$ | $-(CH_2)_2CH_3$ | H | H | H | H | —OMe | H |
| 435 | $-CH_2CH_3$ | $-CH(CH_3)_2$ | H | H | H | H | —OMe | H |
| 436 | $-CH_2CH_3$ | $-(CH_2)_3CH_3$ | H | H | H | H | —OMe | H |
| 437 | $-CH_2CH_3$ | $-CH_2-HC=CH_2$ | H | H | H | H | —OMe | H |
| 438 | $-(CH_2)_2CH_3$ | $-(CH_2)_2CH_3$ | H | H | H | H | —OMe | H |
| 439 | $-(CH_2)_2CH_3$ | $-CH(CH_3)_2$ | H | H | H | H | —OMe | H |
| 440 | $-(CH_2)_2CH_3$ | $-(CH_2)_3CH_3$ | H | H | H | H | —OMe | H |
| 441 | $-(CH_2)_2CH_3$ | $-CH_2-HC=CH_2$ | H | H | H | H | —OMe | H |
| 442 | $-CH(CH_3)_2$ | $-CH(CH_3)_2$ | H | H | H | H | —OMe | H |
| 443 | $-CH(CH_3)_2$ | $-(CH_2)_3CH_3$ | H | H | H | H | —OMe | H |
| 444 | $-CH(CH_3)_2$ | $-CH_2-HC=CH_2$ | H | H | H | H | —OMe | H |
| 445 | $-(CH_2)_3CH_3$ | $-(CH_2)_3CH_3$ | H | H | H | H | —OMe | H |
| 446 | $-(CH_2)_3CH_3$ | $-CH_2-HC=CH_2$ | H | H | H | H | —OMe | H |
| 447 | $-CH_2-HC=CH_2$ | $-CH_2-HC=CH_2$ | H | H | H | H | —OMe | H |
| 448 | $-CH_3$ | $-CH_3$ | H | H | H | H | —OMe | $-CH_2CH_3$ |
| 449 | $-CH_3$ | $-CH_2CH_3$ | H | H | H | H | —OMe | $-CH_2CH_3$ |
| 450 | $-CH_3$ | $-(CH_2)_2CH_3$ | H | H | H | H | —OMe | $-CH_2CH_3$ |
| 451 | $-CH_3$ | $-CH(CH_3)_2$ | H | H | H | H | —OMe | $-CH_2CH_3$ |
| 452 | $-CH_3$ | $-(CH_2)_3CH_3$ | H | H | H | H | —OMe | $-CH_2CH_3$ |
| 453 | $-CH_3$ | $-CH_2-HC=CH_2$ | H | H | H | H | —OMe | $-CH_2CH_3$ |
| 454 | $-CH_2CH_3$ | $-CH_2CH_3$ | H | H | H | H | —OMe | $-CH_2CH_3$ |
| 455 | $-CH_2CH_3$ | $-(CH_2)_2CH_3$ | H | H | H | H | —OMe | $-CH_2CH_3$ |
| 456 | $-CH_2CH_3$ | $-CH(CH_3)_2$ | H | H | H | H | —OMe | $-CH_2CH_3$ |
| 457 | $-CH_2CH_3$ | $-(CH_2)_3CH_3$ | H | H | H | H | —OMe | $-CH_2CH_3$ |
| 458 | $-CH_2CH_3$ | $-CH_2-HC=CH_2$ | H | H | H | H | —OMe | $-CH_2CH_3$ |
| 459 | $-(CH_2)_2CH_3$ | $-(CH_2)_2CH_3$ | H | H | H | H | —OMe | $-CH_2CH_3$ |
| 460 | $-(CH_2)_2CH_3$ | $-CH(CH_3)_2$ | H | H | H | H | —OMe | $-CH_2CH_3$ |
| 461 | $-(CH_2)_2CH_3$ | $-(CH_2)_3CH_3$ | H | H | H | H | —OMe | $-CH_2CH_3$ |
| 462 | $-(CH_2)_2CH_3$ | $-CH_2-HC=CH_2$ | H | H | H | H | —OMe | $-CH_2CH_3$ |
| 463 | $-CH(CH_3)_2$ | $-CH(CH_3)_2$ | H | H | H | H | —OMe | $-CH_2CH_3$ |
| 464 | $-CH(CH_3)_2$ | $-(CH_2)_3CH_3$ | H | H | H | H | —OMe | $-CH_2CH_3$ |
| 465 | $-CH(CH_3)_2$ | $-CH_2-HC=CH_2$ | H | H | H | H | —OMe | $-CH_2CH_3$ |
| 466 | $-(CH_2)_3CH_3$ | $-(CH_2)_3CH_3$ | H | H | H | H | —OMe | $-CH_2CH_3$ |
| 467 | $-(CH_2)_3CH_3$ | $-CH_2-HC=CH_2$ | H | H | H | H | —OMe | $-CH_2CH_3$ |
| 468 | $-CH_2-HC=CH_2$ | $-CH_2-HC=CH_2$ | H | H | H | H | —OMe | $-CH_2CH_3$ |
| 469 | $-CH_3$ | cyclopropyl | H | H | H | H | —OMe | H |
| 470 | $-CH_2CH_3$ | cyclopropyl | H | H | H | H | —OMe | H |
| 471 | $-(CH_2)_2CH_3$ | cyclopropyl | H | H | H | H | —OMe | H |
| 472 | $-CH(CH_3)_2$ | cyclopropyl | H | H | H | H | —OMe | H |
| 473 | $-(CH_2)_3CH_3$ | cyclopropyl | H | H | H | H | —OMe | H |
| 474 | $-CH_2-HC=CH_2$ | cyclopropyl | H | H | H | H | —OMe | H |
| 475 | cyclopropyl | cyclopropyl | H | H | H | H | —OMe | H |
| 476 | $-CH_3$ | cyclopropyl | H | H | H | H | —OMe | $-CH_2CH_3$ |
| 477 | $-CH_2CH_3$ | cyclopropyl | H | H | H | H | —OMe | $-CH_2CH_3$ |
| 478 | $-(CH_2)_2CH_3$ | cyclopropyl | H | H | H | H | —OMe | $-CH_2CH_3$ |
| 479 | $-CH(CH_3)_2$ | cyclopropyl | H | H | H | H | —OMe | $-CH_2CH_3$ |
| 480 | $-(CH_2)_3CH_3$ | cyclopropyl | H | H | H | H | —OMe | $-CH_2CH_3$ |
| 481 | $-CH_2-HC=CH_2$ | cyclopropyl | H | H | H | H | —OMe | $-CH_2CH_3$ |
| 482 | cyclopropyl | cyclopropyl | H | H | H | H | —OMe | $-CH_2CH_3$ |
| 483 | H | $-CH_3$ | H | H | H | H | —OMe | H |
| 484 | H | $-CH_2CH_3$ | H | H | H | H | —OMe | H |
| 485 | H | $-(CH_2)_2CH_3$ | H | H | H | H | —OMe | H |
| 486 | H | $-CH(CH_3)_2$ | H | H | H | H | —OMe | H |
| 487 | H | $-(CH_2)_3CH_3$ | H | H | H | H | —OMe | H |
| 488 | H | $-CH_2-HC=CH_2$ | H | H | H | H | —OMe | H |
| 489 | H | cyclopropyl | H | H | H | H | —OMe | H |
| 490 | H | $-CH_3$ | H | H | H | H | —OMe | $-CH_2CH_3$ |
| 491 | H | $-CH_2CH_3$ | H | H | H | H | —OMe | $-CH_2CH_3$ |
| 492 | H | $-(CH_2)_2CH_3$ | H | H | H | H | —OMe | $-CH_2CH_3$ |
| 493 | H | $-CH(CH_3)_2$ | H | H | H | H | —OMe | $-CH_2CH_3$ |
| 494 | H | $-(CH_2)_3CH_3$ | H | H | H | H | —OMe | $-CH_2CH_3$ |
| 495 | H | $-CH_2-HC=CH_2$ | H | H | H | H | —OMe | $-CH_2CH_3$ |
| 496 | H | cyclopropyl | H | H | H | H | —OMe | $-CH_2CH_3$ |
| 497 | H | $-CD_3$ | H | H | H | H | H | H |
| 498 | H | $-CD_3$ | H | H | —OH | H | H | H |
| 499 | H | $-CD_3$ | H | H | $-OC(O)CH_3$ | H | H | H |
| 500 | H | $-CD_3$ | H | H | H | $-OCH_3$ | H | H |
| 501 | H | $-CD_3$ | H | H | H | H | H | H |
| 502 | H | $-CD_3$ | H | H | —OH | H | H | H |

TABLE 7-continued

| Ref. | X | Y | $R_2$ | $R_3$ | $R_4$ | $R_5$ | $R_6$ | $R_1$ |
|---|---|---|---|---|---|---|---|---|
| 503 | H | $—CD_3$ | H | H | —OC(O)$CH_3$ | H | H | H |
| 504 | H | $—CD_3$ | H | H | H | $—OCH_3$ | H | H |
| 505 | H | $—CD_3$ | H | H | H | H | F | H |
| 506 | H | $—CD_3$ | H | H | —OH | H | F | H |
| 507 | H | $—CD_3$ | H | H | —OC(O)$CH_3$ | H | F | H |
| 508 | H | $—CD_3$ | H | H | H | $—OCH_3$ | F | H |
| 509 | H | $—CD_3$ | H | H | H | H | H | $—CH_2CH_3$ |
| 510 | H | $—CD_3$ | H | H | —OH | H | H | $—CH_2CH_3$ |
| 511 | H | $—CD_3$ | H | H | —OC(O)$CH_3$ | H | H | $—CH_2CH_3$ |
| 512 | H | $—CD_3$ | H | H | H | $—OCH_3$ | H | $—CH_2CH_3$ |
| 513 | H | $—CD_2CD_3$ | H | H | H | H | H | H |
| 514 | H | $—CD_2CD_3$ | H | H | —OH | H | H | H |
| 515 | H | $—CD_2CD_3$ | H | H | —OC(O)$CH_3$ | H | H | H |
| 516 | H | $—CD_2CD_3$ | H | H | H | $—OCH_3$ | H | H |
| 517 | H | $—CD_2CD_3$ | H | H | H | H | H | H |
| 518 | H | $—CD_2CD_3$ | H | H | —OH | H | H | H |
| 519 | H | $—CD_2CD_3$ | H | H | —OC(O)$CH_3$ | H | H | H |
| 520 | H | $—CD_2CD_3$ | H | H | H | $—OCH_3$ | H | H |
| 521 | H | $—CD_2CD_3$ | H | H | H | H | F | H |
| 522 | H | $—CD_2CD_3$ | H | H | —OH | H | F | H |
| 523 | H | $—CD_2CD_3$ | H | H | —OC(O)$CH_3$ | H | F | H |
| 524 | H | $—CD_2CD_3$ | H | H | H | $—OCH_3$ | F | H |
| 525 | H | $—CD_2CD_3$ | H | H | H | H | H | $—CH_2CH_3$ |
| 526 | H | $—CD_2CD_3$ | H | H | —OH | H | H | $—CH_2CH_3$ |
| 527 | H | $—CD_2CD_3$ | H | H | —OC(O)$CH_3$ | H | H | $—CH_2CH_3$ |
| 528 | H | $—CD_2CD_3$ | H | H | H | $—OCH_3$ | H | $—CH_2CH_3$ |
| 529 | H | $—CH_3$ | H | D | H | H | H | H |
| 530 | H | $—CH_2CH_3$ | H | D | H | H | H | H |
| 531 | H | $—(CH_2)_2CH_3$ | H | D | H | H | H | H |
| 532 | H | $—CH(CH_3)_2$ | H | D | H | H | H | H |
| 533 | H | $—(CH_2)_3CH_3$ | H | D | H | H | H | H |
| 534 | H | $—CH_2—HC{=}CH_2$ | H | D | H | H | H | H |
| 535 | H | $—CH_3$ | H | D | —OH | H | H | H |
| 536 | H | $—CH_2CH_3$ | H | D | —OH | H | H | H |
| 537 | H | $—(CH_2)_2CH_3$ | H | D | —OH | H | H | H |
| 538 | H | $—CH(CH_3)_2$ | H | D | —OH | H | H | H |
| 539 | H | $—(CH_2)_3CH_3$ | H | D | —OH | H | H | H |
| 540 | H | $—CH_2—HC{=}CH_2$ | H | D | —OH | H | H | H |
| 541 | H | $—CH_3$ | H | D | —OH | H | F | H |
| 542 | H | $—CH_2CH_3$ | H | D | —OH | H | F | H |
| 543 | H | $—(CH_2)_2CH_3$ | H | D | —OH | H | F | H |
| 544 | H | $—CH(CH_3)_2$ | H | D | —OH | H | F | H |
| 545 | H | $—(CH_2)_3CH_3$ | H | D | —OH | H | F | H |
| 546 | H | $—CH_2—HC{=}CH_2$ | H | D | —OH | H | F | H |
| 547 | H | $—CH_3$ | H | D | H | —OMe | F | H |
| 548 | H | $—CH_2CH_3$ | H | D | H | —OMe | F | H |
| 549 | H | $—(CH_2)_2CH_3$ | H | D | H | —OMe | F | H |
| 550 | H | $—CH(CH_3)_2$ | H | D | H | —OMe | F | H |
| 551 | H | $—(CH_2)_3CH_3$ | H | D | H | —OMe | F | H |
| 552 | H | $—CH_2—HC{=}CH_2$ | H | D | H | —OMe | F | H |
| 553 | H | $—CH_3$ | H | D | H | —OMe | H | H |
| 554 | H | $—CH_2CH_3$ | H | D | H | —OMe | H | H |
| 555 | H | $—(CH_2)_2CH_3$ | H | D | H | —OMe | H | H |
| 556 | H | $—CH(CH_3)_2$ | H | D | H | —OMe | H | H |
| 557 | H | $—(CH_2)_3CH_3$ | H | D | H | —OMe | H | H |
| 558 | H | $—CH_2—HC{=}CH_2$ | H | D | H | —OMe | H | H |
| 559 | H | $—CH_3$ | H | D | —OC(O)$CH_3$ | H | H | H |
| 560 | H | $—CH_2CH_3$ | H | D | —OC(O)$CH_3$ | H | H | H |
| 561 | H | $—(CH_2)_2CH_3$ | H | D | —OC(O)$CH_3$ | H | H | H |
| 562 | H | $—CH(CH_3)_2$ | H | D | —OC(O)$CH_3$ | H | H | H |
| 563 | H | $—(CH_2)_3CH_3$ | H | D | —OC(O)$CH_3$ | H | H | H |
| 564 | H | $—CH_2—HC{=}CH_2$ | H | D | —OC(O)$CH_3$ | H | H | H |
| 565 | H | $—CH_3$ | H | D | —OC(O)$CH_3$ | H | F | H |
| 566 | H | $—CH_2CH_3$ | H | D | —OC(O)$CH_3$ | H | F | H |
| 567 | H | $—(CH_2)_2CH_3$ | H | D | —OC(O)$CH_3$ | H | F | H |
| 568 | H | $—CH(CH_3)_2$ | H | D | —OC(O)$CH_3$ | H | F | H |
| 569 | H | $—(CH_2)_3CH_3$ | H | D | —OC(O)$CH_3$ | H | F | H |
| 570 | H | $—CH_2—HC{=}CH_2$ | H | D | —OC(O)$CH_3$ | H | F | H |

Other exemplary compounds of Formula I include those below in Table 8, which is also represented by Formula Ih:

Formula Ih

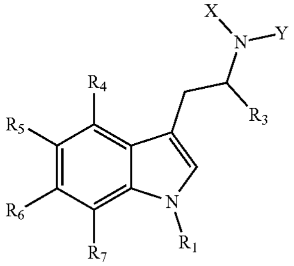

TABLE 8

| Ref. | X | Y | $R_3$ | $R_4$ | $R_5$ | $R_6$ | $R_7$ | $R_1$ |
|---|---|---|---|---|---|---|---|---|
| 1 | $-CH_3$ | $-CH_3$ | H | $-OCH_3$ | H | H | H | $-CH_2CH_3$ |
| 2 | $-CH_3$ | $-CH_2CH_3$ | H | $-OCH_3$ | H | H | H | $-CH_2CH_3$ |
| 3 | $-CH_3$ | $-(CH_2)_2CH_3$ | H | $-OCH_3$ | H | H | H | $-CH_2CH_3$ |
| 4 | $-CH_3$ | $-CH(CH_3)_2$ | H | $-OCH_3$ | H | H | H | $-CH_2CH_3$ |
| 5 | $-CH_3$ | $-(CH_2)_3CH_3$ | H | $-OCH_3$ | H | H | H | $-CH_2CH_3$ |
| 6 | $-CH_3$ | $-CH_2HC{=}CH_2$ | H | $-OCH_3$ | H | H | H | $-CH_2CH_3$ |
| 7 | $-CH_2CH_3$ | $-CH_2CH_3$ | H | $-OCH_3$ | H | H | H | $-CH_2CH_3$ |
| 8 | $-CH_2CH_3$ | $-(CH_2)_2CH_3$ | H | $-OCH_3$ | H | H | H | $-CH_2CH_3$ |
| 9 | $-CH_2CH_3$ | $-CH(CH_3)_2$ | H | $-OCH_3$ | H | H | H | $-CH_2CH_3$ |
| 10 | $-CH_2CH_3$ | $-(CH_2)_3CH_3$ | H | $-OCH_3$ | H | H | H | $-CH_2CH_3$ |
| 11 | $-CH_2CH_3$ | $-CH_2-HC{=}CH_2$ | H | $-OCH_3$ | H | H | H | $-CH_2CH_3$ |
| 12 | $-(CH_2)_2CH_3$ | $-(CH_2)_2CH_3$ | H | $-OCH_3$ | H | H | H | $-CH_2CH_3$ |
| 13 | $-(CH_2)_2CH_3$ | $-CH(CH_3)_2$ | H | $-OCH_3$ | H | H | H | $-CH_2CH_3$ |
| 14 | $-(CH_2)_2CH_3$ | $-(CH_2)_3CH_3$ | H | $-OCH_3$ | H | H | H | $-CH_2CH_3$ |
| 15 | $-(CH_2)_2CH_3$ | $-CH_2-HC{=}CH_2$ | H | $-OCH_3$ | H | H | H | $-CH_2CH_3$ |
| 16 | $-CH(CH_3)_2$ | $-CH(CH_3)_2$ | H | $-OCH_3$ | H | H | H | $-CH_2CH_3$ |
| 17 | $-CH(CH_3)_2$ | $-(CH_2)_3CH_3$ | H | $-OCH_3$ | H | H | H | $-CH_2CH_3$ |
| 18 | $-CH(CH_3)_2$ | $-CH_2-HC{=}CH_2$ | H | $-OCH_3$ | H | H | H | $-CH_2CH_3$ |
| 19 | $-(CH_2)_3CH_3$ | $-(CH_2)_3CH_3$ | H | $-OCH_3$ | H | H | H | $-CH_2CH_3$ |
| 20 | $-(CH_2)_3CH_3$ | $-CH_2-HC{=}CH_2$ | H | $-OCH_3$ | H | H | H | $-CH_2CH_3$ |
| 21 | $-CH_2-HC{=}CH_2$ | $-CH_2-HC{=}CH_2$ | H | $-OCH_3$ | H | H | H | $-CH_2CH_3$ |
| 22 | $-CH_3$ | $-CH_2CH_3$ | H | $-OH$ | H | H | H | $-CH_2CH_3$ |
| 23 | $-CH_3$ | $-(CH_2)_2CH_3$ | H | $-OH$ | H | H | H | $-CH_2CH_3$ |
| 24 | $-CH_3$ | $-CH(CH_3)_2$ | H | $-OH$ | H | H | H | $-CH_2CH_3$ |
| 25 | $-CH_3$ | $-(CH_2)_3CH_3$ | H | $-OH$ | H | H | H | $-CH_2CH_3$ |
| 26 | $-CH_3$ | $-CH_2-HC{=}CH_2$ | H | $-OH$ | H | H | H | $-CH_2CH_3$ |
| 27 | $-CH_2CH_3$ | $-CH_2CH_3$ | H | $-OH$ | H | H | H | $-CH_2CH_3$ |
| 28 | $-CH_2CH_3$ | $-(CH_2)_2CH_3$ | H | $-OH$ | H | H | H | $-CH_2CH_3$ |
| 29 | $-CH_2CH_3$ | $-CH(CH_3)_2$ | H | $-OH$ | H | H | H | $-CH_2CH_3$ |
| 30 | $-CH_2CH_3$ | $-(CH_2)_3CH_3$ | H | $-OH$ | H | H | H | $-CH_2CH_3$ |
| 31 | $-CH_2CH_3$ | $-CH_2-HC{=}CH_2$ | H | $-OH$ | H | H | H | $-CH_2CH_3$ |
| 32 | $-(CH_2)_2CH_3$ | $-(CH_2)_2CH_3$ | H | $-OH$ | H | H | H | $-CH_2CH_3$ |
| 33 | $-(CH_2)_2CH_3$ | $-CH(CH_3)_2$ | H | $-OH$ | H | H | H | $-CH_2CH_3$ |
| 34 | $-(CH_2)_2CH_3$ | $-(CH_2)_3CH_3$ | H | $-OH$ | H | H | H | $-CH_2CH_3$ |
| 35 | $-(CH_2)_2CH_3$ | $-CH_2-HC{=}CH_2$ | H | $-OH$ | H | H | H | $-CH_2CH_3$ |
| 36 | $-CH(CH_3)_2$ | $-CH(CH_3)_2$ | H | $-OH$ | H | H | H | $-CH_2CH_3$ |
| 37 | $-CH(CH_3)_2$ | $-(CH_2)_3CH_3$ | H | $-OH$ | H | H | H | $-CH_2CH_3$ |
| 38 | $-CH(CH_3)_2$ | $-CH_2-HC{=}CH_2$ | H | $-OH$ | H | H | H | $-CH_2CH_3$ |
| 39 | $-(CH_2)_3CH_3$ | $-(CH_2)_3CH_3$ | H | $-OH$ | H | H | H | $-CH_2CH_3$ |
| 40 | $-(CH_2)_3CH_3$ | $-CH_2-HC{=}CH_2$ | H | $-OH$ | H | H | H | $-CH_2CH_3$ |
| 41 | $-CH_2-HC{=}CH_2$ | $-CH_2-HC{=}CH_2$ | H | $-OH$ | H | H | H | $-CH_2CH_3$ |
| 42 | $-CH_3$ | $-CH_3$ | H | $-OC(O)CH_3$ | H | H | H | $-CH_2CH_3$ |
| 43 | $-CH_3$ | $-CH_2CH_3$ | H | $-OC(O)CH_3$ | H | H | H | $-CH_2CH_3$ |
| 44 | $-CH_3$ | $-(CH_2)_2CH_3$ | H | $-OC(O)CH_3$ | H | H | H | $-CH_2CH_3$ |
| 45 | $-CH_3$ | $-CH(CH_3)_2$ | H | $-OC(O)CH_3$ | H | H | H | $-CH_2CH_3$ |
| 46 | $-CH_3$ | $-(CH_2)_3CH_3$ | H | $-OC(O)CH_3$ | H | H | H | $-CH_2CH_3$ |
| 47 | $-CH_3$ | $-CH_2-HC{=}CH_2$ | H | $-OC(O)CH_3$ | H | H | H | $-CH_2CH_3$ |
| 48 | $-CH_2CH_3$ | $-CH_2CH_3$ | H | $-OC(O)CH_3$ | H | H | H | $-CH_2CH_3$ |
| 49 | $-CH_2CH_3$ | $-(CH_2)_2CH_3$ | H | $-OC(O)CH_3$ | H | H | H | $-CH_2CH_3$ |
| 50 | $-CH_2CH_3$ | $-CH(CH_3)_2$ | H | $-OC(O)CH_3$ | H | H | H | $-CH_2CH_3$ |
| 51 | $-CH_2CH_3$ | $-(CH_2)_3CH_3$ | H | $-OC(O)CH_3$ | H | H | H | $-CH_2CH_3$ |
| 52 | $-CH_2CH_3$ | $-CH_2-HC{=}CH_2$ | H | $-OC(O)CH_3$ | H | H | H | $-CH_2CH_3$ |
| 53 | $-(CH_2)_2CH_3$ | $-(CH_2)_2CH_3$ | H | $-OC(O)CH_3$ | H | H | H | $-CH_2CH_3$ |
| 54 | $-(CH_2)_2CH_3$ | $-CH(CH_3)_2$ | H | $-OC(O)CH_3$ | H | H | H | $-CH_2CH_3$ |
| 55 | $-(CH_2)_2CH_3$ | $-(CH_2)_3CH_3$ | H | $-OC(O)CH_3$ | H | H | H | $-CH_2CH_3$ |
| 56 | $-(CH_2)_2CH_3$ | $-CH_2-HC{=}CH_2$ | H | $-OC(O)CH_3$ | H | H | H | $-CH_2CH_3$ |

TABLE 8-continued

| Ref. | X | Y | $R_3$ | $R_4$ | $R_5$ | $R_6$ | $R_7$ | $R_1$ |
|---|---|---|---|---|---|---|---|---|
| 57 | $-CH(CH_3)_2$ | $-CH(CH_3)_2$ | H | $-OC(O)CH_3$ | H | H | H | $-CH_2CH_3$ |
| 58 | $-CH(CH_3)_2$ | $-(CH_2)_3CH_3$ | H | $-OC(O)CH_3$ | H | H | H | $-CH_2CH_3$ |
| 59 | $-CH(CH_3)_2$ | $-CH_2-HC=CH_2$ | H | $-OC(O)CH_3$ | H | H | H | $-CH_2CH_3$ |
| 60 | $-(CH_2)_3CH_3$ | $-(CH_2)_3CH_3$ | H | $-OC(O)CH_3$ | H | H | H | $-CH_2CH_3$ |
| 61 | $-(CH_2)_3CH_3$ | $-CH_2-HC=CH_2$ | H | $-OC(O)CH_3$ | H | H | H | $-CH_2CH_3$ |
| 62 | $-CH_2-HC=CH_2$ | $-CH_2-HC=CH_2$ | H | $-OC(O)CH_3$ | H | H | H | $-CH_2CH_3$ |
| 63 | $-CH_3$ | $-CH_3$ | H | H | $-OCH_3$ | H | H | $-CH_2CH_3$ |
| 64 | $-CH_3$ | $-CH_2CH_3$ | H | H | $-OCH_3$ | H | H | $-CH_2CH_3$ |
| 65 | $-CH_3$ | $-(CH_2)_2CH_3$ | H | H | $-OCH_3$ | H | H | $-CH_2CH_3$ |
| 66 | $-CH_3$ | $-CH(CH_3)_2$ | H | H | $-OCH_3$ | H | H | $-CH_2CH_3$ |
| 67 | $-CH_3$ | $-(CH_2)_3CH_3$ | H | H | $-OCH_3$ | H | H | $-CH_2CH_3$ |
| 68 | $-CH_3$ | $-CH_2-HC=CH_2$ | H | H | $-OCH_3$ | H | H | $-CH_2CH_3$ |
| 69 | $-CH_2CH_3$ | $-CH_2CH_3$ | H | H | $-OCH_3$ | H | H | $-CH_2CH_3$ |
| 70 | $-CH_2CH_3$ | $-(CH_2)_2CH_3$ | H | H | $-OCH_3$ | H | H | $-CH_2CH_3$ |
| 71 | $-CH_2CH_3$ | $-CH(CH_3)_2$ | H | H | $-OCH_3$ | H | H | $-CH_2CH_3$ |
| 72 | $-CH_2CH_3$ | $-(CH_2)_3CH_3$ | H | H | $-OCH_3$ | H | H | $-CH_2CH_3$ |
| 73 | $-CH_2CH_3$ | $-CH_2-HC=CH_2$ | H | H | $-OCH_3$ | H | H | $-CH_2CH_3$ |
| 74 | $-(CH_2)_2CH_3$ | $-(CH_2)_2CH_3$ | H | H | $-OCH_3$ | H | H | $-CH_2CH_3$ |
| 75 | $-(CH_2)_2CH_3$ | $-CH(CH_3)_2$ | H | H | $-OCH_3$ | H | H | $-CH_2CH_3$ |
| 76 | $-(CH_2)_2CH_3$ | $-(CH_2)_3CH_3$ | H | H | $-OCH_3$ | H | H | $-CH_2CH_3$ |
| 77 | $-(CH_2)_2CH_3$ | $-CH_2HC=CH_2$ | H | H | $-OCH_3$ | H | H | $-CH_2CH_3$ |
| 78 | $-CH(CH_3)_2$ | $-CH(CH_3)_2$ | H | H | $-OCH_3$ | H | H | $-CH_2CH_3$ |
| 79 | $-CH(CH_3)_2$ | $-(CH_2)_3CH_3$ | H | H | $-OCH_3$ | H | H | $-CH_2CH_3$ |
| 80 | $-CH(CH_3)_2$ | $-CH_2-HC=CH_2$ | H | H | $-OCH_3$ | H | H | $-CH_2CH_3$ |
| 81 | $-(CH_2)_3CH_3$ | $-(CH_2)_3CH_3$ | H | H | $-OCH_3$ | H | H | $-CH_2CH_3$ |
| 82 | $-(CH_2)_3CH_3$ | $-CH_2-HC=CH_2$ | H | H | $-OCH_3$ | H | H | $-CH_2CH_3$ |
| 83 | $-CH_2-HC=CH_2$ | $-CH_2-HC=CH_2$ | H | H | $-OCH_3$ | H | H | $-CH_2CH_3$ |
| 84 | $-CH_3$ | $-CH_2CH_3$ | H | H | $-OH$ | H | H | $-CH_2CH_3$ |
| 85 | $-CH_3$ | $-(CH_2)_2CH_3$ | H | H | $-OH$ | H | H | $-CH_2CH_3$ |
| 86 | $-CH_3$ | $-CH(CH_3)_2$ | H | H | $-OH$ | H | H | $-CH_2CH_3$ |
| 87 | $-CH_3$ | $-(CH_2)_3CH_3$ | H | H | $-OH$ | H | H | $-CH_2CH_3$ |
| 88 | $-CH_3$ | $-CH_2-HC=CH_2$ | H | H | $-OH$ | H | H | $-CH_2CH_3$ |
| 89 | $-CH_2CH_3$ | $-CH_2CH_3$ | H | H | $-OH$ | H | H | $-CH_2CH_3$ |
| 90 | $-CH_2CH_3$ | $-(CH_2)_2CH_3$ | H | H | $-OH$ | H | H | $-CH_2CH_3$ |
| 91 | $-CH_2CH_3$ | $-CH(CH_3)_2$ | H | H | $-OH$ | H | H | $-CH_2CH_3$ |
| 92 | $-CH_2CH_3$ | $-(CH_2)_3CH_3$ | H | H | $-OH$ | H | H | $-CH_2CH_3$ |
| 93 | $-CH_2CH_3$ | $-CH_2-HC=CH_2$ | H | H | $-OH$ | H | H | $-CH_2CH_3$ |
| 94 | $-(CH_2)_2CH_3$ | $-(CH_2)_2CH_3$ | H | H | $-OH$ | H | H | $-CH_2CH_3$ |
| 95 | $-(CH_2)_2CH_3$ | $-CH(CH_3)_2$ | H | H | $-OH$ | H | H | $-CH_2CH_3$ |
| 96 | $-(CH_2)_2CH_3$ | $-(CH_2)_3CH_3$ | H | H | $-OH$ | H | H | $-CH_2CH_3$ |
| 97 | $-(CH_2)_2CH_3$ | $-CH_2-HC=CH_2$ | H | H | $-OH$ | H | H | $-CH_2CH_3$ |
| 98 | $-CH(CH_3)_2$ | $-CH(CH_3)_2$ | H | H | $-OH$ | H | H | $-CH_2CH_3$ |
| 99 | $-CH(CH_3)_2$ | $-(CH_2)_3CH_3$ | H | H | $-OH$ | H | H | $-CH_2CH_3$ |
| 100 | $-CH(CH_3)_2$ | $-CH_2-HC=CH_2$ | H | H | $-OH$ | H | H | $-CH_2CH_3$ |
| 101 | $-(CH_2)_3CH_3$ | $-(CH_2)_3CH_3$ | H | H | $-OH$ | H | H | $-CH_2CH_3$ |
| 102 | $-(CH_2)_3CH_3$ | $-CH_2-HC=CH_2$ | H | H | $-OH$ | H | H | $-CH_2CH_3$ |
| 103 | $-CH_2-HC=CH_2$ | $-CH_2-HC=CH_2$ | H | H | $-OH$ | H | H | $-CH_2CH_3$ |
| 104 | $-CH_3$ | $-CH_3$ | H | H | $-OC(O)CH_3$ | H | H | $-CH_2CH_3$ |
| 105 | $-CH_3$ | $-CH_2CH_3$ | H | H | $-OC(O)CH_3$ | H | H | $-CH_2CH_3$ |
| 106 | $-CH_3$ | $-(CH_2)_2CH_3$ | H | H | $-OC(O)CH_3$ | H | H | $-CH_2CH_3$ |
| 107 | $-CH_3$ | $-CH(CH_3)_2$ | H | H | $-OC(O)CH_3$ | H | H | $-CH_2CH_3$ |
| 108 | $-CH_3$ | $-(CH_2)_3CH_3$ | H | H | $-OC(O)CH_3$ | H | H | $-CH_2CH_3$ |
| 109 | $-CH_3$ | $-CH_2-HC=CH_2$ | H | H | $-OC(O)CH_3$ | H | H | $-CH_2CH_3$ |
| 110 | $-CH_2CH_3$ | $-CH_2CH_3$ | H | H | $-OC(O)CH_3$ | H | H | $-CH_2CH_3$ |
| 111 | $-CH_2CH_3$ | $-(CH_2)_2CH_3$ | H | H | $-OC(O)CH_3$ | H | H | $-CH_2CH_3$ |
| 112 | $-CH_2CH_3$ | $-CH(CH_3)_2$ | H | H | $-OC(O)CH_3$ | H | H | $-CH_2CH_3$ |
| 113 | $-CH_2CH_3$ | $-(CH_2)_3CH_3$ | H | H | $-OC(O)CH_3$ | H | H | $-CH_2CH_3$ |
| 114 | $-CH_2CH_3$ | $-CH_2HC=CH_2$ | H | H | $-OC(O)CH_3$ | H | H | $-CH_2CH_3$ |
| 115 | $-(CH_2)_2CH_3$ | $-(CH_2)_2CH_3$ | H | H | $-OC(O)CH_3$ | H | H | $-CH_2CH_3$ |
| 116 | $-(CH_2)_2CH_3$ | $-CH(CH_3)_2$ | H | H | $-OC(O)CH_3$ | H | H | $-CH_2CH_3$ |
| 117 | $-(CH_2)_2CH_3$ | $-(CH_2)_3CH_3$ | H | H | $-OC(O)CH_3$ | H | H | $-CH_2CH_3$ |
| 118 | $-(CH_2)_2CH_3$ | $-CH_2-HC=CH_2$ | H | H | $-OC(O)CH_3$ | H | H | $-CH_2CH_3$ |
| 119 | $-CH(CH_3)_2$ | $-CH(CH_3)_2$ | H | H | $-OC(O)CH_3$ | H | H | $-CH_2CH_3$ |
| 120 | $-CH(CH_3)_2$ | $-(CH_2)_3CH_3$ | H | H | $-OC(O)CH_3$ | H | H | $-CH_2CH_3$ |
| 121 | $-CH(CH_3)_2$ | $-CH_2-HC=CH_2$ | H | H | $-OC(O)CH_3$ | H | H | $-CH_2CH_3$ |
| 122 | $-(CH_2)_3CH_3$ | $-(CH_2)_3CH_3$ | H | H | $-OC(O)CH_3$ | H | H | $-CH_2CH_3$ |
| 123 | $-(CH_2)_3CH_3$ | $-CH_2-HC=CH_2$ | H | H | $-OC(O)CH_3$ | H | H | $-CH_2CH_3$ |
| 124 | $-CH_2-HC=CH_2$ | $-CH_2-HC=CH_2$ | H | H | $-OC(O)CH_3$ | H | H | $-CH_2CH_3$ |
| 125 | $-CH_3$ | $-CH_3$ | H | $-OCH_3$ | H | H | $-CH_3$ | H |
| 126 | $-CH_3$ | $-CH_2CH_3$ | H | $-OCH_3$ | H | H | $-CH_3$ | H |
| 127 | $-CH_3$ | $-(CH_2)_2CH_3$ | H | $-OCH_3$ | H | H | $-CH_3$ | H |
| 128 | $-CH_3$ | $-CH(CH_3)_2$ | H | $-OCH_3$ | H | H | $-CH_3$ | H |
| 129 | $-CH_3$ | $-(CH_2)_3CH_3$ | H | $-OCH_3$ | H | H | $-CH_3$ | H |
| 130 | $-CH_3$ | $-CH_2-HC=CH_2$ | H | $-OCH_3$ | H | H | $-CH_3$ | H |
| 131 | $-CH_2CH_3$ | $-CH_2CH_3$ | H | $-OCH_3$ | H | H | $-CH_3$ | H |
| 132 | $-CH_2CH_3$ | $-(CH_2)_2CH_3$ | H | $-OCH_3$ | H | H | $-CH_3$ | H |
| 133 | $-CH_2CH_3$ | $-CH(CH_3)_2$ | H | $-OCH_3$ | H | H | $-CH_3$ | H |
| 134 | $-CH_2CH_3$ | $-(CH_2)_3CH_3$ | H | $-OCH_3$ | H | H | $-CH_3$ | H |

TABLE 8-continued

| Ref. | X | Y | $R_3$ | $R_4$ | $R_5$ | $R_6$ | $R_7$ | $R_1$ |
|---|---|---|---|---|---|---|---|---|
| 135 | $-CH_2CH_3$ | $-CH_2-HC=CH_2$ | H | $-OCH_3$ | H | H | $-CH_3$ | H |
| 135 | $-(CH_2)_2CH_3$ | $-(CH_2)_2CH_3$ | H | $-OCH_3$ | H | H | $-CH_3$ | H |
| 137 | $-(CH_2)_2CH_3$ | $-CH(CH_3)_2$ | H | $-OCH_3$ | H | H | $-CH_3$ | H |
| 138 | $-(CH_2)_2CH_3$ | $-(CH_2)_3CH_3$ | H | $-OCH_3$ | H | H | $-CH_3$ | H |
| 139 | $-(CH_2)_2CH_3$ | $-CH_2-HC=CH_2$ | H | $-OCH_3$ | H | H | $-CH_3$ | H |
| 140 | $-CH(CH_3)_2$ | $-CH(CH_3)_2$ | H | $-OCH_3$ | H | H | $-CH_3$ | H |
| 141 | $-CH(CH_3)_2$ | $-(CH_2)_3CH_3$ | H | $-OCH_3$ | H | H | $-CH_3$ | H |
| 142 | $-CH(CH_3)_2$ | $-CH_2-HC=CH_2$ | H | $-OCH_3$ | H | H | $-CH_3$ | H |
| 143 | $-(CH_2)_3CH_3$ | $-(CH_2)_3CH_3$ | H | $-OCH_3$ | H | H | $-CH_3$ | H |
| 144 | $-(CH_2)_3CH_3$ | $-CH_2-HC=CH_2$ | H | $-OCH_3$ | H | H | $-CH_3$ | H |
| 145 | $-CH_2-HC=CH_2$ | $-CH_2-HC=CH_2$ | H | $-OCH_3$ | H | H | $-CH_3$ | H |
| 146 | $-CH_3$ | $-CH_2CH_3$ | H | $-OH$ | H | H | $-CH_3$ | H |
| 147 | $-CH_3$ | $-(CH_2)_2CH_3$ | H | $-OH$ | H | H | $-CH_3$ | H |
| 148 | $-CH_3$ | $-CH(CH_3)_2$ | H | $-OH$ | H | H | $-CH_3$ | H |
| 149 | $-CH_3$ | $-(CH_2)_3CH_3$ | H | $-OH$ | H | H | $-CH_3$ | H |
| 150 | $-CH_3$ | $-CH_2-HC=CH_2$ | H | $-OH$ | H | H | $-CH_3$ | H |
| 151 | $-CH_2CH_3$ | $-CH_2CH_3$ | H | $-OH$ | H | H | $-CH_3$ | H |
| 152 | $-CH_2CH_3$ | $-(CH_2)_2CH_3$ | H | $-OH$ | H | H | $-CH_3$ | H |
| 153 | $-CH_2CH_3$ | $-CH(CH_3)_2$ | H | $-OH$ | H | H | $-CH_3$ | H |
| 154 | $-CH_2CH_3$ | $-(CH_2)_3CH_3$ | H | $-OH$ | H | H | $-CH_3$ | H |
| 155 | $-CH_2CH_3$ | $-CH_2-HC=CH_2$ | H | $-OH$ | H | H | $-CH_3$ | H |
| 156 | $-(CH_2)_2CH_3$ | $-(CH_2)_2CH_3$ | H | $-OH$ | H | H | $-CH_3$ | H |
| 157 | $-(CH_2)_2CH_3$ | $-CH(CH_3)_2$ | H | $-OH$ | H | H | $-CH_3$ | H |
| 158 | $-(CH_2)_2CH_3$ | $-(CH_2)_3CH_3$ | H | $-OH$ | H | H | $-CH_3$ | H |
| 159 | $-(CH_2)_2CH_3$ | $-CH_2-HC=CH_2$ | H | $-OH$ | H | H | $-CH_3$ | H |
| 160 | $-CH(CH_3)_2$ | $-CH(CH_3)_2$ | H | $-OH$ | H | H | $-CH_3$ | H |
| 161 | $-CH(CH_3)_2$ | $-(CH_2)_3CH_3$ | H | $-OH$ | H | H | $-CH_3$ | H |
| 162 | $-CH(CH_3)_2$ | $-CH_2-HC=CH_2$ | H | $-OH$ | H | H | $-CH_3$ | H |
| 163 | $-(CH_2)_3CH_3$ | $-(CH_2)_3CH_3$ | H | $-OH$ | H | H | $-CH_3$ | H |
| 164 | $-(CH_2)_3CH_3$ | $-CH_2-HC=CH_2$ | H | $-OH$ | H | H | $-CH_3$ | H |
| 165 | $-CH_2-HC=CH_2$ | $-CH_2-HC=CH_2$ | H | $-OH$ | H | H | $-CH_3$ | H |
| 166 | $-CH_3$ | $-CH_3$ | H | $-OC(O)CH_3$ | H | H | $-CH_3$ | H |
| 167 | $-CH_3$ | $-CH_2CH_3$ | H | $-OC(O)CH_3$ | H | H | $-CH_3$ | H |
| 168 | $-CH_3$ | $-(CH_2)_2CH_3$ | H | $-OC(O)CH_3$ | H | H | $-CH_3$ | H |
| 169 | $-CH_3$ | $-CH(CH_3)_2$ | H | $-OC(O)CH_3$ | H | H | $-CH_3$ | H |
| 170 | $-CH_3$ | $-(CH_2)_3CH_3$ | H | $-OC(O)CH_3$ | H | H | $-CH_3$ | H |
| 171 | $-CH_3$ | $-CH_2-HC=CH_2$ | H | $-OC(O)CH_3$ | H | H | $-CH_3$ | H |
| 172 | $-CH_2CH_3$ | $-CH_2CH_3$ | H | $-OC(O)CH_3$ | H | H | $-CH_3$ | H |
| 173 | $-CH_2CH_3$ | $-(CH_2)_2CH_3$ | H | $-OC(O)CH_3$ | H | H | $-CH_3$ | H |
| 174 | $-CH_2CH_3$ | $-CH(CH_3)_2$ | H | $-OC(O)CH_3$ | H | H | $-CH_3$ | H |
| 175 | $-CH_2CH_3$ | $-(CH_2)_3CH_3$ | H | $-OC(O)CH_3$ | H | H | $-CH_3$ | H |
| 176 | $-CH_2CH_3$ | $-CH_2-HC=CH_2$ | H | $-OC(O)CH_3$ | H | H | $-CH_3$ | H |
| 177 | $-(CH_2)_2CH_3$ | $-(CH_2)_2CH_3$ | H | $-OC(O)CH_3$ | H | H | $-CH_3$ | H |
| 178 | $-(CH_2)_2CH_3$ | $-CH(CH_3)_2$ | H | $-OC(O)CH_3$ | H | H | $-CH_3$ | H |
| 179 | $-(CH_2)_2CH_3$ | $-(CH_2)_3CH_3$ | H | $-OC(O)CH_3$ | H | H | $-CH_3$ | H |
| 180 | $-(CH_2)_2CH_3$ | $-CH_2-HC=CH_2$ | H | $-OC(O)CH_3$ | H | H | $-CH_3$ | H |
| 181 | $-CH(CH_3)_2$ | $-CH(CH_3)_2$ | H | $-OC(O)CH_3$ | H | H | $-CH_3$ | H |
| 182 | $-CH(CH_3)_2$ | $-(CH_2)_3CH_3$ | H | $-OC(O)CH_3$ | H | H | $-CH_3$ | H |
| 183 | $-CH(CH_3)_2$ | $-CH_2-HC=CH_2$ | H | $-OC(O)CH_3$ | H | H | $-CH_3$ | H |
| 184 | $-(CH_2)_3CH_3$ | $-(CH_2)_3CH_3$ | H | $-OC(O)CH_3$ | H | H | $-CH_3$ | H |
| 185 | $-(CH_2)_3CH_3$ | $-CH_2-HC=CH_2$ | H | $-OC(O)CH_3$ | H | H | $-CH_3$ | H |
| 186 | $-CH_2-HC=CH_2$ | $-CH_2-HC=CH_2$ | H | $-OC(O)CH_3$ | H | H | $-CH_3$ | H |
| 187 | $-CH_3$ | $-CH_3$ | H | H | $-OCH_3$ | H | $-CH_3$ | H |
| 188 | $-CH_3$ | $-CH_2CH_3$ | H | H | $-OCH_3$ | H | $-CH_3$ | H |
| 189 | $-CH_3$ | $-(CH_2)_2CH_3$ | H | H | $-OCH_3$ | H | $-CH_3$ | H |
| 190 | $-CH_3$ | $-CH(CH_3)_2$ | H | H | $-OCH_3$ | H | $-CH_3$ | H |
| 191 | $-CH_3$ | $-(CH_2)_3CH_3$ | H | H | $-OCH_3$ | H | $-CH_3$ | H |
| 192 | $-CH_3$ | $-CH_2-HC=CH_2$ | H | H | $-OCH_3$ | H | $-CH_3$ | H |
| 193 | $-CH_2CH_3$ | $-CH_2CH_3$ | H | H | $-OCH_3$ | H | $-CH_3$ | H |
| 194 | $-CH_2CH_3$ | $-(CH_2)_2CH_3$ | H | H | $-OCH_3$ | H | $-CH_3$ | H |
| 195 | $-CH_2CH_3$ | $-CH(CH_3)_2$ | H | H | $-OCH_3$ | H | $-CH_3$ | H |
| 196 | $-CH_2CH_3$ | $-(CH_2)_3CH_3$ | H | H | $-OCH_3$ | H | $-CH_3$ | H |
| 197 | $-CH_2CH_3$ | $-CH_2-HC=CH_2$ | H | H | $-OCH_3$ | H | $-CH_3$ | H |
| 198 | $-(CH_2)_2CH_3$ | $-(CH_2)_2CH_3$ | H | H | $-OCH_3$ | H | $-CH_3$ | H |
| 199 | $-(CH_2)_2CH_3$ | $-CH(CH_3)_2$ | H | H | $-OCH_3$ | H | $-CH_3$ | H |
| 200 | $-(CH_2)_2CH_3$ | $-(CH_2)_3CH_3$ | H | H | $-OCH_3$ | H | $-CH_3$ | H |
| 201 | $-(CH_2)_2CH_3$ | $-CH_2-HC=CH_2$ | H | H | $-OCH_3$ | H | $-CH_3$ | H |
| 202 | $-CH(CH_3)_2$ | $-CH(CH_3)_2$ | H | H | $-OCH_3$ | H | $-CH_3$ | H |
| 203 | $-CH(CH_3)_2$ | $-(CH_2)_3CH_3$ | H | H | $-OCH_3$ | H | $-CH_3$ | H |
| 204 | $-CH(CH_3)_2$ | $-CH_2-HC=CH_2$ | H | H | $-OCH_3$ | H | $-CH_3$ | H |
| 205 | $-(CH_2)_3CH_3$ | $-(CH_2)_3CH_3$ | H | H | $-OCH_3$ | H | $-CH_3$ | H |
| 206 | $-(CH_2)_3CH_3$ | $-CH_2-HC=CH_2$ | H | H | $-OCH_3$ | H | $-CH_3$ | H |
| 207 | $-CH_2-HC=CH_2$ | $-CH_2-HC=CH_2$ | H | H | $-OCH_3$ | H | $-CH_3$ | H |
| 208 | $-CH_3$ | $-CH_2CH_3$ | H | H | $-OH$ | H | $-CH_3$ | H |
| 209 | $-CH_3$ | $-(CH_2)_2CH_3$ | H | H | $-OH$ | H | $-CH_3$ | H |
| 210 | $-CH_3$ | $-CH(CH_3)_2$ | H | H | $-OH$ | H | $-CH_3$ | H |
| 211 | $-CH_3$ | $-(CH_2)_3CH_3$ | H | H | $-OH$ | H | $-CH_3$ | H |
| 212 | $-CH_3$ | $-CH_2-HC=CH_2$ | H | H | $-OH$ | H | $-CH_3$ | H |

TABLE 8-continued

| Ref. | X | Y | $R_3$ | $R_4$ | $R_5$ | $R_6$ | $R_7$ | $R_1$ |
|---|---|---|---|---|---|---|---|---|
| 213 | $—CH_2CH_3$ | $—CH_2CH_3$ | H | H | —OH | H | $—CH_3$ | H |
| 214 | $—CH_2CH_3$ | $—(CH_2)_2CH_3$ | H | H | —OH | H | $—CH_3$ | H |
| 215 | $—CH_2CH_3$ | $—CH(CH_3)_2$ | H | H | —OH | H | $—CH_3$ | H |
| 216 | $—CH_2CH_3$ | $—(CH_2)_3CH_3$ | H | H | —OH | H | $—CH_3$ | H |
| 217 | $—CH_2CH_3$ | $—CH_2—HC═CH_2$ | H | H | —OH | H | $—CH_3$ | H |
| 218 | $—(CH_2)_2CH_3$ | $—(CH_2)_2CH_3$ | H | H | —OH | H | $—CH_3$ | H |
| 219 | $—(CH_2)_2CH_3$ | $—CH(CH_3)_2$ | H | H | —OH | H | $—CH_3$ | H |
| 220 | $—(CH_2)_2CH_3$ | $—(CH_2)_3CH_3$ | H | H | —OH | H | $—CH_3$ | H |
| 221 | $—(CH_2)_2CH_3$ | $—CH_2—HC═CH_2$ | H | H | —OH | H | $—CH_3$ | H |
| 222 | $—CH(CH_3)_2$ | $—CH(CH_3)_2$ | H | H | —OH | H | $—CH_3$ | H |
| 223 | $—CH(CH_3)_2$ | $—(CH_2)_3CH_3$ | H | H | —OH | H | $—CH_3$ | H |
| 224 | $—CH(CH_3)_2$ | $—CH_2—HC═CH_2$ | H | H | —OH | H | $—CH_3$ | H |
| 225 | $—(CH_2)_3CH_3$ | $—(CH_2)_3CH_3$ | H | H | —OH | H | $—CH_3$ | H |
| 226 | $—(CH_2)_3CH_3$ | $—CH_2—HC═CH_2$ | H | H | —OH | H | $—CH_3$ | H |
| 227 | $—CH_2—HC═CH_2$ | $—CH_2—HC═CH_2$ | H | H | —OH | H | $—CH_3$ | H |
| 228 | $—CH_3$ | $—CH_3$ | H | H | $—OC(O)CH_3$ | H | $—CH_3$ | H |
| 229 | $—CH_3$ | $—CH_2CH_3$ | H | H | $—OC(O)CH_3$ | H | $—CH_3$ | H |
| 230 | $—CH_3$ | $—(CH_2)_2CH_3$ | H | H | $—OC(O)CH_3$ | H | $—CH_3$ | H |
| 231 | $—CH_3$ | $—CH(CH_3)_2$ | H | H | $—OC(O)CH_3$ | H | $—CH_3$ | H |
| 232 | $—CH_3$ | $—(CH_2)_3CH_3$ | H | H | $—OC(O)CH_3$ | H | $—CH_3$ | H |
| 233 | $—CH_3$ | $—CH_2—HC═CH_2$ | H | H | $—OC(O)CH_3$ | H | $—CH_3$ | H |
| 234 | $—CH_2CH_3$ | $—CH_2CH_3$ | H | H | $—OC(O)CH_3$ | H | $—CH_3$ | H |
| 235 | $—CH_2CH_3$ | $—(CH_2)_2CH_3$ | H | H | $—OC(O)CH_3$ | H | $—CH_3$ | H |
| 236 | $—CH_2CH_3$ | $—CH(CH_3)_2$ | H | H | $—OC(O)CH_3$ | H | $—CH_3$ | H |
| 237 | $—CH_2CH_3$ | $—(CH_2)_3CH_3$ | H | H | $—OC(O)CH_3$ | H | $—CH_3$ | H |
| 238 | $—CH_2CH_3$ | $—CH_2—HC═CH_2$ | H | H | $—OC(O)CH_3$ | H | $—CH_3$ | H |
| 239 | $—(CH_2)_2CH_3$ | $—(CH_2)_2CH_3$ | H | H | $—OC(O)CH_3$ | H | $—CH_3$ | H |
| 240 | $—(CH_2)_2CH_3$ | $—CH(CH_3)_2$ | H | H | $—OC(O)CH_3$ | H | $—CH_3$ | H |
| 241 | $—(CH_2)_2CH_3$ | $—(CH_2)_3CH_3$ | H | H | $—OC(O)CH_3$ | H | $—CH_3$ | H |
| 242 | $—(CH_2)_2CH_3$ | $—CH_2—HC═CH_2$ | H | H | $—OC(O)CH_3$ | H | $—CH_3$ | H |
| 243 | $—CH(CH_3)_2$ | $—CH(CH_3)_2$ | H | H | $—OC(O)CH_3$ | H | $—CH_3$ | H |
| 244 | $—CH(CH_3)_2$ | $—(CH_2)_3CH_3$ | H | H | $—OC(O)CH_3$ | H | $—CH_3$ | H |
| 245 | $—CH(CH_3)_2$ | $—CH_2—HC═CH_2$ | H | H | $—OC(O)CH_3$ | H | $—CH_3$ | H |
| 246 | $—(CH_2)_3CH_3$ | $—(CH_2)_3CH_3$ | H | H | $—OC(O)CH_3$ | H | $—CH_3$ | H |
| 247 | $—(CH_2)_3CH_3$ | $—CH_2—HC═CH_2$ | H | H | $—OC(O)CH_3$ | H | $—CH_3$ | H |
| 248 | $—CH_2—HC═CH_2$ | $—CH_2—HC═CH_2$ | H | H | $—OC(O)CH_3$ | H | $—CH_3$ | H |
| 249 | $—CH_3$ | $—CH_3$ | H | H | H | F | H | H |
| 250 | $—CH_3$ | $—CH_3$ | H | —OH | H | F | H | H |
| 251 | $—CH_3$ | $—CH_3$ | H | $—OC(O)CH_3$ | H | F | H | H |
| 252 | $—CH_3$ | $—CH_3$ | H | $—OCH_3$ | H | F | H | H |
| 253 | $—CH_3$ | $—CH_2CH_3$ | H | H | H | F | H | H |
| 254 | $—CH_3$ | $—CH_2(CH_3)_2$ | H | H | H | F | H | H |
| 255 | $—CH_3$ | $—CH_3$ | H | F | H | H | H | H |
| 256 | $—CH_3$ | $—CH_3$ | $—CH_3$ | H | H | H | H | H |
| 257 | $—CH_3$ | $—CH_3$ | $—CH_3$ | —OH | H | H | H | H |
| 258 | $—CH_3$ | $—CH_3$ | $—CH_3$ | $—OC(O)CH_3$ | H | H | H | H |
| 259 | $—CH_3$ | $—CH_3$ | $—CH_3$ | $—OCH_3$ | H | H | H | H |
| 260 | $—CH_3$ | $—CH_2CH_3$ | $—CH_3$ | H | H | H | H | H |
| 261 | $—CH_3$ | $—CH_2(CH_3)_2$ | $—CH_3$ | H | H | H | H | H |
| 262 | $—CH_3$ | $—CH_3$ | $—CH_3$ | F | H | H | H | H |
| 263 | $—CH_3$ | $—CH_3$ | $—CH_3$ | H | H | F | H | H |
| 264 | $—CH_3$ | $—CH_3$ | $—CH_3$ | —OH | H | F | H | H |
| 265 | $—CH_3$ | $—CH_3$ | $—CH_3$ | $—OC(O)CH_3$ | H | F | H | H |
| 266 | $—CH_3$ | $—CH_3$ | $—CH_3$ | $—OCH_3$ | H | F | H | H |
| 267 | $—CH_3$ | $—CH_2CH_3$ | $—CH_3$ | H | H | F | H | H |
| 268 | $—CH_3$ | $—CH_2(CH_3)_2$ | $—CH_3$ | H | H | F | H | H |
| 269 | $—CH_3$ | $—CH_3$ | $—CH_3$ | F | H | H | H | H |
| 270 | $—CH_3$ | $—CH_3$ | $—CH_3$ | H | H | F | $—CH_3$ | H |
| 271 | $—CH_3$ | $—CH_3$ | $—CH_3$ | —OH | H | F | $—CH_3$ | H |
| 272 | $—CH_3$ | $—CH_3$ | $—CH_3$ | $—OC(O)CH_3$ | H | F | $—CH_3$ | H |
| 273 | $—CH_3$ | $—CH_3$ | $—CH_3$ | $—OCH_3$ | H | F | $—CH_3$ | H |
| 274 | $—CH_3$ | $—CH_2CH_3$ | $—CH_3$ | H | H | F | $—CH_3$ | H |
| 275 | $—CH_3$ | $—CH_2(CH_3)_2$ | $—CH_3$ | H | H | F | $—CH_3$ | H |
| 276 | $—CH_3$ | $—CH_3$ | $—CH_3$ | F | H | H | $—CH_3$ | H |
| 277 | $—CH_3$ | $—CH_3$ | H | H | —OH | H | H | $—CH_3$ |
| 278 | $—CH_3$ | $—CH_3$ | H | H | $—OC(O)CH_3$ | H | H | $—CH_3$ |
| 279 | $—CH_3$ | $—CH_3$ | H | H | $—OCH_3$ | H | H | $—CH_3$ |
| 280 | $—CH_3$ | $—CH_2CH_3$ | H | H | H | H | H | $—CH_3$ |
| 281 | $—CH_3$ | $—CH_2(CH_3)_2$ | H | H | H | H | H | $—CH_3$ |
| 282 | $—CH_3$ | $—CH_3$ | H | H | F | H | H | $—CH_3$ |
| 283 | $—CH_3$ | $—CH_3$ | $—CH_3$ | H | H | H | H | $—CH_3$ |
| 284 | $—CH_3$ | $—CH_3$ | $—CH_3$ | H | —OH | H | H | $—CH_3$ |
| 285 | $—CH_3$ | $—CH_3$ | $—CH_3$ | H | $—OC(O)CH_3$ | H | H | $—CH_3$ |
| 286 | $—CH_3$ | $—CH_3$ | $—CH_3$ | H | $—OCH_3$ | H | H | $—CH_3$ |
| 287 | $—CH_3$ | $—CH_2CH_3$ | $—CH_3$ | H | H | H | H | $—CH_3$ |
| 288 | $—CH_3$ | $—CH_2(CH_3)_2$ | $—CH_3$ | H | H | H | H | $—CH_3$ |
| 289 | $—CH_3$ | $—CH_3$ | $—CH_3$ | H | F | H | H | $—CH_3$ |
| 290 | $—CH_3$ | $—CH_3$ | H | H | H | F | H | $—CH_3$ |

TABLE 8-continued

| Ref. | X | Y | $R_3$ | $R_4$ | $R_5$ | $R_6$ | $R_7$ | $R_1$ |
|---|---|---|---|---|---|---|---|---|
| 291 | $—CH_3$ | $—CH_3$ | H | H | —OH | F | H | $—CH_3$ |
| 292 | $—CH_3$ | $—CH_3$ | H | H | $—OC(O)CH_3$ | F | H | $—CH_3$ |
| 293 | $—CH_3$ | $—CH_3$ | H | H | $—OCH_3$ | F | H | $—CH_3$ |
| 294 | $—CH_3$ | $—CH_2CH_3$ | H | H | H | F | H | $—CH_3$ |
| 295 | $—CH_3$ | $—CH_2(CH_3)_2$ | H | H | H | F | H | $—CH_3$ |
| 296 | $—CH_3$ | $—CH_3$ | H | H | F | F | H | $—CH_3$ |
| 297 | $—CH_3$ | $—CH_3$ | H | H | H | H | $—CH_3$ | $—CH_3$ |
| 298 | $—CH_3$ | $—CH_3$ | H | H | —OH | H | $—CH_3$ | $—CH_3$ |
| 299 | $—CH_3$ | $—CH_3$ | H | H | $—OC(O)CH_3$ | H | $—CH_3$ | $—CH_3$ |
| 300 | $—CH_3$ | $—CH_3$ | H | H | $—OCH_3$ | H | $—CH_3$ | $—CH_3$ |
| 301 | $—CH_3$ | $—CH_2CH_3$ | H | H | H | H | $—CH_3$ | $—CH_3$ |
| 302 | $—CH_3$ | $—CH_2(CH_3)_2$ | H | H | H | H | $—CH_3$ | $—CH_3$ |
| 303 | $—CH_3$ | $—CH_3$ | H | H | H | F | $—CH_3$ | $—CH_3$ |
| 304 | H | $—CH_3$ | H | H | H | H | H | H |
| 305 | H | $CH_2CH_3$ | H | H | H | H | H | H |
| 306 | H | $—(CH_2)_2CH_3$ | H | H | H | H | H | H |
| 307 | H | $—CH(CH_3)_2$ | H | H | H | H | H | H |
| 308 | H | $—(CH_2)_3CH_3$ | H | H | H | H | H | H |
| 309 | H | $—CH_2—HC{=}CH_2$ | H | H | H | H | H | H |
| 310 | H | $—CH_3$ | $—CH_3$ | H | H | H | H | H |
| 310a | H | $—CH_2CH_3$ | $—CH_3$ | H | H | H | H | H |
| 311 | H | $—(CH_2)_2CH_3$ | $—CH_3$ | H | H | H | H | H |
| 312 | H | $—CH(CH_3)_2$ | $—CH_3$ | H | H | H | H | H |
| 313 | H | $—(CH_2)_3CH_3$ | $—CH_3$ | H | H | H | H | H |
| 314 | H | $—CH_2—HC{=}CH_2$ | $—CH_3$ | H | H | H | H | H |
| 315 | H | $—CH_3$ | H | —OH | H | H | H | H |
| 316 | H | $—CH_2CH_3$ | H | —OH | H | H | H | H |
| 317 | H | $—(CH_2)_2CH_3$ | H | —OH | H | H | H | H |
| 318 | H | $—CH(CH_3)_2$ | H | —OH | H | H | H | H |
| 319 | H | $—(CH_2)_3CH_3$ | H | —OH | H | H | H | H |
| 320 | H | $—CH_2—HC{=}CH_2$ | H | —OH | H | H | H | H |
| 321 | H | $—CH_3$ | H | $—OC(O)CH_3$ | H | H | H | H |
| 322 | H | $—CH_2CH_3$ | H | $—OC(O)CH_3$ | H | H | H | H |
| 324 | H | $—(CH_2)_2CH_3$ | H | $—OC(O)CH_3$ | H | H | H | H |
| 325 | H | $—CH(CH_3)_2$ | H | $—OC(O)CH_3$ | H | H | H | H |
| 326 | H | $—(CH_2)_3CH_3$ | H | $—OC(O)CH_3$ | H | H | H | H |
| 327 | H | $—CH_2—HC{=}CH_2$ | H | $—OC(O)CH_3$ | H | H | H | H |
| 328 | H | $—CH_3$ | H | H | $—OCH_3$ | H | H | H |
| 329 | H | $—CH_2CH_3$ | H | H | $—OCH_3$ | H | H | H |
| 330 | H | $—(CH_2)_2CH_3$ | H | H | $—OCH_3$ | H | H | H |
| 331 | H | $—CH(CH_3)_2$ | H | H | $—OCH_3$ | H | H | H |
| 332 | H | $—(CH_2)_3CH_3$ | H | H | $—OCH_3$ | H | H | H |
| 333 | H | $—CH_2—HC{=}CH_2$ | H | H | $—OCH_3$ | H | H | H |
| 334 | H | $—CH_3$ | H | H | H | F | H | H |
| 335 | H | $—CH_2CH_3$ | H | H | H | F | H | H |
| 336 | H | $—(CH_2)_2CH_3$ | H | H | H | F | H | H |
| 337 | H | $—CH(CH_3)_2$ | H | H | H | F | H | H |
| 338 | H | $—(CH_2)_3CH_3$ | H | H | H | F | H | H |
| 339 | H | $—CH_2—HC{=}CH_2$ | H | H | H | F | H | H |
| 340 | H | $—CH_3$ | $—CH_3$ | —OH | H | H | H | $—CH_2CH_3$ |
| 341 | H | $—CH_2CH_3$ | $—CH_3$ | —OH | H | H | H | $—CH_2CH_3$ |
| 342 | H | $—(CH_2)_2CH_3$ | $—CH_3$ | —OH | H | H | H | $—CH_2CH_3$ |
| 343 | H | $—CH(CH_3)_2$ | $—CH_3$ | —OH | H | H | H | $—CH_2CH_3$ |
| 344 | H | $—(CH_2)_3CH_3$ | $—CH_3$ | —OH | H | H | H | $—CH_2CH_3$ |
| 345 | H | $—CH_2—HC{=}CH_2$ | $—CH_3$ | —OH | H | H | H | $—CH_2CH_3$ |
| 346 | H | $—CH_3$ | $—CH_3$ | $—OC(O)CH_3$ | H | H | H | $—CH_2CH_3$ |
| 347 | H | $—CH_2CH_3$ | $—CH_3$ | $—OC(O)CH_3$ | H | H | H | $—CH_2CH_3$ |
| 348 | H | $—(CH_2)_2CH_3$ | $—CH_3$ | $—OC(O)CH_3$ | H | H | H | $—CH_2CH_3$ |
| 349 | H | $—CH(CH_3)_2$ | $—CH_3$ | $—OC(O)CH_3$ | H | H | H | $—CH_2CH_3$ |
| 350 | H | $—(CH_2)_3CH_3$ | $—CH_3$ | $—OC(O)CH_3$ | H | H | H | $—CH_2CH_3$ |
| 351 | H | $—CH_2—HC{=}CH_2$ | $—CH_3$ | $—OC(O)CH_3$ | H | H | H | $—CH_2CH_3$ |
| 352 | H | $—CH_3$ | $—CH_3$ | H | $—OCH_3$ | H | H | $—CH_2CH_3$ |
| 353 | H | $—CH_2CH_3$ | $—CH_3$ | H | $—OCH_3$ | H | H | $—CH_2CH_3$ |
| 354 | H | $—(CH_2)_2CH_3$ | $—CH_3$ | H | $—OCH_3$ | H | H | $—CH_2CH_3$ |
| 355 | H | $—CH(CH_3)_2$ | $—CH_3$ | H | $—OCH_3$ | H | H | $—CH_2CH_3$ |
| 356 | H | $—(CH_2)_3CH_3$ | $—CH_3$ | H | $—OCH_3$ | H | H | $—CH_2CH_3$ |
| 357 | H | $—CH_2—HC{=}CH_2$ | $—CH_3$ | H | $—OCH_3$ | H | H | $—CH_2CH_3$ |
| 358 | H | $—CH_3$ | $—CH_3$ | H | H | F | H | $—CH_2CH_3$ |
| 359 | H | $—CH_2CH_3$ | $—CH_3$ | H | H | F | H | $—CH_2CH_3$ |
| 360 | H | $—(CH_2)_2CH_3$ | $—CH_3$ | H | H | F | H | $—CH_2CH_3$ |
| 361 | H | $—CH(CH_3)_2$ | $—CH_3$ | H | H | F | H | $—CH_2CH_3$ |
| 362 | H | $—(CH_2)_3CH_3$ | $—CH_3$ | H | H | F | H | $—CH_2CH_3$ |
| 363 | H | $—CH_2—HC{=}CH_2$ | $—CH_3$ | H | H | F | H | $—CH_2CH_3$ |
| 364 | H | cyclopropyl | H | H | H | H | H | H |
| 365 | H | cyclopropyl | $—CH_3$ | H | H | H | H | H |
| 366 | H | cyclopropyl | H | —OH | H | H | H | H |
| 367 | H | cyclopropyl | H | $—OC(O)CH_3$ | H | H | H | H |
| 368 | H | cyclopropyl | H | H | $—OCH_3$ | H | H | H |

TABLE 8-continued

| Ref. | X | Y | $R_3$ | $R_4$ | $R_5$ | $R_6$ | $R_7$ | $R_1$ |
|---|---|---|---|---|---|---|---|---|
| 369 | H | cyclopropyl | H | H | H | F | H | H |
| 370 | H | cyclopropyl | H | H | H | H | H | —$CH_2CH_3$ |
| 371 | H | cyclopropyl | —$CH_3$ | —OH | H | F | H | —$CH_2CH_3$ |
| 372 | H | cyclopropyl | —$CH_3$ | —OH | H | H | H | —$CH_2CH_3$ |
| 373 | H | cyclopropyl | —$CH_3$ | —OC(O)$CH_3$ | H | H | H | —$CH_2CH_3$ |
| 374 | H | cyclopropyl | —$CH_3$ | H | —$OCH_3$ | H | H | —$CH_2CH_3$ |
| 375 | H | cyclopropyl | —$CH_3$ | H | H | F | H | —$CH_2CH_3$ |
| 376 | —$CH_3$ | cyclopropyl | H | H | H | H | H | H |
| 377 | —$CH_3$ | cyclopropyl | —$CH_3$ | H | H | H | H | H |
| 378 | —$CH_3$ | cyclopropyl | H | —OH | H | H | H | H |
| 379 | —$CH_3$ | cyclopropyl | H | —OC(O)$CH_3$ | H | H | H | H |
| 380 | —$CH_3$ | cyclopropyl | H | H | —$OCH_3$ | H | H | H |
| 381 | —$CH_3$ | cyclopropyl | H | H | H | F | H | H |
| 382 | —$CH_3$ | cyclopropyl | H | H | H | H | H | —$CH_2CH_3$ |
| 383 | —$CH_3$ | cyclopropyl | —$CH_3$ | —OH | H | F | H | —$CH_2CH_3$ |
| 384 | —$CH_3$ | cyclopropyl | —$CH_3$ | —OH | H | H | H | —$CH_2CH_3$ |
| 385 | —$CH_3$ | cyclopropyl | —$CH_3$ | —OC(O)$CH_3$ | H | H | H | —$CH_2CH_3$ |
| 386 | —$CH_3$ | cyclopropyl | —$CH_3$ | H | —$OCH_3$ | H | H | —$CH_2CH_3$ |
| 387 | —$CH_3$ | cyclopropyl | —$CH_3$ | H | H | F | H | —$CH_2CH_3$ |
| 388 | —$CH_2CH_3$ | cyclopropyl | H | H | H | H | H | H |
| 389 | —$CH_2CH_3$ | cyclopropyl | —$CH_3$ | H | H | H | H | H |
| 390 | —$CH_2CH_3$ | cyclopropyl | H | —OH | H | H | H | H |
| 391 | —$CH_2CH_3$ | cyclopropyl | H | —OC(O)$CH_3$ | H | H | H | H |
| 392 | —$CH_2CH_3$ | cyclopropyl | H | H | —$OCH_3$ | H | H | H |
| 393 | —$CH_2CH_3$ | cyclopropyl | H | H | H | F | H | H |
| 394 | —$CH_2CH_3$ | cyclopropyl | H | H | H | H | H | —$CH_2CH_3$ |
| 395 | —$CH_2CH_3$ | cyclopropyl | —$CH_3$ | —OH | H | F | H | —$CH_2CH_3$ |
| 396 | —$CH_2CH_3$ | cyclopropyl | —$CH_3$ | —OH | H | H | H | —$CH_2CH_3$ |
| 397 | —$CH_2CH_3$ | cyclopropyl | —$CH_3$ | —OC(O)$CH_3$ | H | H | H | —$CH_2CH_3$ |
| 398 | —$CH_2CH_3$ | cyclopropyl | —$CH_3$ | H | —$OCH_3$ | H | H | —$CH_2CH_3$ |
| 399 | —$CH_2CH_3$ | cyclopropyl | —$CH_3$ | H | H | F | H | —$CH_2CH_3$ |
| 400 | —$(CH_2)_2CH_3$ | cyclopropyl | H | H | H | H | H | H |
| 401 | —$(CH_2)_2CH_3$ | cyclopropyl | —$CH_3$ | H | H | H | H | H |
| 402 | —$(CH_2)_2CH_3$ | cyclopropyl | H | —OH | H | H | H | H |
| 403 | —$(CH_2)_2CH_3$ | cyclopropyl | H | —OC(O)$CH_3$ | H | H | H | H |
| 404 | —$(CH_2)_2CH_3$ | cyclopropyl | H | H | —$OCH_3$ | H | H | H |
| 405 | —$(CH_2)_2CH_3$ | cyclopropyl | H | H | H | F | H | H |
| 406 | —$(CH_2)_2CH_3$ | cyclopropyl | H | H | H | H | H | —$CH_2CH_3$ |
| 407 | —$(CH_2)_2CH_3$ | cyclopropyl | —$CH_3$ | —OH | H | F | H | —$CH_2CH_3$ |
| 408 | —$(CH_2)_2CH_3$ | cyclopropyl | —$CH_3$ | —OH | H | H | H | —$CH_2CH_3$ |
| 409 | —$(CH_2)_2CH_3$ | cyclopropyl | —$CH_3$ | —OC(O)$CH_3$ | H | H | H | —$CH_2CH_3$ |
| 410 | —$(CH_2)_2CH_3$ | cyclopropyl | —$CH_3$ | H | —$OCH_3$ | H | H | —$CH_2CH_3$ |
| 411 | —$(CH_2)_2CH_3$ | cyclopropyl | —$CH_3$ | H | H | F | H | —$CH_2CH_3$ |
| 412 | —$CH_2(CH_3)_2$ | cyclopropyl | H | H | H | H | H | H |
| 413 | —$CH_2(CH_3)_2$ | cyclopropyl | —$CH_3$ | H | H | H | H | H |
| 414 | —$CH_2(CH_3)_2$ | cyclopropyl | H | —OH | H | H | H | H |
| 415 | —$CH_2(CH_3)_2$ | cyclopropyl | H | —OC(O)$CH_3$ | H | H | H | H |
| 416 | —$CH_2(CH_3)_2$ | cyclopropyl | H | H | —$OCH_3$ | H | H | H |
| 417 | —$CH_2(CH_3)_2$ | cyclopropyl | H | H | H | F | H | H |
| 418 | —$CH_2(CH_3)_2$ | cyclopropyl | H | H | H | H | H | —$CH_2CH_3$ |
| 419 | —$CH_2(CH_3)_2$ | cyclopropyl | —$CH_3$ | —OH | H | F | H | —$CH_2CH_3$ |
| 420 | —$CH_2(CH_3)_2$ | cyclopropyl | —$CH_3$ | —OH | H | H | H | —$CH_2CH_3$ |
| 421 | —$CH_2(CH_3)_2$ | cyclopropyl | —$CH_3$ | —OC(O)$CH_3$ | H | H | H | —$CH_2CH_3$ |
| 422 | —$CH_2(CH_3)_2$ | cyclopropyl | —$CH_3$ | H | —$OCH_3$ | H | H | —$CH_2CH_3$ |
| 423 | —$CH_2(CH_3)_2$ | cyclopropyl | —$CH_3$ | H | H | F | H | —$CH_2CH_3$ |
| 424 | cyclopropyl | cyclopropyl | —$CH_3$ | H | H | H | H | H |
| 425 | cyclopropyl | cyclopropyl | H | —OH | H | H | H | H |
| 426 | cyclopropyl | cyclopropyl | H | —OC(O)$CH_3$ | H | H | H | H |
| 427 | cyclopropyl | cyclopropyl | H | H | —$OCH_3$ | H | H | H |
| 428 | cyclopropyl | cyclopropyl | H | H | H | F | H | H |
| 429 | cyclopropyl | cyclopropyl | H | H | H | H | H | H |
| 430 | cyclopropyl | cyclopropyl | —$CH_3$ | —OH | H | F | H | —$CH_2CH_3$ |
| 431 | cyclopropyl | cyclopropyl | —$CH_3$ | —OH | H | H | H | —$CH_2CH_3$ |
| 432 | cyclopropyl | cyclopropyl | —$CH_3$ | —OC(O)$CH_3$ | H | H | H | —$CH_2CH_3$ |
| 433 | cyclopropyl | cyclopropyl | —$CH_3$ | H | —$OCH_3$ | H | H | —$CH_2CH_3$ |
| 434 | cyclopropyl | cyclopropyl | —$CH_3$ | H | H | F | H | —$CH_2CH_3$ |
| 435 | H | —$CH_3$ | H | —OH | H | H | —$CH_3$ | H |
| 436 | H | —$CH_2CH_3$ | H | —OH | H | H | —$CH_3$ | H |
| 437 | H | —$(CH_2)_2CH_3$ | H | —OH | H | H | —$CH_3$ | H |
| 438 | H | —$CH(CH_3)_2$ | H | —OH | H | H | —$CH_3$ | H |
| 439 | H | —$(CH_2)_3CH_3$ | H | —OH | H | H | —$CH_3$ | H |
| 440 | H | —$CH_2$—HC═$CH_2$ | H | —OH | H | H | —$CH_3$ | H |
| 441 | H | —$CH_3$ | H | —OC(O)$CH_3$ | H | H | —$CH_3$ | H |
| 442 | H | —$CH_2CH_3$ | H | —OC(O)$CH_3$ | H | H | —$CH_3$ | H |
| 443 | H | —$(CH_2)_2CH_3$ | H | —OC(O)$CH_3$ | H | H | —$CH_3$ | H |
| 444 | H | —$CH(CH_3)_2$ | H | —OC(O)$CH_3$ | H | H | —$CH_3$ | H |
| 445 | H | —$(CH_2)_3CH_3$ | H | —OC(O)$CH_3$ | H | H | —$CH_3$ | H |
| 446 | H | —$CH_2$—HC═$CH_2$ | H | —OC(O)$CH_3$ | H | H | —$CH_3$ | H |

TABLE 8-continued

| Ref. | X | Y | $R_3$ | $R_4$ | $R_5$ | $R_6$ | $R_7$ | $R_1$ |
|---|---|---|---|---|---|---|---|---|
| 447 | H | $-CH_3$ | H | H | $-OCH_3$ | H | $-CH_3$ | H |
| 448 | H | $-CH_2CH_3$ | H | H | $-OCH_3$ | H | $-CH_3$ | H |
| 449 | H | $-(CH_2)_2CH_3$ | H | H | $-OCH_3$ | H | $-CH_3$ | H |
| 450 | H | $-CH(CH_3)_2$ | H | H | $-OCH_3$ | H | $-CH_3$ | H |
| 451 | H | $-(CH_2)_3CH_3$ | H | H | $-OCH_3$ | H | $-CH_3$ | H |
| 452 | H | $-CH_2-HC{=}CH_2$ | H | H | $-OCH_3$ | H | $-CH_3$ | H |
| 453 | H | $-CH_3$ | H | $-OH$ | H | F | H | H |
| 454 | H | $-CH_2CH_3$ | H | $-OH$ | H | F | H | H |
| 455 | H | $-(CH_2)_2CH_3$ | H | $-OH$ | H | F | H | H |
| 456 | H | $-CH(CH_3)_2$ | H | $-OH$ | H | F | H | H |
| 457 | H | $-(CH_2)_3CH_3$ | H | $-OH$ | H | F | H | H |
| 458 | H | $-CH_2-HC{=}CH_2$ | H | $-OH$ | H | F | H | H |
| 459 | H | $-CH_3$ | H | $-OC(O)CH_3$ | H | F | H | H |
| 460 | H | $-CH_2CH_3$ | H | $-OC(O)CH_3$ | H | F | H | H |
| 461 | H | $-(CH_2)_2CH_3$ | H | $-OC(O)CH_3$ | H | F | H | H |
| 462 | H | $-CH(CH_3)_2$ | H | $-OC(O)CH_3$ | H | F | H | H |
| 463 | H | $-(CH_2)_3CH_3$ | H | $-OC(O)CH_3$ | H | F | H | H |
| 464 | H | $-CH_2-HC{=}CH_2$ | H | $-OC(O)CH_3$ | H | F | H | H |
| 465 | H | $-CH_3$ | H | H | $-OCH_3$ | F | H | H |
| 466 | H | $-CH_2CH_3$ | H | H | $-OCH_3$ | F | H | H |
| 467 | H | $-(CH_2)_2CH_3$ | H | H | $-OCH_3$ | F | H | H |
| 468 | H | $-CH(CH_3)_2$ | H | H | $-OCH_3$ | F | H | H |
| 469 | H | $-(CH_2)_3CH_3$ | H | H | $-OCH_3$ | F | H | H |
| 470 | H | $-CH_2-HC{=}CH_2$ | H | H | $-OCH_3$ | F | H | H |
| 471 | H | $-CD_3$ | H | H | H | H | H | H |
| 472 | H | $-CD_3$ | H | $-OH$ | H | H | H | H |
| 473 | H | $-CD_3$ | H | $-OC(O)CH_3$ | H | H | H | H |
| 474 | H | $-CD_3$ | H | H | $-OMe$ | H | H | H |
| 475 | H | $-CD_3$ | H | H | H | F | H | H |
| 476 | H | $-CD_3$ | H | $-OH$ | H | F | H | H |
| 477 | H | $-CD_3$ | H | $-OC(O)CH_3$ | H | F | H | H |
| 478 | H | $-CD_3$ | H | H | $-OMe$ | F | H | H |
| 479 | H | $-CD_3$ | H | H | H | H | $-CH_3$ | H |
| 480 | H | $-CD_3$ | H | $-OH$ | H | H | $-CH_3$ | H |
| 481 | H | $-CD_3$ | H | $-OC(O)CH_3$ | H | H | $-CH_3$ | H |
| 482 | H | $-CD_3$ | H | H | $-OMe$ | H | $-CH_3$ | H |
| 483 | H | $-CD_3$ | H | H | H | H | H | $-CH_2CH_3$ |
| 484 | H | $-CD_3$ | H | $-OH$ | H | H | H | $-CH_2CH_3$ |
| 485 | H | $-CD_3$ | H | $-OC(O)CH_3$ | H | H | H | $-CH_2CH_3$ |
| 486 | H | $-CD_3$ | H | H | $-OMe$ | H | H | $-CH_2CH_3$ |
| 487 | H | $-CD_2CD_3$ | H | H | H | H | H | H |
| 488 | H | $-CD_2CD_3$ | H | $-OH$ | H | H | H | H |
| 489 | H | $-CD_2CD_3$ | H | $-OC(O)CH_3$ | H | H | H | H |
| 490 | H | $-CD_2CD_3$ | H | H | $-OMe$ | H | H | H |
| 491 | H | $-CD_2CD_3$ | H | H | H | F | H | H |
| 492 | H | $-CD_2CD_3$ | H | $-OH$ | H | F | H | H |
| 493 | H | $-CD_2CD_3$ | H | $-OC(O)CH_3$ | H | F | H | H |
| 494 | H | $-CD_2CD_3$ | H | H | $-OMe$ | F | H | H |
| 495 | H | $-CD_2CD_3$ | H | H | H | H | $-CH_3$ | H |
| 496 | H | $-CD_2CD_3$ | H | $-OH$ | H | H | $-CH_3$ | H |
| 497 | H | $-CD_2CD_3$ | H | $-OC(O)CH_3$ | H | H | $-CH_3$ | H |
| 498 | H | $-CD_2CD_3$ | H | H | $-OMe$ | H | $-CH_3$ | H |
| 499 | H | $-CD_2CD_3$ | H | H | H | H | H | $-CH_2CH_3$ |
| 500 | H | $-CD_2CD_3$ | H | $-OH$ | H | H | H | $-CH_2CH_3$ |
| 501 | H | $-CD_2CD_3$ | H | $-OC(O)CH_3$ | H | H | H | $-CH_2CH_3$ |
| 502 | H | $-CD_2CD_3$ | H | H | $-OMe$ | H | H | $-CH_2CH_3$ |
| 503 | H | $-CH_3$ | H | $-OH$ | H | F | $-CH_3$ | H |
| 504 | H | $-CH_2CH_3$ | H | $-OH$ | H | F | $-CH_3$ | H |
| 505 | H | $-(CH_2)_2CH_3$ | H | $-OH$ | H | F | $-CH_3$ | H |
| 506 | H | $-CH(CH_3)_2$ | H | $-OH$ | H | F | $-CH_3$ | H |
| 507 | H | $-(CH_2)_3CH_3$ | H | $-OH$ | H | F | $-CH_3$ | H |
| 508 | H | $-CH_2-HC{=}CH_2$ | H | $-OH$ | H | F | $-CH_3$ | H |
| 509 | H | $-CH_3$ | H | $-OC(O)CH_3$ | H | F | $-CH_3$ | H |
| 510 | H | $-CH_2CH_3$ | H | $-OC(O)CH_3$ | H | F | $-CH_3$ | H |
| 511 | H | $-(CH_2)_2CH_3$ | H | $-OC(O)CH_3$ | H | F | $-CH_3$ | H |
| 512 | H | $-CH(CH_3)_2$ | H | $-OC(O)CH_3$ | H | F | $-CH_3$ | H |
| 513 | H | $-(CH_2)_3CH_3$ | H | $-OC(O)CH_3$ | H | F | $-CH_3$ | H |
| 514 | H | $-CH_2-HC{=}CH_2$ | H | $-OC(O)CH_3$ | H | F | $-CH_3$ | H |
| 515 | H | $-CH_3$ | H | H | $-OCH_3$ | F | $-CH_3$ | H |
| 516 | H | $-CH_2CH_3$ | H | H | $-OCH_3$ | F | $-CH_3$ | H |
| 517 | H | $-(CH_2)_2CH_3$ | H | H | $-OCH_3$ | F | $-CH_3$ | H |
| 518 | H | $-CH(CH_3)_2$ | H | H | $-OCH_3$ | F | $-CH_3$ | H |
| 519 | H | $-(CH_2)_3CH_3$ | H | H | $-OCH_3$ | F | $-CH_3$ | H |
| 520 | H | $-CH_2-HC{=}CH_2$ | H | H | $-OCH_3$ | F | $-CH_3$ | H |
| 521 | H | $-CH_3$ | D | $-OH$ | H | H | $-CH_3$ | H |
| 522 | H | $-CH_2CH_3$ | D | $-OH$ | H | H | $-CH_3$ | H |
| 523 | H | $-(CH_2)_2CH_3$ | D | $-OH$ | H | H | $-CH_3$ | H |
| 524 | H | $-CH(CH_3)_2$ | D | $-OH$ | H | H | $-CH_3$ | H |

TABLE 8-continued

| Ref. | X | Y | $R_3$ | $R_4$ | $R_5$ | $R_6$ | $R_7$ | $R_1$ |
|---|---|---|---|---|---|---|---|---|
| 525 | H | $—(CH_2)_3CH_3$ | D | —OH | H | H | $—CH_3$ | H |
| 526 | H | $—CH_2—HC{=}CH_2$ | D | —OH | H | H | $—CH_3$ | H |
| 527 | H | $—CH_3$ | D | $—OC(O)CH_3$ | H | H | $—CH_3$ | H |
| 528 | H | $—CH_2CH_3$ | D | $—OC(O)CH_3$ | H | H | $—CH_3$ | H |
| 529 | H | $—(CH_2)_2CH_3$ | D | $—OC(O)CH_3$ | H | H | $—CH_3$ | H |
| 530 | H | $—CH(CH_3)_2$ | D | $—OC(O)CH_3$ | H | H | $—CH_3$ | H |
| 531 | H | $—(CH_2)_3CH_3$ | D | $—OC(O)CH_3$ | H | H | $—CH_3$ | H |
| 532 | H | $—CH_2—HC{=}CH_2$ | D | $—OC(O)CH_3$ | H | H | $—CH_3$ | H |
| 533 | H | $—CH_3$ | D | H | $—OCH_3$ | H | $—CH_3$ | H |
| 534 | H | $—CH_2CH_3$ | D | H | $—OCH_3$ | H | $—CH_3$ | H |
| 535 | H | $—(CH_2)_2CH_3$ | D | H | $—OCH_3$ | H | $—CH_3$ | H |
| 536 | H | $—CH(CH_3)_2$ | D | H | $—OCH_3$ | H | $—CH_3$ | H |
| 537 | H | $—(CH_2)_3CH_3$ | D | H | $—OCH_3$ | H | $—CH_3$ | H |
| 538 | H | $—CH_2—HC{=}CH_2$ | D | H | $—OCH_3$ | H | $—CH_3$ | H |
| 539 | H | $—CH_3$ | D | —OH | H | F | H | H |
| 540 | H | $—CH_2CH_3$ | D | —OH | H | F | H | H |
| 541 | H | $—(CH_2)_2CH_3$ | D | —OH | H | F | H | H |
| 542 | H | $—CH(CH_3)_2$ | D | —OH | H | F | H | H |
| 543 | H | $—(CH_2)_3CH_3$ | D | —OH | H | F | H | H |
| 544 | H | $—CH_2—HC{=}CH_2$ | D | —OH | H | F | H | H |
| 545 | H | $—CH_3$ | D | $—OC(O)CH_3$ | H | F | H | H |
| 546 | H | $—CH_2CH_3$ | D | $—OC(O)CH_3$ | H | F | H | H |
| 547 | H | $—(CH_2)_2CH_3$ | D | $—OC(O)CH_3$ | H | F | H | H |
| 548 | H | $—CH(CH_3)_2$ | D | $—OC(O)CH_3$ | H | F | H | H |
| 549 | H | $—(CH_2)_3CH_3$ | D | $—OC(O)CH_3$ | H | F | H | H |
| 550 | H | $—CH_2—HC{=}CH_2$ | D | $—OC(O)CH_3$ | H | F | H | H |
| 551 | H | $—CH_3$ | D | H | $—OCH_3$ | F | H | H |
| 552 | H | $—CH_2CH_3$ | D | H | $—OCH_3$ | F | H | H |
| 553 | H | $—(CH_2)_2CH_3$ | D | H | $—OCH_3$ | F | H | H |
| 554 | H | $—CH(CH_3)_2$ | D | H | $—OCH_3$ | F | H | H |
| 555 | H | $—(CH_2)_3CH_3$ | D | H | $—OCH_3$ | F | H | H |
| 556 | H | $—CH_2—HC{=}CH_2$ | D | H | $—OCH_3$ | F | H | H |
| 557 | H | $—CH_3$ | D | H | H | H | H | H |
| 558 | H | $—CH_2CH_3$ | D | H | H | H | H | H |
| 559 | H | $—(CH_2)_2CH_3$ | D | H | H | H | H | H |
| 560 | H | $—CH(CH_3)_2$ | D | H | H | H | H | H |
| 561 | H | $—(CH_2)_3CH_3$ | D | H | H | H | H | H |
| 562 | H | $—CH_2—HC{=}CH_2$ | D | H | H | H | H | H |

Compositions and Methods

As used herein, the term "5-HT1A" refers to a 5-HT1A receptor. As used herein, the term "5-HT2A" refers to a 5-HT2A receptor.

As used herein, the term "effective amount" in connection with a compound disclosed herein means an amount capable of treating or preventing a disorder, disease or condition, or symptoms thereof, disclosed herein.

As used herein, the term "hallucination" (and related terms such as "hallucinogenic" and "hallucinogen") refers to a perception in the absence of external stimulus that has qualities of real perception. In some embodiments, hallucinations may be vivid, substantial, and are perceived to be located in external objective space. As used herein, hallucinations may occur in any sensory modality including, but not limited to visual, auditory, olfactory, gustatory, tactile, proprioceptive, equilibrioceptive, nociceptive, thermoceptive and chronoceptive. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

As used herein, the terms "prevent" or "preventing" refers to means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein, the term "treat" or "treating" refers to an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

In further embodiments of the present disclosure, described are novel compounds and compositions, as well as methods of administering the same. In some embodiments, a compound provided herein is for use in the methods provided herein. In some embodiments, the disclosure provides the use of a compound provided herein in the preparation of a medicament for treating one or more of the diseases or disorders provided herein.

In certain embodiments, the method comprises administering a serotonin 5-HT1A agonist and a serotonin 5-HT2A agonist. Without being bound to any particular theory, in certain embodiments it has been surprisingly discovered that administering a serotonin 5-HT1A agonist and a serotonin 5-HT2A agonist can be effective in preventing or treating one or more of the conditions described herein. In certain embodiments, it has also been surprisingly discovered that administering a serotonin 5-HT1A agonist and a hallucinogenic 5-HT2A agonist can effectively treat patients without the patients experiencing the hallucinogenic effects of the 5-HT2A agonist. Without intending to be bound by any particular theory, it is believed that the patient can experience a therapeutic effect without experiencing a hallucinogenic manifestation that typically results from the administration of a 5-HT2A agonist because the 5-HT1A agonist can "turn off" the hallucinogenic effects of the of the 5-HT2A agonist without otherwise significantly altering its agonism at a 5-HT2A receptor. In some embodiments, the 5-HT1A agonist is a partial agonist. In some embodiments, the 5-HT1A agonist is a full agonist. In some embodiments, the 5-HT2A agonist is a partial agonist. In some embodiments, the 5-HT2A agonist is a full agonist. In some embodiments, the 5-HT1A and/or 5-HT2A agonists may be selected from compounds of Formula I herein. In some embodiments, the 5-HT1A and the 5-HT2A agonists are the same compound (e.g., a compound of Formula I).

As defined herein, a "full agonist" shall mean an agonist having an Emax % of at least 90% for the relevant serotonin receptor agonist assay (e.g., BRET2, calcium mobilization, beta-arrestin) when compared to an industry-accepted control compound for that particular receptor assay (e.g., serotonin (5-OH-tryptamine)). In some embodiments, a "full agonist" will exhibit an Emax % of at least 90, at least 91, at least 92, at least 93, at least 94, at least 95, at least 96, at least 97, at least 98, or at least 99%. Also defined herein, a "partial agonist" shall mean an agonist having an Emax % of less than 90% for the relevant serotonin receptor when compared to an industry-accepted control compound for that particular receptor (e.g., serotonin (5-OH-tryptamine)). In some embodiments, a "partial agonist" will exhibit an Emax % of less than 85, 80, 75, 70, 65, 60, 55, 50, 45, 40, 35, 30, 25, 20, 15, 10, or even less than 5%. In some embodiments, a partial agonist will exhibit an Emax % of about 0.1 to about 89.9%, such as about 1 to about 89, about 5 to about 85, about 50 to about 88, about 40 to about 85, about 35 to about 75, about 25 to about 65, or about 20 to about 55%.

In some embodiment, the 5-HT1A agonist as used herein is selected from buspirone (8-[4-(4-pyrimidin-2-ylpiperazin-1-yl)butyl]-8-azaspiro[4.5]decane-7,9-dione), 5-OH-buspirone, 6-OH-buspirone, tandospirone ((1R,2R,6S,7S)-4-{4-[4-(pyrimidin-2-yl)piperazin-1-yl]butyl}-4-azatricyclo [5.2.1.02,6]decane-3,5-dione), gepirone (4,4-dimethyl-1-[4-(4-pyrimidin-2-ylpiperazin-1-yl)butyl]piperid-ine-2,6-dione), alnespirone ((+)-4-dihydro-2H-chromen-3-yl]-propylamino]butyl]-8-azaspiro[4.5]decane-7,9-dione), binospirone (8-[2-(2,3-dihydro-1,4-benzodioxin-2-ylmethylamino)ethyl]-8-azaspiro[4.5]-decane-7,9-dione), ipsapirone (9,9-dioxo-8-[4-(4-pyrimidin-2-ylpiperazin-1-yl) butyl]-9.lamda.6-thia-8-azabicyclo[4.3.0]nona-1,3,5-trien-7-one), perospirone (3aR,7aS)-2-{4-[4-(1,2-benzisothiazol-3-yl)piperazin-1-yl]butyl}hexahydro-1H-isoindole-1,3 (2H)-dione, befiradol (F-13,640) (3-chloro-4-fluorophenyl-[4-fluoro-4-([(5-methylpyridin-2-yl)methylamino]methyl) piperidin-1-yl]methanone, repinotan ((R)-(−)-2-[4-[(chroman-2-ylmethyl)-amino]-butyl]-1,1-dioxo-benzo[d] isothiazolone), piclozotan (3-chloro-4-[4-[4-(2-pyridinyl)-1, 2,3,6-tetrahydropyridin-1-yl]butyl]-1,4-benzoxazepin-5 (4H)-one), osemozotan (5-(3-[((2S)-1,4-benzodioxan-2-ylmethyl)amino]propoxy)-1,3-benzodioxole), flesinoxan (4-fluoro-N-[2-[4-[(3S)-3-(hydroxymethyl)-2,3-dihydro-1, 4-benzodioxin-8-yl]piperazin-1-yl]ethyl]benzamide), flibanserin (1-(2-{4-[3-(trifluoromethyl)phenyl]piperazin-1-yl}ethyl)-1,3-dihydro-2H-benzimidazol-2-one), 8-OH-DPAT (7-(Dipropylamino)-5,6,7,8-tetrahydronaphthalen-1-ol), and sarizotan (EMD-128,130) (1-[(2R)-3,4-dihydro-2H-chromen-2-yl]-N-([5-(4-fluorophenyl)pyridin-3-yl]methyl) methanamine), a compound of Formula I, or a prodrug, salt, or derivative thereof.

In some embodiments, the serotonin 5-HT1A agonist and 5-HT2A agonist are administered at the same time. In some embodiments, the serotonin 5-HT1A agonist and 5-HT2A agonist are administered at different times. In some embodiments, the serotonin 5-HT1A agonist and 5-HT2A agonist are administered sequentially. In some embodiments, the serotonin 5-HT1A agonist is administered first, and 5-HT2A agonist is administered second. In some embodiments, the serotonin 5-HT2A agonist is administered about 30 minutes to about 12 hrs after administration of 5-HT1A agonist, such as about 1 hr to about 6 hrs afterwards. In some embodiments, the serotonin 5-HT1A agonist and 5-HT2A agonist are administered at the same time in the same composition. In some embodiments, 5-HT1A agonist is selected from buspirone, 5-OH-buspirone, 6-OH-buspirone, and 8-OH-DPAT. In some embodiments, the 5-HT1A agonist is buspirone. In some embodiments, the 5-HT1A agonist is selected from compounds of Formula I, such as for example compounds of Formula II. In some embodiments, the 5-HT2A agonist is hallucinogenic. In some embodiments, the 5-HT2A agonist is non-hallucinogenic. In some embodiments, the 5-HT2A agonist is selected from compounds of Formula I, such as for example compounds of Formula II.

In some embodiments, the 5-HT2A agonist and the 5-HT1A agonist may comprise the same compound. In some embodiments, the compounds of Formula I described herein (e.g., compounds of Formula II) can act as both 5-HT1A and 5-HT2A receptor agonists. In some embodiments, the compounds described herein are full agonists for both 5-HT1A and 5-HT2A.

In some embodiments, the 5-HT1A agonist and 5-HT2A agonist are full agonists for a 5-HT1A receptor and a 5-HT2A receptor, respectively. In some embodiments, the 5-HT1A agonist exhibits a higher level of molar potency (i.e., lower $EC_{50}$) for activating a 5-HT1A receptor than the 5-HT2A agonist exhibits for activating the 5-HT2A receptor. Without being bound to any particular scientific theory, in certain embodiments it has been surprisingly discovered that compounds that are agonists for 5-HT1A and 5-HT2A—but which exhibit a higher molar potency for 5-HT1A—may be useful to patients needing/desiring non-hallucinogenic 5-HT2A modulation. In other embodiments, the 5-HT1A agonist is a partial agonist (e.g., buspirone) and 5-HT2A agonist is a full agonist for a 5-HT1A receptor and a 5-HT2A receptors, respectively. In other embodiments, the 5-HT1A agonist is a partial agonist (e.g., buspirone) and 5-HT2A agonist is a partial agonist for a 5-HT1A receptor and a 5-HT2A receptors, respectively.

In certain embodiments are described methods for treating, preventing, ameliorating, or curing a disease or disorder via a non-hallucinogenic therapeutic treatment regimen that includes modulation of a 5-HT1A receptor. In certain embodiments, the method comprises identifying a subject in need of treatment for a disease or condition associated with modulation of a 5-HT1A receptor; selecting a compound of Formula I (e.g., Formula II); and administering the compound to the subject in need of treatment, wherein the compound modulates activity at both a 5-HT1A and 5-HT2A receptor. In certain embodiments, the compound of Formula I is a full agonist of a 5-HT1A receptor. In certain embodiments, the compound of Formula I is a full agonist for both 5-HT1A and 5-HT2A receptors. In certain embodiments, the compound of Formula I is a partial agonist for a 5-HT1A receptor and a full agonist for a 5-HT2A receptor. In certain embodiments, the compound of Formula I is a partial agonist for a 5-HT1A receptor and a partial agonist for a 5-HT2A receptor. In certain embodiments, the compound of Formula I, exhibits a higher molar potency (lower $EC_{50}$) for a 5-HT1A receptor when compared to a 5-HT2A receptor.

In certain embodiments, the 5-HT1A agonist has an $EC_{50}$ for activating a 5-HT1A receptor of less than about 100 nM, such as less than about 75 nm, less than about 50 nm, less than about 25 nm, less than about 15 nm, less than about 10 nm, or less than about 5 nm. In certain embodiments, the 5-HT2A agonist has an has an $EC_{50}$ for activating a 5-HT2A receptor of less than about 100 nM, such as less than about 75 nm, less than about 50 nm, less than about 25 nm, less than about 15 nm, less than about 10 nm, or less than about 5 nm. In certain embodiments, the 5-HT1A agonist has an exhibits an $EC_{50}$ for activating a 5-HT1A receptor of about 0.01 nM to about 100 nM, such as about 0.05 to about 50 nm, about 0.1 to about 25 nM, or about 0.5 to about 10 nM. In certain embodiments, the 5-HT2A agonist has an exhibits an $EC_{50}$ for activating a 5-HT2A receptor of about 0.01 nM to about 100 nM, such as about 0.05 to about 50 nm, about 0.1 to about 25 nM, or about 0.5 to about 10 nM. In certain embodiments, the 5-HT2A agonist has an exhibits an $EC_{50}$ for activating a 5-HT2A receptor of about 5 to about 75 nM, such as about 10 to about 60 nm, about 15 to about 50 nM, or about 20 to about 40 nM. In some embodiments, the 5-HT1A agonist/5-HT2A agonist exhibit 5-HT1A receptor: 5-HT2A receptor $EC_{50}$ ratio range of about 1:2 to about 1:100, such as about 1:5 to about 1:50 or about 1:10 to about 1:40. In some embodiments, one or more of the compounds of Formula I independently exhibit a 5-HT1A receptor: 5-HT2A receptor $EC_{50}$ ratio range of about 1:2 to about 1:100, such as about 1:5 to about 1:50 or about 1:10 to about 1:40. Relevant testing parameters to determine full vs. partial agonism (Emax %) and molar potency ($EC_{50}$) include those known to persons of skill in the art, such as the 5-HT Functional Assays described further below.

In some embodiments, also described are novel compounds and compositions, as well as methods of administering the same. In certain embodiments, the method comprises administering a serotonin 5-HT2A agonist and a serotonin 5-HT2B antagonist. Without being bound to any particular theory, in certain embodiments it has been surprisingly discovered that administering a serotonin 5-HT2A agonist and a serotonin 5-HT2B antagonist can be effective in preventing or treating one or more of the conditions described herein. In some embodiments, it has been surprisingly discovered that administering a serotonin 5-HT2A agonist and a serotonin 5-HT2B antagonist can effectively treat patients while also reducing serotonin 5-HT2B-induced cardiotoxicity (e.g., heart valve fibrosis and hypertrophy). In certain embodiments, it has also been surprisingly discovered that administering a serotonin 5-HT2B antagonist and a 5-HT2A agonist can be safely and effectively used treat patients as described herein without the patients experiencing the hallucinogenic effects that can be associated with hallucinogenic 5-HT2A agonists. In some embodiments, the 5-HT2A agonist is a full agonist. In some embodiments, the 5-HT2A agonist is a partial agonist. In some embodiments, the 5-HT2B antagonist is a full antagonist. In some embodiments, the 5-HT2B antagonist is a partial antagonist.

Exemplary serotonin 5-HT2B receptor antagonists include, but are not limited to, agomelatine, amisulpride, ariprazole, carprazine, clozapine, cyproheptadine, mCCP, sarpogrelate, lisuride, tegasurod, metadoxine, and promethazine. In certain embodiments, the 5-HT2B antagonist is not an antagonist at any of the other serotonin 5-HT type receptor subtypes, such as 5-HT1A and 5-HT2A. In certain embodiments, the 5-HT2B receptor antagonist will also be a full or partial agonist at a 5-HT1A and/or 5-HT2A receptor.

In some embodiments, the serotonin 5-HT2A agonist and 5-HT2B antagonist are administered at the same time. In some embodiments, the serotonin 5-HT2A agonist and 5-HT2B antagonist are administered at different times. In some embodiments, the serotonin 5-HT2A agonist and 5-HT2B antagonist are administered at the same time in the same composition. In some embodiments, the serotonin 5-HT1A agonist and 5-HT2B antagonist are administered sequentially. In some embodiments, the serotonin 5-HT2B antagonist is administered first, and 5-HT2A agonist is administered second. In some embodiments, the serotonin 5-HT2A agonist is administered about 30 minutes to about 12 hrs after administration of 5-HT2B antagonist, such as about 1 hr to about 6 hrs afterwards. In some embodiments, the 5-HT2A agonist is hallucinogenic. In some embodiments, the 5-HT2A agonist is non-hallucinogenic. In some embodiments, the 5-HT2A agonist is selected from compounds of Formula I, such as for example compounds of Formula II.

In certain embodiments for compounds of Formula I, Applicant has discovered that size and nature of alkyl groups for X and/or Y can dramatically affect the metabolism of such compounds. For example, it has been theorized that compounds such as 5-MeO-Dimethyltryptamine (5-MeO-DMT) and Dimethyltryptamine (DMT) are inactive upon oral administration due to rapid metabolism of the methylamino residues by monoamine oxidase (MAO) enzymes. It has also been theorized that the oral stability of psilocin (4-OH-dimethyltryptamine), on the other hand, is due largely to intramolecular coordination (hydrogen bonding) between the 4-OH group and the dimethylamino residue, which effectively shields/inhibits rapid MAO degradation.

Without being bound to any particular scientific theory, Applicant has surprisingly found that substituting the alkyl groups X and/or Y with substituents such as deuterium and fluorine can help inhibit MAO degradation of those groups, even in the absence of a hydrogen bond donor (e.g., —OH) at the 4-position (e.g., $R_4$ in Formula I). In addition, or in the alternative, Applicant has discovered that using non-methyl alkyl groups such as ethyl or n-propyl for X and/or Y (or where $W_3$ is $-(CH_2)_n-$, a, b and c are each hydrogen, and n is 1 or 2 in Formula II) can also slow or inhibit rapid MAO metabolism upon oral administration. This, in turn, permits the preparation of orally available compounds of Formula I that are highly active serotonergic drugs that do not require special formulating procedures (e.g., dosages containing MAO inhibitors), or the presence of hydrogen bond-forming donors at the 4-position that—in some cases—can negatively impact the properties of the underlying compound (e.g., reduction of 5-HT1A and/or 5-HT2A agonism).

In some embodiments, Applicant has also surprisingly discovered that alpha-deuteration of the compounds of Formula I (wherein $R_3$ and/or $R_{3'}$ are deuterium) can dramatically improve the pharmacokinetics of those compounds. Without being bound to any particular scientific theory, it is believed that the heavier deuterium isotope disrupts the enzymatic metabolism of those compounds. However, in some embodiments it may not be desirable to "over deuterate" the compound, such as further including deuterated species for residues for X and Y or deuteration at the beta position (i.e., $W_2$), which can further alter the compounds' pharmacokinetic profiles (e.g., greatly extended half lives) in an undesirable manner. Accordingly, in some embodiments, Applicant has discovered that minimal deuteration may be used to achieve the desired pharmacokinetic outcome. For example, in some embodiments adding a single deuterium atom at the alpha position (i.e., $R_3$ or $R_{3'}$) can greatly enhance the desired pharmacokinetic profile. It is theorized that this may be due, in part, to the creation of a stereocenter at the alpha position upon deuteration that impacts the enzymes' ability to metabolize the compound (e.g., hindrance of MAO degradation and/or the ability of enzymes to oxidize the alpha position during metabolic processes).

In one embodiment, the compounds of Formula I, the methods, and the pharmaceutical compositions described herein are used to modulate the activity of a neurotransmitter receptor by administering a therapeutically effective amount of a compound Formula I. Methods include the administration of a therapeutically effective amount of a compound of Formula I to prevent or treat a psychological disorder such as those discussed herein. Compounds of Formula I may be administered neat or as a pharmaceutical composition comprising a compound of Formula I as discussed below.

In some embodiments, the compounds of Formula I may be used to prevent and/or treat a psychological disorder. The disclosure provides a method for preventing and/or treating a psychological disorder by administering to a subject in need thereof a therapeutically effective amount of a compound of Formula I, including the exemplary embodiments discussed above. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

In some embodiments, the compounds of Formula I may be used to prevent and/or treat a brain disorder. The disclosure provides a method for preventing and/or treating a brain disorder by administering to a subject in need thereof a therapeutically effective amount of a compound of Formula I, including the exemplary embodiments discussed above. The brain disorder may be chosen from Huntington's disease, Alzheimer's disease, dementia, and Parkinson's disease.

In some embodiments, the compounds of Formula I may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a compound of Formula I, including the exemplary embodiments discussed above.

In some embodiments, the compounds of Formula I may be used to prevent and/or treat inflammation and/or pain, such as, for example, inflammation and/or pain associated with inflammatory skeletal or muscular diseases or conditions. Accordingly, the disclosure relates to a method for preventing and/or treating inflammation and/or pain by administering to a subject in need thereof a therapeutically effective amount of a compound of Formula I, including the exemplary embodiments discussed herein. Generally speaking, treatable "pain" includes nociceptive, neuropathic, and mix-type. A method of the disclosure may reduce or alleviate the symptoms associated with inflammation, including, but not limited to, treating localized manifestation of inflammation characterized by acute or chronic swelling, pain, redness, increased temperature, or loss of function in some cases. A method of the disclosure may reduce or alleviate the symptoms of pain regardless of the cause of the pain, including, but not limited to, reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include, but are not limited to, musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

In other embodiments, the methods and compositions disclosed herein comprise regulating the activity of a neurotransmitter receptor with a formulation comprising a compound of Formula I. In one embodiment, the methods and compositions disclosed herein comprise administering a first dosage formulation comprising at least one compound of Formula I and a second active compound. In one embodiment, the methods disclosed herein comprise administering a first dosage formulation comprising a compound of Formula I and a neurotransmitter activity modulator (e.g., a second serotonergic drug). In one embodiment, the methods disclosed herein comprise administering a first dosage formulation comprising at least compound of Formula I and a second dosage form comprising at least one cannabinoid, at least one terpene, or a second serotonergic drug.

The present disclosure relates to compositions comprising, consisting essentially of, or consisting of an effective amount of a compound of Formula I and an excipient. The terms "composition" and "formulation" are used interchangeably herein. Other embodiments relate to pharmaceutical compositions comprising, consisting essentially of, or consisting of a therapeutically effective amount of a compound of Formula I, including those discussed above, and a pharmaceutically acceptable excipient (also known as a pharmaceutically acceptable carrier). As discussed above, a compound of Formula I may be therapeutically useful to prevent and/or treat, for example, psychological disorders, brain disorders, pain and inflammation as well as other disorders such as those discussed above.

In some embodiments, the compositions described herein may comprise at least one compound of Formula I, and a second compound selected from at least one of a second serotonergic drug, a cannabinoid, a terpene, or an MAO inhibitor. In certain embodiments, the second compound may be derived from natural sources, such as fungi (e.g., Psilocybe mushrooms; Lion's Mane mushrooms (containing terpenes such as erinacines and hericenones)) and plants (e.g., *Cannabis*). Accordingly, in certain embodiments the second compound may derived or "extracted" from fungus or plant material, meaning said second compound may or may not be "purified" depending on the manner in which it was sourced and extracted.

Within the context of this disclosure, the term “purified” means separated from other compounds or materials, such as plant or fungal material, e.g., protein, chitin, cellulose, or water. In one embodiment, the term “purified” refers to a compound substantially free of other materials. In one embodiment, the term “purified” refers to a compound that is substantially free from a second compound (e.g. an enantiomeric compound of Formula I exhibiting 99% enantiomeric excess after resolution). In one embodiment, the term “purified” refers to a compound substantially free from a biological material, such as mold, fungus, plant mater, or bacteria.

In one embodiment, the term “purified” refers to a compound or composition that has been crystallized. In one embodiment, the term “purified” refers to a compound or composition that has been chromatographed, for example by gas chromatography, liquid chromatography (e.g., LC, HPLC, etc.), etc. In one embodiment, the term “purified” refers to a compound or composition that has been distilled. In one embodiment, the term “purified” refers to a compound or composition that has been sublimed. In one embodiment, the term “purified” refers to a compound or composition that has been subject to two or more steps chosen from crystallization, chromatography, distillation, or sublimation.

In one embodiment, the term “purified” refers to a compound that has a purity ranging from about 80% to about 100%, meaning that the compound makes up about 80% to about 100% of the total mass of the composition. In one embodiment, the term “purified” refers to a compound that is has a purity ranging from about 90% to about 100%, meaning that the compound makes up about 90% to about 100% of the total mass of the composition. In one embodiment, the term “purified” refers to a compound that has a purity ranging from about 95% to about 100%, meaning that the compound makes up about 95% to about 100% of the total mass of the composition. In one embodiment, the term “purified” refers to a compound that has a purity ranging from about 99% to about 100% pure, meaning that the compound makes up about 99% to about 100% of the total mass of the composition. In one embodiment, the term “purified” refers to a compound that has a purity ranging from about 99.9% to about 100%, meaning that the compound makes up about 99.9% to about 100% of the total mass of the composition.

As used herein, the term “particular ratio” refers to the amount of a compound in relation to the amount of another compound or compounds. In one embodiment, there is about 1:1 ratio of a 4-acetoxy-3-[2-(dimethylamino)ethyl]-benzo[b]thiophene) to 4-hydroxy-N,N-dimethyltryptamine. In one embodiment, a particular ratio of compounds is measured by the same unit, e.g., grams, kilograms, pounds, ounces, etc. In one embodiment, a particular ratio of compounds is measured in moles, i.e., molar proportions or molar ratios.

As used herein, the term “particular amount” refers to the quantity of a compound or compounds. In one embodiment, a particular amount is the combined quantity of two compounds within a sample. In one embodiment, a particular amount is measured by dry weight. In one embodiment, the particular amount has 1, 2, 3, or 4 significant figures.

Disclosed herein are compositions comprising a compound of Formula I and a second compound. In one embodiment, the compositions disclosed herein comprise a molar ratio ranging from about 10:1 to about 1:10 of the compound of Formula I (e.g., a 5-HT2A receptor agonist) to the second compound (e.g., a 5-HT1A receptor agonist). In one embodiment, the compositions disclosed herein comprise a molar ratio ranging from about 100:1 to about 1:100 of the compound of Formula I to the second compound. In one embodiment, the compositions disclosed herein comprise a molar ratio ranging from about 1,000:1 to about 1:1,000 of the compound of Formula I to the second compound. In one embodiment, the compositions disclosed herein comprise a molar ratio ranging from about 10,000:1 to about 1:10,000 of the compound of Formula I to the second compound.

Within the context of this disclosure, unless otherwise specified, the serotonergic compounds (e.g., tryptamine compounds) described herein may be present in their protonated or deprotonated (salt or freebase) forms or mixtures thereof depending on the context, for example, the pH of the solution or composition. However, in certain embodiments, the serotonergic compounds described herein will be lipophilic, meaning they will tend to combine with lipids and fats and can readily pass though biological membranes in the body of an animal or human (e.g., blood brain barrier). In certain embodiments, the serotonergic compound in free base form will be lipophilic.

As used herein, the term “salt” refers to a neutralized ionic compound. In one embodiment, a salt is formed from the neutralization of acids and bases. In one embodiment, a salt is electrically neutral.

In one embodiment, the compositions and methods disclosed herein comprise administering a first cannabinoid. In one embodiment, a first cannabinoid is a first purified cannabinoid.

As used herein, the term “cannabinoid” refers to a compound from a class of molecules commonly found in plants of the genus *Cannabis* and their derivatives. In one embodiment, the cannabinoid is endogenous to an animal, i.e., an endocannabinoid. In one embodiment, the cannabinoid is derived from a plant, e.g., a plant of genus *Cannabis*, e.g., a phytocannabinoid. In one embodiment, the cannabinoid is artificially made in a lab, i.e., a synthetic cannabinoid. Many cannabinoids can be identified by the “cannabi” text in their chemical name. There are at least 113 different cannabinoids isolated from *Cannabis*, exhibiting varied (similar and different) effects.

Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN—C2), Cannabinol-C4 (CBN—C4), Cannabinolic acid (CBNA), Cannabiorcool (CBN—C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (.DELTA.8-THC), Delta-8-tetrahydrocannabinolic acid (.DELTA.8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA- B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol.

In one embodiment, the term “cannabinoid” refers to a compound chosen from THC, THCA, THCV, THCVA, CBC, CBCA, CBCV, CBCVA, CBD, CBDA, CBDV, CBDVA, CBG, CBGA, CBGV, or CBGVA.

Within the context of this disclosure, the term “THC” comprises any derivative of Delta-9-tetrahydrocannabinol and/or salts thereof. In one embodiment, the compositions disclosed herein comprise THC and a compound of Formula I. In one embodiment, the THC is purified THC. In one embodiment, methods disclosed herein comprise administering a composition comprising THC and a compound of Formula I. In one embodiment, the THC is purified THC.

Within the context of this disclosure, the term “THCA” comprises any derivative of tetrahydrocannabinolic acid and/or salts thereof. In one embodiment, the compositions disclosed herein comprise THCA and a compound of Formula I. In one embodiment, the THCA is purified THCA. In one embodiment, the methods disclosed herein comprise administering a composition comprising THCA and a compound of Formula I. In one embodiment, the THCA is purified THCA.

Within the context of this disclosure, the term “THCV” comprises any derivative of Delta-9-tetrahydrocannabivarin and/or salts thereof. In one embodiment, the compositions disclosed herein comprise THCV and a compound of Formula I. In one embodiment, the THCV is purified THCV. In one embodiment, the methods disclosed herein comprise administering a composition comprising THCV and a compound of Formula I. In one embodiment, the THCV is purified THCV.

Within the context of this disclosure, the term “THCVA” comprises any derivative of Delta-9-tetrahydrocannabivarinic acid and/or salts thereof. In one embodiment, the compositions disclosed herein comprise THCVA and a compound of Formula I. In one embodiment, the THCVA is purified THCVA. In one embodiment, the methods disclosed herein comprise administering a composition comprising THCVA and a compound of Formula I. In one embodiment, the THCVA is purified THCVA.

Within the context of this disclosure, the term “CBC” comprises any derivative of Cannabichromene and/or salts thereof. In one embodiment, the compositions disclosed herein comprise CBC and a compound of Formula I. In one embodiment, the CBC is purified CBC. In one embodiment, the methods disclosed herein comprise administering a composition comprising CBC and a compound of Formula I. In one embodiment, the CBS is purified CBC.

Within the context of this disclosure, the term “CBCA” comprises any derivative of Cannabichromenic acid and/or salts thereof. In one embodiment, the compositions disclosed herein comprise CBCA and a compound of Formula I. In one embodiment, the CBCA is purified CBCA. In one embodiment, the methods disclosed herein comprise administering a composition comprising CBCA and a compound of Formula I. In one embodiment, the CBCA is purified CBCA.

Within the context of this disclosure, the term “CBCV” comprises any derivative of Cannabichromevarin and/or salts thereof. In one embodiment, the disclosed herein comprise CBCV and a compound of Formula I. In one embodiment, the CBCV is purified CBCV. In one embodiment, the methods disclosed herein comprise administering a composition comprising CBCV and a compound of Formula I. In one embodiment, the CBCV is purified CBCV.

Within the context of this disclosure, the term “CBCVA” comprises any derivative of Cannabichromevarinic acid and/or salts thereof. In one embodiment, the compositions disclosed herein comprise CBCVA and a compound of Formula I. In one embodiment, the CBCVA is purified CBCVA. In one embodiment, the methods disclosed herein comprise administering a composition comprising CBCVA and a compound of Formula I. In one embodiment, the CBCVA is purified CBCVA.

Within the context of this disclosure, the term “CBD” comprises any derivative of Cannabidiol and/or salt thereof. In one embodiment, the compositions disclosed herein comprise CBD and a compound of Formula I. In one embodiment, the CBD is purified CBD. In one embodiment, the methods disclosed herein comprise administering a composition comprising CBD and a compound of Formula I. In one embodiment, the CBD is purified CBD.

Within the context of this disclosure, the term “CBDA” comprises any derivative of Cannabidiolic acid and/or salts thereof. In one embodiment, the compositions disclosed herein comprise CBDA and a compound of Formula I. In one embodiment, the CBDA is purified CBDA. In one embodiment, the methods disclosed herein comprise administering a composition comprising CBDA and a compound of Formula I. In one embodiment, the CBDA is purified CBDA.

Within the context of this disclosure, the term “CBDV” comprises any derivative of Cannabidivarin and/or salts thereof. In one embodiment, the compositions disclosed herein comprise CBDV and a compound of Formula I. In one embodiment, the CBDV is purified CBDV. In one embodiment, the methods disclosed herein comprise administering a composition comprising CBDV and a compound of Formula I. In one embodiment, the CBDV is purified CBDV.

Within the context of this disclosure, the term “CBDVA” comprises any derivative of Cannabidivarinic acid and/or salts thereof. In one embodiment, the compositions disclosed herein comprise CBDVA and a compound of Formula I. In one embodiment, the CBDVA is purified CBDVA. In one embodiment, the methods disclosed herein comprise administering a composition comprising CBDVA and a compound of Formula I. In one embodiment, the CBDVA is purified CBDVA.

Within the context of this disclosure, the term “CBG” comprises any derivative of Cannabigerol and/or salts thereof. In one embodiment, the compositions disclosed herein comprise CBG and a compound of Formula I. In one embodiment, the CBG is purified CBG. In one embodiment, the methods disclosed herein comprise administering a composition comprising CBG and a compound of Formula I. In one embodiment, the CBG is purified CBG.

Within the context of this disclosure, the term “CBGA” comprises any derivative of Cannabigerolic acid and/or salts thereof. In one embodiment, the compositions disclosed herein comprise CBGA and a compound of Formula I. In one embodiment, the CBGA is purified CBGA. In one embodiment, the methods disclosed herein comprise administering a composition comprising CBGA and a compound of Formula I. In one embodiment, the CBGA is purified CBGA.

Within the context of this disclosure, the term "CBGV" comprises any derivative of Cannabigerovarin and/or salts thereof. In one embodiment, the compositions disclosed herein comprise CBGV and a compound of Formula I. In one embodiment, the CBGV is purified CBGV. In one embodiment, the methods disclosed herein comprise administering a composition comprising CBGV and a compound of Formula I. In one embodiment, the CBGV is purified CBGV.

Within the context of this disclosure, the term "CBGVA" comprises any derivative of Cannabigerovarinic acid and/or salts thereof. In one embodiment, the compositions disclosed herein comprise CBGVA and a compound of Formula I. In one embodiment, the CBGVA is purified CBGVA. In one embodiment, the methods disclosed herein comprise administering a composition comprising CBGVA and a compound of Formula I. In one embodiment, the CBGVA is purified CBGVA.

In one embodiment, the compositions disclosed herein comprise a particular ratio (e.g., a molar ratio) ranging from about 100:1 to about 1:100 of the compound of Formula I and a purified cannabinoid. In one embodiment, the compositions disclosed herein comprise a particular ratio (e.g., a molar ratio) ranging from about 75:1 to about 1:75 of the compound of Formula I and a purified cannabinoid. In one embodiment, the compositions disclosed herein comprise a particular ratio (e.g., a molar ratio) ranging from about 50:1 to about 1:50 of the compound of Formula I and a purified cannabinoid. In one embodiment, the compositions disclosed herein comprise a particular ratio (e.g., a molar ratio) ranging from about 25:1 to about 1:25 of the compound of Formula I and a purified cannabinoid. In one embodiment, the compositions disclosed herein comprise a particular ratio (e.g., a molar ratio) ranging from about 10:1 to about 1:10 of the compound of Formula I and a purified cannabinoid. In one embodiment, the compositions disclosed herein comprise a particular ratio (e.g., a molar ratio) ranging from about 5:1 to about 1:5 of the compound of Formula I and a purified cannabinoid.

In one embodiment, the compositions and methods disclosed herein comprise a compound of Formula I, a first purified cannabinoid, and a second purified cannabinoid. In one embodiment, the second purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

In one embodiment, the compositions disclosed herein comprise a particular ratio (e.g., a molar ratio) ranging from about 100:1 to about 1:100 of the compound of Formula I and the sum of the first purified cannabinoid and the second purified cannabinoid. In one embodiment, the compositions disclosed herein comprise a particular ratio (e.g., a molar ratio) ranging from about 75:1 to about 1:75 of a compound of Formula I and the sum of the first purified cannabinoid and the second purified cannabinoid. In one embodiment, the compositions disclosed herein comprise a particular ratio (e.g., a molar ratio) ranging from about 50:1 to about 1:50 of a compound of Formula I and the sum of the first purified cannabinoid and the second purified cannabinoid.

In one embodiment, the compositions disclosed herein comprise a particular ratio (e.g., a molar ratio) ranging from about 25:1 to about 1:25 of the compound of Formula I and the sum of the first purified cannabinoid and the second purified cannabinoid. In one embodiment, the compositions disclosed herein comprise a particular ratio (e.g., a molar ratio) ranging from about 10:1 to about 1:10 of a compound of Formula I and the sum of the first purified cannabinoid and the second purified cannabinoid. In one embodiment, the compositions disclosed herein comprise a particular ratio (e.g., a molar ratio) ranging from about 5:1 to about 1:5 of a compound of Formula I and the sum of the first purified cannabinoid and the second purified cannabinoid.

In one embodiment, the compositions and methods disclosed herein comprise administering a compound of Formula I and a terpene. In one embodiment, the terpene is a purified terpene.

As used herein, the term "terpene" refers to a compound belonging to a large class of compounds often biosynthesized from 5-carbon isoprene units. In one embodiment, a terpene is isolated from a plant, e.g., conifers, *Cannabis*, basil, etc. In one embodiment, a terpene is produced by an insect, e.g., termites or swallowtail butterflies. In one embodiment, a terpene is a volatile compound. In one embodiment, a terpene produces an odor. In one embodiment, a terpene is a major component of a natural resin, e.g., turpentine produced from resin. In one embodiment, a terpene is derived biosynthetically from units of isoprene, which has the molecular formula $C_5H_8$. In one embodiment, the molecular formula of terpenes are multiples of $(C_5Ha)_n$, where n is the number of linked isoprene units, such as 1 to 5.

Within the context of this disclosure when a terpene is modified chemically, such as by oxidation or rearrangement of the carbon skeleton, the resulting compound is referred to as a "terpenoid." In the relevant arts, terpenoids are sometimes referred to as isoprenoids.

In one embodiment, a terpene is the primary constituent or constituents of an essential oil from a plant and/or flower. Essential oils are used widely as fragrances in perfumery, medicine, and alternative medicines, e.g., aromatherapy.

In one embodiment, a terpene is categorized according to the number of isoprene ($C_5H_8$) units in the compound, for example, a monoterpene ($C_{10}H_{16}$), a sesquiterpene ($C_{15}H_{24}$), a diterpene ($C_{20}H_{32}$), a triterpene ($C_{30}H_{48}$), or a tetraterpene ($C_{40}H_{64}$).

Examples of terpenes within the context of this disclosure include acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, alpha-caryophyllene, beta-caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, beta-myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, and vanillin.

In one embodiment, a purified terpene is chosen from bornyl acetate, alpha-bisabolol, borneol, camphene, camphor, carene, beta-caryophyllene, cedrene, cymene, elemene, eucalyptol, eudesmol, farnesene, fenchol, geraniol, guaiacol, humulene, isoborneol, limonene, linalool, menthol, beta-myrcene, nerolidol, ocimene, phellandrene, phytol, pinene, pulegone, sabinene, terpineol, terpinolene, or valencene.

Within the context of this disclosure, the term "bornyl acetate" comprises any derivative and/or salt thereof, including any isomeric, structural and/or enantiomeric, variations thereof. In one embodiment, the compositions disclosed herein comprise bornyl acetate and a compound of Formula I. In one embodiment, the bornyl acetate is purified bornyl acetate. In one embodiment, the methods disclosed herein comprise administering a composition comprising bornyl acetate and a compound of Formula I. In one embodiment, the bornyl acetate is purified bornyl acetate.

Within the context of this disclosure, the term "alpha-bisabolol" comprises any derivative and/or salt thereof, including any isomeric, structural and/or enantiomeric, variations thereof. In one embodiment, the compositions disclosed herein comprise alpha-bisabolol and a compound of Formula I. In one embodiment, the alpha-bisabolol is purified alpha-bisabolol. In one embodiment, the methods disclosed herein comprise administering a composition comprising alpha-bisabolol and a compound of Formula I. In one embodiment, the alpha-bisabolol is purified alpha-bisabolol.

Within the context of this disclosure, the term "borneol" comprises any derivative and/or salt thereof, including any isomeric, structural, and/or enantiomeric, variations thereof. In one embodiment, the compositions disclosed herein comprise borneol and a compound of Formula I. In one embodiment, the borneol is purified borneol. In one embodiment, the methods disclosed herein comprise administering a composition comprising borneol and a compound of Formula I. In one embodiment, the borneol is purified borneol.

Within the context of this disclosure, the term "camphene" comprises any derivative and/or salt thereof, including any isomeric, structural and/or enantiomeric, variations thereof. In one embodiment, the compositions disclosed herein comprise camphene and a compound of Formula I. In one embodiment, the camphene is purified camphene. In one embodiment, the methods disclosed herein comprise administering a composition comprising camphene and a compound of Formula I. In one embodiment, the camphene is purified camphene.

Within the context of this disclosure, the term "camphor" comprises any derivative and/or salt thereof, including any isomeric, structural and/or enantiomeric, variations thereof. In one embodiment, the compositions disclosed herein comprise camphor and a compound of Formula I. In one embodiment, the camphor is purified camphor. In one embodiment, the methods disclosed herein comprise administering a composition comprising camphor and a compound of Formula I. In one embodiment, the camphor is purified camphor.

Within the context of this disclosure, the term "carene" comprises any derivative and/or salt thereof, including any isomeric, structural, and/or enantiomeric, variations thereof. In one embodiment, the compositions disclosed herein comprise carene and a compound of Formula I. In one embodiment, the carene is purified carene. In one embodiment, the methods disclosed herein comprise administering a composition comprising carene and a compound of Formula I. In one embodiment, the carene is purified carene.

Within the context of this disclosure, the term "beta-caryophyllene" comprises any derivative and/or salt thereof, including any isomeric, structural and/or enantiomeric, variations thereof. In one embodiment, the compositions disclosed herein comprise beta-caryophyllene and a compound of Formula I. In one embodiment, the beta-caryophyllene is purified beta-caryophyllene. In one embodiment, the methods disclosed herein comprise administering a composition comprising beta-caryophyllene and a compound of Formula I. In one embodiment, the beta-caryophyllene is purified beta-caryophyllene.

Within the context of this disclosure, the term "cedrene" comprises any derivative and/or salt thereof, including any isomeric, structural, and/or enantiomeric, variations thereof. In one embodiment, the compositions disclosed herein comprise cedrene and a compound of Formula I. In one embodiment, the cedrene is purified cedrene. In one embodiment, the methods disclosed herein comprise administering a composition comprising cedrene and a compound of Formula I. In one embodiment, the cedrene is purified cedrene.

Within the context of this disclosure, the term "cymene" comprises any derivative and/or salt to thereof, including any isomeric, structural and/or enantiomeric, variations thereof. In one embodiment, the compositions disclosed herein comprise cymene and a compound of Formula I. In one embodiment, the cymene is purified cymene. In one embodiment, the methods disclosed herein comprise administering a composition comprising cymene and a compound of Formula I. In one embodiment, the cymene is purified cymene.

Within the context of this disclosure, the term "elemene" comprises any derivative and/or salt thereof, including any isomeric, structural, and/or enantiomeric, variations thereof. In one embodiment, the compositions disclosed herein comprise elemene and a compound of Formula I. In one embodiment, the elemene is purified elemene. In one embodiment, the methods disclosed herein comprise administering a composition comprising elemene and a compound of Formula I. In one embodiment, the elemene is purified elemene.

Within the context of this disclosure, the term "eucalyptol" comprises any derivative and/or salt thereof, including any isomeric, structural and/or enantiomeric, variations thereof. In one embodiment, the compositions disclosed herein comprise eucalyptol and a compound of Formula I. In one embodiment, the eucalyptol is purified eucalyptol. In one embodiment, the methods disclosed herein comprise administering a composition comprising eucalyptol and a compound of Formula I. In one embodiment, the eucalyptol is purified eucalyptol.

Within the context of this disclosure, the term "eudesmol" comprises any derivative and/or salt thereof, including any isomeric, structural, and/or enantiomeric, variations thereof. In one embodiment, the compositions disclosed herein comprise eudesmol and a compound of Formula I. In one embodiment, the eudesmol is purified eudesmol. In one embodiment, the methods disclosed herein comprise administering a composition comprising eudesmol and a compound of Formula I. In one embodiment, the eudesmol is purified eudesmol.

Within the context of this disclosure, the term "farnesene" comprises any derivative and/or salt thereof, including any isomeric, structural, and/or enantiomeric, variations thereof. In one embodiment, the compositions disclosed herein comprise farnesene and a compound of Formula I. In one embodiment, the farnesene is purified farnesene. In one embodiment, the methods disclosed herein comprise administering a composition comprising farnesene and a compound of Formula I. In one embodiment, the farnesene is purified farnesene.

Within the context of this disclosure, the term "fenchol" comprises any derivative and/or salt thereof, including any isomeric, structural, and/or enantiomeric, variations thereof. In one embodiment, the compositions disclosed herein comprise fenchol and a compound of Formula I. In one embodiment, the fenchol is purified fenchol. In one embodiment, the methods disclosed herein comprise administering a composition comprising fenchol and a compound of Formula I. In one embodiment, the fenchol is purified fenchol.

Within the context of this disclosure, the term "geraniol" comprises any derivative and/or salt thereof, including any isomeric, structural and/or enantiomeric, variations thereof. In one embodiment, the compositions disclosed herein comprise geraniol and a compound of Formula I. In one embodiment, the geraniol is purified geraniol. In one embodiment, the methods disclosed herein comprise administering a composition comprising geraniol and a compound of Formula I. In one embodiment, the geraniol is purified geraniol.

Within the context of this disclosure, the term "guaiacol" comprises any derivative and/or salt thereof, including any isomeric, structural, and/or enantiomeric, variations thereof. In one embodiment, the compositions disclosed herein comprise guaiacol and a compound of Formula I. In one embodiment, the guaiacol is purified guaiacol. In one embodiment, the methods disclosed herein comprise administering a composition comprising guaiacol and a compound of Formula I. In one embodiment, the guaiacol is purified guaiacol.

Within the context of this disclosure, the term "humulene" comprises any derivative and/or salt thereof, including any isomeric, structural, and/or enantiomeric, variations thereof. In one embodiment, the compositions disclosed herein comprise humulene and a compound of Formula I. In one embodiment, the humulene is purified humulene. In one embodiment, the methods disclosed herein comprise administering a composition comprising humulene and a compound of Formula I. In one embodiment, the humulene is purified humulene.

Within the context of this disclosure, the term "isoborneol" comprises any derivative and/or salt thereof, including any isomeric, structural, and/or enantiomeric, variations thereof. In one embodiment, the compositions disclosed herein comprise isoborneol and a compound of Formula I. In one embodiment, the isoborneol is purified isoborneol. In one embodiment, the methods disclosed herein comprise administering a composition comprising isoborneol and a compound of Formula I. In one embodiment, the isoborneol purified isoborneol.

Within the context of this disclosure, the term "limonene" comprises any derivative and/or salt thereof, including any isomeric, structural and/or enantiomeric, variations thereof. In one embodiment, the compositions disclosed herein comprise limonene and a compound of Formula I. In one embodiment, the limonene is purified limonene. In one embodiment, the methods disclosed herein comprise administering a composition comprising limonene and a compound of Formula I. In one embodiment, the limonene is purified limonene.

Within the context of this disclosure, the term "linalool" comprises any derivative and/or salt thereof, including any isomeric, structural and/or enantiomeric, variations thereof. In one embodiment, the compositions disclosed herein comprise linalool and a compound of Formula I. In one embodiment, the linalool is purified linalool. In one embodiment, the methods disclosed herein comprise administering a composition comprising linalool and a compound of Formula I. In one embodiment, the linalool is purified linalool.

Within the context of this disclosure, the term "menthol" comprises any derivative and/or salt thereof, including any isomeric, structural and/or enantiomeric, variations thereof. In one embodiment, the compositions disclosed herein comprise menthol and a compound of Formula I. In one embodiment, the menthol is purified menthol. In one embodiment, the methods disclosed herein comprise administering a composition comprising menthol and a compound of Formula I. In one embodiment, the menthol is purified menthol.

Within the context of this disclosure, the term "beta-myrcene" comprises any derivative and/or salt thereof, including any isomeric, structural and/or enantiomeric, variations thereof. In one embodiment, the compositions disclosed herein comprise beta-myrcene and a compound of Formula I. In one embodiment, the beta-myrcene is purified beta-myrcene. In one embodiment, the methods disclosed herein comprise administering a composition comprising beta-myrcene and a compound of Formula I. In one embodiment, the beta-myrcene is purified beta-myrcene.

Within the context of this disclosure, the term "nerolidol" comprises any derivative and/or salt thereof, including any isomeric, structural, and/or enantiomeric, variations thereof. In one embodiment, the compositions disclosed herein comprise nerolidol and a compound of Formula I. In one embodiment, the nerolidol is purified nerolidol. In one embodiment, the methods disclosed herein comprise administering a composition comprising nerolidol and a compound of Formula I. In one embodiment, the nerolidol is purified nerolidol.

Within the context of this disclosure, the term "ocimene" comprises any derivative and/or salt thereof, including any isomeric, structural, and/or enantiomeric, variations thereof. In one embodiment, the compositions disclosed herein comprise ocimene and a compound of Formula I. In one embodiment, the ocimene is purified ocimene. In one embodiment, the methods disclosed herein comprise administering a composition comprising ocimene and a compound of Formula I. In one embodiment, the ocimene is purified ocimene.

Within the context of this disclosure, the term "phellandrene" comprises any derivative and/or salt thereof, including any isomeric, structural, and/or enantiomeric, variations thereof. In one embodiment, the compositions disclosed herein comprise phellandrene and a compound of Formula I. In one embodiment, the phellandrene is purified phellandrene. In one embodiment, the methods disclosed herein comprise administering a composition comprising phellandrene and a compound of Formula I. In one embodiment, the phellandrene is purified phellandrene.

Within the context of this disclosure, the term "phytol" comprises any derivative and/or salt thereof, including any isomeric, structural and/or enantiomeric, variations thereof. In one embodiment, the compositions disclosed herein comprise phytol and a compound of Formula I. In one embodiment, the phytol is purified phytol. In one embodiment, the methods disclosed herein comprise administering a composition comprising phytol and a compound of Formula I. In one embodiment, the phytol is purified phytol.

Within the context of this disclosure, the term "pinene" comprises any derivative and/or salt thereof, including any isomeric, structural, and/or enantiomeric, variations thereof. In one embodiment, the compositions disclosed herein comprise pinene and a compound of Formula I. In one embodiment, the pinene is purified pinene. In one embodiment, the methods disclosed herein comprise administering a composition comprising pinene and a compound of Formula I. In one embodiment, the pinene is purified pinene.

Within the context of this disclosure, the term "pulegone" comprises any derivative and/or salt thereof, including any isomeric, structural, and/or enantiomeric, variations thereof. In one embodiment, the compositions disclosed herein comprise pulegone and a compound of Formula I. In one embodiment, the pulegone is purified pulegone. In one embodiment, the methods disclosed herein comprise administering a composition comprising pulegone and a compound of Formula I. In one embodiment, the pulegone is purified pulegone.

Within the context of this disclosure, the term "sabinene" comprises any derivative and/or salt thereof, including any isomeric, structural, and/or enantiomeric, variations thereof. In one embodiment, the compositions disclosed herein comprise sabinene and a compound of Formula I. In one embodiment, the sabinene is purified sabinene. In one embodiment, the methods disclosed herein comprise administering a composition comprising sabinene and a compound of Formula I. In one embodiment, the sabinene is purified sabinene.

Within the context of this disclosure, the term "terpineol" comprises any derivative and/or salt thereof, including any isomeric, structural, and/or enantiomeric, variations thereof. In one embodiment, the compositions disclosed herein comprise terpineol and a compound of Formula I. In one embodiment, the terpineol is purified terpineol. In one embodiment, the methods disclosed herein comprise administering a composition comprising terpineol and a compound of Formula I. In one embodiment, the terpineol is purified terpineol.

Within the context of this disclosure, the term "terpinolene" comprises any derivative and/or salt thereof, including any isomeric, structural, and/or enantiomeric, variations thereof. In one embodiment, the compositions disclosed herein comprise terpinolene and a compound of Formula I. In one embodiment, the terpinolene is purified terpinolene. In one embodiment, the methods disclosed herein comprise administering a composition comprising terpinolene and a compound of Formula I. In one embodiment, the terpinolene is purified terpinolene.

Within the context of this disclosure, the term "valencene" comprises any derivative and/or salt thereof, including any isomeric, structural, and/or enantiomeric, variations thereof. In one embodiment, the compositions disclosed herein comprise valencene and a compound of Formula I. In one embodiment, the valencene is purified valencene. In one embodiment, the methods disclosed herein comprise administering a composition comprising valencene and a compound of Formula I. In one embodiment, the valencene is purified valencene.

In one embodiment, the compositions and methods disclosed herein include one or more erinacine molecules, which are optionally purified. In one embodiment, the compositions and methods disclosed herein comprise erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K. In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S. In one embodiment, the erinacine molecule is a purified erinacine molecule. In one embodiment, the compositions and methods disclosed herein comprise one or more purified erinacine molecules and purified pyridine-3-carboxylic acid. In one embodiment, the compositions and methods disclosed herein comprise one or more purified erinacine molecules and a purified cannabinoid, such as CBD.

Within the context of this disclosure, the term "erinacine A" comprises any derivative and/or salt thereof, including any isomeric, structural and/or enantiomeric, variations thereof. In one embodiment, the compositions and methods disclosed herein comprise administering a formulation of erinacine A and a compound of Formula I. In one embodiment, the compositions and methods disclosed herein comprise administering a formulation of purified erinacine A and a compound of Formula I.

Within the context of this disclosure, the term "erinacine B" comprises any derivative and/or salt thereof, including any isomeric, structural and/or enantiomeric, variations thereof. In one embodiment, the compositions and methods disclosed herein comprise administering a formulation of erinacine B and a compound of Formula I. In one embodiment, the compositions and methods disclosed herein comprise administering a formulation of purified erinacine B and a compound of Formula I.

Within the context of this disclosure, the term "erinacine C" comprises any derivative and/or salt thereof, including any isomeric, structural and/or enantiomeric, variations thereof. In one embodiment, the compositions and methods disclosed herein comprise administering a formulation of erinacine C and a compound of Formula I. In one embodiment, the compositions and methods disclosed herein comprise administering a formulation of purified erinacine C and a compound of Formula I.

Within the context of this disclosure, the term "erinacine D" comprises any derivative and/or salt thereof, including any isomeric, structural and/or enantiomeric, variations thereof. In one embodiment, the compositions and methods disclosed herein comprise administering a formulation of erinacine D and a compound of Formula I. In one embodiment, the compositions and methods disclosed herein comprise administering a formulation of purified erinacine D a compound of Formula I.

Within the context of this disclosure, the term "erinacine E" comprises any derivative and/or salt thereof, including any isomeric, structural and/or enantiomeric, variations thereof. In one embodiment, the compositions and methods disclosed herein comprise administering a formulation of erinacine E and a compound of Formula I. In one embodiment, the compositions and methods disclosed herein comprise administering a formulation of purified erinacine E and a compound of Formula I.

Within the context of this disclosure, the term "erinacine F" comprises any derivative and/or salt thereof, including any isomeric, structural and/or enantiomeric, variations thereof. In one embodiment, the compositions and methods disclosed herein comprise administering a formulation of erinacine F and a compound of Formula I. In one embodiment, the compositions and methods disclosed herein comprise administering a formulation of purified erinacine F and a compound of Formula I.

Within the context of this disclosure, the term "erinacine G" comprises any derivative and/or salt thereof, including any isomeric, structural and/or enantiomeric, variations thereof. In one embodiment, the compositions and methods disclosed herein comprise administering a formulation of erinacine G and a compound of Formula I. In one embodiment, the compositions and methods disclosed herein comprise administering a formulation of purified erinacine G and a compound of Formula I.

Within the context of this disclosure, the term "erinacine H" comprises any derivative and/or salt thereof, including any isomeric, structural and/or enantiomeric, variations thereof. In one embodiment, the compositions and methods disclosed herein comprise administering a formulation of erinacine H and a compound of Formula I. In one embodiment, the compositions and methods disclosed herein comprise administering a formulation of purified erinacine H and a compound of Formula I.

Within the context of this disclosure, the term "erinacine I" comprises any derivative and/or salt thereof, including any isomeric, structural and/or enantiomeric, variations thereof. In one embodiment, the compositions and methods disclosed herein comprise administering a formulation of erinacine I and a compound of Formula I. In one embodiment, the compositions and methods disclosed herein comprise administering a formulation of purified erinacine I and a compound of Formula I.

Within the context of this disclosure, the term "erinacine J" comprises any derivative and/or salt thereof, including any isomeric, structural and/or enantiomeric, variations thereof. In one embodiment, the compositions and methods disclosed herein comprise administering a formulation of erinacine J and a compound of Formula I. In one embodiment, the compositions and methods disclosed herein comprise administering a formulation of purified erinacine J and a compound of Formula I.

Within the context of this disclosure, the term "erinacine K" comprises any derivative and/or salt thereof, including any isomeric, structural and/or enantiomeric, variations thereof. In one embodiment, the compositions and methods disclosed herein comprise administering a formulation of erinacine K and a compound of Formula I. In one embodiment, the compositions and methods disclosed herein comprise administering a formulation of purified erinacine K and a compound of Formula I.

Within the context of this disclosure, the term "erinacine P" comprises any derivative and/or salt thereof, including any isomeric, structural and/or enantiomeric, variations thereof. In one embodiment, the compositions and methods disclosed herein comprise administering a formulation of erinacine P and a compound of Formula I. In one embodiment, the compositions and methods disclosed herein comprise administering a formulation of purified erinacine P and a compound of Formula I.

Within the context of this disclosure, the term "erinacine Q" comprises any derivative and/or salt thereof, including any isomeric, structural and/or enantiomeric, variations thereof. In one embodiment, the compositions and methods disclosed herein comprise administering a formulation of erinacine Q and a compound of Formula I. In one embodiment, the compositions and methods disclosed herein comprise administering a formulation of purified erinacine Q and a compound of Formula I.

Within the context of this disclosure, the term "erinacine R" comprises any derivative and/or salt thereof, including any isomeric, structural and/or enantiomeric, variations thereof. In one embodiment, the compositions and methods disclosed herein comprise administering a formulation of erinacine R and a compound of Formula I. In one embodiment, the compositions and methods disclosed herein comprise administering a formulation of purified erinacine R and a compound of Formula I.

Within the context of this disclosure, the term "erinacine S" comprises any derivative and/or salt thereof, including any isomeric, structural and/or enantiomeric, variations thereof. In one embodiment, the compositions and methods disclosed herein comprise administering a formulation of erinacine S and a compound of Formula I. In one embodiment, the compositions and methods disclosed herein comprise administering a formulation of purified erinacine S and a compound of Formula I.

The erinacine chemical structures are taken from Li I-C, Lee L-Y, Tzeng T W, et al. Neurohealth properties of Hericium *erinaceus* mycelia enriched with erinacines. In: *Behavioural Neurology.* 2018. doi:10.1155/2018/5802634

In one embodiment, the compositions and methods disclosed herein include one or more hericenone molecules, optionally purified. In one embodiment, the compositions and methods disclosed herein comprise hericenone A. In one embodiment, the compositions and methods disclosed herein comprise hericenone B. In one embodiment, the compositions and methods disclosed herein comprise hericenone C. In one embodiment, the compositions and methods disclosed herein comprise hericenone D. In one embodiment, the compositions and methods disclosed herein comprise hericenone E. In one embodiment, the compositions and methods disclosed herein comprise hericenone F. In one embodiment, the compositions and methods disclosed herein comprise hericenone G. In one embodiment, the compositions and methods disclosed herein comprise purified hericenone H.

Within the context of this disclosure, the term "hericenone A" comprises any derivative and/or salt thereof, including any isomeric, structural and/or enantiomeric, variations thereof. In one embodiment, the compositions and methods disclosed herein comprise administering a formulation of hericenone A and a compound of Formula I. In one embodiment, the compositions and methods disclosed herein comprise administering a formulation of purified hericenone A and a compound of Formula I.

Within the context of this disclosure, the term "hericenone B" comprises any derivative and/or salt thereof, including any isomeric, structural and/or enantiomeric, variations thereof. In one embodiment, the compositions and methods disclosed herein comprise administering a formulation of hericenone B and a compound of Formula I. In one embodiment, the compositions and methods disclosed herein comprise administering a formulation of purified hericenone B and a compound of Formula I.

Within the context of this disclosure, the term "hericenone C" comprises any derivative and/or salt thereof, including any isomeric, structural and/or enantiomeric, variations thereof. In one embodiment, the compositions and methods disclosed herein comprise administering a formulation of hericenone C and a compound of Formula I. In one embodiment, the compositions and methods disclosed herein comprise administering a formulation of purified hericenone C and a compound of Formula I.

Within the context of this disclosure, the term "hericenone D" comprises any derivative and/or salt thereof, including any isomeric, structural and/or enantiomeric, variations thereof. In one embodiment, the compositions and methods disclosed herein comprise administering a formulation of hericenone D and a compound of Formula I. In one embodiment, the compositions and methods disclosed herein comprise administering a formulation of purified hericenone D a compound of Formula I.

Within the context of this disclosure, the term "hericenone E" comprises any derivative and/or salt thereof, including any isomeric, structural and/or enantiomeric, variations thereof. In one embodiment, the compositions and methods disclosed herein comprise administering a formulation of hericenone E and a compound of Formula I. In one embodiment, the compositions and methods disclosed herein comprise administering a formulation of purified hericenone E and a compound of Formula I.

Within the context of this disclosure, the term "hericenone F" comprises any derivative and/or salt thereof, including any isomeric, structural and/or enantiomeric, variations thereof. In one embodiment, the compositions and methods disclosed herein comprise administering a formulation of hericenone F and a compound of Formula I. In one embodiment, the compositions and methods disclosed herein comprise administering a formulation of purified hericenone F and a compound of Formula I.

Within the context of this disclosure, the term "hericenone G" comprises any derivative and/or salt thereof, including any isomeric, structural and/or enantiomeric, variations thereof. In one embodiment, the compositions and methods disclosed herein comprise administering a formulation of hericenone G and a compound of Formula I. In one embodiment, the compositions and methods disclosed herein comprise administering a formulation of purified hericenone G and a compound of Formula I.

Within the context of this disclosure, the term "hericenone H" comprises any derivative and/or salt thereof, including any isomeric, structural and/or enantiomeric, variations thereof. In one embodiment, the compositions and methods disclosed herein comprise administering a formulation of hericenone H and a compound of Formula I. In one embodiment, the compositions and methods disclosed herein comprise administering a formulation of purified hericenone H and a compound of Formula I.

In one embodiment, the compositions and methods disclosed herein comprise one or more purified hericenone molecules and purified pyridine-3-carboxylic acid. In one embodiment, the compositions and methods disclosed herein comprise one or more purified hericenone molecules and a purified cannabinoid, such as CBD.

Within the context of this disclosure, the term "pyridine-3-carboxylic acid" comprises any derivative and/or salt thereof, including any isomeric, structural and/or enantiomeric, variations thereof. In one embodiment, the compositions and methods disclosed herein comprise administering a formulation of pyridine-3-carboxylic acid and a compound of Formula I. In one embodiment, the compositions and methods disclosed herein comprise administering a formulation of purified pyridine-3-carboxylic acid and a compound of Formula I.

In one embodiment, the compositions and methods disclosed herein include one or more purified hericenone molecules and one or more purified erinacine molecules.

In one embodiment, the compositions and methods disclosed herein include one or more purified serotonergic derivatives, one or more purified hericenone molecules and one or more purified erinacine molecules.

In one embodiment, the compositions and methods disclosed herein include one or more purified serotonergic derivatives, one or more purified hericenone molecules, one or more purified erinacine molecules and one or more purified cannabinoids.

In one embodiment, the compositions and methods disclosed herein include one or more purified serotonergic derivatives, one or more purified hericenone molecules, one or more purified erinacine molecules and purified pyridine-3-carboxylic acid.

In one embodiment, the compositions and methods disclosed herein include one or more compounds of Formula I and one or more purified molecules attained by extracting and subsequently purifying one or more compounds from an organism chosen from Bacopa monnieri (for example, the purified molecule bacoside A3), *Centella asiatica* (for example, the purified molecule asiaticoside), *Gingko biloba* (for example, the purified molecule myricetin), *Zingiber officinale* (for example, the purified molecule zingerone), *Ocimum sanctum* (for example, the purified molecule linalool), *Polygonum cuspidatum* (for example, the purified molecule resveratrol), *Origanum vulgare* (for example, the purified molecule carvacrol), *Origanum onites* (for example, the purified molecule thymol), *Rosmarinus officinalis* (for example, the purified molecule rosmarinic acid), *Rosmarinus eriocalyx* (for example, the purified molecule camphor), *Curcuma longa* (for example, the purified molecule curcumin), *Camellia sinensis* (for example, the purified molecule theobromine), *Lavandula spica* (for example, the purified molecule caryophyllene), *Scutellaria lateriflora* (for example, the purified molecule baicalin), *Avena sativa* (for example, the purified molecule avenalin), *Avena byzantina* (for example, the purified molecule beta-glucan), *Salvia divinorum* (for example, the purified molecule salvinorin A), *Banisteriopsis caapi* (for example, the purified molecule harmine), *Psychotria* species (for example, the purified molecule dimethyltryptamine), *Tabernanthe iboga* (for example, the purified molecule ibogaine), *Voacanga africana* (for example, the purified molecule voacangine), *Tabernaemontana undulata* (for example, the purified molecule ibogamine), *Lophophora williamsii* (for example, the purified molecule mescaline), *Ipomoea tricolor* (for example, the purified molecule ergonovine), and/or Argyreia nervosa (for example, the purified molecule ergine).

In one embodiment, the compositions disclosed herein comprise a particular ratio (e.g., a molar ratio) ranging from about 100:1 to about 1:100 of the compound of Formula I derivative and a purified terpene.

In one embodiment, the compositions disclosed herein comprise a particular ratio (e.g., a molar ratio) ranging from about 75:1 to about 1:75 of the compound of Formula I and a purified terpene.

In one embodiment, the compositions disclosed herein comprise a particular ratio (e.g., a molar ratio) ranging from about 50:1 to about 1:50 of the compound of Formula I and a purified terpene.

In one embodiment, the compositions disclosed herein comprise a particular ratio (e.g., a molar ratio) ranging from about 25:1 to about 1:25 of the compound of Formula I and a purified terpene.

In one embodiment, the compositions disclosed herein comprise a particular ratio (e.g., a molar ratio) ranging from about 10:1 to about 1:10 of the compound of Formula I and a purified terpene.

In one embodiment, the compositions disclosed herein comprise a particular ratio (e.g., a molar ratio) ranging from about 5:1 to about 1:5 of the compound of Formula I and a purified terpene.

In one embodiment, the compositions and methods disclosed herein comprise a compound of Formula I, a purified cannabinoid, and a purified terpene.

In one embodiment, the compositions disclosed herein comprise a particular ratio (e.g., a molar ratio) ranging from about 100:1 to about 1:100 of the compound of Formula I and a purified cannabinoid and a particular ratio (e.g., a molar ratio) ranging from about 100:1 to about 1:100 of the compound of Formula I and a purified terpene.

In one embodiment, the compositions disclosed herein comprise a particular ratio (e.g., a molar ratio) ranging from about 75:1 to about 1:75 of compound of Formula I and a purified cannabinoid and a particular ratio (e.g., a molar ratio) ranging from about 75:1 to about 1:75 of the compound of Formula I and a purified terpene.

In one embodiment, the compositions disclosed herein comprise a particular ratio (e.g., a molar ratio) ranging from about 50:1 to about 1:50 of the compound of Formula I and a purified cannabinoid and a particular ratio (e.g., a molar ratio) ranging from about 50:1 to about 1:50 of the compound of Formula I and a purified terpene.

In one embodiment, the compositions disclosed herein comprise a particular ratio (e.g., a molar ratio) ranging from about 25:1 to about 1:25 of the compound of Formula I and a purified cannabinoid and a particular ratio (e.g., a molar ratio) ranging from about 25:1 to about 1:25 of the compound of Formula I and a purified terpene.

In one embodiment, the compositions disclosed herein comprise a particular ratio (e.g., a molar ratio) ranging from about 10:1 to about 1:10 of compound of Formula I and a purified cannabinoid and a particular ratio (e.g., a molar ratio) ranging from about 10:1 to about 1:10 of the compound of Formula I and a purified terpene.

In one embodiment, the compositions disclosed herein comprise a particular ratio (e.g., a molar ratio) ranging from about 5:1 to about 1:5 of the compound of Formula I and a purified cannabinoid and a particular ratio (e.g., a molar ratio) ranging from about 5:1 to about 1:5 of the compound of Formula I and a purified terpene.

In one embodiment, a purified terpene modulates the activity of a neurotransmitter activity modulator, e.g., a compound of Formula I, a serotonergic drug, an adrenergic drug, a dopaminergic drug, a psilocybin derivative, etc.

As used herein, the term "serotonergic drug" refers to a compound that binds to, blocks, or otherwise influences (e.g., via an allosteric reaction) activity at a serotonin receptor. In one embodiment, a serotonergic drug binds to a serotonin receptor. In one embodiment, a serotonergic drug indirectly affects a serotonin receptor, e.g., via interactions affecting the reactivity of other molecules at the serotonin receptor. In one embodiment, a serotonergic drug is an agonist, e.g., a compound activating a serotonin receptor. In one embodiment, a serotonergic drug is an antagonist, e.g., a compound binding but not activating a serotonin receptor, e.g., blocking a receptor. In one embodiment, a serotonergic drug is an effector molecule, e.g., a compound binding to an enzyme for allosteric regulation. In one embodiment, a serotonergic drug acts (either directly or indirectly) at more than one type of receptor (e.g., SHT, dopamine, adrenergic, acetylcholine, etc.).

In one embodiment, a serotonergic drug is an antidepressant.

In one embodiment, a serotonergic drug is an anxiolytic.

In one embodiment, a serotonergic drug is a selective serotonin reuptake inhibitor.

In one embodiment, a serotonergic drug is a selective serotonin norepinephrine reuptake inhibitor.

In some embodiments, the compounds of Formula I are serotonergic drugs. In some embodiments, at least one compound of Formula I is administered with a second serotonergic drug, such as one of the serotonergic drugs identified below.

Some exemplary serotonergic drugs include the following molecules: 4-hydroxy-N-methyltryptamine (aka 3[2-(methylamino)ethyl]-1H-indol-4-ol), aeruginascin (aka [3-[2-(trimethylazaniumyl)ethyl]-1H-indol-4-yl]hydrogen phosphate), baeocystin (aka [3-[2-(methylamino)ethyl]-1H-indol-4-yl]dihydrogen phosphate), bufotenidine (aka 3-[2-(trimethylazaniumypethyl]-1H-indol-5-olate), bufotenin (aka 3-[2-(dimethylamino)ethyl]-1H-indol-5-ol), ethocybin (aka [3-[2-(diethylamino)ethyl]-1H-indol-4-yl]dihydrogen phosphate), norbaeocystin (aka [3-(2-aminoethyl)-1H-indol-4-yl]dihydrogen phosphate), norpsilocin, psilocin (aka 3-[2-(dimethylamino)ethyl]-1H-indol-4-ol), psilocybin (aka [3-[2-(dimethylamino)ethyl]-1H-indol-4-yl]dihydrogen phosphate), serotonin (aka 3-(2-aminoethyl)-1H-indol-5-ol), 1P-LSD (aka (6aR,9R)-N,N-diethyl-7-methyl-4-propanoyl-6,6a,8,9-tetrahydroindolo[4,3-fg]quinoline-9-carboxamide), ALD-52 (aka (6aR,9R)-4-acetyl-N,N-diethyl-7-methyl-6,6a,8,9-tetrahydroindolo[4,3-fg]q-uinoline-9-carboxamide), AL-LAD (aka (6aR,9R)-N,N-diethyl-7-prop-2-enyl-6,6a,8,9-tetrahydro-4H-indolo[4,3-fg]q-uinoline-9-carboxamide), BU-LAD (aka (6aR,9R)-7-butyl-N,N-diethyl-6,6a,8,9-tetrahydro-4H-indolo[4,3-fg]quinoli-ne-9-carboxamide), DAL (aka (6aR,9R)-7-methyl-N,N-bis(prop-2-enyl)-6,6a,8,9-tetrahydro-4H-indolo[4,3-fg]quinoline-9-carboxamide), DAM-57 (aka (6aR,9R)-N,N,7-trimethyl-6,6a,8,9-tetrahydro-4H-indolo[4,3-fg]quinoline-9-carboxamide), EIPLA (aka (6aR,9R)-N-ethyl-7-methyl-N-propan-2-yl-6,6a,8,9-tetrahydro-4H-indolo[4,3-fg]quinoline-9-carboxamide), ETH-LAD (aka (6aR,9R)-N,N,7-triethyl-6,6a,8,9-tetrahydro-4H-indolo[4,3-fg]quinoline-9-carboxamide), LAE-32 (aka (6aR,9R)-N-ethyl-7-methyl-6,6a,8,9-tetrahydro-4H-indolo[4,3-fg]quinoline-9-carboxamide), LPD-824 (aka [(6aR,9R)-7-methyl-6,6a,8,9-tetrahydro-4H-indolo[4,3-fg]quinoline-9-yl]-pyrrolidin-1-ylmethanone), LSB (aka (6aR,9R)-N-butan-2-yl-7-methyl-6,6a,8,9-tetrahydro-4H-indolo[4,3-fg]quino-line-9-carboxamide), LSA (aka (6aR,9R)-7-methyl-6,6a,8,9-tetrahydro-4H-indolo[4,3-fg]quinoline-9-carbox-amide), LSD-25 (aka (6aR,9R)-N,N-diethyl-7-methyl-6,6a,8,9-tetrahydro-4H-indolo[4,3-fg]quinol-ine-9-carboxamide), LSD-PiP (aka (7-methyl-6,6a,8,9-tetrahydro-4H-indolo[4,3-fg]quinoline-9-yl)-piperidin-1-ylmethanone), LSM-775 (aka [(6aR,9R)-7-methyl-6,6a,8,9-tetrahydro-4H-indolo[4,3-fg]quinoline-9-yl]-m-orpholin-4-ylmethanone), LSP (aka (6aR,9R)-7-methyl-N-pentan-3-yl-6,6a,8,9-tetrahydro-4H-indolo[4,3-fg]quinoline-9-carboxamide), LSZ (aka [(6aR,9R)-7-methyl-6,6a,8,9-tetrahydro-4H-indolo[4,3-fg]quinoline-9-yl]-[-(2S,4S)-2,4-dimethylazetidin-1-yl]methanone), methergine (aka (6aR,9R)-N-(1-hydroxybutan-2-yl)-7-methyl-6,6a,8,9-tetrahydro-4H-indolo[4-,3-fg]quinoline-9-carboxamide), MiPLA (aka (6aR,9R)-N,7-dimethyl-N-propan-2-yl-6,6a,8,9-tetrahydro-4H-indolo[4,3-fg]-quinoline-9-carboxamide), NDTDI, PARGY-LAD, PRO-LAD (aka (6aR,9R)-N,N-diethyl-7-propyl-6,6a,8,9-tetrahydro-4H-indolo[4,3-fg]quinol-ine-9-carboxamide), 2-Me-DET (aka N,N-diethyl-2-(2-methyl-1H-indol-3-yl)ethanamine), 2-Me-DMT (aka N,N-dimethyl-2-(2-methyl-1H-indol-3-yl)ethanamine), 2,alpha-DMT (aka 1-(2-methyl-1H-indol-3-yl)propan-2-amine), 4-AcO-DALT (aka [3-[2-[bis(prop-2-enyl)amino]ethyl]-1H-indol-4-yl]acetate), 4-AcO-DET (aka [3-[2-(diethylamino) ethyl]-1H-indol-4-yl]acetate), 4-AcO-DIPT (aka 3-[2-(Diisopropylamino)ethyl]-1H-indol-4-yl acetate), 4-AcO-DMT (aka [3-[2-(dimethylamino)ethyl]-1H-indol-4-yl]acetate), 4-AcO-DPT (aka [3-[2-(dipropylamino)ethyl]-1H-indol-4-yl]acetate), 4-AcO-EPT (aka 3-{2-[Ethyl(propyl)amino] ethyl}-1H-indol-4-yl acetate), 4-AcO-MET (aka [3-[2-[ethyl(methyl)amino]ethyl]-1H-indol-4-yl]acetate), 4-AcO-MIPT (aka [3-[2-[methyl(propan-2-yl)amino]ethyl]-1H-indol-4-yl]acetate), 4-AcO-MPT, 4-HO-DBT (aka 3-[2-(dibutylamino)ethyl]-1H-indol-4-ol), 4-HO-DET (aka 3-[2-(diethylamino)ethyl]-1H-indol-4-ol), 4-HO-DIPT (aka 3-[2-[di(propan-2-yl)amino]ethyl]-1H-indol-4-ol), 4-HO-DPT (aka 3-[2-(dipropylamino)ethyl]-1H-indol-4-ol), 4-HO-EPT, 4-HO-MCPT, 4-HO-MET (aka 3-[2-[ethyl(methyl) amino]ethyl]-1H-indol-4-ol), 4-HO-MIPT (aka 3-[2-[methyl(propan-2-yl)amino]ethyl]-1H-indol-4-ol), 4-HO-MPMI (aka 3-[(1-methylpyrrolidin-2-yl)methyl]-1H-indol-4-ol), 4-HO-MPT (aka 3-[2-[methyl(propyl)amino]ethyl]-1H-indol-4-ol), 4-HO-pyr-T (aka 3-(2-pyrrolidin-1-ylethyl)-1H-indol-4-ol), 4-MeO-MIPT (aka N-[2-(4-methoxy-1H-indol-3-yl)ethyl]-N-methylpropan-2-amine), 4,5-MDO-DIPT (aka N-[2-(6H-[1,3]dioxolo[4,5-e]indol-8-yl)ethyl]-N-propan-2-ylpropan-2-amine-), 4,5-MDO-DMT (aka 2-(6H-[1,3]dioxolo[4,5-e]indol-8-yl)-N,N-dimethyl-ethanamine), 5-BROMO-DMT (aka 2-(5-bromo-1H-indol-3-yl)-N,N-dimethylethanamine), 5-chloro-alpha-MT (aka 1-(5-chloro-1H-indol-3-yl)propan-2-amine), 5-fluoro-AMT (aka 1-(5-fluoro-1H-indol-3-yl)propan-2-amine), 5-MeO-AET (aka 1-(5-methoxy-1H-indol-3-yl)butan-2-amine), 5-MeO-AMT (aka 1-(5-methoxy-1H-indol-3-yl)propan-2-amine), 5-MeO-DALT (aka N-[2-(5-methoxy-1H-indol-3-yl)ethyl]-N-prop-2-enylprop-2-en-1-amine), 5-MeO-DET (aka N,N-diethyl-2-(5-methoxy-1H-indol-3-yl)ethanamine), 5-MeO-DiPT (aka N-[2-(5-methoxy-1H-indol-3-yl)ethyl]-N-propan-2-ylpropan-2-amine), 5-MeO-DMT (aka 2-(5-methoxy-1H-indol-3-yl)-N,N-dimethylethanamine), 5-MeO-DPT (aka N-[2-(5-methoxy-1H-indol-3-yl)ethyl]-N-propylpropan-1-amine), 5-MeO-EiPT (aka N-ethyl-N-[2-(5-methoxy-1H-indol-3-yl)ethyl]propan-2-amine), 5-MeO-MALT (aka N-[2-(5-Methoxy-1H-indol-3-yl)ethyl]-N-methylprop-2-en-1-amine), 5-MeO-MiPT (aka N-[2-(5-methoxy-1H-indol-3-yl)ethyl]-N-methylpropan-2-amine), 5-MeO-NMT (aka 2-(5-methoxy-1H-indol-3-yl)-N-methyl-ethanamine;hydrochloride), 5-MeO-pyr-T (aka 4-fluoro-5-methoxy-3-(2-pyrrolidin-1-ylethyl)-1H-indole), 5-MeO-TMT (aka 2-(5-methoxy-2-methyl-1H-indol-3-yl)-N,N-dimethylethanamine), 5-MeS-DMT (aka N,N-dimethyl-2-(5-methylsulfanyl-1H-indol-3-yl)ethanamine), 5,6-MDO-DIPT (aka N-[2-(5H-[1,3]dioxolo[4,5-f]indol-7-yl)ethyl]-N-propan-2-ylpropan-2-amine-), 5,6-MDO-DMT (aka 2-(5H-[1,3]dioxolo[4,5-f]indol-7-yl)-N,N-dimethyl-ethanamine), 5,6-MDO-MIPT (aka N-[2-(5H-[1,3]dioxolo [4,5-f]indol-7-yl)ethyl]-N-ethylpropan-2-amine), 5,6-MeO-MIPT (aka N-[2-(5,6-dimethoxy-1H-indol-3-yl)ethyl]-N-methylpropan-2-amine), 5,N,N-TMT (aka N,N-dimethyl-2-(5-methyl-1H-indol-3-ethanamine), 6-MeO-THH (aka 6-methoxy-1-methyl-2,3,4,9-tetrahydro-1H-pyrido[3,4-b] indole), alpha-ET (aka 1-(1H-indol-3-yl)butan-2-amine), alpha-MT (aka 1-(1H-indol-3-yl)propan-2-amine), alpha-TMT (aka 1-(1H-indol-3-yl)-N,N-dimethylpropan-2-amine), alpha,N-DMT (aka 2-(1H-indol-3-yl)-N,N-dimethylethanamine), alpha,N,O-TMS (aka 1-(5-methoxy-1H-indol-3-yl)-N-methylpropan-2-amine), alpha,O-DMS (aka 1-(5-methoxy-1H-indol-3-yl)propan-2-amine), DALT (aka N-[2-(1H-indol-3-yl)ethyl]-N-prop-2-enylprop-2-en-1-amine), DBT (aka N-butyl-N-[2-(1H-indol-3-yl)ethyl]butan-1-amine), DET (aka N,N-diethyl-2-(1H-indol-3-yl) ethanamine), DiPT (aka N-[2-(5-methoxy-1H-indol-3-yl) ethyl]-N-propan-2-ylpropan-2-amine), DMT (aka 2-(1H-indol-3-yl)-N,N-dimethylethanamine), DPT (aka N-[2-(1H-indol-3-yl)ethyl]-N-propylpropan-1-amine), EiPT (aka N-ethyl-N-[2-(1H-indol-3-yl)ethyl]propan-2-amine), Harmaline (aka 7-methoxy-1-methyl-3,4-dihydro-2H-pyrido[3,4-b]indole), Harmine (aka 7-methoxy-1-methyl-9H-pyrido [3,4-b]indole), MALT, MBT (aka 3H-1,3-benzothiazole-2-thione), Melatonin (aka N-[2-(5-methoxy-1H-indol-3-yl) ethyl]acetamide), MET (aka N-ethyl-2-(1H-indol-3-yl)-N-methylethanamine), MiPT (aka N-[2-(1H-indol-3-yl)ethyl]-N-methylpropan-2-amine), MPT (aka 3-[2-[methyl(propyl) amino]ethyl]-1H-indol-4-ol), NET (aka N-ethyl-2-(1H-indol-3-yl)ethanamine), NMT (aka 2-(1H-indol-3-yl)-N-methylethanamine), PiPT (aka N-[2-(1H-indol-3-yl)ethyl]-N-propan-2-ylpropan-1-amine), pyr-T (aka 3-(2-pyrrolidin-1-ylethyl)-1H-indole), T (aka 2-(1H-indol-3-yl) ethanamine), Tetrahydroharmine (aka 7-methoxy-1-methyl-2,3,4,9-tetrahydro-1H-pyrido[3,4-b]indole), 2-Br-4,5-MDA (aka 1-(6-bromo-1,3-benzodioxol-5-yl)propan-2-amine), 2-TIM (aka 2-(3,4-dimethoxy-2-methylsulfanylphenyl) ethanamine), 2-TOET (aka 1-(4-ethyl-5-methoxy-2-methylsulfanylphenyl)propan-2-amine), 2-TOM (aka 1-(5-methoxy-4-methyl-2-methylsulfanylphenyl)propan-2-amine), 2,4-DMA (aka 1-(2,4-dimethoxyphenyl)propan-2-amine), 2,5-DMA (aka 1-(2,5-dimethoxyphenyl)propan-2-amine), 2C-B (aka 2-(4-bromo-2,5-dimethoxyphenyl) ethanamine), 2C-C (aka 2-(4-chloro-2,5-dimethoxyphenyl) ethanamine), 2C-D (aka 2-(2,5-dimethoxy-4-methylphenyl) ethanamine), 2C-E (aka 2-(4-ethyl-2,5-dimethoxyphenyl) ethanamine), 2C-F (aka 2-(4-fluoro-2,5-dimethoxyphenyl) ethanamine), 2C-G (aka 2-(2,5-dimethoxy-3,4-dimethylpheny)ethanamine), 2C-G-3 (aka 2-(4,7-dimethoxy-2,3-dihydro-1H-inden-5-yl)ethanamine), 2C-G-4 (aka 2-(1,4-dimethoxy-5,6,7,8-tetrahydronaphthalen-2-yl)ethanamine), 2C-G-5 (aka CAS 207740-20-3), 2C-G-N (aka 2-(1,4-dimethoxynaphthalen-2-yl) ethanamine), 2C-H (aka 2-(2,5-dimethoxyphenyl) ethanamine), 2C-I (aka 2-(4-iodo-2,5-dimethoxyphenyl) ethanamine), 2C-N (aka 2-(2,5-dimethoxy-4-nitrophenyl) ethanamine), 2C—O-4 (aka 2-(2,5-dimethoxy-4-propan-2-yloxyphenyl)ethanamine), 2C-P (aka 2-(2,5-dimethoxy-4-propylphenyl)ethanamine), 2C-SE (aka 2-(2,5-dimethoxy-4-methylselanylphenyl)ethanamine), 2C-T (aka 2-(2,5-dimethoxy-4-methylsulfanylphenyl)ethanamine), 2C-T-13 (aka 2-[2,5-dimethoxy-4-(2-methoxyethylsulfanyl)phenyl] ethanamine), 2C-T-15 (aka 2-(4-cyclopropylsulfanyl-2,5-dimethoxyphenyl)ethanamine), 2C-T-17 (aka 2-(4-butan-2-ylsulfanyl-2,5-dimethoxyphenyl)ethanamine), 2C-T-2 (aka 2-(4-ethylsulfanyl-2,5-dimethoxypheny)ethanamine), 2C-T-2 (aka 2-[4-(2-fluoroethylsulfanyl)-2,5-dimethoxyphenyl]ethanamine), 2C-T-4 (aka 2-(2,5-dimethoxy-4-propan-2-ylsulfanylpheny)ethanamine), 2C-T-7 (aka 2-(2,5-dimethoxy-4-propylsulfanylphenyl)ethanamine), 2C-T-8 (aka 2-[4-(cyclopropylmethylsulfanyl)-2,5-dimethoxyphenyl] ethanamine), 2C-T-9 (aka 2-(4-butylsulfanyl-2,5-dimethoxypheny)ethanamine), 2C-TFM (aka 2-[2,5-dimethoxy-4-(trifluoromethyl)phenyl]ethanamine), 2T-MMDA-3a (aka 1-(4-methylsulfanyl-1,3-benzodioxol-5-yl)propan-2- amine), 3-T-TRIS (aka 2-(3,4-diethoxy-5-ethylsulfanylphenyl)ethanamine), 3-TASB (aka 2-(3-ethoxy-4-ethylsulfanyl-5-methoxyphenyl)ethanamine), 3-TE (aka 2-(4-ethoxy-3-methoxy-5-methylsulfanylphenyl)ethanamine), 3-TFM (aka 2-(2,4-dimethoxy-3-methylsulfanylphenyl)ethanamine), 3-TM (aka 2-(3,4-dimethoxy-5-methylsulfanylpheny) ethanamine), 3-TME (aka 2-(3-ethylsulfanyl-4,5-dimethoxyphenyl)ethanamine), 3-TSB (aka 2-(3-ethoxy-5-ethylsulfanyl-4-methoxyphenyl)ethanamine), 3,4-DMA (aka 1-(3,4-dimethoxyphenyl)propan-2-amine), 3C-BZ (aka 1-(3,5-dimethoxy-4-phenylmethoxyphenyl)propan-2-amine), 3C-E (aka 1-(4-ethoxy-3,5-dimethoxyphenyl)propan-2-amine), 4-Br-3,5-DMA (aka 1-(4-bromo-3,5-dimethoxyphenyl)propan-2-amine), 4-D (aka CAS 1020518-87-9), 4-MA (aka 1-(4-methoxyphenyl)propan-2-amine), 4-T-TRIS (aka 2-(3,5-diethoxy-4-ethylsulfanylphenyl) ethanamine), 4-TASB (aka 2-(3-ethoxy-4-ethylsulfanyl-5-methoxypheny)ethanamine), 4-TE (aka 2-(4-ethylsulfanyl-3,5-dimethoxyphenyl)ethanamine), 4-TIM (aka 2-(2,3-dimethoxy-4-methylsulfanylphenyl)ethanamine), 4-TM (aka 2-(3,5-dimethoxy-4-methylsulfanylphenyl) ethanamine), 4-TME (aka 2-(3-ethoxy-5-methoxy-4-methylsulfanylpheny)ethanamine), 4-TSB (aka 2-(3,5-diethoxy-4-methylsulfanylphenyl)ethanamine), 4T-MMDA-2 (aka 1-(5-methoxy-1,3-benzoxathiol-6-yl)propan-2-amine), 5-TASB (aka 2-(3,4-diethoxy-5-methylsulfanylphenyl) ethanamine), 5-TME (aka 2-(3-ethoxy-4-methoxy-5-methylsulfanylphenyl)ethanamine), 5-TOET (aka 1-(4-ethyl-2-methoxy-5-methylsulfanylphenyl)propan-2-amine), 5-TOM (aka 1-(2-methoxy-4-methyl-5-methylsulfanylphenyl)propan-2-amine), 25B-NBF (aka 2-(4-bromo-2,5-dimethoxyphenyl)-N-[(2-fluorophenyl)methyl]ethanamine-), 25B-NBOH (aka 2-[[2-(4-bromo-2,5-dimethoxypheny) ethylaminolmethyl]phenol), 25B-NBOMe (aka 2-(4-bromo-2,5-dimethoxyphenyl)-N[(2-methoxyphenyl)methyl] ethanamine-), 25C-NB3OMe (aka 2-(4-chloro-2,5-dimethoxyphenyl)-N-[((3-methoxypheny)methyl] ethanamine), 25C-NB4OMe (aka 2-(4-chloro-2,5-dimethoxyphenyl)-N-[(4-methoxyphenyl)methyl] ethanamine), 25C-NBF (aka 2-(4-chloro-2,5-dimethoxyphenyl)-N-[(2-fluorophenyl)methyl]ethanamine), 25C-NBOH (aka 2-(4-chloro-2,5-dimethoxyphenyl)ethylaminolmethyl]phenol), 25C-NBOMe (aka 2-(4-chloro-2,5-dimethoxyphenyl)-N[(2-methoxyphenyl)methyl] ethanamine), 25CN-NBOH (aka 4-[2-[(2-hydroxyphenyl) methylamino]ethyl]-2,5-dimethoxybenzonitrile), 25CN-NBOMe (aka CAS 1354632-16-8), 25D-NBOMe (aka 2-(2,5-dimethoxy-4-methylphenyl)-N-[(2-methoxyphenyl) methyl]ethanamine), 25E-NBOMe (aka 2-(4-ethyl-2,5-dimethoxyphenyl)-N4(2-methoxyphenyl)methyl] ethanamine), 25G-NBOMe (aka 2-(2,5-dimethoxy-3,4-dimethylphenyl)-N-[(2-methoxyphenyl)methyl] ethanamine), 25H-NBOMe (aka 2-(2,5-dimethoxyphenyl)-N-[(2-methoxyphenyl)methyl]ethanamine), 25H-NB34MD (aka N-(1,3-benzodioxol-5-ylmethyl)-2-(4-iodo-2,5-dimethoxyphenyl)ethanamine), 251-NB3OMe (aka 2-(4-iodo-2,5-dimethoxyphenyl)-N-[(3-methoxyphenyl)methyl] ethanamine), 251-NB4OMe (aka 2-(4-iodo-2,5-dimethoxyphenyl)-N-[(4-methoxyphenyl)methyl] ethanamine), 251-NBF (aka N-[(2-fluorophenyl)methyl]-2-(4-iodo-2,5-dimethoxyphenyl)ethanamine), 251-NBMD (aka N-(1,3-benzodioxol-4-ylmethyl)-2-(4-iodo-2,5-dimethoxyphenyl)ethanamine), 251-NBOH (aka 2-[[2-(4-iodo-2,5-dimethoxypheny)ethylamino]methyl]phenol), 251-NBOMe (aka 2-(4-iodo-2,5-dimethoxyphenyl)-N-[(2-methoxyphenyl)methyl]ethanamine), 25iP-NBOMe (aka 2-(2,5-dimethoxy-4-propan-2-ylphenyl)-N-[(2-methoxypheny)methyl]ethanamine), 25N-NBOMe (aka 2-(2,5-dimethoxy-4-nitrophenyl)-N-[(2-methoxypheny)methyl] ethanamine), 25P-NBOMe (aka 2-(2,5-dimethoxy-4-propylphenyl)-N-[(2-methoxyphenyl)methyl]ethanamine), 25TFM-NBOMe (aka 2-[2,5-dimethoxy-4-(trifluoromethyl) phenyl]-N-[(2-methoxyphenyl)methyl]et-hanamine), 2CBCB—NBOMe (aka 1-[(7R)-3-bromo-2,5-dimethoxy-7-bicyclo[4.2.0]octa-1(6),2,4-trienyl]-N—[(-2-methoxypheny)methyl]methanamine), 2CBFIy-NBOMe (aka 2-(4-bromo-2,3,6,7-tetrahydrofuro[2,3-f][1]benzofuran-8-yl)-N-[(2-methoxy-phenyl)methyl]thanamine), AEM (aka 1-(3,4,5-trimethoxyphenyl)butan-2-amine), AL (aka 2-(3,5-dimethoxy-4-prop-2-enoxyphenyl)ethanamine), ALEPH (aka 1-(2,5-dimethoxy-4-methylsulfanylphenyl)propan-2-amine; hydrochloride), ALEPH-2 (aka 1-(4-ethylsulfanyl-2,5-dimethoxyphenyl)propan-2-amine), ALEPH-4 (aka 1-(2,5-dimethoxy-4-propan-2-ylsulfanylphenyl)propan-2-amine), ALEPH-6 (aka 1-(2,5-dimethoxy-4-phenylsulfanylphenyl)propan-2-amine), ALEPH-7 (aka 1-(2,5-dimethoxy-4-propylsulfanylphenyl)propan-2-amine), ARIADNE (aka (2R)-1-(2,5-dimethoxy-4-methylphenyl)butan-2-amine), ASB (aka 2-(3,4-diethoxy-5-methoxyphenyl)ethanamine), B (aka 2-(4-butoxy-3,5-dimethoxyphenyl)ethanamine), BEATRICE (aka 1-(2,5-dimethoxy-4-methylphenyl)-N-methylpropan-2-amine), beta-D (aka 2,2-dideuterio-2-(3,4,5-trimethoxyphenyl) ethanamine), BIS-TOM (aka 1-[4-methyl-2,5-bis(methylsulfanyl)phenyl]propan-2-amine), bk-2C-B (aka 2-amino-1-(4-bromo-2,5-dimethoxyphenyl)ethanone), BOB (aka 2-(4-bromo-2,5-dimethoxyphenyl)-2-methoxyethanamine), BOD (aka 2-(2,5-dimethoxy-4-methylphenyl)-2-methoxyethanamine), BOH (aka 2-(1,3-benzodioxol-5-yl)-2-methoxyethanamine), BOHD (aka 2-amino-1-(2,5-dimethoxy-4-methylpheny)ethanol), BOM (aka 2-methoxy-2-(3,4,5-trimethoxyphenyl)ethanamine), bromo-dragonFLY (aka 1-(4-bromofuro[2,3-f][1]benzofuran-8-yl)propan-2-amine), butylone (aka 1-(1,3-benzodioxl-5-yl)-2-(methylamino)butan-1-one), CPM (aka 2-[4-(cyclopropylmethoxy)-3,5-dimethoxyphenyl]ethanamine), DESOXY (aka 2-(3,5-dimethoxy-4-methylpheny)ethanamine), DMCPA (aka 2-(2,5-dimethoxy-4-methylphenyl)cyclopropan-1-amine), DME (aka 2-amino-1-(3,4-dimethoxyphenyl)ethanol), DMMDA (aka 1-(4,7-dimethoxy-1,3-benzodioxol-5-yl)propan-2-amine), DMMDA-2 (aka 1-(6,7-dimethoxy-1,3-benzodioxol-5-yl)propan-2-amine), DMPEA (aka 2-(3,4-dimethoxyphenyl)ethanamine), DOAM (aka 1-(2,5-dimethoxy-4-pentylphenyl)propan-2-amine), DOB (aka 1-(4-bromo-2,5-dimethoxyphenyl)propan-2-amine), DOBU (aka 1-(4-butyl-2,5-dimethoxyphenyl)propan-2-amine), DOC (aka 1-(4-chloro-2,5-dimethoxyphenyl)propan-2-amine), DOEF (aka 1-[4-(2-fluoroethyl)-2,5-dimethoxyphenyl]propan-2-amine), DOET (aka 1-(4-ethyl-2,5-dimethoxyphenyl)propan-2-amine), DOF (aka 1-(4-fluoro-2,5-dimethoxyphenyl) propan-2-amine), DOI (aka 1-(4-iodo-2,5-dimethoxyphenyl)propan-2-amine), DOM (aka 1-(2,5-dimethoxy-4-methylphenyl)propan-2-amine), DON (aka 1-(2,5-dimethoxy-4-nitrophenyl)propan-2-amine), DOPR (aka 1-(2,5-dimethoxy-4-propylphenyl)propan-2-amine), DOTFM (aka 1-[2,5-dimethoxy-4-(trifluoromethyl)phenyl] propan-2-amine), E (aka 2-(4-ethoxy-3,5-dimethoxyphenyl) ethanamine), EBDP (aka 1-(1,3-benzodioxol-5-yl)-N-ethylpentan-2-amine), EEE (aka 1-(2,4,5-triethoxyphenyl) propan-2-amine), EEM (aka 1-(2,4-diethoxy-5-methoxyphenyl)propan-2-amine), EME (aka 1-(2,5-diethoxy-4-methoxyphenyl)propan-2-amine), EMM (aka 1-(2-ethoxy-4,5-dimethoxyphenyl)propan-2-amine), ETHYL-J (aka 1-(1,3-benzodioxol-5-yl)-N-ethylbutan-2- amine), ETHYL-K (aka 1-(1,3-benzodioxol-5-yl)-N-ethylpentan-2-amine), F-2 (aka 1-(5-methoxy-2-methyl-2,3-dihydro-1-benzofuran-6-yl)propan-2-amine), F-22 (aka 1-(5-methoxy-2,2-dimethyl-3H-1-benzofuran-6-yl)propan-2-amine), FLEA (aka N-[1-(1,3-benzodioxol-5-yl)propan-2-yl]-N-methylhydroxylamine), G-3 (aka 1-(4,7-dimethoxy-2,3-dihydro-1H-inden-5-yl)propan-2-amine), G-4 (aka 1-(1,4-dimethoxy-5,6,7,8-tetrahydronaphthalen-2-yl)propan-2-amine), G-5 (aka 3,6-dimethoxy-4-(2-aminopropyl) benzonorbornane), G-N (aka 1-(1,4-dimethoxynaphthalen-2-yl)propan-2-amine), GANESHA (aka 1-(2,5-dimethoxy-3,4-dimethylphenyl)propan-2-amine), HOT-17 (aka N-[2-(4-butan-2-ylsulfanyl-2,5-dimethoxypheny)ethyl] hydroxylamine), HOT-2 (aka N-[2-(4-ethylsulfanyl-2,5-dimethoxypheny)ethyl]hydroxylamine), HOT-7 (aka N-[2-(2,5-dimethoxy-4-propylsulfanylpheny)ethyl] hydroxylamine), IDNNA (aka 1-(4-iodo-2,5-dimethoxyphenyl)-N,N-dimethylpropan-2-amine), IM (aka 2-(2,3,4-trimethoxyphenyl)ethanamine), IP (aka 2-(3,5-dimethoxy-4-propan-2-yloxyphenyl)ethanamine), IRIS (aka 1-(5-ethoxy-2-methoxy-4-methylphenyl)propan-2-amine), J (aka 1-(1,3-benzodioxol-5-yl)butan-2-amine), jimscaline (aka [(1R)-4,5,6-trimethoxy-2,3-dihydro-1H-inden-1-yl] methanamine), LOPHOPHINE (aka 2-(7-methoxy-1,3-benzodioxol-5-yl)ethanamine), M (aka 2-(3,4,5-trimethoxypheny)ethanamine), MADAM-6 (aka N-methyl-1-(6-methyl-1,3-benzodioxol-5-yl)propan-2-amine), MAL (aka 2-[3,5-dimethoxy-4-(2-methylprop-2-enoxy)phenyl] ethanamine), MDA (aka 1-(1,3-benzodioxol-5-yl)propan-2-amine), MDAL (aka 1-(1,3-benzodioxol-5-yl)-N-prop-2-enylpropan-2-amine), MDBU (aka N-[1-(1,3-benzodioxol-5-yl)propan-2-yl]butan-1-amine), MDBZ (aka 1-(1,3-benzodioxol-5-yl)-N-benzylpropan-2-amine), MDCPM (aka 1-(3a,7a-dihydro-1,3-benzodioxol-5-yl)-N-(cyclopropylmethyl)propan-2-amine), MDDM (aka 1-(1,3-benzodioxol-5-yl)-N,N-dimethylpropan-2-amine), MDE (aka 1-(1,3-benzodioxol-5-yl)-N-ethylpropan-2-amine), MDHOET (aka 2-[1-(1,3-benzodioxol-5-yl)propan-2-ylamino]ethanol), MDIP (aka 1-(1,3-benzodioxol-5-yl)-N-propan-2-ylpropan-2-amine), MDMA (aka 1-(1,3-benzodioxol-5-yl)-N-methylpropan-2-amine), MDMC (aka 1-(2,3-dihydro-1,4-benzodioxin-6-yl)-N-methylpropan-2-amine), MDMEO (aka 1-(1,3-benzodioxol-5-yl)-N-methoxypropan-2-amine), MDMEOET (aka 1-(1,3-benzodioxol-5-yl)-N-(2-methoxyethyl)propan-2-amine), MDMP (aka 1-(1,3-benzodioxol-5-yl)-N,2-dimethylpropan-2-amine), MDOH (aka N-[1-(1,3-benzodioxol-5-yl)propan-2-yl]hydroxylamine), MDPEA (aka 2-(1,3-benzodioxol-5-yl)ethanamine), MDPH (aka 1-(1,3-benzodioxol-5-yl)-2-methylpropan-2-amine), MDPL (aka 1-(1,3-benzodioxol-5-yl)-N-prop-2-ynylpropan-2-amine), MDPR (aka 1-(1,3-benzodioxol-5-yl)-N-propylpropan-2-amine), ME (aka 2-(3-ethoxy-4,5-dimethoxyphenyl) ethanamine), MEDA (aka 1-(5-methoxy-2,3-dihydro-1,4-benzodioxin-7-yl)propan-2-amine), MEE (aka 1-(4,5-diethoxy-2-methoxyphenyl)propan-2-amine), MEM (aka 1-(4-ethoxy-2,5-dimethoxyphenyl)propan-2-amine), MEPEA (aka 2-(4-ethoxy-3-methoxyphenyl)ethanamine), META-DOB (aka 1-(5-bromo-2,4-dimethoxyphenyl)propan-2-amine), META-DOT (aka 1-(2,4-dimethoxy-5-methylsulfanylphenyl)propan-2-amine), METHYL-DMA (aka 1-(2,5-dimethoxyphenyl)-N-methylpropan-2-amine), METHYL-DOB (aka 1-(4-bromo-2,5-dimethoxyphenyl)-N-methylpropan-2-amine), METHYL-J (aka 1-(1,3-benzodioxol-5-yl)-N-methylbutan-2-amine), METHYL-K (aka 1-(1,3-benzodioxol-5-yl)-N-methylpentan-2-amine), METHYL-MA (aka 1-(4-methoxyphenyl)-N-methylpropan-2-amine), METHYL-MMDA-2 (aka 1-(6-methoxy-1,3-benzodioxol-5-yl)-N-methylpropan-2-amine), MMDA (aka 1-(7-methoxy-1,3-benzodioxol-5-yl)propan-2-amine), MMDA-2 (aka 1-(6-methoxy-1,3-benzodioxol-5-yl)propan-2-amine), MMDA-3a (aka 1-(4-methoxy-1,3-benzodioxol-5-yl)propan-2-amine), MMDA-3b (aka 1-(7-methoxy-1,3-benzodioxol-4-yl)propan-2-amine), MME (aka 1-(5-ethoxy-2,4-dimethoxyphenyl)propan-2-amine), MP (aka 2-(3,4-dimethoxy-5-propoxyphenyl)ethanamine), MPM (aka 1-(2,4-dimethoxy-5-propoxyphenyl)propan-2-amine), NBOMe-mescaline (aka N-[(2-methoxyphenyl)methyl]-2-(3,4,5-trimethoxypheny)ethanamine), ORTHO-DOT (aka 1-(4,5-dimethoxy-2-methylsulfanylphenyl)propan-2-amine), P (aka 2-(3,5-dimethoxy-4-propoxyphenyl)ethanamine), PE (aka 2-[3,5-dimethoxy-4-(2-phenylethoxy)phenyl] ethanamine), PEA (aka 2-phenylethanamine), PROPYNYL (aka 2-(3,5-dimethoxy-4-prop-2-ynoxyphenyl)ethanamine), psi-2C-T-4, psi-DOM (aka 1-(2,6-dimethoxy-4-methylphenyl)propan-2-amine), SB (aka 2-(3,5-diethoxy-4-methoxyphenyl)ethanamine), TA (aka 1-(2,3,4,5-tetramethoxyphenyl)propan-2-amine), TB (aka 2-(4-butylsulfanyl-3,5-dimethoxypheny)ethanamine), TCB-2 (aka (3-bromo-2,5-dimethoxy-7-bicyclo[4.2.0]octa-1(6), 2,4-trienyl) methanamine;hydrobromide), TMA (aka 1-(3,4,5-trimethoxyphenyl)propan-2-amine), TMA-2 (aka 1-(2,4,5-trimethoxyphenyl)propan-2-amine), TMA-3 (aka 1-(2,3,4-trimethoxyphenyl)propan-2-amine), TMA-4 (aka 1-(2,3,5-trimethoxyphenyl)propan-2-amine), TMA-5 (aka 1-(2,3,6-trimethoxyphenyl)propan-2-amine), TMA-6 (aka 1-(2,4,6-trimethoxyphenyl)propan-2-amine), TMPEA (aka 2-(2,4,5-trimethoxyphenyl)ethanamine), TOMSO (aka 1-(2-methoxy-4-methyl-5-methylsulfinylphenyl)propan-2-amine), TP (aka 2-(3,5-dimethoxy-4-propylsulfanylphenyl) ethanamine), and TRIS (aka 2-(3,4,5-triethoxyphenyl) ethanamine).

In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof.

In one embodiment, serotonin acts at a serotonin receptor, e.g., by acting as a ligand at a 5-HT receptor. In one embodiment, serotonin is produced by an organism for use as a neurotransmitter within that organism. In one embodiment, the compositions and methods disclosed herein increase the activity at a serotonin receptor. In one embodiment, the compositions and methods disclosed herein decrease the activity at a serotonin receptor.

As used herein, the term “serotonin receptor” refers to a collection of proteins outside a cell capable of receiving signals and activating internal signal transduction pathways causing a cellular response. In one embodiment, a serotonin receptor is found on a cell within the central nervous system of an organism. In one embodiment, a serotonin receptor is found on a cell within the peripheral nervous system of an organism. In one embodiment, serotonin is the natural ligand for a serotonin receptor. In one embodiment, a serotonin receptor modulates the release of a neurotransmitter, e.g., glutamate, gamma-Aminobutyric acid, dopamine, epinephrine (a.k.a. norepinephrine), acetylcholine, etc. In one embodiment, a serotonin receptor modulates the release of a hormone, e.g., oxytocin, prolactin, vasopressin, cortisol, corticotropin, substance P, etc.

Examples of serotonin receptors include, but are not limited to, 5-$HT_{1A}$, 5-$HT_{1B}$, 5-$HT_{1D}$, 5-$HT_{1E}$, 5-$HT_{2A}$, 5-$HT_{2B}$, 5-$HT_{2C}$, 5-$HT_3$, 5-$HT_4$, 5-$HT_{5A}$, 5-$HT_{5B}$, 5-$HT_6$, and 5-$HT_7$.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant.

In one embodiment, an adrenergic drug is a norepinephrine transporter inhibitor.

In one embodiment, an adrenergic drug is a vesicular monoamine transporter inhibitor.

In one embodiment, an adrenergic drug is chosen from adrenaline, agmatine, amoxapine, aptazapine, atomoxetine, bupropion, clonidine, doxepin, duloxetine, esmirtazpine, mianserin, mirabegron, mirtazapine, norepinephrine, phentolamine, phenylephrine, piperoxan, reserpine, ritodrine, setiptiline, tesofensine, timolol, trazodone, trimipramine, or xylazine.

In one embodiment, an adrenergic drug acts at an adrenergic receptor, e.g., by acting as a ligand at an adrenergic receptor. In one embodiment, adrenaline is produced by an organism for use as a neurotransmitter within that organism. In one embodiment, norepinephrine is produced by an organism for use as a neurotransmitter within that organism.

In one embodiment, the compositions and methods disclosed herein increase the activity at an adrenergic receptor. In one embodiment, the compositions and methods disclosed herein decrease the activity at an adrenergic receptor.

As used herein, the term "adrenergic receptor" refers to a collection of proteins outside a cell capable of receiving signals and activating internal signal transduction pathways causing a cellular response. In one embodiment, an adrenergic receptor is found on a cell within the central nervous system of an organism. In one embodiment, an adrenergic receptor is found on a cell within the sympathetic nervous system of an organism.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor.

In one embodiment, a dopaminergic drug is a vesicular monoamine transporter inhibitor.

In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

In one embodiment, a dopaminergic drug acts at a dopamine receptor, e.g., by acting as a ligand at a dopamine receptor. In one embodiment, dopamine is produced by an organism for use as a neurotransmitter within that organism. In one embodiment, the compositions and methods disclosed herein increase the activity at a dopamine receptor. In one embodiment, the compositions and methods disclosed herein decrease the activity at a dopamine receptor.

As used herein, the term "dopamine receptor" refers to a collection of proteins outside a cell capable of receiving signals and activating internal signal transduction pathways causing a cellular response. In one embodiment, a dopamine receptor is found on a cell within the central nervous system of an organism.

In one embodiment, a purified terpene modulates the activity of a neurotransmitter at its native receptor, e.g., serotonin at a serotonin receptor, dopamine at a dopaminergic drug, norephedrine at an adrenergic receptor, etc.

In one embodiment, a purified terpene is active at one or more receptors, e.g., a serotonin receptor, an adrenergic receptor, a dopamine receptor, a GABAergic receptor, a glutaminergic receptor, a histaminergic receptor, a cholinergic receptor, an opioid receptor, or a glycinergic receptor.

In one embodiment, the compositions disclosed herein comprise a monoamine oxidase inhibitor.

As used herein, the term "monoamine oxidase inhibitor" refers to a molecule binding to a monoamine oxidase enzyme thereby reducing the activity of the monoamine oxidase enzyme. Within the context of this disclosure, examples of monoamine oxidase inhibitors include aurorix, deprenyl, eldepryl, emsam, humoryl, hydracarbazine, isocarboxazid, linezolid, manerix, nydrazid, phenelzine, pirazidol, procarbazine, rasagiline, and tranylcypromine. In one embodiment, monoamine oxidase catalyzes the oxidation of a monoamine, e.g., serotonin, dopamine, norepinephrine, amphetamine, adrenaline, etc.

In one embodiment, the compositions disclosed herein comprise a stabilizer. As used herein, the term "stabilizer" refers to a compound useful for preventing the degradation of an active ingredient, e.g., a compound of Formula I, a psilocybin derivative, a cannabinoid, a terpene, etc. In one embodiment, a stabilizer prevents an active ingredient from degrading. In one embodiment, a stabilizer prevents a serotonergic drug from reacting with other compounds in the composition, e.g., a cannabinoid, a terpene, a base, an acid, etc. In one embodiment, a stabilizer prevents a serotonergic drug from reacting with the ambient atmosphere, e.g., heat, light, water, and/or oxygen. In one embodiment, a stabilizer comprises an antioxidant. In one embodiment, a stabilizer comprises a pH buffer.

In one embodiment, the methods and compositions disclosed herein comprise an antioxidant. As used herein, the term "antioxidant" refers to a compound and/or a composition useful for preventing oxidation. In one embodiment, an antioxidant protects an active ingredient from "free radicals". Within the context of this disclosure, a "free radical" is an atom, molecule, or an ion with an unpaired valence electron. In one embodiment, an antioxidant is an electron donor.

In one embodiment, an antioxidant is chosen from ascorbic acid, lycopene, tocopherol, melatonin, retinol, astaxanthin, lutein, apigenin, carnosine, selenium, zinc, cucurmin, and/or a salt or derivative thereof.

In one embodiment, an antioxidant is ascorbic acid and/or its salts or derivatives. Within the context of this disclosure, the term "ascorbic acid" comprises Vitamin C and/or a salt or derivative thereof.

In one embodiment, an antioxidant prevents the oxidation of a composition comprising one or more compounds disclosed herein, e.g., compounds of Formula I, psilocybin derivatives, cannabinoids, terpenes, and/or mixtures thereof. For example, preventing the oxidation of a phenolic group attached to a psilocybin derivative.

As used herein, the term "oxidation" refers to the formal loss of electrons and/or the increase of the formal oxidation state and/or the addition of an oxygen atom or atoms. As used herein, "reduction" refers to the formal gain of electrons and/or the decrease of the formal oxidation state. Zumdahl, Steven S., et al. Chemistry, 7th. Cengage Learning, 2018.

In one embodiment, the methods and compositions disclosed herein comprise a pH buffer.

As used herein, the term "pH buffer" refers to a compound or a composition useful for maintaining the pH of a composition. In one embodiment, a pH buffer comprises a weak acid and a corresponding conjugate base. In one embodiment, a pH buffer comprises a weak base and a corresponding conjugate acid. In one embodiment, a pH buffer does not change the pH of a composition with the addition of a strong acid and/or base.

In one embodiment, a pH buffer maintains the pH of a composition around 7. In one embodiment, a pH buffer maintains the pH of a composition below about 7. In one embodiment, a pH buffer maintains the pH of a composition above about 7. In one embodiment, a pH buffer maintains the pH of a composition ranging from about 2 to about 6. In one embodiment, a pH buffer maintains the pH of a composition ranging from about 5 to about 7. In one embodiment, a pH buffer maintains the pH of a composition ranging from about 6 to about 8. In one embodiment, a pH buffer maintains the pH of a composition ranging from about 7 to about 10.

In one embodiment, a pH buffer comprises citric acid, acetic acid, monosodium phosphate, N-Cyclohexyl-2-aminoethanesulfonic acid, borate, hydrochloric acid, and/or sodium hydroxide.

In one embodiment, the methods disclosed herein comprise administering a composition comprising an acid.

As used herein, the term "acid" refers to a molecule or ion capable of donating a proton, i.e., $H^+$ and/or accepting electrons. In one embodiment, an "acid" refers to a Lewis acid. In one embodiment, an "acid" refers to a Bronsted acid. In one embodiment, an acid is determined by a composition's pH. In one embodiment, a pH below 7 indicates the presence of an acid.

In one embodiment, the compositions and methods disclosed herein comprise administering a formulation comprising a base.

As used herein, the term "base" refers to a molecule or ion capable of accepting a proton, i.e., an H*. In one embodiment, a "base" refers to a molecule capable of donating an electron pair, i.e., a Lewis base. In one embodiment, the presence of a base is determined by a compound's pH. In one embodiment, a pH above 7 indicates the presence of a base.

In one embodiment, the compositions and methods disclosed herein comprise administering a non water soluble composition.

In some embodiments, the compositions described herein are non-aqueous.

As used herein, the term "water soluble" refers to a compound or composition capable of dissolving in water at standard temperature and pressure. In one example, 1 g of a compound dissolves in 1 L of water. In one example, 2 g of a compound dissolves in 1 L of water. In one example, 5 g of a compound dissolves in 1 L of water. In one example, 10 g of a compound dissolves in 1 L of water. In one embodiment, a compound's solubility in water is an inherent property of a compound. In one embodiment, a compound's solubility in water is facilitated by another compound, e.g., an excipient.

In one embodiment, the compositions and methods disclosed herein comprise administering a compound of Formula I present as and/or within a homogenous mixture within a dosage formulation.

In one embodiment, the compositions and methods disclosed herein comprise administering a compound of Formula I and at least one second compound (e.g., serotonergic drug, cannabinoid, terpene, excipient, stabilizer, antioxidant, etc.) present as and/or within a homogenous mixture within a dosage formulation.

As used herein, the term "homogeneous mixture" refers to a solid, liquid, or gaseous composition that has two or more compounds present within one state or thing, e.g., a clear, colorless solution. In one embodiment, the homogeneous mixtures disclosed herein have the same proportion, concentration, and/or ratio of its components across different samples. In one embodiment, the components in the homogeneous mixture are in the same state of matter. In one embodiment, a homogeneous mixture comprises one or more compounds within a solution, e.g., a compound of Formula I and a cannabinoid within a clear solution. In one embodiment, the compositions disclosed herein are present as a homogenous mixture, e.g., a solution with no particulates, a solution with equal concentrations across samples, a powder of similar particle size, etc.

Disclosed herein is a method of modulating activity at a neurotransmitter receptor, comprising:

administering a neurotransmitter activity modulator; and administering a dosage formulation comprising a compound of Formula I to the person in need of treatment, wherein the dosage formulation modulates activity at a neurotransmitter receptor.

As used herein, the term "modulating activity of the neurotransmitter activity modulator" refers to changing, manipulating, and/or adjusting the ability of a compound or composition to affect a neurotransmitter receptor. In one embodiment, modulating the activity of a neurotransmitter activity modulator comprises administering an agonist at a neurotransmitter receptor. In one embodiment, modulating the activity of a neurotransmitter activity modulator comprises administering an antagonist at a neurotransmitter receptor.

As used herein, the term "administering" (e.g., administering a drug) refers to dosing, treating, giving, and/or providing. In one embodiment, administering a neurotransmitter activity modulator comprises providing a neurotransmitter activity modulator to an organism (e.g., a human being) with a neurotransmitter receptor. In one embodiment, administering a neurotransmitter activity modulator comprises providing a neurotransmitter activity modulator along with a compound of Formula I, e.g., a formulation having each of a neurotransmitter activity modulator and a compound of Formula I in a single dosage. In one embodiment, administering a neurotransmitter activity modulator comprises applying a transdermal composition, e.g., applying a topical composition to the skin having each of a neurotransmitter activity modulator and a compound of Formula I. In one embodiment, administering a neurotransmitter activity modulator comprises giving a transmucosal preparation, e.g., providing rapidly dissolving a tablet with an absorption enhancer having each of a neurotransmitter activity modulator and a compound of Formula I.

In one embodiment, the methods disclosed herein comprise administering a composition by inhalation for crossing a blood-brain barrier.

As used herein, the term "neurotransmitter activity modulator" refers to a compound or composition that reacts or influences activity at a neurotransmitter receptor, e.g., a compound of Formula I, a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, a neurotransmitter activity modulator binds on a neurotransmitter receptor. In one embodiment, a neurotransmitter activity modulator indirectly affects a neurotransmitter receptor, e.g., via interactions affecting the reactivity of other molecules at a neurotransmitter receptor. In one embodiment, a neurotransmitter activity modulator is an agonist. In one embodiment, a neurotransmitter activity modulator is an antagonist. In one embodiment, a neurotransmitter activity modulator acts (either directly or indirectly) at more than one type of neurotransmitter receptor.

In one embodiment, a neurotransmitter activity modulator is chosen from aripiprazole, bupropion, citalopram, clomipramine, dextroamphetamine, duloxetine, escitalopram, fluoxetine, fluvoxamine, milnacipran, mirtazapine, paroxetine, quetiapine, reboxetine, risperidone, sertraline, and venlafaxine.

As used herein, the term "first dosage formulation" refers to a compound or compounds selected for the purposes of causing a reaction, effect, and/or result, e.g., causing activity at a neurotransmitter receptor, reacting with other compounds, enhancing the effects of other active ingredients, inhibiting the biosynthesis of a compound, etc., within an organism. In one embodiment, a first dosage formulation comprises a compound of Formula I. In one embodiment, a first dosage formulation comprises a first purified cannabinoid. In one embodiment, a first dosage formulation comprises a first purified terpene. In one embodiment, a first dosage formulation comprises a compound of Formula I and a purified serotonergic derivative. In one embodiment, a first dosage formulation comprises a compound of Formula I and a first purified cannabinoid. In one embodiment, a first dosage formulation a compound of Formula I and a first purified terpene. In one embodiment, a first dosage formulation comprises a compound of Formula I, a first purified cannabinoid, and first purified terpene. In one embodiment, a first dosage formulation comprises a compound of Formula I and a neurotransmitter activity modulator.

In one embodiment, a second dosage formulation comprises a compound of Formula I.

In one embodiment, a second dosage formulation comprises a second compound of Formula I.

In one embodiment, a second dosage formulation comprises second serotonergic drug.

In one embodiment, the methods disclosed herein comprise administering a second dosage formulation. In one embodiment, the methods disclosed herein comprise administering a third dosage formulation. In one embodiment, the methods disclosed herein comprise administering a fourth dosage formulation. In one embodiment, the methods disclosed herein comprise administering more than four dosage formulations.

In certain embodiments, the dosage formulation contains a desired amount of at least one compound of Formula I. In certain embodiments, the dosage formulation contains about 0.01 to about 1,000 mg of the compound, such as about 0.1 to about 500 mg, about 0.5 to about 100 mg, or about 1 to about 50 mg. In certain embodiments, the dosage formulation is calculated to contain an amount of a compound of Formula I based on mg of compound per kg of the subject (mg/kg). In certain embodiments, the mg/kg range can be about 0.001 to about 10 mg/kg, such as about 0.01 to about 5, about 0.05 to about 4, about 0.05 to about 3, about 0.05 to about 3, about 0.05 to about 2, or about 0.05 to about 1 mg/kg. In some embodiments, the compound is dosed in an amount that is less than about 1 mg/kg, such as about 0.001 to about 0.99, about 0.01 to about 0.85, about 0.05 to about 0.75, about 0.01 to about 0.50, about 0.01 to about 0.25 or about 0.01 to about 0.10 mg/kg.

In one embodiment, the methods disclosed herein comprise administering one or more active ingredients, e.g., a compound(s) of Formula I, cannabinoids, terpenes, neurotransmitter activity modulators, etc., in more than two doses.

Disclosed herein is a method of treating a psychological problem, comprising:

identifying a person in need of treatment; and administering a compound of Formula I to the person in need of treatment, wherein the compound of Formula I modulates activity at a neurotransmitter receptor.

As used herein, the term "identifying a person in need of treatment" refers to analyzing, diagnosing, and/or determining whether a person requires treatment for a disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

As used herein, the term "psychological disorder" refers to a condition wherein a person exhibits a pattern of behavioral and/or psychological symptoms that impact multiple life areas and create distress for the person experiencing these symptoms. In one embodiment, a psychological disorder is caused by a genetic disorder. In one embodiment, a psychological disorder is caused by a biological condition, e.g., excess hormone production, a lack of activity at a neurotransmitter receptor, a lack of producing neurotransmitters, etc. In one embodiment, the neurotransmitter receptor is a serotonin receptor.

In one embodiment, the psychological problem is an anxiety disorder. In one embodiment, the psychological problem is a depressive disorder. In one embodiment, the psychological problem is a compulsive disorder. In one embodiment, the psychological problem is characterized by neurodegeneration.

As used herein, the term "anxiety disorder" refers to a state of apprehension, uncertainty, and/or fear resulting from the anticipation of an event and/or situation. An anxiety disorder can disrupt the physical and psychological functions of a person. These disruptions can cause a small hindrance to a debilitating handicap for a person's everyday life. An anxiety disorder can cause a physiological symptom, e.g., muscle tension, heart palpitations, sweating, dizziness, shortness of breath, etc. An anxiety disorder can also cause a psychological symptom, e.g., fear of dying, fear of embarrassment or humiliation, fear of an event occurring, etc.

In one embodiment, an anxiety disorder comprises acute stress disorder, anxiety due to a medical condition, generalized anxiety disorder, panic disorder, panic attack, a phobia, post-traumatic stress disorder, separation anxiety disorder, social anxiety disorder, substance-induced anxiety disorder, or selective mutism.

As used herein, the term "acute stress disorder" refers to a condition developed after exposure to one or more traumatic events. Examples of traumatic events include, but are not limited to, exposure to war, rape or sexual violence, a physical attack, a mugging, childhood physical or sexual violence, kidnapping or being taken hostage, terrorist attacks, torture, natural disasters, and/or severe accidents. In one embodiment, acute stress disorder occurs within a day of experiencing a traumatic event. In one embodiment, acute stress disorder occurs within three days of experiencing a traumatic event. In some instances, acute stress disorder occurs within a week of experiencing a traumatic event. In some instances, acute stress disorder occurs within a month of experiencing a traumatic event.

As used herein, the term "anxiety due to another medical condition" refers to a condition wherein anxiety symptoms are developed because of a physiological and psychological consequence of a non-related disease, injury, and/or illness, e.g., an endocrine disease, a cardiovascular disorder, respiratory illness, a metabolic disturbance, a neurological illness, etc.

As used herein, the term "generalized anxiety disorder" refers to a condition of persistent and excessive anxiety and worry about various domains, e.g., work, school, social settings, etc., that an individual finds difficult to control. In addition, the individual experiences physical symptoms including restlessness, alertness, and/or nervousness; being easily fatigued, difficulty concentrating or mind going blank, irritability, muscle tension, and sleep disturbance.

As used herein, the term "panic disorder" refers to a condition wherein an individual experiences recurrent and unexpected panic attacks. The individual is persistently concerned about having more panic attacks and changes his or her behavior in maladaptive ways because of these panic attacks, e.g. avoidance of exercise, unfamiliar locations, new people, etc.

As used herein, the term "panic attack" refers to an abrupt surge of intense fear or intense discomfort that reaches a peak within a short period of time, e.g., seconds, minutes, hours, etc. In some instances, a panic attack comprises a physical and/or cognitive symptom. Panic attacks may be predictable, such as in response to a typically feared object or situation. In some instances, a panic attack occurs for no apparent reason.

As used herein, the term "phobia" refers to a condition of being fearful, anxious about, or avoidant of a circumscribed object and/or situation. In some instances, a phobia comprises a fear, anxiety, or avoidance that is induced by a situation to a degree that is persistent and out of proportion to the actual risk posed. Examples of phobias include, but are not limited to, a fear or anxiety of an animal, a natural environment, an injection-injury, etc.

As used herein, the term "post-traumatic stress disorder" refers to a condition developed after experiencing and/or witnessing a traumatic event or learning that a traumatic event has happened to a loved one. In some instances, a person shows symptoms of post-traumatic stress disorder within a week of experiencing the traumatic event. In some instances, a person shows symptoms of post-traumatic stress disorder within a month of experiencing the traumatic event. In some instances, a person shows symptoms of post-traumatic stress disorder within a year of experiencing the traumatic event. In some instances, a person shows symptoms of post-traumatic stress disorder after a year or more of experiencing the traumatic event. In some instances, post-traumatic stress disorder comprises a person re-experiencing the trauma event through intrusive distressing recollections of the event, flashbacks, and/or nightmares. In some instances, a symptom of post-traumatic stress disorder comprises emotional numbness and avoidance of places, people, and activities that are reminders of the trauma. In some instances, a symptom of post-traumatic stress disorder comprises increased arousal such as difficulty sleeping and concentrating, feeling anxious, and being easily irritated and angered.

As used herein the term "neurodegeneration" refers to the progressive loss of structure or function of neurons, including but not limited to the death of neurons. Many neurodegenerative diseases—including amyotrophic lateral sclerosis, Parkinson's disease, Alzheimer's disease, and Huntington's disease—occur as a result of neurodegenerative processes. Such diseases are incurable, resulting in progressive degeneration and/or death of neuron cells. Some attempts have been made to treat such diseases and conditions using fungal and plant extracts. But those methods all suffer from a common flaw in that the fungal and/or plants extracts fail to provide consistent or reliable amounts of the therapeutic compounds on account of relying on the highly variable chemical compositions of particular naturally occurring organisms.

As used herein, the term "separation anxiety disorder" refers to a condition wherein an individual is fearful and/or anxious about separation from an attachment figure to a degree that is developmentally inappropriate. In some instances, a separation anxiety disorder comprises a fear or anxiety about harm coming to an attachment figure. In some instances, a separation anxiety disorder comprises a fear of an event leading to the loss of or separation from an attachment figure and reluctance to go away from attachment figures. In some instances, a separation anxiety disorder comprises a nightmare and/or psychical symptom of distress.

As used herein, the term "social anxiety disorder" refers to a condition wherein an individual is fearful, anxious about, or avoidant of social interactions and situations that involve the possibility of being scrutinized. These social interactions and situations include meeting unfamiliar people, situations in which the individual may be observed eating or drinking, situations in which the individual performs in front of others, etc. In some instances, a social anxiety disorder is caused by the fear of being negatively evaluated by others, by being embarrassed, humiliated, rejected, and/or offending others.

As used herein, the term "substance-induced anxiety disorder" refers to a condition wherein anxiety caused by a substance intoxication and/or a withdrawal or to a medical treatment. In some instances, a withdrawal from a substance increases anxiety.

As used herein, the term "selective mutism" refers to a condition characterized by an individual's consistent failure to speak in social situations in which there is an expectation to speak, e.g., school, a lecture, a meeting, etc., even though the individual speaks in other situations. Failure to speak has significant consequences on achievement in academics, occupational settings, and/or otherwise interferes with normal social communication.

In some instances, an anxiety disorder comprises a medical diagnosis based on the criteria and classification from the Diagnostic and Statistical Manual of Medical Disorders, 5th Ed. In some instances, an anxiety disorder comprises a medical diagnosis based on an independent medical evaluation. In some instances, an anxiety disorder comprises a medical diagnosis based on a self-evaluation.

In one embodiment, the methods and compositions disclosed herein comprise administering an anxiolytic drug.

As used herein, the term "anxiolytic drug" refers to a compound or composition that reacts or influences activity at a neurotransmitter receptor, e.g., a compound of Formula I, a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, an anxiolytic drug binds on a neurotransmitter receptor. In one embodiment, an anxiolytic drug indirectly affects a neurotransmitter receptor, e.g., via interactions affecting the reactivity of other molecules at a neurotransmitter receptor. In one embodiment, an anxiolytic drug is an agonist. In one embodiment, an anxiolytic drug is an antagonist. In one embodiment, an anxiolytic drug acts (either directly or indirectly) at more than one type of neurotransmitter receptor.

In one embodiment, an anxiolytic drug is chosen from alprazolam, an alpha blocker, an antihistamine, a barbiturate, a beta blocker, bromazepam, a carbamate, chlordiazepoxide, clonazepam, clorazepate, diazepam, flurazepam, lorazepam, an opioid, oxazepam, temazepam, or triazolam.

As used herein, the term "depressive disorder" refers to a condition of low mood and aversion to activity that can affect a person's thoughts, behavior, feelings, and sense of well-being lasting for a time period. In one embodiment, a depressive disorder disrupts the physical and psychological functions of a person. In one embodiment, a depressive disorder causes a physiological symptom, e.g., weight loss, aches or pains, headaches, cramps, digestive problems, etc. In one embodiment, a depressive disorder causes a psychological symptom, e.g., persistent sadness; anxiety; feelings of hopelessness and irritability; feelings of guilt, worthlessness, or helplessness; loss of interest or pleasure in hobbies and activities; difficulty concentrating, remembering, or making decisions, etc.

In one embodiment, a depressive disorder is chosen from atypical depression, bipolar disorder, catatonic depression, depressive disorder due to a medical condition, major depressive disorder, postpartum depression, premenstrual dysphoric disorder, or seasonal affective disorder.

As used herein, the term "atypical depression" refers to a condition wherein an individual shows signs of mood reactivity (i.e., mood brightens in response to actual or potential positive events), significant weight gain, increase in appetite, hypersomnia, heavy, leaden feelings in arms or legs, and/or long-standing pattern of interpersonal rejection sensitivity that results in significant social or occupational impairment. Exemplary symptoms of atypical depression include, but are not limited to, daily sadness or depressed mood; loss of enjoyment in things that were once pleasurable; major changes in weight (gain or loss) or appetite; insomnia or excessive sleep almost every day; a state of physical restlessness or being rundown that is noticeable by others; daily fatigue or loss of energy; feelings of hopelessness, worthlessness, or excessive guilt almost every day; problems with concentration or making decisions almost every day; recurring thoughts of death or suicide, suicide plan, or suicide attempt.

As used herein, the term "bipolar disorder" refers to a condition that causes an individual to experience unusual shifts in mood, energy, activity levels, and the ability to carry out day-to-day tasks. Individuals with bipolar disorder experience periods of unusually intense emotion, changes in sleep patterns and activity levels, and unusual behaviors. These distinct periods are called "mood episodes." Mood episodes are drastically different from the moods and behaviors that are typical for the person. Exemplary symptoms of mania, excessive behavior, include, but are not limited to, abnormally upbeat, jumpy, or wired behavior; increased activity, energy, or agitation; exaggerated sense of well-being and self-confidence; decreased need for sleep; unusual talkativeness; racing thoughts; distractibility; and poor decision-making—for example, going on buying sprees, taking sexual risks, or making foolish investments.

Exemplary symptoms of depressive episodes, low mood, include, but are not limited by, depressed mood, such as feelings of sadness, emptiness, hopelessness, or tearfulness; marked loss of interest or feeling no pleasure in all—or almost all—activities; significant weight loss, weight gain, or decrease or increase in appetite; insomnia or sleeping too much; restlessness or slowed behavior; fatigue or loss of energy; feelings of worthlessness or excessive or inappropriate guilt; decreased ability to think or concentrate, or indecisiveness; and thinking about, planning or attempting suicide.

As used herein, the term "catatonic depression" refers to a condition causing an individual to remain speechless and motionless for an extended period. Exemplary symptoms of catatonic depression include, but are not limited to, feelings of sadness, which can occur daily, a loss of interest in most activities, sudden weight gain or loss, a change in appetite, trouble falling asleep, trouble getting out of bed, feelings of restlessness, irritability, feelings of worthlessness, feelings of guilt, fatigue, difficulty concentrating, difficulty thinking, difficulty making decisions, thoughts of suicide or death, and/or a suicide attempt.

As used herein, the term "depressive disorder due to a medical condition" refers to a condition wherein an individual experiences depressive symptom caused by another illness. Examples of medical conditions known to cause a depressive disorder include, but are not limited to, HIV/AIDS, diabetes, arthritis, strokes, brain disorders such as Parkinson's disease, Huntington's disease, multiple sclerosis, and Alzheimer's disease, metabolic conditions (e.g. vitamin B12 deficiency), autoimmune conditions (e.g., lupus and rheumatoid arthritis), viral or other infections (hepatitis, mononucleosis, herpes), back pain, and certain cancers (e.g., pancreatic).

As used herein, the term "major depressive disorder" refers to a condition characterized by a time period of low mood that is present across most situations. Major depressive disorder is often accompanied by low self-esteem, loss of interest in normally enjoyable activities, low energy, and pain without a clear cause. In some instances, major depressive order is characterized by two weeks. In some instances, an individual experiences periods of depression separated by years. In some instances, an individual experiences symptom of depression that are nearly always present. Major depressive disorder can negatively affect a person's personal, work, or school life, as well as sleeping, eating habits, and general health. 2-7% of adults with major depressive disorder commit suicide, and up to 60% of people who commit suicide had a major depressive disorder or another related mood disorder. Dysthymia is a subtype of major depressive disorder consisting of the same cognitive and physical problems as a major depressive disorder with less severe but longer-lasting symptoms. Exemplary symptoms of a major depressive disorder include, but are not limited to, feelings of sadness, tearfulness, emptiness or hopelessness; angry outbursts, irritability or frustration, even over small matters; loss of interest or pleasure in most or all normal activities; sleep disturbances, including insomnia or sleeping too much; tiredness and lack of energy; reduced appetite, weight loss or gain; anxiety, agitation or restlessness; slowed thinking, speaking, or body movements; feelings of worthlessness or guilt, fixating on past failures or self-blame; trouble thinking, concentrating, making decisions, and remembering things; frequent thoughts of death, suicidal thoughts, suicide attempts, or suicide; and unexplained physical problems, such as back pain or headaches.

As used herein, the term "postpartum depression" refers to a condition as the result of childbirth and hormonal changes, psychological adjustment to parenthood, and/or fatigue. Postpartum depression is often associated with women, but men can also suffer from postpartum depression as well. Exemplary symptoms of postpartum depression include, but are not limited to, feelings of sadness, hopeless, emptiness, or overwhelmed; crying more often than usual or for no apparent reason; worrying or feeling overly anxious; feeling moody, irritable, or restless; oversleeping, or being unable to sleep even when the baby is asleep; having trouble concentrating, remembering details, and making decisions; experiencing anger or rage; losing interest in activities that are usually enjoyable; suffering from physical aches and pains, including frequent headaches, stomach problems, and muscle pain; eating too little or too much; withdrawing from or avoiding friends and family; having trouble bonding or forming an emotional attachment with the baby; persistently doubting his or ability to care for the baby; and thinking about harming themselves or the baby.

As used herein, the term "premenstrual dysphoric disorder" refers to a condition wherein an individual expresses mood lability, irritability, dysphoria, and anxiety symptoms that occur repeatedly during the premenstrual phase of the cycle and remit around the onset of menses or shortly thereafter. Exemplary symptoms of premenstrual dysphoric disorder include, but are not limited to, lability (e.g., mood swings), irritability or anger, depressed mood, anxiety, and tension, decreased interest in usual activities, difficulty in concentration, lethargy and lack of energy, change in appetite (e.g., overeating or specific food cravings), hypersomnia or insomnia, feeling overwhelmed or out of control, physical symptoms (e.g., breast tenderness or swelling, joint or muscle pain, a sensation of 'bloating' and weight gain), self-deprecating thoughts, feelings of being keyed up or on edge, decreased interest in usual activities (e.g., work, school, friends, hobbies), subjective difficulty in concentration, and easy fatigability.

As used herein, the term "seasonal affective disorder" refers to a condition wherein an individual experiences mood changes based on the time of the year. In some instances, an individual experiences low mood, low energy, or other depressive symptoms during the fall and/or winter season. In some instances, an individual experiences low mood, low energy, or other depressive symptoms during the spring and/or summer season. Exemplary symptoms of seasonal affective disorder include, but are not limited to, feeling depressed most of the day or nearly every day; losing interest in activities once found enjoyable; having low energy; having problems with sleeping; experiencing changes in appetite or weight; feeling sluggish or agitated; having difficulty concentrating; feeling hopeless, worthless, or guilty; and having frequent thoughts of death or suicide.

In one embodiment, a depressive disorder comprises a medical diagnosis based on the criteria and classification from Diagnostic and Statistical Manual of Medical Disorders, 5th Ed.

In one embodiment, a depressive disorder comprises a medical diagnosis based on an independent medical evaluation.

In one embodiment, the methods and compositions disclosed herein comprise administering an antidepressant.

As used herein, the term "antidepressant" refers to a compound or compounds that reacts or influences activity at a neurotransmitter receptor, e.g., a compound of Formula I, a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, an antidepressant binds on a neurotransmitter receptor. In one embodiment, an antidepressant indirectly affects a neurotransmitter receptor, e.g., via interactions affecting the reactivity of other molecules at a neurotransmitter receptor. In one embodiment, an antidepressant is an agonist. In one embodiment, an antidepressant is an antagonist. In one embodiment, an antidepressant acts (either directly or indirectly) at more than one type of neurotransmitter receptor.

In one embodiment, an antidepressant is chosen from bupropion, citalopram, duloxetine, escitalopram, fluoxetine, fluvoxamine, milnacipran, mirtazapine, paroxetine, reboxetine, sertraline, and venlafaxine.

Disclosed herein is a method of treating headaches and/or migraines, comprising identifying a person in need of treatment and administering a composition disclosed herein to the person in need of treatment.

Disclosed herein is a method of treating nicotine addiction, comprising identifying a person in need of treatment and administering a composition disclosed herein to the person in need of treatment.

Disclosed herein is a method of treating drug addiction, comprising identifying a person in need of treatment and administering a composition disclosed herein to the person in need of treatment.

Disclosed herein is a method of treating alcohol addiction, comprising identifying a person in need of treatment and administering a composition disclosed herein to the person in need of treatment.

The compositions disclosed herein are useful for the treatment of compulsive disorders in humans, a variety of intractable psychiatric disorders, chronic depression, post-traumatic stress disorder, and drug or alcohol dependency. The compositions disclosed herein are also useful within the context of meditative, spiritual, and religious practices within a variety of contexts.

As used herein, the term "compulsive disorder" refers to a condition wherein an individual has an obsession causing a feeling of anxiety, fear, apprehension, etc., and has a compulsion to perform tasks to relieve said feeling of anxiety. An obsession is a thought that recurs and persists despite the efforts of an individual to ignore or confront them. In some instances, an obsession is relatively vague involving a general sense of disarray or tension accompanied by a belief that life cannot proceed as normal while the imbalance remains. In other instances, an obsession is more intense and could be a preoccupation with the thought or image of someone close to them dying or intrusions related to relationship rightness. Other obsessions concern the possibility that someone or something other than oneself—such as God, the Devil, or disease—will harm either the person, the people or things that the person cares about. In some instances, individuals perform compulsive rituals because they inexplicably feel they have to. In some instances, individuals perform compulsive rituals to mitigate the anxiety that stems from a particular obsession. The person feels that these actions will somehow either prevent a dreaded event from occurring or will push the event from their thoughts.

In one embodiment, a compulsive disorder is chosen from addiction, body dysmorphic disorder, excoriation disorder, hoarding disorder, obsessive-compulsive disorder, and trichotillomania.

As used herein, the term "addiction" refers to a physical and/or psychological dependence on a substance, activity, and/or any other habit. In one embodiment, an addiction is caused by the altered brain chemistry of an individual in response to a stimulus, e.g., a substance releasing large amounts of serotonin, an activity releasing large amounts of adrenaline, etc. In one embodiment, an addiction is a dependence on a substance, e.g., a drug, an alcohol, nicotine, a food, etc. In one embodiment, an addiction is a dependence on an activity, e.g., gambling, eating, shopping, etc.

As used herein, the term "body dysmorphic disorder" refers to a condition characterized by the obsessive idea that some aspect of an individual's appearance is severely flawed and warrants exceptional measures to hide or fix it. Exemplary symptoms of body dysmorphic disorder includes, but are not limited to, being extremely preoccupied with a perceived flaw in appearance that to others can't be seen or appears minor; a belief that a defect in appearance makes an individual ugly or deformed; a belief that others take special notice of an individual's appearance in a negative way or mock the individual; engaging in behaviors aimed at fixing or hiding the perceived flaw that are difficult to resist or control, such as frequently checking the mirror, grooming, or skin picking; attempting to hide perceived flaws with styling, makeup, or clothes; constantly comparing one's appearance with others; always seeking reassurance about one's appearance from others; having perfectionist tendencies; seeking frequent cosmetic procedures with little satisfaction; avoiding social situations; and being so preoccupied with one's appearance that it causes major distress or problems in a person's social life, work, school, or other areas of functioning.

As used herein, the term "excoriation disorder" refers to a condition of having a repeated urge to pick at one's own skin. In some instances, an excoriation disorder causes a person to often to pick their skin to the extent that damage is caused.

As used herein, the term "hoarding disorder" refers to a condition of persistent difficulty in discarding or parting with possessions, regardless of their value. Exemplary symptoms of a hoarding disorder include, but are not limited to, inability to throw away possessions; severe anxiety when attempting to discard items; great difficulty categorizing or organizing possessions; indecision about what to keep or where to put things; distress, such as feeling overwhelmed or embarrassed by possessions; suspicion of other people touching items; obsessive thoughts and actions; fear of running out of an item or of needing it in the future; checking the trash for accidentally discarded objects; and functional impairments, e.g., loss of living space, social isolation, family or marital discord, financial difficulties, health hazards, etc.

As used herein, the term "obsessive-compulsive disorder" refers to a condition in which an individual has uncontrollable, reoccurring thoughts and behaviors that he or she feels the urge to repeat over and over. In some instances, an obsessive-compulsive disorder manifests itself as an individual needing to clean in order to reduce the fear that germs, dirt, or chemicals will contaminate the individual and the individual will spend many hours washing themselves or cleaning their surroundings. In some instances, an obsessive-compulsive disorder manifests itself as an individual needing to dispel anxiety. An individual may utter a name, phrase or repeat a behavior several times. The individual knows these repetitions will not actually prevent injury, but fear of harm will occur if the repetitions are not performed. In some instances, an obsessive-compulsive disorder manifests itself as an individual needing to reduce the fear of harming oneself or by others by, e.g., forgetting to lock the door or turning off appliances, developing checking rituals, etc. In some instances, an obsessive-compulsive disorder manifests itself as an individual needing to order and arrange his or her surroundings to reduce discomfort, e.g., putting objects in a certain order, arranging household items in a particular manner or in a symmetric fashion, etc. In some instances, an obsessive-compulsive disorder manifests itself as an individual needing to respond to intrusive obsessive thoughts, e.g., praying or saying phrases to reduce anxiety or prevent a dreaded future event. In some instances, obsessive-compulsive disorder is caused by another medical condition. In some instances, obsessive-compulsive disorder is caused by a substance.

As used herein, the term "trichotillomania" refers to a condition of self-induced and recurrent loss of hair, e.g., pulling one's own hair out. In some instances, trichotillomania comprises an individual pulling their hair out at one location. In some instances, trichotillomania comprises an individual pulling their hair out at multiple locations. Exemplary symptoms of trichotillomania include, but are not limited to, recurrent pulling out of one's hair resulting in noticeable hair loss; an increased sense of tension immediately before pulling out the hair or when resisting the behavior; pleasure, gratification, or relief when pulling out the hair; the disturbance is not accounted for by another mental disorder and is not due to a general medical condition (i.e., dermatological condition); repeated attempts have been made to decrease or stop hair pulling; disturbances caused significant distress or impairment in social, occupational, or other important areas of functioning; distress including feelings of loss of control, embarrassment, shame; and impairment due to avoidance of work, school, or other public situations.

In one embodiment, a compulsive disorder comprises a medical diagnosis based on the criteria and classification from Diagnostic and Statistical Manual of Medical Disorders, 5th Ed. In one embodiment, a compulsive disorder comprises a medical diagnosis based on an independent medical evaluation.

In some embodiments, the compositions described herein further comprise at least one compound not acting on a serotonin receptor.

In some embodiments, the compositions described herein comprise a serotonergic drug, wherein the serotonergic drug is selected from Formula I. In some embodiments, the composition comprises a single serotonergic drug. In some embodiments, the serotonergic drug consists essentially of a compound of Formula I.

Although the disclosed disclosure has been described with reference to various exemplary embodiments, it is to be understood that these embodiments are merely illustrative of the principles and applications of the present disclosure. Those having skill in the art would recognize that various modifications to the exemplary embodiments may be made, without departing from the scope of the disclosure.

Where reference is made to a particular compound, it should be understood that this disclosure also contemplates salts and derivatives of that compound as well as degradation products, such as oxidized versions of explicitly disclosed molecules.

Moreover, it should be understood that various features and/or characteristics of differing embodiments herein may be combined with one another. It is, therefore, to be understood that numerous modifications may be made to the illustrative embodiments and that other arrangements may be devised without departing from the scope of the disclosure.

Furthermore, other embodiments of the disclosure will be apparent to those skilled in the art from consideration of the specification and practice of the disclosure disclosed herein. It is intended that the specification and examples be considered as exemplary only, with a scope and spirit being indicated by the claims.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, the terms "about" and "approximately" mean±20%, ±10%, ±5%, or ±1% of the indicated range, value, or structure, unless otherwise indicated.

EXAMPLES

Synthetic Scheme A:

Benzothiophene and Thienopyridine Analogs

Benzothiophene and thienopyridine compounds of Formula I can be synthesized in the following exemplary manner:

Scheme 1A

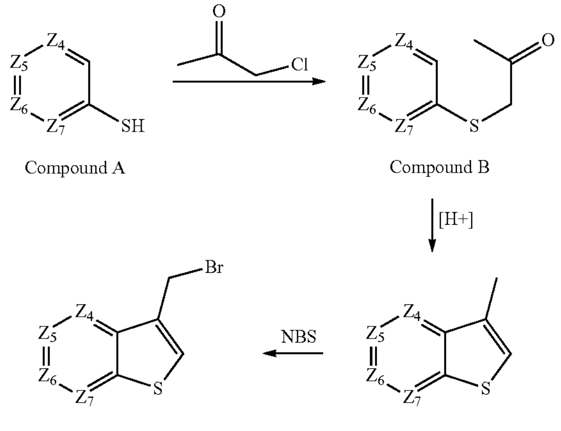

Compound A
Compound B
Compound D
Compound C

Compound A, a thiophenol starting compound, is alkylated with chloroacetone and the resulting thioether (Compound B) is cyclized under dehydrating acidic conditions to yield 3-methylbenzothiophene intermediate (Compound C). Compound C is then mono-brominated with N-bromosuccinimide (NBS) to provide the 3-bromomethylbenzothiophene, Compound D.

Scheme 2A

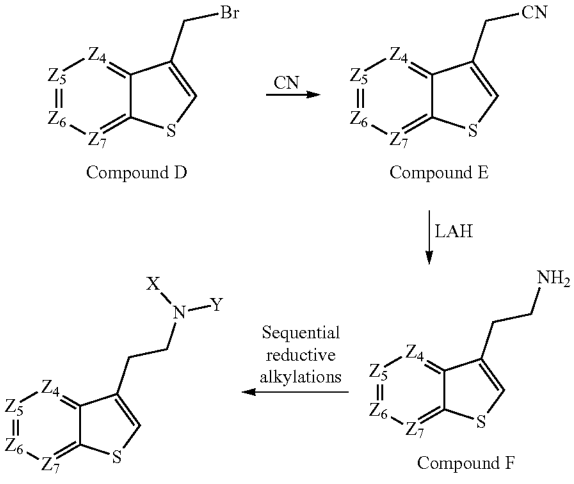

Compound D
Compound E
Compound F
Compound G

The nitrile intermediate, Compound E, is prepared by nucleophilic displacement of bromine of Compound D with cyanide. The nitrile group is then reduced with lithium aluminum hydride in $Et_2O$ to provide 3-aminoethylbenzothiophene intermediate Compound F. From there, a single reductive alkylation can be formed using the corresponding aldehyde X—CHO in a suitable solvent (e.g., THF, DCM, etc.) to form secondary aminic residues and compounds such as Refs. 319 and 320 listed in Table 1. Subsequent reductive alkylation using aldehyde Y—CHO can be used to prepare the dialkylated variants of Compound G.

Scheme 3A

Numerous variations of benzothiophene and thienopyridine compounds of the present disclosure, including compounds generally represented by Compound H, may be synthesized from starting materials purchased commercially from companies such as Sigma-Aldrich® (e.g., benzothiophene, 2-methylthianaphthene, benzothiophene-2-methanol), Fisher Scientific® (e.g., 5-methylbenzothiophene), SpiroChem (e.g., 7-methoxy-5-methylbenzothiophene), and then used in accordance with the methods set forth in Zhang et al., *J. Org. Chem.* 2000, 65, 4732-4735, which is incorporated herein by reference in its entirety. That exemplary scheme is set out below, wherein $X_1$ is an alkyl group (e.g., $C_1$-$C_8$ alkyl such as methyl or ethyl) derived from the corresponding alkyl glyoxylate:

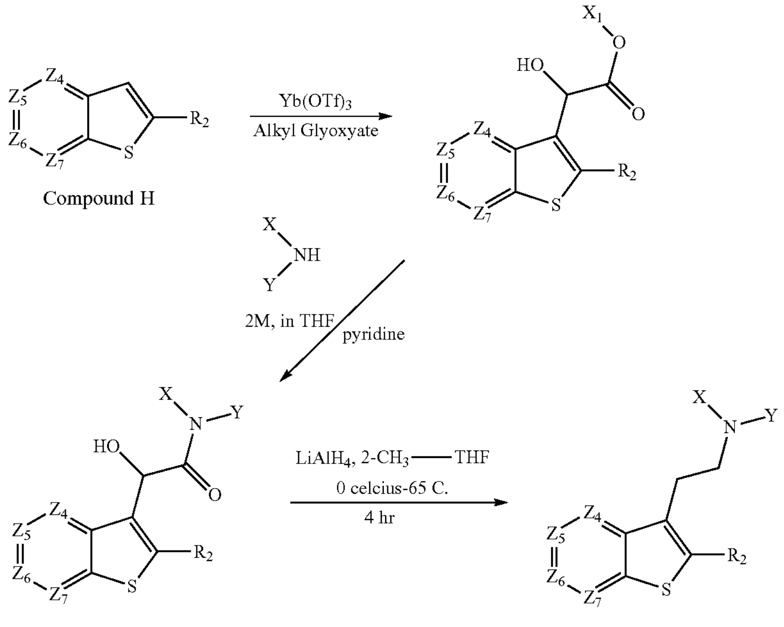

In some embodiments, compounds of Formula I wherein $W_1$ is S(O) or $SO_2$, such compounds may be prepared by commencing with the thio precursors of those compounds (i.e., wherein $W_1$=S) and subjecting the thio precursors to oxidative conditions, such as those set forth in Thiemann et al., "The chemistry of thiophene S-oxides and related compounds," *Issue 5th Eurasian Conference on Heterocyclic Chemistry*, ARKIVOC 2009 (ix) 96-113, incorporated herein by reference for all purposes.

Example 1A. Production of 4-methoxy-3-N,N-dimethylaminoethylbenzothiophene (aka 4-methoxy Thiopsil™)

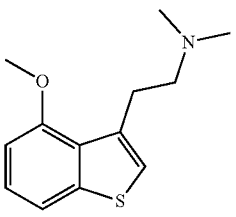

4-methoxy Thiopsil™

3-methoxythiophenol is used as Compound A and carried through Scheme 1A to provide 4-methoxy-3-bromomethyl benzothiophene (used as Compound D). Through Scheme 2A, Compound D is reacted a cyanide salt to provide 4-methoxy-3-cyanomethyl benzothiophene (used as Compound E). Compound E is then reduced with $LiAlH_4$ to provide 4-methoxy-3-aminoethyl benzothiophene (Compound F), which is then reductively alkylated using the corresponding aldehydes X—CHO and Y—CHO in two separate steps using a suitable solvent (e.g., THF, DCM, etc.), followed by aqueous workup of the crude reaction mixture, and purification via silica gel column chromatography, to provide 4-methoxy-3-N,N-dimethylaminoethylbenzothiophene.

Example 2A. Production of 4-hydroxy-3-N,N-dimethylaminoethylbenzosthiophene (aka Thiopsil™)

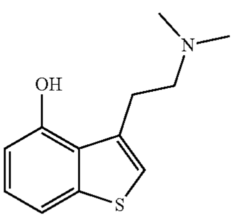

Thiopsil™

To a suspension of NaH (0.024 mol) in 25 ml of dry DMF, ethanethiol (0.024 mol) is added at 0° C. under nitrogen and vigorous stirring. After 1 h a solution of the Example 1 product (0.01 mol) in 20 ml of dry DMF is added all at once and the reaction mixture is refluxed for 1 h. The solvent is removed under vacuum and the residue is purified via silica gel column chromatography (EtOAC/hexanes) to provide 4-hydroxy-3-N,N-dimethylaminoethylbenzothiophene (aka Thiopsil).

Example 3A. Production of 4-acetoxy-3-N,N-dimethylaminoethylbenzothiophene (aka Thiopsilacetin™)

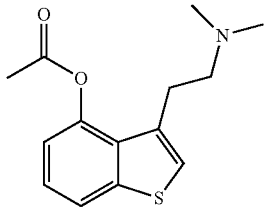

Thiopsilacetin™

To a solution of the product of Example 2A (0.01 mol) in pyridine under a nitrogen blanket and stirred at 25° C. is added a catalytic amount of DMAP and $Ac_2O$ (0.011 mol) in pyridine (0.012 mol). Stirring is continued for 1 hr. After quenching with aqueous workup, the solvent is removed under vacuum and the residue is purified via silica gel column chromatography to provide Thiopsilacetin.

Example 4A. Production of 5-methoxy-3-N,N-dimethylaminoethylbenzothiophene (aka Bufothiophene™)

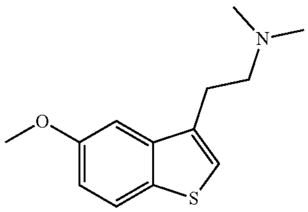

Bufothiophene™

The synthetic procedure of Example 1A is repeated with 4-methoxythiophenol acid as the starting material to yield 5-methoxy-3-N,N dimethylaminoethylbenzothiophene.

Example 5. Production of N-isopropyl-N-methylaminoethylbenzothiophene

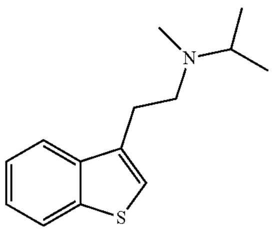

The synthetic procedure of Example 11A was repeated with using isopropylmethylamine as the secondary amine to provide N-isopropyl-N-methylaminoethylbenzothiophene.

Example 6A. Production of N-ethyl-N-methylaminoethylbenzothiophene

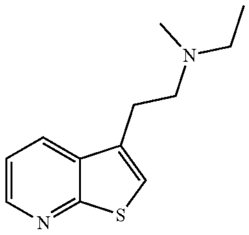

The synthetic procedure of Example 1A is repeated with 2-mercaptopyridine as the starting material and $CH_3$—CHO and $CH_3CH_2$—CHO as the alkylating agents, yielding the N-ethyl-N-methylaminoethylthiopheno[2,3-b]pyridine target compound.

Example 7A. Production of N-ethyl-N-propylaminoethylbenzothiophene

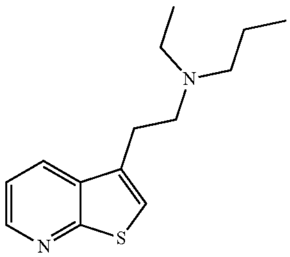 [SMILES: CCCN(CC)CCc1csc2ncccc12]

The synthetic procedure of Example 1A is repeated with 2-amino-3-pyridinecarboxylic acid as the starting material and $CH_3CH_2$—CHO and $CH_3(CH_2)_2$—CHO as the alkylating agents to yield the N-ethyl-N-propylaminoethylthiopheno[2,3-b]pyridine target compound.

Example 8A. Production of 3-(N,N-dimethylaminoethyl)benzo[b]thiophen-4-yl phosphate (aka Thiocybin™)

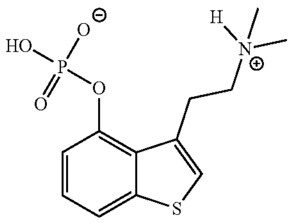

Thiocybin™

A 2000 mL, four-necked, round-bottomed flask is equipped with an overhead stirrer, J-Kem temperature controller, a 100 mL dropping funnel, and rubber septum through which a positive pressure of dry $N_2$ is inserted. The septum is removed and the flask is charged sequentially with Thiopsil produced in accordance with the method of Example 2A (60.2 mmol) and anhyd THE (500 mL). The mixture is stirred for 15 min and the flask is immersed in a solid $CO_2$/acetone cooling bath at −78° C. When the internal temperature of the reaction reaches −67° C., a solution of 2.5 M BuLi in hexanes (28.9 mL, 72.3 mmol) is added dropwise over a period of a few min and maintained at an internal temperature reading below −60° C. After stirring the reaction mixture for 10 min, tetrabenzyl pyrophosphate (35.7 g, 66.2 mmol) is added in one portion and the mixture is stirred well. After 1.5 h, the solid $CO_2$/acetone cooing bath is removed and the temperature is allowed to slowly rise to −25° C. over 2 h.

Amino bound silica gel (30 g) is added in one portion and the reaction is diluted with EtOAc (600 mL). The mixture is filtered through a pad of Celite and washed with EtOAc (400 mL). The filter cake is reslurried for 10 min with EtOAc (400 mL) and again filtered. The combined filtrates are concentrated and transferred into a 500 mL single-necked roundbottom flask. If necessary, the resulting oil is redissolved in DCM (100 mL) and heated with a heat gun to boiling for 5 min. The flask is allowed to reach rt and then held at 4° C. overnight. The crude reaction product (zwitterion precipitate) is filtered via Büchner funnel, then triturated with DCM (4 Å~100 mL). The zwitterion precipitate is then transferred into a 250 mL single-necked round-bottomed flask and thoroughly dried in the vacuum oven at 40° C. overnight to provide benzyl {3-[2-(Benzyldimethyl-ammonio)ethyl]-benzo[b]thiophen-4-yl}Phosphate.

Into a 2000 mL round-bottomed flask is added the benzyl phosphate product produced according to the method in the preceding paragraph (35.6 mmol) followed by $CH_3OH$ (1200 mL). The mixture is degassed and refilled with $N_2$. 10% Pd/C (1.1 g) is added and the mixture is degassed and refilled with a $H_2$ balloon at 1 atm. The reaction mixture is stirred overnight at rt. The flask is degassed, refilled with $N_2$ and the suspension is filtered through a pad of Celite via Büchner funnel. The filter pad is washed with $CH_3OH$ (500 mL) and the filtrate is concentrated and dried overnight under vacuum to give a crude solid. The crude solid is suspended in i-PrOH (200 mL) and boiled for 30 min, then filtered hot (50 to 60° C.). The collected solid is washed with acetone to give a colored solid. The solid is then suspended in 25% $CH_3OH$/i-PrOH and boiled for 30 min and filtered hot, washing with 25% $CH_3OH$/i-PrOH to give a colored solid, which is the Thiocybin product.

Example 9A. Production of N-ethyl-N-methylaminoethylbenzothiophene

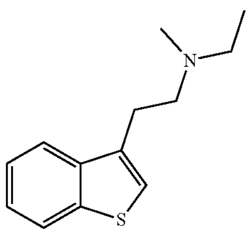

The synthetic procedure of Example 16A was repeated using ethylmethylamine as the secondary amine to provide the desired product in good purity.

Example 10A. Production of N-ethyl-N-propylaminoethylbenzothiophene

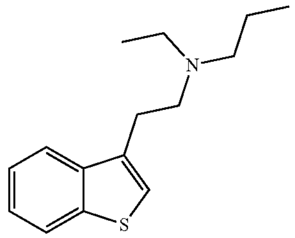 [SMILES: CCCN(CC)CCc1csc2ccccc12]

The synthetic procedure of Example 11A was repeated with using ethyl-n-propylamine as the secondary amine to provide N-ethyl-N-propylaminoethylbenzothiophene.

Example 11A. Production of N-methyl-N-n-propylaminoethylbenzothiophene

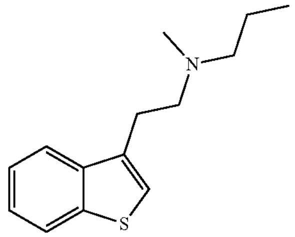 [SMILES: CCCN(C)CCc1csc2ccccc12]

Benzo[b]thiophene (1 eq.) was charged under nitrogen to a dry reaction flask equipped with a glass stir bar and containing 5 mol % ytterbium triflate. Excess ethyl glyoxylate was distilled (according to the method set forth below*) and collected directly into the reaction flask. The reaction was stirred under nitrogen at room temperature for 24 hrs. The resulting crude ester intermediate was concentrated under vacuum and purified via flash chromatography using 5:1 EtOAc:hexanes.

Purified ester intermediate was charged to a dry reaction flask under nitrogen followed by anhydrous methanol and 1.2 eq of the secondary amine methyl n-propylamine. The reaction was stirred at room temperature for 24 hrs or until the ester was consumed as judged by TLC (9:1 DCM:MeOH).

Crude, dry hydroxy amide intermediate was charged under nitrogen to a reaction flask containing a stir bar. To this was added 2Me-THF followed by 3 eq of $LiAlH_4$ as a 2.0 M Solution of $LiAlH_4$ in 2Me-THF over the course of 1 minute. The reaction exothermed slightly and was then heated to 65° C. for 4 hrs. The reaction mixture was then cooled to 0-20° C. and quenched slowly with THF/$H_2O$ (4:1) under stirring for about 30 mins. The reaction mixture was then carefully diluted with DCM/MeOH (9:1) and then filtered through a pad of celite. The filtered solution was then concentrated under reduced pressure and purified via flash chromatography using 5:1 EtOAc:hexanes to provide the desired product as a colorless oil.

*50% ethyl glyoxylate oligomer in toluene (Fluka) was distilled at atmospheric pressure using a short (2 in) Vigreaux column and oil bath temperature 130-185° C. (gradually increased over 30 min period) until only a small residue remained. First few mL were discarded, and then the entire volume collected. The obtained yellowish distillate containing toluene-ethyl glyoxylate mixture was immediately re-distilled at 30 Torr. After toluene reaction, pure ethyl glyoxylate distilled at 48-50° C./30 Torr.

Example 12A. Production of N-ethylaminoethylbenzothiophene

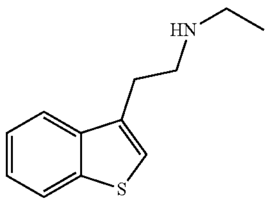

To a vigorously stirred solution of the carbaldehyde prepared according to the method of Example 15A (1 mmol) in MeCN (10 mL) at 0° C. was added $EtNH_3Cl$ (5 mmol) and NaOAc (5 mmol). The reaction mixture was allowed to stir at 0° C. for 15 min before addition of an excess of $NaHB(OAc)_3$. The reaction mixture was stirred at 0° C. for 5 hours before being allowed to warm slowly to room temperature overnight. The reaction mixture was quenched by the addition of 1 M HCl and diluted with diethyl ether. The phases were separated and the organic phase washed with 1M HCl (×2). The combined acidic aqueous phases were basified by the addition of solid NaOH. The aqueous phase was extracted with DCM (×3-5), dried over anhydrous sodium sulfate. After filtration the solvent was removed in vacuo to afford a crude oil.

The target compound was purified by silica gel column chromatography (load with DCM, elute with 1% MeOH/DCM then 5% MeOH/DCM doped with 1% $NEt_3$) as a tannish solid.

Example 13A. Production of N-isopropylaminoethylbenzothiophene

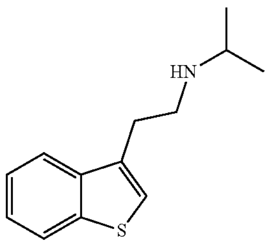

The synthesis of Example 16A was repeated and isopropylamine was used as the amine, to afford the target compound as a tannish semisolid in 65% yield.

Example 14A. Production of N-cyclopropylaminoethylbenzothiophene

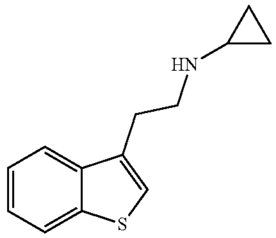 [SMILES: c1ccc2c(CCNC3CC3)csc2c1]

The synthetic procedure of Example 16A is repeated, except the secondary amine is replaced with cyclopropylamine to yield the desired product.

Example 15A. Production of Benzothiophene Extended Carbaldehyde Intermediate

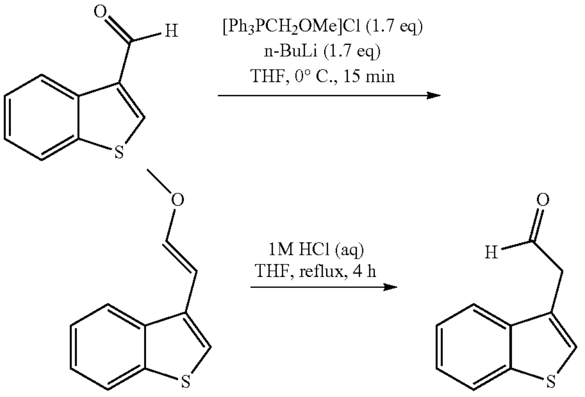

To a stirred suspension of Wittig salt (3.60 g, 10.5 mmol, 1.7 eq) in THF at 0° C. was added a solution n-BuLi (4.2 mL, 10.5 mmol, 1.7 eq, 2.5 M in hexane) dropwise. The resulting reaction mixture turned homogenous and red. Carbaldehyde (1.0 g, 6.2 mmol, 1.0 eq) was added as a solid at once to the reaction mixture. After 15 min, the reaction mixture was diluted by with diethyl ether and quenched with 1 M HCl (aq). The phases were separated and the aqueous extracted with diethyl ether (×2). The combined organic extracts were washed with water and brine and dried over anhydrous sodium sulfate. After filtration, the solvent was removed in vacuo. The enol ether could be isolated from the crude by column chromatography (load with PhMe, elute with 0 to 5% ethyl acetate in hexane) as a pale-yellow oil (862 mg, 73%).

To a solution of enol ether (607 mg, 3.19 mmol, 1.0 eq) in THF (12.8 mL) was added 1 M HCl (aq., 19.2 mL). The reaction mixture was refluxed for 4 hours before cooling to room temperature and diluting with water and diethyl ether. The phases were separated and the aqueous extracted with diethyl ether (×2). The combined organic extracts were washed with water and brine and dried over anhydrous sodium sulfate. After filtration, the solvent was removed in vacuo to afford a crude oil (553 mg) that was the desired extended carbaldehyde.

Example 16A. Production of N,N-Dimethylaminoethylbenzothiophene

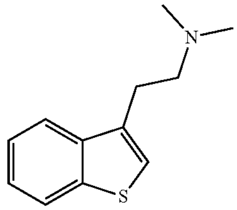

To a solution of the target extended carbaldehyde produced according to the method of Example 15A (1.0 eq) in acetonitrile (0.1 M) was added dimethylamine (2-5 eq) and a few beads of activated whole 3A MS. After stirring at room temperature for 10 min, $NaHB(OAc)_3$ (>5 eq) was added at once. The reaction mixture was allowed to stir 18-24 hours at room temperature before being quenched by the addition of 1M HCl and diluted with diethyl ether. The phases were separated, and the organic phase washed with 1M HCl (×2). The combined aqueous phases were basified by the addition of solid NaOH. The aqueous phase was extracted with DCM (×3) and the combined DCM washes were dried over anhydrous sodium sulfate. Analytical purity was achieved by purification on column chromatography (DCM to 1% MeOH/DCM to remove major impurities, then eluted with 5% MeOH/DCM doped with ~1% $NEt_3$) to afford the product as a colorless oil.

Example 17A. Production of N-isopropyl-N-methylaminoethylbenzothiophene

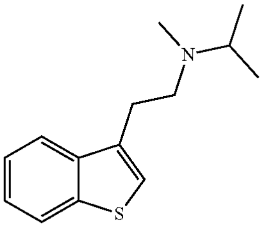 [SMILES: CC(C)N(C)CCc1csc2ccccc12]

The synthetic procedure of Example 16A was repeated using isopropylmethylamine as the secondary amine to provide the desired product as a colorless oil in 68% yield.

Example 18A. Production of N-methylaminoethylbenzothiophene

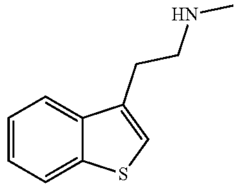

The method of Example 12A was repeated using methylamine hydrochloride as the primary amine to afford target compound in 61% yield as an off-white solid.

Example 19A. Production of Hydrofumarate Salts (Aka [1:1] Fumarate Salts)

[1:1]hydrofumarate salts of each one of the compounds are separately produced from the compounds of Examples 1-7A, 9-14A, and 16-18A using the following procedure:

1 equiv of the free base product is dissolved in acetone and is added dropwise to a boiling solution of fumaric acid (1 equiv) in acetone. A precipitate forms immediately and the precipitate/acetone is stored overnight at −20° C. The solids are then filtered and washed with ice-cold acetone to yield the desired crystalline hydrofumarate salt.

Example 20A. Production of Fumarate Salts (Aka [2:1] Fumarate Salts)

[2:1] fumarate salts of each one of the compounds are separately produced from the compounds of Examples 1-7A, 9-14A, and 16-18A using the following procedure:

1 equiv of the free base product is dissolved in acetone and is added dropwise to a boiling solution of fumaric acid (0.5 equiv) in acetone. A precipitate forms immediately and the precipitate/acetone is stored overnight at −20° C. The solids are then filtered and washed with ice-cold acetone to yield the desired crystalline fumarate salt.

Synthetic Scheme B:

Benzoselenophene and Selenophenopyridine Analogs

As illustrated below, Compound A starting material can be converted into benzoselenophene and selenophenopyridine compounds of Formula I:

Scheme 1B

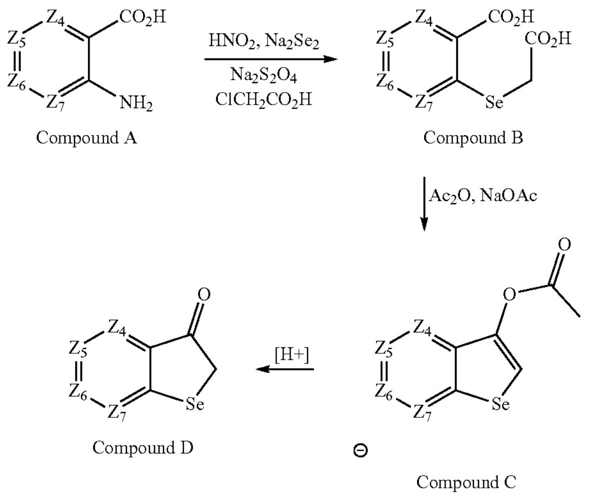

Compound A, a 2-amino benzoic acid (aka anthranilic acid analog) starting compound, is treated with $HNO_2$ (from HCl and $NaNO_2$) to form the diazonium salt in situ. From there, the in situ diazonium salt is treated with $Na_2Se_2$ (prepared from NaOH, water, Se, and rongalite), and after 1 hr activated charcoal is added and the basic solution is filtered. After acidification with conc. HCl, the crude product is filtered, washed with water and oven dried to yield a cream-powder (which may turn red on standing). This diselenide is then dissolved in NaOH and anhydrous $Na_2CO_3$ is added. The solution is warmed to 70° C. and $Na_2S_2O_4$ is introduced. The mixture is refluxed for 1 h, cooled to 60° C., and a neutral aqueous solution of chloroacetic acid is added and refluxed for 2 h. After cooling, concentrated HCl is added until pH=1, and the precipitate is collected and washed with water. Recrystallization yields diacid intermediate Compound B.

Compound B is then mixed with acetic anhydride and dry sodium acetate under reflux for 2 h. After elimination of the reagents and usual work-up, the solid residue is purified by liquid chromatography and recrystallized to provide acetate intermediate Compound C. From there, Compound C is treated with HCl under reflux for 3 h. After elimination of the solvent and usual work-up, the selenoindoxyl Compound D is purified by silica gel column chromatography.

Scheme 2B

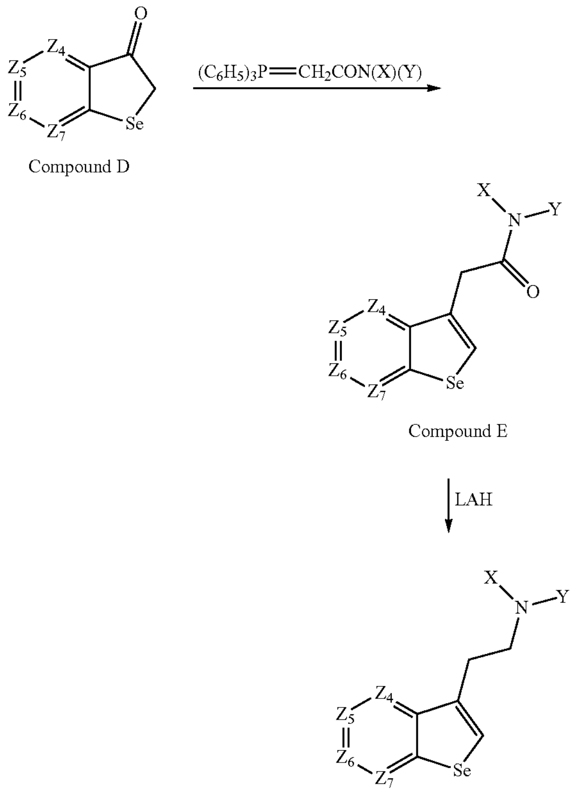

Compound D

Compound E

Compound F

Dialkylcarbamoylmethylenetriphenylphosphorane preparation: a solution of triphenylphosphine and the desired dialkylchloroacetamide is refluxed conditions for 2 h. After cooling the solid is filtered and air dried. White crystals of the phosphonium salt intermediate are obtained. The phosphonium salt is suspended in water and $CHCl_3$. After dropwise addition of NaOH, the mixture is vigorously stirred for 2 h. After decantation and elimination of the solvent, the solid is recrystallized to provide the phosphorane intermediate.

The selenoindoxyl intermediate, Compound D, is combined with the phosphorane and refluxed in dry toluene for 24 h under nitrogen. After elimination of the solvent, the residue is recrystallized to provide amide Compound E, which can be further purified by chromatography.

To a suspension of LiAlH in dry THE (50 ml) a solution of amide Compound E in dry THE is added dropwise. The mixture is refluxed for 1 h, cooled (0° C.) and hydrolyzed successively water and NaOH. After filtration of the salts, the cake is washed with THE and the organic phases are dried and evaporated under vacuum to yield Compound F.

In certain embodiments, Compound F may comprise an alkoxy group (e.g., methoxy) at $R_4$ or $R_5$. To convert the alkoxy residue to a hydroxyl group, Compound F can be treated NaH in dry DMF, with ethanethiol being added at 0° C. under nitrogen and vigorous stirring. After 1 h a solution of Compound F in dry DMF is added all at once and the reaction mixture is refluxed for 1 h. The solvent is removed under vacuum and the residue is diluted with water. Extraction and column chromatography can provide purified compound.

Scheme 3B

Numerous variations of benzoselenophene and selenophenopyridine compounds of the present disclosure, including compounds generally represented by Compound H, may be synthesized from starting materials purchased commercially from companies such as Accela® (e.g., benzoselenophene), and then used in accordance with the methods set forth in Zhang et al., *J. Org. Chem.* 2000, 65, 4732-4735, which is incorporated herein by reference in its entirety. That exemplary scheme is set out below, wherein $X_1$ is an alkyl group (e.g., $C_1$-$C_8$ alkyl such as methyl or ethyl) derived from the corresponding alkyl glyoxylate:

Scheme 4B

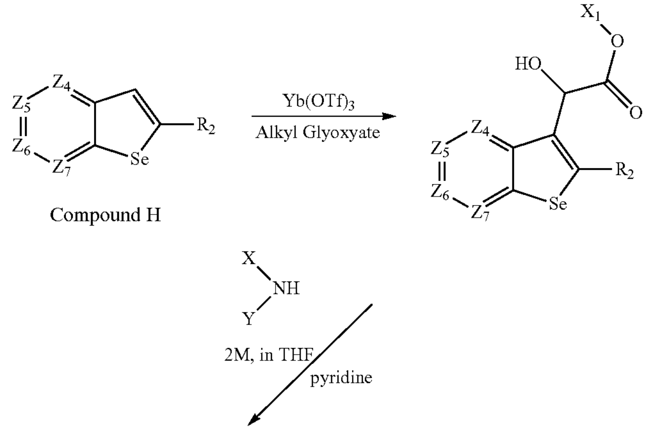

Compound H

-continued

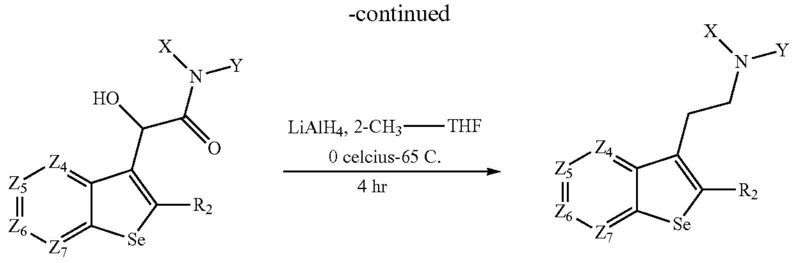

Numerous variations of benzoselenophene and selenophenopyridine compounds of the present disclosure, including compounds generally represented by Compound O, may be synthesized from starting materials purchased commercially from companies such as Accela® (e.g., bromobenzene), and then used in accordance with the methods set forth in E. Paegle, et al., *Chem Asian J*2016 *Vol.* 11 *Issue* 13 Pages 1929-38 which is incorporated herein by reference in its entirety. The exemplary scheme is set out below.

Scheme 4B

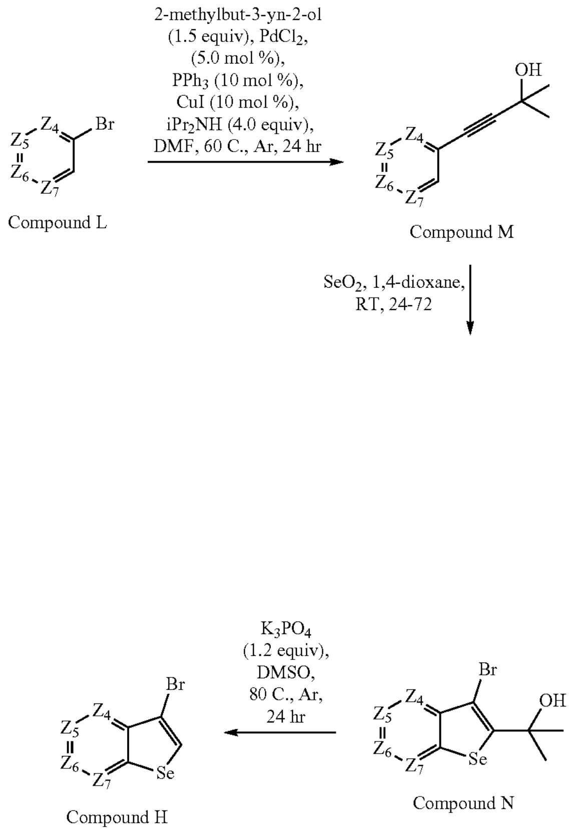

Compound L

Compound M

Compound N

Compound H

In some embodiments, compounds of Formula I wherein $W_1$ is Se(O) or $SeO_2$, such compounds may be prepared by commencing with the seleno precursors of those compounds (i.e., wherein $W_1$=Se) and subjecting the seleno precursors to oxidative conditions, such as those set forth in Nakayama et al., "Oxidation of Tetraarylselenophenes and Benzo[b] selenophene with m-Chloroperbenzoic Acd," *Chemistry Letters,* 495 (1995), incorporated herein by reference for all purposes.

Example 1B. Production of 4-methoxy-3-N,N-dimethylaminoethylbenzoselenophene (aka 4-methoxy Selenopsil™)

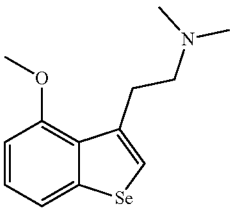

4-methoxy Selenopsil™

6-methoxyanthranilic acid is used as Compound A and carried through Scheme 1B to provide 4-methoxybenzo[b] selenophen-3(2h)-one (used as Compound D). Through Scheme 2B, Compound D is reacted with the desired phosphorane, which is prepared from triphenylphosphine and dimethylchloroacetamide, to provide 4-methoxy-N,N-dimethylbenzo[b]selenophene-3-acetamide (used as Compound E). Compound E is then reduced with $LiAlH_4$ to complete Scheme 2 and provide a crude reaction mixture of 4-methoxy Selenopsil, which is quenched, extracted via aqueous workup, and purified via silica gel column chromatography (EtOAC/hexanes) to provide 4-methoxy-3-N, N-dimethylaminoethylbenzoselenophene.

Example 2B. Production of 4-hydroxy-3-N,N-dimethylaminoethylbenzoselenophene (aka Selenopsil™)

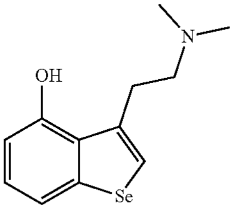

Selenopsil™

To a suspension of NaH (0.024 mol) in 25 ml of dry DMF, ethanethiol (0.024 mol) is added at 0° C. under nitrogen and vigorous stirring. After 1 h a solution of the Example 1 product (0.01 mol) in 20 ml of dry DMF is added all at once and the reaction mixture is refluxed for 1 h. The solvent is removed under vacuum and the residue is purified via silica gel column chromatography (EtOAC/hexanes) to provide 4-hydroxy-3-N,N-dimethylaminoethylbenzoselenophene (aka Selenopsil).

Example 3B. Production of 4-acetoxy-3-N,N-dimethylaminoethylbenzoselenophene (aka Selenopsilacetin™)

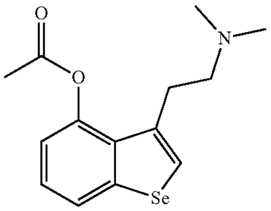

Selenopsilacetin™

To a solution of the product of Example 2B (0.01 mol) in pyridine under a nitrogen blanket and stirred at 25° C. is added a catalytic amount of DMAP and $Ac_2O$ (0.011 mol) in pyridine (0.012 mol). Stirring is continued for 1 hr. After quenching with aqueous workup, the solvent is removed under vacuum and the residue is purified via silica gel column chromatography to provide Selenopsilacetin.

Example 4B. Production of 5-methoxy-3-N,N-dimethylaminoethylbenzoselenophene (aka Bufoselenophene™)

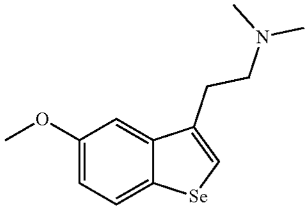

Bufoselenophene™

The synthetic procedure of Example 1B is repeated with 5-methoxyanthranilic acid as the starting material to yield 5-methoxy-3-N,N dimethylaminoethylbenzoselenophene.

Example 5B. Production of N-isopropyl-N-methylaminoethylbenzoselenophene

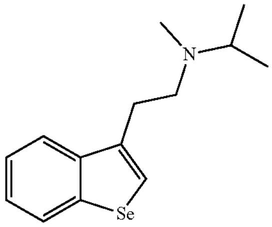 [SMILES: CC(C)N(C)CCc1c[se]c2ccccc12]

The synthetic procedure of Example 11B was repeated with using isopropylmethylamine as the secondary amine to provide the N-isopropyl-N-methylaminoethylbenzoselenophene target compound.

Example 6B. Production of N-ethyl-N-methylaminoethylbenzoselenophen[2,3-b]pyridine

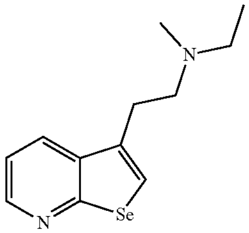

The synthetic procedure of Example 1B is repeated with 2-amino-3-pyridinecarboxylic acid as the starting material and 2-chloro-N-ethyl-N-methylacetamide to form the desired phosphorane, ultimately yielding the N-ethyl-N-methylaminoethylselenopheno[2,3-b]pyridine target compound.

Example 7B. Production of N-ethyl-N-propylaminoethylbenzoselenopheno[2,3-b]pyridine

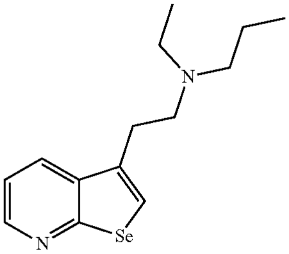 [SMILES: CCCN(CC)CCc1c[se]c2ncccc12]

The synthetic procedure of Example 1B is repeated with 2-amino-3-pyridinecarboxylic acid as the starting material and 2-chloro-N-ethyl-N-propylacetamide to form the desired phosphorane, ultimately yielding the N-ethyl-N-propylaminoethylselenopheno[2,3-b]pyridine target compound.

Example 8B. Production of 3-(N,N-dimethylaminoethyl)benzo[b]selenophen-4-yl phosphate (aka Selenocybin™)

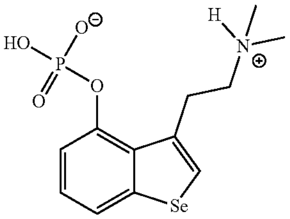

Selenocybin™

A 2000 mL, four-necked, round-bottomed flask is equipped with an overhead stirrer, J-Kem temperature controller, a 100 mL dropping funnel, and rubber septum through which a positive pressure of dry $N_2$ is inserted. The septum is removed and the flask is charged sequentially with Selenopsil produced in accordance with the method of Example 2 (60.2 mmol) and anhyd THE (500 mL). The mixture is stirred for 15 min and the flask is immersed in a solid $CO_2$/acetone cooling bath at −78° C. When the internal temperature of the reaction reaches −67° C., a solution of 2.5 M BuLi in hexanes (28.9 mL, 72.3 mmol) is added dropwise over a period of a few min and maintained at an internal temperature reading below −60° C. After stirring the reaction mixture for 10 min, tetrabenzyl pyrophosphate (35.7 g, 66.2 mmol) is added in one portion and the mixture is stirred well. After 1.5 h, the solid $CO_2$/acetone cooing bath is removed and the temperature is allowed to slowly rise to −25° C. over 2 h.

Amino bound silica gel (30 g) is added in one portion and the reaction is diluted with EtOAc (600 mL). The mixture is filtered through a pad of Celite and washed with EtOAc (400 mL). The filter cake is reslurried for 10 min with EtOAc (400 mL) and again filtered. The combined filtrates are concentrated and transferred into a 500 mL single-necked roundbottom flask. If necessary, the resulting oil is redissolved in DCM (100 mL) and heated with a heat gun to boiling for 5 min. The flask is allowed to reach rt and then held at 4° C. overnight. The crude reaction product (zwitterion precipitate) is filtered via Büchner funnel, then triturated with DCM (4 Å~100 mL). The zwitterion precipitate is then transferred into a 250 mL single-necked round-bottomed flask and thoroughly dried in the vacuum oven at 40° C. overnight to provide benzyl {3-[2-(Benzyldimethylammonio)ethyl]-benzo[b]selenophen-4-yl}Phosphate.

Into a 2000 mL round-bottomed flask is added the benzyl phosphate product produced according to the method in the preceding paragraph (35.6 mmol) followed by $CH_3OH$ (1200 mL). The mixture is degassed and refilled with $N_2$. 10% Pd/C (1.1 g) is added and the mixture is degassed and refilled with a $H_2$ balloon at 1 atm. The reaction mixture is stirred overnight at rt. The flask is degassed, refilled with $N_2$ and the suspension is filtered through a pad of Celite via Büchner funnel. The filter pad is washed with $CH_3OH$ (500 mL) and the filtrate is concentrated and dried overnight under vacuum to give a crude solid. The crude solid is suspended in i-PrOH (200 mL) and boiled for 30 min, then filtered hot (50 to 60° C.). The collected solid is washed with acetone to give a colored solid. The solid is then suspended in 25% $CH_3OH$/i-PrOH and boiled for 30 min and filtered hot, washing with 25% $CH_3OH$/i-PrOH to give a colored solid, which is the Selenocybin product.

Example 9B. Production of N-ethyl-N-methylaminoethylbenzoselenophene

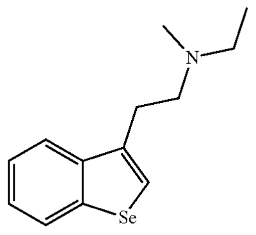

The synthesis of Example 16A was repeated, except the extended carbaldehyde of Example 16B was used as the starting material and ethylmethylamine was used as the secondary amine, to afford the target compound as a brownish oil in 62% yield.

Example 10B. Production of N-ethyl-N-propylaminoethylbenzoselenophene

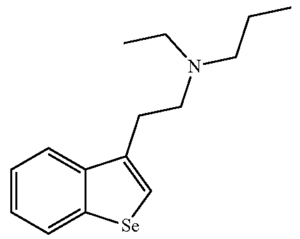 [SMILES: CCCN(CC)CCc1c[se]c2ccccc12]

The synthetic procedure of Example 11B was repeated with using ethyl-n-propylamine as the secondary amine to provide the N-ethyl-N-propylaminoethylbenzoselenophene target compound.

Example 11B. Production of N-methyl-N-n-propylaminoethylbenzoselenophene

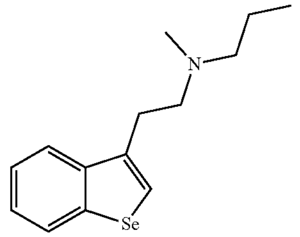 [SMILES: CCCN(C)CCc1c[se]c2ccccc12]

Benzo[b]selenophene (1 eq.) was charged under nitrogen to a dry reaction flask equipped with a glass stir bar and containing 5 mol % ytterbium triflate. Excess ethyl glyoxylate was distilled (according to the method set forth below*) and collected directly into the reaction flask. The reaction was stirred under nitrogen at room temperature for 24 hrs. The resulting crude ester intermediate was concentrated under vacuum and purified via flash chromatography using 5:1 EtOAc:hexanes.

Purified ester intermediate was charged to a dry reaction flask under nitrogen followed by anhydrous methanol and 1.2 eq of the secondary amine methyl n-propylamine. The reaction was stirred at room temperature for 24 hrs or until the ester was consumed as judge by TLC (9:1 DCM:MeOH).

Crude, dry hydroxy amide intermediate was charged under nitrogen to a reaction flask containing a stir bar. To this was added 2Me-THF followed by 3 eq of $LiAlH_4$ as a 2.0 M Solution of $LiAlH_4$ in 2Me-THF over the course of 1 minute. The reaction exothermed slightly and was then heated to 65° C. for 4 hrs. The reaction mixture was then cooled to 0-20° C. and quenched slowly with THF/$H_2O$ (4:1) under stirring for about 30 mins. The reaction mixture was then carefully diluted with DCM/MeOH (9:1) and then filtered through a pad of celite. The filtered solution was then concentrated under reduced pressure and purified via flash chromatography using 5:1 EtOAc:hexanes to provide the desired product.

*50% ethyl glyoxylate oligomer in toluene (Fluka) was distilled at atmospheric pressure using a short (2 in) Vigreaux column and oil bath temperature 130-185° C. (gradually increased over 30 min187ibend) until only a small residue remained. First few mL were discarded, and then the entire volume collected. The obtained yellowish distillate containing toluene-ethyl glyoxylate mixture was immediately re-distilled at 30 Torr. After toluene reaction, pure ethyl glyoxylate distilled at 48-50° C./30 Torr.

Example 12B. Production of N-ethylaminoethylbenzoselenophene

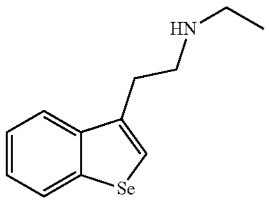

The synthesis of Example 12A was repeated, except the extended carbaldehyde of Example 16B was used as the starting material and ethylamine hydrochloride was used as the primary amine, to afford the target compound as a tannish semisolid in 59% yield.

Example 13B. Production of N-isopropylaminoethylbenzoselenophene

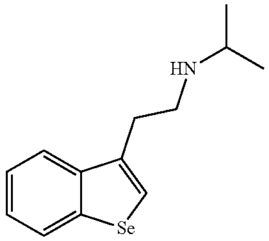

11.9 mg of 3-(aminoethyl)benzoselenophene was suspended in 7 mL of THF under nitrogen followed by acetone as a standard solution in THE. Acetic acid, also as a standard solution in THF, and sodium triacetoxyborohydride were then added and the reaction mixture was stirred for 24 hrs. The reaction was quenched with $NaHCO_3$ and extracted with $Et_2O$, and then concentrated under reduced pressure. The crude product was purified using $SiO_2$ chromatography with 10% MeOH in DCM as eluent to yield the desired product.

Example 14B. Production of N-cyclopropylaminoethylbenzoselenophene

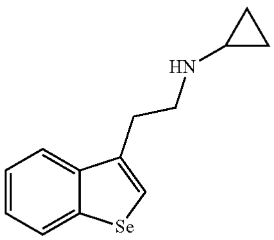 [SMILES: c1ccc2c(CCNC3CC3)c[se]c2c1]

The synthesis of Example 16A was repeated, except the extended carbaldehyde of Example 16B was used as the starting material, and cyclopropylamine was used as the amine, to afford the target compound as tannish solid in 45% yield.

Example 15B. Production of Selenophene Carbaldehyde Intermediate

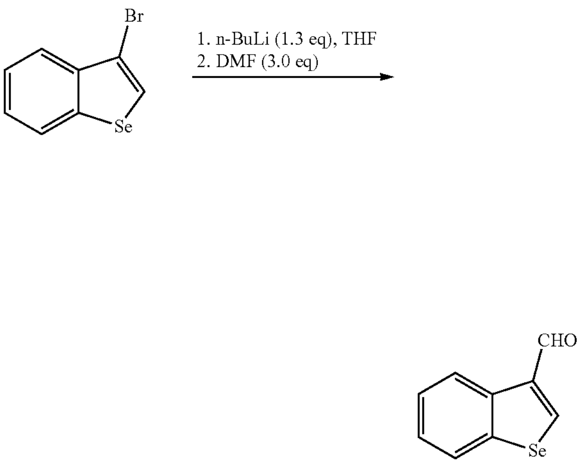

To a solution of 3-bromoselenophene (3.6 mmol) in THE (15 mL) at −78° C. was added n-BuLi (4.7 mmol) dropwise. The reaction mixture was allowed to stir at this temperature for 15 min before DMF (10.8 mmol) was added dropwise. The reaction mixture was allowed to warm to room temperature before being quenched by the addition of water. The phases were separated and the aqueous phase was extracted with diethyl ether (×3). The combined organic extracts were washed with water and brine, and dried over anhydrous sodium sulfate. After filtration, the solvent was removed in vacuo to afford a crude oil. The carbaldehyde was isolated from the crude mixture by silica gel chromatography (eluent 0, 2, 5, 7% ethyl acetate in hexane) as a pale orange solid (39% yield).

Example 16B. Production Extended Carbaldehyde Intermediate

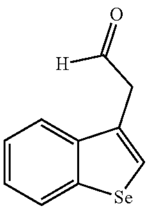 [SMILES: O=CCc1c[se]c2ccccc12]

The target extended selenophene carbaldehyde intermediate was produced using the method of Example 15A, except the carbaldehyde intermediate produced in Example 15B was used as the starting material, to produce the target extended carbaldehyde as a brownish oil in 64% yield.

Example 17B. Production of N,N-dimethylaminoethyl benzoselenophene

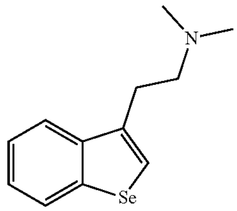

The synthesis of Example 16A was repeated, except the extended carbaldehyde of Example 16B was used as the starting material, to afford the target compound as a colorless oil in 66% yield.

Example 18B. Production of N-methyl benzoselenophene

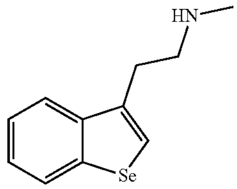

The synthesis of Example 12A was repeated, except the extended carbaldehyde of Example 16B was used as the starting material methylamine hydrochloride was used as the primary amine, to afford the target compound as a whiteish oil in 54% yield.

Example 19B. Production of Hydrofumarate Salts (Aka [1:1] Fumarate Salts)

[1:1]hydrofumarate salts of each one of the compounds are separately produced from the compounds of Examples 1-7B, 9-14B and 17-18B using the following procedure:

1 equiv of the free base product is dissolved in acetone and is added dropwise to a boiling solution of fumaric acid (1 equiv) in acetone. A precipitate forms immediately and the precipitate/acetone is stored overnight at −20° C. The solids are then filtered and washed with ice-cold acetone to yield the desired crystalline hydrofumarate salt.

Example 20B. Production of Fumarate Salts (Aka [2:1] Fumarate Salts)

[2:1] fumarate salts of each one of the compounds are separately produced from the compounds of Examples 1-7B, 9-14B and 17-18B using the following procedure:

1 equiv of the free base product is dissolved in acetone and is added dropwise to a boiling solution of fumaric acid (0.5 equiv) in acetone. A precipitate forms immediately and the precipitate/acetone is stored overnight at −20° C. The solids are then filtered and washed with ice-cold acetone to yield the desired crystalline fumarate salt.

Synthetic Scheme C:

Benzofuran and Furopyridine Analogs

As illustrated below, Compound A starting material can be converted into benzofuran and furopyridine compounds of Formula I:

Scheme 1C

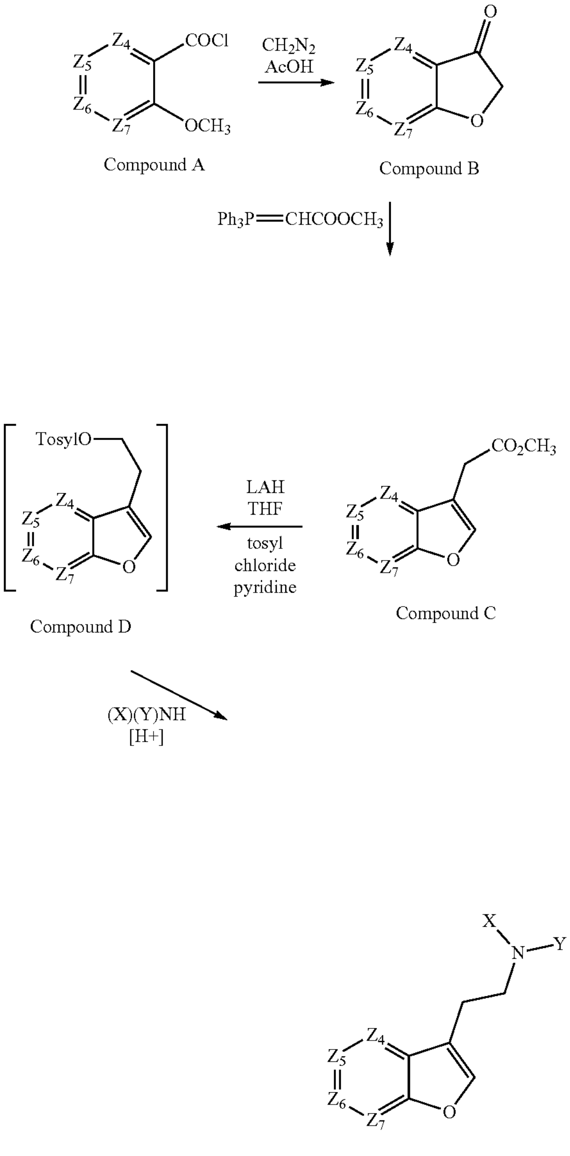

Compound A

Compound B

Compound D

Compound C

Scheme 2C

Numerous variations of benzofuran and furopyridine starting materials, including compounds generally represented by Compound H, can be purchased commercially from companies such as Sigma Aldrich® (e.g., benzofuran, 2-methylbenzofuran, 5-bromobenzofuran, 2-phenylbenzofuran) and then used in accordance with the exemplary scheme is set out below to produce Compound K, which can be subsequently alkylated using the appropriate alkyl halide in the presence of a base using known methods to form the desired monoalkyl or dialkylaminoethyl analogs of Formula I:

Scheme 2C

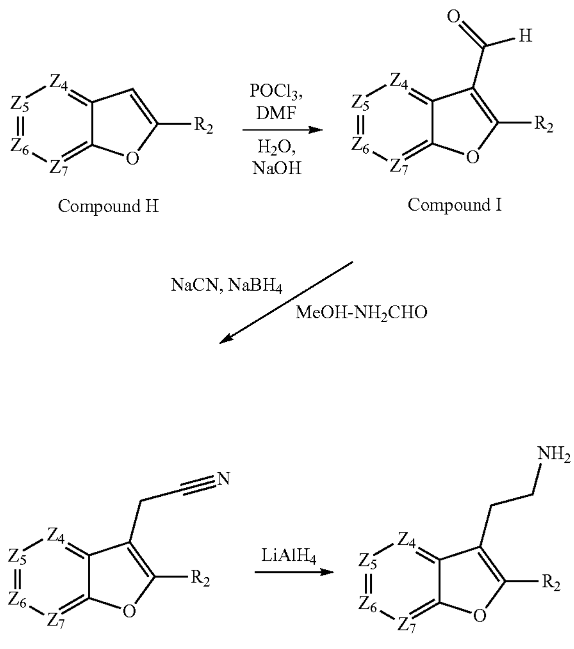

Compound H
Compound I
Compound J
Compound K

Scheme 3C

Numerous variations of benzofuran and furanopyridine compounds of the present disclosure, including compounds generally represented by Compound H, may be synthesized from starting materials purchased commercially from companies such as Sigma® (e.g., benzofuran) and Santa Cruz® (e.g., 5-methoxybenzofuran), and then used in accordance with the methods set forth in Zhang et al., *J. Org. Chem.* 2000, 65, 4732-4735, which is incorporated herein by reference in its entirety. That exemplary scheme is set out below, wherein $X_1$ is an alkyl group (e.g., $C_1$-$C_8$ alkyl such as methyl or ethyl) derived from the corresponding alkyl glyoxylate:

Scheme 3C

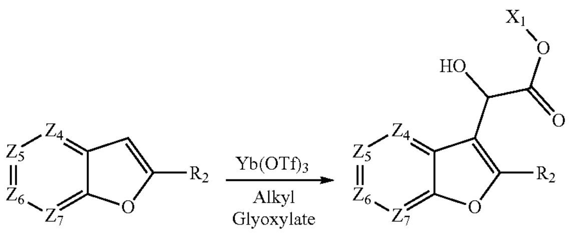

Compound H

-continued

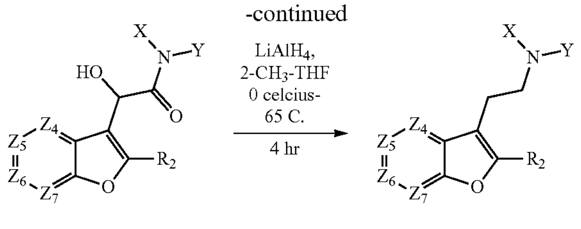

Example 1C. Production of 4-methoxy-3-N,N-dimethylaminoethylbenzofuran (aka 4-methoxy Furanopsil™)

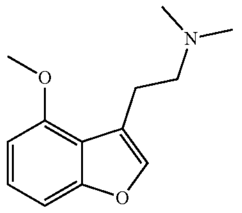

4-methoxy Furanopsil™

2,6-dimethoxybenzoyl chloride is used as Compound A and carried through Scheme 1 to provide 4-methoxybenzo[b]furan-3(2h)-one (Compound B). Compound B is reacted with methyl (triphenylphosphoranylidene)acetate provide 4-methoxy-N,N-dimethylbenzo[b]furan-3-acetamide (Compound C), which is subsequently reduced with $LiAlH_4$ to the primary alcohol and tosylated to form Compound D. The tosylate is then displaced with dimethylamine under acidic conditions and the reaction mixture is quenched, extracted via aqueous workup, and purified via silica gel column chromatography (EtOAC/hexanes) to provide 4-methoxy-3-N,N-dimethylaminoethylbenzofuran.

Example 2C. Production of 4-hydroxy-3-N,N-dimethylaminoethylbenzofuran (aka Furanopsil™)

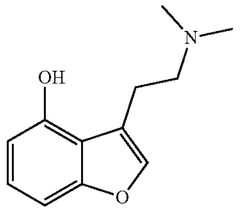

Furanopsil™

To a suspension of NaH (0.024 mol) in 25 ml of dry DMF, ethanethiol (0.024 mol) is added at 0° C. under nitrogen and vigorous stirring. After 1 h a solution of the Example 1 product (0.01 mol) in 20 ml of dry DMF is added all at once and the reaction mixture is refluxed for 1 h. The solvent is removed under vacuum and the residue is purified via silica gel column chromatography (EtOAC/hexanes) to provide 4-hydroxy-3-N,N-dimethylaminoethylbenzofuran (aka Furanopsil).

Example 3C. Production of 4-acetoxy-3-N,N-dimethylaminoethylbenzofuran (aka Furanopsilacetin™)

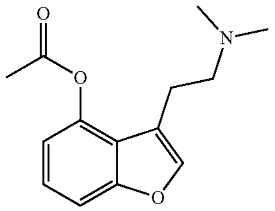

Furanopsilacetin™

To a solution of the product of Example 2C (0.01 mol) in pyridine under a nitrogen blanket and stirred at 25° C. is added a catalytic amount of DMAP and $Ac_2O$ (0.011 mol) in pyridine (0.012 mol). Stirring is continued for 1 hr. After quenching with aqueous workup, the solvent is removed under vacuum and the residue is purified via silica gel column chromatography to provide Furanopsilacetin.

Example 4C. Production of 5-methoxy-3-N,N-dimethylaminoethylbenzofuran (aka Bufofuranopsil™)

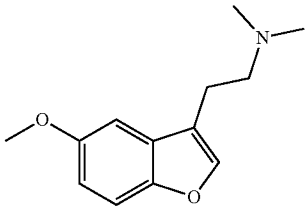

Bufofuranopsil™

The synthetic procedure of Example 1C is repeated with 2,5-dimethoxybenzoyl chloride as the starting material to yield 5-methoxy-3-N,N-dimethylaminoethylbenzofuran.

Example 5C. Production of N-isopropyl-N-methylaminoethylbenzofuran

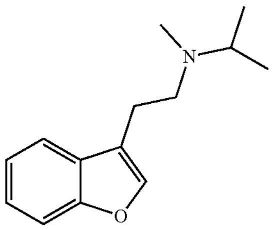 [SMILES: CC(C)N(C)CCc1coc2ccccc12]

The synthetic procedure of Example 11C was followed using isopropylmethylamine as the secondary amine to provide the N-isopropyl-N-methylaminoethylbenzofuran target compound.

Example 6C. Production of N-ethyl-N-methylaminoethylfuro[2,3-b]pyridine

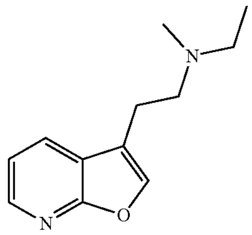

The synthetic procedure of Example 4C is repeated with 2-methoxy-3-pyridinecarbonyl chloride and methyl ethylamine, ultimately yielding the N-ethyl-N-methylaminoethylfuro[2,3-b]pyridine target compound.

Example 7C. Production of N-ethyl-N-propylaminoethylfuro[2,3-b]pyridine

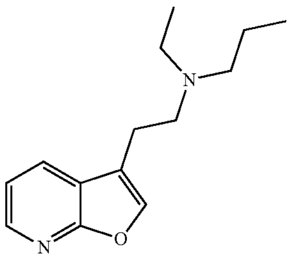 [SMILES: CCCN(CC)CCc1coc2ncccc12]

The synthetic procedure of Example 5C is repeated with ethyl n-propylamine instead of methyl ethylamine, ultimately yielding the N-ethyl-N-propylaminoethylfuro[2,3-b]pyridine target compound.

Example 8C. Production of 3-(N,N-dimethylaminoethyl)benzo[b]furan-4-yl phosphate (aka Furocybin™)

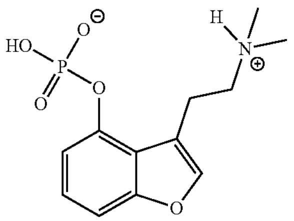

Furocybin™

A 2000 mL, four-necked, round-bottomed flask is equipped with an overhead stirrer, J-Kem temperature controller, a 100 mL dropping funnel, and rubber septum through which a positive pressure of dry $N_2$ is inserted. The septum is removed and the flask is charged sequentially with Furanopsil produced in accordance with the method of Example 2 (60.2 mmol) and anhyd THE (500 mL). The mixture is stirred for 15 min and the flask is immersed in a solid $CO_2$/acetone cooling bath at −78° C. When the internal temperature of the reaction reaches −67° C., a solution of 2.5 M BuLi in hexanes (28.9 mL, 72.3 mmol) is added dropwise over a period of a few min and maintained at an internal temperature reading below −60° C. After stirring the reaction mixture for 10 min, tetrabenzyl pyrophosphate (35.7 g, 66.2 mmol) is added in one portion and the mixture is stirred well. After 1.5 h, the solid $CO_2$/acetone cooing bath is removed and the temperature is allowed to slowly rise to −25° C. over 2 h.

Amino bound silica gel (30 g) is added in one portion and the reaction is diluted with EtOAc (600 mL). The mixture is filtered through a pad of Celite and washed with EtOAc (400 mL). The filter cake is reslurried for 10 min with EtOAc (400 mL) and again filtered. The combined filtrates are concentrated and transferred into a 500 mL single-necked roundbottom flask. If necessary, the resulting oil is redissolved in DCM (100 mL) and heated with a heat gun to boiling for 5 min. The flask is allowed to reach rt and then held at 4° C. overnight. The crude reaction product (zwitterion precipitate) is filtered via Büchner funnel, then triturated with DCM (4 Å~100 mL). The zwitterion precipitate is then transferred into a 250 mL single-necked round-bottomed flask and thoroughly dried in the vacuum oven at 40° C. overnight to provide benzyl {3-[2-(Benzyldimethyl-ammonio)ethyl]-benzo[b]furan-4-yl}Phosphate.

Into a 2000 mL round-bottomed flask is added the benzyl phosphate product produced according to the method in the preceding paragraph (35.6 mmol) followed by $CH_3OH$ (1200 mL). The mixture is degassed and refilled with $N_2$. 10% Pd/C (1.1 g) is added and the mixture is degassed and refilled with a $H_2$ balloon at 1 atm. The reaction mixture is stirred overnight at rt. The flask is degassed, refilled with $N_2$ and the suspension is filtered through a pad of Celite via Büchner funnel. The filter pad is washed with $CH_3OH$ (500 mL) and the filtrate is concentrated and dried overnight under vacuum to give a crude solid. The crude solid is suspended in i-PrOH (200 mL) and boiled for 30 min, then filtered hot (50 to 60° C.). The collected solid is washed with acetone to give a colored solid. The solid is then suspended in 25% $CH_3OH$/i-PrOH and boiled for 30 min and filtered hot, washing with 25% $CH_3OH$/i-PrOH to give a colored solid, which is the Furanocybin product.

Example 9C. Production of N-ethyl-N-methylaminoethylbenzofuran

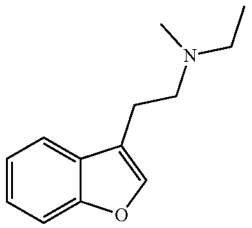

The synthetic procedure of Example 11C was repeated with using ethylmethylamine as the secondary amine to provide the N-ethyl-N-methylaminoethylbenzosfuran target compound.

Example 10C. Production of N-ethyl-N-propylaminoethylbenzofuran

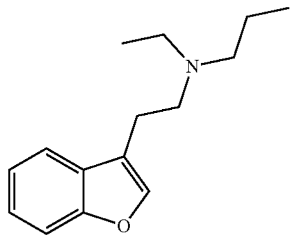 [SMILES: CCCN(CC)CCc1coc2ccccc12]

The synthetic procedure of Example 11C was repeated with using ethyl-n-propylamine as the secondary amine to provide the N-ethyl-N-propylaminoethylbenzofuran target compound.

Example 11C. Production of N-methyl-N-n-propylaminoethylbenzofuran

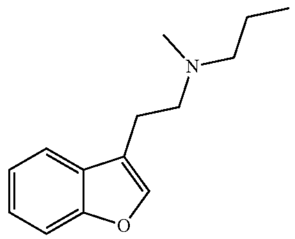 [SMILES: CCCN(C)CCc1coc2ccccc12]

Benzo[b]furan (1 eq.) was charged under nitrogen to a dry reaction flask equipped with a glass stir bar and containing 5 mol % ytterbium triflate. Excess ethyl glyoxylate was distilled (according to the method set forth below*) and collected directly into the reaction flask. The reaction was stirred under nitrogen at room temperature for 24 hrs. The resulting crude ester intermediate was concentrated under vacuum and purified via flash chromatography using 5:1 EtOAc:hexanes.

Purified ester intermediate was charged to a dry reaction flask under nitrogen followed by anhydrous methanol and 1.2 eq of the secondary amine methyl n-propylamine. The reaction was stirred at room temperature for 24 hrs or until the ester was consumed as judged by TLC (9:1 DCM: MeOH).

Crude, dry hydroxy amide intermediate was charged under nitrogen to a reaction flask containing a stir bar. To this was added 2Me-THF followed by 3 eq of $LiAlH_4$ as a 2.0 M Solution of $LiAlH_4$ in 2Me-THF over the course of 1 minute. The reaction exothermed slightly and was then heated to 65° C. for 4 hrs. The reaction mixture was then cooled to 0-20° C. and quenched slowly with THF/$H_2O$ (4:1) under stirring for about 30 mins. The reaction mixture was then carefully diluted with DCM/MeOH (9:1) and then filtered through a pad of celite. The filtered solution was then concentrated under reduced pressure and purified via flash chromatography using 5:1 EtOAc:hexanes to provide the desired product.

*50% ethyl glyoxylate oligomer in toluene (Fluka) was distilled at atmospheric pressure using a short (2 in) Vigreaux column and oil bath temperature 130-185° C.

(gradually increased over 30 min period) until only a small residue remained. First few mL were discarded, and then the entire volume collected. The obtained yellowish distillate containing toluene-ethyl glyoxylate mixture was immediately re-distilled at 30 Torr. After toluene reaction, pure ethyl glyoxylate distilled at 48-50° C./30 Torr.

Example 12C. Production of N-ethylaminoethylbenzofuran

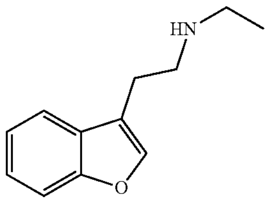

The synthesis of Example 12A was repeated, except the extended carbaldehyde of Example 16C was used as the starting material and ethylamine hydrochloride was used as the primary amine, to afford the target compound as a whiteish solid in 15% yield.

Example 13C. Production of N-isopropylaminoethylbenzofuran

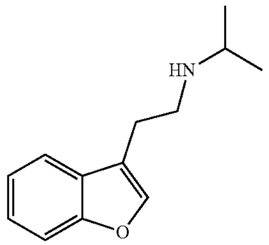

The synthesis of Example 16A was repeated, except the extended carbaldehyde of Example 16C was used as the starting material and isopropylamine was used as the amine, to afford the target compound as a whiteish solid in 27% yield.

Example 14C. Production of N-cyclopropylaminoethylbenzofuran

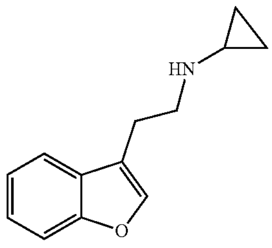 [SMILES: c1ccc2c(CCNC3CC3)coc2c1]

The synthesis of Example 16A was repeated, except the extended carbaldehyde of Example 16C was used as the starting material and cyclopropylamine was used as the amine, to afford the target compound as a whiteish solid in 22% yield overall.

Example 15C. Production of (2R)- and (2S)-1-(benzofuran-3-yl)-N-methylpropan-2-amine Racemic 1-(benzofuran-3-yl)-N-methylpropan-2-amine hydrochloride (Cayman Chemical) was converted to the free base and subjected to HPLC separation to provide two separate compositions enriched with the (S) and (R) enantiomers, respectively:

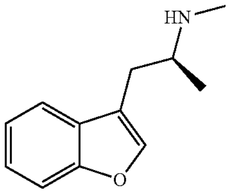

(2S)

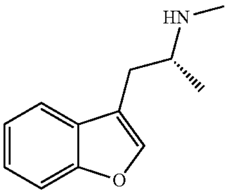

(2R)

Example 16C. Production Extended Benzocarbaldehyde Intermediate

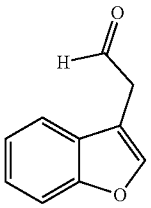 [SMILES: O=CCc1coc2ccccc12]

The target extended benzofurano carbaldehyde intermediate was produced using the method of Example 15A, except benzofurano-3-carbaldehyde was used as the starting material, to produce the target extended carbaldehyde as a light orange oil in 54% crude yield.

Example 17C. Production of N,N-dimethylaminoethyl benzofuran

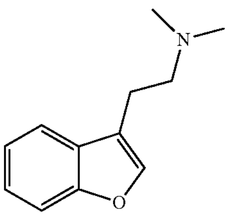

The synthesis of Example 16A was repeated, except the extended carbaldehyde of Example 16C was used as the starting material, to afford the target compound as a yellow oil in 20% yield.

Example 18C. Production of N-methylaminoethyl benzofuran

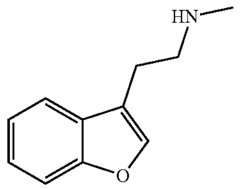

The synthesis of Example 16A was repeated, except the extended carbaldehyde of Example 16C was used as the starting material and methylamine hydrochloride was used as the primary amine, to afford the target compound as a whiteish solid in 35% yield.

Example 19C. Production of 6-methoxy-N,N-dimethylaminoethyl benzofuran

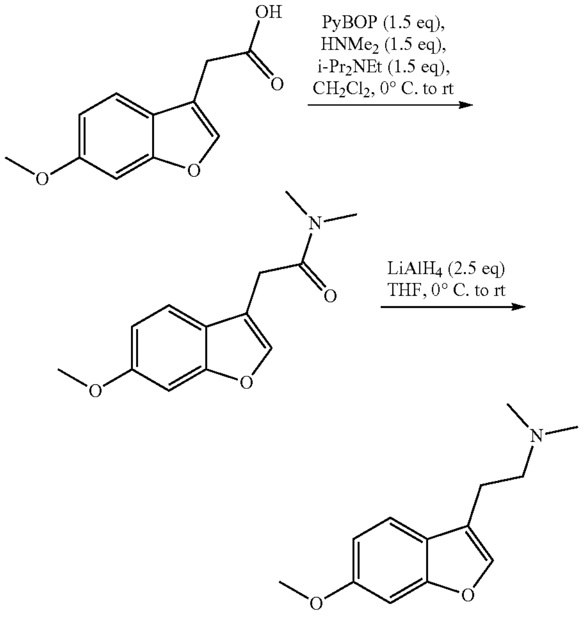

To a solution of carboxylic acid (1 eq) in dichloromethane at 0° C. under $N_2$ atmosphere was added PyBOP (1.5 eq), $i-Pr_2NEt$ (1.5-3.0 eq), and dimethylamine (1.5 eq) sequentially. The reaction mixture was warmed to rt and stirred for 2 h. Following completion of the reaction, the mixture was concentrated in vacuo and the crude oil was purified on silica gel chromatography (50% ethyl acetate in hexanes) to give the dimethylamide as an off-white solid in 90% yield.

The dimethylamide intermediate (1 eq) was dissolved in THF under an inert atmosphere and cooled to 0° C. A solution of $LiAlH_4$ in 2-Me-THF (2.3M, 2.5 eq) was added dropwise. The reaction mixture was warmed to rt and stirred for 16 h. The mixture was quenched by addition of $Et_2O$ and water at 0° C. and filtered over a pad of Celite. The aqueous layer was extracted with EtOAc (3×) and the combined organic layer was washed with brine (3×), dried over $Na_2SO_4$, and concentrated in vacuo. The crude oil was purified on silica gel chromatography (5% MeOH in $CH_2Cl_2$) to afford the target amine as a yellow solid in 43% yield.

Example 20C. Production of 6-methoxy-N-ethylaminoethyl benzofuran

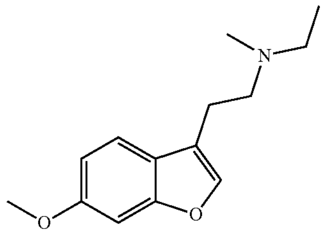 [SMILES: CCN(C)CCc1coc2cc(OC)ccc12]

The procedure of Example 19C was repeated, except ethylmethylamine was used as the secondary amine, to produce the target compound as a yellowish oil in 38% yield.

Example 21C. Production of 6-methoxy-N-ethyl-N-methylaminoethyl benzofuran

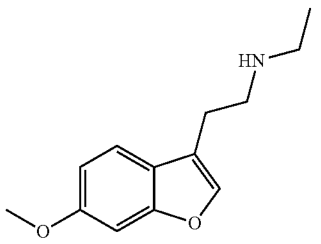 [SMILES: CCNCCc1coc2cc(OC)ccc12]

The procedure of Example 19C was repeated, except ethylamine hydrochloride was used as the primary amine, to produce the target compound as a whiteish solid in 41% yield.

Example 22C. Production of 6-methoxy-N-methylaminoethyl benzofuran

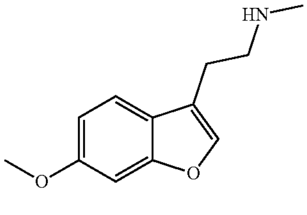

The procedure of Example 19C was repeated, except methylamine hydrochloride was used as the primary amine, to produce the target compound as a tannish solid in 32% yield.

*Other modifications to Example 19C procedure: used 3.5 eq of LAH and refluxed for 36 hrs.

Example 23C. Production of Hydrofumarate Salts (Aka [1:1] Fumarate Salts)

[1:1]hydrofumarate salts of each one of the compounds are separately produced from the compounds of Examples 1-7C, 9-15C and 17-22C using the following procedure:

1 equiv of the free base product is dissolved in acetone and is added dropwise to a boiling solution of fumaric acid (1 equiv) in acetone. A precipitate forms immediately and the precipitate/acetone is stored overnight at −20° C. The solids are then filtered and washed with ice-cold acetone to yield the desired crystalline hydrofumarate salt.

Example 24C. Production of Fumarate Salts (Aka [2:1] Fumarate Salts)

[2:1] fumarate salts of each one of the compounds are separately produced from the compounds of Examples 1-7C, 9-15C and 17-22C using the following procedure:

1 equiv of the free base product is dissolved in acetone and is added dropwise to a boiling solution of fumaric acid (0.5 equiv) in acetone. A precipitate forms immediately and the precipitate/acetone is stored overnight at −20° C. The solids are then filtered and washed with ice-cold acetone to yield the desired crystalline fumarate salt.

Synthetic Scheme D:

Indole and Azaindole Analogs

As illustrated below, indole and azaindole compounds of Formula I can be synthesized in the following exemplary manner:

Scheme 1D

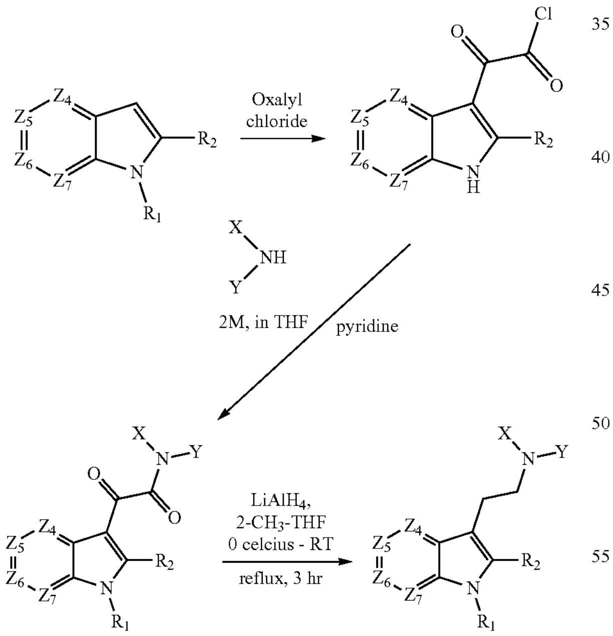

Indole, 4-azaindole, 5-azaindole, 6-azaindole, and 7-azaindoles can be prepared using the general synthetic scheme set forth above and starting with the relevant indole starting material. Exemplary indole starting materials include 4-benzyloxy-7-methylindole (VulcanChem), 6-fluoroindole (Sigma), 5-methoxy-6-fluoroindole (Biosynth Carbosynth), 1-ethylindole, etc. Exemplary azaindole starting materials can be purchased from including: 4-azaindole, 5-azaindole, 6-azaindole, and 7-azaindole (Sigma); 6-fluoro-4-azaindole (Synthonix); 5-methoxy-7-methyl-4-azaindole (Sigma); 6-fluoro-7-azaindole (Shanghai Jizhi); 5-methoxy-7-azaindole and 6-fluoro-5-methoxy-7-azaindole (Achemblock), etc.

Example 1D. Production of 5-methoxy ketoamide Intermediate

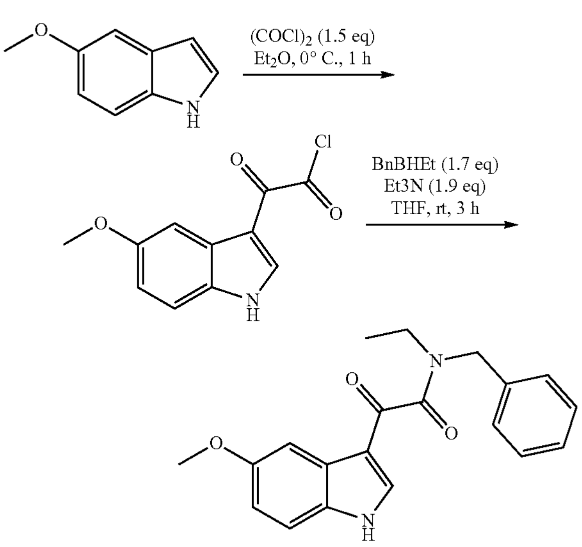

A 3-neck round bottom flask fitted with addn. funnel was charged with oxalyl chloride (0.185 mL, 2.18 mmol, 1.5 eq) in 5 mL of anhyd. $Et_2O$ under inert atmosphere. The flask was cooled to 0° C. and a solution of 5-methoxyindole (240 mg, 1.45 mmol, 1 eq) in 5 mL of ether was added dropwise via the addition funnel. After complete addition, the reaction was stirred at 0° C. for 1 h. The reaction mixture was diluted with anhyd. hexanes. The resulting bright orange solid was filtered through Hirsche funnel and washed several times with (3/1) hexanes/$Et_2O$ mixture. The solid was used in the next step without further purification.

In 2-neck round bottom flask, the acid chloride intermediate (336 mg, 1.31 mmol, 1 eq) was dissolved in THF (10 mL) under inert atmosphere. Benzylethylamine (0.33 mL, 2.2 mmol, 1.7 eq) and triethylamine (0.26 mL, 1.9 mmol, 1.5 eq) was added via syringe. The reaction mixture was stirred at rt for 3 h. Anhyd. hexanes (10 mL) was added and allowed to stir at 40° C. for 30 min. The resulting hydrochloride salt was filtered via Hirsche funnel and the ketoamide precipitated as an off-white solid from the mother liquor. The solids were collected and use for the next step without further purification.

Example 2D. Production of 3-(ethylaminoethyl)-5-methoxyindole

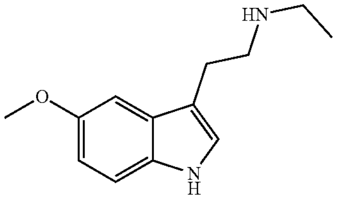 [SMILES: CCNCCc1c[nH]c2ccc(OC)cc12]

In 2-neck round bottom flask fitted with condenser, the ketoamide produced according to the method of Example 1 D (100 mg, 0.28 mmol, 1 eq) was dissolved in THE (5 mL) under inert atmosphere. The flask was cooled to 0° C. and LAH (53 mg, 1.4 mmol, 5 eq) was added and the mixture was heated to reflux for 4 h. The reaction mixture was quench by addition of DI $H_2O$ (10 mL) and the aqueous layer was extracted with $Et_2O$ (3×5 mL). The combined organic layer was washed with brine (3×10 ml), dried over anhyd. sodium sulfate and concentrated in vacuo. The crude solid was purified in via $SiO_2$ column chromatography to give the benzylethylamine intermediate product as a yellow oil.

To the purified benzylmethylamine intermediate (1 mmol) in MeOH (10 mL) was added 10 wt/wt % Pd/C (10-15%). The reaction mixture was degassed to remove oxygen and stirred under a hydrogen atmosphere (1 atm) for 18-24 hours. Upon completion, the reaction mixture was filtered over a pad of Celite and the solvent removed in vacuo to afford a crude oil. The target ethylamine product was isolated from the crude by purification on silica gel chromatography (load with DCM, elute with 1% MeOH/DCM then 5% MeOH/DCM doped with 1% $NEt_3$) as a whitish solid.

Example 3D. Production of 3-(ethylaminoethyl)-6-fluoro-5-methoxy-7-azaindole

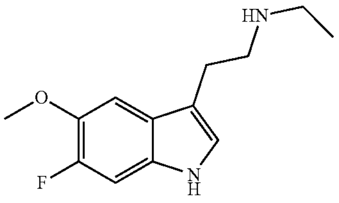 [SMILES: CCNCCc1c[nH]c2cc(F)c(OC)cc12]

The synthetic procedures of Examples 1 D & 2D were repeated, except 6-fluoro-5-methoxy indole was used as the starting material, to provide the desired product as a yellowish solid in 75% yield.

Example 4D. Production of 3-(ethylaminoethyl)-5-methoxy-7-azaindole

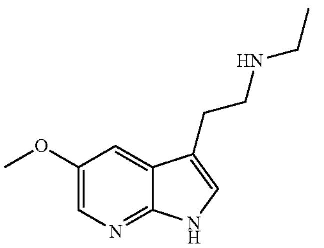 [SMILES: CCNCCc1c[nH]c2ncc(OC)cc12]

The synthetic procedures of Examples 1 D & 2D are repeated, except 5-methoxy-7-azaindole is used as the starting material, to provide the desired product in good yield.

Example 5D. Production of 3-(ethylaminoethyl)-4-hydroxy-7-methylindole

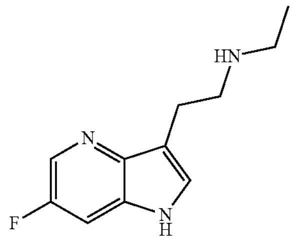

The synthetic procedures of Examples 1 D & 2D are repeated, except 6-fluoro-4-azaindole as the starting material, to provide the desired product in good yield.

Example 6D. Production of Indole Carbaldehyde Intermediate

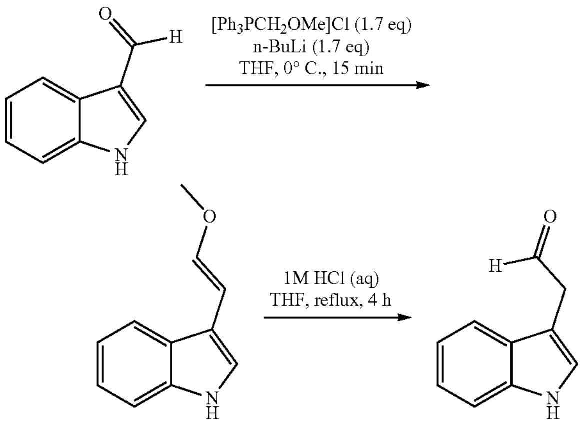

To a stirred suspension of the Wittig salt (10.5 mmol, 1.7 eq) in THF at 0° C. was added a solution n-BuLi (10.5 mmol, 1.7 eq, 2.5 M in hexane) dropwise. The resulting reaction mixture turned homogenous and red. Carbaldehyde starting material (6.2 mmol, 1.0 eq) was added as a solid at once to the reaction mixture. After 15 min, the reaction mixture was diluted by with diethyl ether and quenched with 1M HCl (aq). The phases were separated and the aqueous extracted with diethyl ether (×2). The combined organic extracts were washed with water and brine and dried over anhydrous sodium sulfate. After filtration, the solvent was removed in vacuo. The enol ether could be isolated from the crude by column chromatography (load with PhMe, elute with 0 to 5% ethyl acetate in hexane) as an oil.

To a solution of enol ether (1 mmol, 1.0 eq) in THF (4.8 mL) was added 1 M HCl (aq., 7.2 mL). The reaction mixture was refluxed for 4 hours before cooling to room temperature and diluting with water and diethyl ether. The phases were separated and the aqueous extracted with diethyl ether (×2). The combined organic extracts were washed with water and brine and dried over anhydrous sodium sulfate. After filtration, the solvent was removed in vacuo to afford a crude oil that was used in the next step without further purification.

Example 7D. Production of 3-(ethylaminoethyl)-indole

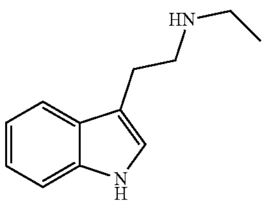

To a solution of the carbaldehyde intermediate produced according to the method of Example 6D (1.0 eq) in acetonitrile (0.1 M) was added benzylethylamine (2-5 eq) and a few beads of activated whole 3A MS. After stirring at room temperature for 10 min, $NaHB(OAc)_3$ (>5 eq) was added at once. The reaction mixture was allowed to stir 18-24 hours at room temperature before being quenched by the addition of 1M HCl and diluted with diethyl ether. The phases were separated, and the organic phase washed with 1M HCl (×2). The combined aqueous phases were basified by the addition of solid NaOH. The aqueous phase was extracted with DCM (×3) and the combined DCM washes were dried over anhydrous sodium sulfate. After filtration, the solvent was removed in vacuo to afford the benzylethylamine intermediate compound in good yield purity. Analytical purity was achieved by purification on column chromatography (DCM to 1% MeOH/DCM to remove major impurities, then eluted with 5% MeOH/DCM doped with –1% $NEt_3$).

To a solution of benzylethylamine intermediate (1 mmol) in MeOH (10 mL) was added 10 wt/wt % Pd/C (10-15%). The reaction mixture was degassed to remove oxygen and stirred under a hydrogen atmosphere (1 atm) for 18-24 hours. Upon completion, the reaction mixture was filtered over a pad of Celite and the solvent removed in vacuo to afford a crude oil. The target ethylamine was isolated from the crude by purification on silica gel chromatography (load with DCM, elute with 1% MeOH/DCM then 5% MeOH/DCM doped with 1% $NEt_3$) as an off-white solid in 56% yield.

Example 8D. Production of 1-ethyl-3-(ethylaminoethyl)-indole

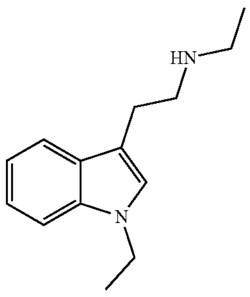 [SMILES: CCNCCc1cn(CC)c2ccccc12]

The procedure of Examples 6D & 7D were repeated, with 1-ethylindole-3-carbaldehyde as the starting material, to provide the desired product in good yield as a whiteish semi-solid in good yield.

Example 8D. Production of 7-methyl-3-(ethylaminoethyl)-indole

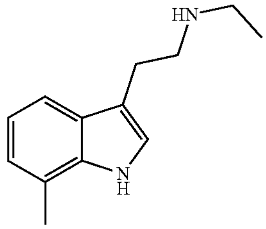

The procedures of Examples 6D & 7D were repeated, with 7-methyindole-3-carbaldehyde as the starting material, to provide the desired product as a whiteish solid in 65% yield.

Example 9D. Production of 1-ethyl-5-methoxy-3-(ethylaminoethyl)-indole

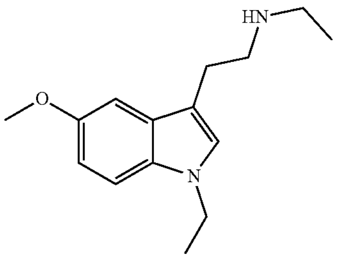 [SMILES: CCNCCc1cn(CC)c2ccc(OC)cc12]

The procedures of Examples 6D & 7D were repeated, with 5-methoxy-1-ethyindole-3-carbaldehyde as the starting material, to provide the desired product in good yield.

Example 10D. Production of 3-(N,N-dimethylaminoethyl)-pyrrolo[3,2-b]pyridine

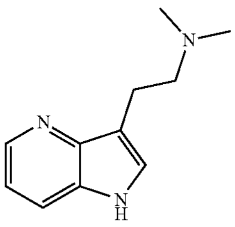

The procedures of Examples 6D & 7D were repeated, except with 1H-pyrrolo[3,2-b]pyridine-3-carbaldehyde as the starting material and dimethylamine as the secondary amine (no Pd/C debenzylation necessary), to provide the desired product as a whiteish oil in about 10% yield overall.

Example 11D. Production of 3-(N-ethyl-N-methylaminoethyl)-pyrrolo[3,2-b]pyridine

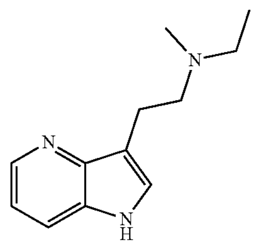

The procedures of Example 10D were repeated, except with ethylmethylamine as the secondary amine, to provide the desired product as a whiteish oil in about 32% yield overall.

Example 12D. Production of 3-(N-methylaminoethyl)-pyrrolo[3,2-b]pyridine

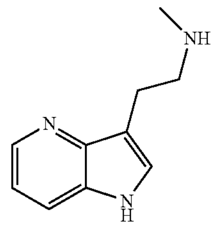

The procedures of Example 10D were repeated, except with methylamine hydrochloride as the secondary amine, to provide the desired product as a whiteish oil in about 14% yield overall.

Example 13D. Production of 3-(N-ethylaminoethyl)-pyrrolo[3,2-b]pyridine

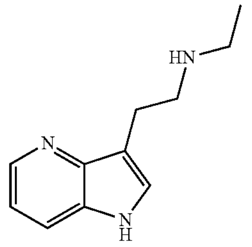

The procedures of Example 10D were repeated, except with ethylamine hydrochloride as the secondary amine, to provide the desired product as a whiteish oil in about 31% yield overall.

Example 14D. Production of 3-(N,N-dimethylaminoethyl)-pyrrolo[3,2-c]pyridine

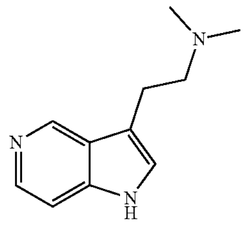

The procedures of Example 10D were repeated, except with 1H-pyrrolo[3,2-b]pyridine-3-carbaldehyde as the starting material, to provide the desired product as a whiteish oil in about 30% yield overall.

Example 15D. Production of 3-(N-ethyl-N-methylaminoethyl)-pyrrolo[3,2-c]pyridine

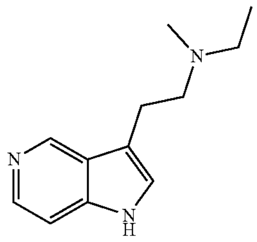

The procedures of Example 11 D were repeated except with 1H-pyrrolo[3,2-b]pyridine-3-carbaldehyde as the starting material, to provide the desired product as a whiteish oil in about 29% yield overall.

Example 16D. Production of 3-(N-methylaminoethyl)-pyrrolo[3,2-c]pyridine

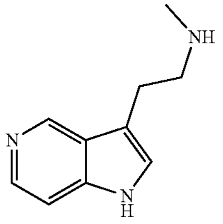

The procedures of Example 12D were repeated, except with 1H-pyrrolo[3,2-b]pyridine-3-carbaldehyde as the starting material, to provide the desired product as a whiteish solid in about 26% yield overall.

Example 17D. Production of 3-(N-ethylaminoethyl)-pyrrolo[3,2-c]pyridine

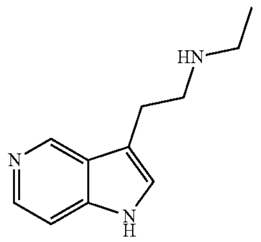

The procedures of Example 13D were repeated, except with 1H-pyrrolo[3,2-b]pyridine-3-carbaldehyde as the starting material, to provide the desired product as a whiteish solid in about 29% yield overall.

Example 18D. Production of 3-(N,N-dimethylaminoethyl)-pyrrolo[2,3-c]pyridine

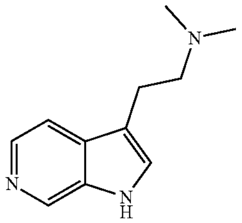

The procedures of Example 10D were repeated, except with 1H-pyrrolo[2,3-c]pyridine-3-carbaldehyde as the starting material, to provide the desired product as a whiteish solid in about 22% yield overall.

Example 19D. Production of 3-(N-ethyl-N-methylaminoethyl)-pyrrolo[2,3-c]pyridine

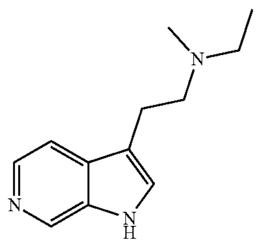

The procedures of Example 11 D were repeated, except with 1H-pyrrolo[2,3-c]pyridine-3-carbaldehyde as the starting material, to provide the desired product as a whiteish oil in about 25% yield overall.

Example 20D. Production of 3-(N-methylaminoethyl)-pyrrolo[2,3-c]pyridine

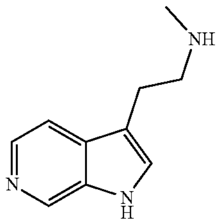

The procedures of Example 12D were repeated, except with 1H-pyrrolo[2,3-c]pyridine-3-carbaldehyde as the starting material, to provide the desired product as a whiteish solid in about 27% yield overall.

Example 21D. Production of 3-(N-ethylaminoethyl)-pyrrolo[2,3-c]pyridine

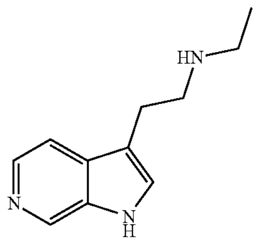

The procedures of Example 13D were repeated, except with 1H-pyrrolo[2,3-c]pyridine-3-carbaldehyde as the starting material, to provide the desired product as a whiteish oil in about 20% yield overall.

Example 22D. Production of 3-(N,N-dimethylaminoethyl)-pyrrolo[2,3-b]pyridine

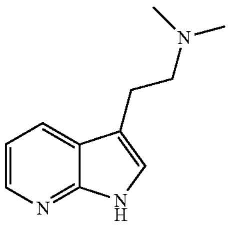

The procedures of Example 10D were repeated, except with 1H-pyrrolo[2,3-b]pyridine-3-carbaldehyde as the starting material, to provide the desired product as a whiteish solid in about 31% yield overall.

Example 23D. Production of 3-(N-ethyl-N-methyl-aminoethyl)-pyrrolo[2,3-b]pyridine

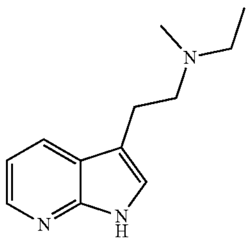

The procedures of Example 11 D were repeated, except with 1H-pyrrolo[2,3-b]pyridine-3-carbaldehyde as the starting material, to provide the desired product as a whiteish oil in about 40% yield overall.

Example 24D. Production of 3-(N-methylamino-ethyl)-pyrrolo[2,3-b]pyridine

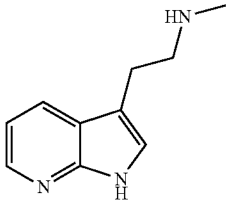

The procedures of Example 12D were repeated, except with 1H-pyrrolo[2,3-b]pyridine-3-carbaldehyde as the starting material, to provide the desired product as a whiteish solid in about 34% yield overall.

Example 25D. Production of 3-(N-ethylamino-ethyl)-pyrrolo[2,3-b]pyridine

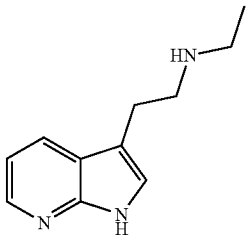

The procedures of Example 13D were repeated, except with 1H-pyrrolo[2,3-b]pyridine-3-carbaldehyde as the starting material, to provide the desired product as a whiteish solid in about 35% yield overall.

Example 26D. Production of 4-benzyloxy-3-(N-benzyl-N-ethylaminoethyl)indole

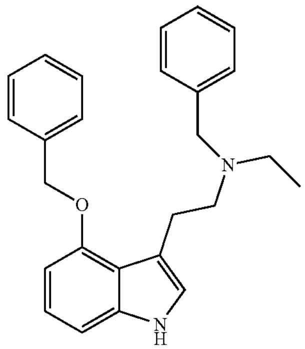 [SMILES: CCN(CCc1c[nH]c2cccc(OCc3ccccc3)c12)Cc1ccccc1]

The procedures of Examples 1 D & 2D were repeated, except 4-benzyloxyindole was used as the starting indole and benzylethylamine was used as the secondary amine (and Pd/C debenzylation step of Example 2D was not performed), to provide the desired product as a whiteish solid.

Example 27D. Production of 4-acetoxy-3-(N-ethylaminoethyl)indole

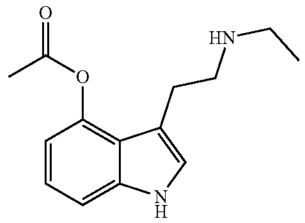 [SMILES: CCNCCc1c[nH]c2cccc(OC(C)=O)c12]

To a solution of benzylethylamine intermediate produced according to the procedure of Example 26D (1 mmol) in MeOH (10 mL) was added 10 wt/wt % Pd/C (10-15%). The reaction mixture was degassed to remove oxygen and stirred under a hydrogen atmosphere (1 atm) for 18-24 hours. Upon completion, the reaction mixture was filtered over a pad of Celite and the solvent removed in vacuo to afford a crude oil, which represented the debenzylated phenolic indole.

The debenzylated phenolic intermediate was dissolved in anhydrous DCM (10 mL) under nitrogen and cooled to 0° C. $Et_3N$ (1.2 eq) was added to solution followed by Boc-anhydride (1.1 eq) in a dropwise manner, and the reaction mixture stirred at rt until the disappearance of the starting material as monitored by TLC. The reaction mix was them diluted with DCM (20 mL) and sequentially washed with water and brine. The organic layer was then dried with sodium sulfate concentrated to yield the N—BOC protected intermediate.

The N—BOC protected intermediate was then taken up in DCM (15 mL) and the solution was cooled to 0° C. $Et_3N$ (2.1 eq) was added to the solution followed by the dropwise addition of acetyl chloride (1.3 eq) in a dropwise manner and the contents were then stirred at room temperature until the disappearance of the starting material (per TLC). After completion, the reaction mixture was diluted with DCM and washed with water and brine washes. The organic layer was removed and dried under sodium sulfate and reduced under pressure to yield an oily residue.

The residue was then taken up in anhydrous DCM, to which HCl in ether (2N, 10 equiv) was added in a dropwise manner to the solution being stirred at 0° C. Stirring was continued until the starting material was consumed by TLC monitoring. The resulting precipitate after the completion of the reaction was filtered and washed with cold DCM, diethyl ether and dried under vacuum to yield the desired compound as a yellowish solid at 33% overall yield.

Example 28D. Production of 3-(N-methylaminoethyl)indole

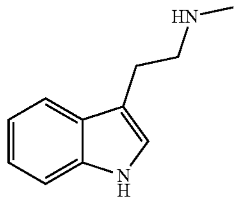

The method according to Example 7D was repeated, except benzylmethylamine was used as the secondary amine, to afford the desired product as a whiteish solid in 52% yield.

Example 29D. Production of 7-methyl-3-(methylaminoethyl)-indole

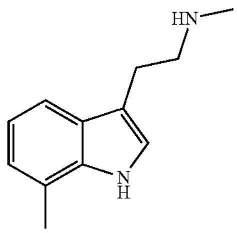

The procedures of Examples 6D & 7D were repeated, with 7-methyindole-3-carbaldehyde as the starting material and methylbenzylamine as the secondary amine, to provide the desired product as a whiteish solid in 62% yield.

Example 30D. Production of 6-fluoro-5-methoxy-3-(N-methylaminoethyl)indole

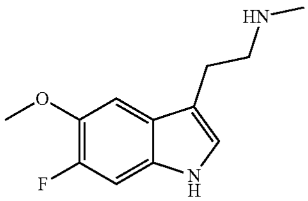

The procedures of Examples 1 D & 2D were repeated, except 6-fluoro-5-methoxyindole was used as the starting indole and benzylmethylamine was used as the secondary amine, to provide the desired product as a whiteish solid in about 34% overall yield.

Example 31D. Production of 6-fluoro-5-methoxy-3-(N,N-dimethylaminoethyl)indole

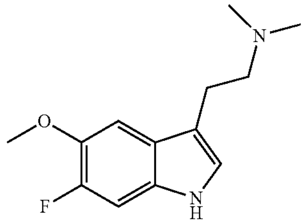

The procedures of Examples 1 D & 2D were repeated, except 6-fluoro-5-methoxyindole was used as the starting indole and dimethylamine was used as the secondary amine (and Pd/C debenzylation step of Example 2D was not performed), to provide the desired product as a whiteish solid in about 40% overall yield.

Example 32D. Production of 6-fluoro-5-methoxy-3-(N-ethyl-N-methylaminoethyl)indole

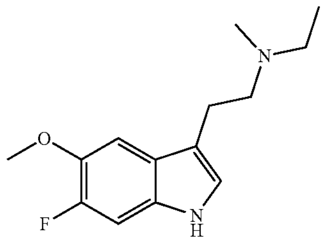 [SMILES: CCN(C)CCc1c[nH]c2cc(F)c(OC)cc12]

The procedures of Examples 1 D & 2D were repeated, except 6-fluoro-5-methoxyindole was used as the starting indole and ethylmethylamine was used as the secondary amine (and Pd/C debenzylation step of Example 2D was not performed), to provide the desired product as a yellowish solid in about 48% overall yield.

Example 33D. Production of 5-methoxy-7-methyl-3-(N-methylaminoethyl)indole

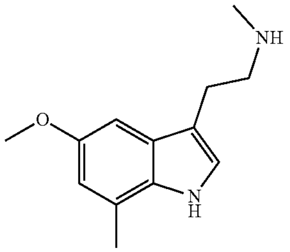 [SMILES: CNCCc1c[nH]c2c(C)cc(OC)cc12]

The procedures of Examples 1D & 2D were repeated, except 5-methoxy-7-methylindole was used as the starting indole and benzylmethylamine was used as the secondary amine, to provide the desired product as a whiteish solid in about 32% overall yield.

Example 34D. Production of 5-methoxy-7-methyl-3-(N-ethylaminoethyl)indole

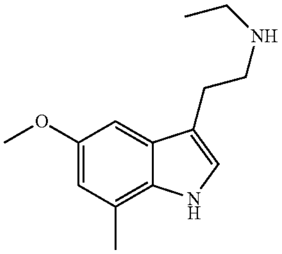 [SMILES: CCNCCc1c[nH]c2c(C)cc(OC)cc12]

The procedures of Examples 1 D & 2D were repeated, except 5-methoxy-7-methylindole was used as the starting indole and benzylethylamine was used as the secondary amine, to provide the desired product as a whiteish solid in about 36% overall yield.

Example 35D. Production of 5-methoxy-7-methyl-3-(N,N-dimethylaminoethyl)indole

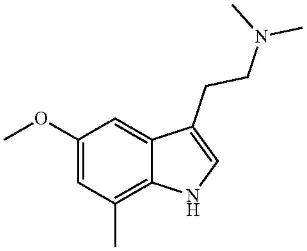

The procedures of Examples 1 D & 2D were repeated, except 5-methoxy-7-methylindole was used as the starting indole and dimethylamine was used as the secondary amine (and Pd/C debenzylation step of Example 2D was not performed), to provide the desired product as a whiteish solid in about 48% overall yield.

Example 36D. Production of 5-methoxy-7-methyl-3-(N-ethyl-N-methylaminoethyl)indole

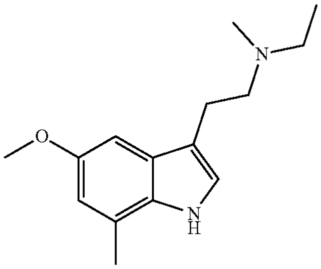 [SMILES: CCN(C)CCc1c[nH]c2c(C)cc(OC)cc12]

The procedures of Examples 1 D & 2D were repeated, except 5-methoxy-7-methylindole was used as the starting indole and ethylmethylamine was used as the secondary amine (and Pd/C debenzylation step of Example 2D was not performed), to provide the desired product as a yellowish solid in about 52% overall yield.

Example 37D. Production of 4-acetoxy-7-methyl-3-(N-methylaminoethyl)indole

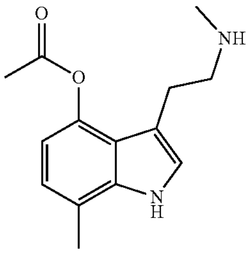 [SMILES: CNCCc1c[nH]c2c(C)ccc(OC(C)=O)c12]

The procedures of Examples 26D & 27D were repeated, except 4-benzyloxy-7-methylindole was used as the starting indole and benzylmethylamine was used as the secondary amine, to provide the desired product as a whiteish solid in about 27% overall yield.

Example 38D. Production of 4-acetoxy-7-methyl-3-(N-ethylaminoethyl)indole

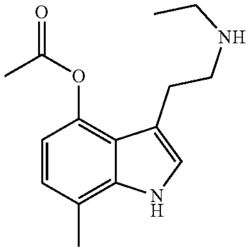 [SMILES: CCNCCc1c[nH]c2c(C)ccc(OC(C)=O)c12]

The procedures of Examples 26D & 27D were repeated, except 4-benzyloxy-7-methylindole was used as the starting indole and benzylethylamine was used as the secondary amine, to provide the desired product as a whiteish solid in about 45% overall yield.

Example 39D. Production of 4-acetoxy-7-methyl-3-(N,N-dimethylaminoethyl)indole

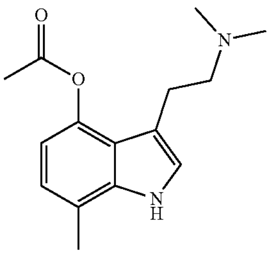 [SMILES: CC(=O)Oc1ccc(C)c2[nH]cc(CCN(C)C)c12]

The procedures of Examples 26D & 27D were repeated, except 4-benzyloxy-7-methylindole was used as the starting indole and dimethylamine was used as the secondary amine to provide the desired product as a pale oil in about 39% overall yield.

Example 40D. Production of 4-acetoxy-7-methyl-3-(N-ethyl-N-methylaminoethyl)indole

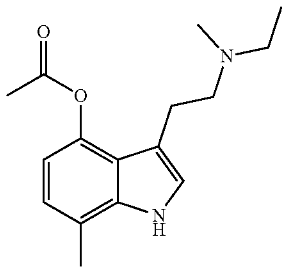 [SMILES: CCN(C)CCc1c[nH]c2c(C)ccc(OC(C)=O)c12]

The procedures of Examples 26D & 27D were repeated, except 4-benzyloxy-7-methylindole was used as the starting indole and ethylmethylamine was used as the secondary amine to provide the desired product as a pale oil in about 37% overall yield.

Example 41D. Production of 4-hydroxy-7-methyl-3-(N-methylaminoethyl)indole

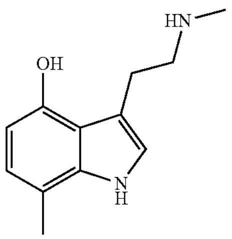

To a solution of acetoxy amine prepared according to the procedure of Example 37D (1.0 mmol) in aqueous methanol (4:1, 0.1 M) was added ammonium acetate (617 mg, 8 mmol) under an inert atmosphere and stirred at room temperature for 4 hours. Methanol was removed in vacuo and the residue was extracted with ethyl acetate (3×) and washed with brine before drying over anhydrous sodium sulfate. Concentration of the dry organic phase resulted in crude phenol which was purified via silica gel chromatography (5% MeOH in $CH_2Cl_2$) to afford the target phenol as a white solid in 86% yield.

Example 42D. Production of 4-hydroxy-7-methyl-3-(N-ethylaminoethyl)indole

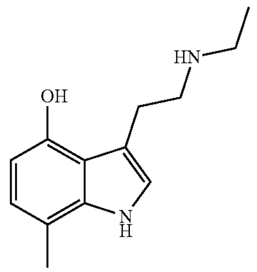 [SMILES: CCNCCc1c[nH]c2c(C)ccc(O)c12]

The procedures of Example 41 D was repeated, except the acetoxy indole of Example 38D served as the starting material, to provide the desired product as a white solid in 90% yield.

Example 43D. Production of 4-hydroxy-7-methyl-3-(N,N-dimethylaminoethyl)indole

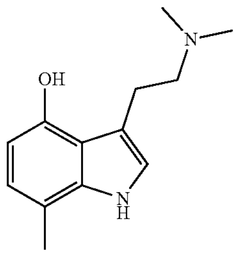 [SMILES: Cc1ccc(O)c2c(CCN(C)C)c[nH]c12]

The procedures of Example 41 D was repeated, except the acetoxy indole of Example 39D served as the starting material, to provide the desired product as a white solid in 96% yield.

Example 44D. Production of 4-hydroxy-7-methyl-3-(N-ethyl-N-methylaminoethyl)indole

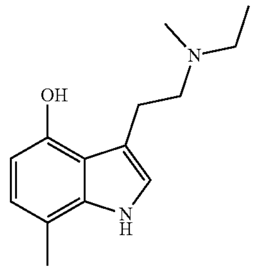 [SMILES: CCN(C)CCc1c[nH]c2c(C)ccc(O)c12]

The procedures of Example 41 D was repeated, except the acetoxy indole of Example 40D served as the starting material, to provide the desired product as a white solid in 92% yield.

Example 45D. Production of 4-acetoxy-6-fluoro-3-(N-methylaminoethyl)indole

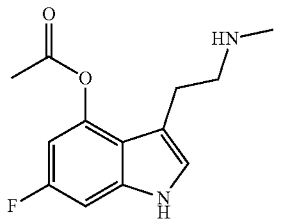 [SMILES: CNCCc1c[nH]c2cc(F)cc(OC(C)=O)c12]

The procedures of Examples 26D & 27D were repeated, except 4-benzyloxy-6-fluoroindole was used as the starting indole and benzylmethylamine was used as the secondary amine, to provide the desired product as a whiteish solid in about 22% overall yield.

Example 46D. Production of 4-acetoxy-6-fluoro-3-(N-ethylaminoethyl)indole

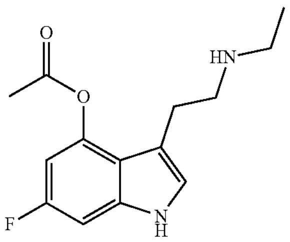 [SMILES: CCNCCc1c[nH]c2cc(F)cc(OC(C)=O)c12]

The procedures of Examples 26D & 27D were repeated, except 4-benzyloxy-6-fluoroindole was used as the starting indole and benzylethylamine was used as the secondary amine, to provide the desired product as a whiteish solid in about 45% overall yield.

Example 47D. Production of 4-acetoxy-7-methyl-3-(N,N-dimethylaminoethyl)indole

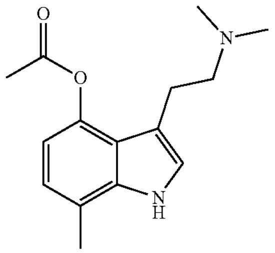 [SMILES: CC(=O)Oc1ccc(C)c2[nH]cc(CCN(C)C)c12]

The procedures of Examples 26D & 27D were repeated, except 4-benzyloxy-7-methylindole was used as the starting indole and dimethylamine was used as the secondary amine to provide the desired product as a pale oil in about 39% overall yield.

Example 48D. Production of 4-acetoxy-7-methyl-3-(N-ethyl-N-methylaminoethyl)indole

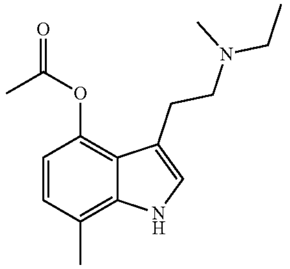 [SMILES: CCN(C)CCc1c[nH]c2c(C)ccc(OC(C)=O)c12]

The procedures of Examples 26D & 27D were repeated, except 4-benzyloxy-7-methylindole was used as the starting indole and ethylmethylamine was used as the secondary amine to provide the desired product as a pale oil in about 37% overall yield.

Example 49D. Production of 4-hydroxy-6-fluoro-7-methyl-3-(N-ethylaminoethyl)indole

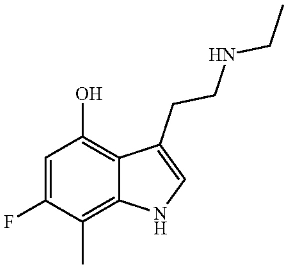 [SMILES: CCNCCc1c[nH]c2c(C)c(F)cc(O)c12]

The procedure of Example 1 D is repeated, except 6-fluoro-7-methyl-1-(triisopropyl silyl)indole is used as the starting indole, to provide the desired silyl-protected keto-amide intermediate without further purification.

The TIPS-protected ketoamide (1 eq), $Pd(OAc)_2$ (0.1 eq), and glycine (4 eq), are charged to a flame dried reaction flask, followed by the addition of HFIP/AcOH (3/2) 1 mL via syringe under air. The reaction mixture is stirred at room temperature for 10 minutes, then placed in a preheated oil bath at 80° C. for 17 hours before diluting with ethyl acetate and quenching with $NaHCO_3$. The reaction mixture is extracted with ethyl acetate thrice and dried using anhydrous sodium sulfate which is then filtered and concentrated in vacuo to provide the 4-acetylated ketoamide intermediate.

To a solution of 4-acetylated ketoamide (1 eq) in THE at 0° C. under an inert atmosphere is added $LiAlH_4$ (53 mg, 1.4 mmol, 5 eq) in one portion and mixture is heated at reflux for 4 hours. The reaction is quench by addition of water and the aqueous layer is extracted with $Et_2O$. The combined organic layer is washed with brine, dried over anhyd. sodium sulfate and concentrated in vacuo to provide the crude benzylethyl amine intermediate.

The benzylethylamine intermediate harboring the TIPs protecting group (1 eq) is suspended in THE under an inert atmosphere at room temperature before the addition of a 1 M solution of tetrabutylammonium fluoride (TBAF) in tetrahydrofuran. The solution is stirred for 10 min at room temperature, then poured into a saturated solution of sodium carbonate and extracted with dichloromethane (3×10 mL). The combined organic layers are washed with water, dried over sodium sulfate, and evaporated under reduced pressure. The residue is purified via silica gel chromatography (5 to 9% MeOH in DCM) to afford the deprotected benzethylamine intermediate.

To a solution of the deprotected benzylethylamine intermediate (1 equiv) in MeOH is added 10 wt/wt % Pd/C (10-15%). The reaction mixture is degassed to remove oxygen and stirred under a hydrogen atmosphere (1 atm) for 18-24 hours. Upon completion, the reaction mixture is filtered over a pad of celite and the solvent removed in vacuo. The target debenzylated ethylamine target compound could be isolated from the crude by purification on silica gel chromatography (load with DCM, elute with 1% MeOH/DCM then 5% MeOH/DCM doped with 1% $NEt_3$).

Example 50D. Production of 4-hydroxy-6-fluoro-7-methyl-3-(N-methylaminoethyl)indole

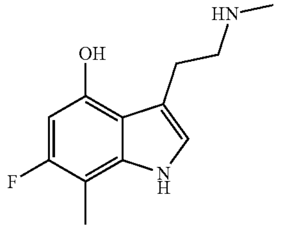 [SMILES: CNCCc1c[nH]c2c(C)c(F)cc(O)c12]

The procedure of Example 49D is repeated, except benzylmethylamine is used as the secondary amine, to provide the desired product.

Example 51D. Production of 4-hydroxy-6-fluoro-7-methyl-3-(N,N-dimethylaminoethyl)indole

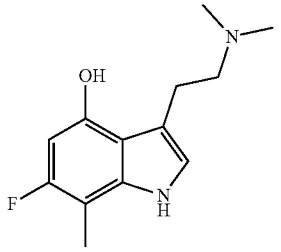 [SMILES: Cc1c(F)cc(O)c2c(CCN(C)C)c[nH]c12]

The procedure of Example 50D is repeated, except dimethylamine is used as the secondary amine (and the final Pd/C debenzylation step is not conducted), to provide the desired product.

Example 52D. Production of 4-hydroxy-6-fluoro-7-methyl-3-(N-ethyl-N-methylaminoethyl)indole

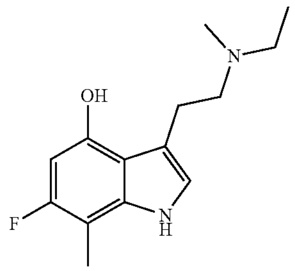 [SMILES: CCN(C)CCc1c[nH]c2c(C)c(F)cc(O)c12]

The procedure of Example 50D is repeated, except ethylmethylamine is used as the secondary amine (and the final Pd/C debenzylation step is not conducted), to provide the desired product.

Example 53D. Production of 4-acetoxy-6-fluoro-7-methyl-3-(N-ethylaminoethyl)indole

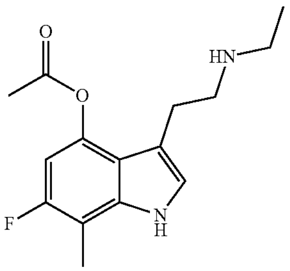 [SMILES: CCNCCc1c[nH]c2c(C)c(F)cc(OC(C)=O)c12]

The 4-hydroxyl product prepared according to the method of Example 49D (1 eq) is dissolved in anhydrous DCM under nitrogen and cooled to 0° C. $Et_3N$ (1.2 eq) was added to solution followed by Boc-anhydride (1.1 eq) in a dropwise manner, and the reaction mixture stirred at rt until the disappearance of the starting material as monitored by TLC. The reaction mix is then diluted with DCM and sequentially washed with water and brine. The organic layer is then dried with sodium sulfate concentrated to yield the N—BOC protected intermediate.

The N—BOC protected intermediate is then taken up in DCM and the solution was cooled to 0° C. $Et_3N$ (2.1 eq) was added to the solution followed by the dropwise addition of acetyl chloride (1.3 eq) in a dropwise manner and the reaction is then stirred at room temperature until the disappearance of the starting material (per TLC). After completion, the reaction mixture is diluted with DCM and washed with water and brine washes. The organic layer is removed and dried under sodium sulfate and reduced under pressure to yield an oily residue.

The residue is then taken up in anhydrous DCM, to which HCl in ether (2M; 12 equiv) was added in a dropwise manner to the solution being stirred at 0° C. Stirring is continued until the starting material was consumed by TLC monitoring. The resulting precipitate after the completion of the reaction is filtered and washed with cold DCM, diethyl ether and dried under vacuum to yield the desired compound.

Example 54D. Production of 4-acetoxy-6-fluoro-7-methyl-3-(N-methylaminoethyl)indole

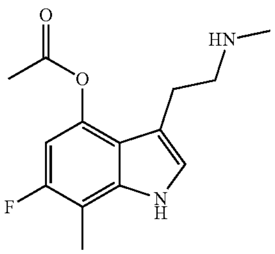 [SMILES: CNCCc1c[nH]c2c(C)c(F)cc(OC(C)=O)c12]

The procedure of Example 53D is repeated, the product prepared according to the method of Example 50D is used as starting material, to provide the desired product.

Example 55D. Production of 4-acetoxy-6-fluoro-7-methyl-3-(N,N-dimethylaminoethyl)indole

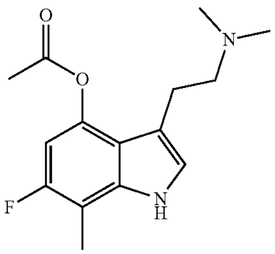 [SMILES: CC(=O)Oc1cc(F)c(C)c2[nH]cc(CCN(C)C)c12]

The procedure of Example 53D is repeated, except the product prepared according to the method of Example 51 D is used as starting material, to provide the desired product.

Example 56D. Production of 4-acetoxy-6-fluoro-7-methyl-3-(N-ethyl-N-methylaminoethyl)indole

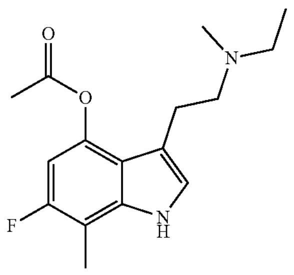 [SMILES: CCN(C)CCc1c[nH]c2c(C)c(F)cc(OC(C)=O)c12]

The procedure of Example 55D is repeated, except with the product prepared by Example 52D, to provide the desired product.

Example 57D. Production of 4-fluoro-3-(N-ethylaminoethyl)indole

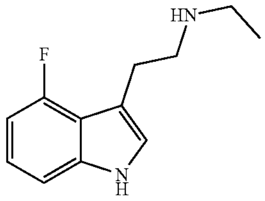

The procedure of Example 1 D and 2D are repeated, except 4-fluoroindole is used as the starting material, to provide the desired product.

Example 58D. Production of 3-(N-n-propylaminoethyl)indole

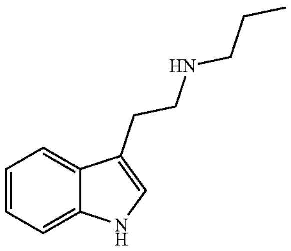

The procedure of Example 1D and 2D are repeated, except indole is used as the starting material and benzyl-n-propylamine is used as the secondary amine, to provide the desired product.

Example 59D. Production of 4-hydroxy-3-(N-ethylaminoethyl)indole

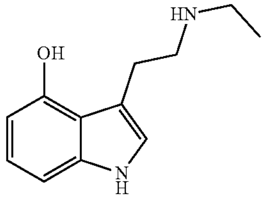

The procedures of Example 38D and 42D were followed, except 4-benzyloxyindole was used as the starting indole, to provide the desired product in good yield.

Example 60D. Production of 3-(N-2-fluoroethylaminoethyl)indole

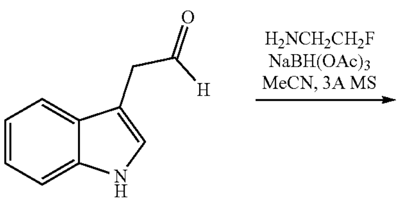

-continued

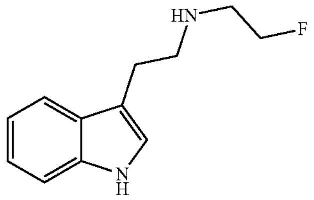

To a solution of homologated aldehyde (1.0 eq) in acetonitrile (0.1 M) is added 2-fluoroethylamine (2-5 eq) and a few beads of activated whole 3A MS. After stirring at room temperature for 10 min, $NaHB(OAc)_3$ (>5 eq) is added at once. The reaction mixture is allowed to stir 18-24 hours at room temperature before being quenched by the addition of 1M HCl and diluted with diethyl ether. The phases are separated and the organic phase washed with 1 M HCl (×2). The combined aqueous phases are basified by the addition of solid NaOH. The aqueous phase is extracted with DCM (×3) and the combined DCM washes are dried over anhydrous sodium sulfate. After filtration, the solvent is removed in vacuo and purified via $SiO_2$ chromatography eluting with 1 to 5% MeOH in DCM to afford the desired product.

Example 61D. Production of 3-(N-ethyl-d2-aminoethyl)indole

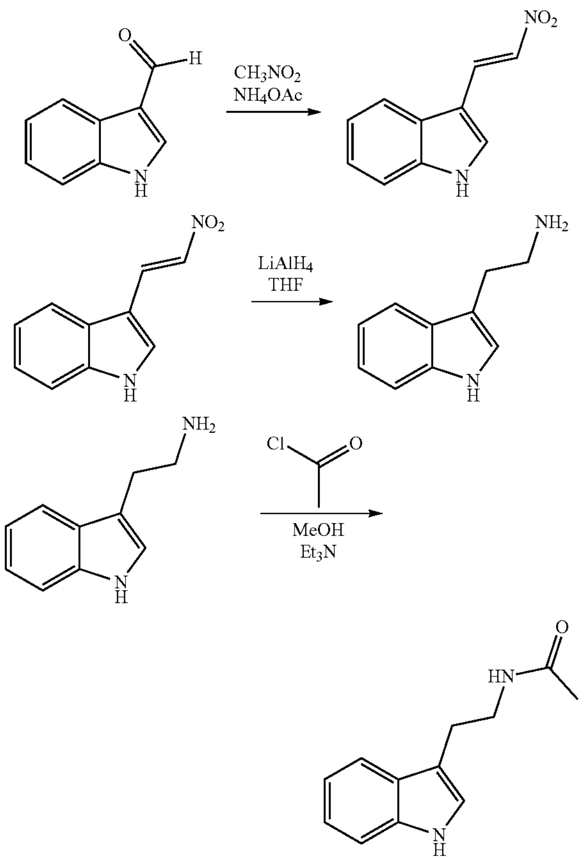

-continued

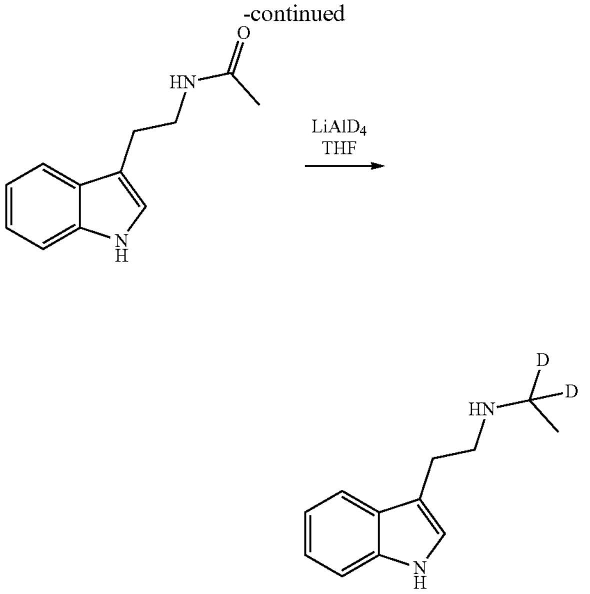

A solution C-3 carbaldehyde (2.5 mmol) and ammonium acetate (1.94 mmol, 0.8 eq) in nitromethane (8 mL) is heated at reflux under an inert atmosphere for 3 hrs or until the reaction is complete by TLC. The resulting reaction mixture is cooled to room temperature and the precipitated solid is collected via filtration over a Buchner funnel to afford the alpha-beta unsaturated nitro adduct.

To a solution of lithium aluminum hydride (18.4 mmol, 5.3 equiv) in anhydrous THE (15 mL) is added alpha beta unsaturated nitro compound (3.48 mmol) portionwise. The resulting solution is stirred at room temperature under an inert atmosphere for 24 hours. Ethyl acetate (15 mL) is then slowly added to the reaction mixture followed by water (1 mL) and sodium sulfate hexahydrate. The resulting mixture is stirred for an additional hour before filtering through Celite and concentrating under reduced pressure. The residual oil is purified via $SiO_2$ chromatography eluting with MeOH:TEA:EA (3:2:15) to afford the primary amine.

The primary amine (0.68 mmol) and triethylamine (1.02 mmol) are dissolved in methanol, then cooled to 0° C. before acetyl chloride (0.68 mmol, 1.0 eq) is added dropwise. The resulting mixture is allowed to warm to room temperature and stirred for 4 hours. When the starting material is consumed, according to TLC, it is concentrated in vacuo and the residue is taken up in dichloromethane before washing with 10% citric acid, saturated sodium bicarbonate, and brine. The organic layers are combined and dried using sodium sulfate, filtered and concentrated to afford the desired amide intermediate.

To a solution of the amide intermediate (1.0 mmol) in THE (15 mL) under an inert atmosphere at 0° C. is added $LiAlD_4$ powder (3.5 eq) portionwise before heating at reflux for 24 hours. The reaction is quenched using $Et_2O$ (20 mL) and water (2 mL) at 0° C. followed by filtration through a pad of Celite. The aqueous phase is extracted with ethyl acetate thrice and the combined organic layers are washed with brine three times before drying over anhydrous sodium sulfate and concentrating in vacuo. The crude product is purified via $SiO_2$ chromatography using 5% MeOH in DCM to afford the desired product.

Example 62D. Production of 3-(N-ethyl-d2-aminoethyl-d2)indole

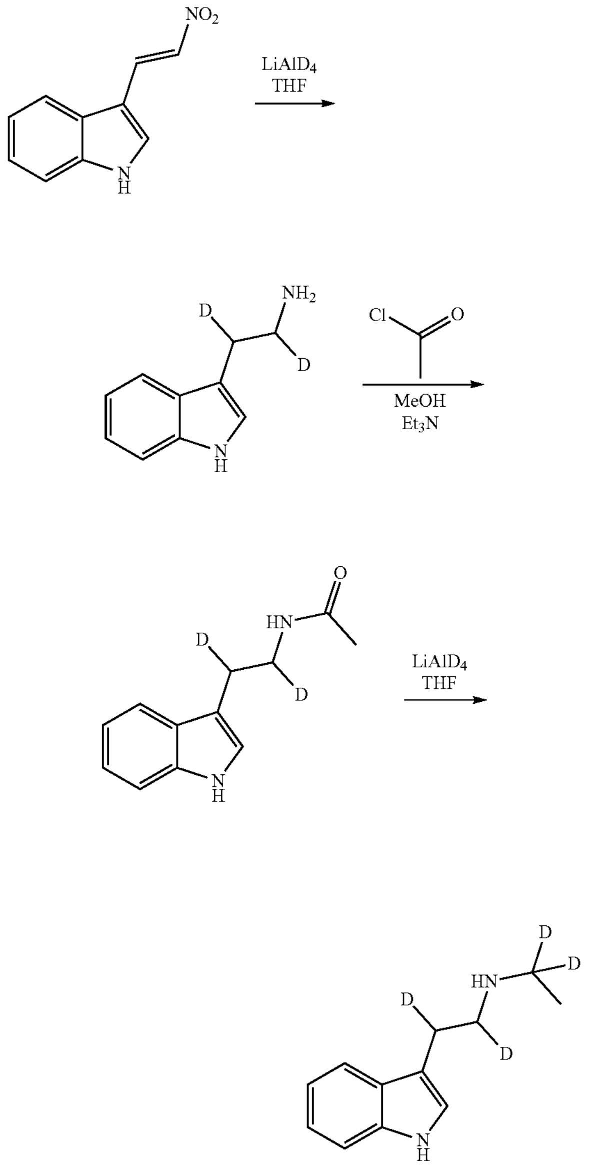

The alpha-beta unsaturated nitro starting material is prepared according to the method of Example 61D. To a solution of lithium aluminum deuteride (18.4 mmol, 5.3 equiv) in anhydrous THF (15 mL) is added alpha beta unsaturated nitro compound (3.48 mmol) portionwise. The resulting solution is stirred at room temperature under an inert atmosphere for 24 hours. Ethyl acetate (15 mL) is then slowly added to the reaction mixture followed by water (1 mL) and sodium sulfate hexahydrate. The resulting mixture is stirred for an additional hour before filtering through Celite and concentrating under reduced pressure. The residue is purified via $SiO_2$ chromatography eluting with MeOH:TEA:EA (3:2:15) to afford the d4 primary amine. Acetylation of the d4 primary amine and deuteride reduction proceeds according to the procedure of Example 61 D to afford the desired d5 indole product.

Example 63D. Production of 3-(N-ethylaminoethyl-d2)indole

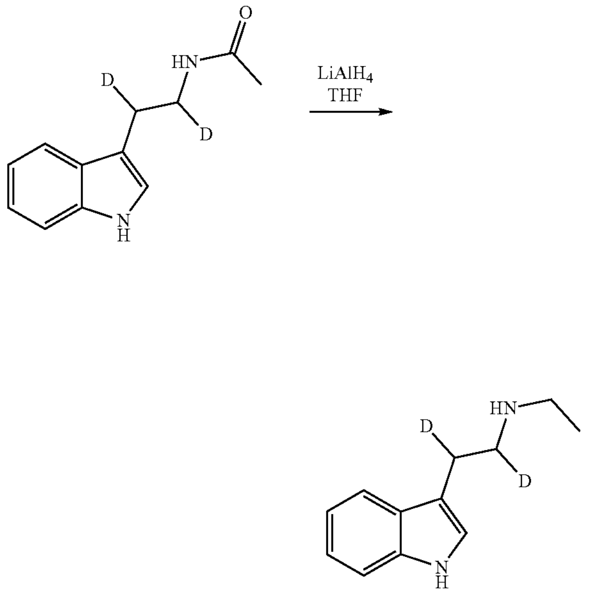

The procedure of Example 62D is repeated, except reduction of the amide is conducted with lithium aluminum hydride instead of lithium aluminum deuteride, to afford the desired deuterated indole.

Example 64D. Production of 3-(N-2-fluoroethylaminoethyl-d1)indole

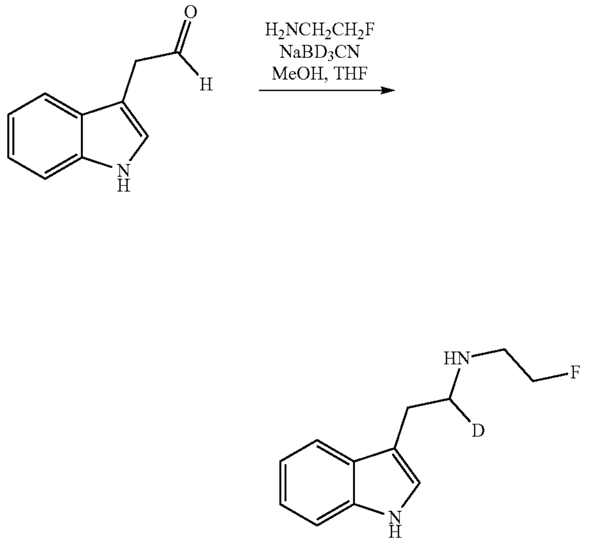

The procedure of Example 60D is repeated, except sodium cyano borodeuteride is used instead of sodium triacetoxyborohydride and the reaction is run in a MeOH and THF solvent system to afford the desired deuterated indole.

Example 65D. Production of 3-(N-ethylaminoethyl-d1)indole

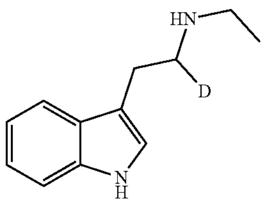

The procedure of Example 64D is repeated, except benzylethylamine is used instead of 2-F-ethylmine, which is then debenzylated according to 27D, to afford the desired deuterated indole.

Example 66D. Production of Tryptamine d1

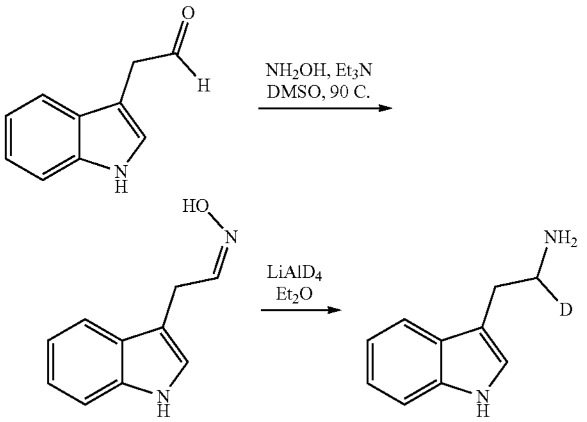

To a vial equipped with a stir bar was added homologated aldehyde (1 eq) followed by triethylamine (1.5 eq) hydroxylamine hydrochloride (1.2 eq) and DMSO. The vial was capped and heated at 90° C. for 1 h. The reaction mixture was cooled to room temperature and water and ether were added to the vial. The aqueous layer was removed and extracted with ether. The combined ethereal layers were washed with water then brine, dried over $MgSO_4$, and concentrated under reduced pressure. The resulting pale residue was used crude without further purification.

To a solution of lithium aluminum deuteride (5.3 eq) in anhydrous ether was added oxime (3.48 mmol) in ether was slowly added. The resulting solution was refluxed under an inert atmosphere for 8 hrs. After cooling, the excess hydride was decomposed by the dropwise addition of water. The complex was hydrolyzed by the addition of 30% sodium hydroxide solution. The mixture was stirred at room temperature for 30 min. and then an additional aliquot of water was added. The ether layer was then decanted from the granular residue of metal hydroxides. The residue was washed several times with ether, and all washings were combined with the original ether fraction and filtered through Celite. The combined ether fraction was then solvent was then concentrated under reduced pressure and purified via $SiO_2$ chromatography eluting with MeOH:TEA:EA (3:2:15) to afford the desired primary amine.

Example 67D. Production of 3-(N-ethylaminoethyl-d1)indole

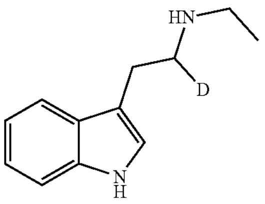

The procedures of Examples 62D and 63D are repeated, except the alpha deuterated tryptamine of Example 66D is utilized to form the amide and LAH is used as the reducing agent, to produce the desired deuterated indole.

Example 68D. Resolution of 3-(N-ethylaminoethyl-d1)indole

The product produced according to Example 67D is resolved using known methods of enantiomeric resolution, such as HPLC or the method of cyclic crystallization of bitartrate diastereomers described in Foreman et al., *J. Pharm. Sci.,* 58(2): 189-192 (1969), which is incorporated herein by reference in its entirety for all purposes, two provide two separate compositions enriched with the (S) and (R) enantiomers, respectively:

(2S)

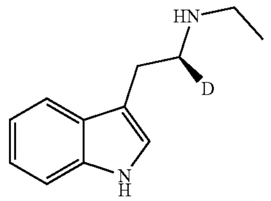

(2R)

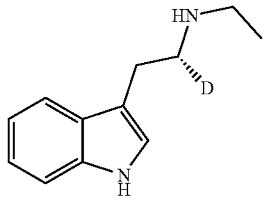

Example 69D. Production of Hydrofumarate Salts (Aka [1:1] Fumarate Salts)

[1:1]hydrofumarate salts of each one of the compounds are separately produced from the compounds of Examples 2-5D, 7-25D and 27-68D using the following procedure:

1 equiv of the free base product is dissolved in acetone and is added dropwise to a boiling solution of fumaric acid (1 equiv) in acetone. A precipitate forms immediately and the precipitate/acetone is stored overnight at −20° C. The solids are then filtered and washed with ice-cold acetone to yield the desired crystalline hydrofumarate salt.

Example 70D. Production of Fumarate Salts (Aka [2:1] Fumarate Salts)

[2:1] fumarate salts of each one of the compounds are separately produced from the compounds of Examples 2-5D, 7-25D and 27-68D using the following procedure:

1 equiv of the free base product is dissolved in acetone and is added dropwise to a boiling solution of fumaric acid (0.5 equiv) in acetone. A precipitate forms immediately and the precipitate/acetone is stored overnight at −20° C. The solids are then filtered and washed with ice-cold acetone to yield the desired crystalline fumarate salt.

Biological Studies

Head-Twitch Response (HTR) Experiments.

Dose-response studies. Dose-response studies for compounds of Formula I are performed in four consecutive steps:

(a). Formulation work. A suitable (non-toxic) vehicle will be identified that can be used to dissolve the compound.

(b). Pilot dose-finding study. HTR-inducing drugs typically have biphasic bell-shaped (inverted U-shaped) dose-response functions, with ascending and descending phases. To quantify the potency of a drug in a HTR dose-response study, doses covering the entire extent of the ascending phase should be included, as well as at least one dose that falls on the descending phase. A pilot dose-finding study is performed to identify a set of doses that matches those requirements. For the pilot, male C57BL/6J mice will be injected with a range of doses (typically 0.3-30 mg/kg) by the IP or SC route and then behavior will be recorded in a magnetometer chamber for up to 150 minutes.

(c). Dose-response study. Groups of male C57BL/6J mice with a magnet implant are injected with vehicle or 4-5 doses of the compound (n=5-7 mice/group) by the IP or SC route and then behavior will be recorded in a magnetometer chamber for at least 30 minutes.

(d). Repeated testing. Although potency can typically be quantified based on a single dose-response study, in some instances repeated testing may be necessary. For example, the doses selected for testing may not have been ideal to calculate the median effective dose (ED50 value). If necessary, a second or third dose-response study will be performed.

Analysis: The following analyses will be performed for dose-response studies:

HTR counts will be analyzed using a 1-way ANOVA followed by a post-hoc test (Dunnett's test).

The median effective dose ($ED_{50}$ value) for the compounds (in mg/kg or moles/kg) will calculated by nonlinear regression using a gaussian or sigmoidal model. The potencies of compounds and other reference compounds can also be compared statistically using an extra-sum-of-squares F-test.

HTR counts can be binned (e.g., blocks of 1, 2, 5, or 10 minutes) and analyzed using a 2-way ANOVA (drug×time) followed by a post-hoc test (Dunnett's test or Tukey's test).

$5\text{-HT}_{2A}$ Antagonist blockade studies. Four groups of male C57BL/6J mice with a magnet implant are pretreated SC with the selective $5\text{-HT}_{2A}$ antagonist M100907 (vehicle, 0.001, 0.01, or 0.1 mg/kg). Twenty minutes later, all of the animals will be injected IP or SC with one dose of the compound (n=5-7 mice/group) and then behavior will be recorded in a magnetometer chamber for 30 minutes.

$5\text{-HT}_{1A}$ Antagonist blockade studies. Four groups of male C57BL/6J mice (n=5-7 mice/group) with a magnet implant are pretreated SC with the selective $5\text{-HT}_{1A}$ antagonist WAY-100635 (vehicle or 1 mg/kg). Twenty minutes later, the animals will be injected IP or SC with vehicle or one dose of the compound and then behavior will be recorded in a magnetometer chamber for at least 30 minutes.

Extended time-course studies. Male C57BL/6J mice with a magnet implant are injected IP or SC with up to three different treatments (n=5-6 mice/group) and then behavior will be recorded in a magnetometer chamber for up to 5 hours (the exact assessment period used will depend on the duration-of-action of the Material being tested).

Brain penetration testing. These studies are used to test whether 5-HT2A ligands that do not induce the HTR are brain penetrant in mice. Male C57BL/6J mice with a magnet implant are pretreated IP or SC with vehicle or three doses of the 5-HT2A ligand (n=5-7 mice/group); 20 minutes later, all of the mice are injected IP with 1 mg/kg (±)-DOI HCl, and then behavior will be recorded in a magnetometer chamber for 20-30 minutes.

hERG Inhibition Studies.

All experiments are conducted manually using a HEKA EPC-10 amplifier at room temperature in the whole-cell mode of the patch-clamp technique. HEK293 cells stably expressing hKv11.1 (hERG) under G418 selection can be sourced from the University of Wisconsin, Madison. Cells are cultured in DMEM containing 10% fetal bovine serum, 2 mM glutamine, 1 mM sodium pyruvate, 100 U ml-1 streptomycin, and 500 mg ml-1 penicillin, 100 μg ml-1 G418. The cell line is not authenticated or tested for mycoplasma contamination. Before experiments, cells are grown to 60-80% confluency, lifted using TrypLE, and plated onto poly-I-lysine-coated coverslips. Patch pipettes are pulled from soda lime glass (micro-haematocrit tubes) and should exhibit resistances of 2-4 MO. For the external solution, normal sodium Ringer is used (160 mM NaCl, 4.5 mM KCl, 2 mM $CaCl_2$, 1 mM $MgCl_2$, 10 mM HEPES, pH 7.4 and 290-310 mOsm). The internal solution used is potassium fluoride with ATP (160 mM KF, 2 mM MgCl2, 10 mM EGTA, 10 mM HEPES, 4 mM NaATP, pH=7.2 and 300-320 mOsm). A two-step pulse (applied every 10 s) from −80 mV initially to 40 mV for 2 s and then to −60 mV for 4 s, is used to elicit hERG currents. The percentage reduction of tail current amplitude by the compounds of Formula I that are tested is determined and data are shown as mean±s.d. (n=3-4 per data point). For all experiments, solutions of the drugs are prepared fresh from 10 mM stocks in DMSO. The final DMSO concentration never exceeds 1%.

Serotonin and Opioid Receptor Functional Assays.

Functional assay screens at 5-HT and opioid receptors are performed in parallel using the same compound dilutions and 384-well-format high-throughput assay platforms. Assays are used to assess activity at all human isoforms of the receptors, except where noted for the mouse $5\text{-HT}_2A$ receptor. Receptor constructs in pcDNA vectors are generated from the Presto-Tango GPCR library39 with minor modifications. All tested compounds of Formula I are serially diluted in drug buffer (HBSS, 20 mM HEPES, pH 7.4 supplemented with 0.1% bovine serum albumin and 0.01% ascorbic acid) and dispensed into 384-well assay plates using a FLIPR Tetra automated dispenser head (Molecular Devices). Every plate includes a positive control such as 5-HT (for all 5-HT receptors), DADLE (DOR), salvinorin A (KOR), and DAMGO (MOR). For measurements of $5\text{-HT}_{2A}$ $5\text{-HT}_{2B}$, and $5\text{-HT}_{2C}$ Gq-mediated calcium flux function, HEK Flp-In 293, T-Rex stable cell lines (Invitrogen) are loaded with Fluo-4 dye for one hour, stimulated with compounds and read for baseline (0-10 s) and peak fold-over-basal fluorescence (5 min) at 25° C. on the FLIPR Tetra system. For measurement of $5\text{-HT}_6$ Gs and $5\text{-HT}_{7a}$ functional assays, -mediated cAMP accumulation is detected using the split-luciferase GloSensor assay in HEKT cells measuring luminescence on a Microbeta Trilux (Perkin Elmer) with a 15 min drug incubation at 25° C. For $5\text{-HT}_{1A}$, $5\text{-HT}_{1B}$, $5\text{-HT}_{1F}$, MOR, KOR and DOR functional assays, Gi/o, -mediated cAMP inhibition is measured using the split-luciferase GloSensor assay in HEKT cells, conducted similarly to that above, but in combination with either 0.3 μM isoproterenol (5-$HT_{1A}$, 5-$HT_{1B}$, 5-$HT_{1F}$) or 1 μM forskolin (MOR, KOR and DOR) to stimulate endogenous cAMP accumulation. For measurement of 5-$HT_{1D}$, 5-$HT_{1E}$, 5-$HT_4$, and 5-$HT_{5A}$ functional assays, 3-arrestin2 recruitment is measured by the Tango assay using HTLA cells expressing tobacco etch virus (TEV) fused-β-arrestin2, as described previously with minor modifications. Cell lines were not authenticated, but they ae purchased mycoplasma-free and tested for mycoplasma contamination. Data for all assays are plotted and nonlinear regression is performed using "log(agonist) vs. response" in GraphPad Prism to yield estimates of the efficacy (Emax and half-maximal effective concentration ($EC_{50}$)).

Pharmacokinetic Studies.

Male and female C57/BL6J mice (12 weeks old) are administered a compound of Formula I via i.p. injection at doses of either 50 mg kg-1, 10 mg kg-1 or 1 mg kg-1. Mice are euthanized 15 min or 3 h after injection by cervical dislocation. Two males and two females are used per dose and time point. Brain and liver are collected, flash-frozen in liquid nitrogen, and stored at −80° C. until metabolomic processing. Whole brain and liver sections are lyophilized overnight to complete dryness, then homogenized with 3.2 mm diameter stainless-steel beads using a GenoGrinder for 50 s at 1,500 rpm. Ground tissue is then extracted using 225 μl cold methanol, 190 μl water, 750 μl methyl tert-butyl ether (MTBE). Seven method blanks and seven quality-control samples (pooled human serum, BioIVT) are extracted at the same time as the samples. The nonpolar fraction of MTBE is dried under vacuum and reconstituted in 60 μl of 90:10 (v/v) methanol:toluene containing 1-cyclohexyldodecanoic acid urea as an internal standard. Samples are then vortexed, sonicated and centrifuged before analysis.

For analysis of the tested compound in liver and brain, samples are randomized before injection with method blanks and quality-control samples are analyzed between every ten study samples. A six-point calibration curve is analyzed after column equilibration using blank injections, and then after all study samples. Blanks are injected after the calibration curve to ensure no that none of the tested compound is retained on the column and carried over to samples. Reconstituted sample (5 μl) is injected onto a Waters Acquity UPLC CSH C18 column (100 mm×2.1 mm, 1.7 μm particle size) with an Acquity UPLC CSH C18 VanGuard precolumn (Waters) using a Vanquish UHPLC coupled to a TSQ Altis triple quadrupole mass spectrometer (Thermo Fisher Scientific). Mobile phase A consists of 60:40 v/v acetonitrile/water with 10 mM ammonium formate and 0.1% formic acid. Mobile phase B consists of 90:10 v/v isopropanol/acetonitrile with 10 mM ammonium formate and 0.1% formic acid. Gradients are run from 0-2 min at 15% B; 2-2.5 min 30% B; 2.5-4.5 min 48% B; 4.5-7.3 min 99% B; 7.3-10 min 15% B. The flow rate is 0.600 ml/min and the column is heated to 65° C. Mass spectrometer conditions are optimized for the target compound by direct infusion. Selected reaction monitoring is performed for the top five ions, with collision energy, source fragmentation, and radiofrequency optimized for the test compound. Data are processed with TraceFinder 4.1 (Thermo Fisher Scientific). Organ weights are recorded. The concentration in the brain is calculated using the experimentally determined number of moles of the target compound in the whole organ divided by the weight of the organ.

5-HT Receptor Functional Assays.

Various assays for measuring serotonin receptor activation are known to those of skill in the art, including those methods described in Olsen et al., *Nat. Chem. Biol.,* 2020 August; 16(8):841-49, incorporated herein by reference in its entirety for all purposes. The assays described therein may be utilized to measure the functional activity of any of the serotonin receptor subtypes described herein, including 5-HT1A, 5-HT2A, 5-HT2B, and 5-HT2C. In certain embodiments, serotonin (5-hydroxytryptamine) is used as the reference compound.

Cell Culture

HEK293T cells are maintained, passaged, and transfected in DMEM medium containing 10% FBS, 100 Units/mL penicillin, and 100 μg/mL streptomycin (Gibco-ThermoFisher, Waltham, MA) in a humidified atmosphere at 37° C. and 5% CO2. After transfection, cells are plated in DMEM containing 1% dialyzed FBS, 100 Units/mL penicillin, and 100 μg/mL streptomycin for BRET2, calcium, and GloSensor assays.

BRET2 Assays

Cells are plated either in six-well dishes at a density of 700,000-800,000 cells/well, or 10-cm dishes at 7-8 million cells/dish. Cells are transfected 2-4 hours later, using a 1:1:1:1 DNA ratio of receptor:Gα-RLuc8:Gβ:Gγ-GFP2 (100 ng/construct for six-well dishes, 750 ng/construct for 10-cm dishes), except for the Gγ-GFP2 screen, where an ethanol co-precipitated mixture of Gβ1-4- is used at twice its normal ratio (1:1:2:1). Transit 2020 (Mirus Biosciences, Madison, WI) is used to complex the DNA at a ratio of 3 μl Transit/μg DNA, in OptiMEM (Gibco-ThermoFisher, Waltham, MA) at a concentration of 10 ng DNA/μL OptiMEM. The next day, cells are harvested from the plate using Versene (0.1M PBS+0.5 mM EDTA, pH 7.4), and plated in poly-D-lysine-coated white, clear bottom 96-well assay plates (Greiner Bio-One, Monroe, NC) at a density of 30,000-50,000 cells/well.

One day after plating in 96-well assay plates, white backings (Perkin Elmer, Waltham, MA) are applied to the plate bottoms, and growth medium is carefully aspirated and replaced immediately with 60 μL of assay buffer (1×HBSS+20 mM HEPES, pH 7.4), followed by a 10 μL addition of freshly prepared 50 μM coelenterazine 400a (Nanolight Technologies, Pinetop, AZ). After a five-minute equilibration period, cells are treated with 30 μl of drug for an additional 5 minutes. Plates are then read in an LB940 Mithras plate reader (Berthold Technologies, Oak Ridge, TN) with 395 nm (RLuc8-coelenterazine 400a) and 510 nm (GFP2) emission filters, at 1 second/well integration times. Plates are read serially six times, and measurements from the sixth read were used in all analyses. BRET2 ratios are computed as the ratio of the GFP2 emission to RLuc8 emission.

Calcium Mobilization Assays

Cells are plated in 10-cm plates as described in the BRET2 protocol and co-transfected with receptor (1 μg) and Gα-subunit (1 μg) cDNA. The next day, cells are plated at 15,000 cells/well in poly-D-lysine coated black, clear bottom 384-well plates (Greiner Bio-One, Monroe, NC). The following day, growth medium are aspirated and replaced with 20 μL assay buffer containing 1× Fluo-4 Direct Calcium Dye (ThermoFisher Scientific, Waltham, MA) and incubated for 60 minutes at 37° C. (no $CO_2$). Plates were brought to RT for 10 minutes in the dark before being loaded into a FLIPR Tetra® liquid-handling robot and plate reader (Molecular Devices, San Jose, CA). Baseline fluorescence measurements were taken for 10 seconds followed by robotic drug addition (10 µL) and a 60-second measurement (1 measurement/second). For antagonist assays, cells are first treated with antagonist and kept in the dark at room temperature for ten minutes before agonist addition by the FLIPR Tetra® robot. Maximal response during this time is used to calculate amplitude of the calcium transients. Measurements were analyzed as percentage of maximum signal amplitude for the construct.

Glosensor cAMP Assays

Cells are plated in 10-cm plates as previously described. Cells are transfected with plasmids encoding cDNA for the Glosensor reporter (Promega, Madison, WI), receptor, and Gα-subunit at a ratio of 2:1:1 (2 µg: 1 µg: 1 µg). The next day, cells are plated in black, clear-bottom, 384-well white plates. After aspiration of the medium on the day of the assay, cells are incubated for 60 minutes at 37° C. with 20 µL of 5 mM luciferin substrate (GoldBio, St. Louis, MO) freshly prepared in assay buffer. For Gas activity, 10 µL of drugs are added using the FLIPR Tetra® liquid-handling robot and read after 15 minutes in a Spectramax luminescence plate reader (Molecular Devices, San Jose, CA) with a 0.5 second signal integration time. For Gai activity, 10 µL of drugs are added for a 15-minute incubation period. Subsequently, 10 µL of isoproterenol (final concentration of 200 nM) are added and incubated for an additional 15-minute period before reading.

EXEMPLARY EMBODIMENTS

Embodiment 1: A compound of Formula I:

Formula I

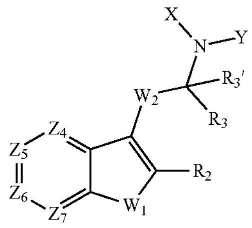

wherein

- X and Y are each independently selected from hydrogen, deuterium, optionally substituted $C_1$-$C_8$ alkyl, and optionally substituted $C_2$-$C_8$ alkenyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;
- $W_1$ is selected from $NR_1$, Se, Se(O), $SeO_2$, O, S, S(O), and $SO_2$;
- $W_2$ is selected from —$CD_2$-, —$(CD_2)_2$-, —CHD-, —$CH_2$— and —$(CH_2)_2$—;
- $Z_4$ is selected from N and $CR_4$;
- $Z_5$ is selected from N and $CR_5$;
- $Z_6$ is selected from N and $CR_6$;
- $Z_7$ is selected from N and $CR_7$;
- $R_2$, $R_3$, $R_{3'}$, $R_6$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$;
- $R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, —$C_1$-$C_8$alkoxy, —$OC(O)R_8$, —$OC(O)OR_8$, —$OP(O)O_2(R_9)_2$, and —$OSO_2R_8$;
- $R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)O_2(R_9)_2$, —$C(O)N(R_9)_2$, —$SOR_8$, and —$SO_2R_8$;
- $R_5$ is selected from optionally substituted $C_1$-$C_8$ alkyl, optionally substituted $C_2$-$C_8$ alkenyl, and optionally substituted aryl;
- $R_9$ is independently selected from hydrogen, deuterium, optionally substituted $C_1$-$C_8$alkyl, optionally substituted $C_2$-$C_8$ alkenyl, and optionally substituted aryl;

and salts, solvates, hydrates, and prodrugs thereof.

Embodiment 2: The compound of Embodiment 1, wherein X and Y are each independently selected from hydrogen, deuterium and $C_1$-$C_8$ alkyl.

Embodiment 3: The compound according to any one of the preceding Embodiments, wherein $R_2$, $R_3$, $R_3$, $R_6$ and $R_7$ are each independently selected from hydrogen, halo, optionally substituted $C_1$-$C_8$ alkyl, and optionally substituted $C_2$-$C_8$ alkenyl.

Embodiment 4: The compound according to any one of the preceding Embodiments, wherein X is unsubstituted $C_1$-$C_8$ alkyl.

Embodiment 5: The compound according to Embodiment 4, wherein X is methyl.

Embodiment 6: The compound according to Embodiment 4, wherein X is ethyl.

Embodiment 7: The compound according to Embodiment 4, wherein X is n-propyl.

Embodiment 8: The compound according to Embodiment 4, wherein X is isopropyl.

Embodiment 9: The compound according to any one of the preceding Embodiments, wherein Y is hydrogen or deuterium.

Embodiment 10: The compound according to any one of Embodiments 1-8, wherein Y is unsubstituted $C_1$-$C_8$ alkyl.

Embodiment 11: The compound according to Embodiment 10, wherein Y is methyl.

Embodiment 12: The compound according to Embodiment 10, wherein Y is ethyl.

Embodiment 13: The compound according to Embodiment 10, wherein Y is n-propyl.

Embodiment 14: The compound according to Embodiment 10, wherein Y is isopropyl.

Embodiment 15: The compound according to any one of the preceding Embodiments, wherein at least one of $Z_4$, $Z_5$, $Z_6$ or $Z_7$ is N.

Embodiment 16: The compound according to any one of the preceding Embodiments, wherein $Z_4$ is $CR_4$.

Embodiment 17: The compound according to any one of the preceding Embodiments, wherein $Z_5$ is $CR_5$.

Embodiment 18: The compound according to any one of the preceding Embodiments, wherein $Z_6$ is $CR_6$.

Embodiment 19: The compound according to any one of the preceding Embodiments, wherein $Z_7$ is $CR_7$.

Embodiment 20: The compound according to any one of the preceding Embodiments, wherein $R_4$ is hydrogen and $R_5$ is selected from optionally substituted $C_1$-$C_8$ alkyl, optionally substituted $C_2$-$C_8$ alkenyl, halo, hydroxyl, —$C_1$-$C_8$ alkoxy, —OC(O)$R_8$, —OC(O)O$R_8$, —OP(O)$O_2$($R_9$)$_2$, and —O$SO_2$$R_8$.

Embodiment 21: The compound according to Embodiment 20, wherein $R_5$ is selected from unsubstituted $C_1$-$C_8$ alkyl, hydroxyl, —$C_1$-$C_8$ alkoxy, —OC(O)$R_8$, —OC(O)O$R_8$, —OP(O)$O_2$($R_9$)$_2$, and —O$SO_2$$R_8$.

Embodiment 22: The compound according to Embodiment 20, wherein $R_5$ is selected from unsubstituted $C_1$-$C_8$ alkyl, hydroxyl, —$C_2$-$C_8$ alkoxy, —OC(O)$R_8$, —OC(O)O$R_8$, —OP(O)$O_2$($R_9$)$_2$, and —O$SO_2$$R_8$.

Embodiment 23: The compound according to Embodiment 22, wherein $R_5$ is hydroxy.

Embodiment 24: The compound according to Embodiment 22, wherein $R_5$ is —OC(O)$R_8$.

Embodiment 25: The compound according to Embodiment 24, wherein $R_5$ is unsubstituted $C_1$-$C_4$ alkyl.

Embodiment 26: The compound according to Embodiment 21, wherein $R_5$ is methoxy.

Embodiment 27: The compound according to any one of Embodiments 1-19, wherein $R_5$ is hydrogen and $R_4$ is selected from optionally substituted $C_1$-$C_8$ alkyl, optionally substituted $C_2$-$C_8$ alkenyl, halo, hydroxyl, —$C_1$-$C_8$ alkoxy, —OC(O)$R_8$, —OC(O)O$R_8$, —OP(O)$O_2$($R_9$)$_2$, and —O$SO_2$$R_8$.

Embodiment 28: The compound according to Embodiment 27, wherein $R_4$ is selected from unsubstituted $C_1$-$C_8$ alkyl, hydroxyl, —$C_1$-$C_8$ alkoxy, —OC(O)$R_8$, —OC(O)O$R_8$, —OP(O)$O_2$($R_9$)$_2$, and —O$SO_2$$R_8$.

Embodiment 29: The compound according to Embodiment 27, wherein $R_4$ is selected from unsubstituted $C_1$-$C_8$ alkyl, —$C_2$-$C_8$ alkoxy, —OC(O)$R_8$, —OC(O)O$R_8$, —OP(O)$O_2$($R_9$)$_2$, and —O$SO_2$$R_8$.

Embodiment 30: The compound according to Embodiment 28, wherein $R_4$ is —OC(O)$R_8$.

Embodiment 31: The compound according to Embodiment 30, wherein $R_5$ is unsubstituted $C_1$-$C_4$ alkyl.

Embodiment 32: The compound according to Embodiment 31, wherein $R_5$ is methyl.

Embodiment 33: The compound according to Embodiment 25, wherein $R_5$ is methyl.

Embodiment 34: The compound according to Embodiment 27, wherein $R_4$ is fluoro.

Embodiment 35: The compound according to Embodiment 28, wherein $R_4$ is hydroxy.

Embodiment 36: The compound according to any one of the preceding Embodiments, wherein $R_2$ is hydrogen.

Embodiment 37: The compound according to any one of the preceding Embodiments, wherein $R_6$ and $R_7$ are each independently selected from hydrogen, halo, and optionally substituted $C_1$-$C_4$ alkyl.

Embodiment 38: The compound according to any one of the preceding Embodiments, wherein $R_6$ is hydrogen or halo.

Embodiment 39: The compound according to any one of the preceding Embodiments, wherein $R_6$ is hydrogen or fluorine.

Embodiment 40: The compound according to any one of the preceding Embodiments, wherein $R_7$ is selected from hydrogen and optionally substituted $C_1$-$C_4$ alkyl.

Embodiment 41: The compound according to any one of the preceding Embodiments, wherein $R_7$ is selected from hydrogen, methyl, and ethyl.

Embodiment 42: The compound according to any one of the preceding Embodiments, wherein $W_2$ is —$CH_2$— or —CHD-.

Embodiment 43: The compound according to any one of the preceding Embodiments, wherein $W_1$ is N$R_1$.

Embodiment 44: The compound according to Embodiment 43, wherein $R_1$ is selected from hydrogen and unsubstituted $C_1$-$C_4$ alkyl.

Embodiment 45: The compound according to Embodiment 44, wherein $R_1$ is selected from methyl, ethyl and propyl.

Embodiment 46: The compound according to any one of Embodiments 1-42, wherein $W_1$ is S.

Embodiment 47: The compound according to any one of Embodiments 1-42, wherein $W_1$ is Se.

Embodiment 48: The compound according to any one of Embodiments 1-42, wherein $W_1$ is O.

Embodiment 49: The compound according to any one of the preceding Embodiments, wherein $R_3$ is hydrogen.

Embodiment 50: The compound according to any one of Embodiments 1-48, wherein $R_3$ is methyl.

Embodiment 51: The compound according to any one of the preceding Embodiments, wherein the compound comprises a [1:1] salt.

Embodiment 52: The compound according to any one of Embodiments 1-50, wherein the compound comprises a [2:1] salt.

Embodiment 53: The compound according to Embodiment 52, wherein the [2:1] salt comprises an oxalate salt or a fumarate salt.

Embodiment 54: The compound according to any one of the preceding Embodiments, wherein the compound is crystalline.

Embodiment 55: A composition comprising, consisting essentially of, or consisting of a compound according to any one of Embodiments 1-54 and an excipient.

Embodiment 56: A composition according to Embodiment 55, wherein the composition is a pharmaceutical composition comprising, consisting essentially of, or consisting of a therapeutically effective amount of a compound according to any one of Embodiments 1-54 and a pharmaceutically acceptable excipient.

Embodiment 57: A composition comprising, consisting essentially of, or consisting of as a first component: a compound according to any one of Embodiments 1-54; and as a second component selected from (a) a serotonergic drug, (b) a cannabinoid and (c) a terpene; and a pharmaceutically acceptable excipient.

Embodiment 58: The composition according to Embodiment 57, wherein the second component is purified.

Embodiment 59: A method of preventing or treating a psychological disorder comprising administering to a subject in need thereof a therapeutically effective amount of a compound according to any one of Embodiments 1-54 or a composition according to any one of Embodiments 55-58.

Embodiment 60: A method of preventing or treating inflammation and/or pain comprising administering to a subject in need thereof a therapeutically effective amount of a compound according to any one of Embodiments 1-54 or a composition according to any one of Embodiments 55-58.

Embodiment 61: A method of modulating activity at a neurotransmitter receptor, comprising:

- identifying a subject in need of treatment for a disease or condition associated with modulation of a 5-HT2A receptor; and
- administering a compound according to any one of Embodiments 1-54 or a composition according to any one of Embodiments 55-58 to the subject in need of treatment.

Embodiment 62: The method according to Embodiment 61, wherein a therapeutically effective amount of the compound is administered to a human subject.

Embodiment 63: A compound of Formula III:

Formula III

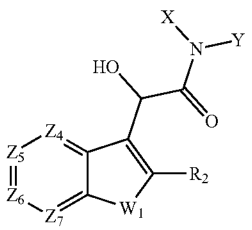

wherein

X and Y are each independently selected from hydrogen, deuterium, optionally substituted $C_1$-$C_8$ alkyl, and optionally substituted $C_2$-$C_8$ alkenyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from $NR_1$, O, Se, Se(O), $SeO_2$, S, S(O), and $SO_2$;

$Z_4$ is selected from N and $CR_4$;

$Z_5$ is selected from N and $CR_5$;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)O_2(R_9)_2$, —$C(O)N(R_9)_2$, —$SOR_8$, and —$SO_2R_8$;

$R_2$, $R_5$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$;

$R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, —$C_1$-$C_8$alkoxy, —$OC(O)R_8$, —$OC(O)OR_8$, —$OP(O)O_2(R_9)_2$, and —$OSO_2R_8$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$alkyl, optionally substituted $C_2$-$C_8$ alkenyl, and optionally substituted aryl; and salts, solvates, hydrates, and prodrugs thereof.

Embodiment 64: The compound according to Embodiment 63, provided that X and Y are not both hydrogen when $Z_4$ is $CR_4$, $Z_5$ is $CR_5$, $Z_e$ is $CR_5$, $Z_7$ is $CR_7$, $R_4$ is hydrogen, $R_5$ is hydrogen, $R_6$ is hydrogen, $R_7$ is hydrogen, and $R_2$ is hydrogen.

Embodiment 65: The compound according to any one of Embodiments 63-64, provided that X is not methyl, or 3-heptyl when Y is hydrogen, $Z_4$ is $CR_4$, $Z_5$ is $CR_5$, $Z_6$ is $CR_6$, $Z_7$ is $CR_7$, $R_4$ is hydrogen, $R_5$ is methyl or chloro, $R_6$ is hydrogen, $R_7$ is hydrogen, and $R_2$ is hydrogen.

Embodiment 66: The compound according to any one of Embodiments 63-65, wherein X and Y are each independently selected from optionally substituted $C_1$-$C_8$ alkyl and optionally substituted $C_2$-$C_8$ alkenyl.

Embodiment 67: The compound according to any one of Embodiments 63-66, wherein $R_2$, $R_5$ and $R_7$ are each independently selected from hydrogen, halo, optionally substituted $C_1$-$C_8$alkyl, and optionally substituted $C_2$-$C_8$ alkenyl.

Embodiment 68: The compound according to any one of Embodiments 63-67, wherein X is unsubstituted $C_1$-$C_8$ alkyl.

Embodiment 69: The compound according to Embodiment 68, wherein X is methyl.

Embodiment 70: The compound according to Embodiment 68, wherein X is ethyl.

Embodiment 71: The compound according to Embodiment 68, wherein X is n-propyl.

Embodiment 72: The compound according to Embodiment 68, wherein X is isopropyl.

Embodiment 73: The compound according to any one of Embodiments 63-72, wherein Y is unsubstituted $C_1$-$C_8$ alkyl.

Embodiment 74: The compound according to Embodiment 73, wherein Y is methyl.

Embodiment 75: The compound according to Embodiment 73, wherein Y is ethyl.

Embodiment 76: The compound according to Embodiment 73, wherein Y is n-propyl.

Embodiment 77: The compound according to Embodiment 73, wherein Y is isopropyl.

Embodiment 78: The compound according to any one of Embodiments 63-72, wherein Y is hydrogen.

Embodiment 79: The compound according to any one of Embodiments 63-78, wherein $W_1$ is S, O, or Se.

Embodiment 80: A compound of Formula IV:

Formula IV

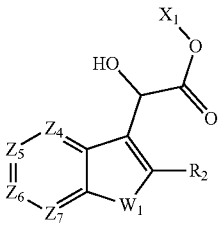

wherein $X_1$ selected from hydrogen, deuterium, optionally substituted $C_1$-$C_8$ alkyl, and optionally substituted $C_2$-$C_8$ alkenyl;

$W_1$ is selected from $NR_1$, O, Se, Se(O), $SeO_2$, S, S(O), and $SO_2$;

$Z_4$ is selected from N and $CR_4$;

$Z_5$ is selected from N and $CR_5$;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)O_2(R_9)_2$, —$C(O)N(R_9)_2$, —$SOR_8$, and —$SO_2R_8$;

$R_2$, $R_6$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl;

$R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, —$C_1$-$C_8$ alkoxy, —$OC(O)R_8$, —OC(O)$OR_8$, —$OP(O)O_2(R_9)_2$, and —$OSO_2R_8$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$alkyl, optionally substituted $C_2$-$C_8$ alkenyl, and optionally substituted aryl; and salts, solvates, hydrates, and prodrugs thereof.

Embodiment 81: The compound according to Embodiment 80, wherein $X_1$ is unsubstituted $C_1$-$C_8$ alkyl.

Embodiment 82: A compound of Formula II:

Formula II

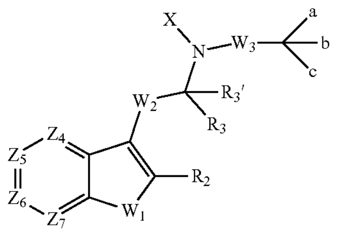

wherein

X is hydrogen or deuterium;

$W_3$ is absent or is selected from —$(CZ'_2)_n$—, wherein n is an integer selected from 1 and 2, and each Z' is independently selected from hydrogen, deuterium, and fluorine;

a, b and c are each independently selected from hydrogen, deuterium, and fluorine;

$W_1$ is selected from $NR_1$, Se, Se(O), $SeO_2$, O, S, S(O), and $SO_2$;

$W_2$ is selected from —$CD_2$-, —CHD-, —$(CD_2)_2$-, —$CH_2$— and —$(CH_2)_2$—;

$Z_4$ is selected from N and $CR_4$;

$Z_5$ is selected from N and $CR_5$;

$Z_6$ is selected from N and $CR_6$;

$Z_7$ is selected from N and $CR_7$;

$R_2$, $R_3$, $R_{3'}$, $R_6$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl;

$R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, —$C_1$-$C_8$alkoxy, —$OC(O)R_8$, —OC(O)$OR_8$, —$OP(O)O_2(R_9)_2$, and —$OSO_2R_8$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)O_2(R_9)_2$, —C(O)$N(R_9)_2$, —$SOR_8$, and —$SO_2R_8$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$alkyl, optionally substituted $C_2$-$C_8$ alkenyl, and optionally substituted aryl; and salts, solvates, hydrates, and prodrugs thereof.

Embodiment 83: The compound according to Embodiment 82, wherein $W_3$ is absent.

Embodiment 84: The compound according to Embodiment 82, wherein $W_3$ is —$(CZ'_2)_n$— and n=1.

Embodiment 85: The compound according to Embodiment 84, wherein $W_3$ is selected from —$CH_2$—, —CHF—, —$CF_2$—, and —$CD_2$-.

Embodiment 86: The compound according to Embodiment 85, wherein $W_3$ is —$CD_2$-.

Embodiment 87: The compound according to any one of Embodiments 82-86, wherein a is fluorine, and b and c are each hydrogen.

Embodiment 88: The compound according to any one of Embodiments 82-86, wherein a is hydrogen, and b and c are each fluorine.

Embodiment 89: The compound according to any one of Embodiments 82-86, wherein a, b and c are all fluorine.

Embodiment 90: The compound according to any one of Embodiments 82-86, wherein a, b and c are all hydrogen.

Embodiment 91: The compound according to any one of Embodiments 82-86, wherein a, b and c are all deuterium.

Embodiment 92: The compound according to any one of Embodiments 82-91, wherein at least one of $Z_4$, $Z_5$, $Z_6$ or $Z_7$ is N.

Embodiment 93: The compound according to any one of Embodiments 82-92, wherein $Z_4$ is $CR_4$.

Embodiment 94: The compound according to any one of Embodiments 82-93, wherein $Z_5$ is CRS.

Embodiment 95: The compound according to any one of Embodiments 82-94, wherein $Z_6$ is $CR_6$.

Embodiment 96: The compound according to any one of Embodiments 82-95, wherein $Z_7$ is $CR_7$.

Embodiment 97: The compound according to any one of Embodiments 82-96, wherein $R_4$ is hydrogen or fluorine and $R_5$ is selected from hydrogen, optionally substituted $C_1$-$C_8$alkyl, optionally substituted $C_2$-$C_8$ alkenyl, halo, hydroxyl, —$C_1$-$C_8$ alkoxy, —$OC(O)R_8$, —$OC(O)OR_8$, —$OP(O)O_2(R_9)_2$, and —$OSO_2R_8$.

Embodiment 98: The compound according to Embodiment 97, wherein $R_5$ is selected from unsubstituted $C_1$-$C_8$ alkyl, hydroxyl, —$C_1$-$C_8$ alkoxy, —$OC(O)R_8$, —OC(O)$OR_8$, —$OP(O)O_2(R_9)_2$, and —$OSO_2R_8$.

Embodiment 99: The compound according to Embodiment 98, wherein $R_5$ is methoxy.

Embodiment 100: The compound according to any one of Embodiments 82-96, wherein $R_5$ is hydrogen or fluorine and $R_4$ is selected from hydrogen, optionally substituted $C_1$—$C_8$ alkyl, optionally substituted $C_2$-$C_8$ alkenyl, halo, hydroxyl, —$C_1$-$C_8$ alkoxy, —$OC(O)R_8$, —$OC(O)OR_8$, —$OP(O)O_2$$(R_9)_2$, and —$OSO_2R_8$.

Embodiment 101: The compound according to Embodiment 100, wherein $R_4$ is selected from fluorine, hydroxyl, —$OC(O)R_8$, and —$OC(O)OR_8$.

Embodiment 102: The compound according to Embodiment 101, wherein $R_5$ is unsubstituted $C_1$-$C_4$ alkyl.

Embodiment 103: The compound according to Embodiment 102, wherein $R_5$ is selected from methyl, ethyl, n-propyl, isopropyl, n-butyl, isobutyl, and sec-butyl.

Embodiment 104: The compound according to any one of Embodiments 82-103, wherein $R_2$ is hydrogen.

Embodiment 105: The compound according to any one of Embodiments 82-104, wherein $R_6$ and $R_7$ are each independently selected from hydrogen, halo, and optionally substituted $C_1$-$C_4$ alkyl.

Embodiment 106: The compound according to Embodiment 105, wherein $R_6$ is hydrogen or halo.

Embodiment 107: The compound according to Embodiment 105, wherein $R_6$ is hydrogen or fluorine.

Embodiment 108: The compound according to any one of Embodiments 82-107, wherein $R_7$ is selected from hydrogen and optionally substituted $C_1$-$C_4$ alkyl.

Embodiment 109: The compound according to any one of Embodiments 82-107, wherein $R_7$ is selected from hydrogen, methyl, and ethyl.

Embodiment 110: The compound according to any one of Embodiments 82-109, wherein $W_2$ is —$CH_2$— or —CHD-.

Embodiment 111: The compound according to any one of Embodiments 82-110, wherein $W_1$ is $NR_1$.

Embodiment 112: The compound according to Embodiment 111, wherein $R_1$ is selected from hydrogen and unsubstituted $C_1$-$C_4$ alkyl.

Embodiment 113: The compound according to Embodiment 111, wherein $R_1$ is selected from methyl, ethyl and propyl.

Embodiment 114: The compound according to any one of Embodiments 82-110, wherein $W_1$ is S.

Embodiment 115: The compound according to any one of Embodiments 82-110, wherein $W_1$ is Se.

Embodiment 116: The compound according to any one of Embodiments 82-110, wherein $W_1$ is O.

Embodiment 117: The compound according to any one of Embodiments 82-116, wherein $R_3$ is hydrogen.

Embodiment 118: The compound according to any one of Embodiments 82-116, wherein $R_3$ is methyl.

Embodiment 119: The compound according to any one of Embodiments 82-118, wherein $R_3$ is hydrogen.

Embodiment 120: The compound according to any one of Embodiments 82-118, wherein $R_3$ is deuterium.

Embodiment 121: The compound according to any one of Embodiments 82-120, wherein at least one of $R_4$, $R_6$, and a is fluorine.

Embodiment 122: The compound according to Embodiment 121, wherein $R_4$ is fluorine.

Embodiment 123: The compound according to Embodiment 121, wherein $R_6$ is fluorine.

Embodiment 124: The compound according to Embodiment 123, wherein $R_4$ is not fluorine.

Embodiment 125: The compound according to Embodiment 123, wherein $R_1$ is hydrogen.

Embodiment 126: The compound according to Embodiment 123, wherein at least one of $R_4$, $R_5$ or $R_7$ is not hydrogen.

Embodiment 127: The compound according to Embodiment 121, wherein a is fluorine.

Embodiment 128: A compound according to any one of Embodiments 82-127, wherein the compound comprises a [1:1] salt.

Embodiment 129: A compound according to any one of Embodiments 82-127, wherein the compound comprises a [2:1] salt.

Embodiment 130: The compound according to Embodiment 129, wherein the [2:1] salt comprises an oxalate salt or a fumarate salt.

Embodiment 131: A compound according to any one of Embodiments 82-130, wherein the compound is crystalline.

Embodiment 132: A composition comprising, consisting essentially of, or consisting of a compound according to any one of Embodiments 82-131 and an excipient.

Embodiment 133: A composition of Embodiment 132, wherein the composition is a pharmaceutical composition comprising, consisting essentially of, or consisting of a therapeutically effective amount of a compound according to any one of Embodiments 82-130 and a pharmaceutically acceptable excipient.

Embodiment 134: A method of preventing or treating a psychological disorder comprising administering to a subject in need thereof a therapeutically effective amount of a compound according to any one of Embodiments 82-131 or a composition according to any one of Embodiments 132-133.

Embodiment 135: A method of preventing or treating inflammation and/or pain comprising administering to a subject in need thereof a therapeutically effective amount of a compound according to any one of Embodiments 82-131 or a composition according to any one of Embodiments 132-133.

Embodiment 136: A method of modulating activity at a neurotransmitter receptor, comprising identifying a subject in need of treatment for a disease or condition associated with modulation of a 5-HT1A receptor;

selecting a compound according to any one of Embodiments 82-131; and administering a therapeutically effective amount of the compound to the subject in need of treatment.

Embodiment 137: The method according to Embodiment 136, wherein to the subject is a human subject.

Embodiment 138: The method according to any one of Embodiments 134-137, wherein the compound is a full agonist of a 5-HT1A receptor.

Embodiment 139: The method according to any one of Embodiments 134-138, wherein the compound is a full agonist of a 5-HT2A receptor.

Embodiment 140: The method according to any one of Embodiments 134-139, wherein the compound exhibits an $EC_{50}$ for activating a 5-HT1A receptor that is lower than the $EC_{50}$ it exhibits for activating a 5-HT2A receptor.

Embodiment 141: The method according to Embodiment 140, wherein the compound exhibits an $EC_{50}$ for activating a 5-HT1A receptor of less than about 10 nM.

Embodiment 142: The method according to Embodiment 141, wherein the compound exhibits an $EC_{50}$ for activating a 5-HT2A receptor of about 20 to about 40 nM.

Embodiment 143: The method according to any one of Embodiments 134-142, wherein the compound exhibits an Emax % of at least about 90% for agonism of a 5-HT1A receptor when compared to 5-hydroxytryptamine.

Embodiment 144: The method according to any one of Embodiments 134-142, wherein the compound exhibits an Emax % of at least about 95% for agonism of a 5-HT1A receptor when compared to 5-hydroxytryptamine.

Embodiment 145: The method according to any one of Embodiments 134-142, wherein the compound exhibits an Emax % of at least about 99% for agonism of a 5-HT1A receptor when compared to 5-hydroxytryptamine.

Embodiment 146: The method according to any one of Embodiments 134-145, wherein the compound exhibits an Emax % of at least about 90% for agonism of a 5-HT2A receptor when compared to 5-hydroxytryptamine.

Embodiment 147: The method according to any one of Embodiments 134-145, wherein the compound exhibits an Emax % of at least about 95% for agonism of a 5-HT2A receptor when compared to 5-hydroxytryptamine.

Embodiment 148: The method according to any one of Embodiments 134-145, wherein the compound exhibits an Emax % of at least about 99% for agonism of a 5-HT2A receptor when compared to 5-hydroxytryptamine.

Embodiment 149: The method according to any one of Embodiments 134-145, wherein the subject does not experience audio or visual hallucinations triggered by the compound.

Embodiment 150: The method according to any one of Embodiments 134-149, wherein the compound is administered to the subject in a dosage form.

Embodiment 151: The method according to Embodiment 150, wherein the dosage form contains about 1 to about 100 mg of the compound.

Embodiment 152: The method according to any one of Embodiments 134-151, wherein the compound is administered to the subject in an amount that is less than about 1 mg/kg.

Embodiment 153: The method according to any one of Embodiments 134-151, wherein the compound is administered to the subject in an amount of about 0.05 to about 0.75 mg/kg.

Embodiment 154: The method according to any one of Embodiments 134-151, wherein the compound is administered to the subject in an amount of about 0.01 to about 0.50 mg/kg.

Embodiment 155: The method according to any one of Embodiments 136-154, wherein the compound modulates activity at both a 5-HT1A receptor and a 5-HT2A receptor.

Finally, it is noted that, as used in this specification and the appended claims, the singular forms "a," "an," and "the," include plural referents unless expressly and unequivocally limited to one referent and vice versa. As used herein, the term "include" or "comprising" and its grammatical variants are intended to be non-limiting, such that recitation of an item or items is not to the exclusion of other like items that can be substituted or added to the recited item(s).

What is claimed is:

1. A compound of Formula I:

Formula I

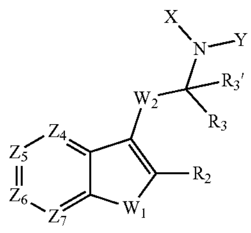

wherein

X is selected from hydrogen, deuterium, optionally substituted $C_1$-$C_8$ alkyl, and optionally substituted $C_2$-$C_8$ alkenyl;

Y is an optionally substituted $C_1$-$C_8$ cyclic alkyl or a $C_1$-$C_4$ alkyl that is substituted with at least one aryl group, at least one halo, at least one heteroaryl group, or at least one $C_1$-$C_8$ cyclic alkyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from O, Se, Se(O), $SeO_2$, S, S(O), $NR_1$, and $SO_2$;

$W_2$ is selected from —$CD_2$-, -CHD-, —$(CD_2)_2$-, —$CH_2$— and —$(CH_2)_2$—;

$Z_4$ is $CR_4$;

$Z_5$ is $CR_5$;

$Z_6$ is $CR_6$;

$Z_7$ is N;

$R_2$, $R_3$, $R_{3'}$, $R_6$ and $R_7$ are each independently selected from hydrogen, deuterium, —$N(R_9)_2$, —$SR_9$, halo, optionally substituted $C_1$-$C_8$ alkyl, —$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$;

$R_4$ and $R_5$ are each independently selected from hydrogen, deuterium, optionally substituted $C_1$-$C_8$ alkyl, optionally substituted $C_2$-$C_8$ alkenyl, halo, hydroxyl, —$N(R_9)_2$, —$SR_9$, optionally substituted $C_1$-$C_8$ alkoxy, —$OC(O)R_8$, —$OC(O)OR_8$, —$OP(O)(OR_9)_2$, and —$OSO_2R_8$, wherein at least one of $R_4$ or $R_5$ is not hydrogen;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —$C(O)N(R_9)_2$, —$SOR_8$, and —$SO_2R_8$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$ alkyl, optionally substituted $C_2$-$C_8$ alkenyl, and optionally substituted aryl;

and salts, solvates, hydrates, and prodrugs thereof.

2. The compound of claim 1, wherein X is an optionally substituted $C_1$-$C_8$ alkyl that is cyclic.

3. The compound of claim 2, wherein Y is an optionally substituted $C_1$-$C_8$ cyclic alkyl or a $C_1$-$C_4$ alkyl that is substituted with at least one aryl group, at least one halo, at least one heteroaryl group, or at least one $C_1$-$C_8$ cyclic alkyl.

4. The compound of claim 3, wherein Y is a $C_1$-$C_8$ cyclic alkyl group optionally substituted with at least one fluoro group.

5. The compound of claim 4, wherein Y is selected from cyclopropyl and cyclobutyl.

6. The compound of claim 3, wherein Y is methyl substituted with an optionally substituted aryl group.

7. The compound of claim 6, wherein Y is methyl substituted with a phenyl group, wherein the phenyl group is optionally substituted with a halo group or a $C_1$-$C_8$ alkoxy group.

8. The compound of claim 7, wherein Y is methyl substituted with a phenyl group, wherein the phenyl group is optionally substituted with fluoro group or a methoxy group.

9. The compound of claim 1, wherein $R_6$ is hydrogen.

10. The compound of claim 9, wherein $R_4$ is selected from hydrogen, halo, hydroxyl, optionally substituted $C_1$-$C_8$ alkoxy and —$OC(O)R_8$.

11. The compound of claim 10, wherein $R_4$ is hydrogen.

12. The compound of claim 11, wherein $R_5$ is selected from halo, hydroxyl, optionally substituted $C_1$-$C_8$ alkyl, optionally substituted $C_1$-$C_8$ alkoxy, and —$OC(O)R_8$.

13. The compound of claim 12, wherein $R_5$ is halo.

14. The compound of claim 13, wherein $R_5$ is fluoro.

15. The compound of claim 12, wherein $R_5$ is $C_1$-$C_8$ alkoxy substituted with at least one halo.

16. The compound of claim 1, wherein Y is taken together with X and the nitrogen atom therebetween to form a 3- to 7-membered heterocyclic ring optionally including 1 to 2 additional ring heteromoieties selected from O, S, S(O), $SO_2$, and $NR_9$.

17. The compound of claim 1, wherein Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$.

18. The compound of claim 1, wherein $W_1$ is selected from S and O.
19. The compound of claim 1, wherein $W_1$ is $NR_1$.
20. The compound of claim 19, wherein the compound is selected from:
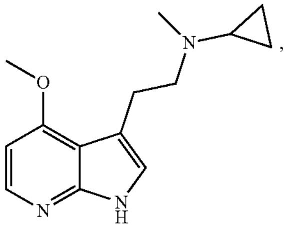
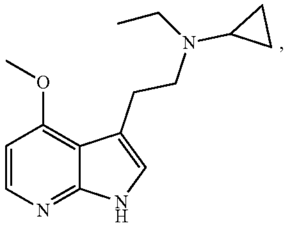
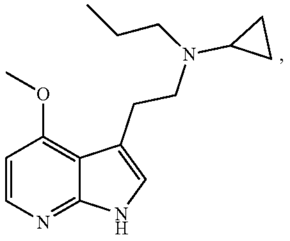
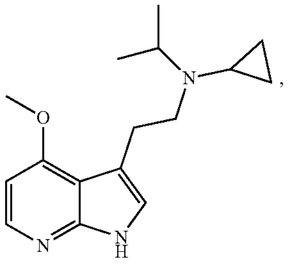
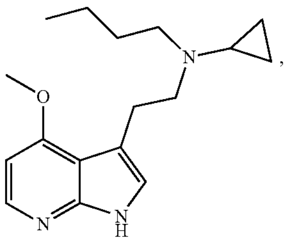
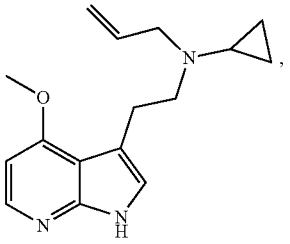
-continued
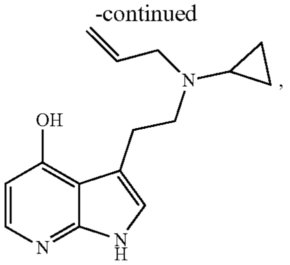
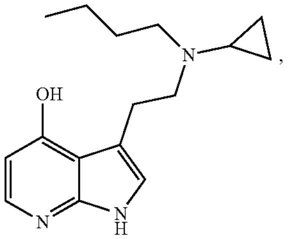
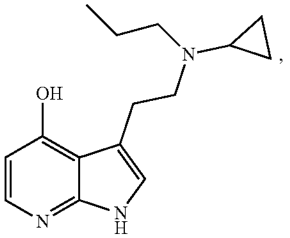
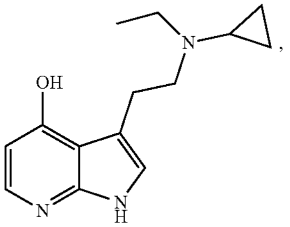
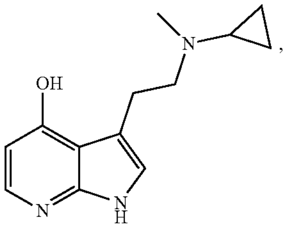
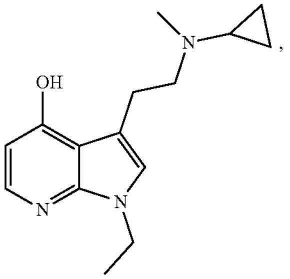
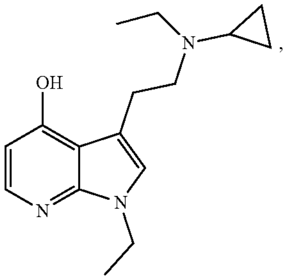

-continued
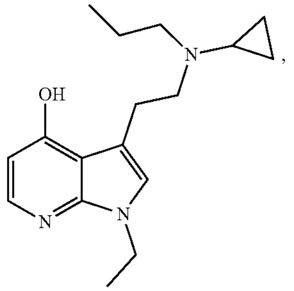
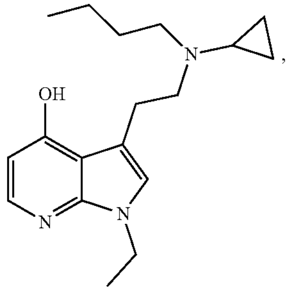
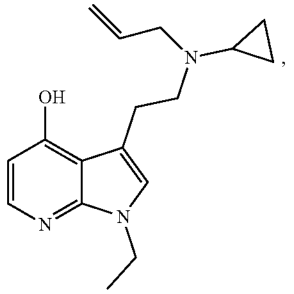
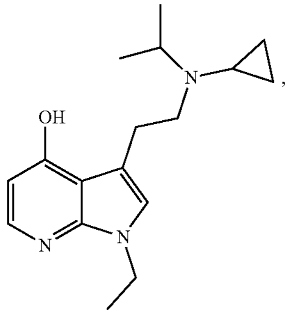
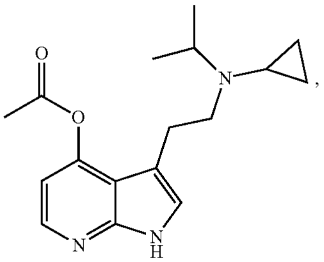
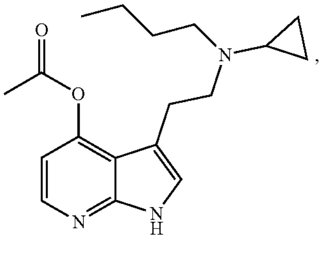
-continued
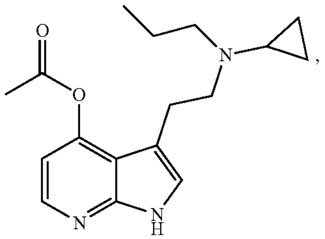
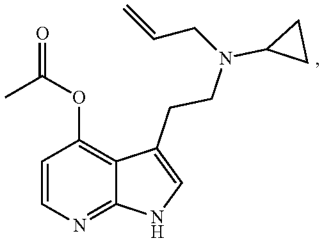
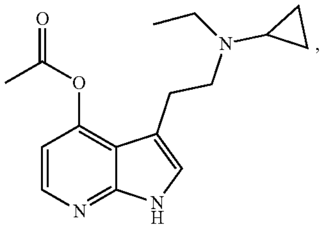
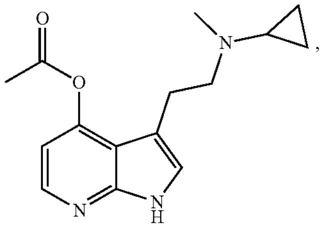
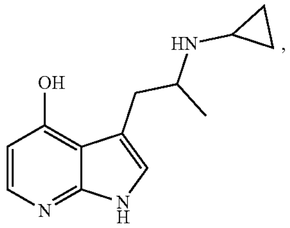
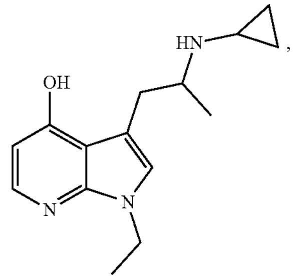
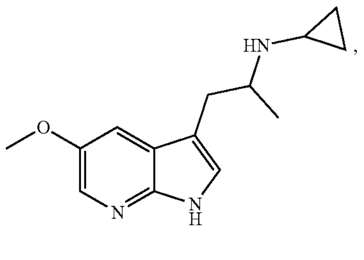

-continued
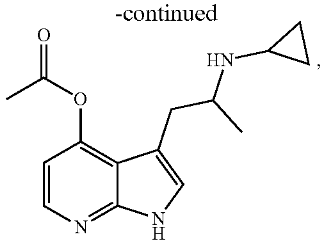
,
and salts, solvates, hydrates, and prodrugs thereof.
* * * * *